US008202883B2

(12) United States Patent
Gerlach et al.

(10) Patent No.: US 8,202,883 B2
(45) Date of Patent: Jun. 19, 2012

(54) SUBSTITUTED PYRIDO[2,3-B]PYRAZINE COMPOUNDS AS MODULATORS OF TYROSINE KINASES

(75) Inventors: Matthias Gerlach, Brachttal (DE); Irene Seipelt, Offenbach (DE); Eckhard Guenther, Maintal (DE); Emmanuel Polymeropoulos, Frankfurt (DE); Tilmann Schuster, Grossostheim (DE); Eckhard Claus, Frankfurt (DE)

(73) Assignee: Aeterna Zentaris GmbH, Frankfurt am Main (DE)

( * ) Notice: Subject to any disclaimer, the term of this patent is extended or adjusted under 35 U.S.C. 154(b) by 385 days.

(21) Appl. No.: 12/117,942

(22) Filed: May 9, 2008

(65) Prior Publication Data
US 2009/0275534 A1 Nov. 5, 2009

Related U.S. Application Data

(60) Provisional application No. 60/917,129, filed on May 10, 2007.

(30) Foreign Application Priority Data

May 10, 2007 (EP) .................... 07107976

(51) Int. Cl.
*A61K 31/44* (2006.01)
(52) U.S. Cl. ....................... 514/303; 544/350
(58) Field of Classification Search .............. 514/303; 544/350
See application file for complete search history.

(56) References Cited

U.S. PATENT DOCUMENTS 3,898,216 A * 8/1975 Weaver .............. 544/345

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*

* cited by examiner

*Primary Examiner* — James O Wilson
*Assistant Examiner* — Douglas M Willis
(74) *Attorney, Agent, or Firm* — Oblon, Spivak, McClelland, Maier & Neustadt, L.L.P.

(57) ABSTRACT

The invention relates to pyrido[2,3-b]pyrazine compounds of formulae (Ia) and (Ib) which have activity to the modulation of misdirected cellular signal transduction processes such as tyrosine kinases, serine/threonine kinases and/or lipid kinases, their preparation and use as medicaments, especially for the treatment of malignant disorders and other disorders based on pathological cell proliferations:

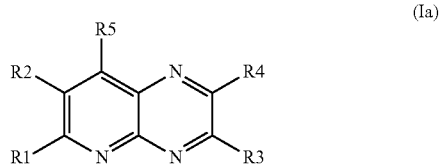

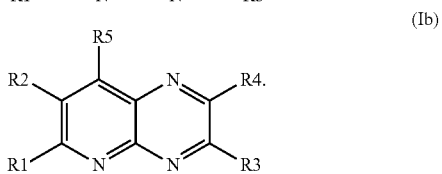

24 Claims, No Drawings

SUBSTITUTED PYRIDO[2,3-B]PYRAZINE COMPOUNDS AS MODULATORS OF TYROSINE KINASES

BACKGROUND OF THE INVENTION

1. Field of the Invention

The invention relates to novel pyrido[2,3-b]pyrazine derivatives, to processes of manufacturing and use thereof, in particular as medicaments for the modulation of misdirected cellular signal transduction processes, such as modulation of tyrosine kinases, serine/threonine kinases and/or lipid kinases and for the treatment or prophylaxis of malignant or benign oncoses and other disorders based on pathological cell proliferation, for example restenosis, psoriasis, arteriosclerosis and cirrhosis of the liver.

2. Description of Related Art

The activation of protein kinases is a central event in cellular signal transduction processes. Aberrant kinase activation is observed in various pathological states. Targeted inhibition of kinases is therefore a fundamental therapeutic aim.

The phosphorylation of proteins is generally initiated by extracellular signals and represents a universal mechanism for controlling various cellular events, for example metabolic processes, cell growth, cell migration, cell differentiation, membrane trans-port and apoptosis. The kinase protein family is responsible for protein phosphorylation. These enzymes catalyse transfer of phosphate to specific substrate proteins. Based on the substrate specificity, the kinases are divided into three main classes, tyrosine kinases, serine/threonine kinases and lipid kinases. Both receptor tyrosine kinases and cytoplasmic tyrosine, serine/threonine and lipid kinases are important proteins in cellular signal transduction. Overexpression or overactivation of these proteins plays an important part in disorders based on pathological cell proliferations. These include metabolic disorders, disorders of the connective tissue and of the blood vessels, and malignant and benign oncoses. In tumor initiation and development they frequently occur as oncogens, i.e. as aberrant, constitutively active kinase proteins. The consequences of this excessive kinase activation are, for example, uncontrolled cell growth and reduced cell death. Stimulation of tumor-induced growth factors may also be the cause of overstimulation of kinases. The development of kinase modulators is therefore of particular interest for all pathogenic processes influenced by kinases.

Ras-Raf-Mek-Erk and PI3K-Akt signal transduction cascades play a central role in cell growth, cell proliferation, apoptosis, adhesion, migration and glucose metabolism. Thus, the fundamental involvement in the pathogenesis of disorders such as cancer, neurodegeneration and inflammatory disorders has been demonstrated both for ras-Raf-Mek-Erk and for PI3K-Akt signaling pathway. Therefore, the individual components of these signal cascades constitute important therapeutic points of attack for the intervention in the various disease processes (Weinstein-Oppenheimer C R et al., Pharmacol Ther. 2000, 88(3):229-279, Chang F et al., Leukemia 2003, 17(3):590-603; Chang F et al., Leukemia 2003, 17(7):1263-1293; Katso R et al., Annu Rev Cell Dev Biol. 2001, 17:615-675; and Lu Y et al., Rev Clin Exp Hematol. 2003, 7(2):205-228; Hennessy B T et al., Nat Rev Drug Discov 2005, 4, 988-1004).

In the following, the molecular and biochemical properties of the two signaling pathways are first described separately.

A multitude of growth factors, cytokines and oncogens transduce their growth-promoting signals via the activation of G-protein-coupled ras, which leads to the activation of serine-threonine kinase Raf and to the activation of mitogen-activated protein kinase kinase 1 and 2 (MAPKK1/2 or Mek1/2), and results in the phosphorylation and activation of MAPK 1 and 2—also known as extracellular signal-regulated kinase (Erk1 and 2). Compared to other signaling pathways, ras-Raf-Mek-Erk signaling pathway combines a large number of proto-oncogenes, including ligands, tyrosine kinase receptors, G proteins, kinases and nuclear transcription factors. Tyrosine-kinases, for example EGFR (Mendelsohn J et al., Oncogene. 2000, 19(56):6550-6565) mediate, in the course of tumor process, caused by overexpression and mutation, frequently constitutively active signals to downstream ras-Raf-Mek-Erk signaling pathway. Ras is mutated in 30% of all human tumors (Khleif S N et al., J Immunother. 1999, 22(2): 155-165; Marshall C, Curr Opin Cell Biol. 1999, 11(6):732-736) the highest incidence at 90% being in pancreas carcinomas (Friess H et al., J Mol. Med. 1996, 74(1):35-42; Sirivatanauksorn V et al., Langenbecks Arch Surg. 1998, 383(2):105-115). As for c-Raf, deregulated expression and/or activation have been described in various tumors (Hoshino R et al., Oncogene 1999, 18(3):813-822; McPhillips F et al., Br J Cancer 2001, 85(11):1753-1758). B-Raf point mutants have been detected in 66% of all human malignant melanomas, 14% of ovarian carcinomas and 12% of colon carcinomas (Davies H et al., Nature 2002, 417(6892):949-954). It is therefore not surprising that Erk1/2 is involved at primary stage in many cellular processes, such as cell growth, cell proliferation and cell differentiation (Lewis T S et al., Adv Cancer Res. 1998, 74:49-139; Chang F et al., Leukemia 2003, 17(3):590-603; Chang F et al., Leukemia 2003, 17(7):1263-1293).

In addition, members of Raf kinases also have Mek-Erk-independent, anti-apoptotic functions whose molecular steps have not yet been fully described. Possible interaction partners described for the Mek-Erk-independent Raf activity have been Ask1, Bcl-2, Akt and Bag1 (Chen J et al., Proc Natl Acad Sci USA 2001, 98(14):7783-7788; Troppmair J et al., Biochem Pharmacol 2003, 66(8):1341-1345; Rapp U R et al., Biochim Biophys Acta 2004, 1644(2-3):149-158; Gotz R et al., Nat Neurosci 2005, 8(9):1169-1178). It is now assumed that both Mek-Erk-dependent and Mek-Erk-independent signal transduction mechanisms control the activation of upstream ras and Raf stimuli.

The isoenzymes of the phosphatidylinositol 3-kinases (PI3Ks) function primarily as lipid kinases and catalyse the D3 phosphorylation of second messenger lipids PtdIns (phosphatidylinositol) to PtdIns(3)P, PtdIns(3,4)$P_2$, PtdIns(3,4,5)$P_3$ phosphatidylinositol phosphates. PI3Ks of class I are composed in structural terms of catalytic subunit (p110alpha, beta, gamma, delta) and of regulatory subunit (p85alpha, beta or p101gamma). In addition, class II (PI3K-C2alpha, PI3K-C2beta) and class III (Vps34p) enzymes also belong to the family of PI3 kinases (Wymann M P et al., Biochim Biophys Acta 1998, 1436(1-2):127-150; Vanhaesebroeck B et al., Annu Rev Biochem 2001, 70:535-602). PIP rise induced by PI3Ks activates proliferative ras-Raf-Mek-Erk signaling pathway via the coupling of ras (Rodriguez-Viciaria P et al., Nature 1994, 370(6490):527-532) and stimulates the anti-apoptotic signaling pathway by recruiting Akt to the cell membrane and consequently overactivating this kinase (Alessi D R et al., EMBO J. 1996, 15(23):6541-6551; Chang H W et al., Science 1997, 276(5320):1848-1850; Moore S M et al., Cancer Res 1998, 58(22):5239-5247). Thus, activation of PI3Ks fulfils at least two crucial mechanisms of tumor development, specifically activation of cell growth and cell differentiation, and inhibition of apoptosis. In addition, PI3Ks also have protein-phosphorylating properties (Dhand R et al., EMBO J. 1994, 13(3):522-533; Bondeva T et al., Science 1998, 282(5387):293-296; Bondev A et al., Biol Chem 1999, 380(11):1337-1340; Vanhaesebroeck B et al., EMBO J. 1999, 18(5):1292-1302), which, for example, can induce serine autophosphorylation which intrinsically regulates PI3Ks. It is also known that PI3Ks have kinase-independent, regulating effector properties, for example in the control of heart contraction (Crackower M A et al., Cell 2002, 110 (6):737-749; Patrucco E et al., Cell. 2004, 118(3):375-387). It has also been demonstrated that PI3 Kdelta and PI3 Kgamma are expressed specifically on haematopoietic cells and are thus potential points of attack for isoenzyme-specific PI3 Kdelta and PI3 Kgamma inhibitors in the treatment of inflammatory disorders, such as rheumatism, asthmas, allergies and in the treatment of B cell and T cell lymphomas (Okkenhaug K et al., Nat Rev Immunol 2003, 3(4):317-330; Ali K et al., Nature 2004, 431(7011): 1007-1011; Sujobert P et al., Blood 2005, 106(3):1063-1066). PI3Kalpha, which has recently been identified as a proto-oncogen (Shayesteh L et al., Nat Genet. 1999, 21(1):99-102; Ma Y Y et al., Oncogene 2000, 19(23):2739-2744; Samuels Y et al., Science 2004, 304(5670):554; Campbell I G, et al., Cancer Res 2004, 64(21):7678-7681; Levine D A et al., Clin Cancer Res 2005, 11(8):2875-2878) is an important target in the therapy of tumor disorders. The significance of the PI3K species as a target for active pharmaceutical ingredient (API) development is therefore extremely wide (Chang F et al., Leukemia 2003, 17(3):590-603).

Of equally great interest are PI3K-related kinases (PIKKs), which include serine/threonine kinases mTOR, ATM, ATR, h-SMG-1 and DNA-PK (Sabatini D M, Nat Rev Canc 2006, 6:729-34; Chiang G G et al., Methods Mol Biol 2004, 281: 125-141). Their catalytic domains have a high sequence homology to the catalytic domains of PI3Ks.

Moreover, loss of tumor suppressor protein PTEN (Li J et al., Science 1997, 275(5308):1943-1947; Steck P A et al., Nat Genet. 1997, 15(4):356-362; Cully M et al., Nat Rev Canc 2006, 6:184-192)—whose function is the reversal of the phosphorylation initiated by PI3K—contributes to overactivation of Akt and its downstream cascade components and hence underlines the causal significance of PI3K as a target molecule for tumor therapy.

Various inhibitors of individual components of ras-Raf-Mek-Erk and PI3K-Akt signaling pathways have already been published and patented.

The current state of development in the field of the kinase-inhibitors, particularly of ras-Raf-Mek-Erk and of PI3K-Akt pathway, is detailed in the reviews by J. S. Sebolt-Leopold et al., Nat Rev Cancer 2004, 4(12):937-947; R. Wetzker et al., Curr Pharm Des 2004, 10(16):1915-1922; Z. A. Knight et al., Biochem Soc Trans. 2007, 35(Pt 2):245-9; R. A. Smith et al., Curr. Top. Med. Chem. 2006, 6, 1071-89; S. Faivre et al., Nat Rev Drug Discov 2006, 5, 671-688. Said publications contain a comprehensive list of published patent applications and patents which describe the synthesis and use of low molecular weight ras-Raf-Mek-Erk and PI3K inhibitors.

European Commission has granted marketing authorization to Nexavar® (sorafenib, Bay 43-9006; WO 99/32111, WO 03/068223 in July 2006 for the treatment of patients with advanced renal cell carcinoma who have failed prior interferon-alpha or interleukin-2 based therapy or are considered unsuitable for such therapy. Nexavar (Bay 43-9006) exhibits a relatively unspecific inhibition pattern of serine/threonine kinases and of tyrosine kinases, such as Raf, VEGFR2/3, Flt-3, PDGFR, c-Kit and further kinases. Great significance is attributed to this inhibitor in advanced tumor disorders induced by angiogenesis (for example in the case of kidney cell carcinoma) but also in the case of melanomas with high B-Raf mutation rate. The clinical action of Bay 43-9006 is currently also being determined in patients having refractory solid tumors in combination, for example, with docetaxel. To date, mild side effects and promising anti-tumor effects have been described. Inhibition of the kinases in the PI3K-Akt signaling pathway has neither been described nor disclosed for Bay 43-9006. Recent advances in the research and development of Raf Kinase inhibitors are described in a review of R. A. Smith et al., Curr. Top. Med. Chem. 2006, 6, 1071-89.

Mek1/2 inhibitor PD0325901 (WO 02/06213) is currently in phase II clinical trials for lung cancer and phase I/II clinical trials for the treatment of other solid tumors. The precursor substance CI-1040 (WO 00/35435, WO 00/37141) was noticeable by its high Mek specificity and target affinity. However, this compound was found to be metabolically unstable in phase I/II studies. Clinical data for the current successor substance PD0325901 are still to come. However, neither interaction with Erk1 or Erk2 nor a function inhibiting the PI3K-Akt signaling pathway or their simultaneous modulation has been published or disclosed for this Mek inhibitor.

A phase II study in malignant melanoma is under way for AZD-6244 (ARRY-142886), a selective MEK inhibitor from Array BioPharmaArray.

The PI3K/mTOR inhibitor BEZ-235 from Novartis (WO 06122806) entered a phase I clinical program as a targeted anticancer agent. The compound inhibited mTOR (IC50=21 nM), p110alpha, p110alpha E542K, p110alpha H107R and p110alpha E545K(IC50=4, 5, 18 and 4 nM, respectively) and p110beta, gamma and delta (IC50=76, 5 and 7 nM, respectively), while preserving selectivity over a panel of other kinases Recent developments at Piramed have resulted in the synthesis of two series of compounds that act as phosphatidylinositol 3-kinase of class Ib (PI3K-Ib) inhibitors and are described as possessing potent anticancer activity. Additional indications include immune disorders, cardiovascular diseases, metabolism/endocrine disorders, neurodegenerative diseases and bacterial or viral infections (WO 06046035, WO 06046040).

Semafore recently initiated a phase I trial of its lead phosphoinositide 3-kinase (PI3K) inhibitor, SF-1126 (WO 04089925), in patients with solid tumor cancers. SF-1126 is a small-molecule conjugate containing a pan-PI3K inhibitor that selectively inhibits all PI3K class IA isoforms and other key members of the PI3K superfamily, including DNA PK and mTOR. Preclinically, SF-1126 has been shown to inhibit angiogenesis and cellular proliferation, induce apoptosis, block pro-survival signals and produce synergistic antitumor effects in combination with chemotherapy.

ICOS disclosed a PI3K inhibitor IC87114 with high PI3Kdelta isoenzyme specificity (WO 01/81346). For PI103 (WO 04/017950).

Exelixis has submitted an IND for XL-147, a novel anticancer compound. XL-147 is an orally available small-molecule inhibitor of phosphoinositide-3 kinase (PI3K). Inactivation of PI3K has been shown to inhibit growth and induce apoptosis in tumor cells. In preclinical studies, XL-147 slowed tumor growth or caused tumor shrinkage in multiple preclinical cancer models, including breast, lung, ovarian and prostate cancers, and gliomas.

Moreover, a highly noted field of research exists in the early development of PI3K inhibitors (see reviews of Z. A. Knight et al., Biochem Soc Trans. 2007, 35(Pt 2):245-9; R. Wetzker et al., Curr Pharm Des 2004, 10(16):1915-19222004).

Inhibitors of SAPK signaling pathway, either of Jnk or of p38, are described in the literature (Gum R J et al., J Biol Chem 1998, 273(25):15605-15610; Bennett B L et al., Proc Natl Acad Sci USA. 2001, 98(24):13681-13686; Davies S P et al., Biochem J. 2000, 351(Pt 1):95-105). However, no function of inhibiting the PI3Ks nor any specific inhibition of Erk1 or Erk2 or else any specific inhibition of SAPKs, Erk1, Erk2, or PI3Ks has been disclosed for these SAPK inhibitors.

6- or 7-substituted pyrido[2,3-b]pyrazine derivatives find wide use in pharmaceutical chemistry as pharmacologically active compounds and as synthetic units.

Patent applications WO 04/104002 and WO 04/104003, for example, describe pyrido[2,3-b]pyrazines which may be 6- or 7-substituted by urea, thiourea, amidine or guanidine groups. These compounds have properties as inhibitors or modulators of kinases, especially of tyrosine and serine/threonine kinases. The use as a medicament is reported. In contrast, use of these compounds as modulators of lipid kinases, alone or in combination with tyrosine and serine/threonine kinases, has not been described.

Moreover, WO 99/17759 describes pyrido[2,3-b]pyrazines which bear, in 6-position, inter alia, alkyl-, aryl- and heteroaryl-substituted carbamates. These compounds are intended to be used for the modulation of serine-threonine protein kinase function.

Patent application WO 05/007099 describes, inter alia, urea-substituted pyrido[2,3-b]pyrazines as inhibitors of serine/threonine kinase PKB. However, the document does not further define the R radical, which describes the range of possible substitutions on urea. Therefore, the range of possible substitution on urea is thus not clearly disclosed. As for these compounds, use in the treatment of cancer disorders is reported. However, no specific examples of urea-substituted pyridopyrazines having the claimed biological properties are given. In addition, the pyridopyrazines described here differ significantly in structure from the novel pyrido[2,3-b]pyrazines described in this invention.

Further examples of 6- and 7-urea-substituted pyrido[2,3-b]pyrazines are reported in WO 05/056547. However, the compounds disclosed there have additional carbonyl, sulphoxy, sulphone or imine substitution in the 2- or 3-position, which means that the compounds differ structurally significantly from the novel pyrido[2,3-b]pyrazines described in this invention. The pyridopyrazines reported in WO 05/056547 are described as inhibitors of protein kinases, especially of GSK-3, Syk and JAK-3. Uses reported include use in the treatment of proliferative disorders. Use of these compounds as modulators of lipid kinases, alone or in combination with serine/threonine kinases, is not described.

WO 04/005472 describes, inter alia, 6-carbamate-substituted pyrido[2,3-b]pyrazines which, as antibacterial substances, inhibit the growth of bacteria. Antitumor action is not described.

Certain diphenylquinoxalines and -pyrido[2,3-b]pyrazines with specific alkylpyrrolidine, alkylpiperidine or alkylsulphonamide radicals on a phenyl ring, which may additionally also bear urea or carbamate substitutions in 6- or 7-position, are described in patent applications WO 03/084473, WO 03/086394 and WO 03/086403 as inhibitors of serine/threonine kinase Akt. For these compounds, use in the treatment of cancer disorders is reported. For pyrido[2,3-b]pyrazine example compounds described there, no defined indication of biological action is specified. Moreover, there is a significant structural difference to the novel pyrido[2,3-b]pyrazines described in this invention.

Moreover, patent application WO 03/024448 describes amide- and acrylamide-substituted pyrido[2,3-b]pyrazines which also contain carbamates as additional substitutents and can be used as histone deacetylase inhibitors for the treatment of cell proliferation disorders.

A further publication (Temple, C. Jr.; J. Med. Chem. 1990: 3044-3050) exemplarily describes the synthesis of a 6-ethyl carbamate-substituted pyrido[2,3-b]pyrazine derivative. Antitumor action is neither disclosed nor rendered obvious.

The synthesis of further derivatives of 6-ethyl carbamate-substituted pyrido[2,3-b]pyrazine is described in a publication by R. D. Elliott (Elliott R D, J. Org. Chem. 1968: 2393-2397). Biological action of these compounds is neither described nor rendered obvious.

The publication by C. Temple (Temple, C. Jr., J. Med. Chem. 1968:1216-1218) describes the synthesis and examination of 6-ethyl carbamate-substituted pyrido[2,3-b]pyrazines as potential active antimalarial ingredients. Antitumor action is neither disclosed nor rendered obvious.

WO 2005/021513 is directed to the preparation of condensed n-pyrazinyl-sulfonamides and their use in the treatment of chemokine mediated diseases. Antitumor action is neither disclosed nor rendered obvious.

JP 2006137723 describes the preparation of sulfonamides, their use as CCL17 and/or 22 regulators, and pharmaceuticals containing them for treatment of the chemokine-associated diseases. Antitumor action is neither disclosed nor rendered obvious.

Sako M. (Sako M., Houben-Weyl, Science of Synthesis 2004, 16.20:1269-1290) gives a general overview about the synthesis of pyridopyrazines. Antitumor action is neither disclosed nor rendered obvious.

U.S. Pat. No. 4,082,845 discloses 3-(1-piperazinyl)-pyrido [2,3-b]pyrazines. Antitumor action is neither disclosed nor rendered obvious.

WO 04/005472 relates to antibacterial inhibitors of Ftsz protein. Pyridopyrazines are not explicitly mentioned. Antitumor action is neither disclosed nor rendered obvious.

WO 02/090355 describes the preparation of N-aroyl cyclic amines as orexin antagonists. Pyrido[2,3-b]pyrazines are not mentioned.

JP 50053394 discloses 3-substituted 5-alkyl-5,8-dihydro-8-oxopyrido[2,3-b]pyrazine-7-carboxylic acids and their esters. Antitumor action is neither disclosed nor rendered obvious.

U.S. Pat. No. 3,209,004 relates to 3,6-diamino—N-(2,2-dialkoxyethyl)pyrido[2,3-b]pyrazine-2-carboxamides. Antitumor action is neither disclosed nor rendered obvious.

U.S. Pat. No. 3,180,868 describes 3,6-diamino—N-(substituted)pyrido[2,3-b]pyrazine-2-carboxamides. Antitumor action is neither disclosed nor rendered obvious.

Chen J J et al. (Chen J J et al., J. Am. Chem. Soc. 1996, 118:8953-8954) discuss the synthesis of pyrido[2,3-b]pyrazines from pyrazine C-nucleosides. Antitumor action is neither disclosed nor rendered obvious.

Nagel A et al. (Nagel A et al., J. Heterocyclic Chem. 1979, 16:301-304) show NMR data of pyrido[2,3-b]pyrazine derivatives. Antitumor action is neither disclosed nor rendered obvious.

Tanaka T et al. (Tanaka T et al., Yakugaku Zasshi 1975, 95(9):1092-1097) describe the synthesis of certain pyrido[2,3-b]pyrazine derivatives. Antitumor action is neither disclosed nor rendered obvious.

Osdene T S et al. (Osdene T S et al., J. Chem. Soc. 1955, pp. 2032-2035) discuss the synthesis of 3,6-diaminopyridopyrazine and derived compounds with potential anti-folic acid activity. Antitumor action is neither disclosed nor rendered obvious.

WO 2006/128172 is directed to a method for treating B cell regulated autoimmune disorders. Pyrido[2,3-b]pyrazines are not disclosed. Antitumor action is neither disclosed nor rendered obvious.

WO 2006/091395 relates to inhibitors of serine/threonine kinase Akt activity. Pyrido[2,3-b]pyrazine derivatives are comprised. However, possible pyrido[2,3-b]pyrazine derivatives are substituted with substituted phenyl and (C3-C8) cycloalkyl, aryl, heteroaryl and heterocyclyl.

WO 06/081179, WO 06/017326, WO 06/017468, WO 06/014580, WO 06/012396, WO 06/002047 and WO 06/020561 are all directed to antibacterial agents. Pyrido[2,3-b]pyrazines are not disclosed. Antitumor action is neither disclosed nor rendered obvious.

WO 2006/074147 discloses 4-arylamino-quinazolines as activatots of caspases and inducers of apoptosis. Pyrido[2,3-b]pyrazines are not disclosed. Antitumor action is neither disclosed nor rendered obvious.

WO 2006/024666 relates to the preparation of pyridine methylene thioxothiazolidinones as phosphoinositide inhibitors. Pyrido[2,3-b]pyrazine derivatives are comprised. However, the displayed pyrido[2,3-b]pyrazine derivatives are not substituted at their pyrazine moiety.

WO 06/021448 is directed to compounds with antibacterial action. Pyrido[2,3-b]pyrazines are not disclosed. Antitumor action is neither disclosed nor rendered obvious.

WO 2005/123733 describes pyrido[2,3-b]pyrazine derivatives as agents for combatting phytopathogenic fungi. However, possible pyrido[2,3-b]pyrazine derivatives are substituted with aryl, heteraryl, halogen or substituted amino at their pyridine moiety.

WO 2005/123698 describes agents for combatting phytopathogenic fungi. Pyrido[2,3-b]pyrazine derivatives are comprised. However, the comprised pyrido[2,3-b]pyrazine derivatives are substituted with aryl, heteraryl, halogen or substituted amino at their pyridine moiety.

US 2005/0272736 relates to tri- and bi-cyclic heteroaryl histamine-3 receptor ligands. Pyrido[2,3-b]pyrazines are not disclosed. Antitumor action is neither disclosed nor rendered obvious.

US 2005/0272728 discloses bicyclic amines bearing heterocyclic substituents as H3 receptor ligands. Pyrido[2,3-b]pyrazines are not disclosed. Antitumor action is neither disclosed nor rendered obvious.

US 2005/0256309 relates to tri- and bi-cyclic heteroaryl histamine-3 receptor ligands. Pyrido[2,3-b]pyrazines are not disclosed. Antitumor action is neither disclosed nor rendered obvious.

US 2005/0256118 discloses bicyclic amines bearing heterocyclic substituents as H3 receptor ligands. Pyrido[2,3-b]pyrazines are not disclosed. Antitumor action is neither disclosed nor rendered obvious.

US 2005/0165028 is directed to N-heteroaryl substituted benzamides as vanilloid receptor ligands. Pyrido[2,3-b]pyrazines are not disclosed. Antitumor action is neither disclosed nor rendered obvious.

WO 05/023807 describes bicyclic quinazolin-4-ylamine derivatives as capsaicin receptor modulators. Pyrido[2,3-b]pyrazines are not disclosed. Antitumor action is neither disclosed nor rendered obvious.

EP 1661889, which corresponds to WO 2005/07099, relates to pyridinyl benzene-sulfonylamide derivatives as chemokine receptor antagonist. Pyrido[2,3-b]pyrazine derivatives are comprised. However, the comprised pyrido[2,3-b]pyrazine derivatives are concomitantly substituted with sulfonamides and cyclic structures.

WO 04/055003 discloses quinazolin-4-yl)amines as capsaicin receptor modulators. Pyrido[2,3-b]pyrazines are not disclosed. Antitumor action is neither disclosed nor rendered obvious.

US 2004/0092521 discloses bicyclic amines bearing heterocyclic substituents as H3 receptor ligands. Pyrido[2,3-b]pyrazines are not disclosed. Antitumor action is neither disclosed nor rendered obvious.

WO 2004/030635 is directed to vasculostatic agents. Pyrido[2,3-b]pyrazine derivatives are comprised. However, the comprised pyrido[2,3-b]pyrazine derivatives are substituted with aryl or heteraryl at their pyrazine moiety.

WO 03/064421 describes aminopiperidine derivatives as antibacterial agents. Pyrido[2,3-b]pyrazines are not disclosed. Antitumor action is neither disclosed nor rendered obvious.

WO 03/064431 also describes aminopiperidine derivatives as antibacterial agents. Pyrido[2,3-b]pyrazines are not disclosed. Antitumor action is neither disclosed nor rendered obvious.

WO 02/055079 relates to 8-hydroxy-1,6-naphthyridine-7-carboxamides as inhibitors of HIV integrase and HIV replication. Pyrido[2,3-b]pyrazines are not disclosed. Antitumor action is neither disclosed nor rendered obvious.

WO 00/12497 discloses quinazoline derivatives as TGF-beta and p38-alpha kinase inhibitors. However, pyrido[2,3-b]pyrazines are not disclosed.

WO 99/43681 is directed to N-(4-piperidinylmethyl) thieno[3,2-b]pyridin-7-amines and related compounds as GABA brain receptor ligands. Pyrido[2,3-b]pyrazines are not disclosed. Antitumor action is neither disclosed nor rendered obvious.

WO 95/15758 describes aryl and heteroaryl quinazoline compounds which inhibit CSF-1R receptor tyrosine kinase. Pyrido[2,3-b]pyrazines are not disclosed.

U.S. Pat. No. 5,480,883 describes bis mono- and bicyclic aryl and heteroaryl compounds which inhibit EGF and/or PDGF receptor tyrosine kinase. Pyrido[2,3-b]pyrazine derivatives are comprised. However, the comprised pyrido[2,3-b]pyrazine derivatives are directly substituted with aryl or heteraryl at their pyrazine moiety.

WO 2006/059103 relates to substituted pyridines and derivatives thereof. Pyrido[2,3-b]pyrazines are not disclosed.

WO 2007/023186 discloses pyrazine derivatives and their use as PI3K inhibitors. Pyrido[2,3-b]pyrazine derivatives are comprised. However, the comprised pyrido[2,3-b]pyrazine derivatives are directly substituted with sulfonamides at their pyrazine moiety.

WO 2007/044729 also describes pyrazine derivatives and their use as PI3K inhibitors. Pyrido[2,3-b]pyrazine derivatives are comprised. However, the comprised pyrido[2,3-b]pyrazine derivatives are directly substituted with sulfonamides at their pyrazine moiety.

WO 2004/108702 is directed to indole derivatives. Pyrido[2,3-b]pyrazine derivatives are comprised. However, the comprised pyrido[2,3-b]pyrazine derivatives are directly substituted with glyoxyl-indolyl at their pyrimidine moiety.

DESCRIPTION OF THE INVENTION

The present invention has the object to provide novel pyrido[2,3-b]pyrazine derivatives that act as kinase modulators.

The object of the present invention has surprisingly been solved in one aspect by providing pyrido[2,3-b]pyrazine derivatives according to general formula (Ia)

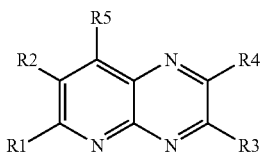

(Ia)

wherein:
one of radicals R3, R4 independently is selected, or both of radicals R3, R4 independently from each other are selected from the group consisting of:
(1) "—NR6R7";
wherein radicals R6, R7 are independently from each other selected from the group consisting of:
(a) "hydrogen, alkyl, arylalkyl, heteroarylalkyl";
with the first proviso that radicals R6, R7 are not both hydrogen, alkyl, arylalkyl or heteroarylalkyl at the same time;
with the second proviso that, if one of radicals R6, R7 independently is "hydrogen", radical R5 is not selected from the group consisting of:"—NH-cycloalkyl, —NH-heterocyclyl, —NH-aryl, —NH-heteroaryl, halogen, —F, —Cl, —Br, —I, —$NR_aR_b$", with Ra, Rb being independently selected from the group consisting of: "H, alkyl, cycloalkyl, cycloalkylalkyl, aryl, arylalkyl, heteroaryl, heteroarylalkyl, —$NR_cR_d$", $R_c$, $R_d$ in turn being independently selected from the group consisting of:"H, alkyl, cycloalkyl, cycloalkylalkyl, aryl, arylalkyl, heteroaryl, heteroarylalkyl";
(b) "—C(Y1)NR8R9, —C(Y1b)OR9b, —C(=NR10R11, —C(Y2)NR12-Y3-R13";
wherein Y1, Y1b, Y2 are independently from each other selected from the group consisting of:"=O, =S, =NH, =NR14";
wherein Y3 is independently selected from the group consisting of:"O, S";
wherein radicals R8, R9, R9b, R10, R11, R12, R13, R14 are independently from each other selected from the group consisting of:
(I) "hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —$CF_3$, —$N_3$, —$NH_2$, —NHX1, —NX2X3, —$NO_2$, —OH, —$OCF_3$, —$OCHF_2$, —SH, —O—$SO_3$H, —OP(O)(OH)$_2$, —CHO, —COOH, —C(O)—$NH_2$, —$SO_3$H, —P(O)(OH)$_2$, —C(O)—X4, —C(O)—O—X5, —C(O)—NH—X6, —C(O)NX7X8, —O—X9, —O(—X10-O)$_a$—H (a=1, 2, 3, 4, 5), —O(—X11-O)$_b$—X12 (b=1, 2, 3, 4, 5), —OC(O)—X13, —OC(O)—O—X14, —OC(O)—NHX15, —O—C(O)—NX16X17, —OP(O)(OX18)(OX19), —OSi(X20)(X21)(X22), —OS(O$_2$)—X23, —NHC(O)—$NH_2$, —NHC(O)—X24, —NX25C(O)—X26, —NH—C(O)—O—X27, —NH—C(O)—NH—X28, —NH—C(O)—NX29X30, —NX31-C(O)—O—X32, —NX33-C(O)—NH—X34, —NX35-C(O)—NX36X37, —NHS(O$_2$)—X38, —NX39S(O$_2$)—X40, —S—X41, —S(O)—X42, —S(O$_2$)—X43, —S(O$_2$)—NH—X44, —S(O$_2$)NX45X46, —S(O$_2$)O—X47, —P(O)(OX48)(OX49), —Si(X50)(X51)(X52), —C(NH)—$NH_2$, —C(NX53)-$NH_2$, —C(NH)—NHX54, —C(NH)—NX55X56, —C(NX57)-NHX58, —C(NX59)-NX60X61, —NH—C(O)—NH—O—X62, —NH—C(O)—NX63-O—X64, —NX65-C(O)—NX66-O—X67, —N(—C(O)—NH—O—X68)$_2$, —N(—C(O)—NX69-O—X70)$_2$, —N(—C(O)—NH—O—X71)(—C(O)—NX72-O—X73), —C(S)—X74, —C(S)—O—X75, —C(S)—NH—X76, —C(S)—NX77X78, —C(O)—NH—O—X79, —C(O)—NX80-O—X81, —C(S)—NH—O—X82, —C(S)—NX83-O—X84, —C(O)—NH—NH—X85, —C(O)—NH—NX86X87, —C(O)—NX88-NX89X90, —C(S)—NH—NH—X91, —C(S)—NH—NX92X93, —C(S)—NX94-NX95X96, —C(O)—C(O)—O—X97, —C(O)—C(O)—$NH_2$, —C(O)—C(O)—NHX98, —C(O)—C(O)—NX99X100, —C(S)—C(O)—O—X101, —C(O)—C(S)—O—X102, —C(S)—C(S)—O—X103, —C(S)—C(O)—$NH_2$, —C(S)—C(O)—NHX104, —C(S)—C(O)—NX105X106, —C(S)—C(S)—$NH_2$, —C(S)—C(S)—NHX107, —C(S)—C(S)—NX108X109, —C(O)—C(S)—$NH_2$, —C(O)—C(S)—NHX110, —C(O)—C(S)—NX111X112";
wherein X1, X2, X3, X4, X5, X6, X7, X8, X9, X10, X11, X12, X13, X14, X15, X16, X17, X18, X19, X20, X21, X22, X23, X24, X25, X26, X27, X28, X29, X30, X31, X32, X33, X34, X35, X36, X37, X38, X39, X40, X41, X42, X43, X44, X45, X46, X47, X48, X49, X50, X51, X52, X53, X54, X55, X56, X57, X58, X59, X60, X61, X62, X63, X64, X65, X66, X67, X68, X69, X70, X71, X72, X73, X74, X75, X76, X77, X78, X79, X80, X81, X82, X83, X84, X85, X86, X87, X88, X89, X90, X91, X92, X93, X94, X95, X96, X97, X98, X99, X100, X101, X102, X103, X104, X105, X106, X107, X108, X109, X110, X111, X112 are independently from each other selected from the group consisting of:"hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and wherein alternatively X7, X8 and/or X16, X17 and/or X29, X30 and/or X36, X37 and/or X45, X46 and/or X55, X56 and/or X60, X61 and/or X77, X78 and/or X86, X87 and/or X89, X90 and/or X92, X93 and/or X95, X96 and/or X99, X100 and/or X105, X106 and/or X108, X109 and/or X111, X112 and/or respectively together can also form "heterocyclyl";
wherein optionally above substituents of substituents group (I)—if not hydrogen—can in turn independently from each other be substituted with at least one substituent, identical or different, selected from the group consisting of:
(i) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —$CF_3$, —$N_3$, —$NH_2$, —NHX201, —NX202X203, —$NO_2$, —OH, =O, —$OCF_3$, —$OCHF_2$, —SH, —O—$SO_3$H, —OP(O)(OH)$_2$, —CHO, —COOH, —C(O)—$NH_2$, —$SO_3$H, —P(O)(OH)$_2$, —C(O)—X204, —C(O)—O—X205, —C(O)—NH—X206, —C(O)—NX207X208, —O—X209, —O(—X210-O)$_c$—H (c=1, 2, 3, 4, 5), —O(—X211-O)$_d$—X212 (d=1, 2, 3, 4, 5), —OC(O)—X213, —OC(O)—O—X214, —OC(O)—NHX215, —O—C(O)—NX216X217, —OP(O)(OX218)(OX219), —OSi(X220)(X221)(X222), —OS(O$_2$)—X223, —NHC(O)—$NH_2$, —NHC(O)—X224, —NX225C(O)—X226, —NH—C(O)—O—X227, —NH—C(O)—NH—X228, —NH—C(O)—NX229X230, —NX231-C(O)—O—X232, —NX233-C(O)—NH—X234, —NX235-C(O)—NX236X237, —NHS(O$_2$)—X238, —NX239S(O$_2$)—X240, —S—X241, —S(O)—X242, —S(O$_2$)—X243, —S(O$_2$)—NH—X244, —S(O$_2$)NX245X246, —S(O$_2$)O—X247, —P(O)(OX248)(OX249), —Si(X250)(X251)(X252), —C(NH)—NH$_2$, —C(NX253)-NH$_2$, —C(NH)—NHX254, —C(NH)—NX255X256, —C(NX257)-NHX258, —C(NX259)-NX260X261, —NH—C(O)—NH—O—X262, —NH—C(O)—NX263-O—X264, —NX265-C(O)—NX266-O—X267, —N(—C(O)—NH—O—X268)$_2$, —N(—C(O)—NX269-O—X270)$_2$, —N(—C(O)—NH—O—X271)(—C(O)—NX272-O—X273), —C(S)—X274, —C(S)—O—X275, —C(S)—NH—X276, —C(S)—NX277X278, —C(O)—NH—O—X279, —C(O)—NX280-O—X281, —C(S)—NH—O—X282, —C(S)—NX283-O—X284, —C(O)—NH—NH—X285, —C(O)—NH—NX286X287, —C(O)—NX288-NX289X290, —C(S)—NH—NH—X291, —C(S)—NH—NX292X293, —C(S)—NX294-NX295X296, —C(O)—C(O)—O—X297, —C(O)—C(O)—NH$_2$, —C(O)—C(O)—NHX298, —C(O)—C(O)—NX299X300, —C(S)—C(O)—O—X301, —C(O)—C(S)—O—X302, —C(S)—C(S)—O—X303, —C(S)—C(O)—NH$_2$, —C(S)—C(O)—NHX304, —C(S)—C(O)—NX305X306, —C(S)—C(S)—NH$_2$, —C(S)—C(S)—NHX307, —C(S)—C(S)—NX308X309, —C(O)—C(S)—NH$_2$, —C(O)—C(S)—NHX310, —C(O)—C(S)—NX311X312";

wherein X201, X202, X203, X204, X205, X206, X207, X208, X209, X210, X211, X212, X213, X214, X215, X216, X217, X218, X219, X220, X221, X222, X223, X224, X225, X226, X227, X228, X229, X230, X231, X232, X233, X234, X235, X236, X237, X238, X239, X240, X241, X242, X243, X244, X245, X246, X247, X248, X249, X250, X251, X252, X253, X254, X255, X256, X257, X258, X259, X260, X261, X262, X263, X264, X265, X266, X267, X268, X269, X270, X271, X272, X273, X274, X275, X276, X277, X278, X279, X280, X281, X282, X283, X284, X285, X286, X287, X288, X289, X290, X291, X292, X293, X294, X295, X296, X297, X298, X299, X300, X301, X302, X303, X304, X305, X306, X307, X308, X309, X310, X311, X312 are independently from each other selected from the group consisting of:"hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively X207, X208 and/or X216, X217 and/or X229, X230 and/or X236, X237 and/or X245, X246 and/or X255, X256 and/or X260, X261 and/or X277, X278 and/or X286, X287 and/or X289, X290 and/or X292, X293 and/or X295, X296 and/or X299, X300 and/or X305, X306 and/or X308, X309 and/or X311, X312 and/or respectively together can also form "heterocyclyl";

wherein optionally above substituents of substituents group (i) can in turn independently from each other be substituted with at least one substituent, identical or different, selected from the group consisting of:

(ii) "alkyl, (C$_9$-C$_{30}$)alkyl, cycloalkyl, cycloalkyalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHX401, —NX402X403, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)—X404, —C(O)—O—X405, —C(O)—NH—X406, —C(O)—NX407X408, —O—X409, —O(—X410-O)$_e$—H (e=1, 2, 3, 4, 5), —O(—X411-O)$_f$X412 (f=1, 2, 3, 4, 5), —OC(O)—X413, —OC(O)—O—X414, —OC(O)—NHX415, —O—C(O)—NX416X417, —OP(O)(OX418)(OX419), —OSi(X420)(X421)(X422), —OS(O$_2$)—X423, —NHC(O)—NH$_2$, —NHC(O)—X424, —NX425C(O)—X426, —NH—C(O)—O—X427, —NH—C(O)—NH—X428, —NH—C(O)—NX429X430, —NX431-C(O)—O—X432, —NX433-C(O)—NH—X434, —NX435-C(O)—NX436X437, —NHS(O$_2$)—X438, —NX439S(O$_2$)—X440, —S—X441, —S(O)—X442, —S(O$_2$)—X443, —S(O$_2$)—NH—X444, —S(O$_2$)NX445X446, —S(O$_2$)O—X447, —P(O)(OX448)(OX449), —Si(X450)(X451)(X452), —C(NH)—NH$_2$, —C(NX453)-NH$_2$, —C(NH)—NHX454, —C(NH)—NX455X456, —C(NX457)-NHX458, —C(NX459)-NX460X461, —NH—C(O)—NH—O—X462, —NH—C(O)—NX463-O—X464, —NX465-C(O)—NX466-O—X467, —N(—C(O)—NH—O—X468)$_2$, —N(—C(O)—NX469-O—X470)$_2$, —N(—C(O)—NH—O—X471)(—C(O)—NX472-O—X473), —C(S)—X474, —C(S)—O—X475, —C(S)—NH—X476, —C(S)—NX477X478, —C(O)—NH—O—X479, —C(O)—NX480-O—X481, —C(S)—NH—O—X482, —C(S)—NX483-O—X484, —C(O)—NH—NH—X485, —C(O)—NH—NX486X487, —C(O)—NX488-NX489X490, —C(S)—NH—NH—X491, —C(S)—NH—NX492X493, —C(S)—NX494-NX495X496, —C(O)—C(O)—O—X497, —C(O)—C(O)—NH$_2$, —C(O)—C(O)—NHX498, —C(O)—C(O)—NX499X500, —C(S)—C(O)—O—X501, —C(O)—C(S)—O—X502, —C(S)—C(S)—O—X503, —C(S)—C(O)—NH$_2$, —C(S)—C(O)—NHX504, —C(S)—C(O)—NX505X506, —C(S)—C(S)—NH$_2$, —C(S)—C(S)—NHX507, —C(S)—C(S)—NX508X509, —C(O)—C(S)—NH$_2$, —C(O)—C(S)—NHX510, —C(O)—C(S)—NX511X512";

wherein X401, X402, X403, X404, X405, X406, X407, X408, X409, X410, X411, X412, X413, X414, X415, X416, X417, X418, X419, X420, X421, X422, X423, X424, X425, X426, X427, X428, X429, X430, X431, X432, X433, X434, X435, X436, X437, X438, X439, X440, X441, X442, X443, X444, X445, X446, X447, X448, X449, X450, X451, X452, X453, X454, X455, X456, X457, X458, X459, X460, X461, X462, X463, X464, X465, X466, X467, X468, X469, X470, X471, X472, X473, X474, X475, X476, X477, X478, X479, X480, X481, X482, X483, X484, X485, X486, X487, X488, X489, X490, X491, X492, X493, X494, X495, X496, X497, X498, X499, X500, X501, X502, X503, X504, X505, X506, X507, X508, X509, X510, X511, X512 are independently from each other selected from the group consisting of:"hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and wherein alternatively X407, X408 and/or X416, X417 and/or X429, X430 and/or X436, X437 and/or X445, X446 and/or X455, X456 and/or X460, X461 and/or X477, X478 and/or X486, X487 and/or X489, X490 and/or X492, X493 and/or X495, X496 and/or X499, X500 and/or X505, X506 and/or X508, X509 and/or X511, X512 and/or respectively together can also form "heterocyclyl";

wherein optionally above substituents of substituents group (ii) can in turn independently from each other be substituted with at least one substituent, identical or different, selected from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHX601, —NX602X603, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)—X604, —C(O)O—X605, —C(O)NH—X606, —C(O)NX607X608, —O—X609, —O(—X610-O)$_e$—H (e=1, 2, 3, 4, 5), —O(—X611-O)$_f$—X612 (f=1, 2, 3, 4, 5), —OC(O)—X613, —OC(O)—O—X614, —OC(O)—NHX615, —O—C(O)—NX616X617, —OP(O)(OX618)(OX619), —OSi(X620)(X621)(X622), —OS(O$_2$)—X623, —NHC(O)—NH$_2$, —NHC(O)—X624, —NX625C(O)—X626, —NH—C(O)—O—X627, —NH—C(O)—NH—X628, —NH—C(O)—NX629X630, —NX631-C(O)—O—X632, —NX633-C(O)—NH—X634, —NX635-C(O)—NX636X637, —NHS(O$_2$)—X638, —NX639S(O$_2$)—X640, —S—X641, —S(O)—X642, —S(O$_2$)—X643, —S(O$_2$)NH—X644, —S(O$_2$)NX645X646, —S(O$_2$)O—X647, —P(O)(OX648)(OX649), —Si(X650)(X651)(X652), —C(NH)—NH$_2$, —C(NX653)-NH$_2$, —C(NH)—NHX654, —C(NH)—NX655X656, —C(NX657)-NHX658, —C(NX659)-NX660X661, —NH—C(O)—NH—O—X662, —NH—C(O)—NX663-O—X664, —NX665-C(O)—NX666-O—X667, —N(—C(O)—NH—O—X668)$_2$, —N(—C(O)—NX669-O—X670)$_2$, —N(—C(O)—NH—O—X671)(—C(O)—NX672-O—X673), —C(S)—X674, —C(S)—O—X675, —C(S)—NH—X676, —C(S)—NX677X678, —C(O)—NH—O—X679, —C(O)—NX680-O—X681, —C(S)—NH—O—X682, —C(S)—NX683-O—X684, —C(O)—NH—NH—X685, —C(O)—NH—NX686X687, —C(O)—NX688-NX689X690, —C(S)—NH—NH—X691, —C(S)—NH—NX692X693, —C(S)—NX694—NX695X696, —C(O)—C(O)—O—X697, —C(O)—C(O)—NH$_2$, —C(O)—C(O)—NHX698, —C(O)—C(O)—NX699X700, —C(S)—C(O)—O—X701, —C(O)—C(S)—O—X702, —C(S)—C(S)—O—X703, —C(S)—C(O)—NH$_2$, —C(S)—C(O)—NHX704, —C(S)—C(O)—NX705X706, —C(S)—C(S)—NH$_2$, —C(S)—C(S)—NHX707, —C(S)—C(S)—NX708X709, —C(O)—C(S)—NH$_2$, —C(O)—C(S)—NHX710, —C(O)—C(S)—NX711X712";

wherein X601, X602, X603, X604, X605, X606, X607, X608, X609, X610, X611, X612, X613, X614, X615, X616, X617, X618, X619, X620, X621, X622, X623, X624, X625, X626, X627, X628, X629, X630, X631, X632, X633, X634, X635, X636, X637, X638, X639, X640, X641, X642, X643, X644, X645, X646, X647, X648, X649, X650, X651, X652, X653, X654, X655, X656, X657, X658, X659, X660, X661, X662, X663, X664, X665, X666, X667, X668, X669, X670, X671, X672, X673, X674, X675, X676, X677, X678, X679, X680, X681, X682, X683, X684, X685, X686, X687, X688, X689, X690, X691, X692, X693, X694, X695, X696, X697, X698, X699, X700, X701, X702, X703, X704, X705, X706, X707, X708, X709, X710, X711, X712 are independently from each other selected from the group consisting of:"hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and wherein alternatively X607, X608 and/or X616, X617 and/or X629, X630 and/or X636, X637 and/or X645, X646 and/or X655, X656 and/or X660, X661 and/or X677, X678 and/or X686, X687 and/or X689, X690 and/or X692, X693 and/or X695, X696 and/or X699, X700 and/or X705, X706 and/or X708, X709 and/or X711, X712 and/or respectively together can also form "heterocyclyl";

with the first proviso that if "—C(Y1)-NR8R9" is selected from the group consisting of:"—C(O)—NR$_a$R$_b$", with Ra, Rb independently from each other being selected from the group consisting of:"hydrogen, alkyl, (C9-C30)alkyl, aryl, arylalkyl, heteroaryl, heteroarylalkyl, cycloalkyl, cycloalkylalkyl, heterocyclyl, heterocyclylalkyl" or with Ra, Rb forming together "heterocyclyl", one of radicals R1, R2 is not "hydrogen" and the other one of radicals R1, R2 is not "—NR$_c$R$_d$ with Rc, Rd independently from each other being selected from the group consisting of:"hydrogen, alkyl, ($C_9$-$C_{30}$alkyl), cycloalkyl, cycloalkylalkyl, heterocyclyl, heterocyclylalkyl, aryl, arylalkyl, heteroaryl, heteroarylalkyl, —C(Ya1)NXa16Xa17, —C(=NXa18)-Xa19, —C(Ya2)NXa20-Ya3-Xa21"; with the proviso that Rc, Rd are not "hydrogen" or "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" at the same time, with the further proviso that if one of radicals Rc, Rd is "hydrogen" or "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl", the other radical Rc, Rd is "—C(Ya1)NXa16Xa17", "—C(=NXa18)-Xa19" oder "—C(Ya2)NXa20-Ya3-Xa21", where Ya1, Ya2, Ya3 are independently from each other selected from the group consisting of "O, S, =NH, =NXa22"; where Xa16, Xa17, Xa18, Xa19, Xa20, Z21, Z22 are independently from each other selected from the group consisting of:hydrogen, alkyl, ($C_9$-$C_{30}$)alkyl, cycloalkyl, cycloalkylalkyl, aryl, arylalkyl, heteroaryl, heteroarylalkyl, heterocyclyl, heterocyclylalkyl";

with the second proviso that if at least one of radicals R1, R2 is "—NXa26Xa27" with at least one of radicals Xa26, Xa27 being "—C(O)—NR$_e$R$_f$ where at least one of radicals R$_e$, R$_f$ is selected from the group consisting of:"alkyl, cycloalkyl, heterocyclyl, aryl, heteroaryl, C(O)-alkyl, C(O)-aryl, C(O)-heteroaryl, (C$_9$-C$_{30}$)alkyl, cycloalkylalkyl, heterocyclylalkyl, arylalkyl, heteroarylalkyl, —C(O)—(C$_9$-C$_{30}$)alkyl, —C(O)cycloalkyl, —C(O)cycloalkylalkyl, —C(O)arylalkyl, —C(O)-heteroarylalkyl, —C(O)heterocyclyl, —C(O)heterocyclylalkyl, —S(O$_2$)alkyl, —S(O$_2$)(C$_9$-C$_{30}$)alkyl, —S(O$_2$)cycloalkyl, —S(O$_2$)-cycloalkylalkyl, —S(O$_2$)-aryl, —S(O$_2$)-arylalkyl, —S(O$_2$)-heteroaryl, —S(O$_2$)-heteroarylalkyl, —S(O$_2$)-heterocyclyl, —S(O$_2$)-heterocyclylalkyl", radicals R3, R4 are not "—C(O) NXa1135Xa1136 with Xa1135, Xa1136 independently being selected from the group consisting of:hydrogen, alkyl, (C9-C30alkyl), cycloalkyl, cycloalkylalkyl, heterocyclyl, heterocyclylalkyl, aryl, arylalkyl, heteroaryl, heteroarylalkyl" or with Xa1135, Xa1136 forming together "heterocyclyl";

with the third proviso that, if "—C(Y1)-NR8R9" independently is selected from the group consisting of:"—C(O)—N[C(O)—O-alkyl]$_2$, —C(O)—N[C(O)-alkyl]$_2$, —C(O)—N[S(O$_2$)-alkyl]$_2$, —C(O)—N[S(O$_2$)-cycloalkyl]$_2$, —C(O)—N[S(O$_2$)-cycloalkylalkyl]$_2$, —C(O)—N[S(O$_2$)-aryl]$_2$, —C(O)—N[S(O$_2$)-heterocyclyl]$_2$", radicals R1, R2 independently from each other are not "phenyl";

with the fourth proviso that, if "—C(Y2)-NR12-Y3-R13" independently is selected from the group consisting of:"—C(O)—N[O-alkyl]$_2$", radicals R1, R2 independently from each other are not "phenyl";

(c) "—C(O)—C(O)—R16";

wherein radical R16 is independently selected from the group consisting of:

(II) "hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHZ1, —NZ2Z3, —NO$_2$, —OH, —OCF$_3$, —OCHF$_2$, —SH, —O—SO$_3$H, —OP(O)(OH)$_2$, —CHO, —COOH, —C(O)NH$_2$, —SO$_3$H, —P(O)(OH)$_2$, —C(O)-Z4, —C(O)—O-Z5, —C(O)—NH-Z6, —C(O)NZ7Z8, —O-Z9, —O(-Z10-O)$_a$—H (a=1, 2, 3, 4, 5), —O(-Z11-O)$_b$-Z12 (b=1, 2, 3, 4, 5), —OC(O)-Z13, —OC(O)—O-Z14, —OC(O)—NHZ15, —O—C(O)—NZ16Z17, —OP(O)(OZ18)(OZ19), —OSi(Z20)(Z21)(Z22), —OS(O$_2$)-Z23, —NHC(O)—NH$_2$, —NHC(O)-Z24, —NZ25C(O)-Z26, —NH—C(O)—O-Z27, —NH—C(O)—NH-Z28, —NH—C(O)—NZ29Z30, —NZ31-C(O)—O-Z32, —NZ33-C(O)—NH-Z34, —NZ35-C(O)—NZ36Z37, —NHS(O$_2$)-Z38, —NZ39S(O$_2$)-Z40, —S-Z41, —S(O)-Z42, —S(O$_2$)-Z43, —S(O$_2$)—NH-Z44, —S(O$_2$)NZ45Z46, —S(O$_2$)O-Z47, —P(O)(OZ48)(OZ49), —Si(Z50)(Z51)(Z52), —C(NH)—NH$_2$, —C(NZ53)-NH$_2$, —C(NH)—NHZ54, —C(NH)—NZ55Z56, —C(NZ57)-NHZ58, —C(NZ59)-NZ60Z61, —NH—C(O)—NH—O-Z62, —NH—C(O)—NZ63-O-Z64, —NZ65-C(O)—NZ66-O-Z67, —N(—C(O)—NH—O-Z68)$_2$, —N(—C(O)—NZ69-O-Z70)$_2$, —N(—C(O)—NH—O-Z71)(—C(O)—NZ72-O-Z73), —C(S)-Z74, —C(S)-O-Z75, —C(S)—NH-Z76, —C(S)—NZ77Z78, —C(O)—NH—O-Z79, —C(O)—NZ80-O-Z81, —C(S)—NH—O-Z82, —C(S)—NZ83-O-Z84, —C(O)—NH—NH-Z85, —C(O)—NH—NZ86Z87, —C(O)—NZ88-NZ89Z90, —C(S)—NH—NH-Z91, —C(S)—NH—NZ92Z93, —C(S)—NZ94-NZ95Z96, —C(O)—C(O)—O-Z97, —C(O)—C(O)—NH$_2$, —C(O)—C(O)—NHZ98, —C(O)—C(O)—NZ99Z100, —C(S)—C(O)—O-Z101, —C(O)—C(S)—O-Z102, —C(S)—C(S)—O-Z103, —C(S)—C(O)—NH$_2$, —C(S)—C(O)—NHZ104, —C(S)—C(O)—NZ105Z106, —C(S)—C(S)—NH$_2$, —C(S)—C(S)—NHZ107, —C(S)—C(S)—NZ108Z109, —C(O)—C(S)—NH$_2$, —C(O)—C(S)—NHZ110, —C(O)—C(S)—NZ111Z112";

wherein Z1, Z2, Z3, Z4, Z5, Z6, Z7, Z8, Z9, Z10, Z11, Z12, Z13, Z14, Z15, Z16, Z17, Z18, Z19, Z20, Z21, Z22, Z23, Z24, Z25, Z26, Z27, Z28, Z29, Z30, Z31, Z32, Z33, Z34, Z35, Z36, Z37, Z38, Z39, Z40, Z41, Z42, Z43, Z44, Z45, Z46, Z47, Z48, Z49, Z50, Z51, Z52, Z53, Z54, Z55, Z56, Z57, Z58, Z59, Z60, Z61, Z62, Z63, Z64, Z65, Z66, Z67, Z68, Z69, Z70, Z71, Z72, Z73, Z74, Z75, Z76, Z77, Z78, Z79, Z80, Z81, Z82, Z83, Z84, Z85, Z86, Z87, Z88, Z89, Z90, Z91, Z92, Z93, Z94, Z95, Z96, Z97, Z98, Z99, Z100, Z101, Z102, Z103, Z104, Z105, Z106, Z107, Z108, Z109, Z110, Z111, Z112 are independently from each other selected from the group consisting of:"hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively Z7, Z8 and/or Z16, Z17 and/or Z29, Z30 and/or Z36, Z37 and/or Z45, Z46 and/or Z55, Z56 and/or Z60, Z61 and/or Z77, Z78 and/or Z86, Z87 and/or Z89, Z90 and/or Z92, Z93 and/or Z95, Z96 and/or Z99, Z100 and/or Z105, Z106 and/or Z108, Z109 and/or Z111, Z112 and/or respectively together can also form "heterocyclyl";

wherein optionally above substituents of substituents group (II)—if not hydrogen—can in turn independently from each other be substituted with at least one substituent, identical or different, selected from the group consisting of:

(i) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHZ201, —NZ202Z203, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)-Z204, —C(O)—O-Z205, —C(O)—NH-Z206, —C(O)—NZ207Z208, —O-Z209, —O(-Z210-O)$_c$—H (c=1, 2, 3, 4, 5), —O(-Z211—O)$_d$-Z212 (d=1, 2, 3, 4, 5), —OC(O)-Z213, —OC(O)—O-Z214, —OC(O)—NHZ215, —O—C(O)—NZ216Z217, —OP(O)(OZ218)(OZ219), —OSi(Z220)(Z221)(Z222), —OS(O$_2$)-Z223, —NHC(O)—NH$_2$, —NHC(O)-Z224, —NZ225C(O)-Z226, —NH—C(O)—O-Z227, —NH—C(O)—NH-Z228, —NH—C(O)—NZ229Z230, —NZ231-C(O)—O-Z232, —NZ233-C(O)—NH-Z234, —NZ235-C(O)—NZ236Z237, —NHS(O$_2$)-Z238, —NZ239S(O$_2$)-Z240, —S-Z241, —S(O)-Z242, —S(O$_2$)-Z243, —S(O$_2$)—NH-Z244, —S(O$_2$)—NZ245Z246, —S(O$_2$)O-Z247, —P(O)(OZ248)(OZ249), —Si(Z250)(Z251)(Z252), —C(NH)—NH$_2$, —C(NZ253)-NH$_2$, —C(NH)—NHZ254, —C(NH)—NZ255Z256, —C(NZ257)-NHZ258, —C(NZ259)-NZ260Z261, —NH—C(O)—NH—O-Z262, —NH—C(O)—NZ263-O-Z264, —NZ265-C(O)—NZ266-O-Z267, —N(—C(O)—NH—O-Z268)$_2$, —N(—C(O)—NZ269-O-Z270)$_2$, —N(—C(O)—NH—O-Z271)(—C(O)—NZ272-O-Z273), —C(S)-Z274, —C(S)—O-Z275, —C(S)—NH-Z276, —C(S)—NZ277Z278, —C(O)—NH—O-Z279, —C(O)—NZ280-O-Z281, —C(S)—NH—O-Z282, —C(S)—NZ283-O-Z284, —C(O)—NH—NH-Z285, —C(O)—NH—NZ286Z287, —C(O)—NZ288-NZ289Z290, —C(S)—NH—NH-Z291, —C(S)—NH—NZ292Z293, —C(S)—NZ294-NZ295Z296, —C(O)—C(O)—O-Z297, —C(O)—C(O)—NH$_2$, —C(O)—C(O)—NHZ298, —C(O)—C(O)—NZ299Z300, —C(S)—C(O)—O-Z301, —C(O)—C(S)—O-Z302, —C(S)—C(S)—O-Z303, —C(S)—C(O)—NH$_2$, —C(S)—C(O)—NHZ304, —C(S)—C(O)—NZ305Z306, —C(S)—C(S)—NH$_2$, —C(S)—C(S)—NHZ307, —C(S)—C(S)—NZ308Z309, —C(O)—C(S)—NH$_2$, —C(O)—C(S)—NHZ310, —C(O)—C(S)—NZ311Z312";

wherein Z201, Z202, Z203, Z204, Z205, Z206, Z207, Z208, Z209, Z210, Z211, Z212, Z213, Z214, Z215, Z216, Z217, Z218, Z219, Z220, Z221, Z222, Z223, Z224, Z225, Z226, Z227, Z228, Z229, Z230, Z231, Z232, Z233, Z234, Z235, Z236, Z237, Z238, Z239, Z240, Z241, Z242, Z243, Z244, Z245, Z246, Z247, Z248, Z249, Z250, Z251, Z252, Z253, Z254, Z255, Z256, Z257, Z258, Z259, Z260, Z261, Z262, Z263, Z264, Z265, Z266, Z267, Z268, Z269, Z270, Z271, Z272, Z273, Z274, Z275, Z276, Z277, Z278, Z279, Z280, Z281, Z282, Z283, Z284, Z285, Z286, Z287, Z288, Z289, Z290, Z291, Z292, Z293, Z294, Z295, Z296, Z297, Z298, Z299, Z300, Z301, Z302, Z303, Z304, Z305, Z306, Z307, Z308, Z309, Z310, Z311, Z312 are independently from each other selected from the group consisting of:"hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and wherein alternatively Z207, Z208 and/or Z216, Z217 and/or Z229, Z230 and/or Z236, Z237 and/or Z245, Z246 and/or Z255, Z256 and/or Z260, Z261 and/or Z277, Z278 and/or Z286, Z287 and/or Z289, Z290 and/or Z292, Z293 and/or Z295, Z296 and/or Z299, Z300 and/or Z305, Z306 and/or Z308, Z309 and/or Z311, Z312 and/or respectively together can also form "heterocyclyl";

wherein optionally above substituents of substituents group (i) can in turn independently from each other be substituted with at least one substituent, identical or different, selected from the group consisting of:

(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHZ401, —NZ402Z403, —NO$_2$, —OH, =O, —OCF$_3$, —OCHF$_2$, —SH, —O—SO$_3$H, —OP(O)(OH)$_2$, —CHO, —COOH, —C(O)NH$_2$, —SO$_3$H, —P(O)(OH)$_2$, —C(O)-Z404, —C(O)O-Z405, —C(O)NH-Z406, —C(O)NZ407Z408, —O-Z409, —O(-Z410-O)$_e$—H (e=1, 2, 3, 4, 5), —O(-Z411-O)$_f$-Z412 (f=1, 2, 3, 4, 5), —OC(O)-Z413, —OC(O)—O-Z414, —OC(O)—NHZ415, —O—C(O)—NZ416Z417, —OP(O)(OZ418)(OZ419), —OSi(Z420)(Z421)(Z422), —OS(O$_2$)-Z423, —NHC(O)—NH$_2$, —NHC(O)-Z424, —NZ425C(O)-Z426, —NH—C(O)—O-Z427, —NH—C(O)—NH-Z428, —NH—C(O)—NZ429Z430, —NZ431-C(O)—O-Z432, —NZ433-C(O)—NH-Z434, —NZ435-C(O)—NZ436Z437, —NHS(O$_2$)-Z438, —NZ439S(O$_2$)-Z440, —S-Z441, —S(O)-Z442, —S(O$_2$)-Z443, —S(O$_2$)NH-Z444, —S(O$_2$)NZ445Z446, —S(O$_2$)O-Z447, —P(O)(OZ448)(OZ449), —Si(Z450)(Z451)(Z452), —C(NH)—NH$_2$, —C(NZ453)-NH$_2$, —C(NH)—NHZ454, —C(NH)—NZ455Z456, —C(NZ457)-NHZ458, —C(NZ459)-NZ460Z461, —NH—C(O)—NH—O-Z462, —NH—C(O)—NZ463-O-Z464, —NZ465-C(O)—NZ466-O-Z467, —N(—C(O)—NH—O-Z468)$_2$, —N(—C(O)—NZ469-O-Z470)$_2$, —N(—C(O)—NH—O-Z471)(—C(O)—NZ472-O-Z473), —C(S)-Z474, —C(S)—O-Z475, —C(S)—NH-Z476, —C(S)—NZ477Z478, —C(O)—NH—O-Z479, —C(O)—NZ480-O-Z481, —C(S)—NH—O-Z482, —C(S)—NZ483-O-Z484, —C(O)—NH—NH-Z485, —C(O)—NH—NZ486Z487, —C(O)—NZ488-NZ489Z490, —C(S)—NH—NH-Z491, —C(S)—NH—NZ492Z493, —C(S)—NZ494-NZ495Z496, —C(O)—C(O)—O-Z497, —C(O)—C(O)—NH$_2$, —C(O)—C(O)—NHZ498, —C(O)—C(O)—NZ499Z500, —C(S)—C(O)—O-Z501, —C(O)—C(S)—O-Z502, —C(S)—C(S)—O-Z503, —C(S)—C(O)—NH$_2$, —C(S)—C(O)—NHZ504, —C(S)—C(O)—NZ505Z506, —C(S)—C(S)—NH$_2$, —C(S)—C(S)—NHZ507, —C(S)—C(S)—NZ508Z509, —C(O)—C(S)—NH$_2$, —C(O)—C(S)—NHZ510, —C(O)—C(S)—NZ511Z512";

wherein Z401, Z402, Z403, Z404, Z405, Z406, Z407, Z408, Z409, Z410, Z411, Z412, Z413, Z414, Z415, Z416, Z417, Z418, Z419, Z420, Z421, Z422, Z423, Z424, Z425, Z426, Z427, Z428, Z429, Z430, Z431, Z432, Z433, Z434, Z435, Z436, Z437, Z438, Z439, Z440, Z441, Z442, Z443, Z444, Z445, Z446, Z447, Z448, Z449, Z450, Z451, Z452, Z453, Z454, Z455, Z456, Z457, Z458, Z459, Z460, Z461, Z462, Z463, Z464, Z465, Z466, Z467, Z468, Z469, Z470, Z471, Z472, Z473, Z474, Z475, Z476, Z477, Z478, Z479, Z480, Z481, Z482, Z483, Z484, Z485, Z486, Z487, Z488, Z489, Z490, Z491, Z492, Z493, Z494, Z495, Z496, Z497, Z498, Z499, Z500, Z501, Z502, Z503, Z504, Z505, Z506, Z507, Z508, Z509, Z510, Z511, Z512 are independently from each other selected from the group consisting of:"hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and wherein alternatively Z407, Z408 and/or Z416, Z417 and/or Z429, Z430 and/or Z436, Z437 and/or Z445, Z446 and/or Z455, Z456 and/or Z460, Z461 and/or Z477, Z478 and/or Z486, Z487 and/or Z489, Z490 and/or Z492, Z493 and/or Z495, Z496 and/or Z499, Z500 and/or Z505, Z506 and/or Z508, Z509 and/or Z511, Z512 and/or respectively together can also form "heterocyclyl";

wherein optionally above substituents of substituents group (ii) can in turn independently from each other be substituted with at least one substituent, identical or different, selected from the group consisting of:

(iii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHZ601, —NZ602Z603, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)-Z604, —C(O)—O-Z605, —C(O)—NH-Z606, —C(O)—NZ607Z608, —O-Z609, —O(-Z610-O)$_e$—H (e=1, 2, 3, 4, 5), —O(-Z611-O)$_f$Z612 (f=1, 2, 3, 4, 5), —OC(O)-Z613, —OC(O)—O-Z614, —OC(O)—NHZ615, —O—C(O)—NZ616Z617, —OP(O)(OZ618)(OZ619), —OSi(Z620)(Z621)(Z622), —OS(O$_2$)-Z623, —NHC(O)—NH$_2$, —NHC(O)-Z624, —NZ625C(O)-Z626, —NH—C(O)—O-Z627, —NH—C(O)—NH-Z628, —NH—C(O)—NZ629Z630, —NZ631-C(O)—O-Z632, —NZ633-C(O)—NH-Z634, —NZ635-C(O)—NZ636Z637, —NHS(O$_2$)-Z638, —NZ639S(O$_2$)-Z640, —S-Z641, —S(O)-Z642, —S(O$_2$)-Z643, —S(O$_2$)NH-Z644, —S(O$_2$)NZ645Z646, —S(O$_2$)O-Z647, —P(O)(OZ648)(OZ649), —Si(Z650)(Z651)(Z652), —C(NH)—NH$_2$, —C(NZ653)-NH$_2$, —C(NH)—NHZ654, —C(NH)—NZ655Z656, —C(NZ657)-NHZ658, —C(NZ659)-NZ660Z661, —NH—C(O)—NH—O-Z662, —NH—C(O)—NZ663-O-Z664, —NZ665-C(O)—NZ666-O-Z667, —N(—C(O)—NH—O-Z668)$_2$, —N(—C(O)—NZ669-O-Z670)$_2$, —N(—C(O)—NH—O-Z671)(—C(O)—NZ672-O-Z673), —C(S)-Z674, —C(S)—O-Z675, —C(S)—NH-Z676, —C(S)—NZ677Z678, —C(O)—NH—O-Z679, —C(O)—NZ680-O-Z681, —C(S)—NH—O-Z682, —C(S)—NZ683-O-Z684, —C(O)—NH—NH-Z685, —C(O)—NH—NZ686Z687, —C(O)—NZ688-NZ689Z690, —C(S)—NH—NH-Z691, —C(S)—NH—NZ692Z693, —C(S)—NZ694—NZ695Z696, —C(O)—C(O)—O-Z697, —C(O)—C(O)—NH$_2$, —C(O)—C(O)—NHZ698, —C(O)—C(O)—NZ699Z700, —C(S)—C(O)—O-Z701, —C(O)—C(S)—O-Z702, —C(S)—C(S)—O-Z703, —C(S)—C(O)—NH$_2$, —C(S)—C(O)—NHZ704, —C(S)—C(O)—NZ705Z706, —C(S)—C(S)—NH$_2$, —C(S)—C(S)—NHZ707, —C(S)—C(S)—NZ708Z709, —C(O)—C(S)—NH$_2$, —C(O)—C(S)—NHZ710, —C(O)—C(S)—NZ711Z712";

wherein Z601, Z602, Z603, Z604, Z605, Z606, Z607, Z608, Z609, Z610, Z611, Z612, Z613, Z614, Z615, Z616, Z617, Z618, Z619, Z620, Z621, Z622, Z623, Z624, Z625, Z626, Z627, Z628, Z629, Z630, Z631, Z632, Z633, Z634, Z635, Z636, Z637, Z638, Z639, Z640, Z641, Z642, Z643, Z644, Z645, Z646, Z647, Z648, Z649, Z650, Z651, Z652, Z653, Z654, Z655, Z656, Z657, Z658, Z659, Z660, Z661, Z662, Z663, Z664, Z665, Z666, Z667, Z668, Z669, Z670, Z671, Z672, Z673, Z674, Z675, Z676, Z677, Z678, Z679, Z680, Z681, Z682, Z683, Z684, Z685, Z686, Z687, Z688, Z689, Z690, Z691, Z692, Z693, Z694, Z695, Z696, Z697, Z698, Z699, Z700, Z701, Z702, Z703, Z704, Z705, Z706, Z707, Z708, Z709, Z710, Z711, Z712 are independently from each other selected from the group consisting of:"hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively Z607, Z608 and/or Z616, Z617 and/or Z629, Z630 and/or Z636, Z637 and/or Z645, Z646 and/or Z655, Z656 and/or Z660, Z661 and/or Z677, Z678 and/or Z686, Z687 and/or Z689, Z690 and/or Z692, Z693 and/or Z695, Z696 and/or Z699, Z700 and/or Z705, Z706 and/or Z708, Z709 and/or Z711, Z712 and/or respectively together can also form "heterocyclyl";

with the proviso that radical R16 is not "indol-yl";

(d) "—S(O$_2$)—R18";

wherein radical R18 is independently selected from the group consisting of:

(III) "—F, —Cl, —Br, —I, —CN, —CF$_3$, —N$_3$, —NH$_2$, —NHW1, —NW2W3, —NO$_2$, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)—W4, —C(O)—O—W5, —C(O)—NH—W6, —C(O)—NW7W8, —O—W9, —O(—W10-O)$_a$—H (a=1, 2, 3, 4, 5), —O(—W$_{11}$—O)$_b$—W12 (b=1, 2, 3, 4, 5), —OC(O)—W13, —OC(O)-0-W14, —OC(O)—NHW15, —O—C(O)—NW16W17, —OP(O)(OW18)(OW19), —OSi(W20)(W21)(W22), —OS(O$_2$)—W23, —NHC(O)—NH$_2$, —NHC(O)—W24, —NW25C(O)—W26, —NH—C(O)—O—W27, —NH—C(O)—NH—W28, —NH—C(O)—NW29W30, —NW31-C(O)—O—W32, —NW33-C(O)—NH—W34, —NW35-C(O)—NW36W37, —NHS(O$_2$)—W38, —NW39S(O$_2$)—W40, —S—W41, —S(O)—W42, —S(O$_2$)—W43, —S(O$_2$)—NH—W44, —S(O$_2$)—NW45W46, —S(O$_2$)O—W47, —P(O)(OW48)(OW49), —Si(W50)(W51)(W52), —C(NH)—NH$_2$, —C(NW53)-NH$_2$, —C(NH)—NHW54, —C(NH)—NW55W56, —C(NW57)-NHW58, —C(NW59)-NW60W61, —NH—C(O)—NH—O—W62, —NH—C(O)—NW63-O—W64, —NW65-C(O)—NW66-O—W67, —N(—C(O)—NH—O—W68)$_2$, —N(—C(O)—NW69-O—W70)$_2$, —N(—C(O)—NH—O—W71)(—C(O)—NW72-O—W73), —C(S)—W74, —C(S)—O—W75, —C(S) NH—W76, —C(S)—NW77W78, —C(O)—NH—O—W79, —C(O)—NW80-O—W81, —C(S)—NH—O—W82, —C(S)—NW83-O—W84, —C(O)—NH—NH—W85, —C(O)—NH—NW86W87, —C(O)—NW88-NW89W90, —C(S)—NH—NH—W91, —C(S)—NH—NW92W93, —C(S)—NW94-NW95W96, —C(O)—C(O)—O—W97, —C(O)—C(O)—NH$_2$, —C(O)—C(O)—NHW98, —C(O)—C(O)—NW99W100, —C(S)—C(O)—O—W101, —C(O)—C(S)—O—W102, —C(S)—C(S)—O—W103, —C(S)—C(O)—NH$_2$, —C(S)—C(O)—NHW104, —C(S)—C(O)—NW105W106, —C(S)—C(S)—NH$_2$, —C(S)—C(S)—NHW107, —C(S)—C(S)—NW108W109, —C(O)—C(S)—NH$_2$, —C(O)—C(S)—NHW110, —C(O)—C(S)—NW111W112";

wherein W1, W2, W3, W4, W5, W6, W7, W8, W9, W10, W11, W12, W13, W14, W15, W16, W17, W18, W19, W20, W21, W22, W23, W24, W25, W26, W27, W28, W29, W30, W31, W32, W33, W34, W35, W36, W37, W38, W39, W40, W41, W42, W43, W44, W45, W46, W47, W48, W49, W50, W51, W52, W53, W54, W55, W56, W57, W58, W59, W60, W61, W62, W63, W64, W65, W66, W67, W68, W69, W70, W71, W72, W73, W74, W75, W76, W77, W78, W79, W80, W81, W82, W83, W84, W85, W86, W87, W88, W89, W90, W91, W92, W93, W94, W95, W96, W97, W98, W99, W100, W101, W102, W103, W104, W105, W106, W107, W108, W109, W110, W111, W112 are independently from each other selected from the group consisting of:"hydrogen, alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl" and wherein alternatively W7, W8 and/or W16, W17 and/or W29, W30 and/or W36, W37 and/or W45, W46 and/or W55, W56 and/or W60, W61 and/or W77, W78 and/or W86, W87 and/or W89, W90 and/or W92, W93 and/or W95, W96 and/or W99, W100 and/or W105, W106 and/or W108, W109 and/or W111, W112 and/or respectively together can also form "heterocyclyl";

wherein optionally above substituents of substituents group (III) can in turn independently from each other be substituted with at least one substituent, identical or different, selected from the group consisting of:

(i) "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl", —F, —Cl, —Br, —I, —CN, —CF$_3$, —N$_3$, —NH$_2$, —NHW201, —NW202W203, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)—W204, —C(O)—O—W205, —C(O)—NH—W206, —C(O)—NW207W208, —O—W209, —O(—W210-O)$_c$—H (c=1, 2, 3, 4, 5), —O(—W211-O)$_d$—W212 (d=1, 2, 3, 4, 5), —OC(O)—W213, —OC(O)—O—W214, —OC(O)—NHW215, —O—C(O)—NW216W217, —OP(O)(OW218)(OW219), —OSi(W220)(W221)(W222), —OS(O$_2$)—W223, —NHC(O)—NH$_2$, —NHC(O)—W224, —NW225C(O)—W226, —NH—C(O)—O—W227, —NH—C(O)—NH—W228, —NH—C(O)—NW229W230, —NW231-C(O)—O—W232, —NW233-C(O)—NH—W234, —NW235-C(O)—NW236W237, —NHS(O$_2$)—W238, —NW239S(O$_2$)—W240, —S—W241, —S(O)—W242, —S(O$_2$)—W243, —S(O$_2$)NH—W244, —S(O$_2$)—NW245W246, —S(O$_2$)O—W247, —P(O)(OW248)(OW249), —Si(W250)(W251)(W252), —C(NH)—NH$_2$, —C(NW253)-NH$_2$, —C(NH)—NHW254, —C(NH)—NW255W256, —C(NW257)-NHW258, —C(NW259)-NW260W261, —NH—C(O)—NH—O—W262, —NH—C(O)—NW263-O—W264, —NW265-C(O)—NW266-O—W267, —N(—C(O)—NH—O—W268)$_2$, —N(—C(O)—NW269-O—W270)$_2$, —N(—C(O)—NH—O—W271)(—C(O)—NW272-O—W273), —C(S)—W274, —C(S)—O—W275, —C(S)—NH—W276, —C(S)—NW277W278, —C(O)—NH—O—W279, —C(O)—NW280-O—W281, —C(S)—NH—O—W282, —C(S)—NW283-O—W284, —C(O)—NH—NH—W285, —C(O)—NH—NW286W287, —C(O)—NW288-NW289W290, —C(S)—NH—NH—W291, —C(S)—NH—NW292W293, —C(S)—NW294-NW295W296, —C(O)—C(O)—O—W297, —C(O)—C(O)—NH$_2$, —C(O)—C(O)—NHW298, —C(O)—C(O)—NW299W300, —C(S)—C(O)—O—W301, —C(O)—C(S)—O—W302, —C(S)—C(S)—O—W303, —C(S)—C(O)—NH$_2$, —C(S)—C(O)—NHW304, —C(S)—C(O)—NW305W306, —C(S)—C(S)—NH$_2$, —C(S)—C(S)—NHW307, —C(S)—C(S)—NW308W309, —C(O)—C(S)—NH$_2$, —C(O)—C(S)—NHW310, —C(O)—C(S)—NW311W312";

wherein W201, W202, W203, W204, W205, W206, W207, W208, W209, W210, W211, W212, W213, W214, W215, W216, W217, W218, W219, W220, W221, W222, W223, W224, W225, W226, W227, W228, W229, W230, W231, W232, W233, W234, W235, W236, W237, W238, W239, W240, W241, W242, W243, W244, W245, W246, W247, W248, W249, W250, W251, W252, W253, W254, W255, W256, W257, W258, W259, W260, W261, W262, W263, W264, W265, W266, W267, W268, W269, W270, W271, W272, W273, W274, W275, W276, W277, W278, W279, W280, W281, W282, W283, W284, W285, W286, W287, W288, W289, W290, W291, W292, W293, W294, W295, W296, W297, W298, W299, W300, W301, W302, W303, W304, W305, W306, W307, W308, W309, W310, W311, W312 are independently from each other selected from the group consisting of:"hydrogen, alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl" and wherein alternatively W207, W208 and/or W216, W217 and/or W229, W230 and/or W236, W237 and/or W245, W246 and/or W255, W256 and/or W260, W261 and/or W277, W278 and/or W286, W287 and/or W289, W290 and/or W292, W293 and/or W295, W296 and/or W299, W300 and/or W305, W306 and/or W308, W309 and/or W311, W312 and/or respectively together can also form "heterocyclyl";

wherein optionally above substituents of substituents group (i) can in turn independently from each other be substituted with at least one substituent, identical or different, selected from the group consisting of:

(ii) "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl", —F, —Cl, —Br, —I, —CN, —CF$_3$, —N$_3$, —NH$_2$, —NHW401, —NW402W403, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)—W404, —C(O)—O—W405, —C(O)—NH—W406, —C(O)—NW407W408, —O—W409, —O(—W410-O)$_e$—H (e=1, 2, 3, 4, 5), —O(—W411-O)$_f$—W412 (f=1, 2, 3, 4, 5), —OC(O) W413, —OC(O)—O—W414, —OC(O)—NHW415, —O—C(O)—NW416W417, —OP(O)(OW418)(OW419), —OSi(W420)(W421)(W422), —OS(O$_2$)—W423, —NHC(O)—NH$_2$, —NHC(O)—W424, —NW425C(O)—W426, —NH—C(O)—O—W427, —NH—C(O)—NH—W428, —NH—C(O)—NW429W430, —NW431-C(O)—O—W432, —NW433-C(O)—NH—W434, —NW435-C(O)—NW436W437, —NHS(O$_2$)—W438, —NW439S(O$_2$)—W440, —S—W441, —S(O)—W442, —S(O$_2$)—W443, —S(O$_2$)NH—W444, —S(O$_2$)—NW445W446, —S(O$_2$)O—W447, —P(O)(OW448)(OW449), —Si(W450)(W451)(W452), —C(NH)—NH$_2$, —C(NW453)-NH$_2$, —C(NH)—NHW454, —C(NH)—NW455W456, —C(NW457)-

NHW458, —C(NW459)-NW460W461, —NH—C(O)—NH—O—W462, —NH—C(O)—NW463-O—W464, —NW465-C(O)—NW466-O—W467, —N(—C(O)—NH—O—W468)$_2$, —N(—C(O)—NW469-O—W470)$_2$, —N(—C(O)—NH—O—W471)(—C(O)—NW472-O—W473), —C(S)—W474, —C(S)—O—W475, —C(S)—NH—W476, —C(S)—NW477W478, —C(O)—NH—O—W479, —C(O)—NW480-O—W481, —C(S)—NH—O—W482, —C(S)—NW483-O—W484, —C(O)—NH—NH—W485, —C(O)—NH—NW486W487, —C(O)—NW488-NW489W490, —C(S)—NH—NH—W491, —C(S)—NH—NW492W493, —C(S)—NW494-NW495W496, —C(O)—C(O)—O—W497, —C(O)—C(O)—NH$_2$, —C(O)—C(O)—NHW498, —C(O)—C(O)—NW499W500, —C(S)—C(O)—O—W501, —C(O)—C(S)—O—W502, —C(S)—C(S)—O—W503, —C(S)—C(O)—NH$_2$, —C(S)—C(O)—NHW504, —C(S)—C(O)—NW505W506, —C(S)—C(S)—NH$_2$, —C(S)—C(S)—NHW507, —C(S)—C(S)—NW508W509, —C(O)—C(S)—NH$_2$, —C(O)—C(S)—NHW510, —C(O)—C(S)—NW511W512";

wherein W401, W402, W403, W404, W405, W406, W407, W408, W409, W410, W411, W412, W413, W414, W415, W416, W417, W418, W419, W420, W421, W422, W423, W424, W425, W426, W427, W428, W429, W430, W431, W432, W433, W434, W435, W436, W437, W438, W439, W440, W441, W442, W443, W444, W445, W446, W447, W448, W449, W450, W451, W452, W453, W454, W455, W456, W457, W458, W459, W460, W461, W462, W463, W464, W465, W466, W467, W468, W469, W470, W471, W472, W473, W474, W475, W476, W477, W478, W479, W480, W481, W482, W483, W484, W485, W486, W487, W488, W489, W490, W491, W492, W493, W494, W495, W496, W497, W498, W499, W500, W501, W502, W503, W504, W505, W506, W507, W508, W509, W510, W511, W512 are independently from each other selected from the group consisting of:"hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and wherein alternatively W407, W408 and/or W416, W417 and/or W429, W430 and/or W436, W437 and/or W445, W446 and/or W455, W456 and/or W460, W461 and/or W477, W478 and/or W486, W487 and/or W489, W490 and/or W492, W493 and/or W495, W496 and/or W499, W500 and/or W505, W506 and/or W508, W509 and/or W511, W512 and/or respectively together can also form "heterocyclyl"; wherein optionally above substituents of substituents group (ii) can in turn independently from each other be substituted with at least one substituent, identical or different, selected from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHW601, —NW602W603, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)—W604, —C(O)—O—W605, —C(O)—NH—W606, —C(O)—NW607W608, —O—W609, —O(—W610-O)$_e$—H (e=1, 2, 3, 4, 5), —O(—W611-0)$_f$—W612 (f=1, 2, 3, 4, 5), —OC(O)—W613, —OC(O)—O—W614, —OC(O)—NHW615, —O—C(O)—NW616W617, —OP(O)(OW618)(OW619), —OSi(W620)(W621)(W622), —OS(O$_2$)—W623, —NHC(O)—NH$_2$, —NHC(O)—W624, —NW625C(O)—W626, —NH—C(O)—O—W627, —NH—C(O)—NH—W628, —NH—C(O)—NW629W630, —NW631-C(O)—O—W632, —NW633-C(O)—NH—W634, —NW635-C(O)—NW636W637, —NHS(O$_2$)—W638, —NW639S(O$_2$)—W640, —S—W641, —S(O)—W642, —S(O$_2$)—W643, —S(O$_2$)—NH—W644, —S(O$_2$)—NW645W646, —S(O$_2$)O—W647, —P(O)(OW648)(OW649), —Si(W650)(W651)(W652), —C(NH)—NH$_2$, —C(NW653)-NH$_2$, —C(NH)—NHW654, —C(NH)—NW655W656, —C(NW657)-NHW658, —C(NW659)-NW660W661, —NH—C(O)—NH—O—W662, —NH—C(O)—NW663-O—W664, —NW665-C(O)—NW666-O—W667, —N(—C(O)—NH—O—W668)$_2$, —N(—C(O)—NW669-O—W670)$_2$, —N(—C(O)—NH—O—W671)(—C(O)—NW672-O—W673), —C(S)—W674, —C(S)—O—W675, —C(S)—NH—W676, —C(S)—NW677W678, —C(O)—NH—O—W679, —C(O)—NW680-O—W681, —C(S)—NH—O—W682, —C(S)—NW683-O—W684, —C(O)—NH—NH—W685, —C(O)—NH—NW686W687, —C(O)—NW688—NW689W690, —C(S)—NH—NH—W691, —C(S)—NH—NW692W693, —C(S)—NW694NW695W696, —C(O)—C(O)—O—W697, —C(O)—C(O)—NH$_2$, —C(O)—C(O)—NHW698, —C(O)—C(O)—NW699W700, —C(S)—C(O)—O—W701, —C(O—C(S)—O—W702, —C(S)—C(S)—O—W703, —C(S)—C(O)—NH$_2$, —C(S)—C(O)—NHW704, —C(S)—C(O)—NW705W706, —C(S)—C(S)—NH$_2$, —C(S)—C(S)—NHW707, —C(S)—C(S)—NW708W709, —C(O)—C(S)—NH$_2$, —C(O)—C(S)—NHW710, —C(O)—C(S)—NW711W712";

wherein W601, W602, W603, W604, W605, W606, W607, W608, W609, W610, W611, W612, W613, W614, W615, W616, W617, W618, W619, W620, W621, W622, W623, W624, W625, W626, W627, W628, W629, W630, W631, W632, W633, W634, W635, W636, W637, W638, W639, W640, W641, W642, W643, W644, W645, W646, W647, W648, W649, W650, W651, W652, W653, W654, W655, W656, W657, W658, W659, W660, W661, W662, W663, W664, W665, W666, W667, W668, W669, W670, W671, W672, W673, W674, W675, W676, W677, W678, W679, W680, W681, W682, W683, W684, W685, W686, W687, W688, W689, W690, W691, W692, W693, W694, W695, W696, W697, W698, W699, W700, W701, W702, W703, W704, W705, W706, W707, W708, W709, W710, W711, W712 are independently from each other selected from the group consisting of:"hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and wherein alternatively W607, W608 and/or W616, W617 and/or W629, W630 and/or W636, W637 and/or W645, W646 and/or W655, W656 and/or W660, W661 and/or W677, W678 and/or W686, W687 and/or W689, W690 and/or W692, W693 and/or W695, W696 and/or W699, W700 and/or W705, W706 and/or W708, W709 and/or W711, W712 and/or respectively together can also form "heterocyclyl";

with the first proviso that radical R18 is not selected from the group consisting of:"—O-alkyl, —O—(C9-C30)alkyl, —O-aryl, —O-arylalkyl, —O-heteroaryl, —O-heteroarylalkyl, —O-cycloalkyl, —O-cycloalkylalkyl, —O-heterocyclyl, —O-heterocyclylalkyl";

with the second proviso that, if radical R18 independently is selected from the group consisting of:"—$NR_aR_b$", with Ra, Rb independently from each other being selected from the group consisting of:"hydrogen, alkyl, (C9-C30)alkyl, aryl, arylalkyl, heteroaryl, heteroarylalkyl, cycloalkyl, cycloalkylalkyl, heterocyclyl, heterocyclylalkyl", radical R1 is not selected from the group consisting of:"heterocyclylalkyl being substituted with =O, where heterocyclyl is 5-membered; alkyl being substituted with heterocyclyl, where heterocyclyl is 5-membered and substituted with =O";

and one of radicals R3, R4 or neither of radicals R3, R4 independently is selected from the group consisting of:

(2) "hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —$CF_3$, —$N_3$, —$NH_2$, —NHA1, —NA2A3, —$NO_2$, —OH, —$OCF_3$, —$OCHF_2$, —SH, —O—$SO_3H$, —OP(O)(OH)$_2$, —CHO, —COOH, —C(O)—$NH_2$, —$SO_3H$, —P(O)(OH)$_2$, —C(O)-A4, —C(O)—O-A5, —C(O)—NH-A6, —C(O)—NA7A8, —O-A9, —O(-A10-O)$_a$—H (a=1, 2, 3, 4, 5), —O(-A11-O)$_b$-A12 (b=1, 2, 3, 4, 5), —OC(O)-A13, —OC(O)—O-A14, —OC(O)—NHA15, —O—C(O)—NA16A17, —OP(O)(OA18)(OA19), —OSi(A20)(A21)(A22), —OS($O_2$)-A23, —NHC(O)—$NH_2$, —NHC(O)-A24, —NA25C(O)-A26, —NH—C(O)-0-A27, —NH—C(O)—NH-A28, —NH—C(O)—NA29A30, —NA31—C(O)—O-A32, —NA33-C(O)—N—H-A34, —NA35-C(O)—NA36A37, —NHS($O_2$)-A38, —NA39S($O_2$)-A40, —S-A41, —S(O)-A42, —S($O_2$)-A43, —S($O_2$)—NH-A44, —S($O_2$)NA45A46, —S($O_2$)O-A47, —P(O)(OA48)(OA49), —Si(A50)(A51)(A52), —C(NH)—$NH_2$, —C(NA53)-$NH_2$, —C(NH)—NHA54, —C(NH)—NA55A56, —C(NA57)-NHA58, —C(NA59)-NA60A61, —NH—C(O)—NH—O-A62, —NH—C(O)—NA63-O-A64, —NA65-C(O)—NA66-O-A67, —N(—C(O)—NH—O-A68)$_2$, —N(—C(O)—NA69-O-A70)$_2$, —N(—C(O)—NH—O-A71)(—C(O)—NA72-O-A73), —C(S)-A74, —C(S)—O-A75, —C(S)—NH-A76, —C(S)—NA77A78, —C(O)—NH—O-A79, —C(O)—NA80-O-A81, —C(S)—NH—O-A82, —C(S)—NA83-O-A84, —C(O)—NH—NH-A85, —C(O)—NH—NA86A87, —C(O)—NA88—NA89A90, —C(S)—NH—NH-A91, —C(S)—NH—NA92A93, —C(S)—NA94NA95A96, —C(O)—C(O)—O-A97, —C(O)—C(O)—$NH_2$, —C(O)—C(O)—NHA98, —C(O)—C(O)—NA99A100, —C(S)—C(O)—O-A101, —C(O)—C(S)—O-A102, —C(S)—C(O)—O-A103, —C(S)—C(O)—$NH_2$, —C(S)—C(O)—NHA104, —C(S)—C(O)—NA105A106, —C(S)—C(S)—$NH_2$, —C(S)—C(S)—NHA107, —C(S)—C(S)—NA108A109, —C(O)—C(S)—$NH_2$, —C(O)—C(S)—NHA110, —C(O)—C(S)—NA111A112";

wherein A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, A36, A37, A38, A39, A40, A41, A42, A43, A44, A45, A46, A47, A48, A49, A50, A51, A52, A53, A54, A55, A56, A57, A58, A59, A60, A61, A62, A63, A64, A65, A66, A67, A68, A69, A70, A71, A72, A73, A74, A75, A76, A77, A78, A79, A80, A81, A82, A83, A84, A85, A86, A87, A88, A89, A90, A91, A92, A93, A94, A95, A96, A97, A98, A99, A100, A101, A102, A103, A104, A105, A106, A107, A108, A109, A110, A111, A112 are independently from each other selected from the group consisting of:"hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and wherein alternatively A7, A8 and/or A16, A17 and/or A29, A30 and/or A36, A37 and/or A45, A46 and/or A55, A56 and/or A60, A61 and/or A77, A78 and/or A86, A87 and/or A89, A90 and/or A92, A93 and/or A95, A96 and/or A99, A100 and/or A105, A106 and/or A108, A109 and/or A111, A112 and/or respectively together can also form "heterocyclyl";

wherein optionally above substituents of substituents group (2)—if not hydrogenn—can in turn independently from each other be substituted with at least one substituent, identical or different, selected from the group consisting of:

(i) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —$CF_3$, —$N_3$, —$NH_2$, —NHA201, —NA202A203, —$NO_2$, —OH, =O, —$OCF_3$, —$OCHF_2$, —SH, —O—$SO_3H$, —OP(O)(OH)$_2$, —CHO, —COOH, —C(O)—$NH_2$, —$SO_3H$, —P(O)(OH)$_2$, —C(O)-A204, —C(O)—O-A205, —C(O)—NH-A206, —C(O)—NA207A208, —O-A209, —O(-A210-O), —H (c=1, 2, 3, 4, 5), —O(-A211-O)$_d$-A212 (d=1, 2, 3, 4, 5), —OC(O)-A213, —OC(O)—O-A214, —OC(O)—NHA215, —O—C(O)—NA216A217, —OP(O)(OA218)(OA219), —OSi(A220)(A221)(A222), —OS($O_2$)-A223, —NHC(O)—$NH_2$, —NHC(O)-A224, —NA225C(O)-A226, —NH—C(O)—O-A227, —NH—C(O)—NH-A228, —NH—C(O)—NA229A230, —NA231-C(O)—O-A232, —NA233-C(O)—NH-A234, —NA235-C(O)—NA236A237, —NHS($O_2$)-A238, —NA239S($O_2$)-A240, —S-A241, —S(O)-A242, —S($O_2$)-A243, —S($O_2$)—NH-A244, —S($O_2$)NA245A246, —S($O_2$)O—-A247, —P(O)(OA248)(OA249), —Si(A250)(A251)(A252), —C(NH)—$NH_2$, —C(NA253)-$NH_2$, —C(NH)—NHA254, —C(NH)—NA255A256, —C(NA257)-NHA258, —C(NA259)-NA260A261, —NH—C(O)—NH—O-A262, —NH—C(O)—NA263-O-A264, —NA265-C(O)—NA266-O-A267, —N(—C(O)—NH—O-A268)$_2$, —N(—C(O)—NA269-O-A270)$_2$, —N(—C(O)—NH—O-A271)(—C(O)—NA272-O-A273), —C(S)-A274, —C(S)—O-A275, —C(S)—NH-A276, —C(S)—NA277A278, —C(O)—NH—O-A279, —C(O)—NA280-O-A281, —C(S)—NH—O-A282, —C(S)—NA283-O-A284, —C(O)—NH—NH-A285, —C(O)—NH—NA286A287, —C(O)—NA288—NA289A290, —C(S)—NH—NH-A291, —C(S)—NH—NA292A293, —C(S)—NA294—

NA295A296, —C(O)—C(O)—O-A297, —C(O)—C(O)—NH$_2$, —C(O)—C(O)—NHA298, —C(O)—C(O)—NA299A300, —C(S)—C(O)—O-A301, —C(O)—C(S)—O-A302, —C(S)—C(S)—O-A303, —C(S)—C(O)—NH$_2$, —C(S)—C(O)—NHA304, —C(S)—C(O)—NA305A306, —C(S)—C(S)—NH$_2$, —C(S)—C(S)—NHA307, —C(S)—C(S)—NA308A309, —C(O)—C(S)—NH$_2$, —C(O)—C(S)—NHA310, —C(O)—C(S)—NA311A312";

wherein A201, A202, A203, A204, A205, A206, A207, A208, A209, A210, A211, A212, A213, A214, A215, A216, A217, A218, A219, A220, A221, A222, A223, A224, A225, A226, A227, A228, A229, A230, A231, A232, A233, A234, A235, A236, A237, A238, A239, A240, A241, A242, A243, A244, A245, A246, A247, A248, A249, A250, A251, A252, A253, A254, A255, A256, A257, A258, A259, A260, A261, A262, A263, A264, A265, A266, A267, A268, A269, A270, A271, A272, A273, A274, A275, A276, A277, A278, A279, A280, A281, A282, A283, A284, A285, A286, A287, A288, A289, A290, A291, A292, A293, A294, A295, A296, A297, A298, A299, A300, A301, A302, A303, A304, A305, A306, A307, A308, A309, A310, A311, A312 are independently from each other selected from the group consisting of:"hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively A207, A208 and/or A216, A217 and/or A229, A230 and/or A236, A237 and/or A245, A246 and/or A255, A256 and/or A260, A261 and/or A277, A278 and/or A286, A287 and/or A289, A290 and/or A292, A293 and/or A295, A296 and/or A299, A300 and/or A305, A306 and/or A308, A309 and/or A311, A312 and/or respectively together can also form "heterocyclyl";

wherein optionally above substituents of substituents group (i) can in turn independently from each other be substituted with at least one substituent, identical or different, selected from the group consisting of:

(ii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHA401, —NA402A403, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)-A404, —C(O)—O-A405, —C(O)—NH-A406, —C(O)—NA407A408, —O-A409, —O(-A410-O)$_e$—H (e=1, 2, 3, 4, 5), —O(-A411-O)$_f$-A412 (f=1, 2, 3, 4, 5), —OC(O)-A413, —OC(O)—O-A414, —OC(O)—NHA415, —O—C(O)—NA416A417, —OP(O)(OA418)(OA419), —OSi(A420)(A421)(A422), —OS(O$_2$)-A423, —NHC(O)—NH$_2$, —NHC(O)-A424, —NA425C(O)-A426, —NH—C(O)—O-A427, —NH—C(O)—NH-A428, —NH—C(O)—NA429A430, —NA431-C(O)—O-A432, —NA433-C(O)—NH-A434, —NA435-C(O)—NA436A437, —NHS(O$_2$)-A438, —NA439S(O$_2$)-A440, —S-A441, —S(O)-A442, —S(O$_2$)— A443, —S(O$_2$)—NH-A444, —S(O$_2$)NA445A446, —S(O$_2$)O-A447, —P(O)(OA448)(OA449), —Si(A450)(A451)(A452), —C(NH)—NH$_2$, —C(NA453)-NH$_2$, —C(NH)—NHA454, —C(NH)—NA455A456, —C(NA457)NHA458, —C(NA459)-NA460A461, —NH—C(O)—NH—O-A462, —NH—C(O)—NA463-O-A464, —NA465-C(O)—NA466-O-A467, —N(—C(O)—NH—O-A468)$_2$, —N(—C(O)—NA469-O-A470)$_2$, —N(—C(O)—NH—O-A471)(—C(O)—NA472-O-A473), —C(S)-A474, —C(S)—O-A475, —C(S)—NH-A476, —C(S)—NA477A478, —C(O)—NH—O-A479, —C(O)—NA480-O-A481, —C(S)—NH—O-A482, —C(S)$_y$NA483-O-A484, —C(O)—NH—NH-A485, —C(O)—NH—NA486A487, —C(O)—NA488NA489A490, —C(S)—NH—NH-A491, —C(S)—NH—NA492A493, —C(S)—NA494—NA495A496, —C(O)—C(O)—O-A497, —C(O)—C(O)—NH$_2$, —C(O)—C(O)—NHA498, —C(O)—C(O)—NA499A500, —C(S)—C(O)—O-A501, —C(O)—C(S)—O-A502, —C(S)—C(S)—O-A503, —C(S)—C(O)—NH$_2$, —C(S)—C(O)—NHA504, —C(S)—C(O)—NA505A506, —C(S)—C(S)—NH$_2$, —C(S)—C(S)—NHA507, —C(S)—C(S)—NA508A509, —C(O)—C(S)—NH$_2$, —C(O)—C(S)—NHA510, —C(O)—C(S)—NA511A512";

wherein A401, A402, A403, A404, A405, A406, A407, A408, A409, A410, A411, A412, A413, A414, A415, A416, A417, A418, A419, A420, A421, A422, A423, A424, A425, A426, A427, A428, A429, A430, A431, A432, A433, A434, A435, A436, A437, A438, A439, A440, A441, A442, A443, A444, A445, A446, A447, A448, A449, A450, A451, A452, A453, A454, A455, A456, A457, A458, A459, A460, A461, A462, A463, A464, A465, A466, A467, A468, A469, A470, A471, A472, A473, A474, A475, A476, A477, A478, A479, A480, A481, A482, A483, A484, A485, A486, A487, A488, A489, A490, A491, A492, A493, A494, A495, A496, A497, A498, A499, A500, A501, A502, A503, A504, A505, A506, A507, A508, A509, A510, A511, A512 are independently from each other selected from the group consisting of:"hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively A407, A408 and/or A416, A417 and/or A429, A430 and/or A436, A437 and/or A445, A446 and/or A455, A456 and/or A460, A461 and/or A477, A478 and/or A486, A487 and/or A489, A490 and/or A492, A493 and/or A495, A496 and/or A499, A500 and/or A505, A506 and/or A508, A509 and/or A511, A512 and/or respectively together can also form "heterocyclyl";

wherein optionally above substituents of substituents group (ii) can in turn independently from each other be substituted with at least one substituent, identical or different, selected from the group consisting of:

(iii) "alkyl, (C$_9$-C$_{30}$)alkyl, cycloalkyl, cycloalkylalkyl, heterocyclyl, heterocyclylalkyl, aryl, arylalkyl; heteroaryl, heteroarylalkyl, —F, —Cl, —Br, —I, —CN, —CF$_3$, —N$_3$, —NH$_2$, —NHA601, —NA602A603, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)-A604, —C(O)—O-A605, —C(O)—NH-A606, —C(O)—NA607A608, —O-A609, —O(-A610-O)$_e$—H (e=1, 2, 3, 4, 5), —O(-A611-O)$_f$-A612 (f=1, 2, 3, 4, 5), —OC(O)-A613, —OC(O)—O-A614, —OC(O)—NHA615, —O—C(O)—NA616A617, —OP(O)(OA618)(OA619), —OSi(A620)(A621)(A622), —OS(O$_2$)-A623, —NHC(O)—NH$_2$, —NHC(O)-A624, —NA625C(O)-A626, —NH—C(O)—O-A627, —NH—C(O)—NH-A628, —NH—C(O)—NA629A630, —NA631-C(O)—O-A632, —NA633-C(O)—NH-A634, —NA635-C(O)—NA636A637, —NHS(O$_2$)-A638, —NA639S(O$_2$)-A640, —S-A641, —S(O)-A642, —S(O$_2$)-A643, —S(O$_2$)—NH-A644, —S(O$_2$)NA645A646, —S(O$_2$)O-A647, —P(O)(OA648)(OA649), —Si(A650)(A651)(A652), —C(NH)—NH$_2$, —C(NA653)-NH$_2$, —C(NH)—NHA654, —C(NH)—NA655A656, —C(NA657)-NHA658, —C(NA659)-NA660A661, —NH—C(O)—NH—O-A662, —NH—C(O)—NA663-O-A664, —NA665-C(O)—NA666-O-A667, —N(—C(O)—NH—O-A668)$_2$, —N(—C(O)—NA669-O-A670)$_2$, —N(—C(O)—NH—O-A671)(—C(O)—NA672-O-A673), —C(S)-A674, —C(S)—O-A675, —C(S)—NH-A676, —C(S)—NA677A678, —C(O)—NH—O-A679, —C(O)—NA680-O-A681, —C(S) NH—O-A682, —C(S)—NA683-O-A684, —C(O)—NH—NH-A685, —C(O)—NH—NA686A687, —C(O)—NA688—NA689A690, —C(S)—NH—NH-A691, —C(S)—NH—NA692A693, —C(S)—NA694—NA695A696, —C(O)—C(O)—O-A697, —C(O)—C(O)—NH$_2$, —C(O)—C(O)—NHA698, —C(O)—C(O)—NA699A700, —C(S)—C(O)—O-A701, —C(O)—C(S)—O-A702, —C(S)—C(S)—O-A703, —C(S)—C(O)—NH$_2$, —C(S)—C(O)—NHA704, —C(S)—C(O)—NA705A706, —C(S)—C(S)—NH$_2$, —C(S)—C(S)—NHA707, —C(S)—C(S)—NA708A709, —C(O)—C(S)—NH$_2$, —C(O)—C(S)—NHA710, —C(O)—C(S)—NA711A712";

wherein A601, A602, A603, A604, A605, A606, A607, A608, A609, A610, A611, A612, A613, A614, A615, A616, A617, A618, A619, A620, A621, A622, A623, A624, A625, A626, A627, A628, A629, A630, A631, A632, A633, A634, A635, A636, A637, A638, A639, A640, A641, A642, A643, A644, A645, A646, A647, A648, A649, A650, A651, A652, A653, A654, A655, A656, A657, A658, A659, A660, A661, A662, A663, A664, A665, A666, A667, A668, A669, A670, A671, A672, A673, A674, A675, A676, A677, A678, A679, A680, A681, A682, A683, A684, A685, A686, A687, A688, A689, A690, A691, A692, A693, A694, A695, A696, A697, A698, A699, A700, A701, A702, A703, A704, A705, A706, A707, A708, A709, A710, A711, A712 are independently from each other selected from the group consisting of:"hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively A607, A608 and/or A616, A617 and/or A629, A630 and/or A636, A637 and/or A645, A646 and/or A655, A656 and/or A660, A661 and/or A677, A678 and/or A686, A687 and/or A689, A690 and/or A692, A693 and/or A695, A696 and/or A699, A700 and/or A705, A706 and/or A708, A709 and/or A711, A712 and/or respectively together can also form "heterocyclyl";

and radicals R1, R2, R5 independently from each other are selected from the group consisting of:

(3) "hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHB1, —NB2B3, —NO$_2$, —OH, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)—B4, —C(O)—O—B5, —C(O)—NH—B6, —C(O)—NB7B8, —O—B9, —O(—B10-O)$_a$—H (a=1, 2, 3, 4, 5), —O(—B11-O)$_b$—B12 (b=1, 2, 3, 4, 5), —OC(O)—B13, —OC(O)—O—B14, —OC(O)—NHB15, —O—NB16B17, —OP(O)(OB18)(OB19), —OSi(B20)(B21)(B22), —OS(O$_2$)—B23, —NHC(O)—NH$_2$, —NHC(O)—B24, —NB25C(O)—B26, —NH—C(O)—O—B27, —NH—C(O)—NH—B28, —NH—C(O)—NB29B30, —NB31-C(O)—O—B32, —NB33-C(O)—NH—B34, —NB35-C(O)—NB36B37, —NHS(O$_2$)—B38, —NB39S(O$_2$)—B40, —S—B41, —S(O)—B42, —S(O$_2$)—B43, —S(O$_2$)—NH—B44, —S(O$_2$)—NB45B46, —S(O$_2$)O—B47, —P(O)(OB48)(OB49), —Si(B50)(B51)(B52), —C(NH)—NH$_2$, —C(NB53)-NH$_2$, —C(NH)—NHB54, —C(NH)—NB55B56, —C(NB57)-NHB58, —C(NB59)-NB60B61, —NH—C(O)—NH—O—B62, —NH—C(O)—NB63-O—B64, —NB65-C(O)—NB66-O—B67, —N(—C(O)—NH—O—B68)$_2$, —N(—C(O)—NB69-O—B70)$_2$, —N(—C(O)—NH—O—B71)(—C(O)—NB72-O—B73), —C(S)—B74, —C(S)—O—B75, —C(S)—NH—B76, —C(S)—NB77B78, —C(O)—NH—O—B79, —C(O)—NB80-O—B81, —C(S)—NH—O—B82, —C(S)—NB83-O—B84, —C(O)—NH—NH—B85, —C(O)—NH—NB86B87, —C(O)—NB88-NB89B90, —C(S)—NH—NH—B91, —C(S)—NH—NB92B93, —C(S)—N B94-NB95B96, —C(O)—C(O)—O—B97, —C(O)—C(O)—NH$_2$, —C(O)—C(O)—NHB98, —C(O)—C(O)—NB99B100, —C(S)—C(O)—O—B101, —C(O)—C(S)—O—B102, —C(S)—C(S)—O—B103, —C(S)—C(O)—NH$_2$, —C(S)—C(O)—NHB104, —C(S)—C(O)—NB105B106, —C(S)—C(S)—NH$_2$, —C(S)—C(S)—NHB107, —C(S)—C(S)—NB108B109, —C(O)—C(S)—NH$_2$, —C(O)—C(S)—NHB110, —C(O)—C(S)—NB111B112";

wherein B1, B2, B3, B4, B5, B6, B7, B8, B9, B10, B11, B12, B13, B14, B15, B16, B17, B18, B19, B20, B21, B22, B23, B24, B25, B26, B27, B28, B29, B30, B31, B32, B33, B34, B35, B36, B37, B38, B39, B40, B41, B42, B43, B44, B45, B46, B47, B48, B49, B50, B51, B52, B53, B54, B55, B56, B57, B58, B59, B60, B61, B62, B63, B64, B65, B66, B67, B68, B69, B70, B71, B72, B73, B74, B75, B76, B77, B78, B79, B80, B81, B82, B83, B84, B85, B86, B87, B88, B89, B90, B91, B92, B93, B94, B95, B96, B97, B98, B99, B100, B101, B102, B103, B104, B105, B106, B107, B108, B109, B110, B111, B112 are independently from each other selected from the group consisting of:"hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively B2, B3 and/or B7, B8 and/or B16, B17 and/or B29, B30 and/or B36, B37 and/or B45, B46 and/or B55, B56 and/or B60, B61 and/or B77, B78 and/or B86, B87 and/or B89, B90 and/or B92, B93 and/or B95, B96 and/or B99, B100 and/or B105, B106 and/or B108, B109 and/or B111, B112 and/or respectively together can also form "heterocyclyl";

wherein optionally above substituents of substituents group (3)—if not hydrogen—can in turn independently from each other be substituted with at least one substituent, identical or different, selected from the group consisting of:

(i) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHB201, —NB202B203, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)—B204, —C(O)—O—B205, —C(O)—NH—B206, —C(O)—NB207B208, —O—B209, —O(—B210-O)$_c$—H (c=1, 2, 3, 4, 5), —O(—B211-O)$_d$—B212 (d=1, 2, 3, 4, 5), —OC(O)—B213, —OC(O)—O—B214, —OC(O)—NHB215, —O—C(O)—NB216B217, —OP(O)(OB218)(OB219), —OSi(B220)(B221)(B222), —OS(O$_2$)—B223, —NHC(O)—NH$_2$, —NHC(O)—B224, —NB225C(O)—B226, —NH—C(O—O—B227, —NH—C(O)—NH—B228, —NH—C(O)—NB229B230, —NB231-C(O)—O—B232, —NB233-C(O)—NH—B234, —NB235-C(O)—NB236B237, —NHS(O$_2$)—B238, —NB239S(O$_2$)—B240, —S—B241, —S(O)—B242, —S(O$_2$)—B243, —S(O$_2$)—NH—B244, —S(O$_2$)—NB245B246, —S(O$_2$)O—B247, —P(O)(OB248)(OB249), —Si(B250)(B251)(B252), —C(NH)—NH$_2$, —C(NB253Y NH$_2$, —C(NH)—NHB254, —C(NH)—NB255B256, —C(NB257)-NHB258, —C(NB259)-NB260B261, —NH—C(O)—NH—O—B262, —NH—C(O)—NB263-O—B264, —NB265-C(O)—NB266-O—B267, —N(—C(O)—NH—O—B268)$_2$, —N(—C(O)—N B269-O—B270)$_2$, —N(—C(O)—NH—O—B271)(—C(O)—NB272-O—B273), —C(S)—B274, —C(S)—O—B275, —C(S)—NH—B276, —C(S)—NB277B278, —C(O)—NH—O—B279, —C(O)—NB280-O—B281, —C(S)—NH—O—B282, —C(S)—NB283-O—B284, —C(O)—NH—NH—B285, —C(O)—NH—NB286B287, —C(O)NB288—NB289B290, —C(S)—NH—NH—B291, —C(S)—NH—NB292B293, —C(S)—NB294—NB295B296, —C(O)—C(O)—O—B297, —C(O)—C(O)—NH$_2$, —C(O)—C(O)—NHB298, —C(O)—C(O)—NB299B300, —C(S)—C(O)—O—B301, —C(O)—C(S)—O—B302, —C(S)—C(S)—O—B303, —C(S)—C(O)—NH$_2$, —C(S)—C(O)—NHB304, —C(S)—C(O)—NB305B306, —C(S)—C(S)—NH$_2$, —C(S)—C(S)—NHB307, —C(S)—C(S)—NB308B309, —C(O)—C(S)—NH$_2$, —C(O)—C(S)—NHB310, —C(O)—C(S)—NB311B312";

wherein B201, B202, B203, B204, B205, B206, B207, B208, B209, B210, B211, B212, B213, B214, B215, B216, B217, B218, B219, B220, B221, B222, B223, B224, B225, B226, B227, B228, B229, B230, B231, B232, B233, B234, B235, B236, B237, B238, B239, B240, B241, B242, B243, B244, B245, B246, B247, B248, B249, B250, B251, B252, B253, B254, B255, B256, B257, B258, B259, B260, B261, B262, B263, B264, B265, B266, B267, B268, B269, B270, B271, B272, B273, B274, B275, B276, B277, B278, B279, B280, B281, B282, B283, B284, B285, B286, B287, B288, B289, B290, B291, B292, B293, B294, B295, B296, B297, B298, B299, B300, B301, B302, B303, B304, B305, B306, B307, B308, B309, B310, B311, B312 are independently from each other selected from the group consisting of:"hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively B207, B208 and/or B216, B217 and/or B229, B230 and/or B236, B237 and/or B245, B246 and/or B255, B256 and/or B260, B261 and/or B277, B278 and/or B286, B287 and/or B289, B290 and/or B292, B293 and/or B295, B296 and/or B299 and/or B305, B306 and/or B308, B309 and/or B311, B312 and/or respectively together can also form "heterocyclyl";
wherein optionally above substituents of substituents group (i) can in turn independently from each other be substituted with at least one substituent, identical or different, selected from the group consisting of:

(ii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHB401, —NB402B403, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)—B404, —C(O)—O—B405, —C(O)—NH—B406, —C(O)—NB407B408, —O—B409, —O(—B410-O)$_e$—H (e=1, 2, 3, 4, 5), —O(—B411-O)$_f$—B412 (f=1, 2, 3, 4, 5), —OC(O)—B413, —OC(O)—O—B414, —OC(O)—NHB415, —O—C(O)—NB416B417, —OP(O)(OB418)(OB419), —OSi(B420)(B421)(B422), —OS(O$_2$)—B423, —NHC(O)—NH$_2$, —NHC(O)—B424, —NB425C(O)—B426, —NH—C(O)—O—B427, —NH—C(O)—NH—B428, —NH—C(O)—NB429B430, —NB431-C(O)—O—B432, —NB433-C(O)—NH—B434, —NB435-C(O)—NB436B437, —NHS(O$_2$)—B438, —NB439S(O$_2$)—B440, —S—B441, —S(O)—B442, —S(O$_2$)—B443, —S(O$_2$)—NH—B444, —S(O$_2$)—NB445B446, —S(O$_2$)O—B447, —P(O)(OB448)(OB449), —Si(B450)(B451)(B452), —C(NH)—NH$_2$, —C(NB453)-NH$_2$, —C(NH)—NHB454, —C(NH)—NB455B456, —C(NB457)-NHB458, —C(NB459)-NB460B461, —NH—C(O)—NH—O—B462, —NH—C(O)—NB463-O—B464, —NB465-C(O)—NB466-O—B467, —N(—C(O)—NH—O—B468)$_2$, —N(—C(O)—NB469-O—B470)$_2$, —N(—C(O)—NH—O—B471)(—C(O)—NB472-O—B473), —C(S)—B474, —C(S)—O—B475, —C(S)—NH—B476, —C(S)—NB477B478, —C(O)—NH—O—B479, —C(O)—NB480-O—B481, —C(S)—NH—O—B482, —C(S)—NB483-O—B484, —C(O)—NH—NH—B485, —C(O)—NH—NB486B487, —C(O)—NB488—NB489B490, —C(S)—NH—NH—B491, —C(S)—NH—NB492B493, —C(S)—NB494-NB495B496, —C(O)—C(O)—O—B497, —C(O)—C(O)—NH$_2$, —C(O)—C(O)—NHB498, —C(O)—C(O)—NB499B500, —C(S)—C(O)—O—B501, —C(O)—C(S)—O—B502, —C(S)—C(S)—O—B503, —C(S)—C(O)—NH$_2$, —C(S)—C(O)—NHB504, —C(S)—C(O)—NB505B506, —C(S)—C(S)—NH$_2$, —C(S)—C(S)—NHB507, —C(S)—C(S)—NB508B509, —C(O)—C(S)—NH$_2$, —C(O)—C(S)—NHB510, —C(O)—C(S)—NB511B512";

wherein B401, B402, B403, B404, B405, B406, B407, B408, B409, B410, B411, B412, B413, B414, B415, B416, B417, B418, B419, B420, B421, B422, B423, B424, B425, B426, B427, B428, B429, B430, B431, B432, B433, B434, B435, B436, B437, B438, B439, B440, B441, B442, B443, B444, B445, B446, B447, B448, B449, B450, B451, B452, B453, B454, B455, B456, B457, B458, B459, B460, B461, B462, B463, B464, B465, B466, B467, B468, B469, B470, B471, B472, B473, B474, B475, B476, B477, B478, B479, B480, B481, B482, B483, B484, B485, B486, B487, B488, B489, B490, B491, B492, B493, B494, B495, B496, B497, B498, B499, B500, B501, B502, B503, B504, B505, B506, B507, B508, B509, B510, B511, B512 are independently from each other selected from the group consisting of:"hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively B407, B408 and/or B416, B417 and/or B429, B430 and/or B436, B437 and/or B445, B446 and/or B455, B456 and/or B460, B461 and/or B477, B478 and/or B486, B487 and/or B489, B490 and/or B492, B493 and/or B495, B496 and/or B499, B500 and/or B505, B506 and/or B508, B509 and/or B511, B512 and/or respectively together can also form "heterocyclyl";
wherein optionally above substituents of substituents group (ii) can in turn independently from each other be substituted with at least one substituent, identical or different, selected from the group consisting of:
(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —$CF_3$, —$N_3$, —$NH_2$, —NHB601, —NB602B603, —$NO_2$, —OH, ═O, —$OCF_3$, —$OCHF_2$, —SH, —O—$SO_3H$, —OP(O)(OH)$_2$, —CHO, —COOH, —C(O)—$NH_2$, —$SO_3H$, —P(O)(OH)$_2$, —C(O)—B604, —C(O)—O—B605, —C(O)—NH—B606, —C(O)—NB607B608, —O—B609, —O(—B610-O)$_e$—H (e=1, 2, 3, 4, 5), —O(—B611-O)$_f$—B612 (f=1, 2, 3, 4, 5), —OC(O)—B613, —OC(O)—O—B614, —OC(O)—NHB615, —O—C(O)—NB616B617, —OP(O)(OB618)(OB619), —OSi(B620)(B621)(B622), —OS($O_2$)—B623, —NHC(O)—$NH_2$, —NHC(O)—B624, —NB625C(O)—B626, —NH—C(O)—O—B627, —NH—C(O)—NH—B628, —NH—C(O)—NB629B630, —NB631-C(O)—O—B632, —NB633-C(O)—NH—B634, —NB635-C(O)—NB636B637, —NHS($O_2$)—B638, —NB639S($O_2$)—B640, —S—B641, —S(O)—B642, —S($O_2$)—B643, —S($O_2$)—NH—B644, —S($O_2$)N B645B646, —S($O_2$)O—B647, —P(O)(OB648)(OB649), —Si(B650)(B651)(B652), —C(NH)—$NH_2$, —C(NB653)-$NH_2$, —C(NH)—NHB654, —C(NH)—NB655B656, —C(NB657)-NHB658, —C(NB659)-NB660B661, —NH—C(O)—NH—O—B662, —NH—C(O)—NB663-O—B664, —NB665-C(O)—NB666-O—B667, —N(—C(O)—NH—O—B668)$_2$, —N(—C(O)—NB669-O—B670)$_2$, —N(—C(O)—NH—O—B671)(—C(O)—NB672-O—B673), —C(S)—B674, —C(S)—O—B675, —C(S)—NH—B676, —C(S)—NB677B678, —C(O)—NH—O—B679, —C(O)—NB680-O—B681, —C(S)—NH—O—B682, —C(S)—NB683-O—B684, —C(O)—NH—NH—B685, —C(O)—NH—NB686B687, —C(O)—NB688-NB689B690, —C(S)—NH—NH—B691, —C(S)—NH—NB692B693, —C(S)—NB694-NB695B696, —C(O)—C(O)—O—B697, —C(O)—C(O)—$NH_2$, —C(O)—C(O)—NHB698, —C(O)—C(O)—NB699B700, —C(S)—C(O)—O—B701, —C(O)—C(S)—O—B702, —C(S)—C(S)—O—B703, —C(S)—C(O)—$NH_2$, —C(S)—C(O)—NHB704, —C(S)—C(O)—NB705B706, —C(S)—C(S)—$NH_2$, —C(S)—C(S)—NHB707, —C(S)—C(S)—NB708B709, —C(O)—C(S)—$NH_2$, —C(O)—C(S)—NHB710, —C(O)—C(S)—NB711B712";
wherein B601, B602, B603, B604, B605, B606, B607, B608, B609, B610, B611, B612, B613, B614, B615, B616, B617, B618, B619, B620, B621, B622, B623, B624, B625, B626, B627, B628, B629, B630, B631, B632, B633, B634, B635, B636, B637, B638, B639, B640, B641, B642, B643, B644, B645, B646, B647, B648, B649, B650, B651, B652, B653, B654, B655, B656, B657, B658, B659, B660, B661, B662, B663, B664, B665, B666, B667, B668, B669, B670, B671, B672, B673, B674, B675, B676, B677, B678, B679, B680, B681, B682, B683, B684, B685, B686, B687, B688, B689, B690, B691, B692, B693, B694, B695, B696, B697, B698, B699, B700, B701, B702, B703, B704, B705, B706, B707, B708, B709, B710, B711, B712 are independently from each other selected from the group consisting of:"hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and wherein alternatively B607, B608 and/or B616, B617 and/or B629, B630 and/or B636, B637 and/or B645, B646 and/or B655, B656 and/or B660, B661 and/or B677, B678 and/or B686, B687 and/or B689, B690 and/or B692, B693 and/or B695, B696 and/or B699, B700 and/or B705, B706 and/or B708, B709 and/or B711, B712 and/or respectively together can also form "heterocyclyl".

The object of the present invention has surprisingly been solved in one aspect by providing pyrido[2,3-b]pyrazine derivatives according to general formula (Ib)

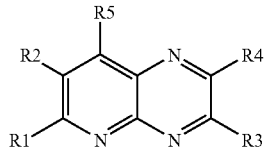

(Ib)

wherein:
one of radicals R3, R4 independently is selected, or both of radicals R3, R4 independently from each other are selected from the group consisting of:
(1) "—NR6R7";
wherein radicals R6, R7 are independently from each other selected from the group consisting of:
(a) "hydrogen";
  with the first proviso that radicals R6, R7 are not both hydrogen at the same time;
  with the second proviso that, if one of radicals R6, R7 independently is "hydrogen", radical R5 is not selected from the group consisting of:"—NH-cycloalkyl, —NH-heterocyclyl, —NH-aryl, —NH-heteroaryl, halogen, —F, —Cl, —Br, —I, —NR$_a$R$_b$", with Ra, Rb being independently selected from the group consisting of: "H, alkyl, cycloalkyl, cycloalkylalkyl, aryl, arylalkyl, heteroaryl, heteroarylalkyl, —NR$_c$R$_d$", Rc, Rd in turn being independently selected from the group consisting of:"H, alkyl, cycloalkyl, cycloalkylalkyl, aryl, arylalkyl, heteroaryl, heteroarylalkyl";
(b) "—C(Y1)NR8R9, —C(═NR10)-R11, —C(Y2)NR12-Y3-R13";
  wherein Y1, Y2 are independently from each other selected from the group consisting of:"═O, ═S, ═NH, ═NR14";
  wherein Y3 is independently selected from the group consisting of:"O, S";
  wherein radicals R8, R9, R10, R11, R12, R13, R14 are independently from each other selected from the group consisting of:
  (I) "hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHX1, —NX2X3, —NO$_2$, —OH, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)—X4, —C(O)O—X5, —C(O)—NH—X6, —C(O)—NX7X8, —O—X9, —O(—X10-O)$_a$—H (a=1, 2, 3, 4, 5), —O(—X11-O)$_b$—X12 (b=1, 2, 3, 4, 5), —OC(O)—X13, —OC(O)—O—X14, —OC(O)—NHX15, —O—C(O)—NX16X17, —OP(O)(OX18)(OX19), —OSi(X20)(X21)(X22), —OS(O$_2$)—X23, —NHC(O)—NH$_2$, —NHC(O)—X24, —NX25C(O)—X26, —NH—C(O)—O—X27, —NH—C(O)—NH—X28, —NH—C(O)—NX29X30, —NX31-C(O)—O—X32, —NX33-C(O)—NH—X34, —NX35-C(O)—NX36X37, —NHS(O$_2$)—X38, —NX39S(O$_2$)—X40, —S—X41, —S(O) X42, —S(O$_2$)—X43, —S(O$_2$)—NH—X44, —S(O$_2$)NX45X46, —S(O$_2$)O—X47, —P(O)(OX48)(OX49), —Si(X50)(X51)(X52), —C(NH)—NH$_2$, —C(NX53)-NH$_2$, —C(NH)—NHX54, —C(NH)—NX55X56, —C(NX57)-NHX58, —C(NX59)-NX60X61, —NH—C(O)—NH—O—X62, —NH—C(O)—NX63-O—X64, —NX65-C(O)—NX66-O—X67, —N(—C(O)—NH—O—X68)$_2$, —N(—C(O)—NX69-O—X70)$_2$, —N(—C(O)—NH—O—X71)(—C(O)—NX72-O—X73), —C(S)—X74, —C(S)—O—X75, —C(S)—NH—X76, —C(S)—NX77X78, —C(O)—NH—O—X79, —C(O)—NX80-O—X81, —C(S)—NH—O—X82, —C(S)—NX83-O—X84, —C(O)—NH—NH—X85, —C(O)—NH—NX86X87, —C(O)—NX88-NX89X90, —C(S)—NH—NH—X91, —C(S)—NH—NX92X93, —C(S)—NX94-NX95X96, —C(O)—C(O)—O—X97, —C(O)—C(O)—NH$_2$, —C(O)—C(O)—NHX98, —C(O)—C(O)—NX99X100, —C(S)—C(O)—O—X101, —C(O)—C(S)—O—X102, —C(S)—C(S)—O—X103, —C(S)—C(O)—NH$_2$, —C(S)—C(O)—NHX104, —C(S)—C(O)—NX105X106, —C(S)—C(S)—NH$_2$, —C(S)—C(S)—NHX107, —C(S)—C(S)—NX108X109, —C(O)—C(S)—NH$_2$, —C(O)—C(S)—NHX110, —C(O)—C(S)—NX111X12";

wherein X1, X2, X3, X4, X5, X6, X7, X8, X9, X10, X11, X12, X13, X14, X15, X16, X17, X18, X19, X20, X21, X22, X23, X24, X25, X26, X27, X28, X29, X30, X31, X32, X33, X34, X35, X36, X37, X38, X39, X40, X41, X42, X43, X44, X45, X46, X47, X48, X49, X50, X51, X52, X53, X54, X55, X56, X57, X58, X59, X60, X61, X62, X63, X64, X65, X66, X67, X68, X69, X70, X71, X72, X73, X74, X75, X76, X77, X78, X79, X80, X81, X82, X83, X84, X85, X86, X87, X88, X89, X90, X91, X92, X93, X94, X95, X96, X97, X98, X99, X100, X101, X102, X103, X104, X105; X106, X107, X108, X109, X110, X111, X112 are independently from each other selected from the group consisting of:"hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively X7, X8 and/or X16, X17 and/or X29, X30 and/or X36, X37 and/or X45, X46 and/or X55, X56 and/or X60, X61 and/or X77, X78 and/or X86, X87 and/or X89, X90 and/or X92, X93 and/or X95, X96 and/or X99, X100 and/or X105, X106 and/or X108, X109 and/or X111, X112 and/or respectively together can also form "heterocyclyl";

wherein optionally above substituents of substituents group (I)—if not hydrogen—can in turn independently from each other be substituted with at least one substituent, identical or different, selected from the group consisting of:

(i) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHX201, —NX202X203, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)—X204, —C(O)O—X205, —C(O)NH—X206, —C(O)NX207X208, —O—X209, —O(—X210-O)$_c$—H (c=1, 2, 3, 4, 5), —O(—X211-O)$_d$—X212 (d=1, 2, 3, 4, 5), —OC(O)—X213, —OC(O)—O—X214, —OC(O)—NHX215, —O—C(O)—NX216X217, —OP(O)(OX218)(OX219), —OSi(X220)(X221)(X222), —OS(O$_2$)—X223, —NHC(O)—NH$_2$, —NHC(O)—X224, —NX225C(O)—X226, —NH—C(O)—O—X227, —NH—C(O)—NH—X228, —NH—C(O)—NX229X230, —NX231-C(O)—O—X232, —NX233-C(O)—NH—X234, —NX235-C(O)—NX236X237, —NHS(O$_2$)—X238, —NX239S(O$_2$)—X240, —S—X241, —S(O)—X242, —S(O$_2$)—X243, —S(O$_2$)—NH—X244, —S(O$_2$)NX245X246, —S(O$_2$)O—X247, —P(O)(OX248)(OX249), —Si(X250)(X251)(X252), —C(NH)—NH$_2$, —C(NX253)-NH$_2$, —C(NH)—NHX254, —C(NH)—NX255X256, —C(NX257)-NHX258, —C(NX259)-NX260X261, —NH—C(O)—NH—O—X262, —NH—C(O)—NX263-O—X264, —NX265-C(O)—NX266-O—X267, —N(—C(O)—NH—O—X268)$_2$, —N(—C(O)—NX269-O—X270)$_2$, —N(—C(O)—NH—O—X271)(—C(O)—NX272-O—X273), —C(S)—X274, —C(S)—O—X275, —C(S)—NH—X276, —C(S)—NX277X278, —C(O)—NH—O—X279, —C(O)—NX280-O—X281, —C(S)—NH—O—X282, —C(S)—NX283-O—X284, —C(O)—NH—NH—X285, —C(O)—NH—NX286X287, —C(O)—NX288-NX289X290, —C(S)—NH—NH—X291, —C(S)—NH—NX292X293, —C(S)—NX294-NX295X296, —C(O)—C(O)—O—X297, —C(O)—C(O)—NH$_2$, —C(O)—C(O)—NHX298, —C(O)—C(O)—NX299X300, —C(S)—C(O)—O—X301, —C(O)—C(S)—O—X302, —C(S)—C(S)—O—X303, —C(S)—C(O)—NH$_2$, —C(S)—C(O)—NHX304, —C(S)—C(O)—NX305X306, —C(S)—C(S)—NH$_2$, —C(S)—C(S)—NHX307, —C(S)—C(S)—NX308X309, —C(O)—C(S)—NH$_2$, —C(O)—C(S)—NHX310, —C(O)—C(S)—NX311X312";

wherein X201, X202, X203, X204, X205, X206, X207, X208, X209, X210, X211, X212, X213, X214, X215, X216, X217, X218, X219, X220, X221, X222, X223, X224, X225, X226, X227, X228, X229, X230, X231, X232, X233, X234, X235, X236, X237, X238, X239, X240, X241, X242, X243, X244, X245, X246, X247, X248, X249, X250, X251, X252, X253, X254, X255, X256, X257, X258, X259, X260, X261, X262, X263, X264, X265, X266, X267, X268, X269, X270, X271, X272, X273, X274, X275, X276, X277, X278, X279, X280, X281, X282, X283, X284, X285, X286, X287, X288, X289, X290, X291, X292, X293, X294, X295, X296, X297, X298, X299, X300, X301, X302, X303, X304, X305, X306, X307, X308, X309, X310, X311, X312 are independently from each other selected from the group consisting of: "hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and wherein alternatively X207, X208 and/or X216, X217 and/or X229, X230 and/or X236, X237 and/or X245, X246 and/or X255, X256 and/or X260, X261 and/or X277, X278 and/or X286, X287 and/or X289, X290 and/or X292, X293 and/or X295, X296 and/or X299, X300 and/or X305, X306 and/or X308, X309 and/or X311, X312 and/or respectively together can also form "heterocyclyl";

wherein optionally above substituents of substituents group (i) can in turn independently from each other be substituted with at least one substituent, identical or different, selected from the group consisting of:

(ii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHX401, —NX402X403, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)—X404, —C(O)—O—X405, —C(O)—NH—X406, —C(O)—NX407X408, —O—X409, —O(—X410-O)$_e$—H (e=1, 2, 3, 4, 5), —O(—X411-O)$_f$—X412 (f=1, 2, 3, 4, 5), —OC(O)—X413, —OC(O)—O—X414, —OC(O)—NHX415, —O—C(O)—NX416X417, —OP(O)(OX418)(OX419), —OSi(X420)(X421)(X422), —OS(O$_2$)—X423, —NHC(O)—NH$_2$, —NHC(O)—X424, —NX425C(O)—X426, —NH—C(O)—O—X427, —NH—C(O)—NH—X428, —NH—C(O)—NX429X430, —NX431-C(O)—O—X432, —NX433-C(O)—NH—X434, —NX435-C(O)—NX436X437, —NHS(O$_2$)—X438, —NX439S(O$_2$)—X440, —S—X441, —S(O)—X442, —S(O$_2$)—X443, —S(O$_2$)—NH—X444, —S(O$_2$)NX445X446, —S(O$_2$)O—X447, —P(O)(OX448)(OX449), —Si(X450)(X451)(X452), —C(NH)—NH$_2$, —C(NX453)-NH$_2$, —C(NH)—NHX454, —C(NH)—NX455X456, —C(NX457)-NHX458, —C(NX459)-NX460X461, —NH—C(O)—NH—O—X462, —NH—C(O)—NX463-O—X464, —NX465-C(O)—NX466-O—X467, —N(—C(O)—NH—O—X468)$_2$, —N(—C(O)—NX469-O—X470)$_2$, —N(—C(O)—NH—O—X471)(—C(O)—NX472-O—X473), —C(S)—X474, —C(S)—O—X475, —C(S)—NH—X476, —C(S)—NX477X478, —C(O)—NH—O—X479, —C(O)—NX480-O—X481, —C(S)—NH—O—X482, —C(S)—NX483-O—X484, —C(O)—NH—NH—X485, —C(O)—NH—NX486X487, —C(O)—NX488-NX489X490, —C(S)—NH—NH—X491, —C(S)—NH—NX492X493, —C(S)—NX494-NX495X496, —C(O)—C(O)—O—X497, —C(O)—C(O)—NH$_2$, —C(O)—C(O)—NHX498, —C(O)—C(O)—NX499X500, —C(S)—C(O)—O—X501, —C(O)—C(S)—O—X502, —C(S)—C(S)—O—X503, —C(S)—C(O)—NH$_2$, —C(S)—C(O)—NHX504, —C(S)—C(O)—NX505X506, —C(S)—C(S)—NH$_2$, —C(S)—C(S)—NHX507, —C(S)—C(S)—NX508X509, —C(O)—C(S)—NH$_2$, —C(O)—C(S)—NHX510, —C(O)—C(S)—NX511X512";

wherein X401, X402, X403, X404, X405, X406, X407, X408, X409, X410, X411, X412, X413, X414, X415, X416, X417, X418, X419, X420, X421, X422, X423, X424, X425, X426, X427, X428, X429, X430, X431, X432, X433, X434, X435, X436, X437, X438, X439, X440, X441, X442, X443, X444, X445, X446, X447, X448, X449, X450, X451, X452, X453, X454, X455, X456, X457, X458, X459, X460, X461, X462, X463, X464, X465, X466, X467, X468, X469, X470, X471, X472, X473, X474, X475, X476, X477, X478, X479, X480, X481, X482, X483, X484, X485, X486, X487, X488, X489, X490, X491, X492, X493, X494, X495, X496, X497, X498, X499, X500, X501, X502, X503, X504, X505, X506, X507, X508, X509, X510, X511, X512 are independently from each other selected from the group consisting of: "hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and wherein alternatively X407, X408 and/or X416, X417 and/or X429, X430 and/or X436, X437 and/or X445, X446 and/or X455, X456 and/or X460, X461 and/or X477, X478 and/or X486, X487 and/or X489, X490 and/or X492, X493 and/or X495, X496 and/or X499, X500 and/or X505, X506 and/or X508, X509 and/or X511, X512 and/or respectively together can also form "heterocyclyl";

wherein optionally above substituents of substituents group (ii) can in turn independently from each other be substituted with at least one substituent, identical or different, selected from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHX601, —NX602X603, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)—X604, —C(O)—O—X605, —C(O)—NH—X606, —C(O)—NX607X608, —O—X609, —O(—X610-O)$_e$H (e=1, 2, 3, 4, 5), —O(—X611-O)$_f$—X612 (f=1, 2, 3, 4, 5), —OC(O)—X613, —OC(O)—O—X614, —OC(O)—NHX615, —O—C(O)—NX616X617, —OP(O)(OX618)(OX619), —OSi(X620)(X621)(X622), —OS(O$_2$)—X623, —NHC(O)—NH$_2$, —NHC(O)—X624, —NX625C(O)—X626, —NH—C(O)—O—X627, —NH—C(O)—NH—X628, —NH—C(O)—NX629X630, —NX631-C(O)—O—X632, —NX633-C(O)—NH—X634, —NX635-C(O)—NX636X637, —NHS(O$_2$)—X638, —NX639S(O$_2$)—X640, —S—X641, —S(O)—X642, —S(O$_2$)—X643, —S(O$_2$)—NH—X644, —S(O$_2$)NX645X646, —S(O$_2$)O—X647, —P(O)(OX648)(OX649), —Si(X650)(X651)(X652), —C(NH)—NH$_2$, —C(NX653)-NH$_2$, —C(NH)—NHX654, —C(NH)—NX655X656, —C(NX657)-NHX658, —C(NX659)-NX660X661, —NH—C(O)—NH—O—X662, —NH—C(O)—NX663-O—X664, —NX665-C(O)—NX666-O—X667, —N(—C(O)—NH—O—X668)$_2$, —N(—C(O)—NX669-O—X670)$_2$, —N(—C(O)—NH—O—X671)(—C(O)—NX672-O—X673), —C(S)—X674, —C(S)—O—X675, —C(S)—NH—X676, —C(S)—NX677X678, —C(O)—NH—O—X679, —C(O)—NX680-O—X681, —C(S)—NH—O—X682, —C(S)—NX683-O—X684, —C(O)—NH—NH—X685, —C(O)—NH—NX686X687, —C(O)—NX688-NX689X690, —C(S)—NH—NH—X691, —C(S)—NH—NX692X693, —C(S)—NX694—NX695X696, —C(O)—C(O)—O—X697, —C(O)—C(O)—NH$_2$, —C(O)—C(O)—NHX698, —C(O)—C(O)—NX699X700, —C(S)—C(O)—O—X701, —C(O)—C(S)—O—X702, —C(S)—C(S)—O—X703, —C(S)—C(O)—NH$_2$, —C(S)—C(O)—NHX704, —C(S)—C(O)—NX705X706, —C(S)—C(S)—NH$_2$, —C(S)—C(S)—NHX707, —C(S)—C(S)—NX708X709, —C(O)—C(S)—NH$_2$, —C(O)—C(S)—NHX710, —C(O)—C(S)—NX711X712";

wherein X601, X602, X603; X604, X605, X606, X607, X608, X609, X610, X611, X612, X613, X614, X615, X616, X617, X618, X619, X620, X621, X622, X623, X624, X625, X626, X627, X628, X629, X630, X631, X632, X633, X634, X635, X636, X637, X638, X639, X640, X641, X642, X643, X644, X645, X646, X647, X648, X649, X650, X651, X652, X653, X654, X655, X656, X657, X658, X659, X660, X661, X662, X663, X664, X665, X666, X667, X668, X669, X670, X671, X672, X673, X674, X675, X676, X677, X678, X679, X680, X681, X682, X683, X684, X685, X686, X687, X688, X689, X690, X691, X692, X693, X694, X695, X696, X697, X698, X699, X700, X701, X702, X703, X704, X705, X706, X707, X708, X709, X710, X711, X712 are independently from each other selected from the group consisting of:"hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively X607, X608 and/or X616, X617 and/or X629, X630 and/or X636, X637 and/or X645, X646 and/or X655, X656 and/or X660, X661 and/or X677, X678 and/or X686, X687 and/or X689, X690 and/or X692, X693 and/or X695, X696 and/or X699, X700 and/or X705, X706 and/or X708, X709 and/or X711, X712 and/or respectively together can also form "heterocyclyl";

with the first proviso that "—C(Y1)-NR8R9" is not selected from the group consisting of:"—C(O)—NR$_a$R$_b$", with Ra, Rb independently from each other being selected from the group consisting of:"hydrogen, alkyl, (C$_9$-C$_{30}$)alkyl, aryl, arylalkyl, heteroaryl, heteroarylalkyl, cycloalkyl, cycloalkylalkyl, heterocyclyl, heterocyclylalkyl"

with the second proviso that, if "—C(Y1)-NR8R9" independently is selected from the group consisting of:"—C(O)—N[C(O)—O-alkyl]$_2$, —C(O)—N[C(O)alkyl]$_2$, —C(O)—N[S(O$_2$)alkyl]$_2$, —C(O)—N[S(O$_2$)-cycloalkyl]$_2$, —C(O)—N[S(O$_2$)-cycloalkylalkyl]$_2$, —C(O)—N[S(O$_2$)-aryl]$_2$, —C(O)—N[S(O$_2$)-heterocyclyl]$_2$", radicals R1, R2 independently from each other are not "phenyl";

with the third proviso that, if "—C(Y2)-NR12-Y3-R13" independently is selected from the group consisting of:"—C(O)—N[O-alkyl]$_2$", radicals R1, R2 independently from each other are not "phenyl";

(c) "—C(O)—C(O)—R16";

wherein radical R16 is independently selected from the group consisting of:

(II) "hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHZ1, —NZ2Z3, —NO$_2$, —OH, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)-Z4, —C(O)—O-Z5, —C(O)—NH-Z6, —C(O)—NZ7Z8, —O-Z9, —O(-Z10-O)$_a$—H (a=1, 2, 3, 4, 5), —O(-Z11-O)$_b$-Z12 (b=1, 2, 3, 4, 5), —OC(O)-Z13, —OC(O)—O-Z14, —OC(O)—NHZ15, —O—C(O)—NZ16Z17, —OP(O)(OZ18)(OZ19), —OSi(Z20)(Z21)(Z22), —OS(O$_2$)-Z23, —NHC(O)—NH$_2$, —NHC(O)-Z24, —NZ25C(O)-Z26, —NH—C(O)—O-Z27, —NH—C(O)—NH-Z28, —NH—C(O)—NZ29Z30, —NZ31-C(O)—O-Z32, —NZ33-C(O)—NH-Z34, —NZ35-C(O)—NZ36Z37, —NHS(O$_2$)-Z38, —NZ39S(O$_2$)-Z40, —S-Z41, —S(O)-Z42, —S(O$_2$)-Z43, —S(O$_2$)—NH-Z44, —S(O$_2$)NZ45Z46, —S(O$_2$)O-Z47, —P(O)(OZ48)(OZ49), —Si(Z50)(Z51)(Z52), —C(NH)—NH$_2$, —C(NZ53)-NH$_2$, —C(NH)—NHZ54, —C(NH)—NZ55Z56, —C(NZ57)-NHZ58, —C(NZ59)-NZ60Z61, —NH—C(O)—NH—O-Z62, —NH—C(O)—NZ63-O-Z64, —NZ65-C(O)—NZ66-O-Z67, —N(—C(O)—NH—O-Z68)$_2$, —N(—C(O)—NZ69-O-Z70)$_2$, —N(—C(O)—NH—O-Z71)(—C(O)—NZ72-O-Z73), —C(S)-Z74, —C(S)—O-Z75, —C(S)—NH-Z76, —C(S)—NZ77Z78, —C(O)—NH—O-Z79, —C(O)—NZ80-O-Z81, —C(S)—NH—O-Z82, —C(S)—NZ83-O-Z84, —C(O)—NH—NH-Z85, —C(O)—NH—NZ86Z87, —C(O)—NZ88-NZ89Z90, —C(S)—NH—NH-Z91, —C(S)—NH—NZ92Z93, —C(S)—NZ94-NZ95Z96, —C(O)—C(O)—O-Z97, —C(O)—C(O)—NH$_2$, —C(O)—C(O)—NHZ98, —C(O)—C(O)—NZ99Z100, —C(S)—C(O)—O-Z101, —C(O)—C(S)—O-Z102, —C(S)—C(S)—O-Z103, —C(S)—C(O)—NH$_2$, —C(S)—C(O)—NHZ104, —C(S)—C(O)—NZ105Z106, —C(S)—C(S)—NH$_2$, —C(S)—C(S)—NHZ107, —C(S)—C(S)—NZ108Z109, —C(O)—C(S)—NH$_2$, —C(O)—C(S)—NHZ110, —C(O)—C(S)—NZ111Z112";

wherein Z1, Z2, Z3, Z4, Z5, Z6, Z7, Z8, Z9, Z10, Z11, Z12, Z13, Z14, Z15, Z16, Z17, Z18, Z19, Z20, Z21, Z22, Z23, Z24, Z25, Z26, Z27, Z28, Z29, Z30, Z31, Z32, Z33, Z34, Z35, Z36, Z37, Z38, Z39, Z40, Z41, Z42, Z43, Z44, Z45, Z46, Z47, Z48, Z49, Z50, Z51, Z52, Z53, Z54, Z55, Z56, Z57, Z58, Z59, Z60, Z61, Z62, Z63, Z64, Z65, Z66, Z67, Z68, Z69, Z70, Z71, Z72, Z73, Z74, Z75, Z76, Z77, Z78, Z79, Z80, Z81, Z82, Z83, Z84, Z85, Z86, Z87, Z88, Z89, Z90, Z91, Z92, Z93, Z94, Z95, Z96, Z97, Z98, Z99, Z100, Z101, Z102, Z103, Z104, Z105, Z106, Z107, Z108, Z109, Z110, Z111, Z112 are independently from each other selected from the group consisting of:"hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively Z7, Z8 and/or Z16, Z17 and/or Z29, Z30 and/or Z36, Z37 and/or Z45, Z46 and/or Z55, Z56 and/or Z60, Z61 and/or Z77, Z78 and/or Z86, Z87 and/or Z89, Z90 and/or Z92, Z93 and/or Z95, Z96 and/or Z99, Z100 and/or Z105, Z106 and/or Z108, Z109 and/or Z111, Z112 and/or respectively together can also form "heterocyclyl";

wherein optionally above substituents of substituents group (II)—if not hydrogen—can in turn independently from each other be substituted with at least one substituent, identical or different, selected from the group consisting of:

(i) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHZ201, —NZ202Z203, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)-Z204, —C(O)O-Z205, —C(O)NH-Z206, —C(O)NZ207Z208, —O-Z209, —O(-Z210-O)$_c$—H (c=1, 2, 3, 4, 5), —O(-Z211—O)$_d$-Z212 (d=1, 2, 3, 4, 5), —OC(O)-Z213, —OC(O)—O-Z214, —OC(O)—NHZ215, —O—C(O)—NZ216Z217, —OP(O)(OZ218)(OZ219), —OSi(Z220)(Z221)(Z222), —OS(O$_2$)-Z223, —NHC(O)—NH$_2$, —NHC(O)-Z224, —NZ225C(O)-Z226, —NH—C(O)—O-Z227, —NH—C(O)—NH-Z228, NH—C(O)—NZ229Z230, —NZ231-C(O)—O-Z232, —NZ233-C(O)—NH-Z234, —NZ235-C(O)—NZ236Z237, —NHS(O$_2$)-Z238, —NZ239S(O$_2$)-Z240, —S-Z241, —S(O)-Z242, —S(O$_2$)-Z243, —S(O$_2$)—NH-Z244, —S(O$_2$)NZ245Z246, —S(O$_2$)O-Z247, —P(O)(OZ248)(OZ249), —Si(Z250)(Z251)(Z252), —C(NH)—NH$_2$, —C(NZ253)-NH$_2$, —C(NH)—NHZ254, —C(NH)—NZ255Z256, —C(NZ257)-NHZ258, —C(NZ259)-NZ260Z261, —NH—C(O)—NH—O-Z262, —NH—C(O)—NZ263-O-Z264, —NZ265-C(O)—NZ266-O-Z267, —N(—C(O)—NH—O-Z268)$_2$, —N(—C(O)—NZ269-O-Z270)$_2$, —N(—C(O)—NH—O-Z271)(—C(O)—NZ272-O-Z273), —C(S)-Z274, —C(S)—O-Z275, —C(S)—NH-Z276, —C(S)-NZ277Z278, —C(O)—NH—O-Z279, —C(O)—NZ280-O-Z281, —C(S)—NH—O-Z282, —C(S)—NZ283-O-Z284, —C(O)—NH—NH-Z285, —C(O)—NH—NZ286Z287, —C(O)—NZ288-NZ289Z290, —C(S)—NH—NH-Z291, —C(S)—NH—NZ292Z293, —C(S)—NZ294-NZ295Z296, —C(O)—C(O)—O-Z297, —C(O)—C(O)—NH$_2$, —C(O)—C(O)—NHZ298, —C(O)—C(O)—NZ299Z300, —C(S)—C(O)—O-Z301, —C(O)—C(S)—O-Z302, —C(S)—C(S)—O-Z303, —C(S)—C(O)—NH$_2$, —C(S)—C(O)—NHZ304, —C(S)—C(O)—NZ305Z306, —C(S)—C(S)—NH$_2$, —C(S)—C(S)—NHZ307, —C(S)—C(S)—NZ308Z309, —C(O)—C(S)—NH$_2$, —C(O)—C(S)—NHZ310, —C(O)—C(S)—NZ311Z312";

wherein Z201, Z202, Z203, Z204, Z205, Z206, Z207, Z208, Z209, Z210, Z211, Z212, Z213, Z214, Z215, Z216, Z217, Z218, Z219, Z220, Z221, Z222, Z223, Z224, Z225, Z226, Z227, Z228, Z229, Z230, Z231, Z232, Z233, Z234, Z235, Z236, Z237, Z238, Z239, Z240, Z241, Z242, Z243, Z244, Z245, Z246, Z247, Z248, Z249, Z250, Z251, Z252, Z253, Z254, Z255, Z256, Z257, Z258, Z259, Z260, Z261, Z262, Z263, Z264, Z265, Z266, Z267, Z268, Z269, Z270, Z271, Z272, Z273, Z274, Z275, Z276, Z277, Z278, Z279, Z280, Z281, Z282, Z283, Z284, Z285, Z286, Z287, Z288, Z289, Z290, Z291, Z292, Z293, Z294, Z295, Z296, Z297, Z298, Z299, Z300, Z301, Z302, Z303, Z304, Z305, Z306, Z307, Z308, Z309, Z310, Z311, Z312 are independently from each other selected from the group consisting of:"hydrogen, alkyl, $(C_9-C_{30})$alkyl, cycloalkyl, cycloalkylalkyl, heterocyclyl, heterocyclylalkyl, aryl, arylalkyl, heteroaryl, heteroarylalkyl" and wherein alternatively Z207, Z208 and/or Z216, Z217 and/or Z229, Z230 and/or Z236, Z237 and/or Z245, Z246 and/or Z255, Z256 and/or Z260, Z261 and/or Z277, Z278 and/or Z286, Z287 and/or Z289, Z290 and/or Z292, Z293 and/or Z295, Z296 and/or Z299, Z300 and/or Z305, Z306 and/or Z308, Z309 and/or Z311, Z312 and/or respectively together can also form "heterocyclyl";

wherein optionally above substituents of substituents group (i) can in turn independently from each other be substituted with at least one substituent, identical or different, selected from the group consisting of:

(ii) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHZ401, —NZ402Z403, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)-Z404, —C(O)—O-Z405, —C(O)—NH-Z406, —C(O)NZ407Z408, —O-Z409, —O(-Z410-O)$_e$—H (e=1, 2, 3, 4, 5), —O(-Z411-O)$_f$Z412 (f=1, 2, 3, 4, 5), —OC(O)-Z413, —OC(O)—O-Z414, —OC(O)—NHZ415, —O—C(O)—NZ416Z417, —OP(O)(OZ418)(OZ419), —OSi(Z420)(Z421)(Z422), —OS(O$_2$)-Z423, —NHC(O—NH$_2$, —NHC(O)-Z424, —NZ425C(O)-Z426, —NH—C(O)—O-Z427, —NH—C(O)—NH-Z428, —NH—C(O)—NZ429Z430, —NZ431-C(O)—O-Z432, —NZ433-C(O)—NH-Z434, —NZ435-C(O)—NZ436Z437, —NHS(O$_2$)-Z438, —NZ439S(O$_2$)-Z440, —S-Z441, —S(O)-Z442, —S(O$_2$)-Z443, —S(O$_2$)—NH-Z444, —S(O$_2$)NZ445Z446, —S(O$_2$)O-Z447, —P(O)(OZ448)(OZ449), —Si(Z450)(Z451)(Z452), —C(NH)—NH$_2$, —C(NZ453)-NH$_2$, —C(NH)—NHZ454, —C(NH)—NZ455Z456, —C(NZ457)-NHZ458, —C(NZ459)-NZ460Z461, —NH—C(O)—NH—O-Z462, —NH—C(O)—NZ463-O-Z464, —NZ465-C(O)—NZ466-O-Z467, —N(—C(O)—NH—O-Z468)$_2$, —N(—C(O)—NZ469-O-Z470)$_2$, —N(—C(O)—NH—O-Z471)(—C(O)—NZ472-O-Z473), —C(S)-Z474, —C(S)—O-Z475, —C(S)—NH-Z476, —C(S)—NZ477Z478, —C(O)—NH—O-Z479, —C(O)—NZ480-O-Z481, —C(S)—NH—O-Z482, —C(S)—NZ483-O-Z484, —C(O)—NH—NH-Z485, —C(O)—NH—NZ486Z487, —C(O)—NZ488-NZ489Z490, —C(S)—NH—NH-Z491, —C(S)—NH—NZ492Z493, —C(S)—NZ494-NZ495Z496, —C(O)—C(O)—O-Z497, —C(O)—C(O)—NH$_2$, —C(O)—C(O)—NHZ498, —C(O)—C(O)—NZ499Z500, —C(S)—C(O)—O-Z501, —C(O)—C(S)—O-Z502, —C(S)—C(S)—O-Z503, —C(S)—C(O)—NH$_2$, —C(S)—C(O)—NHZ504, —C(S)—C(O)—NZ505Z506, —C(S)—C(S)—NH$_2$, —C(S)—C(S)—NHZ507, —C(S)—C(S)—NZ508Z509, —C(O)—C(S)—NH$_2$, —C(O)—C(S)—NHZ510, —C(O)—C(S)—NZ511Z512";

wherein Z401, Z402, Z403, Z404, Z405, Z406, Z407, Z408, Z409, Z410, Z411, Z412, Z413, Z414, Z415, Z416, Z417, Z418, Z419, Z420, Z421, Z422, Z423, Z424, Z425, Z426, Z427, Z428, Z429, Z430, Z431, Z432, Z433, Z434, Z435, Z436, Z437, Z438, Z439, Z440, Z441, Z442, Z443, Z444, Z445, Z446, Z447, Z448, Z449, Z450, Z451, Z452, Z453, Z454, Z455, Z456, Z457, Z458, Z459, Z460, Z461, Z462, Z463, Z464, Z465, Z466, Z467, Z468, Z469, Z470, Z471, Z472, Z473, Z474, Z475, Z476, Z477, Z478, Z479, Z480, Z481, Z482, Z483, Z484, Z485, Z486, Z487, Z488, Z489, Z490, Z491, Z492, Z493, Z494, Z495, Z496, Z497, Z498, Z499, Z500, Z501, Z502, Z503, Z504, Z505, Z506, Z507, Z508, Z509, Z510, Z511, Z512 are independently from each other selected from the group consisting of:"hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively Z407, Z408 and/or Z416, Z417 and/or Z429, Z430 and/or Z436, Z437 and/or Z445, Z446 and/or Z455, Z456 and/or Z460, Z461 and/or Z477, Z478 and/or Z486, Z487 and/or Z489, Z490 and/or Z492, Z493 and/or Z495, Z496 and/or Z499, Z500 and/or Z505, Z506 and/or Z508, Z509 and/or Z511, Z512 and/or respectively together can also form "heterocyclyl";

wherein optionally above substituents of substituents group (ii) can in turn independently from each other be substituted with at least one substituent, identical or different, selected from the group consisting of:

(iii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHZ601, —NZ602Z603, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)-Z604, —C(O)—O-Z605, —C(O)—NH-Z606, —C(O)—NZ607Z608, —O-Z609, —O(-Z610-O)$_e$—H (e=1, 2, 3, 4, 5), —O(-Z611-O)$_f$Z612 (f=1, 2, 3, 4, 5), —OC(O)-Z613, —OC(O)—O-Z614, —OC(O)—NHZ615, —O—C(O)—NZ616Z617, —OP(O)(OZ618)(OZ619), —OSi(Z620)(Z621)(Z622), —OS(O$_2$)-Z623, —NHC(O)—NH$_2$, —NHC(O)-Z624, —NZ625C(O)-Z626, —NH—C(O)—O-Z627, —NH—C(O)—NH-Z628, —NH—C(O)—NZ629Z630, —NZ631-C(O)—O-Z632, —NZ633-C(O)—NH-Z634, —NZ635-C(O)—NZ636Z637, —NHS(O$_2$)-Z638, —NZ639S(O$_2$)-Z640, —S-Z641, —S(O)-Z642, —S(O$_2$)-Z643, —S(O$_2$)—NH-Z644, —S(O$_2$)NZ645Z646, —S(O$_2$)O-Z647, —P(O)(OZ648)(OZ649), —Si(Z650)(Z651)(Z652), —C(NH)—NH$_2$, —C(NZ653)-NH$_2$, —C(NH)—NHZ654, —C(NZ655)NZ656, —C(NZ657)-NHZ658, —C(NZ659)-NZ660Z661, —NH—C(O)—NH—O-Z662, —NH—C(O)—NZ663-O-Z664, —NZ665-C(O)—NZ666-O-Z667, —N(—C(O)—NH—O-Z668)$_2$, —N(—C(O)—NZ669-O-Z670)$_2$, —N(—C(O)—NH—O-Z671)(—C(O)—NZ672-O-Z673), —C(S)-Z674, —C(S)—O-Z675, —C(S)—NH-Z676, —C(S)—NZ677Z678, —C(O)—NH—O-Z679, —C(O)—NZ680-O-Z681, —C(S)—NH—O-Z682, —C(S)—NZ683-O-Z684, —C(O)—NH—NH-Z685, —C(O)—NH—NZ686Z687, —C(O)—NZ688-NZ689Z690, —C(S)—NH—NH-Z691, —C(S)—NH—NZ692Z693, —C(S)—NZ694-NZ695Z696, —C(O)—C(O)—O-Z697, —C(O)—C(O)—NH$_2$, —C(O)—C(O)—NHZ698, —C(O)—C(O)—NZ699Z700, —C(S)—C(O)—O-Z701, —C(O)—C(S)—O-Z702, —C(S)—C(S)—O-Z703, —C(S)—C(O)—NH$_2$, —C(S)—C(O)—NHZ704, —C(S)—C(O)—NZ705Z706, —C(S)—C(S) NH$_2$, —C(S)—C(S)—NHZ707, —C(S)—C(S)—NZ708Z709, —C(O)—C(S)—NH$_2$, —C(O)—C(S)—NHZ710, —C(O)—C(S)—NZ711Z712";

wherein Z601, Z602, Z603, Z604, Z605, Z606, Z607, Z608, Z609, Z610, Z611, Z612, Z613, Z614, Z615, Z616, Z617, Z618, Z619, Z620, Z621, Z622, Z623, Z624, Z625, Z626, Z627, Z628, Z629, Z630, Z631, Z632, Z633, Z634, Z635, Z636, Z637, Z638, Z639, Z640, Z641, Z642, Z643, Z644, Z645, Z646, Z647, Z648, Z649, Z650, Z651, Z652, Z653, Z654, Z655, Z656, Z657, Z658, Z659, Z660, Z661, Z662, Z663, Z664, Z665, Z666, Z667, Z668, Z669, Z670, Z671, Z672, Z673, Z674, Z675, Z676, Z677, Z678, Z679, Z680, Z681, Z682, Z683, Z684, Z685, Z686, Z687, Z688, Z689, Z690, Z691, Z692, Z693, Z694, Z695, Z696, Z697, Z698, Z699, Z700, Z701, Z702, Z703, Z704, Z705, Z706, Z707, Z708, Z709, Z710, Z711, Z712 are independently from each other selected from the group consisting of:"hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively Z607, Z608 and/or Z616, Z617 and/or Z629, Z630 and/or Z636, Z637 and/or Z645, Z646 and/or Z655, Z656 and/or Z660, Z661 and/or Z677, Z678 and/or Z686, Z687 and/or Z689, Z690 and/or Z692, Z693 and/or Z695, Z696 and/or Z699, Z700 and/or Z705, Z706 and/or Z708, Z709 and/or Z711, Z712 and/or respectively together can also form "heterocyclyl";

with the proviso that radical R16 is not "indol-yl";

(d) "—S(O$_2$)—R18";

wherein radical R18 is independently selected from the group consisting of:

(III) "—F, —Cl, —Br, —I, —CN, —CF$_3$, —N$_3$, —NH$_2$, —NHW1, —NW2W3, —NO$_2$, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)—W4, —C(O)—O—W5, —C(O)—NH—W6, —C(O)—NW7W8, —O—W9, —O(—W10-O)$_a$—H (a=1, 2, 3, 4, 5), —O(—W11-O)$_b$—W12 (b=1, 2, 3, 4, 5), —OC(O)—W13, —OC(O)—O—W14, —OC(O)—NHW15, —O—C(O)—NW16W17, —OP(O)(OW18)(OW19), —OSi(W20)(W21)(W22), —OS(O$_2$)—W23, —NHC(O)—NH$_2$, —NHC(O)—W24, —NW25C(O)—W26, —NH—C(O)—O—W27, —NH—C(O)—NH—W28,

—NH—C(O)—NW29W30, —NW31-C(O)—O—W32, —NW33-C(O)—NH—W34, —NW35-C(O)—NW36W37, —NHS(O$_2$)—W38, —NW39S(O$_2$)—W40, —S—W41, —S(O)—W42, —S(O$_2$)—W43, —S(O$_2$)—NH—W44, —S(O$_2$)—NW45W46, —S(O$_2$)O—W47, —P(O)(OW48)(OW49), —Si(W50)(W51)(W52), —C(NH)—NH$_2$, —C(NW53)-NH$_2$, —C(NH)—NHW54, —C(NH)—NW55W56, —C(NW57)-NHW58, —C(NW59)-NW60W61, —NH—C(O)—NH—O—W62, —NH—C(O)—NW63-O—W64, —NW65-C(O)—NW66-O—W67, —N(—C(O)—NH—O—W68)$_2$, —N(—C(O)—NW69-O—W70)$_2$, —N(—C(O)—NH—O—W71)(—C(O)—NW72-O—W73), —C(S)—W74, —C(S)—O—W75, —C(S)—NH—W76, —C(S)—NW77W78, —C(O)—NH—O—W79, —C(O)—NW80-O—W81, —C(S)—NH—O—W82, —C(S)—NW83-O—W84, —C(O)—NH—NH—W85, —C(O)—NH—NW86W87, —C(O)—NW88-NW89W90, —C(S)—NH—NH—W91, —C(S)—NH—NW92W93, —C(S)—NW94-NW95W96, —C(O)—C(O)—O—W97, —C(O)—C(O)—NH$_2$, —C(O)—C(O)—NHW98, —C(O)—C(O)—NW99W100, —C(S)—C(O)—O—W101, —C(O)—C(S)—O—W102, —C(S)—C(S)—O—W103, —C(S)—C(O)—NH$_2$, —C(S)—C(O)—NHW104, —C(S)—C(O)—NW105W106, —C(S)—C(S)—NH$_2$, —C(S)—C(S)—NHW107, —C(S)—C(S)—NW108W109, —C(O)—C(S)—NH$_2$, —C(O)—C(S)—NHW110, —C(O)—C(S)—NW111W112";

wherein W1, W2, W3, W4, W5, W6, W7, W8, W9, W10, W11, W12, W13, W14, W15, W16, W17, W18, W19, W20, W21, W22, W23, W24, W25, W26, W27, W28, W29, W30, W31, W32, W33, W34, W35, W36, W37, W38, W39, W40, W41, W42, W43, W44, W45, W46, W47, W48, W49, W50, W51, W52, W53, W54, W55, W56, W57, W58, W59, W60, W61, W62, W63, W64, W65, W66, W67, W68, W69, W70, W71, W72, W73, W74, W75, W76, W77, W78, W79, W80, W81, W82, W83, W84, W85, W86, W87, W88, W89, W90, W91, W92, W93, W94, W95, W96, W97, W98, W99, W100, W101, W102, W103, W104, W105, W106, W107, W108, W109, W110, W111, W112 are independently from each other selected from the group consisting of:"hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively W7, W8 and/or W16, W17 and/or W29, W30 and/or W36, W37 and/or W45, W46 and/or W55, W56 and/or W60, W61 and/or W77, W78 and/or W86, W87 and/or W89, W90 and/or W92, W93 and/or W95, W96 and/or W99, W100 and/or W105, W106 and/or W108, W109 and/or W1, W112 and/or respectively together can also form "heterocyclyl";

wherein optionally above substituents of substituents group (III) can in turn independently from each other be substituted with at least one substituent, identical or different, selected from the group consisting of:
(i) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHW201, —NW202W203, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)—W204, —C(O)—O—W205, —C(O)—NH—W206, —C(O)—NW207W208, —O—W209, —O(—W210-O), —H (c=1, 2, 3, 4, 5), —O(—W211-O)$_d$—W212 (d=1, 2, 3, 4, 5), —OC(O)—W213, —OC(O)—O—W214, —OC(O)—NHW215, —O—C(O)—NW216W217, —OP(O)(OW218)(OW219), —OSi(W220)(W221)(W222), —OS(O$_2$)—W223, —NHC(O)—NH$_2$, —NHC(O)—W224, —NW225C(O)—W226, —NH—C(O)—O—W227, —NH—C(O)—NH—W228, —NH—C(O)—NW229W230, —NW231-C(O)—O—W232, —NW233-C(O)—NH—W234, —NW235-C(O)—NW236W237, —NHS(O$_2$)—W238, —NW239S(O$_2$)—W240, —S—W241, —S(O)—W242, —S(O$_2$)—W243, —S(O$_2$)—NH—W244, —S(O$_2$)—NW245W246, —S(O$_2$)O—W247, —P(O)(OW248)(OW249), —Si(W250)(W251)(W252), —C(NH)—NH$_2$, —C(NW253)-NH$_2$, —C(NH)—NHW254, —C(NH)—NW255W256, —C(NW257)-NHW258, —C(NW259)-NW260W261, —NH—C(O)—NH—O—W262, —NH—C(O)—NW263-O—W264, —NW265-C(O)—NW266-O—W267, —N(—C(O)—NH—O—W268)$_2$, —N(—C(O)—NW269-O—W270)$_2$, —N(—C(O)—NH—O—W271)(—C(O)—NW272-O—W273), —C(S)—W274, —C(S)—O—W275, —C(S)—NH—W276, —C(S)—NW277W278, —C(O)—NH—O—W279, —C(O)—NW280-O—W281, —C(S)—NH—O—W282, —C(S)—NW283-O—W284, —C(O)—NH—NH—W285, —C(O)—NH—NW286W287, —C(O)—NW288-NW289W290, —C(S)—NH—NH—W291, —C(S)—NH—NW292W293, —C(S)—NW294-NW295W296, —C(O)—C(O)—O—W297, —C(O)—C(O)—NH$_2$, —C(O)—C(O)—NHW298, —C(O)—C(O)—NW299W300, —C(S)—C(O)—O—W301, —C(O)—C(S)—O—W302, —C(S)—C(S)—O—W303, —C(S)—C(O)—NH$_2$, —C(S)—C(O)—NHW304, —C(S)—C(O)—NW305W306, —C(S)—C(S)—NH$_2$, —C(S)—C(S)—NHW307, —C(S)—C(S)—NW308W309, —C(O)—C(S)—NH$_2$, —C(O)—C(S)—NHW310, —C(O)—C(S)—NW311W312";

wherein W201, W202, W203, W204, W205, W206, W207, W208, W209, W210, W211, W212, W213, W214, W215, W216, W217, W218, W219, W220, W221, W222, W223, W224, W225, W226, W227, W228, W229, W230, W231, W232, W233, W234, W235, W236, W237, W238, W239, W240, W241, W242, W243, W244, W245, W246, W247, W248, W249, W250, W251, W252, W253, W254, W255, W256, W257, W258, W259, W260, W261, W262, W263, W264, W265, W266, W267, W268, W269, W270, W271, W272, W273, W274, W275, W276, W277, W278, W279, W280, W281, W282, W283, W284, W285, W286, W287, W288, W289, W290, W291, W292, W293, W294, W295, W296, W297, W298, W299, W300, W301, W302, W303, W304, W305, W306, W307, W308, W309, W310, W311, W312 are independently from each other selected from the group consisting of:"hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively W207, W208 and/or W216, W217 and/or W229, W230 and/or W236, W237 and/or W245, W246 and/or W255, W256 and/or W260, W261 and/or W277, W278 and/or W286, W287 and/or W289, W290 and/or W292, W293 and/or W295, W296 and/or W299, W300 and/or W305, W306 and/or W308, W309 and/or W311, W312 and/or respectively together can also form "heterocyclyl"; wherein optionally above substituents of substituents group (i) can in turn independently from each other be substituted with at least one substituent, identical or different, selected from the group consisting of:

(ii) "alkyl, $(C_9$-$C_{30})$alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHW401, —NW402W403, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)—W404, —C(O)—O—W405, —C(O)—NH—W406, —C(O)—NW407W408, —O—W409, —O(—W4100-)$_e$—H (e=1, 2, 3, 4, 5), —O(—W411-O)$_f$—W412 (f=1, 2, 3, 4, 5), —OC(O)—W413, —OC(O)—O—W414, —OC(O)—NHW415, —O—C(O)—NW416W417, —OP(O)(OW418)(OW419), —OSi(W420)(W421)(W422), —OS(O$_2$)—W423, —NHC(O)—NH$_2$, —NHC(O)—W424, —NW425C(O)—W426, —NH—C(O)—O—W427, —NH—C(O)—NH—W428, —NH—C(O)—NW429W430, —NW431-C(O)—O—W432, —NW433-C(O)—NH—W434, —NW435-C(O)—NW436W437, —NHS(O$_2$)—W438, —NW439S(O$_2$)—W440, —S—W441, —S(O)—W442, —S(O$_2$)—W443, —S(O$_2$)—NH—W444, —S(O$_2$)—NW445W446, —S(O$_2$)O—W447, —P(O)(OW448)(OW449), —Si(W450)(W451)(W452), —C(NH)—NH$_2$, —C(NW453)-NH$_2$, —C(NH—NHW454, —C(NH)—NW455W456, —C(NW457)-NHW458, —C(NW459)-NW460W461, —NH—C(O)—NH—O—W462, —NH—C(O)—NW463-O—W464, —NW465-C(O)—NW466-O—W467, —N(—C(O)—NH—O—W468)$_2$, —N(—C(O)—NW469-O—W470)$_2$, —N(—C(O)—NH—O—W471)(—C(O)—NW472-O—W473), —C(S)—W474, —C(S)—O—W475, —C(S)—NH—W476, —C(S)—NW477W478, —C(O)—NH—O—W479, —C(O)—NW480-O—W481, —C(S)—NH—O—W482, —C(S)—NW483-O—W484, —C(O)—NH—NH—W485, —C(O)—NH—NW486W487, —C(O)—NW488-NW489W490, —C(S)—NH—NH—W491, —C(S)—NH—NW492W493, —C(S)—NW494-NW495W496, —C(O)—C(O)—O—W497, —C(O)—C(O)—NH$_2$, —C(O)—C(O)—NHW498, —C(O)—C(O)—NW499W500, —C(S)—C(O)—O—W501, —C(O)—C(S)—O—W502, —C(S)—C(S)—O—W503, —C(S)—C(O)—NH$_2$, —C(S)—C(O)—NHW504, —C(S)—C(O)—NW505W506, —C(S)—C(S)—NH$_2$, —C(S)—C(S)—NHW507, —C(S)—C(S)—NW508W509, —C(O)—C(S)—NH$_2$, —C(O)—C(S)—NHW510, —C(O)—C(S)—NW511W512";

wherein W401, W402, W403, W404, W405, W406, W407, W408, W409, W410, W411, W412, W413, W414, W415, W416, W417, W418, W419, W420, W421, W422, W423, W424, W425, W426, W427, W428, W429, W430, W431, W432, W433, W434, W435, W436, W437, W438, W439, W440, W441, W442, W443, W444, W445, W446, W447, W448, W449, W450, W451, W452, W453, W454, W455, W456, W457, W458, W459, W460, W461, W462, W463, W464, W465, W466, W467, W468, W469, W470, W471, W472, W473, W474, W475, W476, W477, W478, W479, W480, W481, W482, W483, W484, W485, W486, W487, W488, W489, W490, W491, W492, W493, W494, W495, W496, W497, W498, W499, W500, W501, W502, W503, W504, W505, W506, W507, W508, W509, W510, W511, W512 are independently from each other selected from the group consisting of:"hydrogen, alkyl, $(C_9$-$C_{30})$alkyl, cycloalkyl, cycloalkylalkyl, heterocyclyl, heterocyclylalkyl, aryl, arylalkyl, heteroaryl, heteroarylalkyl" and wherein alternatively W407, W408 and/or W416, W417 and/or W429, W430 and/or W436, W437 and/or W445, W446 and/or W455, W456 and/or W460, W461 and/or W477, W478 and/or W486, W487 and/or W489, W490 and/or W492, W493 and/or W495, W496 and/or W499, W500 and/or W505, W506 and/or W508, W509 and/or W511, W512 and/or respectively together can also form "heterocyclyl"; wherein optionally above substituents of substituents group (ii) can in turn independently from each other be substituted with at least one substituent, identical or different, selected from the group consisting of:

(iii) "alkyl, $(C_9$-$C_{30})$alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHW601, —NW602W603, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)—W604, —C(O)—O—W605, —C(O)—NH—W606, —C(O)—NW607W608, —O—W609, —O(—W610-O)$_e$—H (e=1, 2, 3, 4, 5), —O(—W611-O)$_f$—W612 (f=1, 2, 3, 4, 5), —OC(O)—W613, —OC(O)—O—W614, —OC(O)—NHW615, —O—C(O)—NW616W617, —OP(O)(OW618)(OW619), —OSi(W620)(W621)(W622), —OS(O$_2$y W623, —NHC(O)—NH$_2$, —NHC(O)—W624, —NW625C(O)—W626, —NH—C(O)—O—W627, —NH—C(O)—NH—W628, —NH—C(O)—NW629W630, —NW631-C(O)—O—W632, —NW633-C(O)—NH—W634, —NW635-C(O)—NW636W637, —NHS(O$_2$)—W638, —NW639S(O$_2$)—W640, —S—W641, —S(O)—W642, —S(O$_2$)—W643, —S(O$_2$)—NH—W644, —S(O$_2$)—NW645W646, —S(O$_2$)O—W647, —P(O)(OW648)(OW649), —Si(W650)(W651)(W652), —C(NH)—NH$_2$, —C(NW653)-NH$_2$, —C(NH)—NHW654, —C(NH)—NW655W656, —C(NW657)-NHW658, —C(NW659)-NW660W661, —NH—C(O)—NH—O—W662, —NH—C(O)—NW663-O—W664, —NW665-C(O)—NW666-O—W667, —N(—C(O)—NH—O—W668)$_2$, —N(—C(O)—NW669-O—W670)$_2$, —N(—C (O)—NH—O—W671)(—C(O)—NW672-O—W673), —C(S)—W674, —C(S)—O—W675, —C(S)—NH—W676, —C(S)—NW677W678, —C(O)—NH—O—W679, —C(O)—NW680-O—W681, —C(S)—NH—O—W682, —C(S)—NW683-O—W684, —C(O)—NH—NH—W685, —C(O)—NH—NW686W687, —C(O)—NW688—NW689W690, —C(S)—NH—NH—W691, —C(S)—NH—NW692W693, —C(S)—NW694-NW695W696, —C(O)—C(O)—O—W697, —C(O)—C(O)—NH$_2$, —C(O)—C(O)—NHW698, —C(O)—C(O)—NW699W700, —C(S)—C(O)—O—W701, —C(O)—C(S)—O—W702, —C(S)—C(S)—O—W703, —C(S)—C(O)—NH$_2$, —C(S)—C(O)—NHW704, —C(S)—C(O)—NW705W706, —C(S)—C(S)—NH$_2$, —C(S)—C(S)—NHW707, —C(S)—C(S)—NW708W709, —C(O)—C(S)—NH$_2$, —C(O)—C(S)—NHW710, —C(O)—C(S)—NW711W712";

wherein W601, W602, W603, W604, W605, W606, W607, W608, W609, W610, W611, W612, W613, W614, W615, W616, W617, W618, W619, W620, W621, W622, W623, W624, W625, W626, W627, W628, W629, W630, W631, W632, W633, W634, W635, W636, W637, W638, W639, W640, W641, W642, W643, W644, W645, W646, W647, W648, W649, W650, W651, W652, W653, W654, W655, W656, W657, W658, W659, W660, W661, W662, W663, W664, W665, W666, W667, W668, W669, W670, W671, W672, W673, W674, W675, W676, W677, W678, W679, W680, W681, W682, W683, W684, W685, W686, W687, W688, W689, W690, W691, W692, W693, W694, W695, W696, W697, W698, W699, W700, W701, W702, W703, W704, W705, W706, W707, W708, W709, W710, W711, W712 are independently from each other selected from the group consisting of:"hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively W607, W608 and/or W616, W617 and/or W629, W630 and/or W636, W637 and/or W645, W646 and/or W655, W656 and/or W660, W661 and/or W677, W678 and/or W686, W687 and/or W689, W690 and/or W692, W693 and/or W695, W696 and/or W699, W700 and/or W705, W706 and/or W708, W709 and/or W711; W712 and/or respectively together can also form "heterocyclyl";

with the first proviso that radical R18 is not selected from the group consisting of:"—O-alkyl, —O—(C$_9$-C$_{30}$)alkyl, —O-aryl, —O-arylalkyl, —O-heteroaryl, —O-heteroarylalkyl, —O-cycloalkyl, —O-cycloalkylalkyl, —O-heterocyclyl, —O-heterocyclylalkyl";

with the second proviso that, if radical R18 independently is selected from the group consisting of:"—NR$_a$R$_b$", with Ra, Rb independently from each other being selected from the group consisting of:"hydrogen, alkyl, (C9-C30)alkyl, aryl, arylalkyl, heteroaryl, heteroarylalkyl, cycloalkyl, cycloalkylalkyl, heterocyclyl, heterocyclylalkyl", radical R1 is not selected from the group consisting of:"heterocyclylalkyl being substituted with =O, where heterocyclyl is 5-membered; alkyl being substituted with heterocyclyl, where heterocyclyl is 5-membered and substituted with =O";

and one of radicals R3, R4 or neither of radicals R3, R4 independently is selected from the group consisting of:
(2) "hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHA1, —NA2A3, —NO$_2$, —OH, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)-A4, —C(O)—O-A5, —C(O)—NH-A6, —C(O)—NA7A8, —O-A9, —O(-A10-O)$_a$—H (a=1, 2, 3, 4, 5), —O(-A11-O)$_b$-A12 (b=1, 2, 3, 4, 5), —OC(O)-A13, —OC(O)—O-A14, —OC(O)—NHA15, —O—C(O)—NA16A17, —OP(O)(OA18)(OA19), —OSi(A20)(A21)(A22), —OS(O$_2$)-A23, —NHC(O)—NH$_2$, —NHC(O)-A24, —NA25C(O)-A26, —NH—C(O)-0-A27, —NH—C(O)—NH-A28, —NH—C(O)—NA29A30, —NA31-C(O)—O-A32, —NA33-C(O)—NH-A34, —NA35-C(O)—NA36A37, —NHS(O$_2$)-A38, —NA39S(O$_2$)-A40, —S-A41, —S(O)-A42, —S(O$_2$)-A43, —S(O$_2$)—NH-A44, —S(O$_2$)NA45A46, —S(O$_2$)O-A47, —P(O)(OA48)(OA49), —Si(A50)(A51)(A52), —C(NH)—NH$_2$, —C(NA53)-NH$_2$, —C(NH)—NHA54, —C(NH)—NA55A56, —C(NA57)-NHA58, —C(NA59)-NA60A61, —NH—C(O)—NH—O-A62, —NH—C(O)—NA63-O-A64, —NA65-C(O)—NA66-O-A67, —N(—C(O)—NH—O-A68)$_2$, —N(—C(O)—NA69-O-A70)$_2$, —N(—C(O)—NH—O-A71)(—C(O)—NA72-O-A73), —C(S)-A74, —C(S)—O-A75, —C(S)—NH-A76, —C(S)—NA77A78, —C(O)—NH—O-A79, —C(O)—NA80-O-A81, —C(S)—NH—O-A82, —C(S)—NA83-O-A84, —C(O)—NH—NH-A85, —C(O)—NH—NA86A87, —C(O)—NA88—NA89A90, —C(S)—NH—NH-A91, —C(S)—NH—NA92A93, —C(S)—NA94—NA95A96, —C(O)—C(O)—O-A97, —C(O)—C(O)—NH$_2$, —C(O)—C(O)—NHA98, —C(O)—C(O)—NA99A100, —C(S)—C(O)—O-A101, —C(O)—C(S)—O-A102, —C(S)—C(S)—O-A103, —C(S)—C(O)—NH$_2$, —C(S)—C(O)—NHA104, —C(S)—C(O)—NA105A106, —C(S)—C(S)—NH$_2$, —C(S)—C(S)—NHA107, —C(S)—C(S)—NA108A109, —C(O)—C(S)—NH$_2$, —C(O)—C(S)—NHA110, —C(O)—C(S)—NA111A112";

wherein A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, A36, A37, A38, A39, A40, A41, A42, A43, A44, A45, A46, A47, A48, A49, A50, A51, A52, A53, A54, A55, A56, A57, A58, A59, A60, A61, A62, A63, A64, A65, A66, A67, A68, A69, A70, A71, A72, A73, A74, A75, A76, A77, A78, A79, A80, A81, A82, A83, A84, A85, A86, A87, A88, A89, A90, A91, A92, A93, A94, A95, A96, A97, A98, A99, A100, A101, A102, A103, A104, A105, A106, A107, A108, A109, A110, A111, A112 are independently from each other selected from the group consisting of:"hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively A7, A8 and/or A16, A17 and/or A29, A30 and/or A36, A37 and/or A45, A46 and/or A55, A56 and/or A60, A61 and/or A77, A78 and/or A86, A87 and/or A89, A90 and/or A92, A93 and/or A95, A96 and/or A99, A100 and/or A105, A106 and/or A108, A109 and/or A111, A112 and/or respectively together can also form "heterocyclyl";

wherein optionally above substituents of substituents group (2)—if not hydrogenn—can in turn independently from each other be substituted with at least one substituent, identical or different, selected from the group consisting of:
(i) "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHA201, —NA202A203, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)-A204, —C(O)—O-A205, —C(O)—NH-A206, —C(O)—NA207A208, —O-A209, —O(-A210-O)$_c$—H (c=1, 2, 3, 4, 5), —O(-A211-O)$_d$-A212 (d=1, 2, 3, 4, 5), —OC(O)-A213, —OC(O)—O-A214, —OC(O)—NHA215, —O—C(O)—NA216A217, —OP(O)(OA218)(OA219), —OSi(A220)(A221)(A222), —OS(O$_2$)-A223, —NHC(O)—NH$_2$, —NHC(O)-A224, —NA225C(O)-A226, —NH—C(O—O-A227, —NH—C(O)—NH-A228, —NH—C(O)—NA229A230, —NA231-C(O—O-A232, —NA233-C(O)—NH-A234, —NA235-C(O)—NA236A237, —NHS(O$_2$)-A238, —NA239S(O$_2$)-A240, —S-A241, —S(O)-A242, —S(O$_2$)-A243, —S(O$_2$)—NH-A244, —S(O$_2$)NA245A246, —S(O$_2$)O-A247, —P(O)(OA248)(OA249), —Si(A250)(A251)(A252), —C(NH)—NH$_2$, —C(NA253)-NH$_2$, —C(NH)—NHA254, —C(NH)—NA255A256, —C(NA257)-NHA258, —C(NA259)-NA260A261, —NH—C(O)—NH—O-A262, —NH—C(O)—NA263-O-A264, —NA265-C(O)—NA266-O-A267, —N(—C(O)—NH—O-A268)$_2$, —N(—C(O)—NA269-O-A270)$_2$, —N(—C(O)—NH—O-A271)(—C(O)—NA272-O-A273), —C(S)-A274, —C(S)—O-A275, —C(S)—NH-A276, —C(S)—NA277A278, —C(O)—NH—O-A279, —C(O)—NA280-O-A281, —C(S)—NH—O-A282, —C(S)—NA283-O-A284, —C(O)—NH—NH-A285, —C(O)—NH—NA286A287, —C(O)—NA288—NA289A290, —C(S)—NH—NH-A291, —C(S)—NH—NA292A293, —C(S)—NA294—NA295A296, —C(O)—C(O)—O-A297, —C(O)—C(O)—NH$_2$, —C(O)—C(O)—NHA298, —C(O)—C(O)—NA299A300, —C(S)—C(O)—O-A301, —C(O)—C(S)—O-A302, —C(S)—C(S)—O-A303, —C(S)—C(O)—NH$_2$, —C(S)—C(O)—NHA304, —C(S)—C(O)—NA305A306, —C(S)—C(S)—NH$_2$, —C(S)—C(S)—NHA307, —C(S)—C(S)—NA308A309, —C(O)—C(S)—NH$_2$, —C(O)—C(S)—NHA310, —C(O)—C(S)—NA311A312";
wherein A201, A202, A203, A204, A205, A206, A207, A208, A209, A210, A211, A212, A213, A214, A215, A216, A217, A218, A219, A220, A221, A222, A223, A224, A225, A226, A227, A228, A229, A230, A231, A232, A233, A234, A235, A236, A237, A238, A239, A240, A241, A242, A243, A244, A245, A246, A247, A248, A249, A250, A251, A252, A253, A254, A255, A256, A257, A258, A259, A260, A261, A262, A263, A264, A265, A266, A267, A268, A269, A270, A271, A272, A273, A274, A275, A276, A277, A278, A279, A280, A281, A282, A283, A284, A285, A286, A287, A288, A289, A290, A291, A292, A293, A294, A295, A296, A297, A298, A299, A300, A301, A302, A303, A304, A305, A306, A307, A308, A309, A310, A311, A312 are independently from each other selected from the group consisting of:"hydrogen, alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl" and wherein alternatively A207, A208 and/or A216, A217 and/or A229, A230 and/or A236, A237 and/or A245, A246 and/or A255, A256 and/or A260, A261 and/or A277, A278 and/or A286, A287 and/or A289, A290 and/or A292, A293 and/or A295, A296 and/or A299, A300 and/or A305, A306 and/or A308, A309 and/or A311, A312 and/or respectively together can also form "heterocyclyl";
wherein optionally above substituents of substituents group (i) can in turn independently from each other be substituted with at least one substituent, identical or different, selected from the group consisting of:
(ii) "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHA401, —NA402A403, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)-A404, —C(O)—O-A405, —C(O)—NH-A406, —C(O)—NA407A408, —O-A409, —O(-A410-O)$_e$—H (e=1, 2, 3, 4, 5), —O(-A411-O)$_f$-A412 (f=1, 2, 3, 4, 5), —OC(O)-A413, —OC(O)—O-A414, —OC(O)—NHA415, —O—C(O)—NA416A417, —OP(O)(OA418)(OA419), —OSi(A420)(A421)(A422), —OS(O$_2$)-A423, —NHC(O)—NH$_2$, —NHC(O)-A424, —NA425C(O)-A426, —NH—C(O)—O-A427, —NH—C(O)—NH-A428, —NH—C(O)—NA429A430, —NA431-C(O)—O-A432, —NA433-C(O)—NH-A434, —NA435-C(O)—NA436A437, —NHS(O$_2$)-A438, —NA439S(O$_2$)-A440, —S-A441, —S(O)-A442, —S(O$_2$)-A443, —S(O$_2$)—NH-A444, —S(O$_2$)NA445A446, —S(O$_2$)O-A447, —P(O)(OA448)(OA449), —Si(A450)(A451)(A452), —C(NH)—NH$_2$, —C(NA453)-NH$_2$, —C(NH)—NHA454, —C(NH)—NA455A456, —C(NA457)-NHA458, —C(NA459)-NA460A461, —NH—C(O)—NH—O-A462, —NH—C(O)—NA463-O-A464, —NA465-C(O)—NA466-O-A467, —N(—C(O)—NH—O-A468)$_2$, —N(—C(O)—NA469-O-A470)$_2$, —N(—C(O)—NH—O-A471)(—C(O)—NA472-O-A473), —C(S)-A474, —C(S)—O-A475, —C(S)—NH-A476, —C(S)—NA477A478, —C(O)—NH—O-A479, —C(O)—NA480-O-A481, —C(S)—NH—O-A482, —C(S)—NA483-O-A484, —C(O)—NH—NH-A485, —C(O)—NH—NA486A487, —C(O)—NA488—NA489A490, —C(S)—NH—NH-A491, —C(S)—NH—NA492A493, —C(S)—NA494—NA495A496, —C(O)—C(O)—O-A497, —C(O)—C(O)—NH$_2$, —C(O)—C(O)—NHA498, —C(O)—C(O)—NA499A500, —C(S)—C(O)—O-A501, —C(O)—C(S)—O-A502, —C(S)—C(S)—O-A503, —C(S)—C(O)—NH$_2$, —C(S)—C(O)—NHA504, —C(S)—C(O)—NA505A506, —C(S)—C(S)—NH$_2$, —C(S)—C(S)—NHA507, —C(S)—C(S)—NA508A509, —C(O)—C(S)—NH$_2$, —C(O)—C(S)—NHA510, —C(O)—C(S)—NA511A512";
wherein A401, A402, A403, A404, A405, A406, A407, A408, A409, A410, A411, A412, A413, A414, A415, A416, A417, A418, A419, A420, A421, A422, A423, A424, A425, A426, A427, A428, A429, A430, A431, A432, A433, A434, A435, A436, A437, A438, A439, A440, A441, A442, A443, A444, A445, A446, A447, A448, A449, A450, A451, A452, A453, A454, A455, A456, A457, A458, A459, A460, A461, A462, A463, A464, A465, A466, A467, A468, A469, A470, A471, A472, A473, A474, A475, A476, A477, A478, A479, A480, A481, A482, A483, A484, A485, A486, A487, A488, A489, A490, A491, A492, A493, A494, A495, A496, A497, A498, A499, A500, A501, A502, A503, A504, A505, A506, A507, A508, A509, A510, A511, A512 are independently from each other selected from the group consisting of:"hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and wherein alternatively A407, A408 and/or A416, A417 and/or A429, A430 and/or A436, A437 and/or A445, A446 and/or A455, A456 and/or A460, A461 and/or A477, A478 and/or A486, A487 and/or A489, A490 and/or A492, A493 and/or A495, A496 and/or A499, A500 and/or A505, A506 and/or A508, A509 and/or A511, A512 and/or respectively together can also form "heterocyclyl"; wherein optionally above substituents of substituents group (ii) can in turn independently from each other be substituted with at least one substituent, identical or different, selected from the group consisting of:

(iii) "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —$CF_3$, —$N_3$, —$NH_2$, —NHA601, —NA602A603, —$NO_2$, —OH, =O, —$OCF_3$, —$OCHF_2$, —SH, —O—$SO_3$H, —OP(O)(OH)$_2$, —CHO, —COOH, —C(O)—$NH_2$, —$SO_3$H, —P(O)(OH)$_2$, —C(O)-A604, —C(O)—O-A605, —C(O)—NH-A606, —C(O)—NA607A608, —O-A609, —O(-A610-O)$_e$—H (e=1, 2, 3, 4, 5), —O(-A611-O)$_f$-A612 (f=1, 2, 3, 4, 5), —OC(O)-A613, —OC(O)—O-A614, —OC(O)—NHA615, —O—C(O)—NA616A617, —OP(O)(OA618)(OA619), —OSi(A620)(A621)(A622), —OS($O_2$)-A623, —NHC(O)—$NH_2$, —NHC(O)-A624, —NA625C(O)-A626, —NH—C(O)—O-A627, —NH—C(O)—NH-A628, —NH—C(O)—NA629A630, —NA631-C(O)—O-A632, —NA633-C(O)—NH-A634, —NA635-C(O)—NA636A637, —NHS($O_2$)-A638, —NA639S($O_2$)-A640, —S-A641, —S(O-A642, —S($O_2$)-A643, —S($O_2$)—NH-A644, —S($O_2$)NA645A646, —S($O_2$)O-A647, —P(O)(OA648)(OA649), —Si(A650)(A651)(A652), —C(NH)—$NH_2$, —C(NA653)-$NH_2$, —C(NH)—NHA654, —C(NH)—NA655A656, —C(NA657)-NHA658, —C(NA659)-NA660A661, —NH—C(O)—NH—O-A662, —NH—C(O)—NA663-O-A664, —NA665-C(O)—NA666-O-A667, —N(—C(O)—NH—O-A668)$_2$, —N(—C(O)—NA669-O-A670)$_2$, —N(—C(O)—NH—O-A671) (—C(O)—NA672-O-A673), —C(S)-A674, —C(S)—O-A675, —C(S)—NH-A676, —C(S)—NA677A678, —C(O)—NH—O-A679, —C(O)—NA680-O-A681, —C(S)—NH—O-A682, —C(S)—NA683-O-A684, —C(O)—NH—NH-A685, —C(O)—NH—NA686A687, —C(O)—NA688—NA689A690, —C(S)—NH—NH-A691, —C(S)—NH—NA692A693, —C(S)—NA694—NA695A696, —C(O)—C(O)—O-A697, —C(O)—C(O)—$NH_2$, —C(O)—C(O)—NHA698, —C(O)—C(O)—NA699A700, —C(S)—C(O)—O-A701, —C(S)—C(O)—O-A702, —C(S)—C(S)—O-A703, —C(S)—C(O)—$NH_2$, —C(S)—C(O)—NHA704, —C(S)—C(O)—NA705A706, —C(S)—C(S)—$NH_2$, —C(S)—C(S)—NHA707, —C(S)—C(S)—NA708A709, —C(O)—C(S)—$NH_2$, —C(O)—C(S)—NHA710, —C(O)—C(S)—NA711A712";

wherein A601, A602, A603, A604, A605, A606, A607, A608, A609, A610, A611, A612, A613, A614, A615, A616, A617, A618, A619, A620, A621, A622, A623, A624, A625, A626, A627, A628, A629, A630, A631, A632, A633, A634, A635, A636, A637, A638, A639, A640, A641, A642, A643, A644, A645, A646, A647, A648, A649, A650, A651, A652, A653, A654, A655, A656, A657, A658, A659, A660, A661, A662, A663, A664, A665, A666, A667, A668, A669, A670, A671, A672, A673, A674, A675, A676, A677, A678, A679, A680, A681, A682, A683, A684, A685, A686, A687, A688, A689, A690, A691, A692, A693, A694, A695, A696, A697, A698, A699, A700, A701, A702, A703, A704, A705, A706, A707, A708, A709, A710, A711, A712 are independently from each other selected from the group consisting of:"hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and wherein alternatively A607, A608 and/or A616, A617 and/or A629, A630 and/or A636, A637 and/or A645, A646 and/or A655, A656 and/or A660, A661 and/or A677, A678 and/or A686, A687 and/or A689, A690 and/or A692, A693 and/or A695, A696 and/or A699, A700 and/or A705, A706 and/or A708, A709 and/or A711, A712 and/or respectively together can also form "heterocyclyl";

and radicals R1, R2, R5 independently from each other are selected from the group consisting of:

(3) "hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —$CF_3$, —$N_3$, —$NH_2$, —NHB1, —NB2B3, —$NO_2$, —OH, —$OCF_3$, —$OCHF_2$, —SH, —O—$SO_3$H, —OP(O)(OH)$_2$, —CHO, —COOH, —C(O)—$NH_2$, —$SO_3$H, —P(O)(OH)$_2$, —C(O)—B4, —C(O)—O—B5, —C(O)—NH—B6, —C(O)—NB7B8, —O—B9, —O(—B10-O)$_a$—H (a=1, 2, 3, 4, 5), —O(—B11-O)$_b$—B12 (b=1, 2, 3, 4, 5), —OC(O)—B13, —OC(O)—O—B14, —OC(O)—NHB15, —O—C(O)—NB16B17, —OP(O)(OB18)(OB19), —OSi(B20)(B21)(B22), —OS($O_2$)—B23, —NHC(O)—$NH_2$, —NHC(O)—B24, —NB25C(O)—B26, —NH—C(O)—O—B27, —NH—C(O)—NH—B28, —NH—C(O)—NB29B30, —NB31-C(O)—O—B32, —NB33-C(O)—NH—B34, —NB35-C(O)—NB36B37, —NHS($O_2$)—B38, —NB39S($O_2$)—B40, —S—B41, —S(O)—B42, —S($O_2$)—B43, —S($O_2$)—NH—B44, —S($O_2$)—NB45B46, —S($O_2$)O—B47, —P(O)(OB48)(OB49), —Si(B50)(B51)(B52), —C(NH)—$NH_2$, —C(NB53)-$NH_2$, —C(NH)—NHB54, —C(NH)—NB55B56, —C(NB57)-NHB58, —C(NB59)-NB60B61, —NH—C(O)—NH—O—B62, —NH—C(O)—NB63-O—B64, —NB65-C(O)—NB66-O—B67, —N(—C(O)—NH—O—B68)$_2$, —N(—C(O)—NB69-O—B70)$_2$, —N(—C(O)—NH—O—B71)(—C(O)—NB72-O—B73), —C(S)—B74, —C(S)—O—B75, —C(S)—NH—B76, —C(S)—NB77B78, —C(O)—NH—O—B79, —C(O)—NB80-O—B81, —C(S)—NH—O—B82, —C(S)—NB83-O—B84, —C(O)—NH—NH—B85, —C(O)—NH—NB86B87, —C(O)—NB88-NB89B90, —C(S)—NH—NH—B91, —C(S)—NH—NB92B93, —C(S)—NB94-NB95B96, —C(O)—C(O)—O—B97, —C(O)—C(O)—$NH_2$, —C(O)—C(O)—NHB98, —C(O)—C(O)—NB99B100, —C(S)—C(O)—O—B101, —C(O)—C(S)—O—B102, —C(S)—C(S)—O—B103, —C(S)—C(O)—NH₂, —C(S)—C(O)—NHB104, —C(S)—C(O)—NB105B106, —C(S)—C(S)—NH₂, —C(S)—C(S)—NHB107, —C(S)—C(S)—NB108B109, —C(O)—C(S)—NH₂, —C(O)—C(S)—NHB110, —C(O)—C(S)—NB111B112";

wherein B1, B2, B3, B4, B5, B6, B7, B8, B9, B10, B11, B12, B13, B14, B15, B16, B17, B18, B19, B20, B21, B22, B23, B24, B25, B26, B27, B28, B29, B30, B31, B32, B33, B34, B35, B36, B37, B38, B39, B40, B41, B42, B43, B44, B45, B46, B47, B48, B49, B50, B51, B52, B53, B54, B55, B56, B57, B58, B59, B60, B61, B62, B63, B64, B65, B66, B67, B68, B69, B70, B71, B72, B73, B74, B75, B76, B77, B78, B79, B80, B81, B82, B83, B84, B85, B86, B87, B88, B89, B90, B91, B92, B93, B94, B95, B96, B97, B98, B99, B100, B101, B102, B103, B104, B105, B106, B107, B108, B109, B110, B11, B112 are independently from each other selected from the group consisting of:"hydrogen, alkyl, (C₉-C₃₀)alkyl, cycloalkyl, cycloalkylalkyl, heterocyclyl, heterocyclylalkyl, aryl, arylalkyl, heteroaryl, heteroarylalkyl" and wherein alternatively B2, B3 and/or B7, B8 and/or B16, B17 and/or B29, B30 and/or B36, B37 and/or B45, B46 and/or B55, B56 and/or B60, B61 and/or B77, B78 and/or B86, B87 and/or B89, B90 and/or B92, B93 and/or B95, B96 and/or B99, B100 and/or B105, B106 and/or B108, B109 and/or B111, B112 and/or respectively together can also form "heterocyclyl";

wherein optionally above substituents of substituents group (3)—if not hydrogen—can in turn independently from each other be substituted with at least one substituent, identical or different, selected from the group consisting of:

(i) "alkyl, (C₉-C₃₀)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF₃, —N₃, —NH₂, —NHB201, —NB202B203, —NO₂, —OH, =O, —OCF₃, —OCHF₂, —SH, —O—SO₃H, —OP(O)(OH)₂, —CHO, —COOH, —C(O)—NH₂, —SO₃H, —P(O)(OH)₂, —C(O)—B204, —C(O)—O—B205, —C(O)—NH—B206, —C(O)—NB207B208, —O—B209, —O(—B210-O)$_c$—H (c=1, 2, 3, 4, 5), —O(—B211-O)$_d$—B212 (d=1, 2, 3, 4, 5), —OC(O)—B213, —OC(O)—O—B214, —OC(O)—NHB215, —O—NB216B217, —OP(O)(OB218)(OB219), —OSi(B220)(B221)(B222), —OS(O₂)—B223, —NHC(O)—NH₂, —NHC(O)—B224, —NB225C(O)—B226, —NH—C(O)—O—B227, —NH—C(O)—NH—B228, —NH—C(O)—NB229B230, —NB231-C(O)—O—B232, —NB233-C(O)—NH—B234, —NB235-C(O)—NB236B237, —NHS(O₂)—B238, —NB239S(O₂)—B240, —S—B241, —S(O)—B242, —S(O₂)—B243, —S(O₂)NH—B244, —S(O₂)—NB245B246, —S(O₂)O—B247, —P(O)(OB248)(OB249), —Si(B250)(B251)(B252), —C(NH)—NH₂, —C(NB253)-NH₂, —C(NH)—NHB254, —C(NH)—NB255B256, —C(NB257)-NHB258, —C(NB259)-NB260B261, —NH—C(O)—NH—O—B262, —NH—C(O)—NB263-O—B264, —NB265-C(O)—NB266-O—B267, —N(—C(O)—NH—O—B268)₂, —N(—C(O)—NB269-O—B270)₂, —N(—C(O)—NH—O—B271)(—C(O)—NB272-O—B273), —C(S)—B274, —C(S)—O—B275, —C(S)—NH—B276, —C(S)—NB277B278, —C(O)—NH—O—B279,
—C(O)—NB280-O—B281, —C(S)—NH—O—B282, —C(S) NB283-O—B284, —C(O)—NH—NH—B285, —C(O)—NH—NB286B287, —C(O)—NB288-NB289B290, —C(S)—NH—NH—B291, —C(S)—NH—NB292B293, —C(S)—NB294—N B295B296, —C(O)—C(O)—O—B297, —C(O)—C(O)—NH₂, —C(O)—C(O)—NHB298, —C(O)—C(O)—NB299B300, —C(S)—C(O)—O—B301, —C(O)—C(S)—O—B302, —C(S)—C(S)—O—B303, —C(S)—C(O)—NH₂, —C(S)—C(O)—NHB304, —C(S)—C(O)—NB305B306, —C(S)—C(S)—NH₂, —C(S)—C(S)—NHB307, —C(S)—C(S)—NB308B309, —C(O)—C(S)—NH₂, —C(O)—C(S)—NHB310, —C(O)—C(S)—NB311B312";

wherein B201, B202, B203, B204, B205, B206, B207, B208, B209, B210, B211, B212, B213, B214, B215, B216, B217, B218, B219, B220, B221, B222, B223, B224, B225, B226, B227, B228, B229, B230, B231, B232, B233, B234, B235, B236, B237, B238, B239, B240, B241, B242, B243, B244, B245, B246, B247, B248, B249, B250, B251, B252, B253, B254, B255, B256, B257, B258, B259, B260, B261, B262, B263, B264, B265, B266, B267, B268, B269, B270, B271, B272, B273, B274, B275, B276, B277, B278, B279, B280, B281, B282, B283, B284, B285, B286, B287, B288, B289, B290, B291, B292, B293, B294, B295, B296, B297, B298, B299, B300, B301, B302, B303, B304, B305, B306, B307, B308, B309, B310, B311, B312 are independently from each other selected from the group consisting of:"hydrogen, alkyl, (C₉-C₃₀)alkyl, cycloalkyl, cycloalkylalkyl, heterocyclyl, heterocyclylalkyl, aryl, arylalkyl, heteroaryl, heteroarylalkyl" and wherein alternatively B207, B208 and/or B216, B217 and/or B229, B230 and/or B236, B237 and/or B245, B246 and/or B255, B256 and/or B260, B261 and/or B277, B278 and/or B286, B287 and/or B289, B290 and/or B292, B293 and/or B295, B296 and/or B299, B300 and/or B305, B306 and/or B308, B309 and/or B311, B312 and/or respectively together can also form "heterocyclyl";

wherein optionally above substituents of substituents group (i) can in turn independently from each other be substituted with at least one substituent, identical or different, selected from the group consisting of:

(ii) "alkyl, (C₉-C₃₀)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF₃, —N₃, —NH₂, —NHB401, —NB402B403, —NO₂, —OH, =O, —OCF₃, —OCHF₂, —SH, —O—SO₃H, —OP(O)(OH)₂, —CHO, —COOH, —C(O)—NH₂, —SO₃H, —P(O)(OH)₂, —C(O)—B404, —C(O)—O—B405, —C(O)—NH—B406, —C(O)—NB407B408, —O—B409, —O(—B410-O)$_e$—H (e=1, 2, 3, 4, 5), —O(—B411-O)$_f$—B412 (f=1, 2, 3, 4, 5), —OC(O)—B413, —OC(O)—O—B414, —OC(O)—NHB415, —O—C(O)—NB416B417, —OP(O)(OB418)(OB419), —OSi(B420)(B421)(B422), —OS(O₂)—B423, —NHC(O)—NH₂, —NHC(O)—B424, —NB425C(O)—B426, —NH—C(O)—O—B427, —NH—C(O)—NH—B428, —NH—C(O)—NB429B430, —NB431-C(O)—O—B432, —NB433-C(O)—NH—B434, —NB435-C(O)—NB436B437, —NHS(O₂)—B438, —NB439S(O₂)—B440, —S—B441, —S(O)—B442, —S(O₂)—B443, —S(O₂)—NH—B444, —S(O₂)—NB445B446, —S(O₂)O—B447, —P(O)(OB448)(OB449), —Si(B450)(B451)(B452), —C(NH)—NH$_2$, —C(NB453)-NH$_2$, —C(NH)—NHB454, —C(NH)—NB455B456, —C(NB457)-NHB458, —C(NB459)—NB460B461, —NH—C(O)—NH—O—B462, —NH—C(O)—NB463-O—B464, —NB465-C(O)—NB466-O—B467, —N(—C(O)—NH—O—B468)$_2$, —N(—C(O)—NB469-O—B470)$_2$, —N(—C(O)—NH—O—B471)(—C(O)—NB472-O—B473), —C(S)—B474, —C(S)—O—B475, —C(S)—NH—B476, —C(S)—NB477B478, —C(O)—NH—O—B479, —C(O)—NB480-O—B481, —C(S)—NH—O—B482, —C(S)—NB483-O—B484, —C(O)—NH—NH—B485, —C(O)—NH—NB486B487, —C(O)—NB488-NB489B490, —C(S)—NH—NH—B491, —C(S)—NH—NB492B493, —C(S)—NB494-NB495B496, —C(O)—C(O)—O—B497, —C(O)—C(O)—NH$_2$, —C(O)—C(O)—NHB498, —C(O)—C(O)—NB499B500, —C(S)—C(O)—O—B501, —C(O)—C(S)—O—B502, —C(S)—C(S)—O—B503, —C(S)—C(O)—NH$_2$, —C(S)—C(O)—NHB504, —C(S)—C(O)—NB505B506, —C(S)—C(S)—NH$_2$, —C(S)—C(S)—NHB507, —C(S)—C(S)—NB508B509, —C(O)—C(S)—NH$_2$, —C(O)—C(S)—NHB510, —C(O)—C(S)—NB511B512";

wherein B401, B402, B403, B404, B405, B406, B407, B408, B409, B410, B411, B412, B413, B414, B415, B416, B417, B418, B419, B420, B421, B422, B423, B424, B425, B426, B427, B428, B429, B430, B431, B432, B433, B434, B435, B436, B437, B438, B439, B440, B441, B442, B443, B444, B445, B446, B447, B448, B449, B450, B451, B452, B453, B454, B455, B456, B457, B458, B459, B460, B461, B462, B463, B464, B465, B466, B467, B468, B469, B470, B471, B472, B473, B474, B475, B476, B477, B478, B479, B480, B481, B482, B483, B484, B485, B486, B487, B488, B489, B490, B491, B492, B493, B494, B495, B496, B497, B498, B499, B500, B501, B502, B503, B504, B505, B506, B507, B508, B509, B510, B511, B512 are independently from each other selected from the group consisting of:"hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively B407, B408 and/or B416, B417 and/or B429, B430 and/or B436, B437 and/or B445, B446 and/or B455, B456 and/or B460, B461 and/or B477, B478 and/or B486, B487 and/or B489, B490 and/or B492, B493 and/or B495, B496 and/or B499, B500 and/or B505, B506 and/or B508, B509 and/or B511, B512 and/or respectively together can also form "heterocyclyl";

wherein optionally above substituents of substituents group (ii) can in turn independently from each other be substituted with at least one substituent, identical or different, selected from the group consisting of:

(iii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHB601, —NB602B603, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —C(O)—B604, —C(O)—O—B605, —C(O)—NH—B606, —C(O)—NB607B608, —O—B609, —O(—B610-O)$_e$—H (e=1, 2, 3, 4, 5), —O(—B611-O)$_f$—B612 (f=1, 2, 3, 4, 5), —OC(O)—B613, —OC(O)—O—B614, —OC(O)—NHB615, —O—C(O)—NB616B617, —OP(O)(OB618)(OB619), —OSi(B620)(B621)(B622), —OS(O$_2$)—B623, —NHC(O)—NH$_2$, —NHC(O)—B624, —NB625C(O)—B626, —NH—C(O)—O—B627, —NH—C(O)—NH—B628, —NH—C(O)—NB629B630, —NB631-C(O)—O—B632, —NB633-C(O)—NH—B634, —NB635-C(O)—NB636B637, —NHS(O$_2$)—B638, —NB639S(O$_2$)—B640, —S—B641, —S(O)—B642, —S(O$_2$)—B643, —S(O$_2$)—NH—B644, —S(O$_2$)—NB645B646, —S(O$_2$)O—B647, —P(O)(OB648)(OB649), —Si(B650)(B651)(B652), —C(NH)—NH$_2$, —C(NB653)-NH$_2$, —C(NH)—NHB654, —C(NH)—NB655B656, —C(NB657)-NHB658, —C(NB659)-NB660B661, —NH—C(O)—NH—O—B662, —NH—C(O)—NB663-O—B664, —NB665-C(O)—NB666-O—B667, —N(—C(O)—NH—O—B668)$_2$, —N(—C(O)—NB669-O—B670)$_2$, —N(—C(O)—NH—O—B671)(—C(O)—NB672-O—B673), —C(S)—B674, —C(S)—O—B675, —C(S)—NH—B676, —C(S)—NB677B678, —C(O)—NH—O—B679, —C(O)—NB680-O—B681, —C(S)—NH—O—B682, —C(S)—NB683-O—B684, —C(O)—NH—NH—B685, —C(O)—NH—NB686B687, —C(O)—NB688-NB689B690, —C(S)—NH—NH—B691, —C(S)—NH—NB692B693, —C(S)—NB694-NB695B696, —C(O)—C(O)—O—B697, —C(O)—C(O)—NH$_2$, —C(O)—C(O)—NHB698, —C(O)—C(O)—NB699B700, —C(S)—C(O)—O—B701, —C(O)—C(S)—O—B702, —C(S)—C(S)—O—B703, —C(S)—C(O)—NH$_2$, —C(S)—C(O)—NHB704, —C(S)—C(O)—NB705B706, —C(S)—C(S)—NH$_2$, —C(S)—C(S)—NHB707, —C(S)—C(S)—NB708B709, —C(O)—C(S)—NH$_2$, —C(O)—C(S)—NHB710, —C(O)—C(S)—NB711B712";

wherein B601, B602, B603, B604, B605, B606, B607, B608, B609, B610, B611, B612, B613, B614, B615, B616, B617, B618, B619, B620, B621, B622, B623, B624, B625, B626, B627, B628, B629, B630, B631, B632, B633, B634, B635, B636, B637, B638, B639, B640, B641, B642, B643, B644, B645, B646, B647, B648, B649, B650, B651, B652, B653, B654, B655, B656, B657, B658, B659, B660, B661, B662, B663, B664, B665, B666, B667, B668, B669, B670, B671, B672, B673, B674, B675, B676, B677, B678, B679, B680, B681, B682, B683, B684, B685, B686, B687, B688, B689, B690, B691, B692, B693, B694, B695, B696, B697, B698, B699, B700, B701, B702, B703, B704, B705, B706, B707, B708, B709, B710, B711, B712 are independently from each other selected from the group consisting of:"hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively B607, B608 and/or B616, B617 and/or B629, B630 and/or B636, B637 and/or B645, B646 and/or B655, B656 and/or B660, B661 and/or B677, B678 and/or B686, B687 and/or B689, B690 and/or B692, B693 and/or B695, B696 and/or B699, B700 and/or B705, B706 and/or B708, B709 and/or B711, B712 and/or respectively together can also form "heterocyclyl".

In order to avoid ambiguities, the cases (1)(a) to (d) detailed above for the general formula (I) are to establish novelty over the prior art as follows:novelty is established by the fact that at least one of radicals R3, R4 must be one of the substituents as illustrated under (1) (a), (b), (c) and (d), whereas the other one of radicals R3, R4 can be either one of the substituents as illustrated under (1) (a), (b), (c) and (d) or it can be one of the substituents as illustrated under (2). Radicals R1, R2 and R5 can in all cases be one of the substituents as illustrated under (3).

In a preferred embodiment, pyrido[2,3-b]pyrazine derivatives according to above general formula (I) are provided, wherein:

radical R1 independently is selected from the group consisting of:
(i) "hydrogen, alkyl, (C9-C30)alkyl, cycloalkyl, cycloalkylalkyl, aryl, arylalkyl, heteroaryl, heteroarylalkyl, heterocyclyl, heterocyclylalkyl, —NH-alkyl, —NH—(C9-C30)alkyl, —NH-cycloalkyl, —NH-cycloalkylalkyl, —NH-aryl, —NH-arylalkyl, —NH-heteroaryl, —NH-heteroarylalkyl, —NH-heterocyclyl, —NH-heterocyclylalkyl";

where above substituents of substituents group (i)—if not hydrogen or nitrogen—may, optionally, additionally be substituted with at least one substituent selected from the group consisting of:"—F, —Cl, —Br, —I, —CN, —CF$_3$, —N$_3$, —NH$_2$, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —NHC(O)—NH$_2$, —C(NH)—NH$_2$, —C(O)—C(O)—NH$_2$, —C(O)—CF$_3$, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, alkyl-OH, alkyl-CN, alkyl-COOH, alkyl-P(O)(O-alkyl)$_2$, cycloalkyl-CN, aryl-OH, aryl(—OH)(-alkyl), —C(O)alkyl, —C(O)heterocyclyl, —C(O)—O-alkyl, —C(O)—O-heterocyclyl, —P(O)(O-alkyl-O—C(O)alkyl)$_2$, —OP(O)(O-alkyl)$_2$, —OS(O$_2$)alkyl, —S-alkyl, —O-alkyl, —O-aryl, —O-arylalkyl, —O-heterocyclyl, —O-heterocyclylalkyl, —O-arylalkyl-(O-alkyl)$_2$, —O-alkyl-O-alkyl, —O-alkyl-N(alkyl)$_2$, —O-alkyl-halogen, —O-alkyl-Cl, —O-alkyl-F, —O-alkyl-Br, —O-alkyl-1, —OC(O)alkyl, —OC(O)—N(alkyl)$_2$, —OC(O)—NH-alkyl, —OC(O)—(C$_9$-C$_{30}$)alkyl, —OC(O)—O-alkyl, —OC(O)—O-alkyl-O-alkyl, —OC(O)—O-aryl, —N(alkyl)$_2$, —N(aryl)$_2$, —NHC(O)alkyl, —NHC(O)alkyl-NH-alkyl, —NHC(O)alkyl-C(O)—O-alkyl, —NHC(O)—O-alkyl, —NHC(O)—O-alkyl-O-alkyl, —NHC(O)—O-alkyl-O-alkyl-O-alkyl, —NHC(O)—NH-alkyl, —NHC(O)—NH-aryl, —NHC(O)—NH-heteroaryl, —NHC(O)—NH-heterocyclyl, —NHC(O)—NH-heterocyclylalkyl, —NHC(O)—NH-alkyl-halogen, —NHC(O)—NH-alkyl-Cl, —NHC(O)—N(alkyl)$_2$, —NHS(O$_2$)alkyl";

radical R2 independently is "hydrogen";

radical R3 independently is selected from the group consisting of:
(i) "—NH—C(O)—NH—C(O)—O-alkyl, —NH—C(O)—NH—C(OO—(C9-C30)alkyl, —NH—C(O)—NH—C(O)—O-cycloalkyl, —NH—C(O)—NH—C(O)—O-cycloalkylalkyl, —NH—C(O)—NH—C(O)—O-aryl, —NH—C(O)—NH—C(O)—O-arylalkyl, —NH—C(O)—NH—C(O)—O-heteroaryl, —NH—C(O)—NH—C(O)—O-heteroarylalkyl, —NH—C(O)—NH—C(O)—O-heterocyclyl, —NH—C(O)—NH—C(O)—O-heterocyclylalkyl —NH—C(S)—NH-alkyl, —NH—C(S)—NH—(C9-C30)alkyl, —NH—C(S)—NH-cycloalkyl, —NH—C(S)—NH-cycloalkylalkyl, —NH—C(S)—NH-aryl, —NH—C(S)—NH-arylalkyl, —NH—C(S)—NH-heteroaryl, —NH—C(S)—NH-heteroarylalkyl, —NH—C(S)—NH-heterocyclyl, —NH—C(S)—NH-heterocyclylalkyl, —NH—C(=NH)alkyl, —NH—C(=NH)—(C9-C30)alkyl, —NH—C(=NH)cycloalkyl, —NH—C(=NH)cycloalkylalkyl, —NH—C(=NH)aryl, —NH—C(=NH)arylalkyl, —NH—C(=NH)heteroaryl, —NH—C(=NH)heteroarylalkyl, —NH—C(=NH)heterocyclyl, —NH—C(=NH) heterocyclylalkyl, —NH—C(O)—C(O)alkyl, —NH—C(O)—C(O)—(C9-C30)alkyl, —NH—C(O)—C(O)-cycloalkyl, —NH—C(O)—C(O)cycloalkylalkyl, —NH—C(O)—C(O) aryl, —NH—C(O)—C(O)arylalkyl, —NH—C(O)—C(O)heteroaryl, —NH—C(O)—C(O) heteroarylalkyl, —NH—C(O)—C(O)heterocyclyl, —NH—C(O)—C(O) heterocyclylalkyl"

where above substituents of substituents group (i)—if not hydrogen or nitrogen—may, optionally, additionally be substituted with at least one substituent selected from the group consisting of:"—F, —Cl, —Br, —I, —CN, —CF$_3$, —N$_3$, —NH$_2$, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —NHC(OyNH$_2$, —C(NH)—NH$_2$, —C(O)—C(O)—NH$_2$, —C(O)—CF$_3$, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, alkyl-OH, alkyl-CN, alkyl-COOH, alkyl-P(O)(O-alkyl)$_2$, cycloalkyl-CN, aryl-OH, aryl(—OH)(-alkyl), —C(O)alkyl, —C(O)heterocyclyl, —C(O)—O-alkyl, —C(O)—O-heterocyclyl, —P(O)(O-alkyl-O—C(O)alkyl)$_2$, —OP(O)(O-alkyl)$_2$, —OS(O$_2$)-alkyl, —S-alkyl, —O-alkyl, —O-aryl, —O-arylalkyl, —O-heterocyclyl, —O-heterocyclylalkyl, —O-arylalkyl-(O-alkyl)$_2$, —O-alkyl-O-alkyl, —O-alkyl-N(alkyl)$_2$, —O-alkyl-halogen, —O-alkyl-Cl, —O-alkyl-F, —O-alkyl-Br, —O-alkyl-1, —OC(O)alkyl, —OC(O)—N(alkyl)$_2$, —OC(O)—NH-alkyl, —OC(O)—(C$_9$-C$_{30}$)alkyl, —OC(O)—O-alkyl, —OC(O)—O-alkyl-O-alkyl, —OC(O)—O-aryl, —N(alkyl)$_2$, —N(aryl)$_2$, —NHC(O)alkyl, —NHC(O)alkyl-NH-alkyl, —NHC(O)alkyl-C(O)—O-alkyl, —NHC(O)—O-alkyl, —NHC(O)—O-alkyl-O-alkyl, —NHC(O)—O-alkyl-O-alkyl-O-alkyl, —NHC(O)—NH-alkyl, —NHC(O)—NH-aryl, —NHC(O)—NH-heteroaryl, —NHC(O)—NH-heterocyclyl, —NHC(O)—NH-heterocyclylalkyl, —NHC(O)—NH-alkyl-halogen, —NHC(O)—NH-alkyl-Cl, —NHC(O)—N(alkyl)$_2$, —NHS(O$_2$)alkyl";

radical R4 independently is selected from the group consisting of:
(i) "hydrogen, alkyl, (C9-C30)alkyl, cycloalkyl, cycloalkylalkyl, aryl, arylalkyl, heteroaryl, heteroarylalkyl, heterocyclyl, heterocyclylalkyl, —NH-alkyl, —NH—(C9-C30)alkyl, —NH-cycloalkyl, —NH-cycloalkylalkyl, —NH-aryl, —NH-arylalkyl, —NH-heteroaryl, —NH-heteroarylalkyl, —NH-heterocyclyl, —NH-heterocyclylalkyl";

where above substituents of substituents group (i)—if not hydrogen or nitrogen—may, optionally, additionally be substituted with at least one substituent selected from the group consisting of:"—F, —Cl, —Br, —I, —CN, —CF$_3$, —N$_3$, —NH$_2$, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —NHC(O)—NH$_2$, —C(NH)—NH$_2$, —C(O)—C(O)—NH$_2$, —C(O)—CF$_3$, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, alkyl- OH, alkyl-CN, alkyl-COOH, alkyl-P(O)(O-alkyl)$_2$, cycloalkyl-CN, aryl-OH, aryl(—OH)(-alkyl), —C(O)-alkyl, —C(O)heterocyclyl, —C(O)—O-alkyl, —C(O)—O-heterocyclyl, —P(O)(O-alkyl-O—C(O) alkyl)$_2$, —OP(O)(O-alkyl)$_2$, —OS(O$_2$)alkyl, —S-alkyl, —O-alkyl, —O-aryl, —O-arylalkyl, —O-heterocyclyl, —O-heterocyclylalkyl, —O-arylalkyl-(O-alkyl)$_2$, —O-alkyl-O-alkyl, —O-alkyl-N(alkyl)$_2$, —O-alkyl-halogen, —O-alkyl-Cl, —O-alkyl-F, —O-alkyl-Br, —O-alkyl-1, —OC(O)alkyl, —OC(O)—N(alkyl)$_2$, —OC(O)—NH-alkyl, —OC(O)(C$_9$-C$_{30}$)alkyl, —OC(O)—O-alkyl, —OC(O)—O-alkyl-O-alkyl, —OC(O)—O-aryl, —N(alkyl)$_2$, —N(aryl)$_2$, —NHC(O)alkyl, —NHC(O)-alkyl-NH-alkyl, —NHC(O)alkyl-C(O)—O-alkyl, —NHC(O)—O-alkyl, —NHC(O)—O-alkyl-O-alkyl, —NHC(O)—O-alkyl-O-alkyl-O-alkyl-O-alkyl, —NHC(O)—NH-alkyl, —NHC(O)—NH-aryl, —NHC(O)—NH-heteroaryl, —NHC(O)—NH-heterocyclyl, —NHC(O)—NH-heterocyclylalkyl, —NHC(O)—NH-alkyl-halogen, —NHC(O)—NH-alkyl-Cl, —NHC(O)—N(alkyl)$_2$, —NHS(O$_2$)alkyl";

radical R5 independently is "hydrogen".

In a further preferred embodiment, pyrido[2,3-b]pyrazine derivatives according to above general formula (I) are provided, wherein:

radical R1 independently is selected from the group consisting of:

(i) "hydrogen, methyl, ethyl, propyl, isopropyl, tert-butyl, hexyl, allyl, propenyl, prop-2-en-1-yl, cyclopropyl, cyclopropylmethyl, cyclopropylethyl, cyclopropylpropyl, cyclopropylbutyl, cyclopentyl, cyclopentylmethyl, cyclopentylethyl, cyclopentylpropyl, cyclopentylbutyl, cyclohexyl, cyclohexylmethyl, cyclohexylethyl, cyclohexylpropyl, cyclohexylbutyl, phenyl, naphthalenyl, naphthalen-1-yl, naphthalen-2-yl, benzyl, phenyl-ethyl, isoxazol, pyridinyl, pyridin-2-yl, pyridin-3-yl, pyridin-4-yl, pyrazolyl, pyrazol-3-yl, pyrazol-4-yl, quinolinyl, quinolin-2-yl, quinolin-3-yl, quinolin-4-yl, quinolin-8-yl, thiophenyl, thiophen-2-yl, thiophen-3-yl, furanyl, furan-2-yl, furan-3-yl, pyrimidinyl, pyrimidin-5-yl, imidazolyl, imidazol-4-yl, imidazol-3-yl, pyrrolo[2,3-b]pyridinyl, pyrrolo[2,3-b]pyridin-5-yl, indolyl, 1H-indol-2-yl, dibenzofuranyl, dibenzofuran-4-yl, piperidinyl, piperidinylmethyl, piperidinylethyl, piperidinylpropyl, piperidinylbutyl, piperidin-1-yl, piperidin-3-yl, piperidin-4-yl, piperazinyl, piperazinylmethyl, piperazinylethyl, piperazinylpropyl, piperazinylbutyl, piperazin-1-yl, diazepanyl, diazepanylmethyl, diazepanylethyl, diazepanylpropyl, diazepanylbuytl, diazepan-1-yl, morpholinyl, morpholinylmethyl, morpholinylethyl, morpholinylpropyl, morpholinylbuytyl, morpholin-4-yl, 2-morpholin-4-yl-ethyl, 1,2,3,4-tetrahydro-isoquinolinyl, 1,2,3,4-tetrahydro-isoquinolinylmethyl, 1,2,3,4-tetrahydro-isoquinolinylethyl, 1,2,3,4-tetrahydro-isoquinolinylpropyl, 1,2,3,4-tetrahydro-isoquinolinylbutyl, 1,2,3,4-tetrahydro-isoquinolin-7-yl, benzo[1,3]dioxolyl, benzo[1,3]dioxolylmethyl, benzo[1,3]dioxolylethyl, benzo[1,3]dioxolylpropyl, benzo[1,3]dioxolylbutyl, benzo[1,3]dioxol-5-yl, benzo[1,4]oxazinyl, benzo[1,4]oxazinylmethyl, benzo[1,4]oxazinylethyl, benzo[1,4]oxazinylpropyl, benzo[1,4]oxazinylbutyl, benzo[1,4]oxazin-6-yl, —NH—R$_{x1}$" with R$_{x1}$ being selected from the group consisting of:"methyl, ethyl, propyl, isopropyl, tert-butyl, hexyl, allyl, propenyl, prop-2-en-1-yl, cyclopropyl, cyclopropylmethyl, cyclopropylethyl, cyclopropylpropyl, cyclopropylbutyl, cyclopentyl, cyclopentylmethyl, cyclopentylethyl, cyclopentylpropyl, cyclopentylbutyl, cyclohexyl, cyclohexylmethyl, cyclohexylethyl, cyclohexylpropyl, cyclohexylbutyl, phenyl, naphthalenyl, naphthalen-1-yl, naphthalen-2-yl, benzyl, phenyl-ethyl, isoxazol, pyridinyl, pyridin-2-yl, pyridin-3-yl, pyridin-4-yl, pyrazolyl, pyrazol-3-yl, pyrazol-4-yl, quinolinyl, quinolin-2-yl, quinolin-3-yl, quinolin-4-yl, quinolin-8-yl, thiophenyl, thiophen-2-yl, thiophen-3-yl, furanyl, furan-2-yl, furan-3-yl, pyrimidinyl, pyrimidin-5-yl, imidazolyl, imidazol-4-yl, imidazol-3-yl, pyrrolo[2,3-b]pyridinyl, pyrrolo[2,3-b]pyridin-5-yl, indolyl, 1H-indol-2-yl, dibenzofuranyl, dibenzofuran-4-yl, piperidinyl, piperidinylmethyl, piperidinylethyl, piperidinylpropyl, piperidinylbutyl, piperidin-1-yl, piperidin-3-yl, piperidin-4-yl, piperazinyl, piperazinylmethyl, piperazinylethyl, piperazinylpropyl, piperazinylbutyl, piperazin-1-yl, diazepanyl, diazepanylmethyl, diazepanylethyl, diazepanylpropyl, diazepanylbuytl, diazepan-1-yl, morpholinyl, morpholinylmethyl, morpholinylethyl, morpholinylpropyl, morpholinylbuytyl, morpholin-4-yl, 2-morpholin-4-yl-ethyl, 1,2,3,4-tetrahydro-isoquinolinyl, 1,2,3,4-tetrahydro-isoquinolinylmethyl, 1,2,3,4-tetrahydro-isoquinolinylethyl, 1,2,3,4-tetrahydro-isoquinolinylpropyl, 1,2,3,4-tetrahydro-isoquinolinylbutyl, 1,2,3,4-tetrahydro-isoquinolin-7-yl, benzo[1,3]dioxolyl, benzo[1,3]dioxolylmethyl, benzo[1,3]dioxolylethyl, benzo[1,3]dioxolylpropyl, benzo[1,3]dioxolylbutyl, benzo[1,3]dioxol-5-yl, benzo[1,4]oxazinyl, benzo[1,4]oxazinylmethyl, benzo[1,4]oxazinylethyl, benzo[1,4]oxazinylpropyl, benzo[1,4]oxazinylbutyl, benzo[1,4]oxazin-6-yl";

where above substituents of substituents group (i)—if not hydrogen or nitrogen—may, optionally, additionally be substituted with at least one substituent selected from the group consisting of:"—F, —Cl, —Br, —I, —CN, —CF$_3$, —N$_3$, —NH$_2$, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —NHC(O)—NH$_2$, —C(NH)—NH$_2$, —C(O)—C(O)—NH$_2$, —C(O)—CF$_3$, alkyl, (C$_9$-C$_{30}$)-alkyl, cycloalkyl, cycloalkylalkyl, heterocyclyl, heterocyclylalkyl, aryl, arylalkyl, heteroaryl, heteroarylalkyl, alkyl-OH, alkyl-CN, alkyl-COOH, alkyl-P(O)(O-alkyl)$_2$, cycloalkyl-CN, aryl-OH, aryl(—OH)(-alkyl), —C(O)-alkyl, —C(O)heterocyclyl, —C(O—O-alkyl, —C(O)—O-heterocyclyl, —P(O)(O-alkyl-O—C(O)-alkyl)$_2$, —OP(O)(O-alkyl)$_2$, —OS(O$_2$)alkyl, —S-alkyl, —O-alkyl, —O-aryl, —O-arylalkyl, —O-heterocyclyl, —O-heterocyclylalkyl, —O-arylalkyl-(O-alkyl)$_2$, —O-alkyl-O-alkyl, —O-alkyl-N(alkyl)$_2$, —O-alkyl-halogen, —O-alkyl-Cl, —O-alkyl-F, —O-alkyl-Br, —O-alkyl-1, —OC(O)alkyl, —OC(O)—N(alkyl)$_2$, —OC(O)—NH-alkyl, —OC(O)—(C$_9$-C$_{30}$)alkyl, —OC(O)—O-alkyl, —OC(O)—O— alkyl-O-alkyl, —OC(O)—O-aryl, —N(alkyl)$_2$, —N(aryl)$_2$, —NHC(O)alkyl, —NHC(O)alkyl-NH-alkyl, —NHC(O)alkyl-C(O)—O-alkyl, —NHC(O)—O-alkyl, —NHC(O)—O-alkyl-O-alkyl, —NHC(O)—O-alkyl-O-alkyl-O-alkyl-O-alkyl, —NHC(O)—NH-alkyl, —NHC(O)—NH-aryl, —NHC(O)—NH-heteroaryl, —NHC(O)—NH-heterocyclyl, —NHC(O)—NH-heterocyclylalkyl, —NHC(O)—NH-alkyl-halogen, —NHC(O)—NH-alkyl-Cl, —NHC(O)—N(alkyl)$_2$, —NHS(O$_2$)-alkyl";

radical R2 independently is "hydrogen";

radical R3 independently is selected from the group consisting of:

(i) "—NH—C(O)—NH—C(O)—O—R$_{x2}$, —NH—C(S)—NH—R$_{x3}$, —NH—C(=NH)—R$_{x4}$, —NH—C(O)—C(O)R$_{x5}$", with R$_{x2}$, R$_{x3}$, R$_{x4}$, R$_{x5}$ independently from each other being selected from the group consisting of:"methyl, ethyl, propyl, isopropyl, tert-butyl, hexyl, allyl, propenyl, prop-2-en-1-yl, cyclopropyl, cyclopropylmethyl, cyclopropylethyl, cyclopropylpropyl, cyclopropylbutyl, cyclopentyl, cyclopentylmethyl, cyclopentylethyl, cyclopentylpropyl, cyclopentylbutyl, cyclohexyl, cyclohexylmethyl, cyclohexylethyl, cyclohexylpropyl, cyclohexylbutyl, phenyl, naphthalenyl, naphthalen-1-yl, naphthalen-2-yl, benzyl, phenyl-ethyl, isoxazol, pyridinyl, pyridin-2-yl, pyridin-3-yl, pyridin-4-yl, pyrazolyl, pyrazol-3-yl, pyrazol-4-yl, quinolinyl, quinolin-2-yl, quinolin-3-yl, quinolin-4-yl, quinolin-8-yl, thiophenyl, thiophen-2-yl, thiophen-3-yl, furanyl, furan-2-yl, furan-3-yl, pyrimidinyl, pyrimidin-5-yl, imidazolyl, imidazol-4-yl, imidazol-3-yl, pyrrolo[2,3-b]pyridinyl, pyrrolo[2,3-b]pyridin-5-yl, indolyl, 1H-indol-2-yl, dibenzofuranyl, dibenzofuran-4-yl, piperidinyl, piperidinylmethyl, piperidinylethyl, piperidinylpropyl, piperidinylbutyl, piperidin-1-yl, piperidin-3-yl, piperidin-4-yl, piperazinyl, piperazinylmethyl, piperazinylethyl, piperazinylpropyl, piperazinylbutyl, piperazin-1-yl, diazepanyl, diazepanylmethyl, diazepanylethyl, diazepanylpropyl; diazepanylbuytl, diazepan-1-yl, morpholinyl, morpholinylmethyl, morpholinylethyl, morpholinylpropyl, morpholinylbuytyl, morpholin-4-yl, 2-morpholin-4-yl-ethyl, 1,2,3,4-tetrahydro-isoquinolinyl, 1,2,3,4-tetrahydro-isoquinolinylmethyl, 1,2,3,4-tetrahydro-isoquinolinylethyl, 1,2,3,4-tetrahydro-isoquinolinylpropyl, 1,2,3,4-tetrahydro-isoquinolinylbutyl, 1,2,3,4-tetrahydro-isoquinolin-7-yl, benzo[1,3]dioxolyl, benzo[1,3]dioxolylmethyl, benzo[1,3]dioxolylethyl, benzo[1,3]dioxolylpropyl, benzo[1,3]dioxolylbutyl, benzo[1,3]dioxol-5-yl, benzo[1,4]oxazinyl, benzo[1,4]oxazinylmethyl, benzo[1,4]oxazinylethyl, benzo[1,4]oxazinylpropyl, benzo[1,4]oxazinylbutyl, benzo[1,4]oxazin-6-yl";

where above substituents of substituents group (i)—if not hydrogen or nitrogen—may, optionally, additionally be substituted with at least one substituent selected from the group consisting of:"—F, —Cl, —Br, —I, —CN, —CF$_3$, —N$_3$, —NH$_2$, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —NHC(O)—NH$_2$, —C(NH)—NH$_2$, —C(O)—C(O)—NH$_2$, —C(O)—CF$_3$, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, alkyl-OH, alkyl-CN, alkyl-COOH, alkyl-P(O)(O-alkyl)$_2$, cycloalkyl-CN, aryl-OH, aryl(—OH)(-alkyl), —C(O)-alkyl, —C(O)heterocyclyl, —C(O)—O-alkyl, —C(O)—O-heterocyclyl, —P(O)(O-alkyl-O—C(O)alkyl)$_2$, —OP(O)(O-alkyl)$_2$, —OS(O$_2$)alkyl, —S-alkyl, —O-alkyl, —O-aryl, —O-arylalkyl, —O-heterocyclyl, —O-heterocyclylalkyl, —O—arylalkyl-(O-alkyl)$_2$, —O-alkyl-O-alkyl, —O-alkyl-N(alkyl)$_2$, —O-alkyl-halogen, —O-alkyl-Cl, —O-alkyl-F, —O-alkyl-Br, —O-alkyl-1, —OC(O)alkyl, —OC(O)—N(alkyl)$_2$, —OC(O)—NH-alkyl, —OC(OH(C$_9$-C$_{30}$)alkyl, —OC(O)—O-alkyl, —OC(O)—O-alkyl-O-alkyl, —OC(O)—O-aryl, —N(alkyl)$_2$, —N(aryl)$_2$, —NHC(O)alkyl, —NHC(O)-alkyl-NH-alkyl, —NHC(O)alkyl-C(O)-alkyl, —NHC(O)—O-alkyl, —NHC(O)-alkyl-O-alkyl, —NHC(O)—O-alkyl-O-alkyl-O-alkyl, —NHC(O)—NH-alkyl, —NHC(O)—NH-aryl, —NHC(O)—NH-heteroaryl, —NHC(O)—NH-heterocyclyl, —NHC(O)—NH-heterocyclylalkyl, —NHC(O)—NH-alkyl-halogen, —NHC(O)—NH-alkyl-Cl, —NHC(O)—N(alkyl)$_2$, —NHS(O$_2$)alkyl";

radical R4 independently is selected from the group consisting of:

(i) "hydrogen, methyl, ethyl, propyl, isopropyl, tert-butyl, hexyl, allyl, propenyl, prop-2-en-1-yl, cyclopropyl, cyclopropylmethyl, cyclopropylethyl, cyclopropyl-propyl, cyclopropylbutyl, cyclopentyl, cyclopentylmethyl, cyclopentylethyl, cyclopentylpropyl, cyclopentylbutyl, cyclohexyl, cyclohexylmethyl, cyclohexylethyl, cyclohexylpropyl, cyclohexylbutyl, phenyl, naphthalenyl, naphthalen-1-yl, naphthalen-2-yl, benzyl, phenyl-ethyl, isoxazol, pyridinyl, pyridin-2-yl, pyridin-3-yl, pyridin-4-yl, pyrazolyl, pyrazol-3-yl, pyrazol-4-yl, quinolinyl, quinolin-2-yl, quinolin-3-yl, quinolin-4-yl, quinolin-8-yl, thiophenyl, thiophen-2-yl, thiophen-3-yl, furanyl, furan-2-yl, furan-3-yl, pyrimidinyl, pyrimidin-5-yl, imidazolyl, imidazol-4-yl, imidazol-3-yl, pyrrolo[2,3-b]pyridinyl, pyrrolo[2,3-b]pyridin-5-yl, indolyl, 1H-indol-2-yl, dibenzofuranyl, dibenzofuran-4-yl, piperidinyl, piperidinylmethyl, piperidinylethyl, piperidinylpropyl, piperidinylbutyl, piperidin-1-yl, piperidin-3-yl, piperidin-4-yl, piperazinyl, piperazinylmethyl, piperazinylethyl, piperazinylpropyl, piperazinylbutyl, piperazin-1-yl, diazepanyl, diazepanylmethyl, diazepanylethyl, diazepanylpropyl, diazepanylbuytl, diazepan-1-yl, morpholinyl, morpholinylmethyl, morpholinylethyl, morpholinylpropyl, morpholinylbuytyl, morpholin-4-yl, 2-morpholin-4-yl-ethyl, 1,2,3,4-tetrahydro-isoq uinolinyl, 1,2,3,4-tetrahydro-isoquinolinylmethyl, 1,2,3,4-tetrahydro-isoquinolinylethyl, 1,2,3,4-tetrahydro-isoquinolinylpropyl, 1,2,3,4-tetrahydro-isoquinolinylbutyl, 1,2,3,4-tetrahydro-isoquinolin-7-yl, benzo[1,3]dioxolyl, benzo[1,3]dioxolylmethyl, benzo[1,3]dioxolylethyl, benzo[1,3]dioxolylpropyl, benzo[1,3]dioxolylbutyl, benzo[1,3]dioxol-5-yl, benzo[1,4]oxazinyl, benzo[1,4]oxazinylmethyl, benzo[1,4]oxazinylethyl, benzo[1,4]oxazinylpropyl, benzo[1,4]oxazinylbutyl, benzo[1,4]oxazin-6-yl, —NH—R$_{x6}$" with R$_{x6}$ being selected from the group consisting of:"methyl, ethyl, propyl, isopropyl, tert-butyl, hexyl, allyl, propenyl, prop-2-en-1-yl, cyclopropyl, cyclopropylmethyl, cyclopropylethyl, cyclopropylpropyl, cyclopropylbutyl, cyclopentyl, cyclopentylmethyl, cyclopentylethyl, cyclopentylpropyl, cyclopentylbutyl, cyclohexyl, cyclohexylmethyl, cyclohexylethyl, cyclohexylpropyl, cyclohexylbutyl, phenyl, naphthalenyl, naphthalen-1-yl, naphthalen-2-yl, benzyl, phenyl-ethyl, isoxazol, pyridinyl, pyridin-2-yl, pyridin-3-yl, pyridin-4-yl, pyrazolyl, pyrazol-3-yl, pyrazol-4-yl, quinolinyl, quinolin-2-yl, quinolin-3-yl, quinolin-4-yl, quinolin-8-yl, thiophenyl, thiophen-2-yl, thiophen-3-yl, furanyl, furan-2-yl, furan-3-yl, pyrimidinyl, pyrimidin-5-yl, imidazolyl, imidazol-4-yl, imidazol-3-yl, pyrrolo[2,3-b]pyridinyl, pyrrolo[2,3-b]pyridin-5-yl, indolyl, 1H-indol-2-yl, dibenzofuranyl, dibenzofuran-4-yl, piperidinyl, piperidinylmethyl, piperidinylethyl, piperidinylpropyl, piperidinylbutyl, piperidin-1-yl, piperidin-3-yl, piperidin-4-yl, piperazinyl, piperazinylmethyl, piperazinylethyl, piperazinylpropyl, piperazinylbutyl, piperazin-1-yl, diazepanyl, diazepanylmethyl, diazepanylethyl, diazepanylpropyl, diazepanylbuytl, diazepan-1-yl, morpholinyl, morpholinylmethyl, morpholinylethyl, morpholinylpropyl, morpholinylbuytyl, morpholin-4-yl, 2-morpholin-4-yl-ethyl, 1,2,3,4-tetrahydro-isoq uinolinyl, 1,2,3,4-tetrahydro-isoquinolinylmethyl, 1,2,3,4-tetrahydro-isoquinolinylethyl, 1,2,3,4-tetrahydro-isoquinolinylpropyl, 1,2,3,4-tetrahydro-isoquinolinylbutyl, 1,2,3,4-tetrahydro-isoquinolin-7-yl, benzo[1,3]dioxolyl, benzo[1,3]dioxolylmethyl, benzo[1,3]dioxolylethyl, benzo[1,3]dioxolylpropyl, benzo[1,3]dioxolylbutyl, benzo[1,3]dioxol-5-yl, benzo[1,4]oxazinyl, benzo[1,4]oxazinylmethyl, benzo[1,4]oxazinylethyl, benzo[1,4]oxazinylpropyl, benzo[1,4]oxazinylbutyl, benzo[1,4]oxazin-6-yl";

where above substituents of substituents group (i)—if not hydrogen or nitrogen -may, optionally, additionally be substituted with at least one substituent selected from the group consisting of:"—F, —Cl, —Br, —I, —CN, —CF$_3$, —N$_3$, —NH$_2$, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —NHC(O)—NH$_2$, —C(NH)—NH$_2$, —C(O)—C(O)—NH$_2$, —C(O)—CF$_3$, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, alkyl-OH, alkyl-CN, alkyl-COOH, alkyl-P(O)(O-alkyl)$_2$, cycloalkyl-CN, aryl-OH, aryl(—OH)(-alkyl), —C(O)alkyl, —C(O)heterocyclyl, —C(O)—O-alkyl, —C(O)—O-heterocyclyl, —P(O)(O-alkyl-O—C(O)-alkyl)$_2$, —OP(O)(O-alkyl)$_2$, —OS(O$_2$)alkyl, —S-alkyl, —O-alkyl, —O-aryl, —O-arylalkyl, —O-heterocyclyl, —O-heterocyclylalkyl, —O-arylalkyl-(O-alkyl)$_2$, —O-alkyl-O-alkyl, —O-alkyl-N(alkyl)$_2$, —O-alkyl-halogen, —O-alkyl-Cl, —O-alkyl-F, —O-alkyl-Br, —O-alkyl-1, —OC(O)alkyl, —OC(O)—N(alkyl)$_2$, —OC(O)—NH-alkyl, —OC(O)—(C$_9$-C$_{30}$)alkyl, —OC(O)—O-alkyl, —OC(O)—O-alkyl-O-alkyl, —OC(O)—O-aryl, —N(alkyl)$_2$, —N(aryl)$_2$, —NHC(O)alkyl, —NHC(O)alkyl-NH-alkyl, —NHC(O)alkyl-C(O)—O-alkyl, —NHC(O)—O-alkyl, —NHC(O)—O-alkyl-O-alkyl, —NHC(O)—O-alkyl-O-alkyl-O-alkyl-O-alkyl, —NHC(O)—NH-alkyl, —NHC(O)—NH-aryl, —NHC(O)—NH-heteroaryl, —NHC(O)—NH-heterocyclyl, —NHC(O)—NH-heterocyclylalkyl, —NHC(O)—NH-alkyl-halogen, —NHC(O)—NH-alkyl-Cl, —NHC(O)—N(alkyl)$_2$, —NHS(O$_2$)alkyl";

radical R5 independently is "hydrogen".

In a further preferred embodiment, pyrido[2,3-b]pyrazine derivatives according to above general formula (I) and preferred embodiments and subsets are provided, wherein:

radical R1 independently is selected from the group consisting of:
(i) "hydrogen, alkyl, (C9-C30)alkyl, cycloalkyl, cycloalkylalkyl, aryl, arylalkyl, heteroaryl, heteroarylalkyl, heterocyclyl, heterocyclylalkyl, —NH-alkyl, —NH—(C9-C30)alkyl, —NH-cycloalkyl, —NH-cycloalkylalkyl, —NH-aryl, —NH-arylalkyl, —NH-heteroaryl, —NH-heteroarylalkyl, —NH-heterocyclyl, —NH-heterocyclylalkyl";

where above substituents of substituents group (i)—if not hydrogen or nitrogen—may, optionally, additionally be substituted with at least one substituent selected from the group consisting of:"—F, —Cl, —Br, —I, —CN, —CF$_3$, —N$_3$, —NH$_2$, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —NHC(O)—NH$_2$, —C(NH)—NH$_2$, —C(O)—C(O)—NH$_2$, —C(O)—CF$_3$, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, alkyl-OH, alkyl-CN, alkyl-COOH, alkyl-P(O)(O-alkyl)$_2$, cycloalkyl-CN, aryl-OH, aryl(—OH)(-alkyl), —C(O)alkyl, —C(O)heterocyclyl, —C(O)—O-alkyl, —C(O)—O-heterocyclyl, —P(O)(O-alkyl-O—C(O)alkyl)$_2$, —OP(O)(O-alkyl)$_2$, —OS(O$_2$)alkyl, —S-alkyl, —O-alkyl, —O-aryl, —O-arylalkyl, —O-heterocyclyl, —O-heterocyclylalkyl, —O-arylalkyl-(O-alkyl)$_2$, —O-alkyl-O-alkyl, —O-alkyl-N(alkyl)$_2$, —O-alkyl-halogen, —O-alkyl-Cl, —O-alkyl-F, —O-alkyl-Br, —O-alkyl-1, —OC(O)alkyl, —OC(O)—N(alkyl)$_2$, —OC(O)—NH-alkyl, —OC(O)—(C$_9$-C$_{30}$)alkyl, —OC(O)—O-alkyl, —OC(O)—O-alkyl-O-alkyl, —OC(O)—O-aryl, —N(alkyl)$_2$, —N(aryl)$_2$, —NHC(O)alkyl, —NHC(O)alkyl-NH-alkyl, —NHC(O)alkyl-C(O)—O-alkyl, —NHC(O)—O-alkyl, —NHC(O)—O-alkyl-O-alkyl, —NHC(O)—O-alkyl-O-alkyl-O-alkyl-O-alkyl, —NHC(O)—NH-alkyl, —NHC(O)—NH-aryl, —NHC(O)—NH-heteroaryl, —NHC(O)—NH-heterocyclyl, —NHC(O)—NH-heterocyclylalkyl, —NHC(O)—NH-alkyl-halogen, —NHC(O)—NH-alkyl-Cl, —NHC(O)—N(alkyl)$_2$, —NHS(O$_2$)alkyl";

radical R2 independently is "hydrogen";

radical R3 independently is selected from the group consisting of:
(i) "—NH—C(O)—NH$_2$, —NH—C(O)—NH-alkyl, —NH—C(O)—NH—(C9-C30)alkyl, —NH—C(O)—NH-cycloalkyl, —NH—C(O)—NH-cycloalkylalkyl, —NH—C(O)—NH-aryl, —NH—C(O)—NH-arylalkyl, —NH—C(O)—NH-heteroaryl, —NH—C(O)—NH-heteroarylalkyl, —NH—C(O)—NH-heterocyclyl, —NH—C(O)—NH-heterocyclylalkyl, —NH—C(O)—O-alkyl, —NH—C(O)—O—(C9-C30)alkyl, —NH—C(O)—O-cycloalkyl, —NH—C(O)—O-cycloalkylalkyl, —NH—C(O)—O-aryl, —NH—C(O)—O-arylalkyl, —NH—C(O)—O-heteroaryl, —NH—C(O)—O-heteroarylalkyl, —NH—C(O)—O-heterocyclyl, —NH—C(O)—O-heterocyclylalkyl, —NH—C(O)alkyl, —NH—C(O)—(C9-C30)alkyl, —NH—C(O)cycloalkyl, —NH—C(O)cycloalkylalkyl, —NH—C(O)aryl, —NH—C(O)-arylalkyl, —NH—C(O)heteroaryl, —NH—C(O)heteroarylalkyl, —NH—C(O)-heterocyclyl, —NH—C(O)heterocyclylalkyl, —NH—S(O$_2$)alkyl, —NH—S(O$_2$)—(C9-C30)alkyl, —NH—S(O$_2$)-cycloalkyl, —NH—S(O$_2$)-cycloalkylalkyl, —NH—S(O$_2$)aryl, —NH—S(O$_2$)arylalkyl, —NH—S(O$_2$)-heteroaryl, —NH—S(O$_2$)-heteroarylalkyl, —NH—S(O$_2$)-heterocyclyl, —NH—S(O$_2$)-heterocyclylalkyl;

where above substituents of substituents group (i)—if not hydrogen, nitrogen or sulphur—may, optionally, additionally be substituted with at least one substituent selected from the group consisting of:"—F, —Cl, —Br, —I, —CN, —CF$_3$, —N$_3$, —NH$_2$, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —NHC(O)—NH$_2$, —C(NH)—NH$_2$, —C(O)—C(O)—NH$_2$, —C(O)—CF$_3$, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, alkyl-OH, alkyl-CN, alkyl-COOH, alkyl-P(O)(O-alkyl)$_2$, cycloalkyl-CN, aryl-OH, aryl(—OH)(-alkyl), —C(O)alkyl, —C(O)heterocyclyl, —C(O)—O-alkyl, —C(O)—O-heterocyclyl, —P(O)(O-alkyl-O—C(O)alkyl)$_2$, —OP(O)(O-alkyl)$_2$, —OS(O$_2$)alkyl, —S-alkyl, —O-alkyl, —O-aryl, —O-arylalkyl, —O-heterocyclyl, —O-heterocyclylalkyl, —O-arylalkyl-(O-alkyl)$_2$, —O-alkyl-O-alkyl, —O-alkyl-N(alkyl)$_2$, —O-alkyl-halogen, —O-alkyl-Cl, —O-alkyl-F, —O-alkyl-Br, —O-alkyl-I, —OC(O)alkyl, —OC(O)—N(alkyl)$_2$, —OC(O)—NH-alkyl, —OC(O)—(C$_9$-C$_{30}$)alkyl, —OC(O)—O-alkyl, —OC(O)—O-alkyl-O-alkyl, —OC(O)—O-aryl, —N(alkyl)$_2$, —N(aryl)$_2$, —NHC(O)alkyl, —NHC(O)alkyl-NH-alkyl, —NHC(O)alkyl-C(O)—O-alkyl, —NHC(O)—O-alkyl, —NHC(O)—O-alkyl-O-alkyl, —NHC(O)—O-alkyl-O-alkyl-O-alkyl-O-alkyl, —NHC(O)—NH-alkyl, —NHC(O)—NH-aryl, —NHC(O)—NH-heteroaryl, —NHC(O)—NH-heterocyclyl, —NHC(O)—NH-heterocyclylalkyl, —NHC(O)—NH-alkyl-halogen, —NHC(O)—NH-alkyl-Cl, —NHC(O)—N(alkyl)$_2$, —NHS(O$_2$)alkyl";

radical R4 independently is selected from the group consisting of:

(i) "hydrogen, alkyl, (C9-C30)alkyl, cycloalkyl, cycloalkylalkyl, aryl, arylalkyl, heteroaryl, heteroarylalkyl, heterocyclyl, heterocyclylalkyl, —NH-alkyl, —NH—(C9-C30)alkyl, —NH-cycloalkyl, —NH-cycloalkylalkyl, —NH-aryl, —NH-arylalkyl, —NH-heteroaryl, —NH-heteroarylalkyl, —NH-heterocyclyl, —NH-heterocyclylalkyl";

where above substituents of substituents group (i)—if not hydrogen or nitrogen—may, optionally, additionally be substituted with at least one substituent selected from the group consisting of:"—F, —Cl, —Br, —I, —CN, —CF$_3$, —N$_3$, —NH$_2$, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —NHC(O)—NH$_2$, —C(NH)—NH$_2$, —C(O$_y$C(O)—NH$_2$, —C(O)—CF$_3$, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, alkyl-OH, alkyl-CN, alkyl-COOH, alkyl-P(O)(O-alkyl)$_2$, cycloalkyl-CN, aryl-OH, aryl(—OH)(-alkyl), —C(O)alkyl, —C(O)heterocyclyl, —C(O)—O-alkyl, —C(O)—O-heterocyclyl, —P(O)(O-alkyl-O—C(O)alkyl)$_2$, —OP(O)(O-alkyl)$_2$, —OS(O$_2$)alkyl, —S-alkyl, —O-alkyl, —O-aryl, —O-arylalkyl, —O-heterocyclyl, —O-heterocyclylalkyl, —O-arylalkyl-(O-alkyl)$_2$, —O-alkyl-O-alkyl, —O-alkyl-N(alkyl)$_2$, —O-alkyl-halogen, —O-alkyl-Cl, —O-alkyl-F, —O-alkyl-Br, —O-alkyl-1, —OC(O)alkyl, —OC(O)—N(alkyl)$_2$, —OC(O)—NH-alkyl, —OC(O)—(C$_9$-C$_{30}$)alkyl, —OC(O)—O-alkyl, —OC(O)—O-alkyl-O-alkyl, —OC(O)—O-aryl, —N(alkyl)$_2$, —N(aryl)$_2$, —NHC(O)alkyl, —NHC(O)alkyl-NH-alkyl, —NHC(O)alkyl-C(O)—O-alkyl, —NHC(O)—O-alkyl, —NHC(O)—O-alkyl-O-alkyl, —NHC(O)—O-alkyl-O-alkyl-O-alkyl-O-alkyl, —NHC(O)—NH-alkyl, —NHC(O)—NH-aryl, —NHC(O)—NH-heteroaryl, —NHC(O)—NH-heterocyclyl, —NHC(O)—NH-heterocyclylalkyl, —NHC(O)—NH-alkyl-halogen, —NHC(O)—NH-alkyl-Cl, —NHC(O)—N(alkyl)$_2$, —NHS(O$_2$)alkyl";

radical R5 independently is selected from the group consisting of:

(i) "hydrogen, alkyl, (C9-C30)alkyl, cycloalkyl, cycloalkylalkyl, aryl, arylalkyl, heteroaryl, heteroarylalkyl, heterocyclyl, heterocyclylalkyl";

where above substituents of substituents group (i)—if not hydrogen—may, optionally, additionally be substituted with at least one substituent selected from the group consisting of:"—F, —Cl, —Br, —I, —CN, —CF$_3$, —N$_3$, —NH$_2$, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —NHC(O)—NH$_2$, —C(NH)—NH$_2$, —C(O)C(O)—NH$_2$, —C(O)—CF$_3$, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, alkyl-OH, alkyl-CN, alkyl-COOH, alkyl-P(O)(O-alkyl)$_2$, cycloalkyl-CN, aryl-OH, aryl(—OH)(-alkyl), —C(O)alkyl, —C(O)heterocyclyl, —C(O)—O-alkyl, —C(O)—O-heterocyclyl, —P(O)(O-alkyl-O—C(O)alkyl)$_2$, —OP(O)(O-alkyl)$_2$, —OS(O$_2$)alkyl, —S-alkyl, —O-alkyl, —O-aryl, —O-arylalkyl, —O-heterocyclyl, —O-heterocyclylalkyl, —O-arylalkyl-(O-alkyl)$_2$, —O-alkyl-O-alkyl, —O-alkyl-N(alkyl)$_2$, —O-alkyl-halogen, —O-alkyl-Cl, —O-alkyl-F, —O-alkyl-Br, —O-alkyl-I, —OC(O)alkyl, —OC(O)—N(alkyl)$_2$, —OC(O)—NH-alkyl, —OC(O)—(C$_9$-C$_{30}$)alkyl, —OC(O)—O-alkyl, —OC(O)—O-alkyl-O-alkyl, —OC(O)—O-aryl, —N(alkyl)$_2$, —N(aryl)$_2$, —NHC(O)alkyl, —NHC(O)alkyl-NH-alkyl, —NHC(O)alkyl-C(O)—O-alkyl, —NHC(O)—O-alkyl, —NHC(O)—O-alkyl-O-alkyl, —NHC(O)—O-alkyl-O-alkyl-O-alkyl-O-alkyl, —NHC(O)—NH-alkyl, —NHC(O)—NH-aryl, —NHC(O)—NH-heteroaryl, —NHC(O)—NH-heterocyclyl, —NHC(O)—NH-heterocyclylalkyl, —NHC(O)—NH-alkyl-halogen, —NHC(O)—NH-alkyl-Cl, —NHC(O)—N(alkyl)$_2$, —NHS(O$_2$)alkyl".

In a yet further preferred embodiment, pyrido[2,3-b]pyrazine derivatives according to above general formula (I) and preferred embodiments and subsets are provided, wherein:

radical R1 independently is selected from the group consisting of:

(i) "hydrogen, methyl, ethyl, propyl, isopropyl, tert-butyl, hexyl, allyl, propenyl, prop-2-en-1-yl, cyclopropyl, cyclopropylmethyl, cyclopropylethyl, cyclopropylpropyl, cyclopropylbutyl, cyclopentyl, cyclopentylmethyl, cyclopentylethyl, cyclopentylpropyl, cyclopentylbutyl, cyclohexyl, cyclohexylmethyl, cyclohexylethyl, cyclohexylpropyl, cyclohexylbutyl, phenyl, naphthalenyl, naphthalen-1-yl, naphthalen-2-yl, benzyl, phenyl-ethyl, isoxazol, pyridinyl, pyridin-2-yl, pyridin-3-yl, pyridin-4-yl, pyrazolyl, pyrazol-3-yl, pyrazol-4-yl, quinolinyl, quinolin-2-yl, quinolin-3-yl, quinolin-4-yl, quinolin-8-yl, thiophenyl, thiophen-2-yl, thiophen-3-yl, furanyl, furan-2-yl, furan-3-yl, pyrimidinyl, pyrimidin-5-yl, imidazolyl, imidazol-4-yl, imidazol-3-yl, pyrrolo[2,3-b]pyridinyl, pyrrolo[2,3-b]pyridin-5-yl, indolyl, 1H-indol-2-yl, dibenzofuranyl, dibenzofuran-4-yl, piperidinyl, piperidinylmethyl, piperidinylethyl, piperidinylpropyl, piperidinylbutyl, piperidin-1-yl, piperidin-3-yl, piperidin-4-yl, piperazinyl, piperazinylmethyl, piperazinylethyl, piperazinylpropyl, piperazinylbutyl, piperazin-1-yl, diazepanyl, diazepanylmethyl, diazepanylethyl, diazepanylpropyl, diazepanylbuytl, diazepan-1-yl, morpholinyl, morpholinylmethyl, morpholinylethyl, morpholinylpropyl, morpholinylbuytyl, morpholin-4-yl, 2-morpholin-4-yl-ethyl, 1,2,3,4-tetrahydro-isoquinolinyl, 1,2,3,4-tetrahydro-isoquinolinylmethyl, 1,2,3,4-tetrahydro-isoquinolinylethyl, 1,2,3,4-tetrahydro-isoquinolinylpropyl, 1,2,3,4-tetrahydro-isoquinolinylbutyl, 1,2,3,4-tetrahydro-isoquinolin-7-yl, benzo[1,3]dioxolyl, benzo[1,3]dioxolylmethyl, benzo[1,3]dioxolylethyl, benzo[1,3]dioxolylpropyl, benzo[1,3]dioxolylbutyl, benzo[1,3]dioxol-5-yl, benzo[1,4]oxazinyl, benzo[1,4]oxazinylmethyl, benzo[1,4]oxazinylethyl, benzo[1,4]oxazinylpropyl, benzo[1,4]oxazinylbutyl, benzo[1,4]oxazin-6-yl, —NH—R$_{y1}$" with R$_{y1}$ being selected from the group consisting of:"methyl, ethyl, propyl, isopropyl, tert-butyl, hexyl, allyl, propenyl, prop-2-en-1-yl, cyclopropyl, cyclopropylmethyl, cyclopropylethyl, cyclopropylpropyl, cyclopropylbutyl, cyclopentyl, cyclopentylmethyl, cyclopentylethyl, cyclopentylpropyl, cyclopentylbutyl, cyclohexyl, cyclohexylmethyl, cyclohexylethyl, cyclohexylpropyl, cyclohexylbutyl, phenyl, naphthalenyl, naphthalen-1-yl, naphthalen-2-yl, benzyl, phenyl-ethyl, isoxazol, pyridinyl, pyridin-2-yl, pyridin-3-yl, pyridin-4-yl, pyrazolyl, pyrazol-3-yl, pyrazol-4-yl, quinolinyl, quinolin-2-yl, quinolin-3-yl, quinolin-4-yl, quinolin-8-yl, thiophenyl, thiophen-2-yl, thiophen-3-yl, furanyl, furan-2-yl, furan-3-yl, pyrimidinyl, pyrimidin-5-yl, imidazolyl, imidazol-4-yl, imidazol-3-yl, pyrrolo[2,3-b]pyridinyl, pyrrolo[2,3-b]pyridin-5-yl, indolyl, 1H-indol-2-yl, dibenzofuranyl, dibenzofuran-4-yl, piperidinyl, piperidinylmethyl, piperidinylethyl, piperidinylpropyl, piperidinylbutyl, piperidin-1-yl, piperidin-3-yl, piperidin-4-yl, piperazinyl, piperazinylmethyl, piperazinylethyl, piperazinylpropyl, piperazinylbutyl, piperazin-1-yl, diazepanyl, diazepanylmethyl, diazepanylethyl, diazepanylpropyl, diazepanylbuytl, diazepan-1-yl, morpholinyl, morpholinylmethyl, morpholinylethyl, morpholinylpropyl, morpholinylbuytyl, morpholin-4-yl, 2-morpholin-4-yl-ethyl, 1,2,3,4-tetrahydro-isoquinolinyl, 1,2,3,4-tetrahydro-isoquinolinylmethyl, 1,2,3,4-tetrahydro-isoquinolinylethyl, 1,2,3,4-tetrahydro-isoquinolinylpropyl, 1,2,3,4-tetrahydro-isoquinolinylbutyl, 1,2,3,4-tetrahydro-isoquinolin-7-yl, benzo[1,3]dioxolyl, benzo[1,3]dioxolylmethyl, benzo[1,3]dioxolylethyl, benzo[1,3]dioxolylpropyl, benzo[1,3]dioxolylbutyl, benzo[1,3]dioxol-5-yl, benzo[1,4]oxazinyl, benzo[1,4]oxazinylmethyl, benzo[1,4]oxazinylethyl, benzo[1,4]oxazinylpropyl, benzo[1,4]oxazinylbutyl, benzo[1,4]oxazin-6-yl";

where above substituents of substituents group (i)—if not hydrogen or nitrogen—may, optionally, additionally be substituted with at least one substituent selected from the group consisting of:"—F, —Cl, —Br, —I, —CN, —CF$_3$, —N$_3$, —NH$_2$, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —NHC(O)—NH$_2$, —C(NH)—NH$_2$, —C(O)—C(O)—NH$_2$, —C(O)—CF$_3$, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, alkyl-OH, alkyl-CN, alkyl-COOH, alkyl-P(O)(O-alkyl)$_2$, cycloalkyl-CN, aryl-OH, aryl(—OH)(-alkyl), —C(O)-alkyl, —C(O)heterocyclyl, —C(O)—O—alkyl, —C(O)—O-heterocyclyl, —P(O)(O-alkyl-O—C(O)alkyl)$_2$, —OP(O)(O-alkyl)$_2$, —OS(O$_2$)-alkyl, —S-alkyl, —O-alkyl, —O-aryl, —O-arylalkyl, —O-heterocyclyl, —O-heterocyclylalkyl, —O-arylalkyl-(O-alkyl)$_2$, —O-alkyl-O-alkyl, —O-alkyl-N(alkyl)$_2$, —O-alkyl-halogen, —O-alkyl-Cl, —O-alkyl-F, —O-alkyl-Br, —O-alkyl-1, —OC(O)alkyl, —OC(O)—N(alkyl)$_2$, —OC(O)—NH-alkyl, —OC(OHC$_9$-C$_{30}$)alkyl, —OC(O)—O-alkyl, —OC(O)—O-alkyl-O-alkyl, —OC(O)—O-aryl, —N(alkyl)$_2$, —N(aryl)$_2$, —NHC(O)alkyl, —NHC(O)alkyl-NH-alkyl, —NHC(O)alkyl-C(O)—O-alkyl, —NHC(O)—O-alkyl, —NHC(O)—O-alkyl-O-alkyl, —NHC(O)—O-alkyl-O-alkyl-O-alkyl, —NHC(O)—NH-alkyl, —NHC(O)—NH-aryl, —NHC(O)—NH-heteroaryl, —NHC(O)—NH-heterocyclyl, —NHC(O)—NH-heterocyclylalkyl, —NHC(O)—NH-alkyl-halogen, —NHC(O)—NH-alkyl-Cl, —NHC(O)—N(alkyl)$_2$, —NHS(O$_2$)alkyl";

radical R2 independently is "hydrogen";

radical R3 independently is selected from the group consisting of:

(i) "—NH—C(O)—NH$_2$, —NH—C(O)—NH—R$_{y2}$, —NH—C(O)—O—R$_{y3}$, —NH—C(O)—R$_{y4}$, —NH—S(O$_2$)R$_{y5}$";

with R$_{y2}$, R$_{y3}$, R$_{y4}$, R$_{y5}$ independently from each other being selected from the group consisting of:"methyl, ethyl, propyl, isopropyl, tert-butyl, hexyl, allyl, propenyl, prop-2-en-1-yl, cyclopropyl, cycloprppylmethyl, cyclopropylethyl, cyclopropylpropyl, cyclopropylbutyl, cyclopentyl, cyclopentylmethyl, cyclopentylethyl, cyclopentylpropyl, cyclopentylbutyl, cyclohexyl, cyclohexylmethyl, cyclohexylethyl, cyclohexylpropyl, cyclohexylbutyl, phenyl, naphthalenyl, naphthalen-1-yl, naphthalen-2-yl, benzyl, phenyl-ethyl, isoxazol, pyridinyl, pyridin-2-yl, pyridin-3-yl, pyridin-4-yl, pyrazolyl, pyrazol-3-yl, pyrazol-4-yl, quinolinyl, quinolin-2-yl, quinolin-3-yl, quinolin-4-yl, quinolin-8-yl, thiophenyl, thiophen-2-yl, thiophen-3-yl, furanyl, furan-2-yl, furan-3-yl, pyrimidinyl, pyrimidin-5-yl, imidazolyl, imidazol-4-yl, imidazol-3-yl, pyrrolo[2,3-b]pyridinyl, pyrrolo[2,3-b]pyridin-5-yl, indolyl, 1H-indol-2-yl, dibenzofuranyl, dibenzofuran-4-yl, piperidinyl, piperidinylmethyl, piperidinylethyl, piperidinylpropyl, piperidinylbutyl, piperidin-1-yl, piperidin-3-yl, piperidin-4-yl, piperazinyl, piperazinylmethyl, piperazinylethyl, piperazinylpropyl, piperazinylbutyl, piperazin-1-yl, diazepanyl, diazepanylmethyl, diazepanylethyl, diazepanylpropyl, diazepanylbuytl, diazepan-1-yl, morpholinyl, morpholinylmethyl, morpholinylethyl, morpholinylpropyl, morpholinylbuytyl, morpholin-4-yl, 2-morpholin-4-yl-ethyl, 1,2,3,4-tetrahydro-isoquinolinyl, 1,2,3,4-tetrahydro-isoquinolinylmethyl, 1,2,3,4-tetrahydro-isoquinolinylethyl, 1,2,3,4-tetrahydro-isoquinolinylpropyl, 1,2,3,4-tetrahydro-isoquinolinylbutyl, 1,2,3,4-tetrahydro-isoquinolin-7-yl, benzo[1,3]dioxolyl, benzo[1,3]dioxolylmethyl, benzo[1,3]dioxolylethyl, benzo[1,3]dioxolylpropyl, benzo[1,3]dioxolylbutyl, benzo[1,3]dioxol-5-yl, benzo[1,4]oxazinyl, benzo[1,4]oxazinylmethyl, benzo[1,4]oxazinylethyl, benzo[1,4]oxazinylpropyl, benzo[1,4]oxazinylbutyl, benzo[1,4]oxazin-6-yl";

where above substituents of substituents group (i)—if not hydrogen, nitrogen or sulphur—may, optionally, additionally be substituted with at least one substituent selected from the group consisting of:"—F, —Cl, —Br, —I, —CN, —CF$_3$, —N$_3$, —NH$_2$, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —NHC(O)—NH$_2$, —C(NH)—NH$_2$, —C(O)—C(O)—NH$_2$, —C(O)—CF$_3$, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, alkyl-OH, alkyl-CN, alkyl-COOH, alkyl-P(O)(O-alkyl)$_2$, cycloalkyl-CN, aryl-OH, aryl(—OH)(-alkyl), —C(O)alkyl, —C(O)heterocyclyl, —C(O)—O—alkyl, —C(O)—O-heterocyclyl, —P(O)(O-alkyl-O—C(O)alkyl)$_2$, —OP(O)(O-alkyl)$_2$, —OS(O$_2$)alkyl, —S-alkyl, —O-alkyl, —O-aryl, —O-arylalkyl, —O-heterocyclyl, —O-heterocyclylalkyl, —O-arylalkyl-(O-alkyl)$_2$, —O-alkyl-O-alkyl, —O-alkyl-N(alkyl)$_2$, —O-alkyl-halogen, —O-alkyl-Cl, —O-alkyl-F, —O-alkyl-Br, —O-alkyl-1, —OC(O)alkyl, —OC(O)—N(alkyl)$_2$, —OC(O)—NH-alkyl, —OC(O)—(C$_9$-C$_{30}$)alkyl, —OC(O)—O-alkyl, —OC(O)—O-alkyl-O-alkyl, —OC(O)—O-aryl, —N(alkyl)$_2$, —N(aryl)$_2$, —NHC(O)alkyl, —NHC(O)alkyl-NH-alkyl, —NHC(O)alkyl-C(O)—O-alkyl, —NHC(O)—O-alkyl, —NHC(O)—O-alkyl-O-alkyl, —NHC(O)—O-alkyl-O-alkyl-O-alkyl- O-alkyl, —NHC(O)—NH-alkyl, —NHC(O)—NH-aryl, —NHC(O)—NH-heteroaryl, —NHC(O)—NH-heterocyclyl, —NHC(O)—NH-heterocyclylalkyl, —NHC(O)—NH-alkyl-halogen, —NHC(O)—NH-alkyl-Cl, —NHC(O)—N(alkyl)$_2$, —NHS(O$_2$)alkyl";

radical R4 independently is selected from the group consisting of:

(i) "hydrogen, methyl, ethyl, propyl, isopropyl, tert-butyl, hexyl, allyl, propenyl, prop-2-en-1-yl, cyclopropyl, cyclopropylmethyl, cyclopropylethyl, cyclopropyl-propyl, cyclopropylbutyl, cyclopentyl, cyclopentylmethyl, cyclopentylethyl, cyclopentylpropyl, cyclopentylbutyl, cyclohexyl, cyclohexylmethyl, cyclohexylethyl, cyclohexylpropyl, cyclohexylbutyl, phenyl, naphthalenyl, naphthalen-1-yl, naphthalen-2-yl, benzyl, phenyl-ethyl, isoxazol, pyridinyl, pyridin-2-yl, pyridin-3-yl, pyridin-4-yl, pyrazolyl, pyrazol-3-yl, pyrazol-4-yl, quinolinyl, quinolin-2-yl, quinolin-3-yl, quinolin-4-yl, quinolin-8-yl, thiophenyl, thiophen-2-yl, thiophen-3-yl, furanyl, furan-2-yl, furan-3-yl, pyrimidinyl, pyrimidin-5-yl, imidazolyl, imidazol-4-yl, imidazol-3-yl, pyrrolo[2,3-b]pyridinyl, pyrrolo[2,3-b]pyridin-5-yl, indolyl, 1H-indol-2-yl, dibenzofuranyl, dibenzofuran-4-yl, piperidinyl, piperidinylmethyl, piperidinylethyl, piperidinylpropyl, piperidinylbutyl, piperidin-1-yl, piperidin-3-yl, piperidin-4-yl, piperazinyl, piperazinylmethyl, piperazinylethyl, piperazinylpropyl, piperazinylbutyl, piperazin-1-yl, diazepanyl, diazepanylmethyl, diazepanylethyl, diazepanylpropyl, diazepanylbuytl, diazepan-1-yl, morpholinyl, morpholinylmethyl, morpholinylethyl, morpholinylpropyl, morpholinylbuytyl, morpholin-4-yl, 2-morpholin-4-yl-ethyl, 1,2,3,4-tetrahydro-isoquinolinyl, 1,2,3,4-tetrahydro-isoquinolinylmethyl, 1,2,3,4-tetrahydro-isoquinolinylethyl, 1,2,3,4-tetrahydro-isoquinolinylpropyl, 1,2,3,4-tetrahydro-isoquinolinylbutyl, 1,2,3,4-tetrahydro-isoquinolin-7-yl, benzo[1,3]dioxolyl, benzo[1,3]dioxolylmethyl, benzo[1,3]dioxolylethyl, benzo[1,3]dioxolylpropyl, benzo[1,3]dioxolylbutyl, benzo[1,3]dioxol-5-yl, benzo[1,4]oxazinyl, benzo[1,4]oxazinylmethyl, benzo[1,4]oxazinylethyl, benzo[1,4]oxazinylpropyl, benzo[1,4]oxazinylbutyl, benzo[1,4]oxazin-6-yl, —NH—R$_{y6}$" with R$_{y6}$ being selected from the group consisting of:"methyl, ethyl, propyl, isopropyl, tert-butyl, hexyl, allyl, propenyl, prop-2-en-1-yl, cyclopropyl, cyclopropylmethyl, cyclopropylethyl, cyclopropylpropyl, cyclopropylbutyl, cyclopentyl, cyclopentylmethyl, cyclopentylethyl, cyclopentylpropyl, cyclopentylbutyl, cyclohexyl, cyclohexylmethyl, cyclohexylethyl, cyclohexylpropyl, cyclohexylbutyl, phenyl, naphthalenyl, naphthalen-1-yl, naphthalen-2-yl, benzyl, phenyl-ethyl, isoxazol, pyridinyl, pyridin-2-yl, pyridin-3-yl, pyridin-4-yl, pyrazolyl, pyrazol-3-yl, pyrazol-4-yl, quinolinyl, quinolin-2-yl, quinolin-3-yl, quinolin-4-yl, quinolin-8-yl, thiophenyl, thiophen-2-yl, thiophen-3-yl, furanyl, furan-2-yl, furan-3-yl, pyrimidinyl, pyrimidin-5-yl, imidazolyl, imidazol-4-yl, imidazol-3-yl, pyrrolo[2,3-b]pyridinyl, pyrrolo[2,3-b]pyridin-5-yl, indolyl, 1H-indol-2-yl, dibenzofuranyl, dibenzofuran-4-yl, piperidinyl, piperidinylmethyl, piperidinylethyl, piperidinylpropyl, piperidinylbutyl, piperidin-1-yl, piperidin-3-yl, piperidin-4-yl, piperazinyl, piperazinylmethyl, piperazinylethyl, piperazinylpropyl, piperazinylbutyl, piperazin-1-yl, diazepanyl, diazepanylmethyl, diazepanylethyl, diazepanylpropyl, diazepanylbuytl, diazepan-1-yl, morpholinyl, morpholinylmethyl, morpholinylethyl, morpholinylpropyl, morpholinylbuytyl, morpholin-4-yl, 2-morpholin-4-yl-ethyl, 1,2,3,4-tetrahydro-isoquinolinyl, 1,2,3,4-tetrahydro-isoquinolinylmethyl, 1,2,3,4-tetrahydro-isoquinolinylethyl, 1,2,3,4-tetrahydro-isoquinolinylpropyl, 1,2,3,4-tetrahydro-isoquinolinylbutyl, 1,2,3,4-tetrahydro-isoquinolin-7-yl, benzo[1,3]dioxolyl, benzo[1,3]dioxolylmethyl, benzo[1,3]dioxolylethyl, benzo[1,3]dioxolylpropyl, benzo[1,3]dioxolylbutyl, benzo[1,3]dioxol-5-yl, benzo[1,4]oxazinyl, benzo[1,4]oxazinylmethyl, benzo[1,4]oxazinylethyl, benzo[1,4]oxazinylpropyl, benzo[1,4]oxazinylbutyl, benzo[1,4]oxazin-6-yl";

where above substituents of substituents group (i)—if not hydrogen or nitrogen—may, optionally, additionally be substituted with at least one substituent selected from the group consisting of:"—F, —Cl, —Br, —I, —CN, —CF$_3$, —N$_3$, —NH$_2$, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —NHC(O)—NH$_2$, —C(NH)—NH$_2$, —C(O)—C(O)—NH$_2$, —C(O)—CF$_3$, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, alkyl-OH, alkyl-CN, alkyl-COOH, alkyl-P(O)(O-alkyl)$_2$, cycloalkyl-CN, aryl-OH, aryl(—OH)(-alkyl), —C(O)-alkyl, —C(O)heterocyclyl, —C(O)—O-alkyl, —C(O)—O-heterocyclyl, —P(O)(O-alkyl-O—C(O)alkyl)$_2$, —OP(O)(O-alkyl)$_2$, —OS(O$_2$)alkyl, —S-alkyl, —O-alkyl, —O-aryl, —O-arylalkyl, —O-heterocyclyl, —O-heterocyclylalkyl, —O-arylalkyl-(O-alkyl)$_2$, —O-alkyl-O-alkyl, —O-alkyl-N(alkyl)$_2$, —O-alkyl-halogen, —O-alkyl-Cl, —O-alkyl-F, —O-alkyl-Br, —O-alkyl-I, —OC(O)alkyl, —OC(O)—N(alkyl)$_2$, —OC(O)—NH-alkyl, —OC(O)—(C$_9$-C$_{30}$)alkyl, —OC(O)—O-alkyl, —OC(O)—O-alkyl-O-alkyl, —OC(O)—O-aryl, —N(alkyl)$_2$, —N(aryl)$_2$, —NHC(O)alkyl, —NHC(O)alkyl-NH-alkyl, —NHC(O)alkyl-C(O)—O-alkyl, —NHC(O)—O-alkyl, —NHC(O)—O-alkyl-O-alkyl, —NHC(O)—O-alkyl-O-alkyl-O-alkyl, —NHC(O)—NH-alkyl, —NHC(O)—NH-aryl, —NHC(O)—NH-heteroaryl, —NHC(O)—NH-heterocyclyl, —NHC(O)—NH-heterocyclylalkyl, —NHC(O)—NH-alkyl-halogen, —NHC(O)—NH-alkyl-Cl, —NHC(O)—N(alkyl)$_2$, —NHS(O$_2$)alkyl";

radical R5 independently is selected from the group consisting of:

(i) "hydrogen, methyl, ethyl, propyl, isopropyl, tert-butyl, hexyl, allyl, propenyl, prop-2-en-1-yl, cyclopropyl, cyclopropylmethyl, cyclopropylethyl, cyclopropylpropyl, cyclopropylbutyl, cyclopentyl, cyclopentylmethyl, cyclopentylethyl, cyclopentylpropyl, cyclopentylbutyl, cyclohexyl, cyclohexylmethyl, cyclohexylethyl, cyclohexylpropyl, cyclohexylbutyl, phenyl, naphthalenyl, naphthalen-1-yl, naphthalen-2-yl, benzyl, phenyl-ethyl, isoxazol, pyridinyl, pyridin-2-yl, pyridin-3-yl, pyridin-4-yl, pyrazolyl, pyrazol-3-yl, pyrazol-4-yl, quinolinyl, quinolin-2-yl, quinolin-3-yl, quinolin-4-yl, quinolin-8-yl, thiophenyl, thiophen-2-yl, thiophen-3-yl, furanyl, furan-2-yl, furan-3-yl, pyrimidinyl, pyrimidin-5-yl, imidazolyl, imidazol-4-yl, imidazol-3-yl, pyrrolo[2,3-b]pyridinyl, pyrrolo[2,3-b]pyridin-5-yl, indolyl, 1H-indol-2-yl, dibenzofuranyl, dibenzofuran-4-yl, piperidinyl, piperidinylmethyl, piperidinylethyl, piperidinylpropyl, piperidinylbutyl, piperidin-1-yl, piperidin-3-yl, piperidin-4-yl, piperazinyl, piperazinylmethyl, piperazinylethyl, piperazinylpropyl, piperazinylbutyl, piperazin-1-yl, diazepanyl, diazepanylmethyl, diazepanylethyl, diazepanylpropyl, diazepanylbuytl, diazepan- 1-yl, morpholinyl, morpholinylmethyl, morpholinylethyl, morpholinylpropyl, morpholinylbuytyl, morpholin-4-yl, 2-morpholin-4-yl-ethyl, 1,2,3,4-tetrahydro-isoquinolinyl, 1,2,3,4-tetrahydro-isoquinolinylmethyl, 1,2,3,4-tetrahydro-isoquinolinylethyl, 1,2,3,4-tetrahydro-isoquinolinylpropyl, 1,2,3,4-tetrahydro-isoquinolinylbutyl, 1,2,3,4-tetrahydro-isoquinolin-7-yl, benzo[1,3]dioxolyl, benzo[1,3]dioxolylmethyl, benzo[1,3]dioxolylethyl, benzo[1,3]dioxolylpropyl, benzo[1,3]dioxolylbutyl, benzo[1,3]dioxol-5-yl, benzo[1,4]oxazinyl, benzo[1,4]oxazinylmethyl, benzo[1,4]oxazinylethyl, benzo[1,4]oxazinylpropyl, benzo[1,4]oxazinylbutyl, benzo[1,4]oxazin-6-yl;

where above substituents of substituents group (i)—if not hydrogen or nitrogen—may, optionally, additionally be substituted with at least one substituent selected from the group consisting of:"—F, —Cl, —Br, —I, —CN, —CF$_3$, —N$_3$, —NH$_2$, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —NHC(O)—NH$_2$, —C(NH)—NH$_2$, —C(O)—C(O)—NH$_2$, —C(O)—CF$_3$, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, alkyl-OH, alkyl-CN, alkyl-COOH, alkyl-P(O)(O-alkyl)$_2$, cycloalkyl-CN, aryl-OH, aryl(—OH)(-alkyl), —C(O)alkyl, —C(O)heterocyclyl, —C(O)—O-alkyl, —C(O)—O-heterocyclyl, —P(O)(O-alkyl-O—C(O)alkyl)$_2$, —OP(O)(O-alkyl)$_2$, —OS(O$_2$)alkyl, —S-alkyl, —O-alkyl, —O-aryl, —O-arylalkyl, —O-heterocyclyl, —O-heterocyclylalkyl, —O-arylalkyl-(O-alkyl)$_2$, —O-alkyl-O-alkyl, —O-alkyl-N(alkyl)$_2$, —O-alkyl-halogen, —O-alkyl-Cl, —O-alkyl-F, —O-alkyl-Br, —O-alkyl-1, —OC(O)alkyl, —OC(O)—N(alkyl)$_2$, —OC(O)—NH-alkyl, —OC(OH(C$_9$-C$_{30}$)alkyl, —OC(O)—O-alkyl, —OC(O)—O-alkyl-O-alkyl, —OC(O)—O-aryl, —N(alkyl)$_2$, —N(aryl)$_2$, —NHC(O)alkyl, —NHC(O)alkyl-NH-alkyl, —NHC(O)alkyl-C(O)—O-alkyl, —NHC(O)—O-alkyl, —NHC(O)—O-alkyl-O-alkyl, —NHC(O)—O-alkyl-O-alkyl-O-alkyl-O-alkyl, —NHC(O)—NH-alkyl, —NHC(O)—NH-aryl, —NHC(O)—NH-heteroaryl, —NHC(O)—NH-heterocyclyl, —NHC(O)—NH-heterocyclylalkyl, —NHC(O)—NH-alkyl-halogen, —NHC(O)—NH-alkyl-Cl, —NHC(O)—N(alkyl)$_2$, —NHS(O$_2$)alkyl";

In another preferred embodiment, pyrido[2,3-b]pyrazine derivatives according to above general formula (I) and preferred embodiments and subsets are provided, wherein:

radical R1 independently is selected from the group consisting of:

(i) "—NH—C(O)—NH$_2$, —NH—C(S)—NH$_2$, —NH—C(O)—NH-alkyl, —NH—C(O)—NH—(C9-C30)alkyl, —NH—C(O)—NH-cycloalkyl, —NH—C(O)—NH-cycloalkylalkyl, —NH—C(O)—NH-aryl, —NH—C(O)—NH-arylalkyl, —NH—C(O)—NH-heteroaryl, —NH—C(O)—NH-heteroarylalkyl, —NH—C(O)—NH-heterocyclyl, —NH—C(O)—NH-heterocyclylalkyl, —NH—C(S)—NH-alkyl, —NH—C(S)—NH—(C9-C30)alkyl, —NH—C(S)—NH-cycloalkyl, —NH—C(S)—NH-cycloalkylalkyl, —NH—C(S)—NH-aryl, —NH—C(S)—NH-arylalkyl, —NH—C(S)—NH-heteroaryl, —NH—C(S)—NH-heteroarylalkyl, —NH—C(S)—NH-heterocyclyl, —NH—C(S)—NH-heterocyclylalkyl, —NH—C(O)—alkyl, —NH—C(O)—(C9-C30)alkyl, —NH—C(O)cycloalkyl, —NH—C(O)—cycloalkylalkyl, —NH—C(O)aryl, —NH—C(O)arylalkyl, —NH—C(O)heteroaryl, —NH—C(O)heteroarylalkyl, —NH—C(O)heterocyclyl, —NH—C(O)—heterocyclylalkyl, —NH—C(S)alkyl, —NH—C(S)—(C9-C30)alkyl, —NH—C(S)cycloalkyl, —NH—C(S)cycloalkylalkyl, —NH—C(S)aryl, —NH—C(S)arylalkyl, —NH—C(S)-heteroaryl, —NH—C(S)-heteroarylalkyl, —NH—C(S)heterocyclyl, —NH—C(S)heterocyclylalkyl";

where above substituents of substituents group (i)—if not hydrogen, nitrogen or sulphur—may, optionally, additionally be substituted with at least one substituent selected from the group consisting of:"—F, —Cl, —Br, —I, —CN, —CF$_3$, —N$_3$, —NH$_2$, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —NHC(O)—NH$_2$, —C(NH)—NH$_2$, —C(O)—C(O)—NH$_2$, —C(O)—CF$_3$, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, alkyl-OH, alkyl-CN, alkyl-COOH, alkyl-P(O)(O-alkyl)$_2$, cycloalkyl-CN, aryl-OH, aryl(—OH)(-alkyl), —C(O)-alkyl, —C(O)-heterocyclyl, —C(O)—O-alkyl, —C(O—O-heterocyclyl, —P(O)(O-alkyl-O—C(O)-alkyl)$_2$, —OP(O)(O-alkyl)$_2$, —OS(O$_2$)alkyl, —S-alkyl, —O-alkyl, —O-aryl, —O-arylalkyl, —O-heterocyclyl, —O-heterocyclylalkyl, —O-arylalkyl-(O-alkyl)$_2$, —O-alkyl-O-alkyl, —O-alkyl-N(alkyl)$_2$, —O-alkyl-halogen, —O-alkyl-Cl, —O-alkyl-F, —O-alkyl-Br, —O-alkyl-1, —OC(O)alkyl, —OC(O)—N(alkyl)$_2$, —OC(O)—NH-alkyl, —OC(O)—(C$_9$-C$_{30}$)alkyl, —OC(O)—O-alkyl, —OC(O)—O-alkyl-O-alkyl, —OC(O)—O-aryl, —N(alkyl)$_2$, —N(aryl)$_2$, —NHC(O)alkyl, —NHC(O)alkyl-NH-alkyl, —NHC(O)alkyl-C(O)—O-alkyl, —NHC(O)—O-alkyl, —NHC(O)—O-alkyl-O-alkyl, —NHC(O)—O-alkyl-O-alkyl-O-alkyl-O-alkyl, —NHC(O)—NH-alkyl, —NHC(O)—NH-aryl, —NHC(O)—NH-heteroaryl, —NHC(O)—NH-heterocyclyl, —NHC(O)—NH-heterocyclylalkyl, —NHC(O)—NH-alkyl-halogen, —NHC(O)—NH-alkyl-Cl, —NHC(O)—N(alkyl)$_2$, —NHS(O$_2$)alkyl";

radical R2 independently is "hydrogen";

radical R3 independently is selected from the group consisting of:

(i) "alkyl, (C9-C30)alkyl, cycloalkyl, cycloalkylalkyl, aryl, arylalkyl, heteroaryl, heteroarylalkyl, heterocyclyl, heterocyclylalkyl, —NH-alkyl, —NH—(C9-C30)alkyl, —NH-cycloalkyl, —NH-cycloalkylalkyl, —NH-aryl, —NH-arylalkyl, —NH-heteroaryl, —NH-heteroarylalkyl, —NH-heterocyclyl, —NH-heterocyclylalkyl";

where above substituents of substituents group (i)—if not hydrogen or nitrogen—may, optionally, additionally be substituted with at least one substituent selected from the group consisting of:"—F, —Cl, —Br, —I, —CN, —CF$_3$, —N$_3$, —NH$_2$, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —NHC(O)—NH$_2$, —C(NH)—NH$_2$, —C(O)—C(O)—NH$_2$, —C(O)—CF$_3$, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, alkyl-OH, alkyl-CN, alkyl-COOH, alkyl-P(O)(O-alkyl)$_2$, cycloalkyl-CN, aryl-OH, aryl(—OH)(-alkyl), —C(O)alkyl, —C(O)heterocyclyl, —C(OO-alkyl, —C(O)—O-heterocyclyl, —P(O)(O-alkyl-O—C(O)alkyl)$_2$, —OP(O)(O-alkyl)$_2$, —OS(O$_2$)alkyl, —S-alkyl, —O-alkyl, —O-aryl, —O-arylalkyl, —O-heterocyclyl, —O-heterocyclylalkyl, —O-arylalkyl-(O-alkyl)$_2$, —O-alkyl-O-alkyl, —O-alkyl-N(alkyl)$_2$, —O-alkyl-halogen, —O-alkyl-Cl, —O-alkyl-F, —O-alkyl-Br, —O-alkyl-1, —OC(O)alkyl, —OC(O)—N(alkyl)$_2$, —OC(O)—NH-alkyl, —OC(O)(C$_9$-C$_{30}$)alkyl, —OC(O)—O-alkyl, —OC(O)—O-alkyl-O-alkyl, —OC(O)—O-aryl, —N(alkyl)$_2$, —N(aryl)$_2$, —NHC(O)alkyl, —NHC(O)-alkyl-NH-alkyl, —NHC(O)alkyl-C(O)—O-alkyl, —NHC(O)—O-alkyl, —NHC(O)—O-alkyl-O-alkyl, —NHC(O)—O-alkyl-O-alkyl-O-alkyl-O-alkyl, —NHC(O)—NH-alkyl, —NHC(O)—NH-aryl, —NHC(O)—NH-heteroaryl, —NHC(O)—NH-heterocyclyl, —NHC(O)—NH-heterocyclylalkyl, —NHC(O)—NH-alkyl-halogen, —NHC(O)—NH-alkyl-Cl, —NHC(O)—N(alkyl)$_2$, —NHS(O$_2$)alkyl";

radical R4 independently is selected from the group consisting of:

(i) "hydrogen, alkyl, (C9-C30)alkyl, cycloalkyl, cycloalkylalkyl, aryl, arylalkyl, heteroaryl, heteroarylalkyl, heterocyclyl, heterocyclylalkyl, —NH-alkyl, —NH—(C9-C30)alkyl, —NH-cycloalkyl, —NH-cycloalkylalkyl, —NH-aryl, —NH-arylalkyl, —NH-heteroaryl, —NH-heteroarylalkyl, —NH-heterocyclyl, —NH-heterocyclylalkyl";

where above substituents of substituents group (i)—if not hydrogen or nitrogen—may, optionally, additionally be substituted with at least one substituent selected from the group consisting of:"—F, —Cl, —Br, —I, —CN, —CF$_3$, —N$_3$, —NH$_2$, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —NHC(O)—NH$_2$, —C(NH)—NH$_2$, —C(O)—C(O)—NH$_2$, —C(O)—CF$_3$, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, alkyl-OH, alkyl-CN, alkyl-COOH, alkyl-P(O)(O-alkyl)$_2$, cycloalkyl-CN, aryl-OH, aryl(—OH)(-alkyl), —C(O)alkyl, —C(O)heterocyclyl, —C(O)—O-alkyl, —C(O)—O-heterocyclyl, —P(O)(O-alkyl-O—C(O)alkyl)$_2$, —OP(O)(O-alkyl)$_2$, —OS(O$_2$)alkyl, —S-alkyl, —O-alkyl, —O-aryl, —O-arylalkyl, —O-heterocyclyl, —O-heterocyclylalkyl, —O-arylalkyl-(O-alkyl)$_2$, —O-alkyl-O-alkyl, —O-alkyl-N(alkyl)$_2$, —O-alkyl-halogen, —O-alkyl-Cl, —O-alkyl-F, —O-alkyl-Br, —Oalkyl-1, —OC(O)alkyl, —OC(O)—N(alkyl)$_2$, —OC(O)—NH-alkyl, —OC(O)(C$_9$-C$_{30}$)alkyl, —OC(O)—O-alkyl, —OC(O)—O-alkyl-O-alkyl, —OC(O)—O-aryl, —N(alkyl)$_2$, —N(aryl)$_2$, —NHC(O)alkyl, —NHC(O)alkyl-NH-alkyl, —NHC(O)alkyl-C(O)—O-alkyl, —NHC(O)—O-alkyl, —NHC(O)—O-alkyl-O-alkyl, —NHC(O)—O-alkyl-O-alkyl-O-alkyl-O-alkyl, —NHC(O)—NH-alkyl, —NHC(O)—NH-aryl, —NHC(O)—NH-heteroaryl, —NHC(O)—NH-heterocyclyl, —NHC(O)—NH-heterocyclylalkyl, —NHC(O)—NH-alkyl-halogen, —NHC(O)—NH-alkyl-Cl, —NHC(O)—N(alkyl)$_2$, —NHS(O$_2$)alkyl";

radical R5 independently is "hydrogen".

In yet another preferred embodiment, pyrido[2,3-b]pyrazine derivatives according to above general formula (I) and preferred embodiments and subsets are provided, wherein:

radical R$_1$ independently is selected from the group consisting of:

(i) "—NH—C(O)—NH$_2$, —NH—C(S)—NH$_2$, —NH—C(O)—NH—R$_{11}$, —NH—C(S)—NH—R$_{12}$, —NH—C(O)—R$_{y3}$, —NH—C(S)—NH—R$_{z4}$", with R$_{z1}$, R$_{z2}$, R$_{z3}$, R$_{z4}$ independently from each other being selected from the group consisting of:"methyl, ethyl, propyl, isopropyl, tert-butyl, hexyl, allyl, propenyl, prop-2-en-1-yl, cyclopropyl, cyclopropylmethyl, cyclopropylethyl, cyclopropylpropyl, cyclopropylbutyl, cyclopentyl, cyclopentylmethyl, cyclopentylethyl, cyclopentylpropyl, cyclopentylbutyl, cyclohexyl, cyclohexylmethyl, cyclohexylethyl, cyclohexylpropyl, cyclohexylbutyl, phenyl, naphthalenyl, naphthalen-1-yl, naphthalen-2-yl, benzyl, phenyl-ethyl, isoxazol, pyridinyl, pyridin-2-yl, pyridin-3-yl, pyridin-4-yl, pyrazolyl, pyrazol-3-yl, pyrazol-4-yl, quinolinyl, quinolin-2-yl, quinolin-3-yl, quinolin-4-yl, quinolin-8-yl, thiophenyl, thiophen-2-yl, thiophen-3-yl, furanyl, furan-2-yl, furan-3-yl, pyrimidinyl, pyrimidin-5-yl, imidazolyl, imidazol-4-yl, imidazol-3-yl, pyrrolo[2,3-b]pyridinyl, pyrrolo[2,3-b]pyridin-5-yl, indolyl, 1H-indol-2-yl, dibenzofuranyl, dibenzofuran-4-yl, piperidinyl, piperidinylmethyl, piperidinylethyl, piperidinylpropyl, piperidinylbutyl, piperidin-1-yl, piperidin-3-yl, piperidin-4-yl, piperazinyl, piperazinylmethyl, piperazinylethyl, piperazinylpropyl, piperazinylbutyl, piperazin-1-yl, diazepanyl, diazepanylmethyl, diazepanylethyl, diazepanylpropyl, diazepanylbuytl, diazepan-1-yl, morpholinyl, morpholinylmethyl, morpholinylethyl, morpholinylpropyl, morpholinylbuytyl, morpholin-4-yl, 2-morpholin-4-yl-ethyl, 1,2,3,4-tetrahydro-isoquinolinyl; 1,2,3,4-tetrahydroisoquinolinylmethyl, 1,2,3,4-tetrahydro-isoquinolinylethyl, 1,2,3,4-tetrahydro-isoquinolinylpropyl, 1,2,3,4-tetrahydro-isoquinolinylbutyl, 1,2,3,4-tetrahydro-isoquinolin-7-yl, benzo[1,3]dioxolyl, benzo[1,3]dioxolylmethyl, benzo[1,3]dioxolylethyl, benzo[1,3]dioxolylpropyl, benzo[1,3]dioxolylbutyl, benzo[1,3]dioxol-5-yl, benzo[1,4]oxazinyl, benzo[1,4]oxazinylmethyl, benzo[1,4]oxazinylethyl, benzo[1,4]oxazinylpropyl, benzo[1,4]oxazinylbutyl, benzo[1,4]oxazin-6-yl";

where above substituents of substituents group (i)- if not hydrogen, nitrogen or sulphur—may, optionally, additionally be substituted with at least one substituent selected from the group consisting of:"—F, —Cl, —Br, —I, —CN, —CF$_3$, —N$_3$, —NH$_2$, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —NHC(O)—NH$_2$, —C(NH)—NH$_2$, —C(O)—C(O)—NH$_2$, —C(O)—CF$_3$, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, alkyl-OH, alkyl-CN, alkyl-COOH, alkyl-P(O)(O-alkyl)$_2$, cycloalkyl-CN, aryl-OH, aryl(—OH)(-alkyl), —C(O)alkyl, —C(O)heterocyclyl, —C(O)—O-alkyl, —C(O)—O-heterocyclyl, —P(O)(O-alkyl-O—C(O)alkyl)$_2$, —OP(O)(O-alkyl)$_2$, —OS(O$_2$)-alkyl, —S-alkyl, —O-alkyl, —O-aryl, —O-arylalkyl, —O-heterocyclyl, —O-heterocyclylalkyl, —O-arylalkyl-(O-alkyl)$_2$, —O-alkyl-O-alkyl, —O-alkyl-N(alkyl)$_2$, —O-alkyl-halogen, —O-alkyl-Cl, —O-alkyl-F, —O-alkyl-Br, —O-alkyl-1, —OC(O)alkyl, —OC(O)—N(alkyl)$_2$, —OC(O)—NH-alkyl, —OC(O)—(C$_9$-C$_{30}$)alkyl, —OC(O)—O-alkyl, —OC(O)—O-alkyl-O-alkyl, —OC(O)—O-aryl, —N(alkyl)$_2$, —N(aryl)$_2$, —NHC(O)alkyl, —NHC(O)alkyl-NH-alkyl, —NHC(O)alkyl-C(O)—O-alkyl, —NHC(O)—O-alkyl, —NHC(O)—O-alkyl-O-alkyl, —NHC(O)—O-alkyl-O-alkyl-O-alkyl, —NHC(O)—NH-alkyl, —NHC(O)—NH-aryl, —NHC(O)—NH-heteroaryl, —NHC(O)—NH-heterocyclyl, —NHC(O)—NH-heterocyclylalkyl, —NH C(O)—NH-alkyl-halogen, —NHC(O)—NH-alkyl-Cl, —NHC(O)—N(alkyl)$_2$, —NHS(O$_2$)alkyl";

radical R2 independently is "hydrogen";

radical R3 independently is selected from the group consisting of:
(i) "methyl, ethyl, propyl, isopropyl, tert-butyl, hexyl, allyl, propenyl, prop-2-en-1-yl, cyclopropyl, cyclopropylmethyl, cyclopropylethyl, cyclopropylpropyl, cyclopropylbutyl, cyclopentyl, cyclopentylmethyl, cyclopentylethyl, cyclopentylpropyl, cyclopentylbutyl, cyclohexyl, cyclohexylmethyl, cyclohexylethyl, cyclohexylpropyl, cyclohexylbutyl, phenyl, naphthalenyl, naphthalen-1-yl, naphthalen-2-yl, benzyl, phenyl-ethyl, isoxazol, pyridinyl, pyridin-2-yl, pyridin-3-yl, pyridin-4-yl, pyrazolyl, pyrazol-3-yl, pyrazol-4-yl, quinolinyl, quinolin-2-yl, quinolin-3-yl, quinolin-4-yl, quinolin-8-yl, thiophenyl, thiophen-2-yl, thiophen-3-yl, furanyl, furan-2-yl, furan-3-yl, pyrimidinyl, pyrimidin-5-yl, imidazolyl, imidazol-4-yl, imidazol-3-yl, pyrrolo[2,3-b]pyridinyl, pyrrolo[2,3-b]pyridin-5-yl, indolyl, 1H-indol-2-yl, dibenzofuranyl, dibenzofuran-4-yl, piperidinyl, piperidinylmethyl, piperidinylethyl, piperidinylpropyl, piperidinylbutyl, piperidiri-1-yl, piperidin-3-yl, piperidin-4-yl, piperazinyl, piperazinylmethyl, piperazinylethyl, piperazinylpropyl, piperazinylbutyl, piperazin-1-yl, diazepanyl, diazepanylmethyl, diazepanylethyl, diazepanylpropyl, diazepanylbuytl, diazepan-1-yl, morpholinyl, morpholinylmethyl, morpholinylethyl, morpholinylpropyl, morpholinylbuytyl, morpholin-4-yl, 2-morpholin-4-yl-ethyl, 1,2,3,4-tetrahydro-isoquinolinyl, 1,2,3,4-tetrahydro-isoquinolinylmethyl, 1,2,3,4-tetrahydro-isoquinolinylethyl, 1,2,3,4-tetrahydro-isoquinolinylpropyl, 1,2,3,4-tetrahydro-isoquinolinylbutyl, 1,2,3,4-tetrahydro-isoquinolin-7-yl, benzo[1,3]dioxolyl, benzo[1,3]dioxolylmethyl, benzo[1,3]dioxolylethyl, benzo[1,3]dioxolylpropyl, benzo[1,3]dioxolylbutyl, benzo[1,3]dioxol-5-yl, benzo[1,4]oxazinyl, benzo[1,4]oxazinylmethyl, benzo[1,4]oxazinylethyl, benzo[1,4]oxazinylpropyl, benzo[1,4]oxazinylbutyl, benzo[1,4]oxazin-6-yl, —NH—$R_{z5}$" with $R_{z5}$ being selected from the group consisting of:"methyl, ethyl, propyl, isopropyl, tert-butyl, hexyl, allyl, propenyl, prop-2-en-1-yl, cyclopropyl, cyclopropylmethyl, cyclopropylethyl, cyclopropylpropyl, cyclopropylbutyl, cyclopentyl, cyclopentylmethyl, cyclopentylethyl, cyclopentylpropyl, cyclopentylbutyl, cyclohexyl, cyclohexylmethyl, cyclohexylethyl, cyclohexylpropyl, cyclohexylbutyl, phenyl, naphthalenyl, naphthalen-1-yl, naphthalen-2-yl, benzyl, phenyl-ethyl, isoxazol, pyridinyl, pyridin-2-yl, pyridin-3-yl, pyridin-4-yl, pyrazolyl, pyrazol-3-yl, pyrazol-4-yl, quinolinyl, quinolin-2-yl, quinolin-3-yl, quinolin-4-yl, quinolin-8-yl, thiophenyl, thiophen-2-yl, thiophen-3-yl, furanyl, furan-2-yl, furan-3-yl, pyrimidinyl, pyrimidin-5-yl, imidazolyl, imidazol-4-yl, imidazol-3-yl, pyrrolo[2,3-b]pyridinyl, pyrrolo[2,3-b]pyridin-5-yl, indolyl, 1H-indol-2-yl, dibenzofuranyl, dibenzofuran-4-yl, piperidinyl, piperidinylmethyl, piperidinylethyl, piperidinylpropyl, piperidinylbutyl, piperidin-1-yl, piperidin-3-yl, piperidin-4-yl, piperazinyl, piperazinylmethyl, piperazinylethyl, piperazinylpropyl, piperazinylbutyl, piperazin-1-yl, diazepanyl, diazepanylmethyl, diazepanylethyl, diazepanylpropyl, diazepanylbuytl, diazepan-1-yl, morpholinyl, morpholinylmethyl, morpholinylethyl, morpholinylpropyl, morpholinylbuytyl, morpholin-4-yl, 2-morpholin-4-yl-ethyl, 1,2,3,4-tetrahydro-isoquinolinyl, 1,2,3,4-tetrahydro-isoquinolinylmethyl, 1,2,3,4-tetrahydro-isoquinolinylethyl, 1,2,3,4-tetrahydro-isoquinolinylpropyl, 1,2,3,4-tetrahydro-isoquinolinylbutyl, 1,2,3,4-tetrahydro-isoquinolin-7-yl, benzo[1,3]dioxolyl, benzo[1,3]dioxolylmethyl, benzo[1,3]dioxolylethyl, benzo[1,3]dioxolylpropyl, benzo[1,3]dioxolylbutyl, benzo[1,3]dioxol-5-yl, benzo[1,4]oxazinyl, benzo[1,4]oxazinylmethyl, benzo[1,4]oxazinylethyl, benzo[1,4]oxazinylpropyl, benzo[1,4]oxazinylbutyl, benzo[1,4]oxazin-6-yl";

where above substituents of substituents group (i)—if not hydrogen or nitrogen—may, optionally, additionally be substituted with at least one substituent selected from the group consisting of:"—F, —Cl, —Br, —I, —CN, —$CF_3$, —$N_3$, —$NH_2$, —$NO_2$, —OH, =O, —$OCF_3$, —$OCHF_2$, —SH, —O—$SO_3H$, —OP(O)(OH)$_2$, —CHO, —COOH, —C(O)—$NH_2$, —$SO_3H$, —P(O)(OH)$_2$, —NHC(O)—$NH_2$, —C(NH)—$NH_2$, —C(O)—C(O)—$NH_2$, —C(O)—$CF_3$, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, alkyl-OH, alkyl-CN, alkyl-COOH, alkyl-P(O)(O-alkyl)$_2$, cycloalkyl-CN, aryl-OH, aryl(—OH)(-alkyl), —C(O)-alkyl, —C(O)-heterocyclyl, —C(O)—O-alkyl, —C(O)—O-heterocyclyl, —P(O)(O-alkyl-O—C(O)-alkyl)$_2$, —OP(O)(O-alkyl)$_2$, —OS(O$_2$)-alkyl, —S-alkyl, —O-alkyl, —O-aryl, —O-arylalkyl, —O-heterocyclyl, —O-heterocyclylalkyl, —O-arylalkyl-(O-alkyl)$_2$, —O-alkyl-O-alkyl, —O-alkyl-N(alkyl)$_2$, —O-alkyl-halogen, —O-alkyl-Cl, —O-alkyl-F, —O-alkyl-Br, —O-alkyl-I, —OC(O)-alkyl, —OC(O)—N(alkyl)$_2$, —OC(O)—NH-alkyl, —OC(O)—($C_9$-$C_{30}$)alkyl, —OC(O)—O-alkyl, —OC(O)—O-alkyl-O-alkyl, —OC(O)—O-aryl, —N(alkyl)$_2$, —N(aryl)$_2$, —NHC(O)-alkyl, —NHC(O)-alkyl-NH-alkyl, —NHC(O)-alkyl-C(O)—O-alkyl, —NHC(O)—O-alkyl, —NHC(O)—O-alkyl-O-alkyl, —NHC(O)—O-alkyl-O-alkyl-O-alkyl, —NHC(O)—NH-alkyl, —NHC(O)—NH-aryl, —NHC(O)—NH-heteroaryl, —NHC(O)—NH-heterocyclyl, —NHC(O)—NH-heterocyclylalkyl, —NHC(O)—NH-alkyl-halogen, —NHC(O)—NH-alkyl-Cl, —NHC(O)—N(alkyl)$_2$, —NHS(O$_2$)-alkyl";

radical R4 independently is selected from the group consisting of:
(i) "hydrogen, methyl, ethyl, propyl, isopropyl, tert-butyl, hexyl, allyl, propenyl, prop-2-en-1-yl, cyclopropyl, cyclopropylmethyl, cyclopropylethyl, cyclopropylpropyl, cyclopropylbutyl, cyclopentyl, cyclopentylmethyl, cyclopentylethyl, cyclopentylpropyl, cyclopentylbutyl, cyclohexyl, cyclohexylmethyl, cyclohexylethyl, cyclohexylpropyl, cyclohexylbutyl, phenyl, naphthalenyl, naphthalen-1-yl, naphthalen-2-yl, benzyl, phenyl-ethyl, isoxazol, pyridinyl, pyridin-2-yl, pyridin-3-yl, pyridin-4-yl, pyrazolyl, pyrazol-3-yl, pyrazol-4-yl, quinolinyl, quinolin-2-yl, quinolin-3-yl, quinolin-4-yl, quinolin-8-yl, thiophenyl, thiophen-2-yl, thiophen-3-yl, furanyl, furan-2-yl, furan-3-yl, pyrimidinyl, pyrimidin-5-yl, imidazolyl, imidazol-4-yl, imidazol-3-yl, pyrrolo[2,3-b]pyridinyl, pyrrolo[2,3-b]pyridin-5-yl, indolyl, 1H-indol-2-yl, dibenzofuranyl, dibenzofuran-4-yl, piperidinyl, piperidinylmethyl, piperidinylethyl, piperidinylpropyl, piperidinylbutyl, piperidin-1-yl, piperidin-3-yl, piperidin-4-yl, piperazinyl, piperazinylmethyl, piperazinylethyl, piperazinylpropyl, piperazinylbutyl, piperazin-1-yl, diazepanyl, diazepanylmethyl, diazepanylethyl, diazepanylpropyl, diazepanylbuytl, diazepan-1-yl, morpholinyl, morpholinylmethyl, morpholinylethyl, morpholinylpropyl, morpholinylbuytyl, morpholin-4-yl, 2-morpholin-4-yl-ethyl, 1,2,3,4-tetrahydro-isoquinolinyl, 1,2,3,4-tetrahydro-isoquinolinylmethyl, 1,2,3,4-tetrahydro-isoquinolinylethyl, 1,2,3,4-tetrahydro-isoquinolinylpropyl, 1,2,3,4-tetrahydro-isoquinolinylbutyl, 1,2,3,4-tetrahydro-isoquinolin-7-yl, benzo[1,3]dioxolyl, benzo[1,3]dioxolylmethyl, benzo[1,3]dioxolylethyl, benzo[1,3]dioxolylpropyl, benzo[1,3]dioxolylbutyl, benzo[1,3]dioxol-5-yl, benzo[1,4]oxazinyl, benzo[1,4]oxazinylmethyl, benzo[1,4]oxazinylethyl, benzo[1,4]oxazinylpropyl, benzo[1,4]oxazinylbutyl, benzo[1,4]oxazin-6-yl";

where above substituents of substituents group (i)—if not hydrogen or nitrogen—may, optionally, additionally be substituted with at least one substituent selected from the group consisting of:"—F, —Cl, —Br, —I, —CN, —CF$_3$, —N$_3$, —NH$_2$, —NO$_2$, —OH, =O, —OCF$_3$, —OCHF$_2$, —SH, —O—SO$_3$H, —OP(O)(OH)$_2$, —CHO, —COOH, —C(O)—NH$_2$, —SO$_3$H, —P(O)(OH)$_2$, —NHC(O)—NH$_2$, —C(NH)—NH$_2$, —C(O)—C(O)—NH$_2$, —C(O)—CF$_3$, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, alkyl-OH, alkyl-CN, alkyl-COOH, alkyl-P(O)(O-alkyl)$_2$, cycloalkyl-CN, aryl-OH, aryl(—OH)(-alkyl), —C(O)-alkyl, —C(O)-heterocyclyl, —C(O)—O-alkyl, —C(O)—O-heterocyclyl, —P(O)(O-alkyl-O—C(O)-alkyl)$_2$, —OP(O)(O-alkyl)$_2$, —OS(O$_2$)-alkyl, —S-alkyl, —O-alkyl, —O-aryl, —O-arylalkyl, —O-heterocyclyl, —O-heterocyclylalkyl, —O-arylalkyl-O)-alkyl)$_2$, —O-alkyl-O-alkyl, —O-alkyl-N(alkyl)$_2$, —O-alkyl-halogen, —O-alkyl-Cl, —O-alkyl-F, —O-alkyl-Br, —O-alkyl-I, —OC(O)-alkyl, —OC(O)—N(alkyl)$_2$, —OC(O)—NH-alkyl, —OC(O)—(C$_9$-C$_{30}$)alkyl, —OC(O)—O-alkyl, —OC(O)—O-alkyl-O-alkyl, —OC(O)—O-aryl, —N(alkyl)$_2$, —N(aryl)$_2$, —NHC(O)-alkyl, —NHC(O)-alkyl-NH-alkyl, —NHC(O)-alkyl-C(O)—O-alkyl, —NHC(O)—O-alkyl, —NHC(O)—O-alkyl-O-alkyl, —NHC(O)—O-alkyl-O-alkyl-O-alkyl-O-alkyl, —NHC(O)—NH-alkyl, —NHC(O)—NH-aryl, —NHC(O)—NH-heteroaryl, —NHC(O)—NH-heterocyclyl, —NHC(O)—NH-heterocyclylalkyl, —NHC(O)—NH-alkyl-halogen, —NHC(O)—NH-alkyl-Cl, —NHC(O)—N(alkyl)$_2$, —NHS(O$_2$)-alkyl";

radical R5 independently is "hydrogen".

In another preferred embodiment, pyrido[2,3-b]pyrazine derivatives according to general formula (I) and above preferred embodiments and subsets are provided that are selected from the group consisting of:

| Compound | Structure | Name |
|---|---|---|
| 1 | 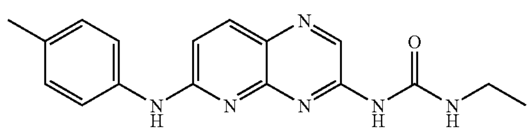 | 1-Ethyl-3-(6-p-tolylamino-pyrido[2,3-b]pyrazin-3-yl)-urea |
| 2 | 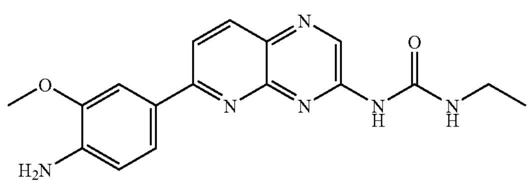 | 1-[6-(4-Amino-3-methoxy-phenyl)-pyrido[2,3-b]pyrazin-3-yl]-3-ethyl-urea |
| 3 | 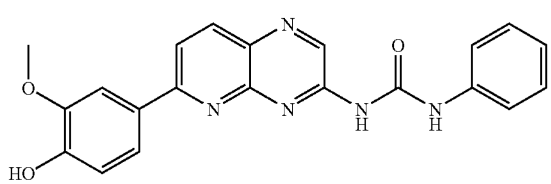 | 1-[6-(4-Hydroxy-3-methoxy-phenyl)-pyrido[2,3-b]pyrazin-3-yl]-3-phenyl-urea |
| 4 | 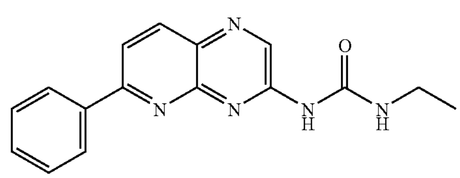 | 1-Ethyl-3-(6-phenyl-pyrido[2,3-b]pyrazin-3-yl)-urea |
| 5 | 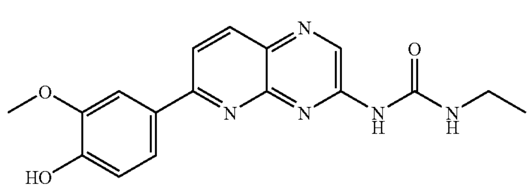 | 1-Ethyl-3-[6-(4-hydroxy-3-methoxy-phenyl)-pyrido[2,3-b]pyrazin-3-yl]-urea |

-continued

| Compound | Structure | Name |
|---|---|---|
| 6 | 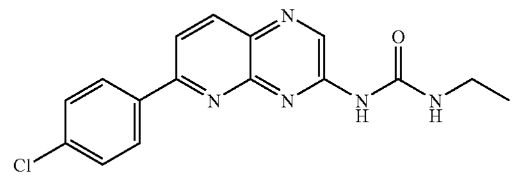 | 1-[6-(4-Chloro-phenyl)-pyrido[2,3-b]pyrazin-3-yl]-3-ethyl-urea |
| 7 | 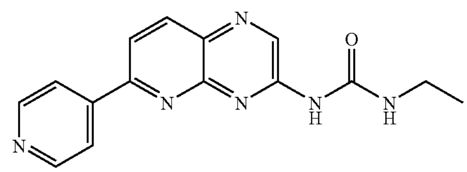 | 1-Ethyl-3-(6-pyridin-4-yl-pyrido[2,3-b]pyrazin-3-yl)-urea |
| 8 | 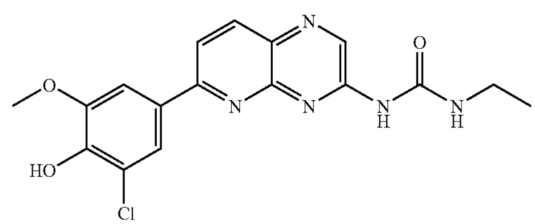 | 1-[6-(3-Chloro-4-hydroxy-5-methoxy-phenyl)-pyrido[2,3-b]pyrazin-3-yl]-3-ethyl-urea |
| 9 | 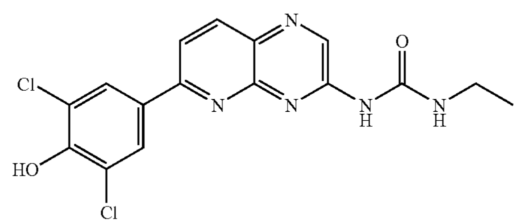 | 1-[6-(3,5-Dichloro-4-hydroxy-phenyl)-pyrido[2,3-b]pyrazin-3-yl]-3-ethyl-urea |
| 10 | 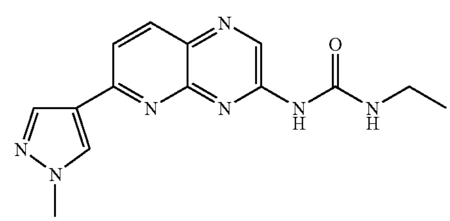 | 1-Ethyl-3-[6-(1-methyl-1H-pyrazol-4-yl)-pyrido[2,3-b]pyrazin-3-yl]-urea |
| 11 | 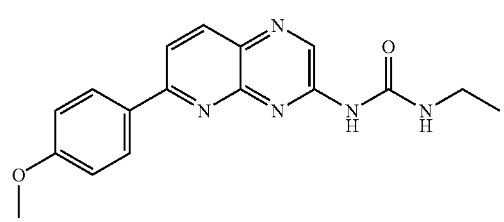 | 1-Ethyl-3-[6-(4-methoxy-phenyl)-pyrido[2,3-b]pyrazin-3-yl]-urea |
| 12 | 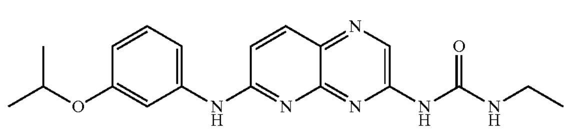 | 1-Ethyl-3-[6-(3-isopropoxy-phenylamino)-pyrido[2,3-b]pyrazin-3-yl]-urea |
| 13 | 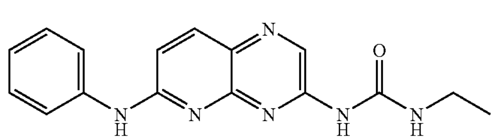 | 1-Ethyl-3-(6-phenylamino-pyrido[2,3-b]pyrazin-3-yl)-urea |

-continued

| Compound | Structure | Name |
|---|---|---|
| 14 | 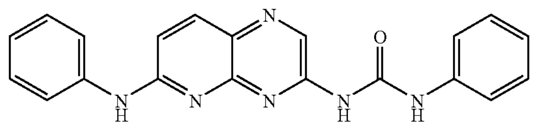 | 1-Phenyl-3-(6-phenylamino-pyrido[2,3-b]pyrazin-3-yl)-urea |
| 15 | 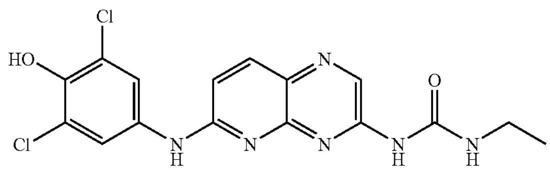 | 1-[6-(3,5-Dichloro-4-hydroxy-phenylamino)-pyrido[2,3-b]pyrazin-3-yl]-3-ethyl-urea |
| 16 | 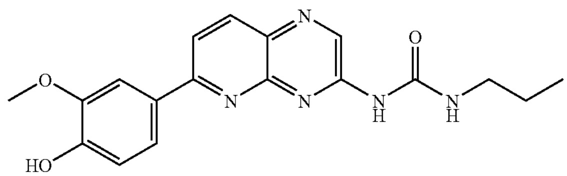 | 1-[6-(4-Hydroxy-3-methoxy-phenyl)-pyrido[2,3-b]pyrazin-3-yl]-3-propyl-urea |
| 17 | 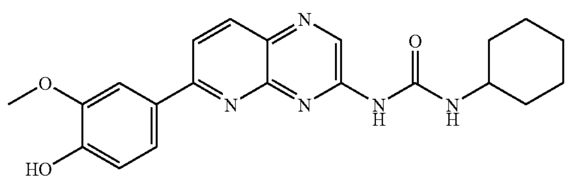 | 1-Cyclohexyl-3-[6-(4-hydroxy-3-methoxy-phenyl)-pyrido[2,3-b]pyrazin-3-yl]-urea |
| 18 | 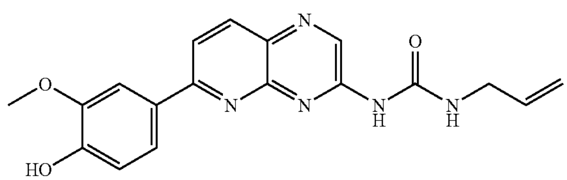 | 1-Allyl-3-[6-(4-hydroxy-3-methoxy-phenyl)-pyrido[2,3-b]pyrazin-3-yl]-urea |
| 19 | 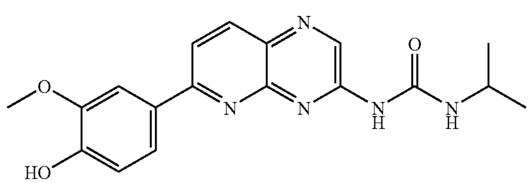 | 1-[6-(4-Hydroxy-3-methoxy-phenyl)-pyrido[2,3-b]pyrazin-3-yl]-3-isopropyl-urea |
| 20 | 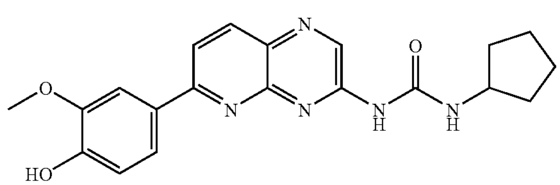 | 1-Cyclopentyl-3-[6-(4-hydroxy-3-methoxy-phenyl)-pyrido[2,3-b]pyrazin-3-yl]-urea |
| 21 | 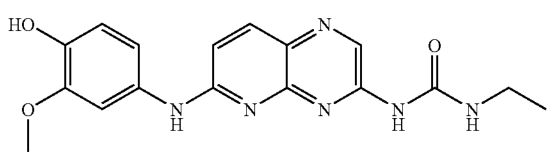 | 1-Ethyl-3-[6-(4-hydroxy-3-methoxy-phenylamino)-pyrido[2,3-b]pyrazin-3-yl]-urea |
| 22 | 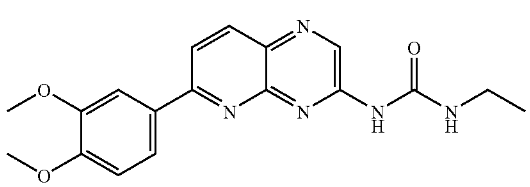 | 1-[6-(3,4-Dimethoxy-phenyl)-pyrido[2,3-b]pyrazin-3-yl]-3-ethyl-urea |

-continued

| Compound | Structure | Name |
|---|---|---|
| 23 | 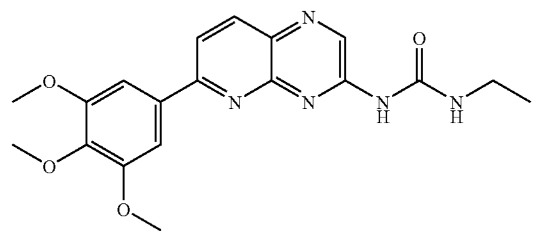 | 1-Ethyl-3-[6-(3,4,5-trimethoxy-phenyl)-pyrido[2,3-b]pyrazin-3-yl]-urea |
| 24 | 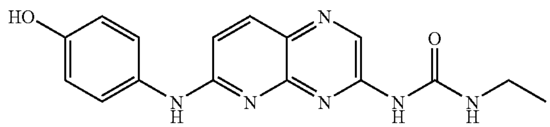 | 1-Ethyl-3-[6-(4-hydroxy-phenylamino)-pyrido[2,3-b]pyrazin-3-yl]-urea |
| 25 | 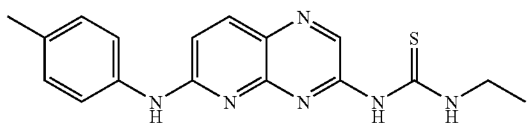 | 1-Ethyl-3-(6-p-tolylamino-pyrido[2,3-b]pyrazin-3-yl)-thiourea |
| 26 | 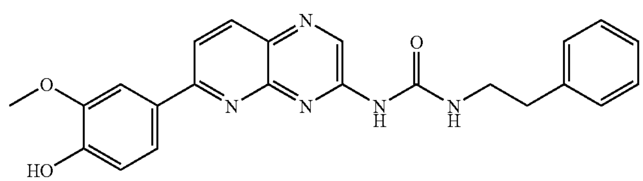 | 1-[6-(4-Hydroxy-3-methoxy-phenyl)-pyrido[2,3-b]pyrazin-3-yl]-3-phenethyl-urea |
| 27 | 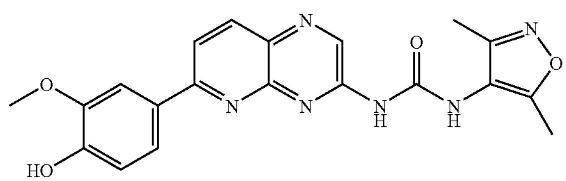 | 1-(3,5-Dimethyl-isoxazol-4-yl)-3-[6-(4-hydroxy-3-methoxy-phenyl)-pyrido[2,3-b]pyrazin-3-yl]-urea |
| 28 | 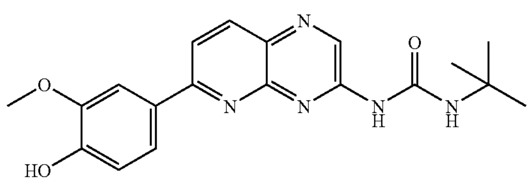 | 1-tert-Butyl-3-[6-(4-hydroxy-3-methoxy-phenyl)-pyrido[2,3-b]pyrazin-3-yl]-urea |
| 29 | 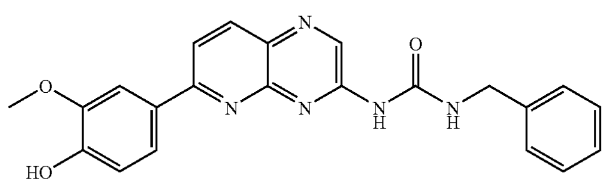 | 1-Benzyl-3-[6-(4-hydroxy-3-methoxy-phenyl)-pyrido[2,3-b]pyrazin-3-yl]-urea |
| 30 | 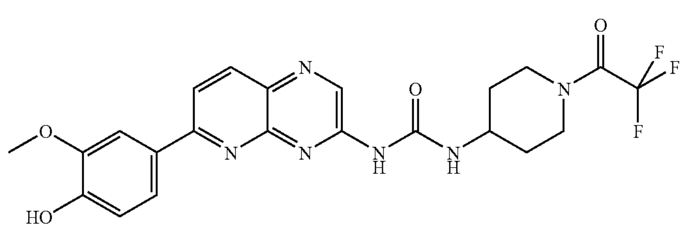 | 1-[6-(4-Hydroxy-3-methoxy-phenyl)-pyrido[2,3-b]pyrazin-3-yl]-3-[1-(2,2,2-trifluoro-acetyl)-piperidin-4-yl]-urea |
| 31 | 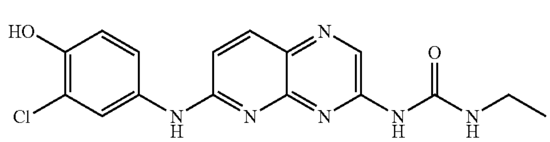 | 1-[6-(3-Chloro-4-hydroxy-phenylamino)-pyrido[2,3-b]pyrazin-3-yl]-3-ethyl-urea |

| Compound | Structure | Name |
|---|---|---|
| 32 | 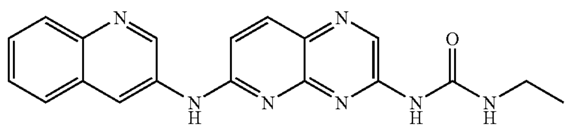 | 1-Ethyl-3-[6-(quinolin-3-ylamino)-pyrido[2,3-b]pyrazin-3-yl]-urea |
| 33 | 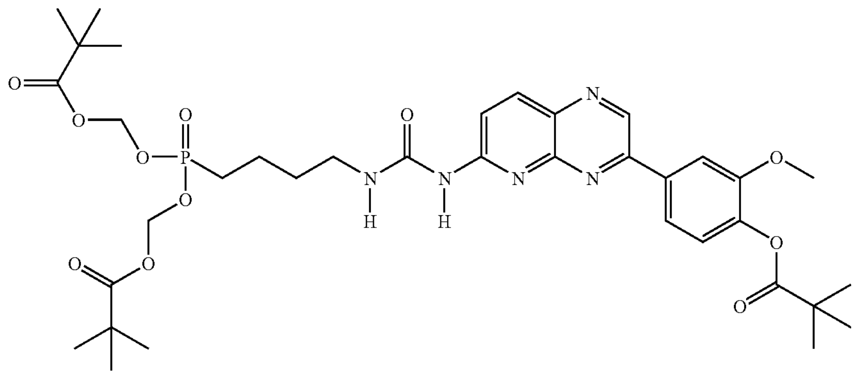 | 2,2-Dimethyl-propionic acid(2,2-dimethyl-propionyloxymeth-oxy)-[4-(3-{3-[4-(2,2-dimethyl-propionyl-oxy)-3-methoxy-phenyl]-pyrido[2,3-b]pyrazin-6-yl}-ureido)-butyl]-phosphinoyloxy-methyl ester |
| 34 | 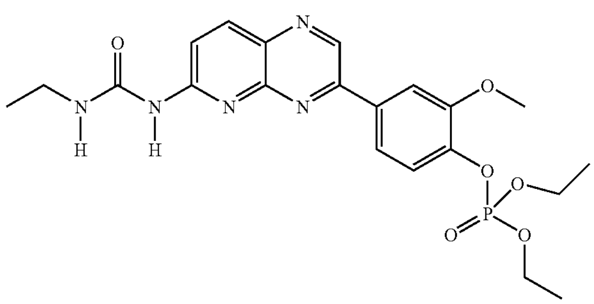 | Phosphoric acid di-ethyl ester 4-[6-(3-ethyl-ureido)-pyrido[2,3-b]-pyrazin-3-yl]-2-methoxy-phenyl ester |
| 35 | 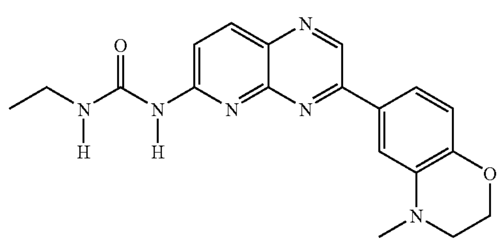 | 1-Ethyl-3-[3-(4-methyl-3,4-dihydro-2H-benzo[1,4]oxazin-6-yl)-pyrido[2,3-b]pyrazin-6-yl]-urea |
| 36 | 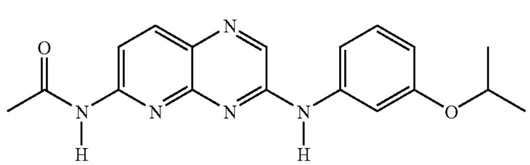 | N-[3-(3-Isopropoxy-phenylamino)-pyrido[2,3-b]pyrazin-6-yl]-acetamide |
| 37 | 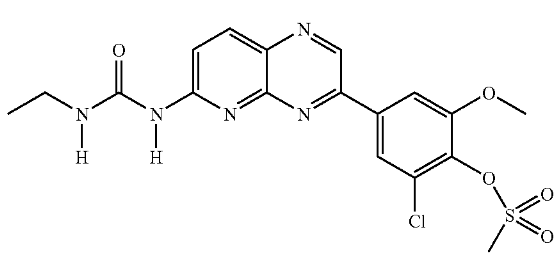 | Methanesulfonic acid 2-chloro-4-[6-(3-ethyl-ureido)-pyrido[2,3-b]pyrazin-3-yl]-6-methoxy-phenyl ester |

-continued

| Compound | Structure | Name |
|---|---|---|
| 38 | 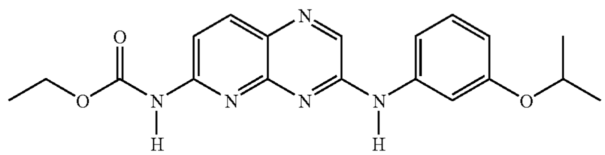 | [3-(3-Isopropoxy-phenylamino)-pyrido[2,3-b]pyrazin-6-yl]-carbamic acid ethyl ester |
| 39 | 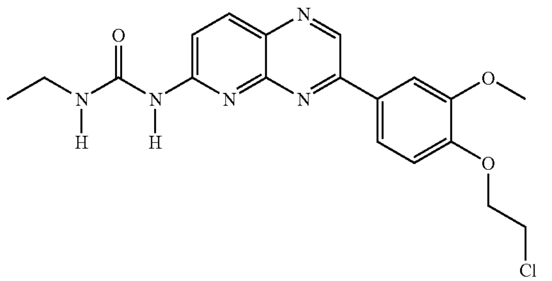 | 1-{3-[4-(2-Chloro-ethoxy)-3-methoxy-phenyl]-pyrido[2,3-b]pyrazin-6-yl}-3-ethyl-urea |
| 40 | 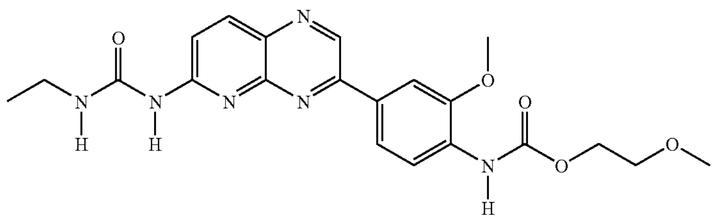 | {4-[6-(3-Ethyl-ureido)-pyrido[2,3-b]pyrazin-3-yl]-2-methoxy-phenyl}-carbamic acid 2-methoxy-ethyl ester |
| 41 | 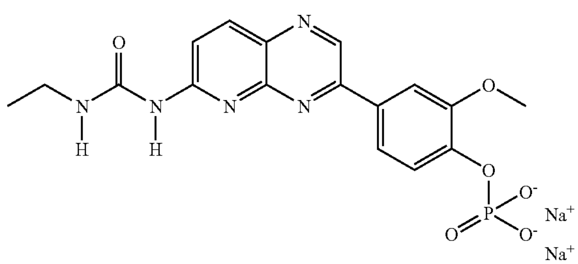 | Phosphoric acid mono-{4-[6-(3-ethyl-ureido)-pyrido-[2,3-b]pyrazin-3-yl]-2-methoxy-phenyl} ester; sodium salt |
| 42 | 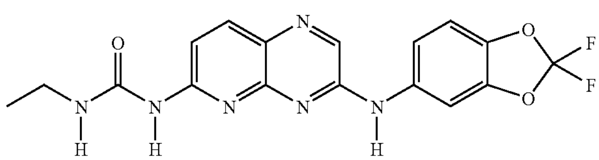 | 1-[3-(2,2-Difluoro-benzo[1,3]dioxol-5-ylamino)-pyrido[2,3-b]pyrazin-6-yl]-3-ethyl-urea |
| 43 | 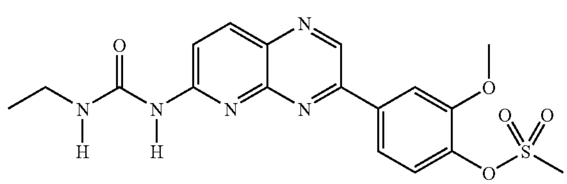 | Methanesulfonic acid 4-[6-(3-ethyl-ureido)-pyrido[2,3-b]pyrazin-3-yl]-2-methoxy-phenyl ester |
| 44 | 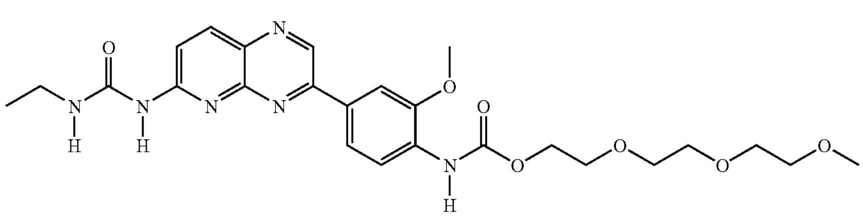 | {4-[6-(3-Ethyl-ureido)-pyrido[2,3-b]pyrazin-3-yl]-2-methoxy-phenyl}-carbamic acid 2-[2-(2-methoxy-ethoxy)-ethoxy]-ethyl ester |

-continued

| Compound | Structure | Name |
|---|---|---|
| 45 | 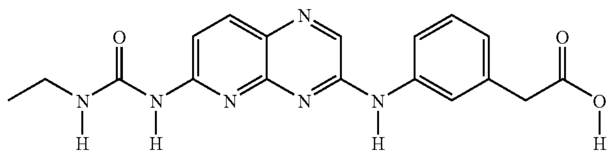 | {3-[6-(3-Ethyl-ureido)-pyrido[2,3-b]-pyrazin-3-ylamino]-phenyl}-acetic acid |
| 46 | 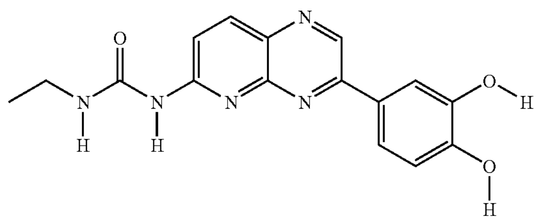 | 1-Ethyl-3-[3-(3-hydroxy-4-methoxy-phenyl)-pyrido[2,3-b]pyrazin-6-yl]-urea |
| 47 | 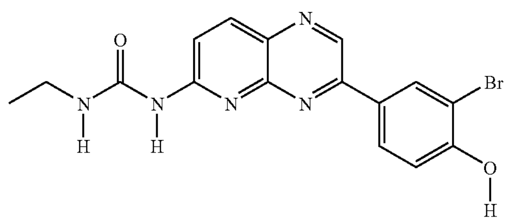 | 1{3-(3-Bromo-4-hydroxy-phenyl)-pyrido[2,3-b]pyrazin-6-yl]-3-ethyl-urea |
| 48 | 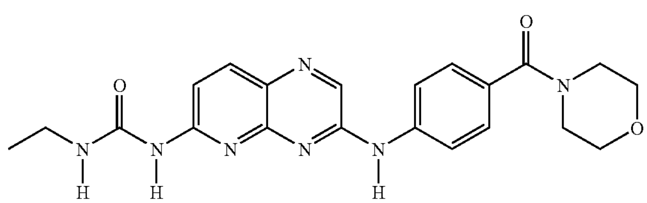 | 1-Ethyl-3-{3-[4-(morpholine-4-carbonyl)-phenylamino]-pyrido[2,3-b]-pyrazin-6-yl}-urea |
| 49 | 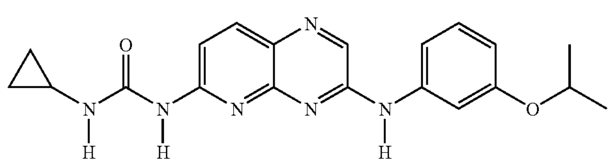 | 1-Cyclopropyl-3-[3-(3-isopropoxy-phenylamino)-pyrido[2,3-b]pyrazin-6-yl]-urea |
| 50 | 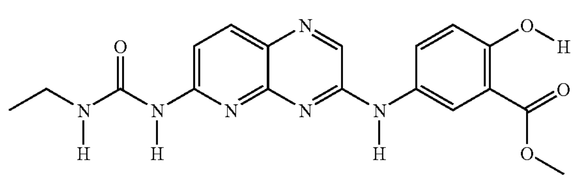 | 5-[6-(3-Ethyl-ureido)-pyrido[2,3-b]-pyrazin-3-ylamino]-2-hydroxy-benzoic acid methyl ester |
| 51 | 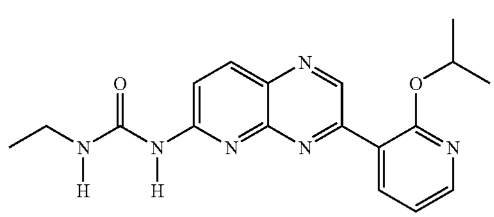 | 1-Ethyl-3-[3-(2-isopropoxy-pyridin-3-yl)-pyrido[2,3-b]pyrazin-6-yl]-urea |
| 52 | 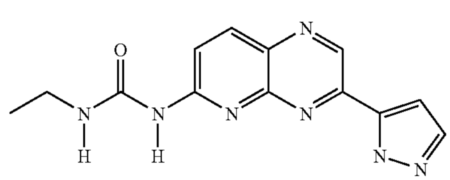 | 1-Ethyl-3-[3-(2H-pyrazol-3-yl)-pyrido[2,3-b]pyrazin-6-yl]-urea |

-continued

| Compound | Structure | Name |
|---|---|---|
| 53 | 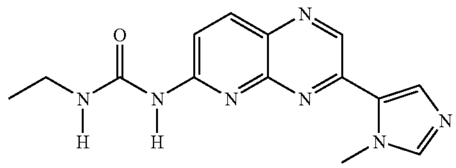 | 1-Ethyl-3-[3-(3-methyl-3H-imidazol-4-yl)-pyrido[2,3-b]pyrazin-6-yl]-urea |
| 54 | 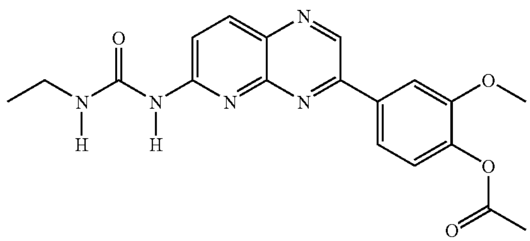 | Acetic acid 4-[6-(3-ethyl-ureido)-pyrido[2,3-b]pyrazin-3-yl]-2-methoxy-phenyl ester |
| 55 | 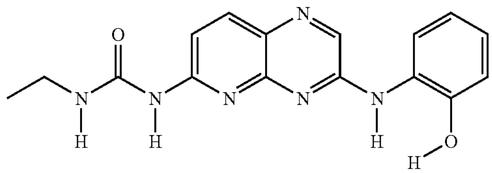 | 1-Ethyl-3-[3-(2-hydroxy-phenylamino)-pyrido[2,3-b]pyrazin-6-yl]-urea |
| 56 | 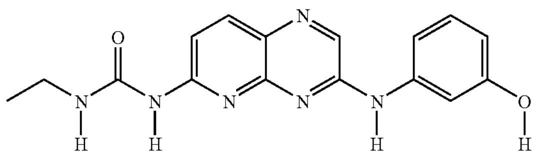 | 1-Ethyl-3-[3-(3-hydroxy-phenylamino)-pyrido[2,3-b]pyrazin-6-yl]-urea |
| 57 | 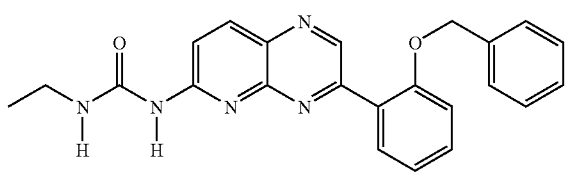 | 1-[3-(2-Benzyloxy-phenyl)-pyrido[2,3-b]pyrazin-6-yl]-3-ethyl-urea |
| 58 | 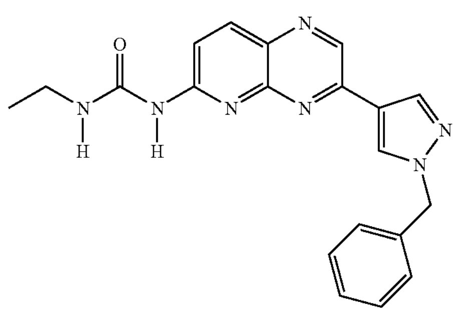 | 1-[3-(1-Benzyl-1H-pyrazol-4-yl)-pyrido[2,3-b]pyrazin-6-yl]-3-ethyl-urea |
| 59 | 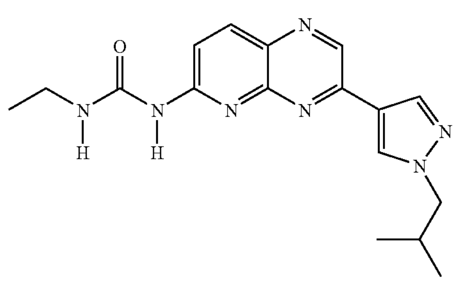 | 1-Ethyl-3-[3-(1-isobutyl-1H-pyrazol-4-yl)-pyrido[2,3-b]pyrazin-6-yl]-urea |

| Compound | Structure | Name |
|---|---|---|
| 60 | 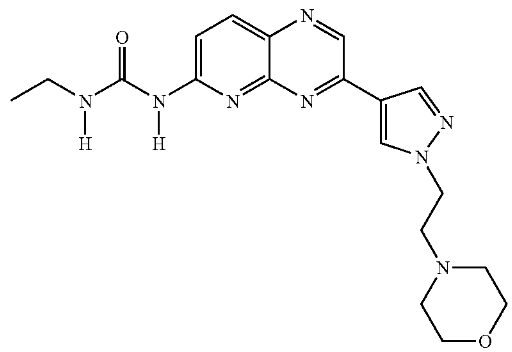 | 1-Ethyl-3-{3-[1-(2-morpholin-4-yl-ethyl)-1H-pyrazol-4-yl]-pyrido[2,3-b]pyrazin-6-yl}-urea |
| 61 | 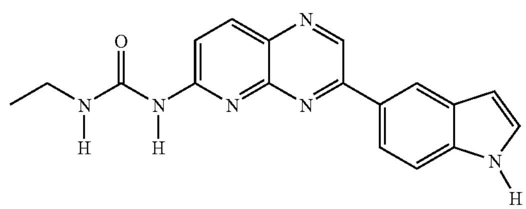 | 1-Ethyl-3-[3-(1H-pyrrolo[2,3-b]pyridin-5-yl)-pyrido[2,3-b]pyrazin-6-yl]-urea |
| 62 | 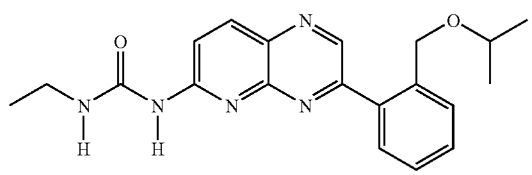 | 1-Ethyl-3-[3-(2-isobutoxy-phenyl)-pyrido[2,3-b]pyrazin-6-yl]-urea |
| 63 | 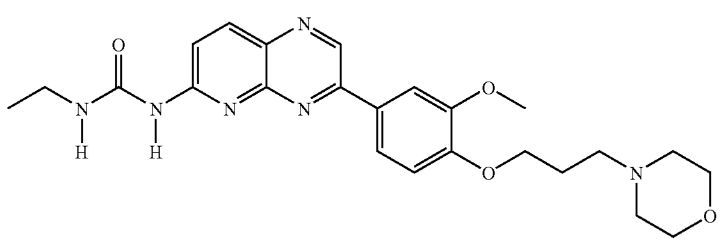 | 1-Ethyl-3-{3-[3-methoxy-4-(3-morpholin-4-yl-propoxy)-phenyl]-pyrido[2,3-b]pyrazin-6-yl}-urea |
| 64 | 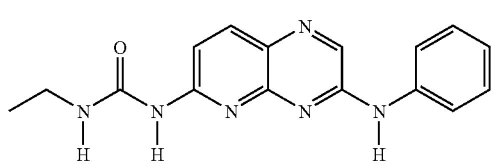 | 1-Ethyl-3-(3-phenylamino-pyrido-[2,3-b]pyrazin-6-yl)-urea |
| 65 | 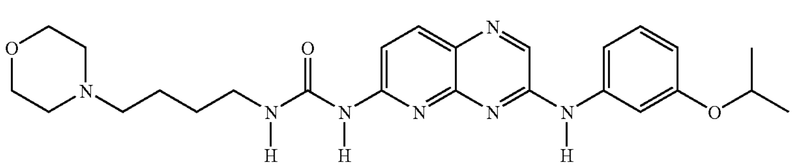 | 1-[3-(3-Isopropoxy-phenylamino)-pyrido[2,3-b]pyrazin-6-yl]-3-(4-morpholin-4-yl-butyl)-urea |
| 66 | 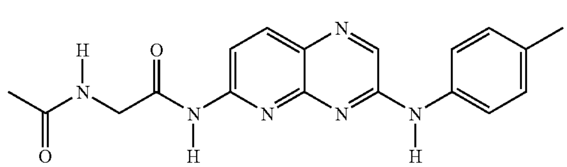 | 2-Acetylamino-N-(3-p-tolylamino-pyrido[2,3-b]pyrazin-6-yl)-acetamide |

| Compound | Structure | Name |
| --- | --- | --- |
| 67 | 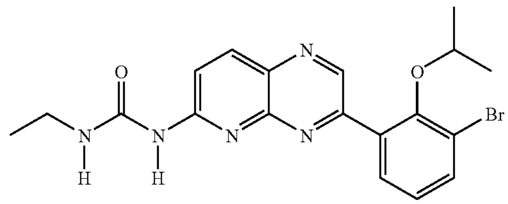 | 1-[3-(3-Bromo-2-isopropoxy-phenyl)-pyrido[2,3-b]pyrazin-6-yl]-3-ethyl-urea |
| 68 | 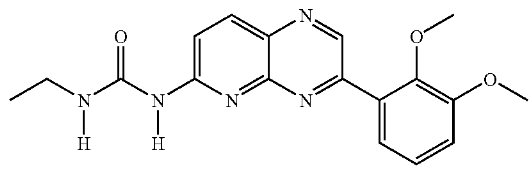 | 1-[3-(2,3-Dimethoxy-phenyl)-pyrido[2,3-b]pyrazin-6-yl]-3-ethyl-urea |
| 70 | 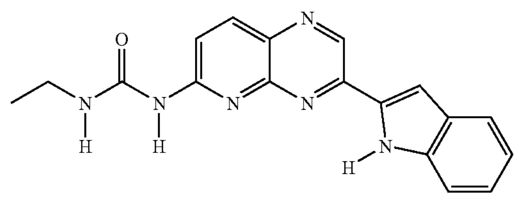 | 1-Ethyl-3-[3-(1H-indol-2-yl)-pyrido[2,3-b]pyrazin-6-yl]-urea |
| 71 | 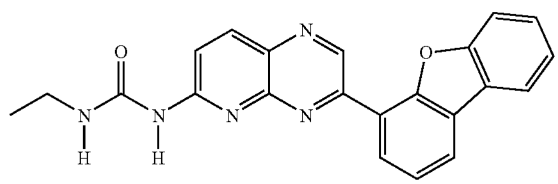 | 1-(3-Dibenzofuran-4-yl-pyrido[2,3-b]pyrazin-6-yl)-3-ethyl-urea |
| 72 | 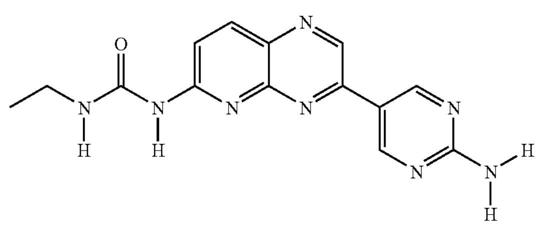 | 1-[3-(2-Amino-pyrimidin-5-yl)-pyrido[2,3-b]pyrazin-6-yl]-3-ethyl-urea |
| 73 | 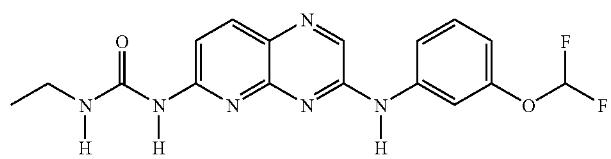 | 1-[3-(3-Difluoromethoxy-phenylamino)-pyrido[2,3-b]pyrazin-6-yl]-3-ethyl-urea |
| 74 | 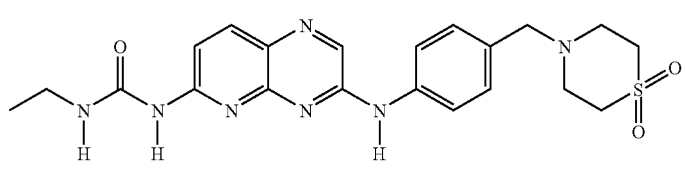 | 1-{3-[4-(1,1-Dioxo-1lambda*6*-thiomorpholin-4-ylmethyl)-phenylamino]-pyrido[2,3-b]pyrazin-6-yl}-3-ethyl-urea |
| 75 | 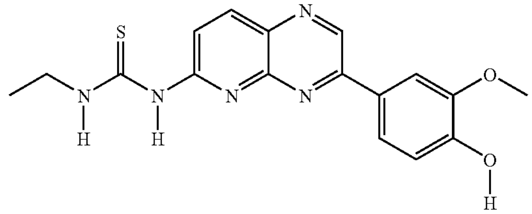 | 1-Ethyl-3-[3-(4-hydroxy-3-methoxy-phenyl)-pyrido[2,3-b]pyrazin-6-yl]-thiourea |

US 8,202,883 B2

-continued

| Compound | Structure | Name |
|---|---|---|
| 76 | 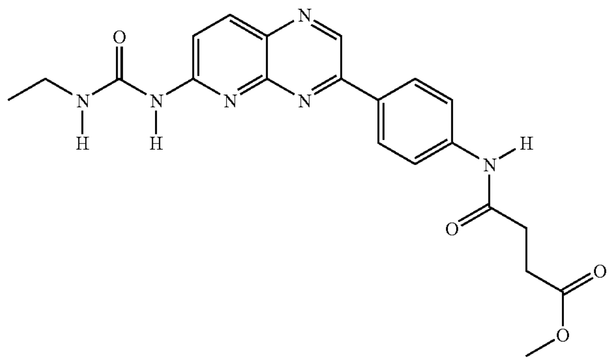 | N-{4-[6-(3-Ethyl-ureido)-pyrido[2,3-b]pyrazin-3-yl]-phenyl}-succinamic acid methyl ester |
| 77 | 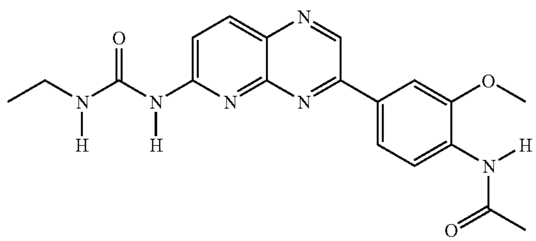 | N-{4-[6-(3-Ethyl-ureido)-pyrido[2,3-b]pyrazin-3-yl]-2-methoxy-phenyl}-acetamide |
| 78 | 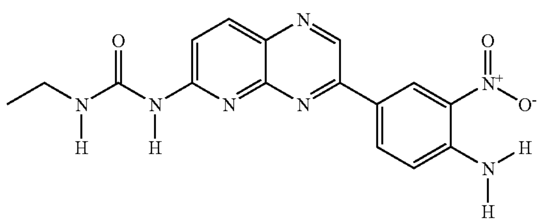 | 1-[3-(4-Amino-3-nitro-phenyl)-pyrido[2,3-b]pyrazin-6-yl]-3-ethyl-urea |
| 79 | 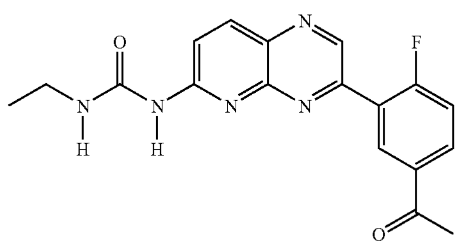 | 1-[3-(5-Acetyl-2-fluoro-phenyl)-pyrido[2,3-b]pyrazin-6-yl]-3-ethyl-urea |
| 80 | 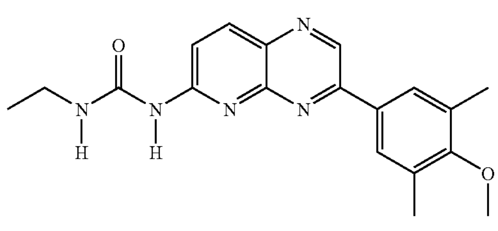 | 1-Ethyl-3-[3-(4-methoxy-3,5-dimethyl-phenyl)-pyrido[2,3-b]pyrazin-6-yl]-urea |
| 81 | 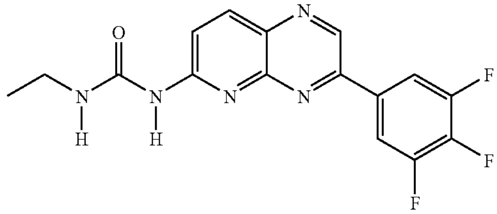 | 1-Ethyl-3-[3-(3,4,5-trifluoro-phenyl)-pyrido[2,3-b]pyrazin-6-yl]-urea |

| Compound | Structure | Name |
| --- | --- | --- |
| 82 | 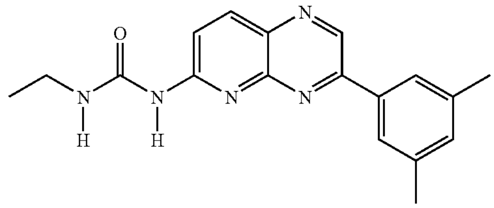 | 1-[3-(3,5-Dimethyl-phenyl)-pyrido[2,3-b]pyrazin-6-yl]-3-ethyl-urea |
| 83 | 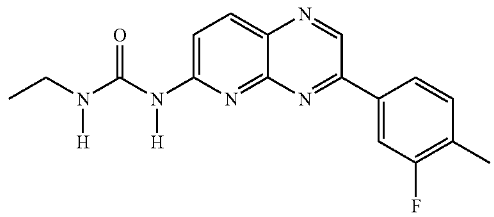 | 1-Ethyl-3-[3-(3-fluoro-4-methyl-phenyl)-pyrido[2,3-b]pyrazin-6-yl]-urea |
| 84 | 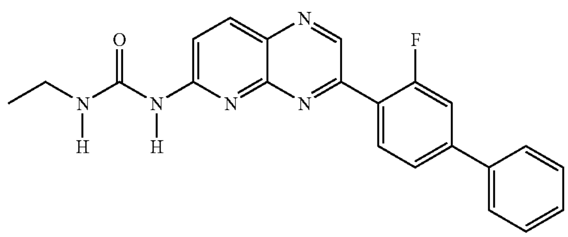 | 1-Ethyl-3-[3-(3-fluoro-biphenyl-4-yl)-pyrido[2,3-bipyrazin-6-yl]-urea |
| 85 | 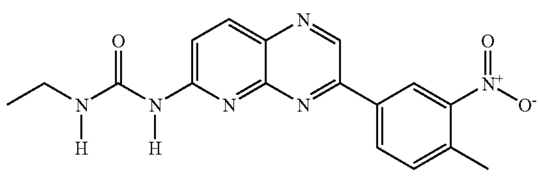 | 1-Ethyl-3-[3-(4-methyl-3-nitro-phenyl)-pyrido[2,3-b]pyrazin-6-yl]-urea |
| 86 | 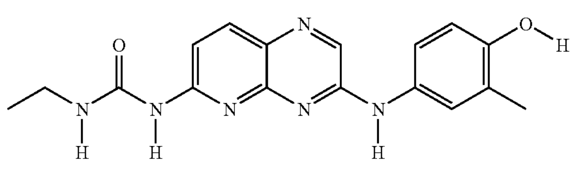 | 1-Ethyl-3-[3-(4-hydroxy-3-methyl-phenylamino)-pyrido[2,3-b]pyrazin-6-yl]-urea |
| 87 | 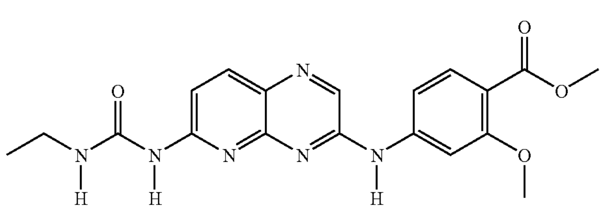 | 4-[6-(3-Ethyl-ureido)-pyrido[2,3-b]pyrazin-3-ylamino]-2-methoxy-benzoic acid methyl ester |

| Compound | Structure | Name |
|---|---|---|
| 88 | 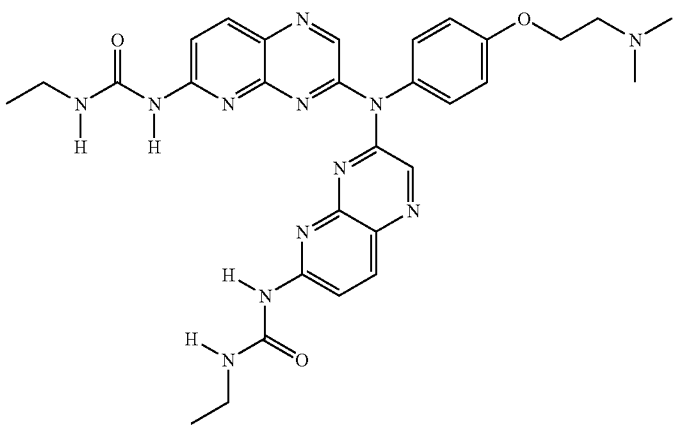 | 1,1'-(3,3'-(4-(2-(dimethyl-amino)ethoxy)phenyl azanediyl)bis(pyrido [2,3-b]pyrazine-6,3-diyl))bis(3-ethylurea) |
| 89 | 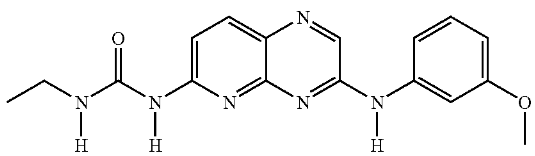 | 1-Ethyl-3-[3-(3-methoxy-phenylamino)-pyrido[2,3-b]pyrazin-6-yl]-urea |
| 90 | 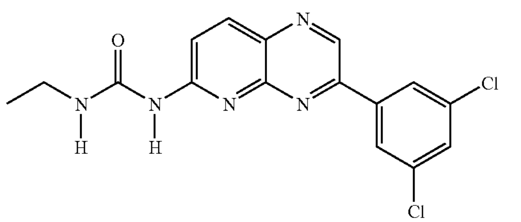 | 1-[3-(3,5-Dichloro-phenyl)-pyrido[2,3-b]pyrazin-6-yl]-3-ethyl-urea |
| 91 | 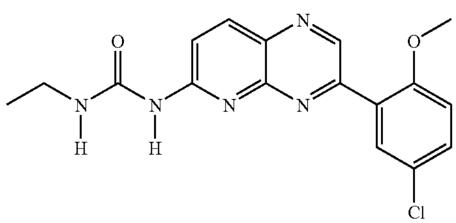 | 1-[3-(5-Chloro-2-methoxy-phenyl)-pyrido[2,3-b]pyrazin-6-yl]-3-ethyl-urea |
| 92 | 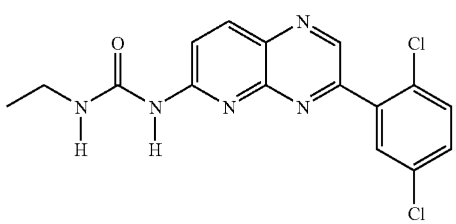 | 1-[3-(2,5-Dichloro-phenyl)-pyrido[2,3-b]pyrazin-6-yl]-3-ethyl-urea |
| 93 | 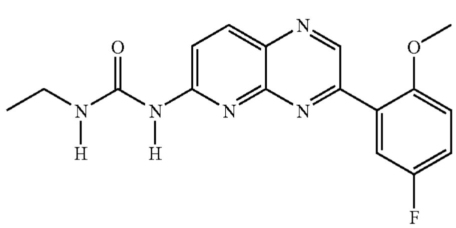 | 1-Ethyl-3-[3-(5-fluoro-2-methoxy-phenyl)-pyrido[2,3-b]pyrazin-6-yl]-urea |

-continued

| Compound | Structure | Name |
|---|---|---|
| 94 | 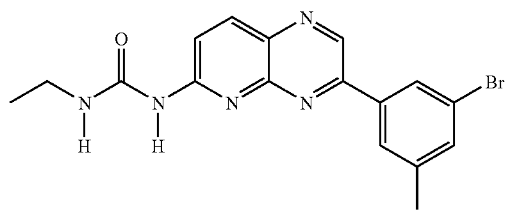 | 1-[3-(3-Bromo-5-methyl-phenyl)-pyrido[2,3-b]pyrazin-6-yl]-3-ethyl-urea |
| 95 | 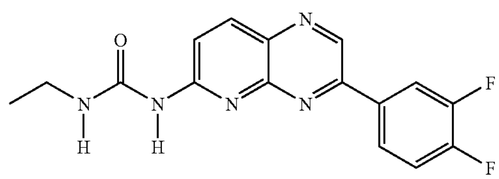 | 1-[3-(3,4-Difluoro-phenyl)-pyrido[2,3-b]pyrazin-6-yl]-3-ethyl-urea |
| 96 | 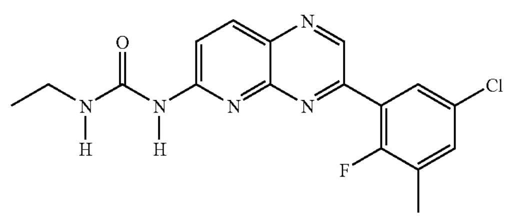 | 1-[3-(5-Chloro-2-fluoro-3-methyl-phenyl)-pyrido[2,3-b]pyrazin-6-yl]-3-ethyl-urea |
| 97 | 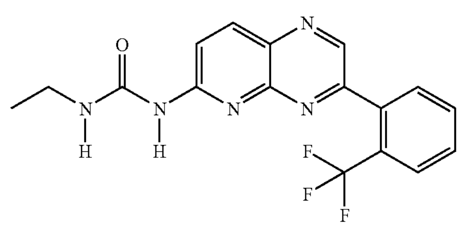 | 1-Ethyl-3-[3-(2-trifluoromethyl-phenyl)-pyrido[2,3-b]pyrazin-6-yl]-urea |
| 98 | 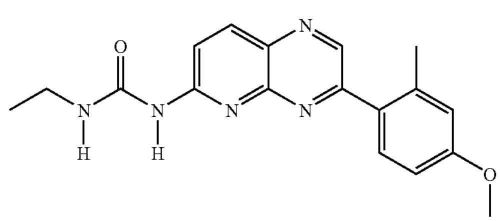 | 1-Ethyl-3-[3-(4-methoxy-2-methyl-phenyl)-pyrido[2,3-b]pyrazin-6-yl]-urea |
| 99 | 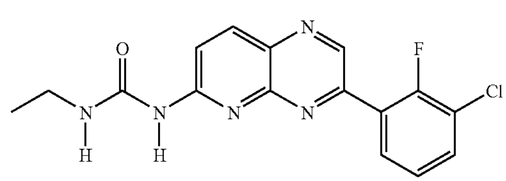 | 1-[3-(3-Chloro-2-fluoro-phenyl)-pyrido[2,3-b]pyrazin-6-yl]-3-ethyl-urea |
| 100 | 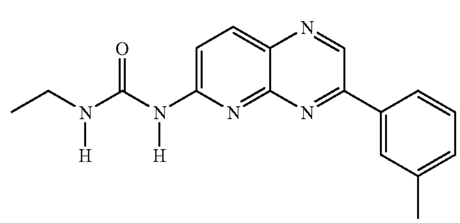 | 1-Ethyl-3-(3-m-tolyl-pyrido[2,3-b]pyrazin-6-yl)-urea |

-continued

| Compound | Structure | Name |
|---|---|---|
| 101 | 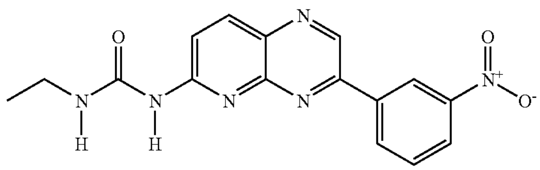 | 1-Ethyl-3-[3-(3-nitro-phenyl)-pyrido[2,3-b]pyrazin-6-yl]-urea |
| 102 | 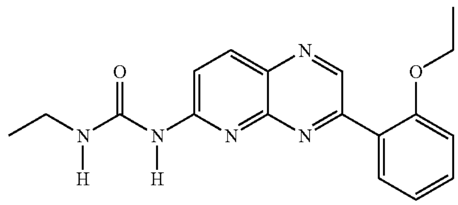 | 1-[3-(2-Ethoxy-phenyl)-pyrido[2,3-b]pyrazin-6-yl]-3-ethyl-urea |
| 103 | 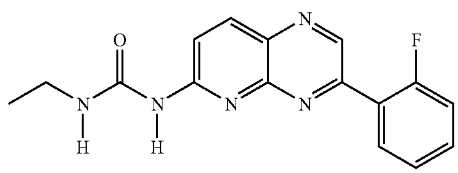 | 1-Ethyl-3-[3-(2-fluoro-phenyl)-pyrido[2,3-b]pyrazin-6-yl]-urea |
| 104 | 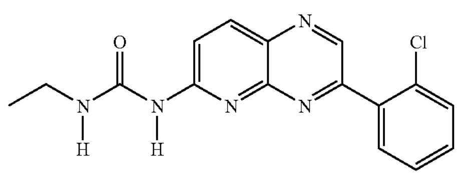 | 1-[3-(2-Chloro-phenyl)-pyrido[2,3-b]pyrazin-6-yl]-3-ethyl-urea |
| 105 | 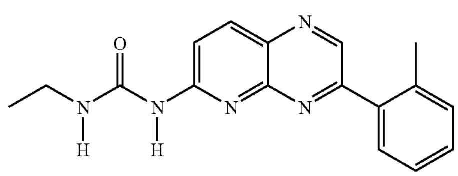 | 1-Ethyl-3-(3-o-tolyl-pyrido[2,3-b]pyrazin-6-yl)-urea |
| 106 | 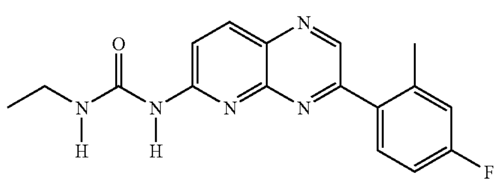 | 1-Ethyl-3-[3-(5-fluoro-2-methyl-phenyl)-pyrido[2,3-b]pyrazin-6-yl]-urea |
| 107 | 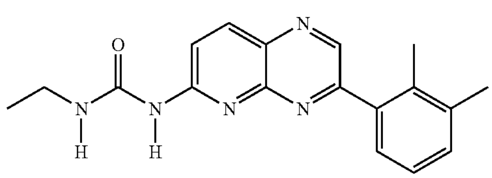 | 1-[3-(2,3-Dimethyl-phenyl)-pyrido[2,3-b]pyrazin-6-yl]-3-ethyl-urea |
| 108 | 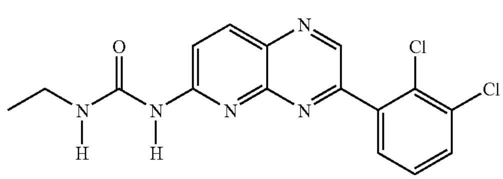 | 1-[3-(2,3-Dichloro-phenyl)-pyrido[2,3-b]pyrazin-6-yl]-3-ethyl-urea |

-continued

| Compound | Structure | Name |
|---|---|---|
| 109 | 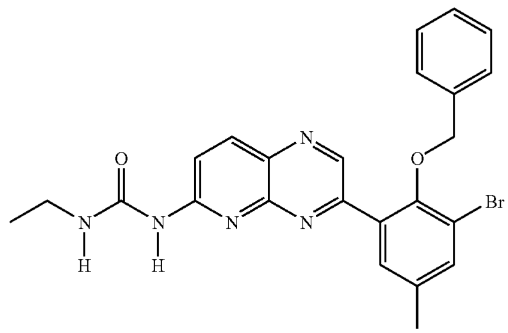 | 1-[3-(2-Benzyloxy-3-bromo-5-methyl-phenyl)-pyrido[2,3-b]pyrazin-6-yl]-3-ethyl-urea |
| 110 | 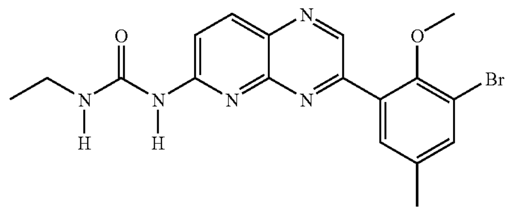 | 1-[3-(3-Bromo-2-methoxy-5-methyl-phenyl)-pyrido[2,3-b]pyrazin-6-yl]-3-ethyl-urea |
| 111 | 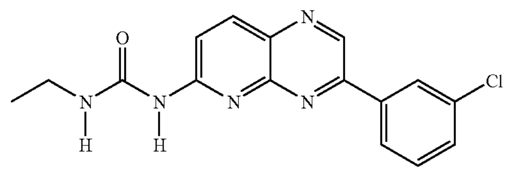 | 1-[3-(3-Chloro-phenyl)-pyrido[2,3-b]pyrazin-6-yl]-3-ethyl-urea |
| 112 | 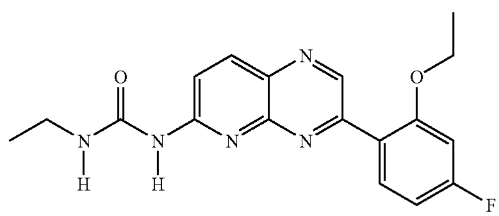 | 1-[3-(2-Ethoxy-4-fluoro-phenyl)-pyrido[2,3-b]pyrazin-6-yl]-3-ethyl-urea |
| 113 | 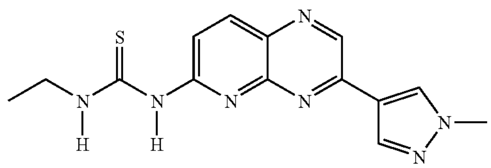 | 1-Ethyl-3-[3-(1-methyl-1H-pyrazol-4-yl)-pyrido[2,3-b]pyrazin-6-yl]-thiourea |
| 114 | 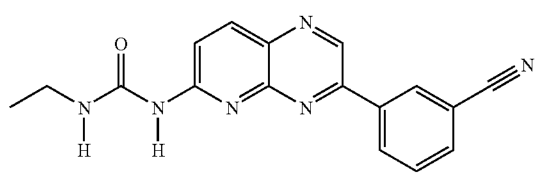 | 1-[3-(3-Cyano-phenyl)-pyrido[2,3-b]pyrazin-6-yl]-3-ethyl-urea |
| 115 | 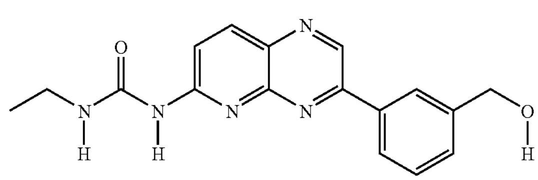 | 1-Ethyl-3-[3-(3-hydroxymethyl-phenyl)-pyrido[2,3-b]pyrazin-6-yl]-urea |

-continued

| Compound | Structure | Name |
|---|---|---|
| 116 | 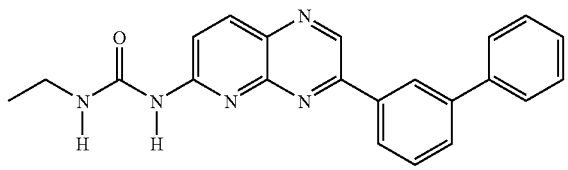 | 1-(3-Biphenyl-3-yl-pyrido[2,3-b]pyrazin-6-yl)-3-ethyl-urea |
| 117 | 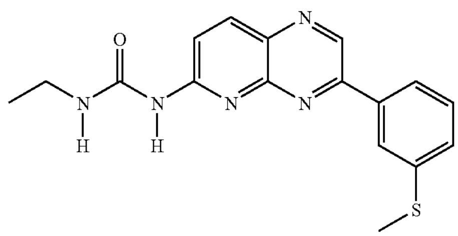 | 1-Ethyl-3-[3-(3-methylsulfanyl-phenyl)-pyrido[2,3-b]pyrazin-6-yl]-urea |
| 118 | 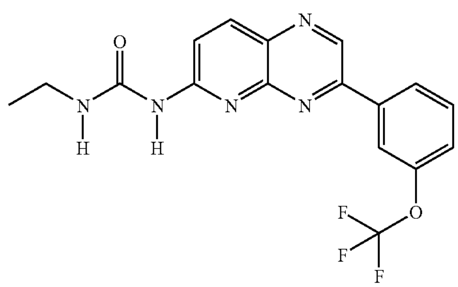 | 1-Ethyl-3-[3-(3-trifluoromethoxy-phenyl)-pyrido[2,3-b]pyrazin-6-yl]-urea |
| 119 | 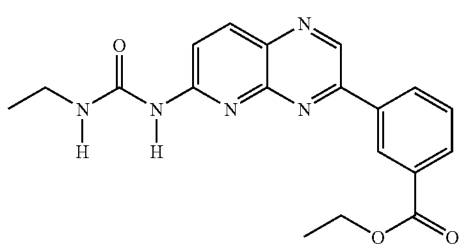 | 3-[6-(3-Ethyl-ureido)-pyrido[2,3-b]pyrazin-3-yl]-benzoic acid ethyl ester |
| 120 | 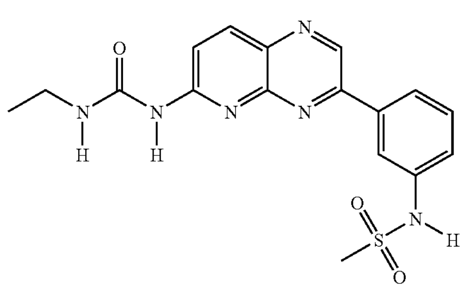 | N-{3-[6-(3-Ethyl-ureido)-pyrido[2,3-b]pyrazin-3-yl]-phenyl}-methanesulfonamide |

-continued

| Compound | Structure | Name |
|---|---|---|
| 121 | 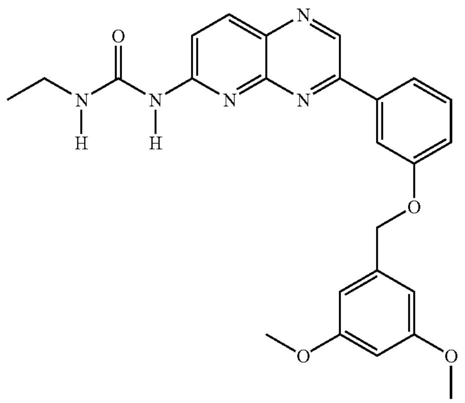 | 1-{3-[3-(3,5-Dimethoxy-benzyloxy)-phenyl]-pyrido[2,3-b]pyrazin-6-yl}-3-ethyl-urea |
| 122 | 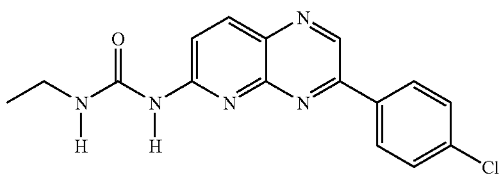 | 1-[3-(4-Chloro-phenyl)-pyrido[2,3-b]pyrazin-6-yl]-3-ethyl-urea |
| 123 | 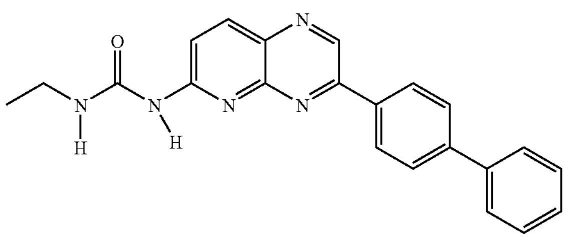 | 1-(3-Biphenyl-4-yl-pyrido[2,3-b]pyrazin-6-yl)-3-ethyl-urea |
| 124 | 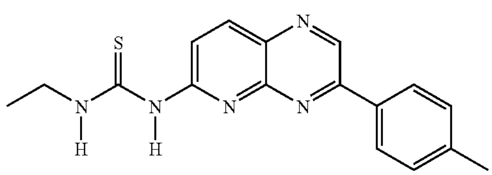 | 1-Ethyl-3-(3-p-tolyl-pyrido[2,3-b]pyrazin-6-yl)-thiourea |
| 125 | 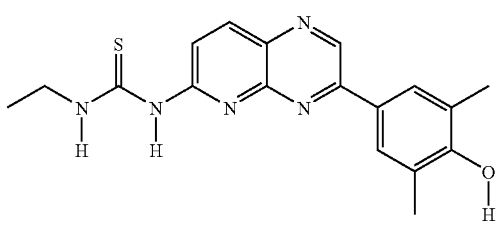 | 1-Ethyl-3-[3-(4-hydroxy-3,5-dimethyl-phenyl)-pyrido[2,3-b]pyrazin-6-yl]-thiourea |
| 126 | 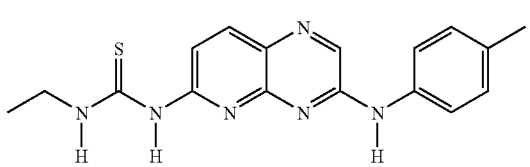 | 1-Ethyl-3-(3-p-tolylamino-pyrido[2,3-b]pyrazin-6-yl)-thiourea |
| 127 | 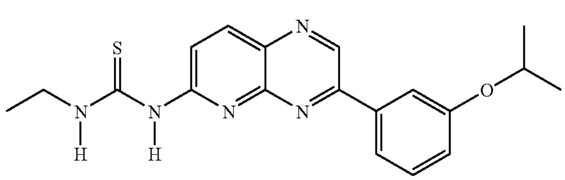 | 1-Ethyl-3-[3-(3-isopropoxy-phenyl)-pyrido[2,3-bipyrazin-6-yl]-thiourea |

| Compound | Name |
|---|---|
| 128 | 1-[3-(4-Diphenylamino-phenyl)-pyrido[2,3-b]pyrazin-6-yl]-3-ethyl-urea |
| 129 | 1-Ethyl-3-[3-(3-fluoro-phenyl)-pyrido[2,3-b]pyrazin-6-yl]-urea |
| 130 | 1-[3-(3-Ethoxy-phenyl)-pyrido[2,3-b]pyrazin-6-yl]-3-ethyl-urea |
| 131 | 1-Ethyl-3-[3-(4-nitro-phenyl)-pyrido[2,3-b]pyrazin-6-yl]-urea |
| 132 | 4-[6-(3-Ethyl-ureido)-pyrido[2,3-b]pyrazin-3-yl]-benzoic acid methyl ester |
| 133 | 1-Ethyl-3-[3-(4-propoxy-phenyl)-pyrido[2,3-b]pyrazin-6-yl]-urea |

-continued

| Compound | Structure | Name |
|---|---|---|
| 134 | 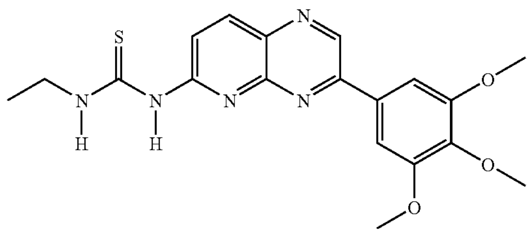 | 1-Ethyl-3-[3-(3,4,5-trimethoxy-phenyl)-pyrido[2,3-b]pyrazin-6-yl]-thiourea |
| 135 | 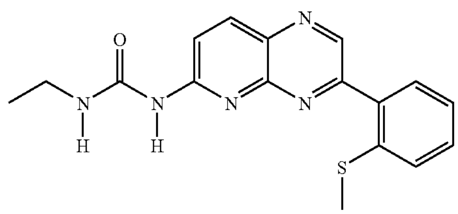 | 1-Ethyl-3-[3-(2-methylsulfanyl-phenyl)-pyrido[2,3-b]pyrazin-6-yl]-urea |
| 136 | 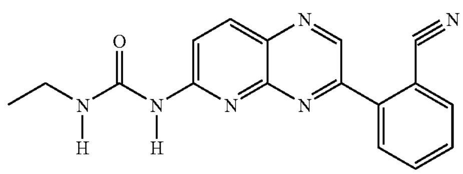 | 1-[3-(3-Cyano-phenyl)-pyrido[2,3-b]pyrazin-6-yl]-3-ethyl-urea |
| 137 | 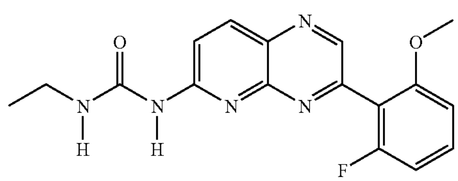 | 1-[3-(2-Chloro-6-methoxy-phenyl)-pyrido[2,3-b]pyrazin-6-yl]-3-ethyl-urea |
| 138 | 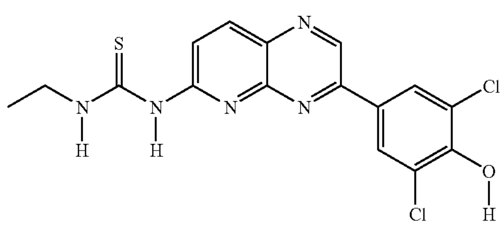 | 1-[3-(3,5-Dichloro-4-hydroxy-phenyl)-pyrido[2,3-b]pyrazin-6-yl]-3-ethyl-thiourea |
| 139 | 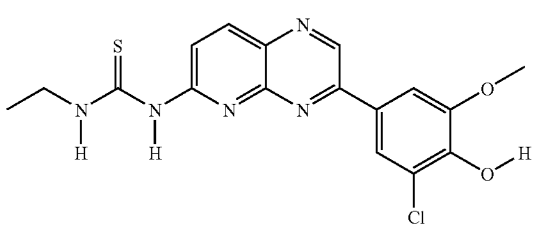 | 1-[3-(3-Chloro-4-hydroxy-5-methoxy-phenyl)-pyrido[2,3-b]pyrazin-6-yl]-3-ethyl-thiourea |
| 140 | 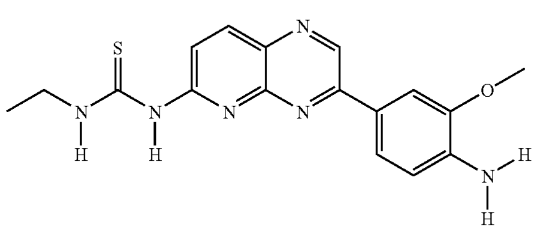 | 1-[3-(4-Amino-3-methoxy-phenyl)-pyrido[2,3-b]pyrazin-6-yl]-3-ethyl-thiourea |

-continued

| Compound | Structure | Name |
|---|---|---|
| 141 | 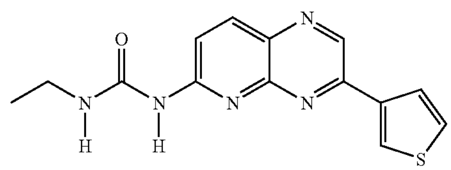 | 1-Ethyl-3-(3-thiophen-3-yl-pyrido[2,3-b]pyrazin-6-yl)-urea |
| 142 | 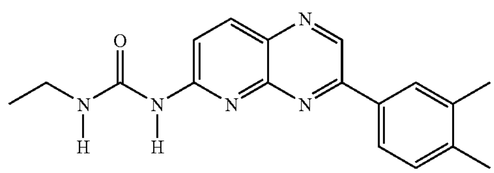 | 1-[3-(3,4-Dimethyl-phenyl)-pyrido[2,3-b]pyrazin-6-yl]-3-ethyl-urea |
| 143 | 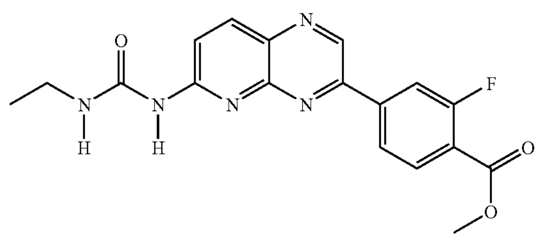 | 4-[6-(3-Ethyl-ureido)-pyrido[2,3-b]pyrazin-3-yl]-2-fluoro-benzoic acid methyl ester |
| 144 | 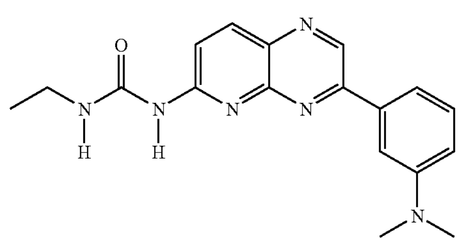 | 1-[3-(3-Dimethylamino-phenyl)-pyrido[2,3-b]pyrazin-6-yl]-3-ethyl-urea |
| 145 | 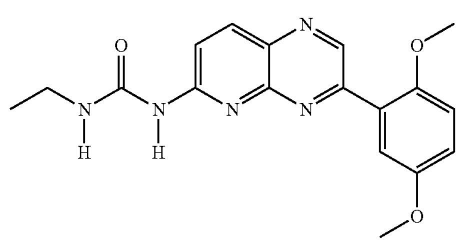 | 1-[3-(2,5-Dimethoxy-phenyl)-pyrido[2,3-b]pyrazin-6-yl]-3-ethyl-urea |
| 146 | 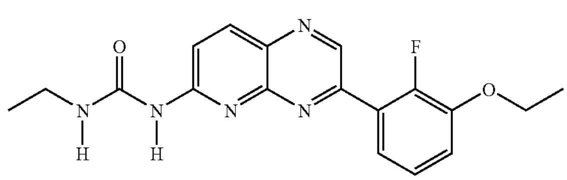 | 1-[3-(3-Ethoxy-2-fluoro-phenyl)-pyrido[2,3-b]pyrazin-6-yl]-3-ethyl-urea |
| 147 | 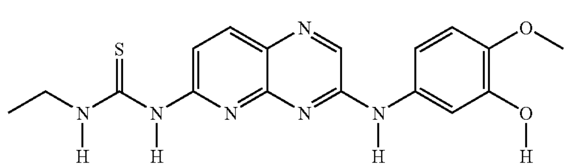 | 1-Ethyl-3-[3-(3-hydroxy-4-methoxy-phenylamino)-pyrido[2,3-b]pyrazin-6-yl]-thiourea |
| 148 | 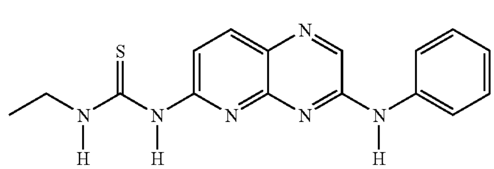 | 1-Ethyl-3-(3-phenylamino-pyrido[2,3-b]pyrazin-6-yl)-thiourea |

| Compound | Structure | Name |
|---|---|---|
| 149 | 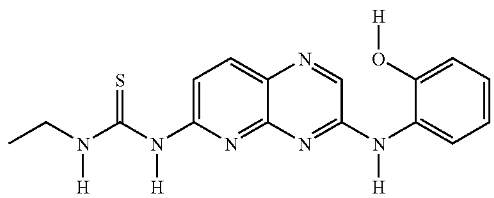 | 1-Ethyl-3-[3-(2-hydroxy-phenylamino)-pyrido[2,3-b]pyrazin-6-yl]-thiourea |
| 150 | 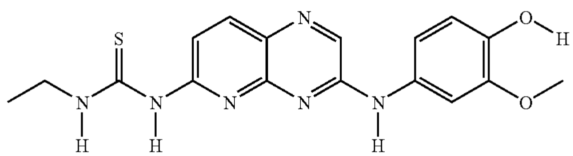 | 1-Ethyl-3-[3-(4-hydroxy-3-methoxy-phenylamino)-pyrido[2,3-b]pyrazin-6-yl]-thiourea |
| 151 | 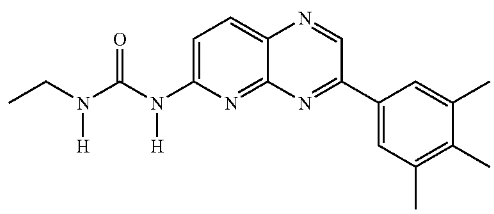 | 1-Ethyl-3-[3-(3,4,5-trimethyl-phenyl)-pyrido[2,3-b]pyrazin-6-yl]-urea |
| 152 | 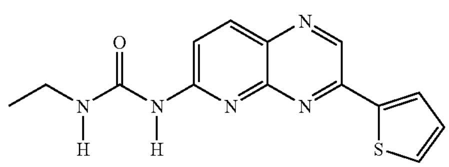 | 1-Ethyl-3-(3-thiophen-2-yl-pyrido[2,3-b]pyrazin-6-yl)-urea |
| 153 | 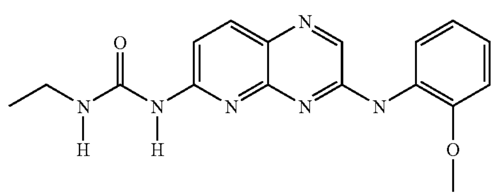 | 1-Ethyl-3-[3-(2-methoxy-phenylamino)-pyrido[2,3-b]pyrazin-6-yl]-urea |
| 154 | 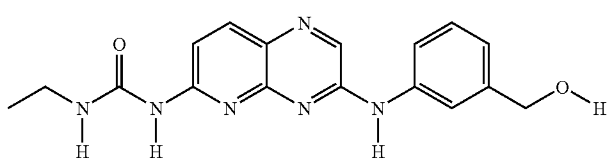 | 1-Ethyl-3-[3-(3-hydroxymethyl-phenylamino)-pyrido[2,3-b]pyrazin-6-yl]-urea |
| 155 | 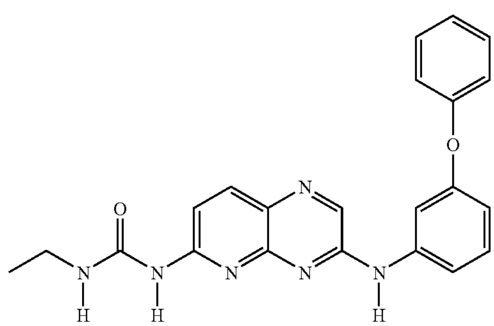 | 1-Ethyl-3-[3-(3-phenoxy-phenylamino)-pyrido[2,3-b]pyrazin-6-yl]-urea |

| Compound | Structure | Name |
|---|---|---|
| 156 | 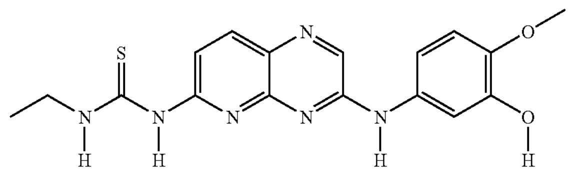 | 1-Ethyl-3-[3-(3-hydroxy-4-methoxy-phenylamino)-pyrido[2,3-b]pyrazin-6-yl]-urea |
| 157 | 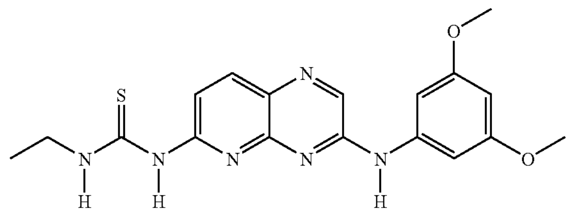 | 1-[3-(3,5-Dimethoxy-phenylamino)-pyrido[2,3-b]pyrazin-6-yl]-3-ethyl-thiourea |
| 158 | 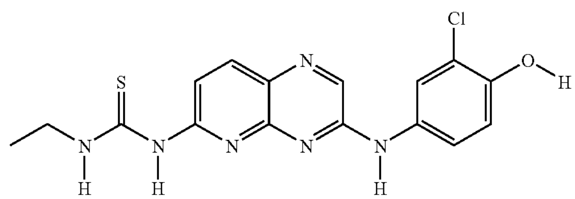 | 1-[3-(3-Chloro-4-hydroxy-phenylamino)-pyrido[2,3-b]pyrazin-6-yl]-3-ethyl-thiourea |
| 159 | 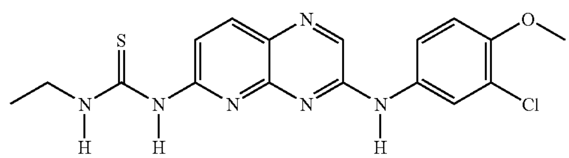 | 1-[3-(3-Chloro-4-methoxy-phenylamino)-pyrido[2,3-b]pyrazin-6-yl]-3-ethyl-thiourea |
| 160 | 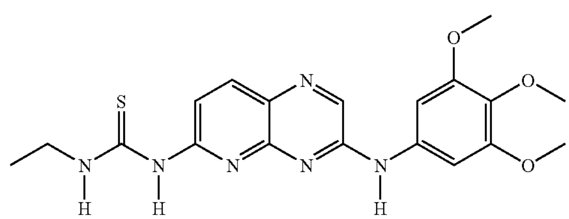 | 1-Ethyl-3-[3-(3,4,5-trimethoxy-phenylamino)-pyrido[2,3-b]pyrazin-6-yl]-thiourea |
| 161 | 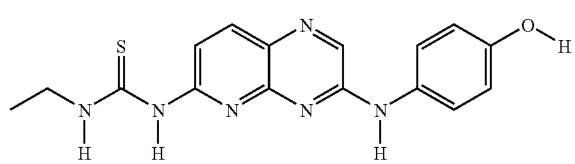 | 1-Ethyl-3-[3-(4-hydroxy-phenylamino)-pyrido[2,3-b]pyrazin-6-yl]-thiourea |
| 162 | 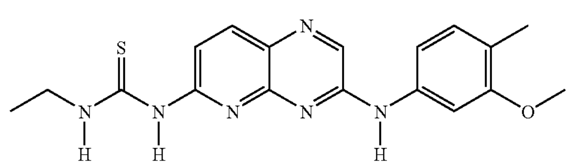 | 1-Ethyl-3-[3-(3-methoxy-4-methyl-phenylamino)-pyrido[2,3-b]pyrazin-6-yl]-thiourea |
| 163 | 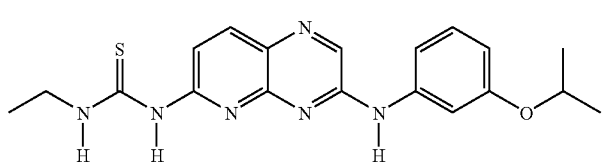 | 1-Ethyl-3-[3-(3-isopropoxy-phenylamino)-pyrido[2,3-b]pyrazin-6-yl]-thiourea |

| Compound | Structure | Name |
|---|---|---|
| 164 | 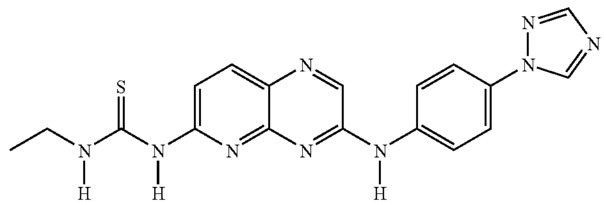 | 1-Ethyl-3-[3-(4-[1,2,4]triazol-1-yl-phenylamino)-pyrido[2,3-b]pyrazin-6-yl]-thiourea |
| 165 | 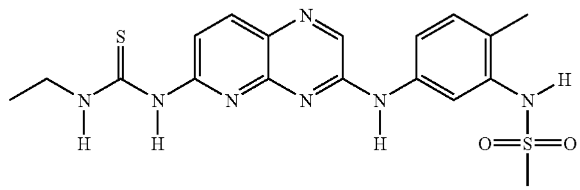 | N-{5-[6-(3-Ethyl-thioureido)-pyrido[2,3-b]pyrazin-3-ylamino]-2-methyl-phenyl}-methanesulfonamide |
| 166 | 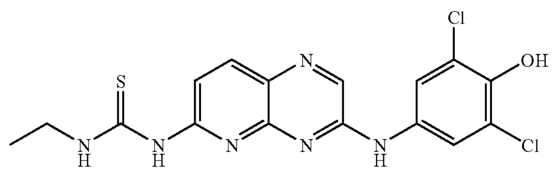 | 1-[3-(3,5-Dichloro-4-hydroxy-phenylamino)-pyrido[2,3-b]pyrazin-6-yl]-3-ethyl-thiourea |
| 167 | 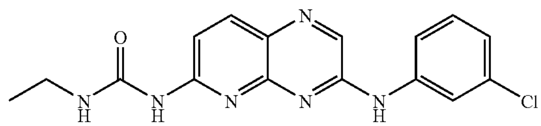 | 1-[3-(3-Chloro-phenylamino)-pyrido[2,3-b]pyrazin-6-yl]-3-ethyl-urea |
| 168 | 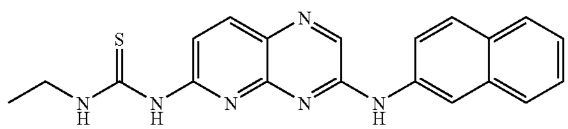 | 1-Ethyl-3-[3-(naphthalen-2-ylamino)-pyrido[2,3-b]pyrazin-6-yl]-thiourea |
| 169 | 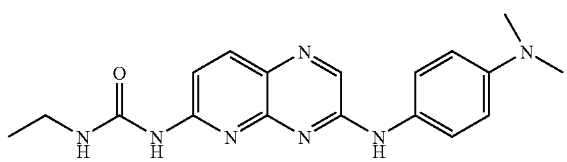 | 1-[3-(4-Dimethylamino-phenylamino)-pyrido[2,3-b]pyrazin-6-yl]-3-ethyl-urea |
| 170 | 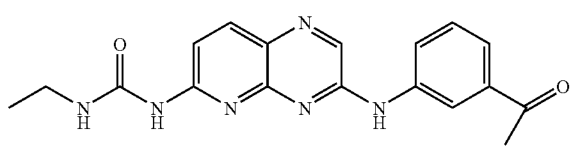 | 1-[3-(3-Acetyl-phenylamino)-pyrido[2,3-b]pyrazin-6-yl]-3-ethyl-urea |
| 171 | 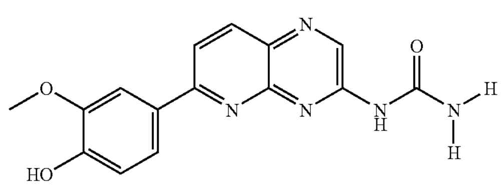 | [6-(4-Hydroxy-3-methoxy-phenyl)-pyrido[2,3-b]pyrazin-3-yl]-urea |
| 172 | 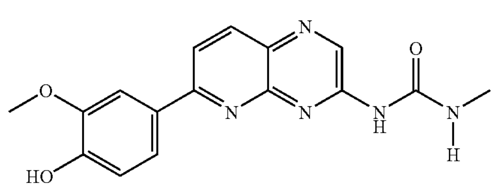 | 1-[6-(4-Hydroxy-3-methoxy-phenyl)-pyrido[2,3-b]pyrazin-3-yl]-3-methyl-urea |

-continued

| Compound | Structure | Name |
|---|---|---|
| 173 | 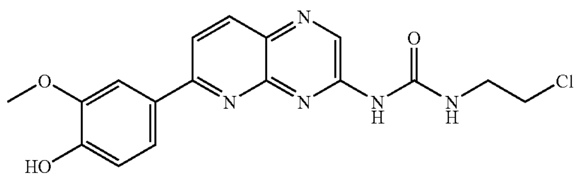 | 1-(2-Chloro-ethyl)-3-[6-(4-hydroxy-3-methoxy-phenyl)-pyrido[2,3-b]pyrazin-3-yl]-urea |
| 174 | 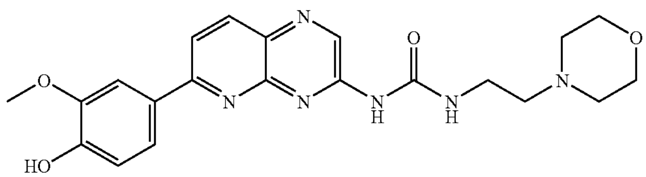 | 1-[6-(4-Hydroxy-3-methoxy-phenyl)-pyrido[2,3-b]pyrazin-3-yl]-3-(2-morpholin-4-yl-ethyl)-urea |
| 175 | 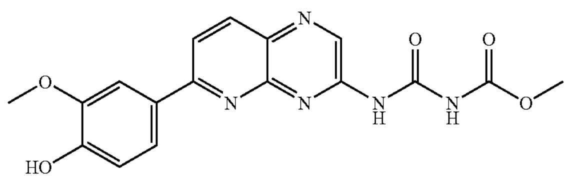 | |
| 176 | 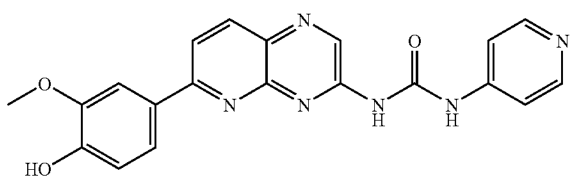 | 1-[6-(4-Hydroxy-3-methoxy-phenyl)-pyrido[2,3-b]pyrazin-3-yl]-3-pyridin-4-yl-urea |
| 177 | 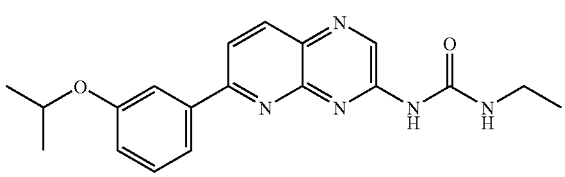 | 1-Ethyl-3-[6-(3-isopropoxy-phenyl)-pyrido[2,3-b]pyrazin-3-yl]-urea |
| 178 | 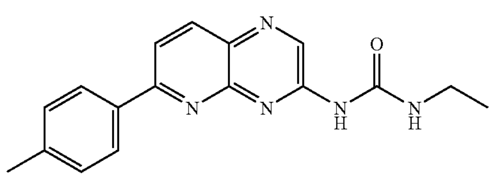 | 1-Ethyl-3-(6-p-tolyl-pyrido[2,3-b]pyrazin-3-yl)-urea |
| 179 | 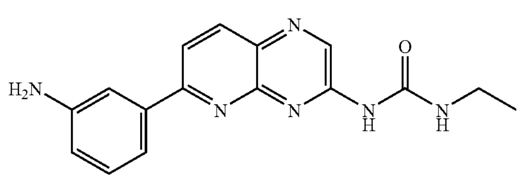 | 1-[6-(3-Amino-phenyl)-pyrido[2,3-b]pyrazin-3-yl]-3-ethyl-urea |
| 180 | 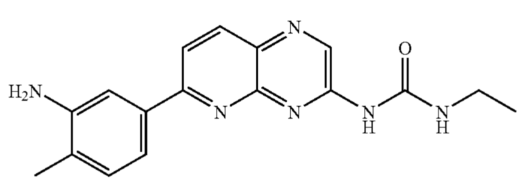 | 1-[6-(3-Amino-4-methyl-phenyl)-pyrido[2,3-b]pyrazin-3-yl]-3-ethyl-urea |

-continued

| Compound | Structure | Name |
|---|---|---|
| 181 | 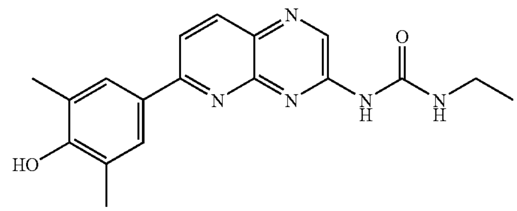 | 1-Ethyl-3-[6-(4-hydroxy-3,5-dimethyl-phenyl)-pyrido[2,3-b]pyrazin-3-yl]-urea |
| 182 | 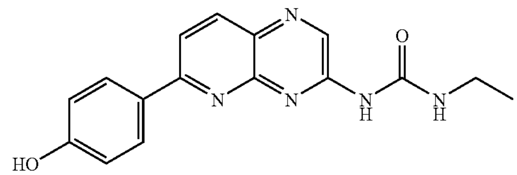 | 1-Ethyl-3-[6-(4-hydroxy-phenyl)-pyrido[2,3-b]pyrazin-3-yl]-urea |
| 183 | 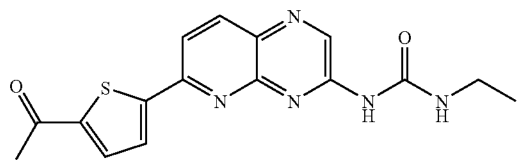 | 1-[6-(5-Acetyl-thiophen-2-yl)-pyrido[2,3-b]pyrazin-3-yl]-3-ethyl-urea |
| 184 | 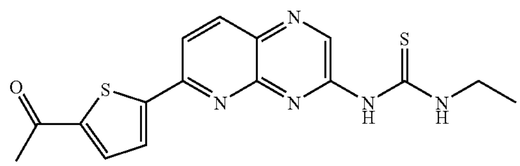 | 1-[6-(5-Acetyl-thiophen-2-yl)-pyrido[2,3-b]pyrazin-3-yl]-3-ethyl-thiourea |
| 185 | 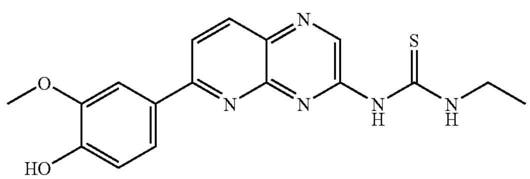 | 1-Ethyl-3-[6-(4-hydroxy-3-methoxy-phenyl)-pyrido[2,3-b]pyrazin-3-yl]-thiourea |
| 186 | 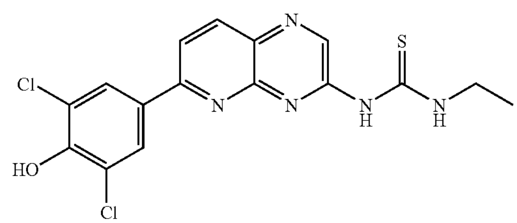 | 1-[6-(3,5-Dichloro-4-hydroxy-phenyl)-pyrido[2,3-b]pyrazin-3-yl]-3-ethyl-thiourea |
| 187 | 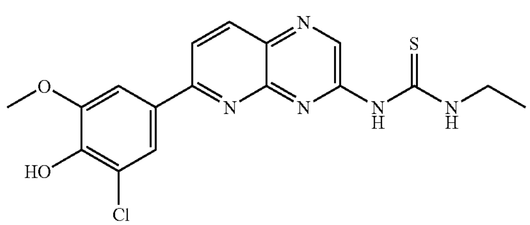 | 1-[6-(3-Chloro-4-hydroxy-5-methoxy-phenyl)-pyrido[2,3-b]pyrazin-3-yl]-3-ethyl-thiourea |
| 188 | 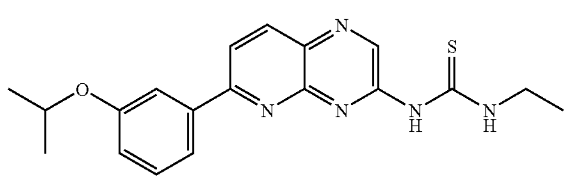 | 1-Ethyl-3-[6-(3-isopropoxy-phenyl)-pyrido[2,3-b]pyrazin-3-yl]-thiourea |

| Compound | Structure | Name |
|---|---|---|
| 189 | 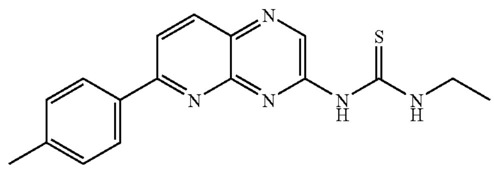 | 1-Ethyl-3-(6-p-tolyl-pyrido[2,3-b]pyrazin-3-yl)-thiourea |
| 190 | 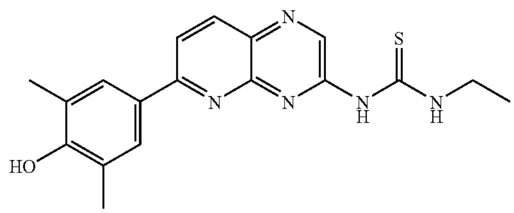 | 1-Ethyl-3-[6-(4-hydroxy-3,5-dimethyl-phenyl)-pyrido[2,3-b]pyrazin-3-yl]-thiourea |
| 191 | 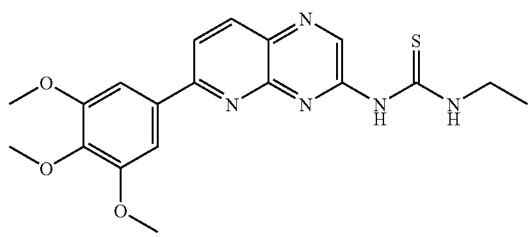 | 1-Ethyl-3-[6-(3,4,5-trimethoxy-phenyl)-pyrido[2,3-b]pyrazin-3-yl]-thiourea |
| 192 | 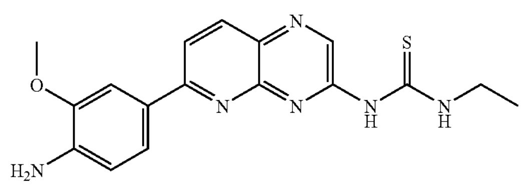 | 1-[6-(4-Amino-3-methoxy-phenyl)-pyrido[2,3-b]pyrazin-3-yl]-3-ethyl-thiourea |
| 193 | 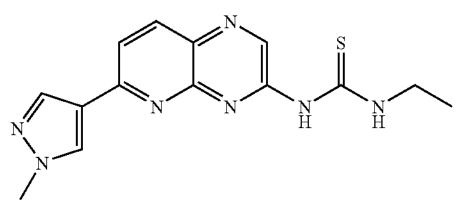 | 1-Ethyl-3-[6-(1-methyl-1H-pyrazol-4-yl)-pyrido[2,3-b]pyrazin-3-yl]-thiourea |
| 194 | 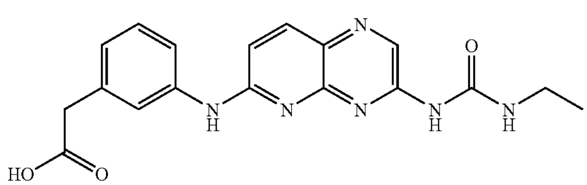 | {3-[3-(3-Ethyl-ureido)-pyrido[2,3-b]pyrazin-6-ylamino]-phenyl}-acetic acid |
| 195 | 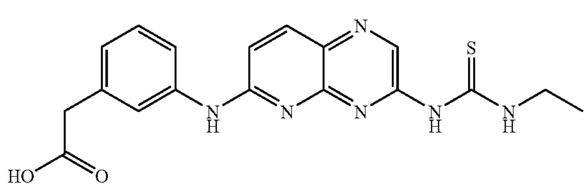 | {3-[3-(3-Ethyl-thioureido)-pyrido[2,3-b]pyrazin-6-ylamino]-phenyl}-acetic acid |
| 196 | 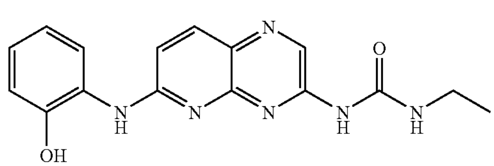 | 1-Ethyl-3-[6-(2-hydroxy-phenylamino)-pyrido[2,3-b]pyrazin-3-yl]-urea |

-continued

| Compound | Structure | Name |
|---|---|---|
| 197 | 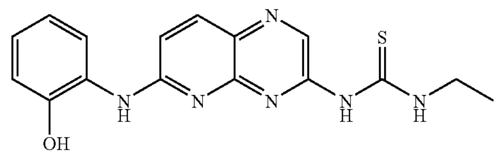 | 1-Ethyl-3-[6-(2-hydroxy-phenylamino)-pyrido[2,3-b]pyrazin-3-yl]-thiourea |
| 198 | 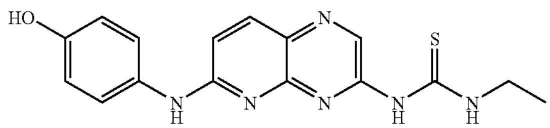 | 1-Ethyl-3-[6-(4-hydroxy-phenylamino)-pyrido[2,3-b]pyrazin-3-yl]-thiourea |
| 199 | 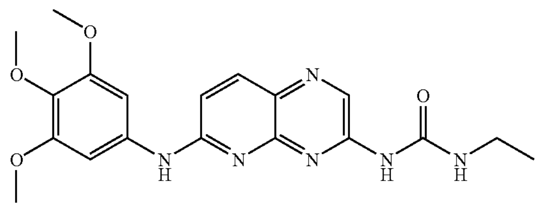 | 1-Ethyl-3-[6-(3,4,5-trimethoxy-phenylamino)-pyrido[2,3-b]pyrazin-3-yl]-urea |
| 200 | 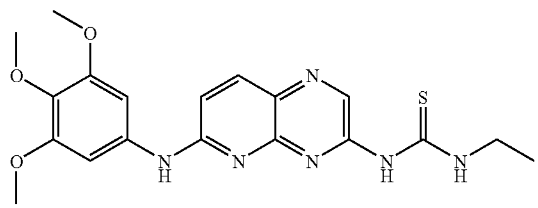 | 1-Ethyl-3-[6-(3,4,5-trimethoxy-phenylamino)-pyrido[2,3-b]pyrazin-3-yl]-thiourea |
| 201 | 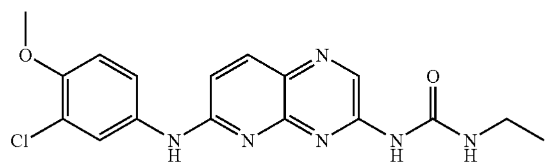 | 1-[6-(3-Chloro-4-methoxy-phenylamino)-pyrido[2,3-b]pyrazin-3-yl]-3-ethyl-urea |
| 202 | 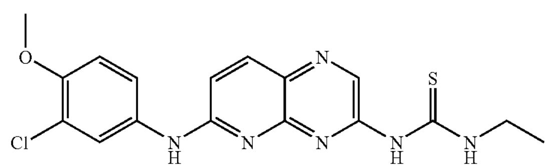 | 1-[6-(3-Chloro-4-methoxy-phenylamino)-pyrido[2,3-b]pyrazin-3-yl]-3-ethyl-thiourea |
| 203 | 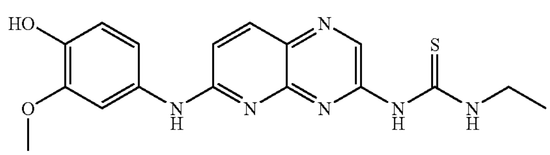 | 1-Ethyl-3-[6-(4-hydroxy-3-methoxy-phenylamino)-pyrido[2,3-b]pyrazin-3-yl]-thiourea |
| 204 | 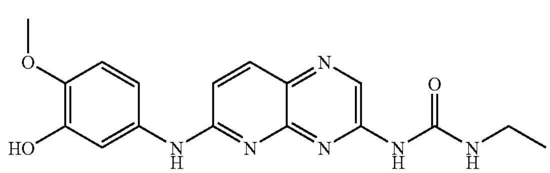 | 1-Ethyl-3-[6-(3-hydroxy-4-methoxy-phenylamino)-pyrido[2,3-b]pyrazin-3-yl]-urea |
| 205 | 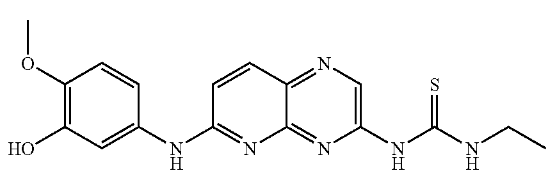 | 1-Ethyl-3-[6-(3-hydroxy-4-methoxy-phenylamino)-pyrido[2,3-b]pyrazin-3-yl]-thiourea |

-continued

| Compound | Structure | Name |
|---|---|---|
| 206 | 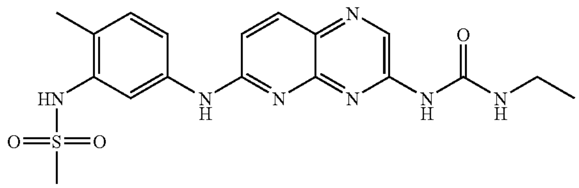 | N-{5-[3-(3-Ethyl-ureido)-pyrido[2,3-b]pyrazin-6-ylamino]-2-methyl-phenyl}-methanesulfonamide |
| 207 | 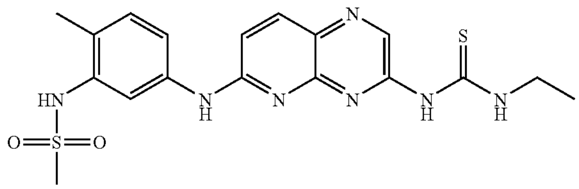 | N-{5-[3-(3-Ethyl-thioureido)-pyrido[2,3-b]pyrazin-6-ylamino]-2-methyl-phenyl}-methanesulfonamide |
| 208 | 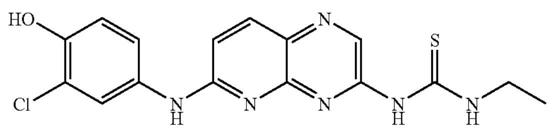 | 1-[6-(3-Chloro-4-hydroxy-phenylamino)-pyrido[2,3-b]pyrazin-3-yl]-3-ethyl-thiourea |
| 209 | 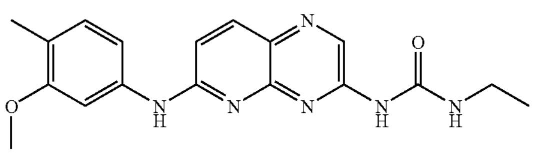 | 1-Ethyl-3-[6-(3-methoxy-4-methyl-phenylamino)-pyrido[2,3-b]pyrazin-3-yl]-urea |
| 210 | 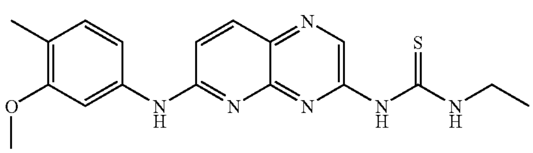 | 1-Ethyl-3-[6-(3-methoxy-4-methyl-phenylamino)-pyrido[2,3-b]pyrazin-3-yl]-thiourea |
| 211 | 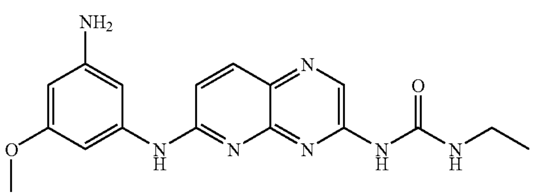 | 1-[6-(3-Amino-5-methoxy-phenylamino)-pyrido[2,3-b]pyrazin-3-yl]-3-ethyl-urea |
| 212 | 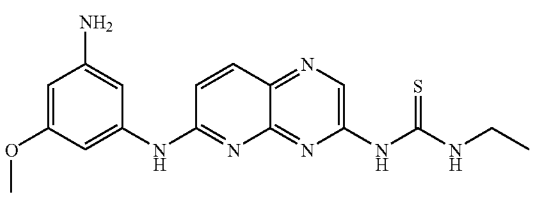 | 1-[6-(3-Amino-5-methoxy-phenylamino)-pyrido[2,3-b]pyrazin-3-yl]-3-ethyl-thiourea |
| 213 | 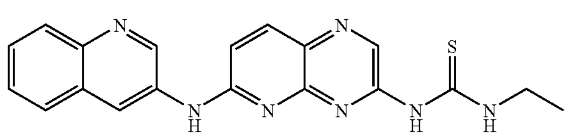 | 1-Ethyl-3-[6-(quinolin-3-ylamino)-pyrido[2,3-b]pyrazin-3-yl]-thiourea |
| 214 | 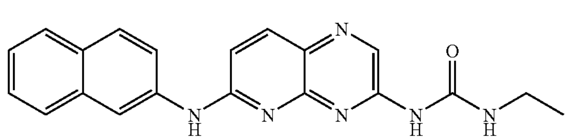 | 1-Ethyl-3-[6-(naphthalen-2-ylamino)-pyrido[2,3-b]pyrazin-3-yl]-urea |

-continued

| Compound | Structure | Name |
|---|---|---|
| 215 | 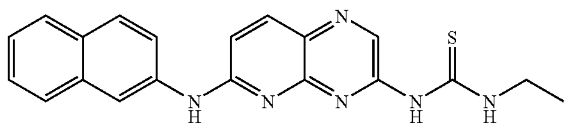 | 1-Ethyl-3-[6-(naphthalen-2-ylamino)-pyrido[2,3-b]pyrazin-3-yl]-thiourea |
| 216 | 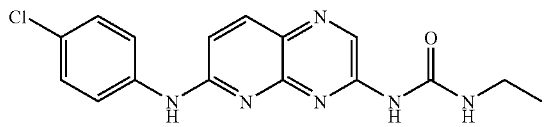 | 1-[6-(4-Chlorophenylamino)-pyrido[2,3-b]pyrazin-3-yl]-3-ethyl-urea |
| 217 | 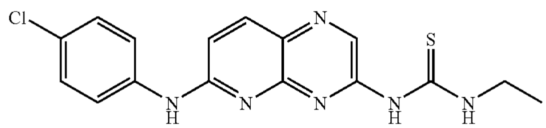 | 1-[6-(4-Chlorophenylamino)-pyrido[2,3-b]pyrazin-3-yl]-3-ethyl-thiourea |
| 218 | 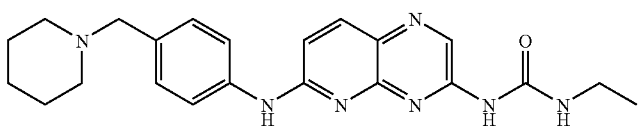 | 1-Ethyl-3-[6-(4-piperidin-1-ylmethyl-phenylamino)-pyrido[2,3-b]pyrazin-3-yl]-urea |
| 219 | 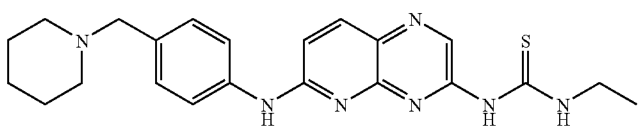 | 1-Ethyl-3-[6-(4-piperidin-1-ylmethyl-phenylamino)-pyrido[2,3-b]pyrazin-3-yl]-thiourea |
| 220 | 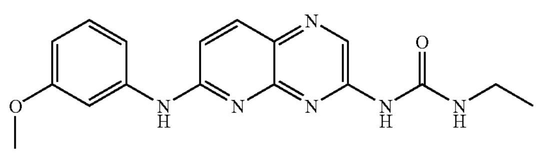 | 1-Ethyl-3-[6-(3-methoxy-phenylamino)-pyrido[2,3-b]pyrazin-3-yl]-urea |
| 221 | 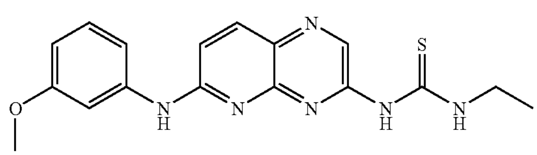 | 1-Ethyl-3-[6-(3-methoxy-phenylamino)-pyrido[2,3-b]pyrazin-3-yl]-thiourea |
| 222 | 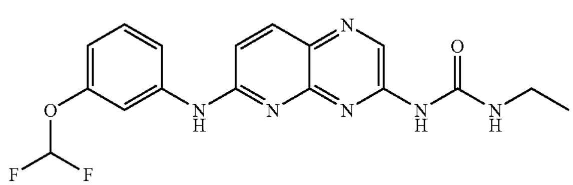 | 1-[6-(3-Difluoromethoxy-phenylamino)-pyrido[2,3-b]pyrazin-3-yl]-3-ethyl-urea |
| 223 | 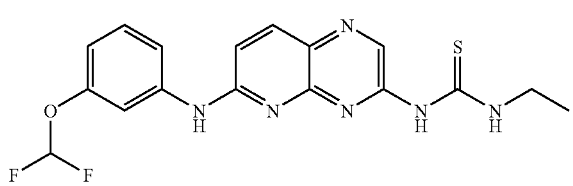 | 1-[6-(3-Difluoromethoxy-phenylamino)-pyrido[2,3-b]pyrazin-3-yl]-3-ethyl-thiourea |
| 224 | 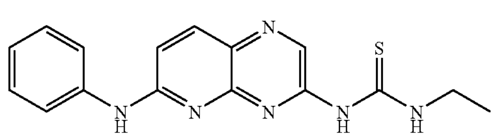 | 1-Ethyl-3-(6-phenylamino-pyrido[2,3-b]pyrazin-3-yl)-thiourea |

-continued

| Compound | Structure | Name |
|---|---|---|
| 225 | 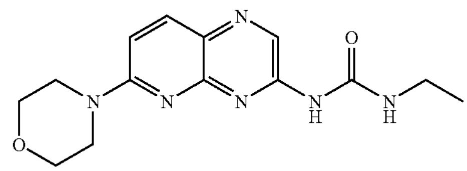 | 1-Ethyl-3-(6-morpholin-4-yl-pyrido[2,3-b]pyrazin-3-yl)-urea |
| 226 | 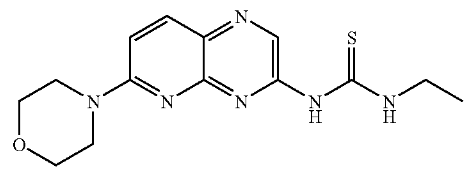 | 1-Ethyl-3-(6-morphoiin-4-yl-pyrido[2,3-b]pyrazin-3-yl)-thiourea |
| 227 | 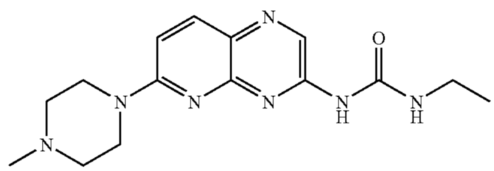 | 1-Ethyl-3-[6-(4-methyl-piperazin-1-yl)-pyrido[2,3-b]pyrazin-3-yl]-urea |
| 228 | 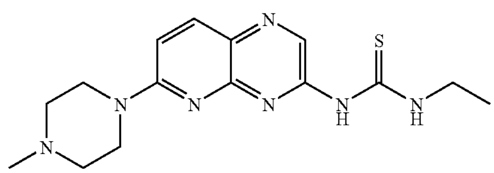 | 1-Ethyl-3-[6-(4-methyl-piperazin-1-yl)-pyrido[2,3-b]pyrazin-3-yl]-thiourea |
| 229 | 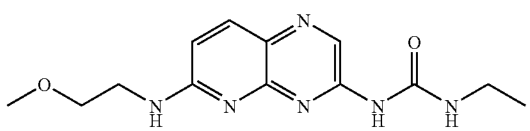 | 1-Ethyl-3-[6-(2-methoxy-ethylamino)-pyrido[2,3-b]pyrazin-3-yl]-urea |
| 230 | 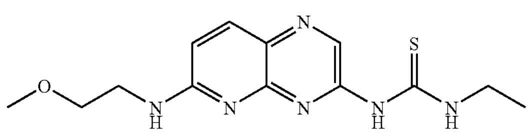 | 1-Ethyl-3-[6-(2-methoxy-ethylamino)-pyrido[2,3-b]pyrazin-3-yl]-thiourea |
| 231 | 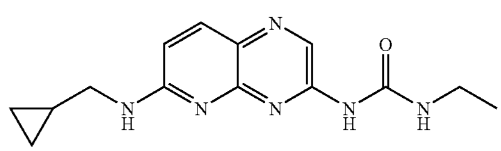 | 1-[6-(Cyclopropylmethyl-amino)-pyrido[2,3-b]pyrazin-3-yl]-3-ethyl-urea |
| 232 | 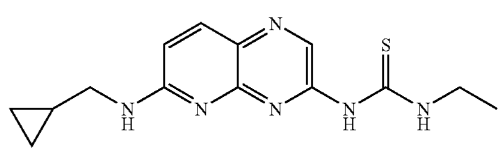 | 1-[6-(Cyclopropylmethyl-amino)-pyrido[2,3-b]pyrazin-3-yl]-3-ethyl-thiourea |
| 233 | 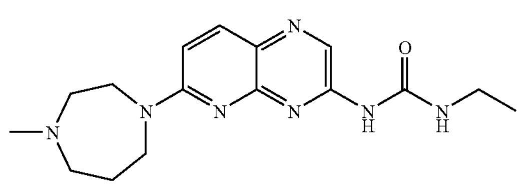 | 1-Ethyl-3-[6-(4-methyl-[1,4]diazepan-1-yl)-pyrido[2,3-b]pyrazin-3-yl]-urea |

| Compound | Structure | Name |
|---|---|---|
| 234 | 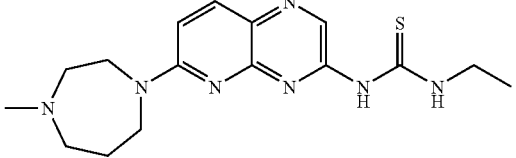 | 1-Ethyl-3-[6-(4-methyl-[1,4]diazepan-1-yl)-pyrido[2,3-b]pyrazin-3-yl]-thiourea |
| 235 | 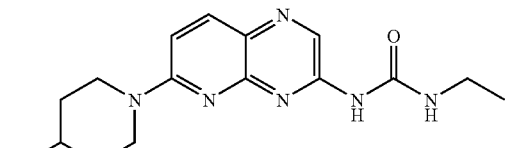 | 1-Ethyl-3-[6-(4-hydroxy-piperidin-1-yl)-pyrido[2,3-b]pyrazin-3-yl]-urea |
| 236 | 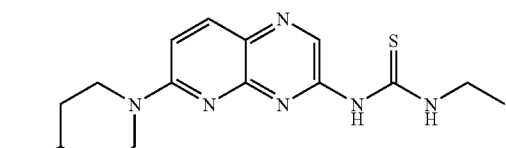 | 1-Ethyl-3-[6-(4-hydroxy-piperidin-1-yl)-pyrido[2,3-b]pyrazin-3-yl]-thiourea |
| 237 | 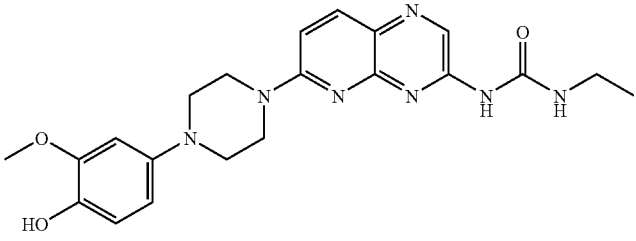 | 1-Ethyl-3-{6-[4-(4-hydroxy-3-methoxy-phenyl)-piperazin-1-yl]-pyrido[2,3-b]pyrazin-3-yl}-urea |
| 238 | 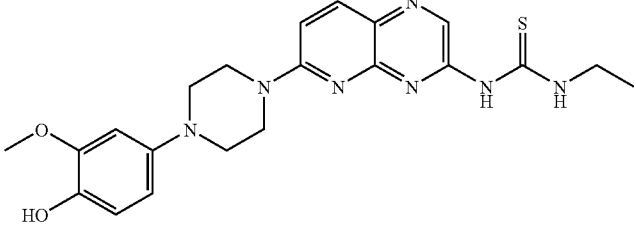 | 1-Ethyl-3-{6-[4-(4-hydroxy-3-methoxy-phenyl)-piperazin-1-yl]-pyrido[2,3-b]pyrazin-3-yl}-thiourea |
| 239 | 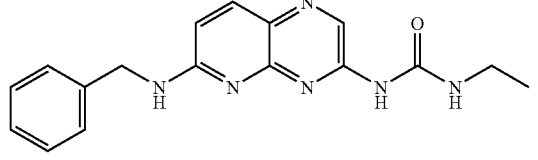 | 1-(6-Benzylamino-pyrido[2,3-b]pyrazin-3-yl)-3-ethyl-urea |
| 240 | 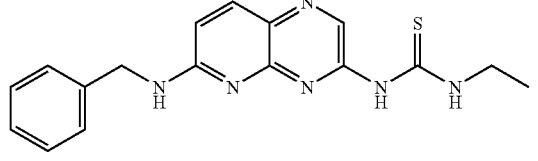 | 1-(6-Benzylamino-pyrido[2,3-b]pyrazin-3-yl)-3-ethyl-thiourea |
| 241 | 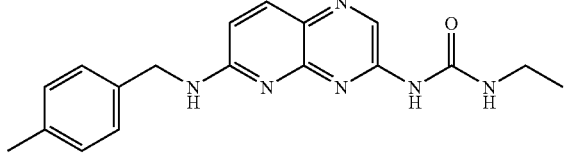 | 1-Ethyl-3-[6-(4-methyl-benzylamino)-pyrido[2,3-b]pyrazin-3-yl]-urea |

-continued

| Compound | Structure | Name |
|---|---|---|
| 242 | 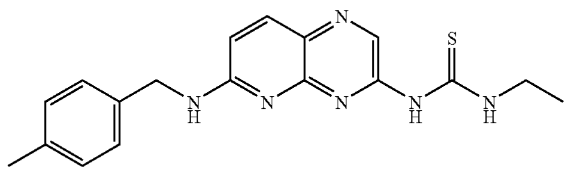 | 1-Ethyl-3-[6-(4-methyl-benzylamino)-pyrido[2,3-b]pyrazin-3-yl]-thiourea |
| 243 | 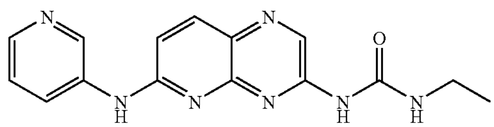 | 1-Ethyl-3-[6-(pyridin-3-ylamino)-pyrido[2,3-b]pyrazin-3-yl]-urea |
| 244 | 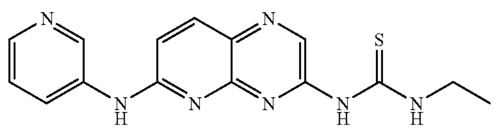 | 1-Ethyl-3-[6-(pyridin-3-ylamino)-pyrido[2,3-b]pyrazin-3-yl]-thiourea |
| 245 | 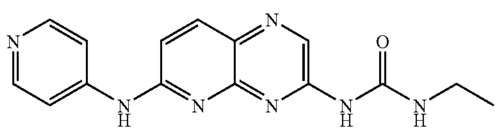 | 1-Ethyl-3-[6-(pyridin-4-ylamino)-pyrido[2,3-b]pyrazin-3-yl]-urea |
| 246 | 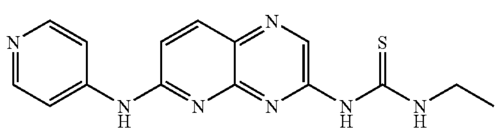 | 1-Ethyl-3-[6-(pyridin-4-ylamino)-pyrido[2,3-b]pyrazin-3-yl]-thiourea |
| 247 | 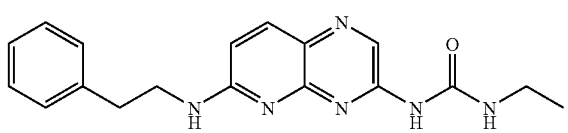 | 1-Ethyl-3-(6-phenethylamino-pyrido[2,3-b]pyrazin-3-yl)-urea |
| 248 | 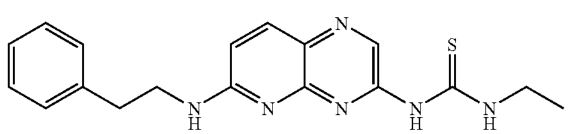 | 1-Ethyl-3-(6-phenethylamino-pyrido[2,3-b]pyrazin-3-yl)-thiourea |
| 249 | 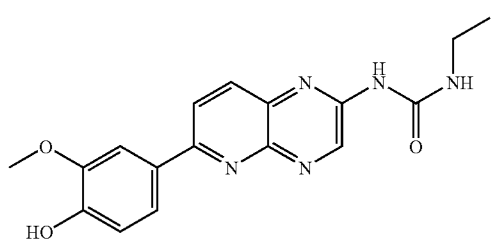 | 1-Ethyl-3-[6-(4-hydroxy-3-methoxy-phenyl)-pyrido[2,3-b]pyrazin-2-yl]-urea |
| 250 | 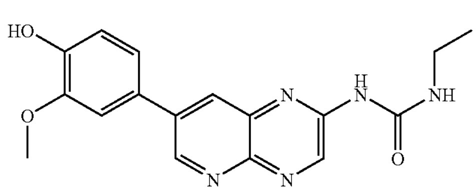 | 1-Ethyl-3-[7-(4-hydroxy-3-methoxy-phenyl)-pyrido[2,3-b]pyrazin-2-yl]-urea |

| Compound | Structure | Name |
|---|---|---|
| 251 | 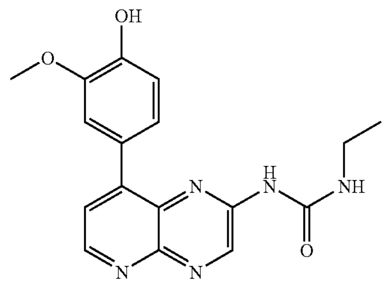 | 1-Ethyl-3-[8-(4-hydroxy-3-methoxy-phenyl)-pyrido[2,3-b]pyrazin-2-yl]-urea |
| 252 | 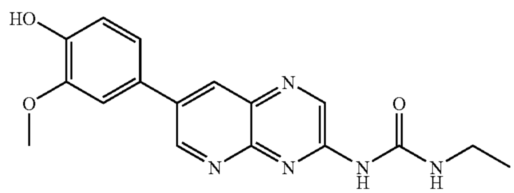 | 1-Ethyl-3-[7-(4-hydroxy-3-methoxy-phenyl)-pyrido[2,3-b]pyrazin-3-yl]-urea |
| 253 | 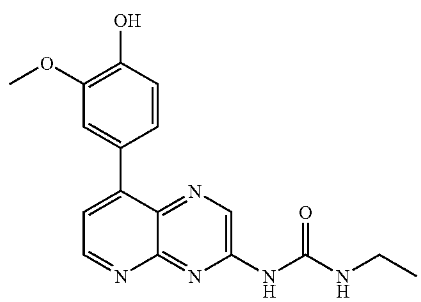 | 1-Ethyl-3-[8-(4-hydroxy-3-methoxy-phenyl)-pyrido[2,3-b]pyrazin-3-yl]-urea |
| 254 | 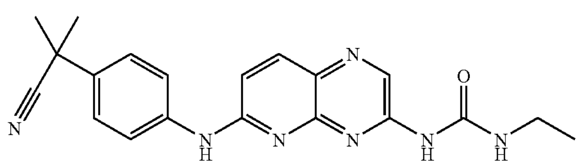 | 1-{6-[4-(Cyano-dimethyl-methyl)-phenylamino]-pyrido[2,3-b]pyrazin-3-yl}-3-ethyl-urea |
| 255 | 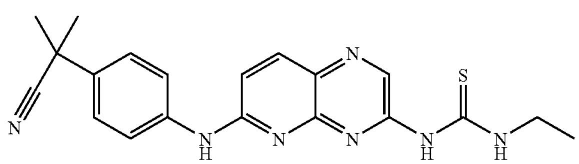 | 1-{6-[4-(Cyano-dimethyl-methyl)-phenylamino]-pyrido[2,3-b]pyrazin-3-yl}-3-ethyl-thiourea |
| 256 | 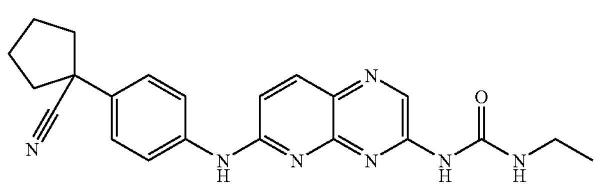 | 1-{6-[4-(1-Cyano-cyclopentyl)-phenylamino]-pyrido[2,3-b]pyrazin-3-yl}-3-ethyl-urea |
| 257 | 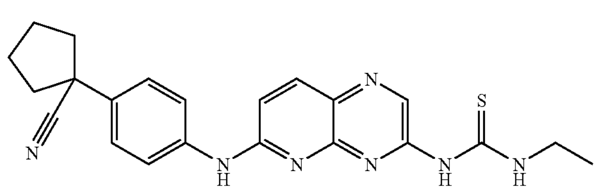 | 1-{6-[4-(1-Cyano-cyclopentyl)-phenylamino]-pyrido[2,3-b]pyrazin-3-yl}-3-ethyl-thiourea |

-continued

| Compound | Structure | Name |
|---|---|---|
| 258 | 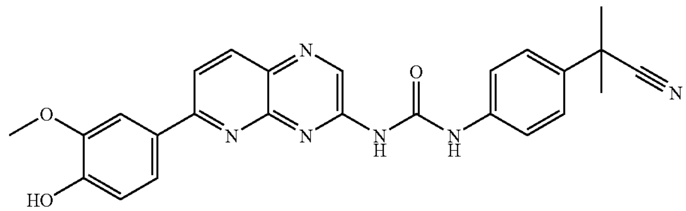 | 1-[4-(Cyano-dimethyl-methyl)-phenyl]-3-[6-(4-hydroxy-3-methoxy-phenyl)-pyrido[2,3-b]pyrazin-3-yl]-urea |
| 259 | 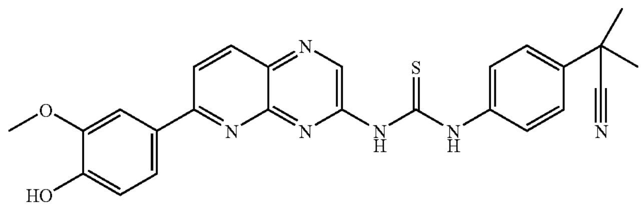 | 1-[4-(Cyano-dimethyl-methy)-phenyl]-3-[6-(4-hydroxy-3-methoxy-phenyl)-pyrido[2,3-b]pyrazin-3-yl]-thiourea |
| 260 | 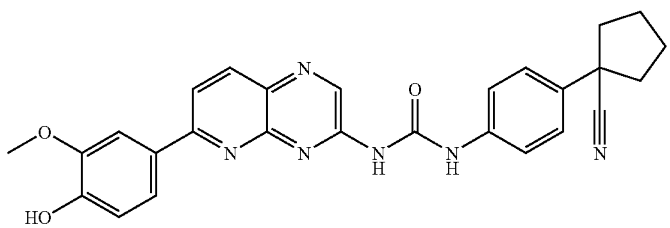 | 1-[4-(1-Cyano-cyclopentyl)-phenyl]-3-[6-(4-hydroxy-3-methoxy-phenyl)-pyrido[2,3-b]pyrazin-3-yl]-urea |
| 261 | 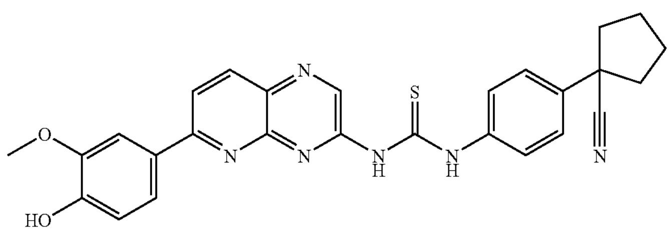 | 1-[4-(1-Cyano-cyclopentyl)-phenyl]-3-[6-(4-hydroxy-3-methoxy-phenyl)-pyrido[2,3-b]pyrazin-3-yl]-thiourea |
| 262 | 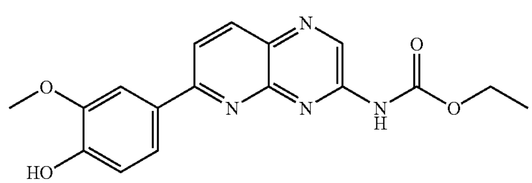 | [6-(4-Hydroxy-3-methoxy-phenyl)-pyrido[2,3-b]pyrazin-3-yl]-carbamic acid ethyl ester |
| 263 | 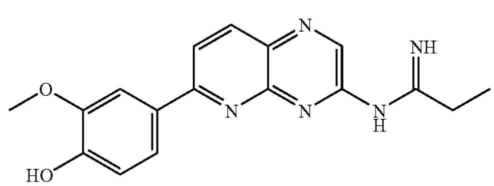 | N-[6-(4-Hydroxy-3-methoxy-phenyl)-pyrido[2,3-b]pyrazin-3-yl]-propionamidine |
| 264 | 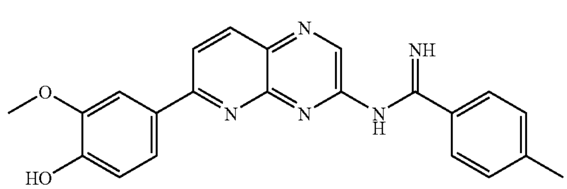 | N-[6-(4-Hydroxy-3-methoxy-phenyl)-pyrido[2,3-b]pyrazin-3-yl]-4-methyl-benzamidine |

| Compound | Structure | Name |
| --- | --- | --- |
| 265 | 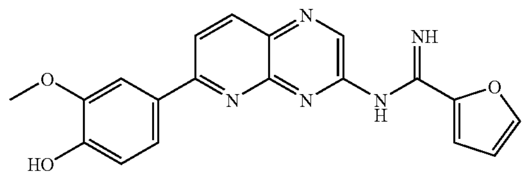 | N-[6-(4-Hydroxy-3-methoxy-phenyl)-pyrido[2,3-b]pyrazin-3-yl]-furan-2-carboxamidine |
| 266 | 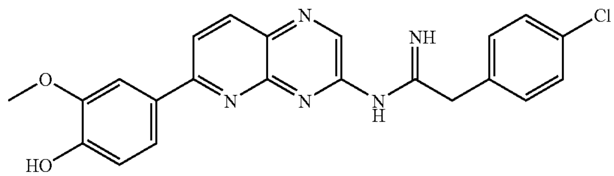 | 2-(4-Chloro-phenyl)-N-[6-(4-hydroxy-3-methoxy-phenyl)-pyrido[2,3-b]pyrazin-3-yl]-acetamidine |
| 267 | 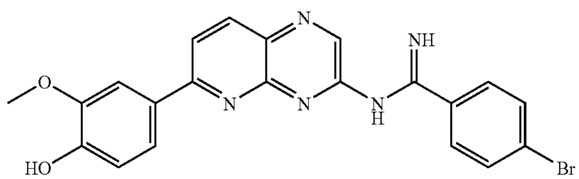 | 4-Bromo-N-[6-(4-hydroxy-3-methoxy-phenyl)-pyrido[2,3-b]pyrazin-3-yl]-benzamidine |
| 268 | 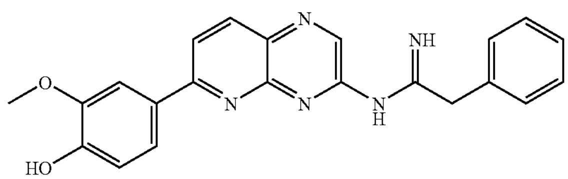 | N-[6-(4-Hydroxy-3-methoxy-phenyl)-pyrido[2,3-b]pyrazin-3-yl]-2-phenyl-acetamidine |
| 269 | 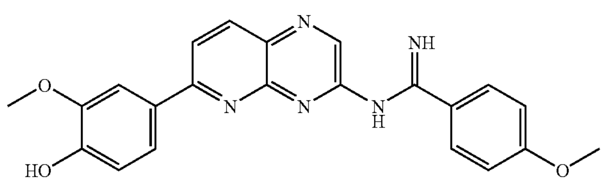 | N-[6-(4-Hydroxy-3-methoxy-phenyl)-pyrido[2,3-b]pyrazin-3-yl]-4-methoxy-benzamidine |
| 270 | 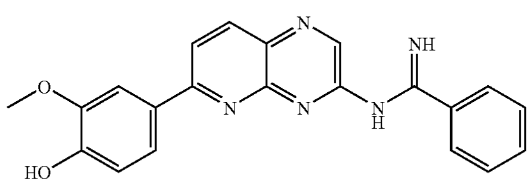 | N-[6-(4-Hydroxy-3-methoxy-phenyl)-pyrido[2,3-b]pyrazin-3-yl]-benzamidine |
| 271 | 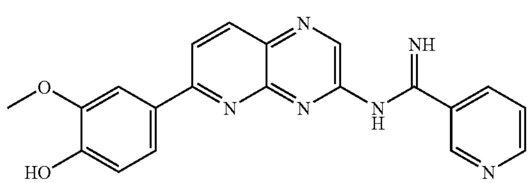 | N-[6-(4-Hydroxy-3-methoxy-phenyl)-pyrido[2,3-b]pyrazin-3-yl]-nicotinamidine |
| 272 | 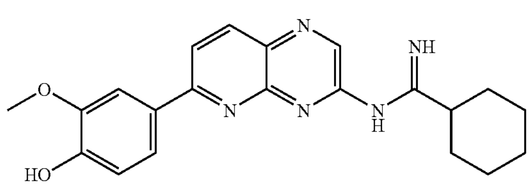 | N-[6-(4-Hydroxy-3-methoxy-phenyl)-pyrido[2,3-b]pyrazin-3-yl]-cyclohexanecarboxamidine |

-continued

| Compound | Structure | Name |
|---|---|---|
| 273 | 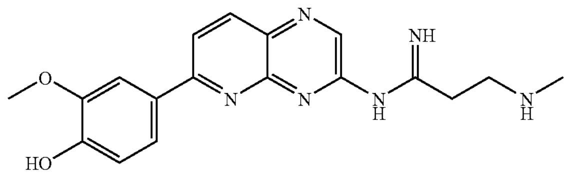 | N-[6-(4-Hydroxy-3-methoxy-phenyl)-pyrido[2,3-b]pyrazin-3-yl]-3-methylamino-propionamidine |
| 274 | 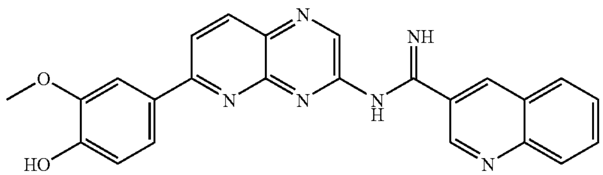 | N-[6-(4-Hydroxy-3-methoxy-phenyl)-pyrido[2,3-b]pyrazin-3-yl]-quinoline-3-carboxamidine |
| 275 | 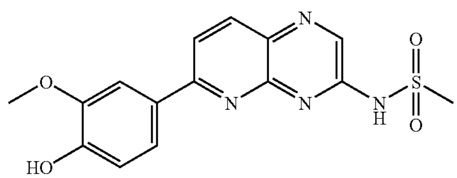 | N-[6-(4-Hydroxy-3-methoxy-phenyl)-pyrido[2,3-b]pyrazin-3-yl]-methanesulfonamide |
| 276 | 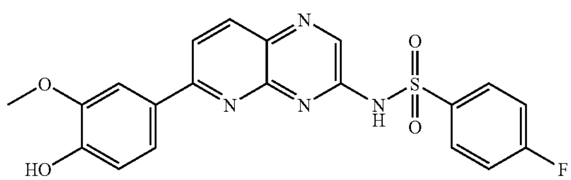 | 4-Fluoro-N-[6-(4-hydroxy-3-methoxy-phenyl)-pyrido[2,3-b]pyrazin-3-yl]-benzenesulfonamide |
| 277 | 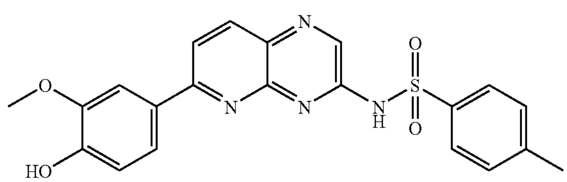 | N-[6-(4-Hydroxy-3-methoxy-phenyl)-pyrido[2,3-b]pyrazin-3-yl]-4-methyl-benzenesulfonamide |
| 278 | 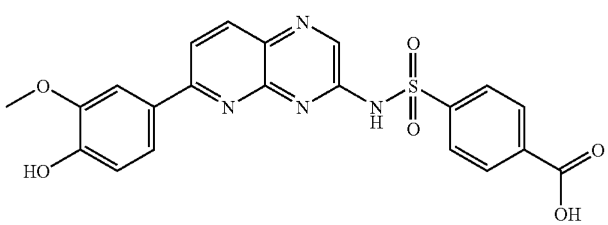 | N-[6-(4-Hydroxy-3-methoxy-phenyl)-pyrido[2,3-b]pyrazin-3-yl]-4-carboxy-benzenesulfonamide |
| 279 | 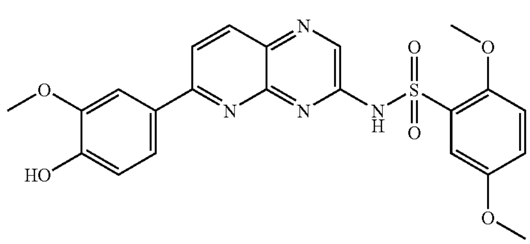 | N-[6-(4-Hydroxy-3-methoxy-phenyl)-pyrido[2,3-b]pyrazin-3-yl]-2,5-dimethoxy-benzenesulfonamide |
| 280 | 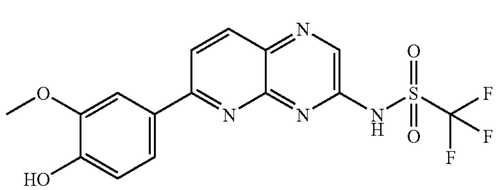 | C,C,C-Trifluoro-N-[6-(4-hydroxy-3-methoxy-phenyl)-pyrido[2,3-b]pyrazin-3-yl]-methanesulfonamide |

-continued

| Compound | Structure | Name |
|---|---|---|
| 281 | 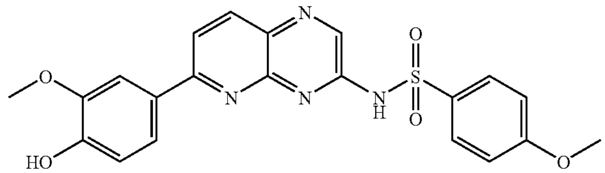 | N-[6-(4-Hydroxy-3-methoxy-phenyl)-pyrido[2,3-b]pyrazin-3-yl]-4-methoxy-benzenesulfonamide |
| 282 | 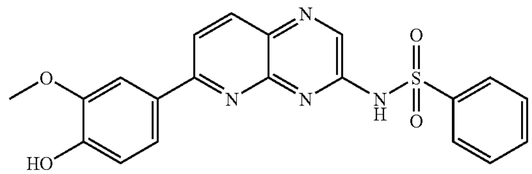 | N-[6-(4-Hydroxy-3-methoxy-phenyl)-pyrido[2,3-b]pyrazin-3-yl]-benzenesulfonamide |
| 283 | 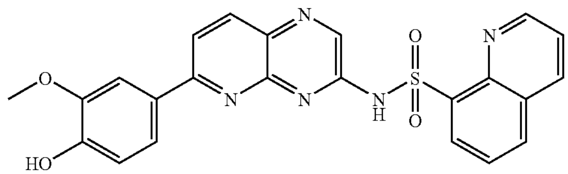 | Quinoline-8-sulfonic acid[6-(4-hydroxy-3-methoxy-phenyl)-pyrido[2,3-b]pyrazin-3-yl]-amide |
| 284 | 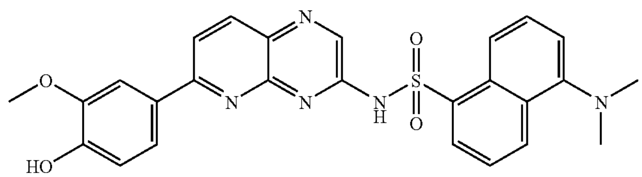 | 5-Dimethylamino-naphthalene-1-sulfonicacid[6-(4-hydroxy-3-methoxy-phenyl)-pyrido[2,3-b]pyrazin-3-yl]-amide |
| 285 | 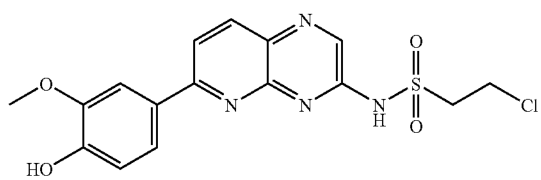 | 2-Chloro-ethanesulfonic acid[6-(4-hydroxy-3-methoxy-phenyl)-pyrido[2,3-b]pyrazin-3-yl]-amide |
| 286 | 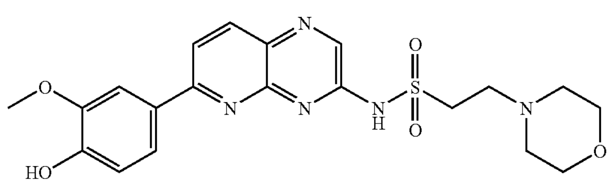 | 2-Morpholin-4-yl-ethanesulfonicacid[6-(4-hydroxy-3-methoxy-phenyl)-pyrido[2,3-b]pyrazin-3-yl]-amide |
| 287 | 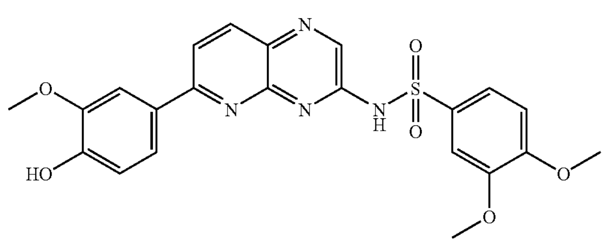 | N-[6-(4-Hydroxy-3-methoxy-phenyl)-pyrido[2,3-b]pyrazin-3-yl]-3,4-dimethoxy-benzenesulfonamide |
| 288 | 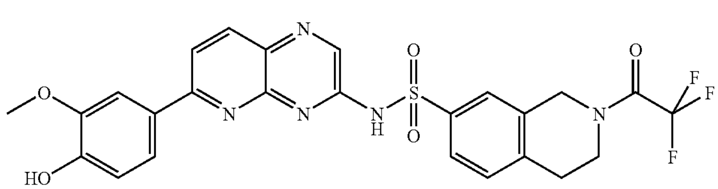 | 2-(2,2,2-Trifluoro-acetyl)-1,2,3,4-tetrahydro-isoquinoline-7-sulfonic acid [6-(4-hydroxy-3-methoxy-phenyl)-pyrido[2,3-b]pyrazin-3-yl]-amide |

-continued

| Compound | Structure | Name |
|---|---|---|
| 289 | 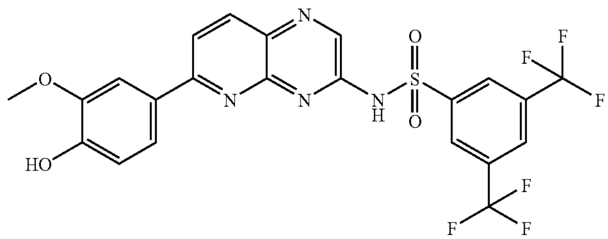 | N-[6-(4-Hydroxy-3-methoxy-phenyl)-pyrido[2,3-b]pyrazin-3-yl]-3,5-bis-trifluoromethyl-benzenesulfonamide |
| 290 | 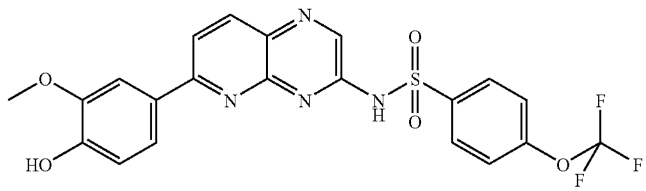 | N-[6-(4-Hydroxy-3-methoxy-phenyl)-pyrido[2,3-b]pyrazin-3-yl]-4-trifluoromethoxy-benzenesulfonamide |
| 291 | 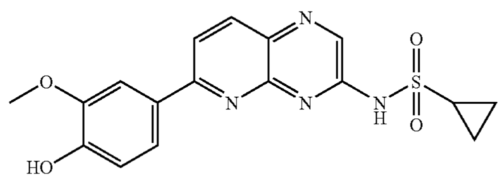 | Cyclopropanesulfonic acid[6-(4-hydroxy-3-methoxy-phenyl)-pyrido[2,3-b]pyrazin-3-yl]-amide |
| 292 | 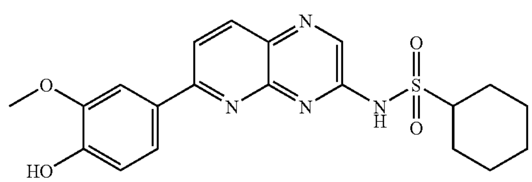 | Cyclohexanesulfonic acid[6-(4-hydroxy-3-methoxy-phenyl)-pyrido[2,3-b]pyrazin-3-yl]-amide |
| 293 | 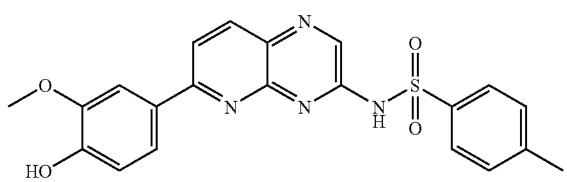 | N-[6-(4-Hydroxy-3-methoxy-phenyl)-pyrido[2,3-b]pyrazin-3-yl]-4-methyl-benzenesulfonamide |
| 294 | 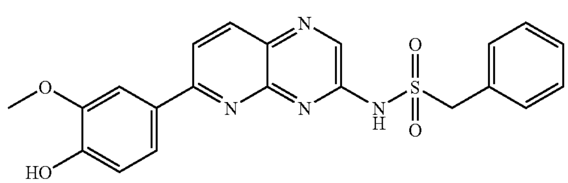 | N-[6-(4-Hydroxy-3-methoxy-phenyl)-pyrido[2,3-b]pyrazin-3-yl]-C-phenyl-methanesulfonamide |
| 295 | 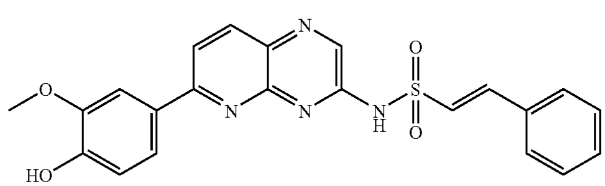 | (E)-2-Phenyl-ethenesulfonic acid [6-(4-hydroxy-3-methoxy-phenyl)-pyrido[2,3-b]pyrazin-3-yl]-amide |
| 296 | 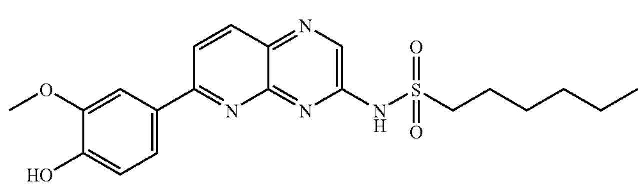 | Hexane-1-sulfonic acid[6-(4-hydroxy-3-methoxy-phenyl)-pyrido[2,3-b]pyrazin-3-yl]-amide |

-continued

| Compound | Structure | Name |
|---|---|---|
| 297 | 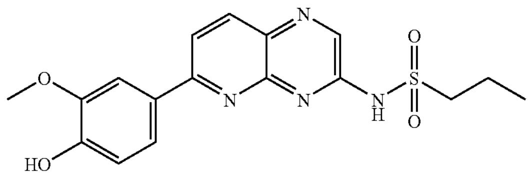 | Propane-1-sulfonic acid[6-(4-hydroxy-3-methoxy-phenyl)-pyrido[2,3-b]pyrazin-3-yl]-amide |
| 298 | 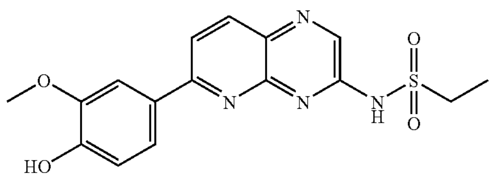 | Ethanesulfonic acid [6-(4-hydroxy-3-methoxy-phenyl)-pyrido[2,3-b]pyrazin-3-yl]-amide |
| 299 | 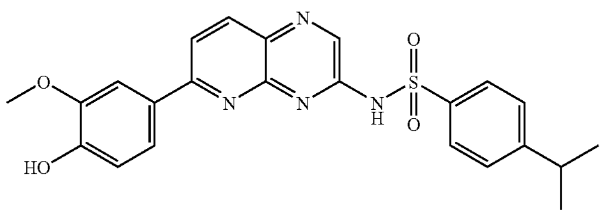 | N-[6-(4-Hydroxy-3-methoxy-phenyl)-pyrido[2,3-b]pyrazin-3-yl]-4-isopropyl-benzenesulfonamide |
| 300 | 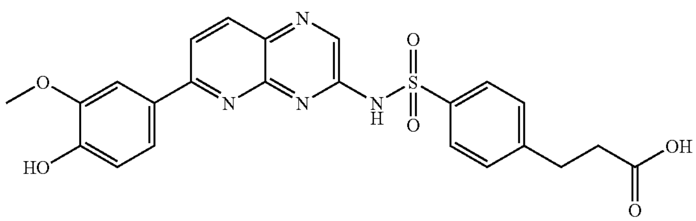 | 3-{4-[6-(4-Hydroxy-3-methoxy-phenyl)-pyrido[2,3-b]pyrazin-3-ylsulfamoyl]-phenyl}-propionic acid |
| 301 | 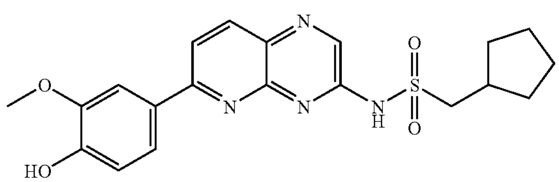 | C-Cyclopentyl-N-[6-(4-hydroxy-3-methoxy-phenyl)-pyrido[2,3-b]pyrazin-3-yl]-methanesulfonamide |
| 302 | 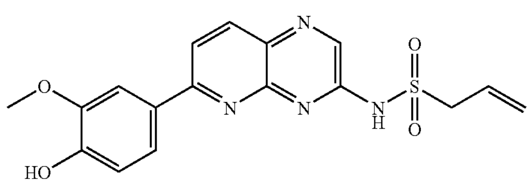 | Prop-2-ene-1-sulfonic acid[6-(4-hydroxy-3-methoxy-phenyl)-pyrido[2,3-b]pyrazin-3-yl]-amide |
| 303 | 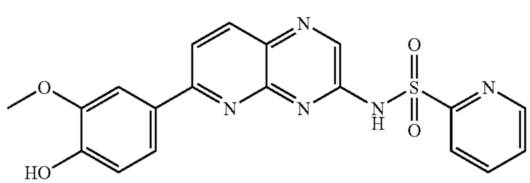 | Pyridine-2-sulfonic acid[6-(4-hydroxy-3-methoxy-phenyl)-pyrido[2,3-b]pyrazin-3-yl]-amide |
| 304 | 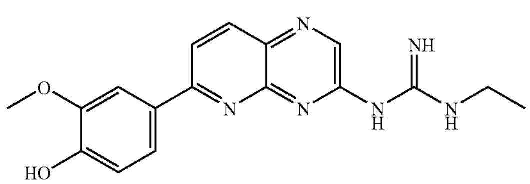 | N-Ethyl-N'-[6-(4-hydroxy-3-methoxy-phenyl)-pyrido[2,3-b]pyrazin-3-yl]-guanidine |

| Compound | Structure | Name |
|---|---|---|
| 305 | 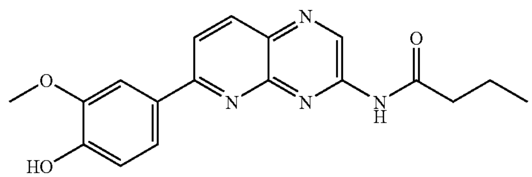 | N-[6-(4-Hydroxy-3-methoxy-phenyl)-pyrido[2,3-b]pyrazin-3-yl]-butyramide |
| 306 | 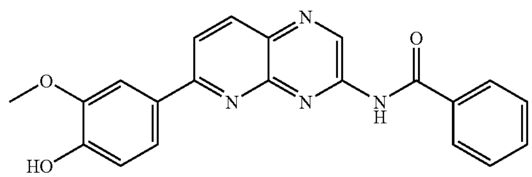 | N-[6-(4-Hydroxy-3-methoxy-phenyl)-pyrido[2,3-b]pyrazin-3-yl]-benzamide |
| 307 | 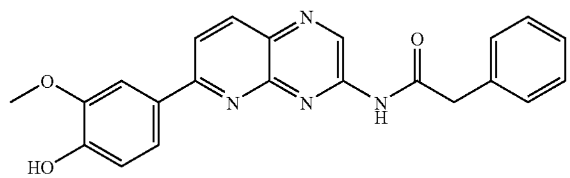 | N-[6-(4-Hydroxy-3-methoxy-phenyl)-pyrido[2,3-b]pyrazin-3-yl]-2-phenyl-acetamide |
| 308 | 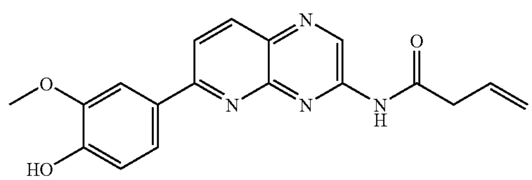 | But-3-enoic acid[6-(4-hydroxy-3-methoxy-phenyl)-pyrido[2,3-b]pyrazin-3-yl]-amide |
| 309 | 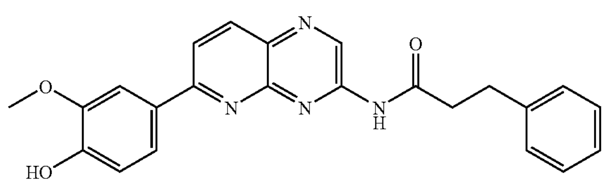 | N-[6-(4-Hydroxy-3-methoxy-phenyl)-pyrido[2,3-b]pyrazin-3-yl]-3-phenyl-propionamide |
| 310 | 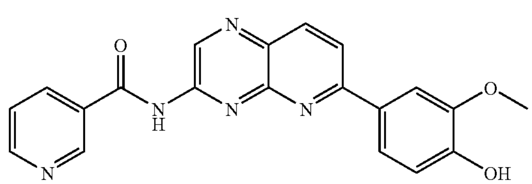 | N-[6-(4-Hydroxy-3-methoxy-phenyl)-pyrido[2,3-b]pyrazin-3-yl]-nicotinamide |
| 311 | 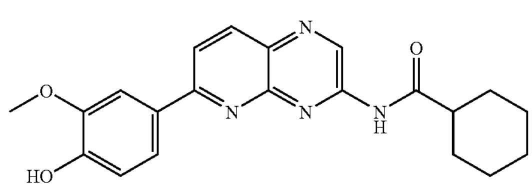 | Cyclohexanecarboxylic acid[6-(4-hydroxy-3-methoxy-phenyl)-pyrido[2,3-b]pyrazin-3-yl]-amide |
| 312 | 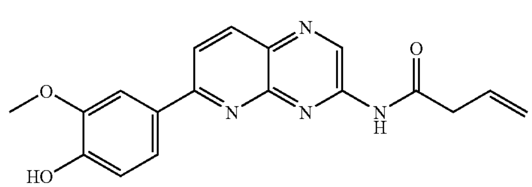 | But-3-enoic acid[6-(4-hydroxy-3-methoxy-phenyl)-pyrido[2,3-b]pyrazin-3-yl]-amide |

| Compound | Structure | Name |
|---|---|---|
| 313 | 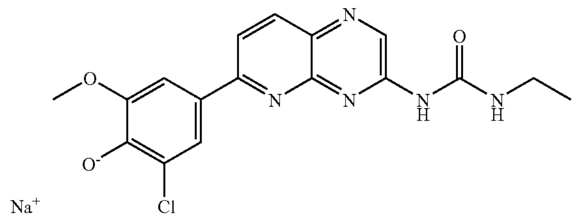 | Sodium; 2-chloro-4-[3-(3-ethyl-ureido)-pyrido[2,3-b]pyrazin-6-yl]-6-methoxy-phenolate |
| 314 | 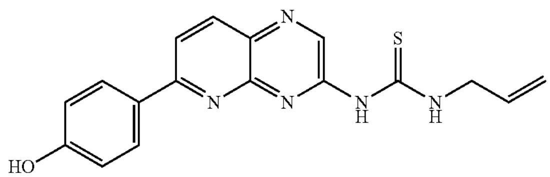 | 1-Allyl-3-[6-(4-hydroxy-phenyl)-pyrido[2,3-b]pyrazin-3-yl]-thiourea |
| 315 | 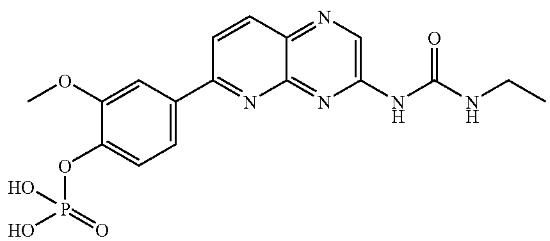 | Phosphoric acid mono-{4-[3-(3-ethyl-ureido)-pyrido[2,3-b]pyrazin-6-yl]-2-methoxy-phenyl} ester |
| 316 | 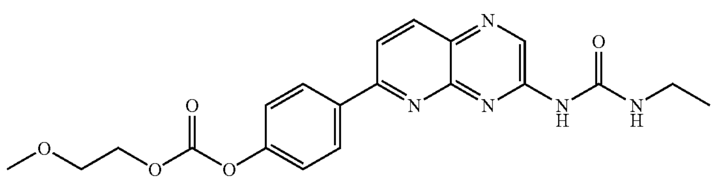 | Carbonic acid 4-[3-(3-ethyl-ureido)-pyrido[2,3-b]pyrazin-6-yl]-phenyl ester 2-methoxy-ethyl ester |
| 317 | 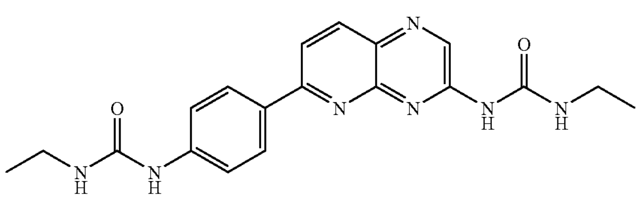 | 1-Ethyl-3-{6-[4-(3-ethyl-ureido)-phenyl]-pyrido[2,3-b]pyrazin-3-yl}-urea |
| 318 | 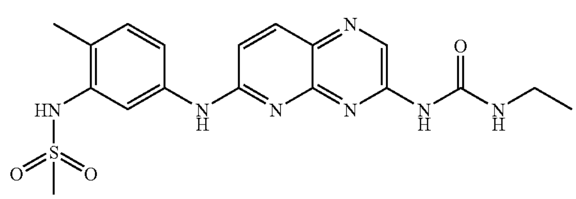 | N-{5-[3-(3-Ethyl-ureido)-pyrido[2,3-b]pyrazin-6-ylamino]-2-methyl-phenyl)-methanesulfonamid |
| 319 | 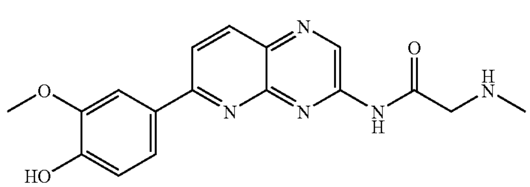 | N-[6-(4-Hydroxy-3-methoxy-phenyl)-pyrido[2,3-b]pyrazin-3-yl]-2-methylamino-acetamide |

-continued

| Compound | Structure | Name |
|---|---|---|
| 320 | 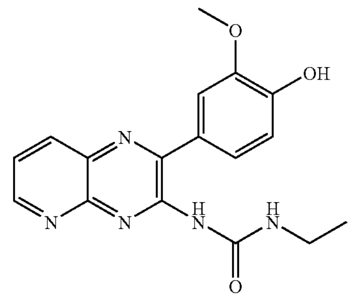 | 1-Ethyl-3-[2-(4-hydroxy-3-methoxy-phenyl)-pyrido[2,3-b]pyrazin-3-yl]-urea |
| 321 | 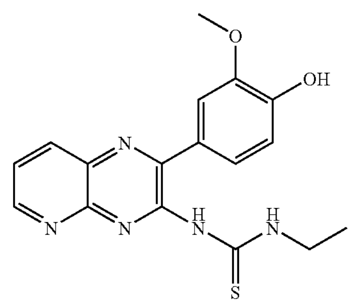 | 1-Ethyl-3-[2-(4-hydroxy-3-methoxy-phenyl)-pyrido[2,3-b]pyrazin-3-yl]-thiourea |
| 322 | 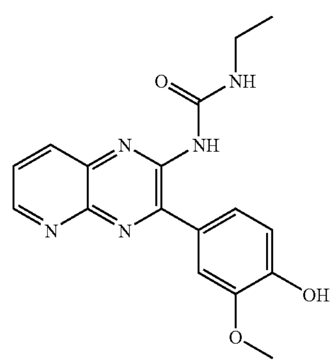 | 1-Ethyl-3-[3-(4-hydroxy-3-methoxy-phenyl)-pyrido[2,3-b]pyrazin-2-yl]-urea |
| 323 | 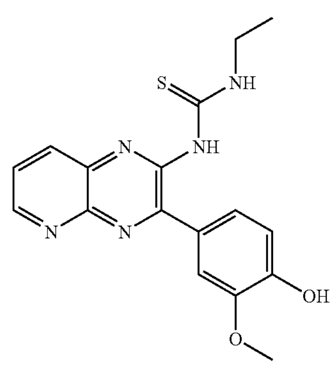 | 1-Ethyl-3-[3-(4-hydroxy-3-methoxy-phenyl)-pyrido[2,3-b]pyrazin-2-yl]-thiourea |

| Compound | Structure | Name |
|---|---|---|
| 324 | 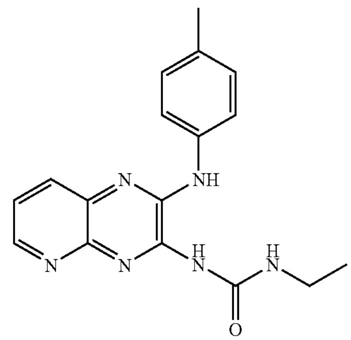 | 1-Ethyl-3-(2-p-tolylamino-pyrido[2,3-b]pyrazin-3-yl)-urea |
| 325 | 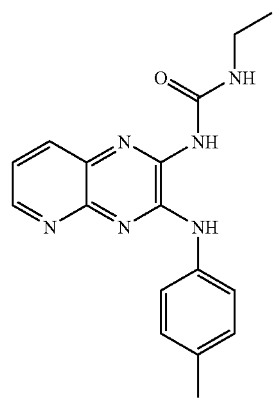 | 1-Ethyl-3-(3-p-tolylamino-pyrido[2,3-b]pyrazin-2-yl)-urea |
| 326 | 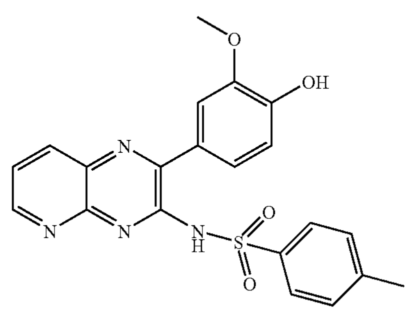 | N-[2-(4-Hydroxy-3-methoxy-phenyl)-pyrido[2,3-b]pyrazin-3-yl]-4-methyl-benzenesulfonamide |
| 327 | 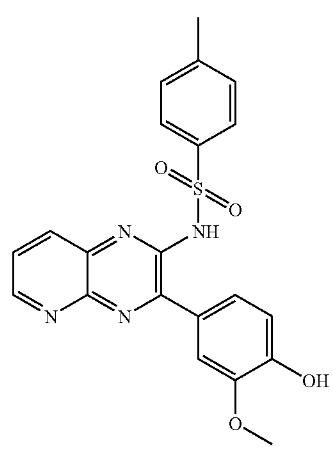 | N-[3-(4-Hydroxy-3-methoxy-phenyl)-pyrido[2,3-b]pyrazin-2-yl]-4-methyl-benzenesulfonamide |

| Compound | Structure | Name |
|---|---|---|
| 328 | 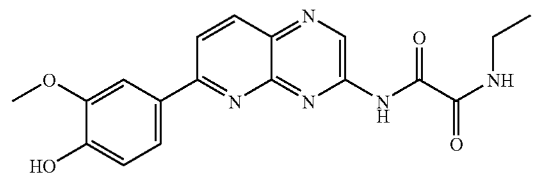 | N-Ethyl-N'-[6-(4-hydroxy-3-methoxy-phenyl)-pyrido[2,3-b]pyrazin-3-yl]-oxalamide |
| 329 | 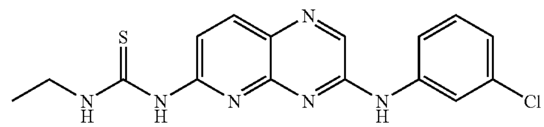 | 1-[3-(3-Chloro-phenylamino)-pyrido[2,3-b]pyrazin-6-yl]-3-ethyl-thiourea |
| 330 | 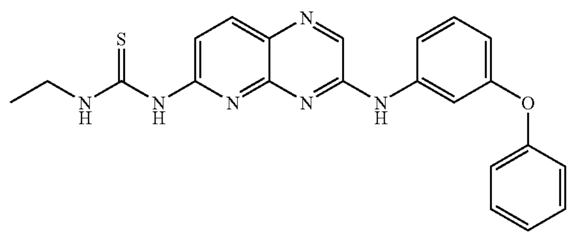 | 1-Ethyl-3-[3-(3-phenoxy-phenylamino)-pyrido[2,3-b]pyrazin-6-yl]-thiourea |
| 331 | 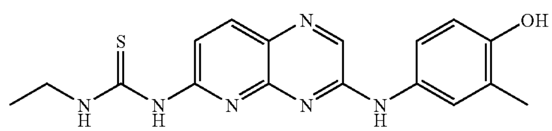 | 1-Ethyl-3-[3-(4-hydroxy-3-methyl-phenylamino)-pyrido[2,3-b]pyrazin-6-yl]-thiourea |
| 332 | 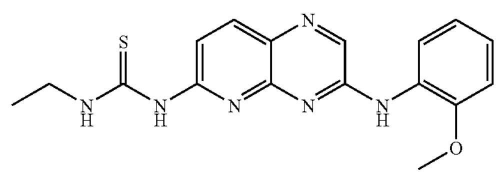 | 1-Ethyl-3-[3-(2-methoxy-phenylamino)-pyrido[2,3-b]pyrazin-6-yl]-thiourea |
| 333 | 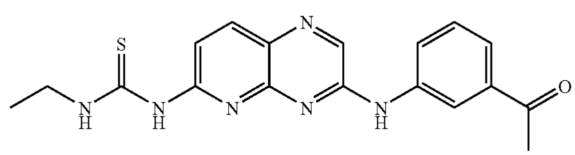 | 1-[3-(3-Acetyl-phenylamino)-pyrido[2,3-b]pyrazin-6-yl]-3-ethyl-thiourea |
| 334 | 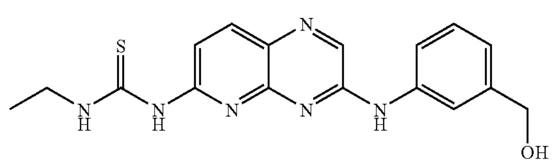 | 1-Ethyl-3-[3-(3-hydroxymethyl-phenylamino)-pyrido[2,3-b]pyrazin-6-yl]-thiourea |
| 335 | 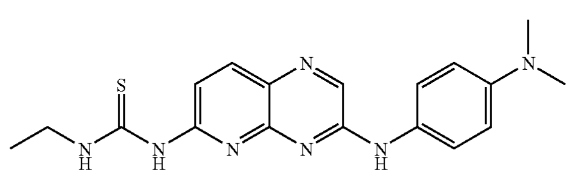 | 1-[3-(4-Dimethylamino-phenylamino)-pyrido[2,3-b]pyrazin-6-yl]-3-ethyl-thiourea |
| 336 | 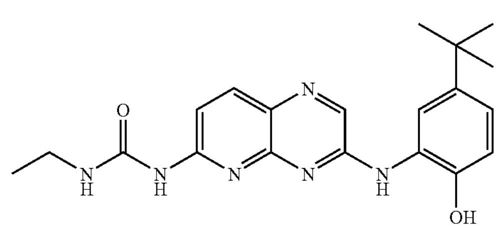 | 1-[3-(5-tert-Butyl-2-hydroxy-phenylamino)-pyrido[2,3-b]pyrazin-6-yl]-3-ethyl-urea |

| Compound | Structure | Name |
|---|---|---|
| 337 | 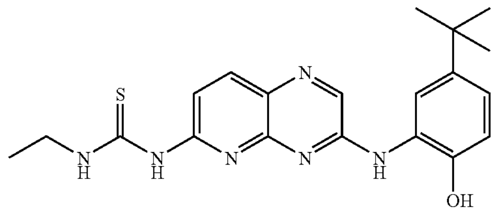 | 1-[3-(5-tert-Butyl-2-hydroxy-phenylamino)-pyrido[2,3-b]pyrazin-6-yl]-3-ethyl-thiourea |
| 338 | 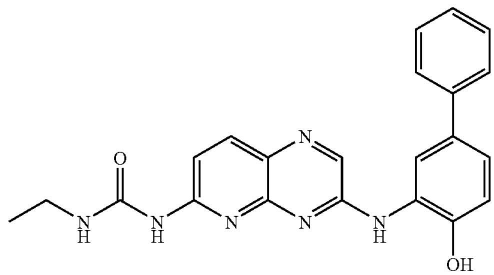 | 1-Ethyl-3-[3-(4-hydroxy-biphenyl-3-ylamino)-pyrido[2,3-b]pyrazin-6-yl]-urea |
| 339 | 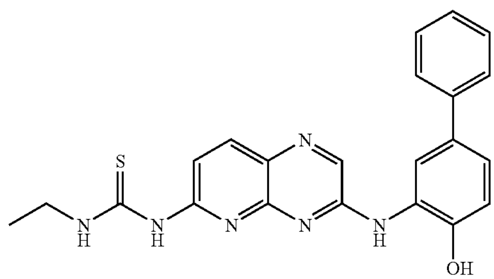 | 1-Ethyl-3-[3-(4-hydroxy-biphenyl-3-ylamino)-pyrido[2,3-b]pyrazin-6-yl]-thiourea |
| 340 | 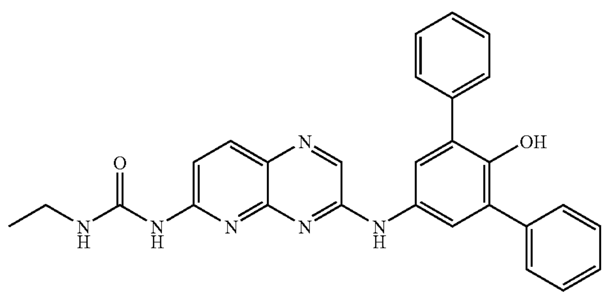 | 1-Ethyl-3-[3-(2'-hydroxy-[1,1';3',1'']terphenyl-5'-ylamino)-pyrido[2,3-b]pyrazin-6-yl]-urea |
| 341 | 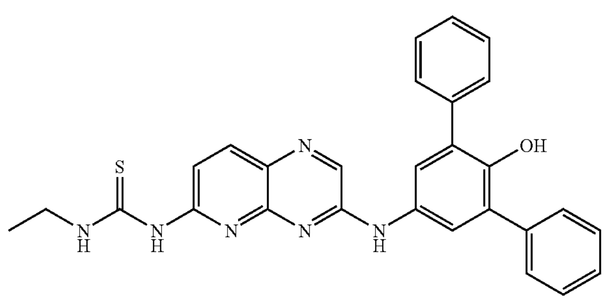 | 1-Ethyl-3-[3-(2'-hydroxy-[1,1';3',1'']terphenyl-5'-ylamino)-pyrido[2,3-b]pyrazin-6-yl]-thiourea |
| 342 | 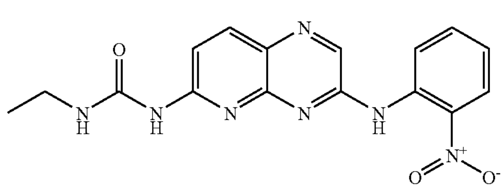 | 1-Ethyl-3-[3-(2-nitro-phenylamino)-pyrido[2,3-b]pyrazin-6-yl]-urea |

-continued

| Compound | Structure | Name |
|---|---|---|
| 343 | 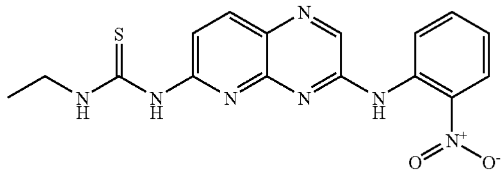 | 1-Ethyl-3-[3-(2-nitro-phenylamino)-pyrido[2,3-b]pyrazin-6-yl]-thiourea |
| 344 | 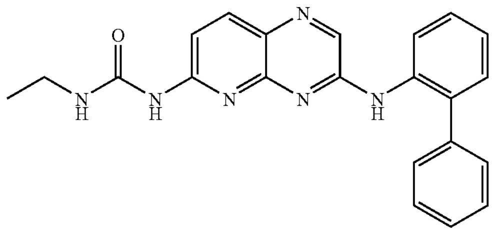 | 1-[3-(Biphenyl-2-ylamino)-pyrido[2,3-b]pyrazin-6-yl]-3-ethyl-urea |
| 345 | 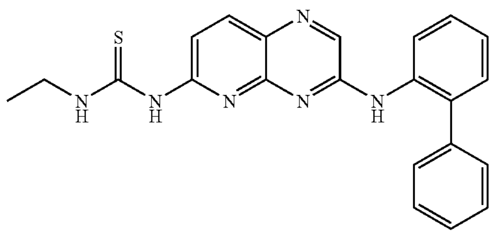 | 1-[3-(Biphenyl-2-ylamino)-pyrido[2,3-b]pyrazin-6-yl]-3-ethyl-thiourea |
| 346 | 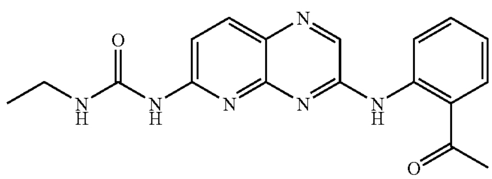 | 1-[3-(2-Acetyl-phenylamino)-pyrido[2,3-b]pyrazin-6-yl]-3-ethyl-urea |
| 347 | 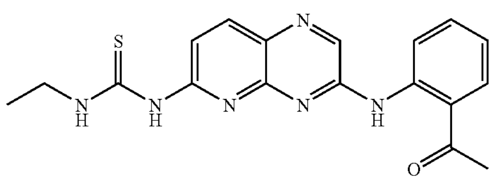 | 1-[3-(2-Acetyl-phenylamino)-pyrido[2,3-b]pyrazin-6-yl]-3-ethyl-thiourea |
| 348 | 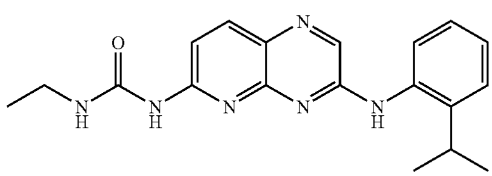 | 1-Ethyl-3-[3-(2-isopropyl-phenylamino)-pyrido[2,3-b]pyrazin-6-yl]-urea |
| 349 | 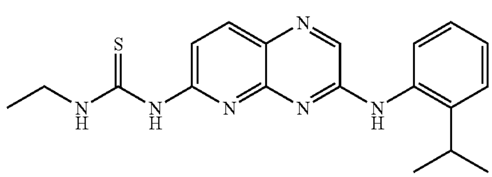 | 1-Ethyl-3-[3-(2-isopropyl-phenylamino)-pyrido[2,3-b]pyrazin-6-yl]-thiourea |
| 350 | 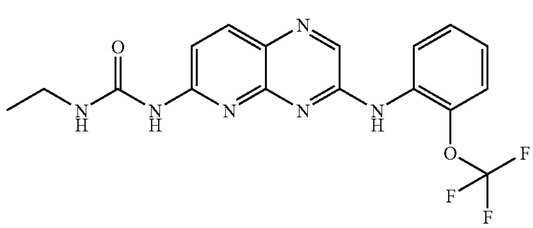 | 1-Ethyl-3-[3-(2-trifluoromethoxy-phenylamino)-pyrido[2,3-b]pyrazin-6-yl]-urea |

| Compound | Structure | Name |
|---|---|---|
| 351 | 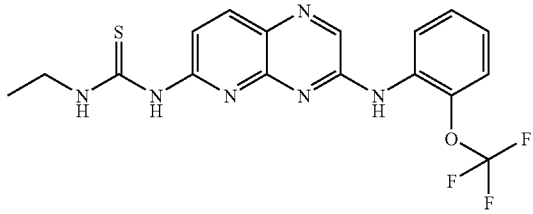 | 1-Ethyl-3-[3-(2-trifluoromethoxy-phenylamino)-pyrido[2,3-b]pyrazin-6-yl]-thiourea |
| 352 | 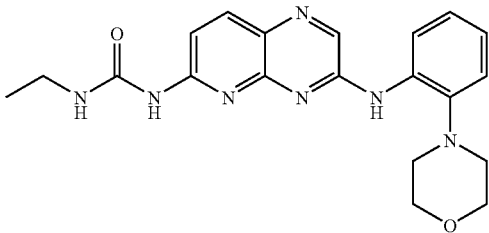 | 1-Ethyl-3-[3-(2-morpholin-4-yl-phenylamino)-pyrido[2,3-b]pyrazin-6-yl]-urea |
| 353 | 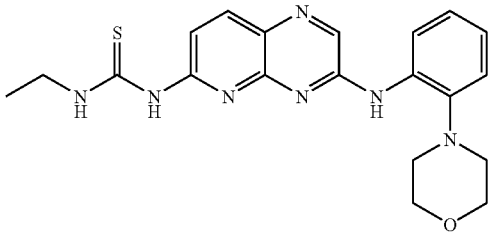 | 1-Ethyl-3-[3-(2-morpholin-4-yl-phenylamino)-pyrido[2,3-b]pyrazin-6-yl]-thiourea |
| 354 | 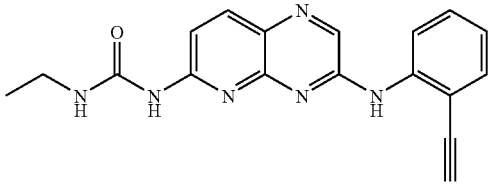 | 1-Ethyl-3-[3-(2-ethynyl-phenylamino)-pyrido[2,3-b]pyrazin-6-yl]-urea |
| 355 | 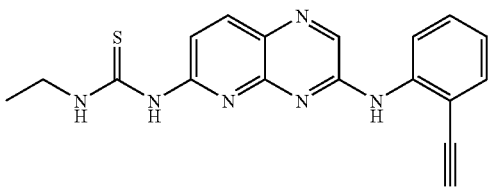 | 1-Ethyl-3-[3-(2-ethynyl-phenylamino)-pyrido[2,3-b]pyrazin-6-yl]-thiourea |
| 356 | 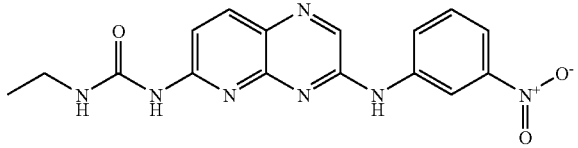 | 1-Ethyl-3-[3-(3-nitro-phenylamino)-pyrido[2,3-b]pyrazin-6-yl]-urea |
| 357 | 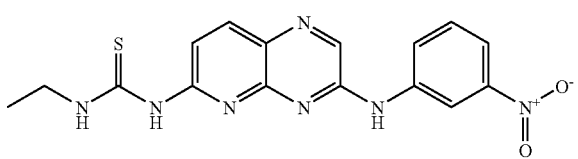 | 1-Ethyl-3-[3-(3-nitro-phenylamino)-pyrido[2,3-b]pyrazin-6-yl]-thiourea |

-continued

| Compound | Structure | Name |
|---|---|---|
| 358 | 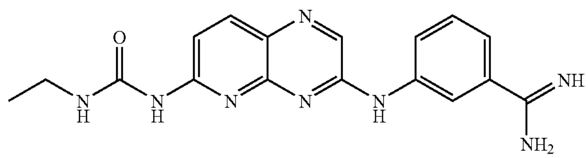 | 3-[6-(3-Ethyl-ureido)-pyrido[2,3-b]pyrazin-3-ylamino]-benzamidine |
| 359 | 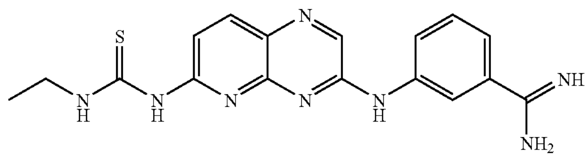 | 3-[6-(3-Ethyl-thioureido)-pyrido[2,3-b]pyrazin-3-ylamino]-benzamidine |
| 360 | 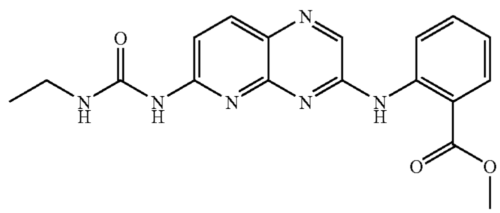 | 2-[6-(3-Ethyl-ureido)-pyrido[2,3-b]pyrazin-3-ylamino]-benzoic acid methyl ester |
| 361 | 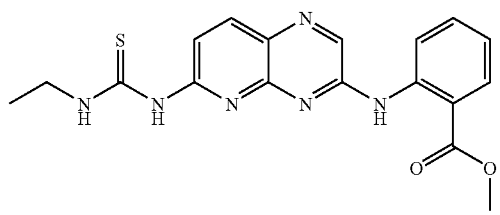 | 2-[6-(3-Ethyl-thioureido)-pyrido[2,3-b]pyrazin-3-ylamino]-benzoic acid methyl ester |
| 362 | 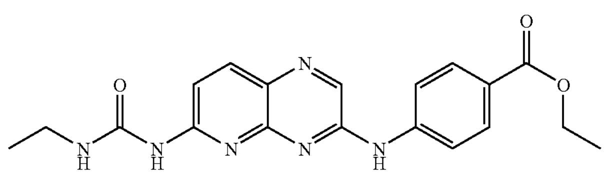 | 4-[6-(3-Ethyl-ureido)-pyrido[2,3-b]pyrazin-3-ylamino]-benzoic acid ethyl ester |
| 363 | 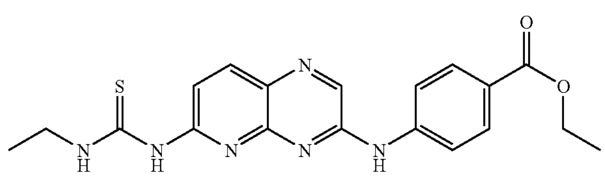 | 4-[6-(3-Ethyl-thioureido)-pyrido[2,3-b]pyrazin-3-ylamino]-benzoic acid ethyl ester |
| 364 | 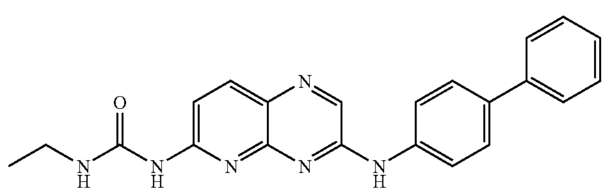 | 1-[3-(Biphenyl-4-ylamino)-pyrido[2,3-b]pyrazin-6-yl]-3-ethyl-urea |
| 365 | 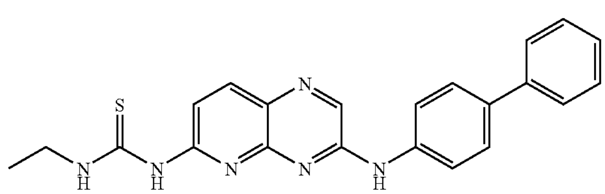 | 1-[3-(Biphenyl-4-ylamino)-pyrido[2,3-b]pyrazin-6-yl]-3-ethyl-thiourea |

-continued

| Compound | Structure | Name |
|---|---|---|
| 366 | 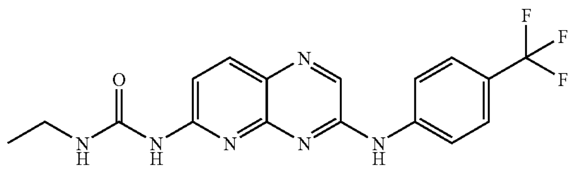 | 1-Ethyl-3-[3-(4-trifluoromethyl-phenylamino)-pyrido[2,3-b]pyrazin-6-yl]-urea |
| 367 | 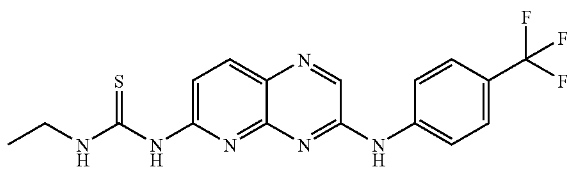 | 1-Ethyl-3-[3-(4-trifluoromethyl-phenylamino)-pyrido[2,3-b]pyrazin-6-yl]-thiourea |
| 368 | 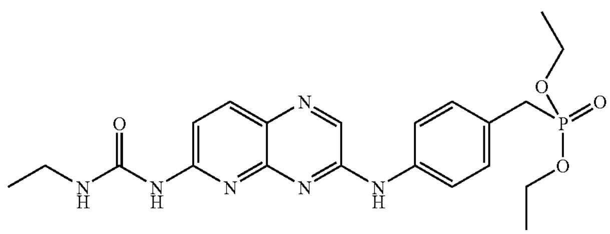 | {4-[6-(3-Ethyl-ureido)-pyrido[2,3-b]pyrazin-3-ylamino]-benzyl}-phosphonic acid di-ethyl ester |
| 369 | 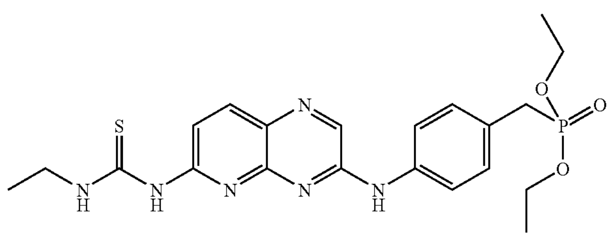 | {4-[6-(3-Ethyl-thioureido)-pyrido[2,3-b]pyrazin-3-ylamino]-benzyl}-phosphonic acid di-ethyl ester |
| 370 | 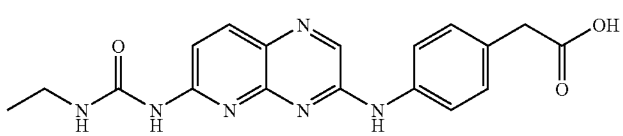 | {4-[6-(3-Ethyl-ureido)-pyrido[2,3-b]pyrazin-3-ylamino]-phenyl}-acetic acid |
| 371 | 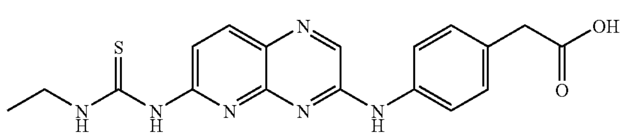 | {4-[6-(3-Ethyl-thioureido)-pyrido[2,3-b]pyrazin-3-ylamino]-phenyl}-acetic acid |
| 372 | 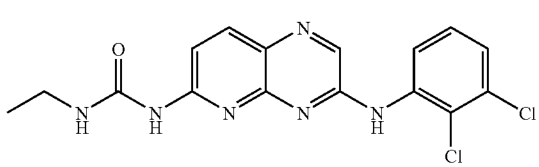 | 1-[3-(2,3-Dichloro-phenylamino)-pyrido[2,3-b]pyrazin-6-yl]-3-ethyl-urea |
| 373 | 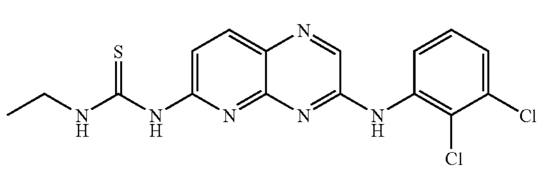 | 1-[3-(2,3-Dichloro-phenylamino)-pyrido[2,3-b]pyrazin-6-yl]-3-ethyl-thiourea |
| 374 | 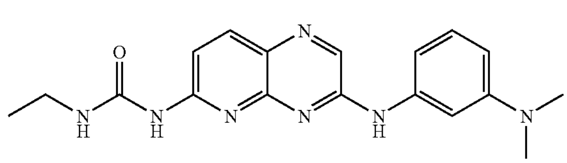 | 1-[3-(3-Dimethylamino-phenylamino)-pyrido[2,3-b]pyrazin-6-yl]-3-ethyl-urea |

-continued

| Compound | Structure | Name |
|---|---|---|
| 375 | 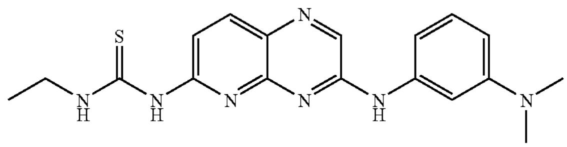 | 1-[3-(3-Dimethylamino-phenylamino)-pyrido[2,3-b]pyrazin-6-yl]-3-ethyl-thiourea |
| 376 | 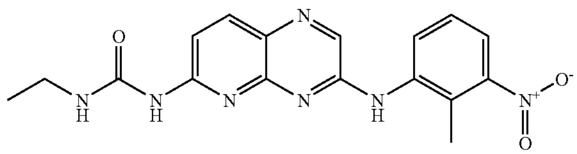 | 1-Ethyl-3-[3-(2-methyl-3-nitro-phenylamino)-pyrido[2,3-b]pyrazin-6-yl]-urea |
| 377 | 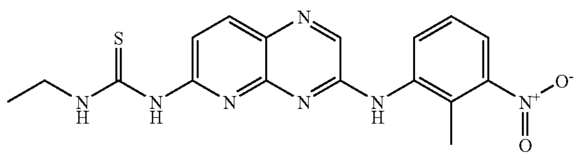 | 1-Ethyl-3-[3-(2-methyl-3-nitro-phenylamino)-pyrido[2,3-b]pyrazin-6-yl]-thiourea |
| 378 | 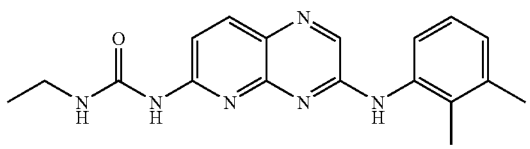 | 1-[3-(2,3-Dimethyl-phenylamino)-pyrido[2,3-b]pyrazin-6-yl]-3-ethyl-urea |
| 379 | 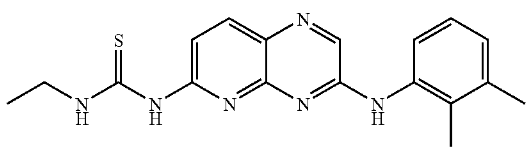 | 1-[3-(2,3-Dimethyl-phenylamino)-pyrido[2,3-b]pyrazin-6-yl]-3-ethyl-thiourea |
| 380 | 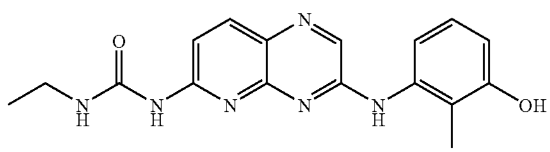 | 1-Ethyl-3-[3-(3-hydroxy-2-methyl-phenylamino)-pyrido[2,3-b]pyrazin-6-yl]-urea |
| 381 | 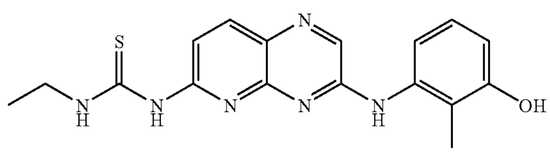 | 1-Ethyl-3-[3-(3-hydroxy-2-methyl-phenylamino)-pyrido[2,3-b]pyrazin-6-yl]-thiourea |
| 382 | 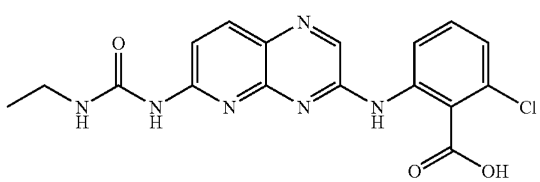 | 2-Chloro-6-[6-(3-ethyl-ureido)-pyrido[2,3-b]pyrazin-3-ylamino]-benzoic acid |
| 383 | 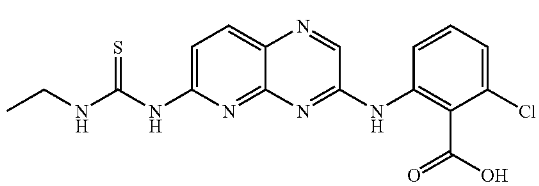 | 2-Chloro-6-[6-(3-ethyl-thioureido)-pyrido[2,3-b]pyrazin-3-ylamino]-benzoic acid |

| Compound | Structure | Name |
|---|---|---|
| 384 | 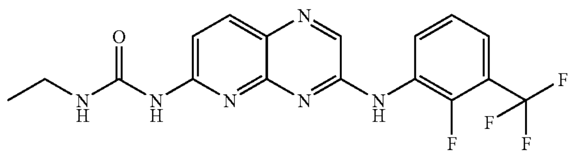 | 1-Ethyl-3-[3-(2-fluoro-3-trifluoromethyl-phenylamino)-pyrido[2,3-b]pyrazin-6-yl]-urea |
| 385 | 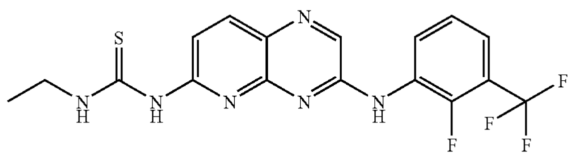 | 1-Ethyl-3-[3-(2-fluoro-3-trifluoromethyl-phenylamino)-pyrido[2,3-b]pyrazin-6-yl]-thiourea |
| 386 | 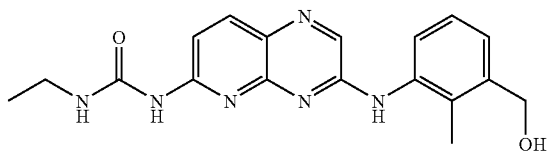 | 1-Ethyl-3-[3-(3-hydroxymethyl-2-methyl-phenylamino)-pyrido[2,3-b]pyrazin-6-yl]-urea |
| 387 | 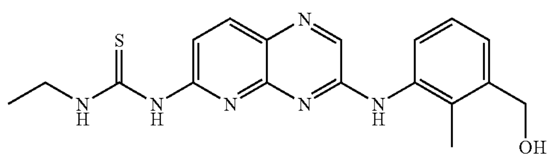 | 1-Ethyl-3-[3-(3-hydroxymethyl-2-methyl-phenylamino)-pyrido[2,3-b]pyrazin-6-yl]-thiourea |
| 388 | 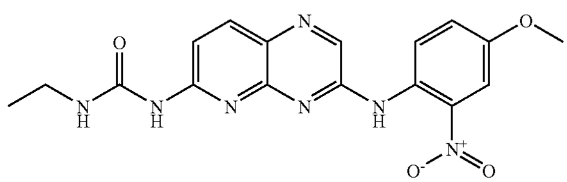 | 1-Ethyl-3-[3-(4-methoxy-2-nitro-phenylamino)-pyrido[2,3-b]pyrazin-6-yl]-urea |
| 389 | 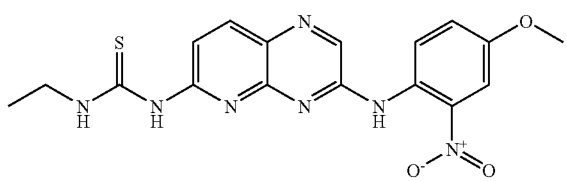 | 1-Ethyl-3-[3-(4-methoxy-2-nitro-phenylamino)-pyrido[2,3-b]pyrazin-6-yl]-thiourea |
| 390 | 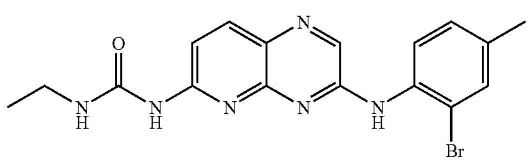 | 1-[3-(2-Bromo-4-methyl-phenylamino)-pyrido[2,3-b]pyrazin-6-yl]-3-ethyl-urea |
| 391 | 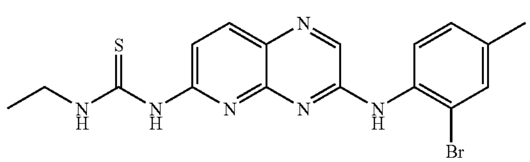 | 1-[3-(2-Bromo-4-methyl-phenylamino)-pyrido[2,3-b]pyrazin-6-yl]-3-ethyl-thiourea |
| 392 | 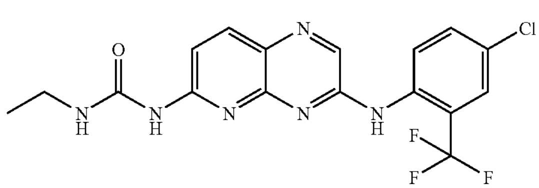 | 1-[3-(4-Chloro-2-trifluoromethyl-phenylamino)-pyrido[2,3-b]pyrazin-6-yl]-3-ethyl-urea |

| Compound | Structure | Name |
|---|---|---|
| 393 | 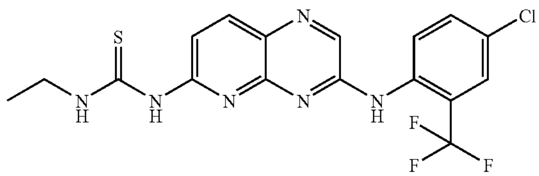 | 1-[3-(4-Chloro-2-trifluoromethyl-phenylamino)-pyrido[2,3-b]pyrazin-6-yl]-3-ethyl-thiourea |
| 394 | 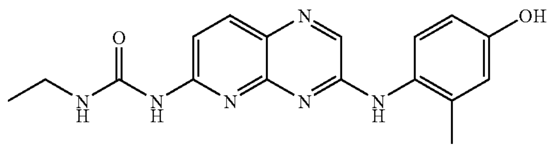 | 1-Ethyl-3-[3-(4-hydroxy-2-methyl-phenylamino)-pyrido[2,3-b]pyrazin-6-yl]-urea |
| 395 | 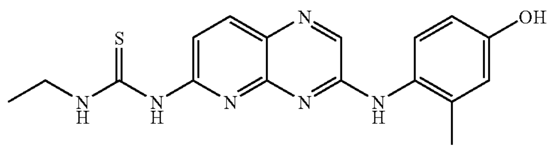 | 1-Ethyl-3-[3-(4-hydroxy-2-methyl-phenylamino)-pyrido[2,3-b]pyrazin-6-yl]-thiourea |
| 396 | 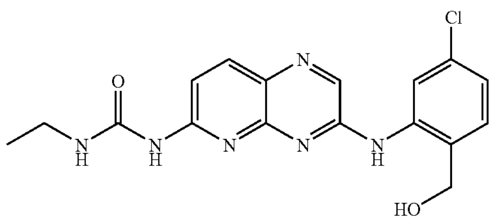 | 1-[3-(5-Chloro-2-hydroxymethyl-phenylamino)-pyrido[2,3-b]pyrazin-6-yl]-3-ethyl-urea |
| 397 | 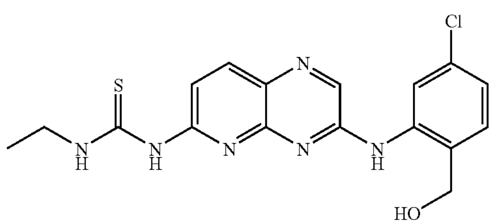 | 1-[3-(5-Chloro-2-hydroxymethyl-phenylamino)-pyrido[2,3-b]pyrazin-6-yl]-3-ethyl-thiourea |
| 398 | 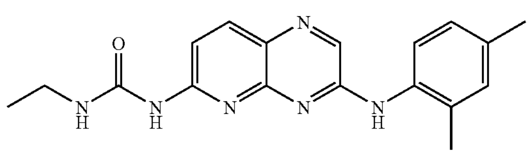 | 1-[3-(2,4-Dimethyl-phenylamino)-pyrido[2,3-b]pyrazin-6-yl]-3-ethyl-urea |
| 399 | 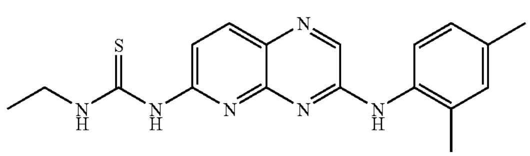 | 1-[3-(2,4-Dimethyl-phenylamino)-pyrido[2,3-b]pyrazin-6-yl]-3-ethyl-thiourea |
| 400 | 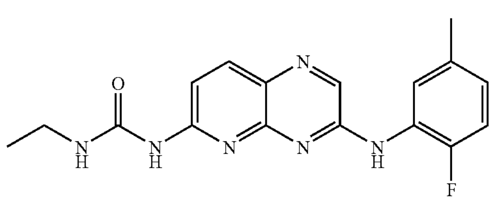 | 1-Ethyl-3-[3-(2-fluoro-5-methyl-phenylamino)-pyrido[2,3-b]pyrazin-6-yl]-urea |

-continued

| Compound | Structure | Name |
|---|---|---|
| 401 | 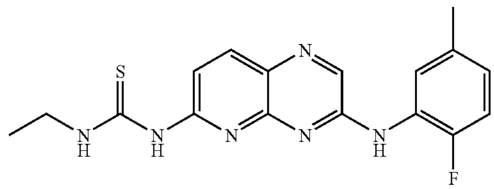 | 1-Ethyl-3-[3-(2-fluoro-5-methyl-phenylamino)-pyrido[2,3-b]pyrazin-6-yl]-thiourea |
| 402 | 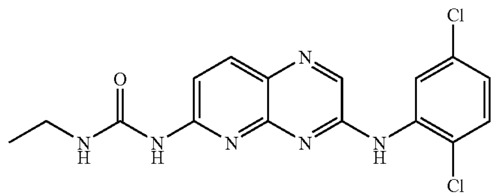 | 1-[3-(2,5-Dichloro-phenylamino)-pyrido[2,3-b]pyrazin-6-yl]-3-ethyl-urea |
| 403 | 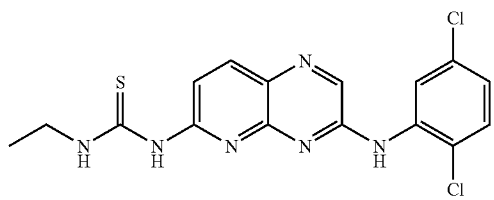 | 1-[3-(2,5-Dichloro-phenylamino)-pyrido[2,3-b]pyrazin-6-yl]-3-ethyl-thiourea |
| 404 | 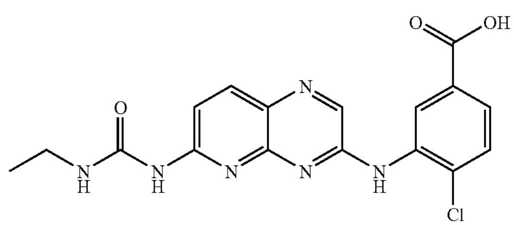 | 4-Chloro-3-[6-(3-ethyl-ureido)-pyrido[2,3-b]pyrazin-3-ylamino]-benzoic acid |
| 405 | 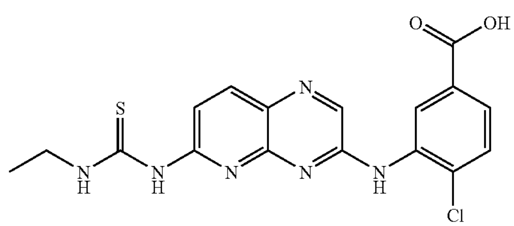 | 4-Chloro-3-[6-(3-ethyl-thioureido)-pyrido[2,3-b]pyrazin-3-ylamino]-benzoic acid |
| 406 | 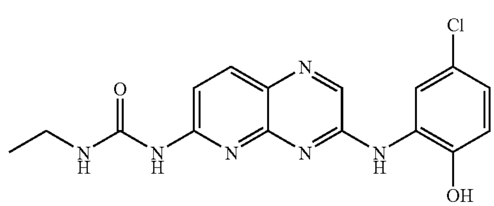 | 1-[3-(5-Chloro-2-hydroxy-phenylamino)-pyrido[2,3-b]pyrazin-6-yl]-3-ethyl-urea |
| 407 | 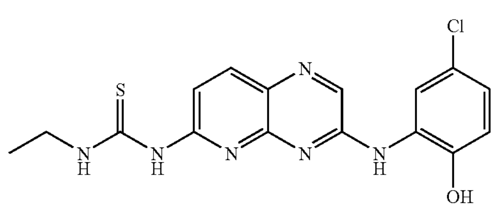 | 1-[3-(5-Chloro-2-hydroxy-phenylamino)-pyrido[2,3-b]pyrazin-6-yl]-3-ethyl-thiourea |

-continued

| Compound | Structure | Name |
|---|---|---|
| 408 | 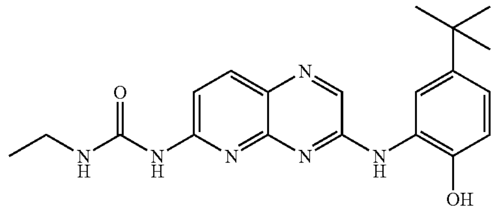 | 1-[3-(5-tert-Butyl-2-hydroxy-phenylamino)-pyrido[2,3-b]pyrazin-6-yl]-3-ethyl-urea |
| 409 | 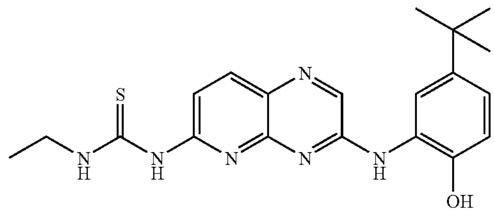 | 1-[3-(5-tert-Butyl-2-hydroxy-phenylamino)-pyrido[2,3-b]pyrazin-6-yl]-3-ethyl-thiourea |
| 410 | 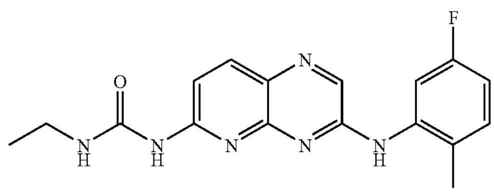 | 1-Ethyl-3-[3-(5-fluoro-2-methyl-phenylamino)-pyrido[2,3-b]pyrazin-6-yl]-urea |
| 411 | 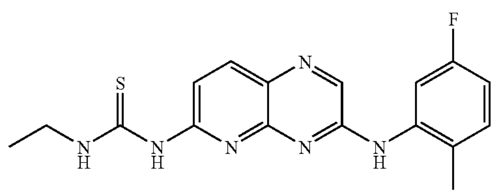 | 1-Ethyl-3-[3-(5-fluoro-2-methyl-phenylamino)-pyrido[2,3-b]pyrazin-6-yl]-thiourea |
| 412 | 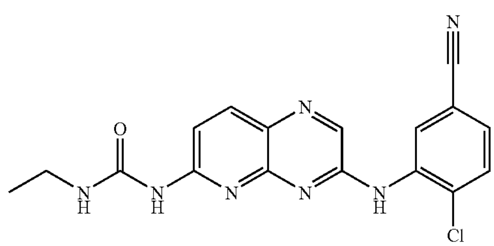 | 1-[3-(2-Chloro-5-cyano-phenylamino)-pyrido[2,3-b]pyrazin-6-yl]-3-ethyl-urea |
| 413 | 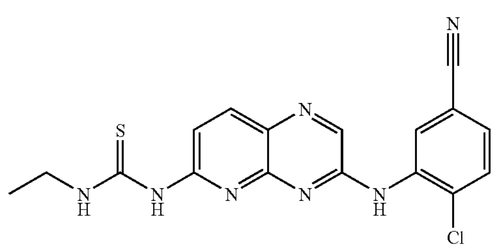 | 1-[3-(2-Chloro-5-cyano-phenylamino)-pyrido[2,3-b]pyrazin-6-yl]-3-ethyl-thiourea |
| 414 | 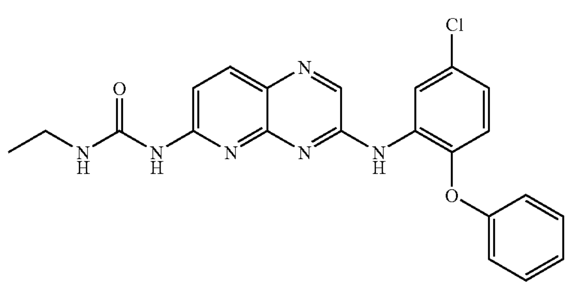 | 1-[3-(5-Chloro-2-phenoxy-phenylamino)-pyrido[2,3-b]pyrazin-6-yl]-3-ethyl-urea |

-continued

| Compound | Structure | Name |
|---|---|---|
| 415 | 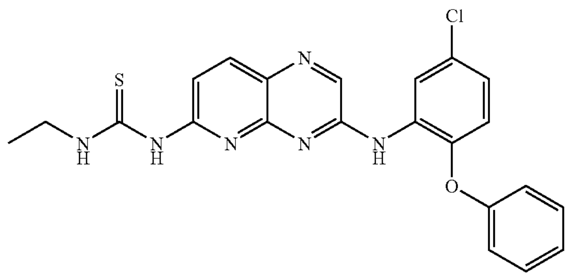 | 1-[3-(5-Chloro-2-phenoxy-phenylamino)-pyrido[2,3-b]pyrazin-6-yl]-3-ethyl-thiourea |
| 416 | 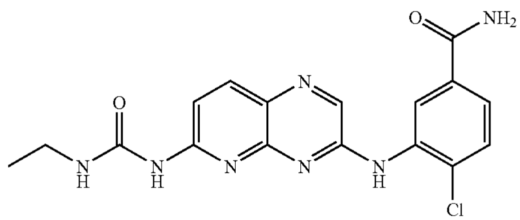 | 4-Chloro-3-[6-(3-ethyl-ureido)-pyrido[2,3-b]pyrazin-3-ylamino]-benzamide |
| 417 | 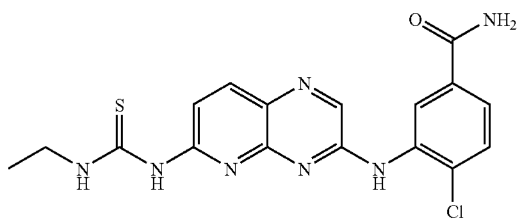 | 4-Chloro-3-[6-(3-ethyl-thioureido)-pyrido[2,3-b]pyrazin-3-ylamino]-benzamide |
| 418 | 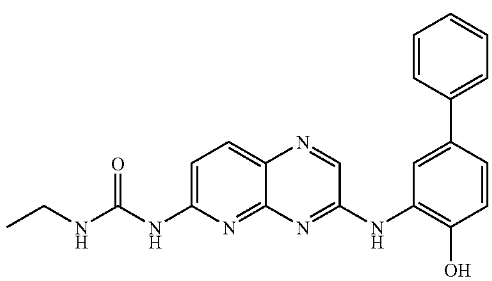 | 1-Ethyl-3-[3-(4-hydroxy-biphenyl-3-ylamino)-pyrido[2,3-b]pyrazin-6-yl]-urea |
| 419 | 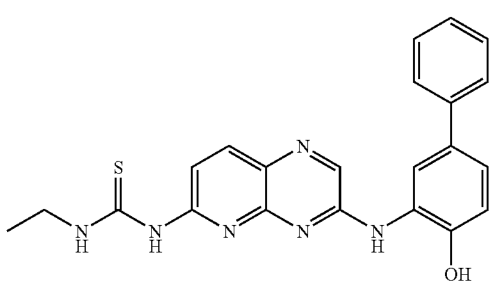 | 1-Ethyl-3-[3-(4-hydroxy-biphenyl-3-ylamino)-pyrido[2,3-b]pyrazin-6-yl]-thiourea |
| 420 | 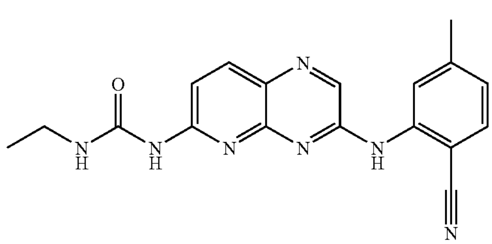 | 1-[3-(2-Cyano-5-methyl-phenylamino)-pyrido[2,3-b]pyrazin-6-yl]-3-ethyl-urea |

| Compound | Structure | Name |
|---|---|---|
| 421 | 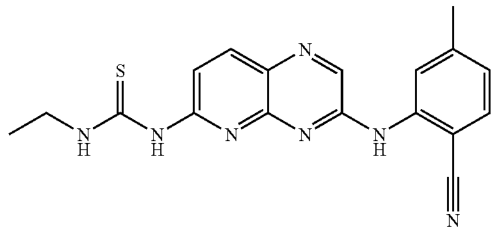 | 1-[3-(2-Cyano-5-methyl-phenylamino)-pyrido[2,3-b]pyrazin-6-yl]-3-ethyl-thiourea |
| 422 | 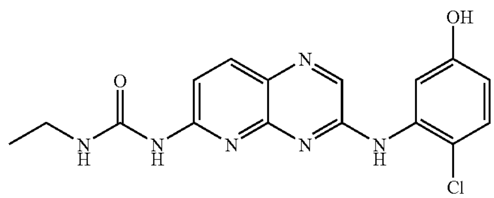 | 1-[3-(2-Chloro-5-hydroxy-phenylamino)-pyrido[2,3-b]pyrazin-6-yl]-3-ethyl-urea |
| 423 | 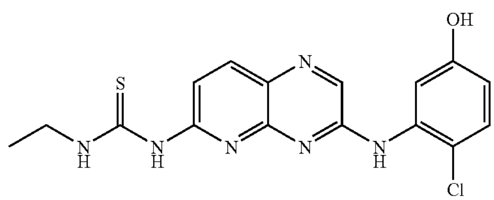 | 1-[3-(2-Chloro-5-hydroxy-phenylamino)-pyrido[2,3-b]pyrazin-6-yl]-3-ethyl-thiourea |
| 424 | 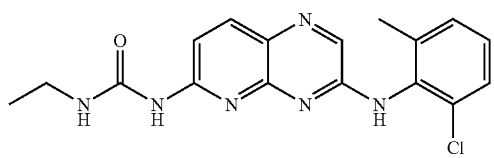 | 1-[3-(2-Chloro-6-methyl-phenylamino)-pyrido[2,3-b]pyrazin-6-yl]-3-ethyl-urea |
| 425 | 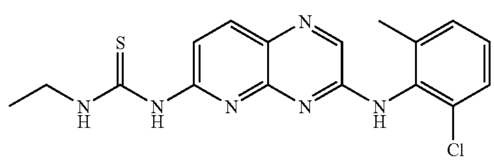 | 1-[3-(2-Chloro-6-methyl-phenylamino)-pyrido[2,3-b]pyrazin-6-yl]-3-ethyl-thiourea |
| 426 | 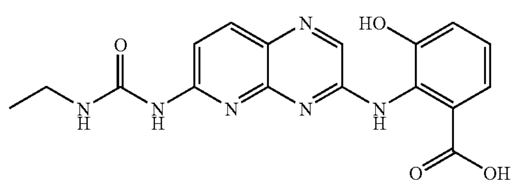 | 2-[6-(3-Ethyl-ureido)-pyrido[2,3-b]pyrazin-3-ylamino]-3-hydroxy-benzoic acid |
| 427 | 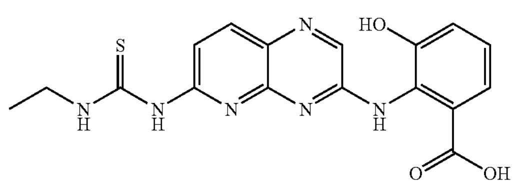 | 2-[6-(3-Ethyl-thioureido)-pyrido[2,3-b]pyrazin-3-ylamino]-3-hydroxy-benzoic acid |
| 428 | 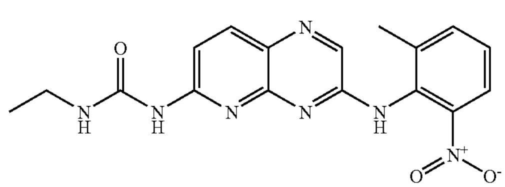 | 1-Ethyl-3-[3-(2-methyl-6-nitro-phenylamino)-pyrido[2,3-b]pyrazin-6-yl]-urea |

| Compound | Structure | Name |
| --- | --- | --- |
| 429 | 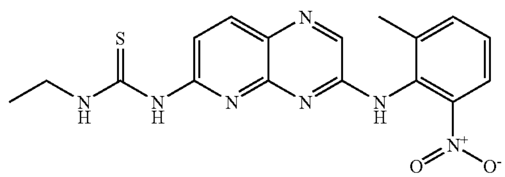 | 1-Ethyl-3-[3-(2-methyl-6-nitro-phenylamino)-pyrido[2,3-b]pyrazin-6-yl]-thiourea |
| 430 | 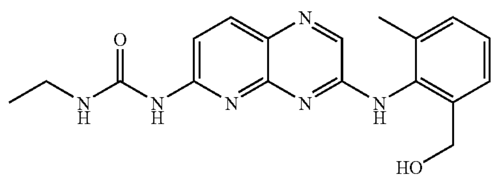 | 1-Ethyl-3-[3-(2-hydroxymethyl-6-methyl-phenylamino)-pyrido[2,3-b]pyrazin-6-yl]-urea |
| 431 | 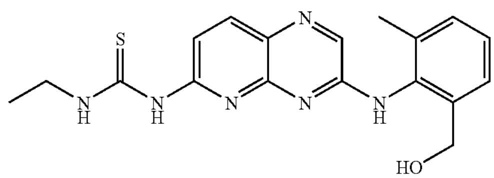 | 1-Ethyl-3-[3-(2-hydroxymethyl-6-methyl-phenylamino)-pyrido[2,3-b]pyrazin-6-yl]-thiourea |
| 432 | 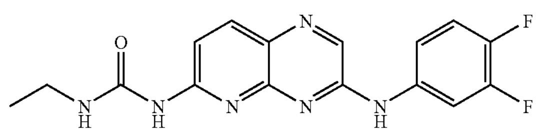 | 1-[3-(3,4-Difluoro-phenylamino)-pyrido[2,3-b]pyrazin-6-yl]-3-ethyl-urea |
| 433 | 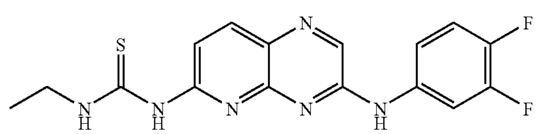 | 1-[3-(3,4-Difluoro-phenylamino)-pyrido[2,3-b]pyrazin-6-yl]-3-ethyl-thiourea |
| 434 | 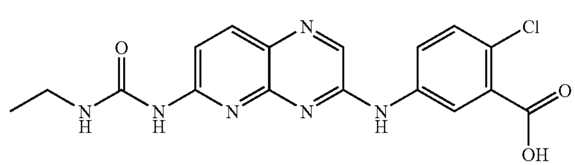 | 2-Chloro-5-[6-(3-ethyl-ureido)-pyrido[2,3-b]pyrazin-3-ylamino]-benzoic acid |
| 435 | 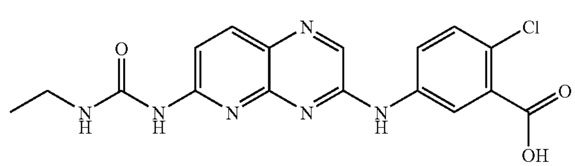 | 2-Chloro-5-[6-(3-ethyl-thioureido)-pyrido[2,3-b]pyrazin-3-ylamino]-benzoic acid |
| 436 | 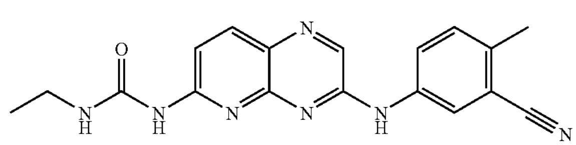 | 1-[3-(3-Cyano-4-methyl-phenylamino)-pyrido[2,3-b]pyrazin-6-yl]-3-ethyl-urea |
| 437 | 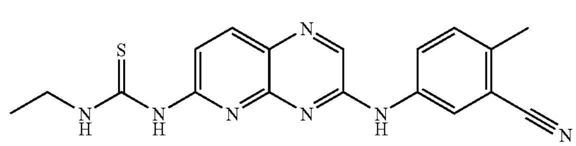 | 1-[3-(3-Cyano-4-methyl-phenylamino)-pyrido[2,3-b]pyrazin-6-yl]-3-ethyl-thiourea |
| 438 | 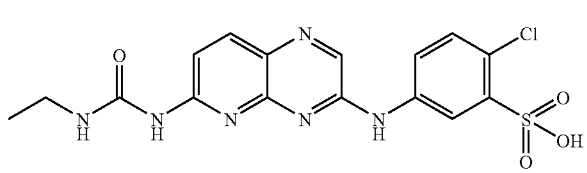 | 2-Chloro-5-[6-(3-ethyl-ureido)-pyrido[2,3-b]pyrazin-3-ylamino]-benzenesulfonic acid |

-continued

| Compound | Structure | Name |
|---|---|---|
| 439 | 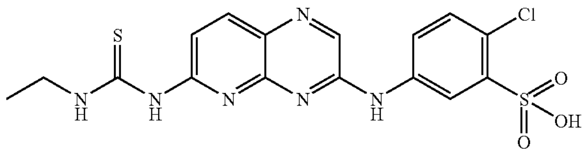 | 2-Chloro-5-[6-(3-ethyl-thioureido)-pyrido[2,3-b]pyrazin-3-ylamino]-benzenesulfonic acid |
| 440 | 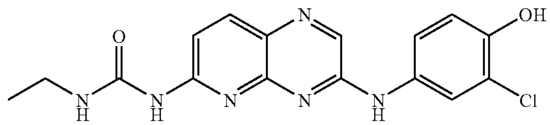 | 1-[3-(3-Chloro-4-hydroxy-phenylamino)-pyrido[2,3-b]pyrazin-6-yl]-3-ethyl-urea |
| 441 | 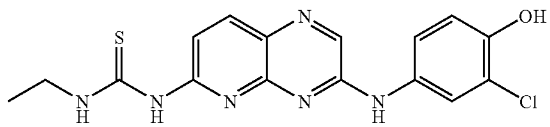 | 1-[3-(3-Chloro-4-hydroxy-phenylamino)-pyrido[2,3-b]pyrazin-6-yl]-3-ethyl-thiourea |
| 442 | 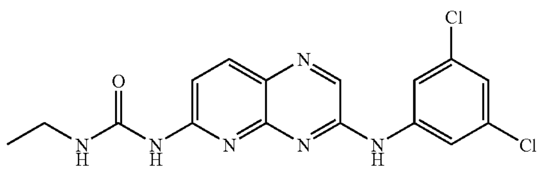 | 1-[3-(3,5-Dichloro-phenylamino)-pyrido[2,3-b]pyrazin-6-yl]-3-ethyl-urea |
| 443 | 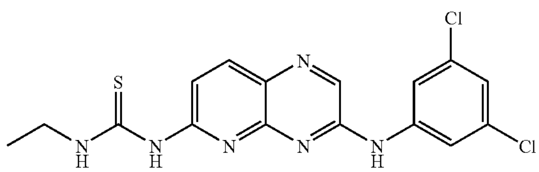 | 1-[3-(3,5-Dichloro-phenylamino)-pyrido[2,3-b]pyrazin-6-yl]-3-ethyl-thiourea |
| 444 | 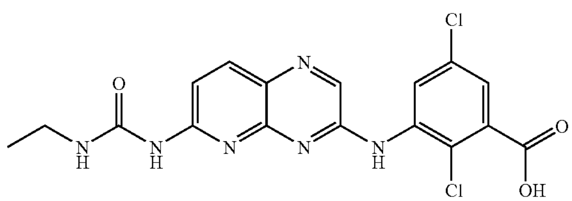 | 2,5-Dichloro-3-[6-(3-ethyl-ureido)-pyrido[2,3-b]pyrazin-3-ylamino]-benzoic acid |
| 445 | 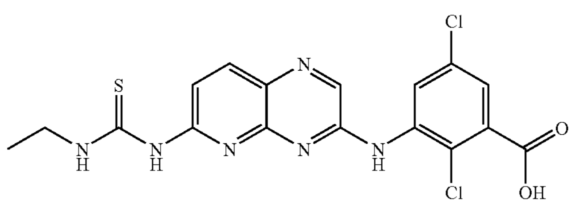 | 2,5-Dichloro-3-[6-(3-ethyl-thioureido)-pyrido[2,3-b]pyrazin-3-ylamino]-benzoic acid |
| 446 | 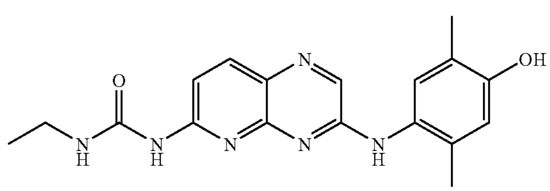 | 1-Ethyl-3-[3-(4-hydroxy-2,5-dimethyl-phenylamino)-pyrido[2,3-b]pyrazin-6-yl]-urea |
| 447 | 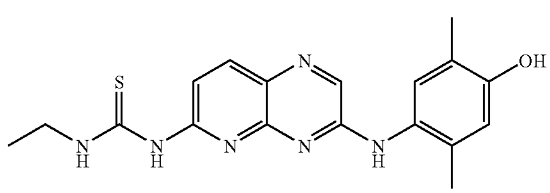 | 1-Ethyl-3-[3-(4-hydroxy-2,5-dimethyl-phenylamino)-pyrido[2,3-b]pyrazin-6-yl]-thiourea |

-continued

| Compound | Structure | Name |
|---|---|---|
| 448 | 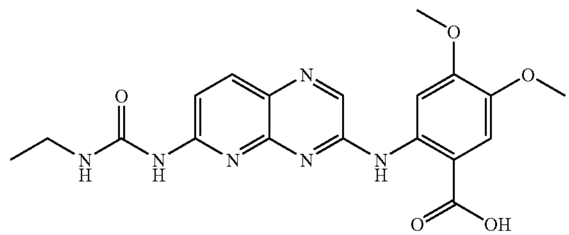 | 2-[6-(3-Ethyl-ureido)-pyrido[2,3-b]pyrazin-3-ylamino]-4,5-dimethoxy-benzoic acid |
| 449 | 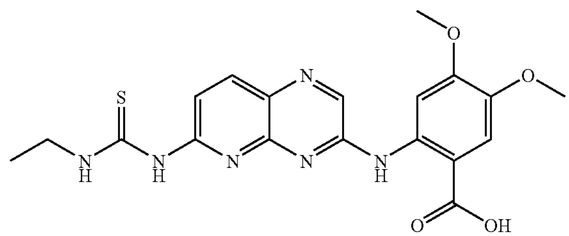 | 2-[6-(3-Ethyl-thioureido)-pyrido[2,3-b]pyrazin-3-ylamino]-4,5-dimethoxy-benzoic acid |
| 450 | 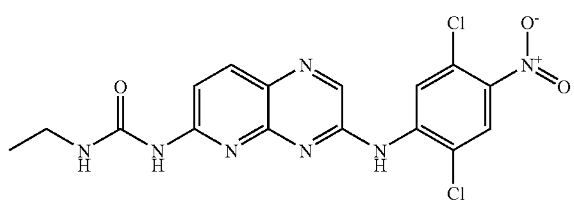 | 1-[3-(2,5-Dichloro-4-nitro-phenylamino)-pyrido[2,3-b]pyrazin-6-yl]-3-ethyl-urea |
| 451 | 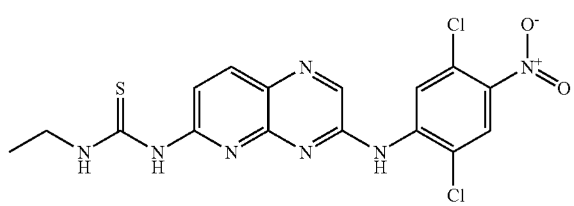 | 1-[3-(2,5-Dichloro-4-nitro-phenylamino)-pyrido[2,3-b]pyrazin-6-yl]-3-ethyl-thiourea |
| 452 | 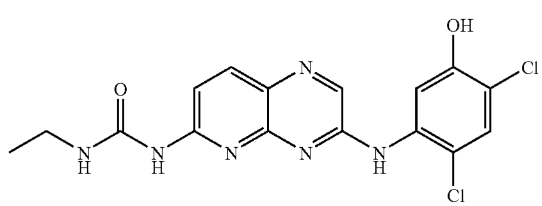 | 1-[3-(2,4-Dichloro-5-hydroxy-phenylamino)-pyrido[2,3-b]pyrazin-6-yl]-3-ethyl-urea |
| 453 | 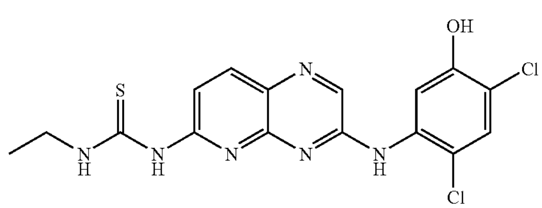 | 1-[3-(2,4-Dichloro-5-hydroxy-phenylamino)-pyrido[2,3-b]pyrazin-6-yl]-3-ethyl-thiourea |
| 454 | 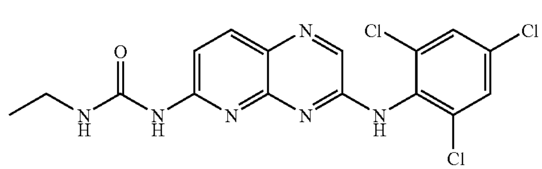 | 1-Ethyl-3-[3-(2,4,6-trichloro-phenylamino)-pyrido[2,3-b]pyrazin-6-yl]-urea |

| Compound | Structure | Name |
|---|---|---|
| 455 | 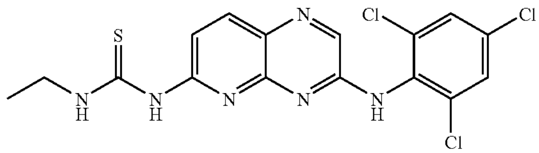 | 1-Ethyl-3-[3-(2,4,6-trichloro-phenylamino)-pyrido[2,3-b]pyrazin-6-yl]-thiourea |
| 456 | 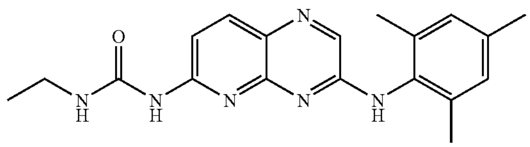 | 1-Ethyl-3-[3-(2,4,6-trimethyl-phenylamino)-pyrido[2,3-b]pyrazin-6-yl]-urea |
| 457 | 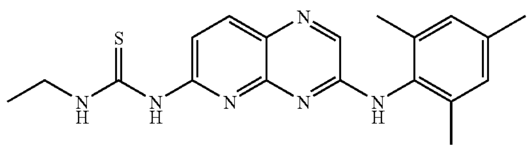 | 1-Ethyl-3-[3-(2,4,6-trimethyl-phenylamino)-pyrido[2,3-b]pyrazin-6-yl]-thiourea |
| 458 | 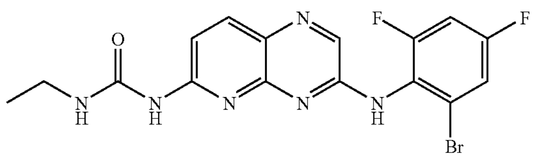 | 1-[3-(2-Bromo-4,6-difluoro-phenylamino)-pyrido[2,3-b]pyrazin-6-yl]-3-ethyl-urea |
| 459 | 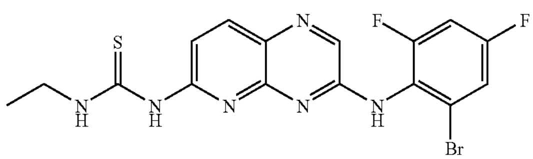 | 1-[3-(2-Bromo-4,6-difluoro-phenylamino)-pyrido[2,3-b]pyrazin-6-yl]-3-ethyl-thiourea |
| 460 | 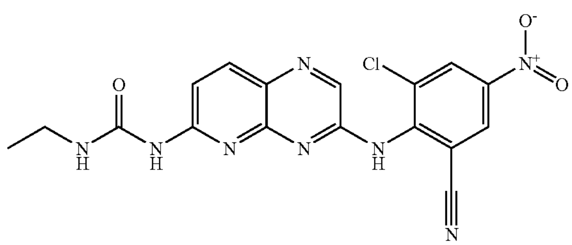 | 1-[3-(2-Chloro-6-cyano-4-nitro-phenylamino)-pyrido[2,3-b]pyrazin-6-yl]-3-ethyl-urea |
| 461 | 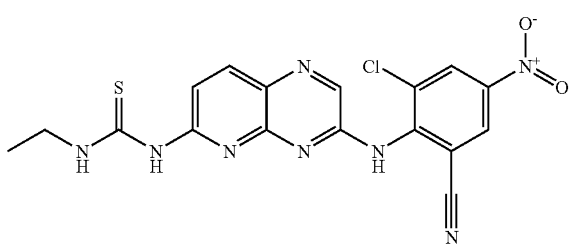 | 1-[3-(2-Chloro-6-cyano-4-nitro-phenylamino)-pyrido[2,3-b]pyrazin-6-yl]-3-ethyl-thiourea |
| 462 | 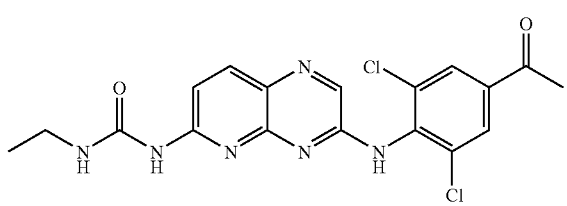 | 1-[3-(4-Acetyl-2,6-dichloro-phenylamino)-pyrido[2,3-b]pyrazin-6-yl]-3-ethyl-urea |

-continued

| Compound | Structure | Name |
|---|---|---|
| 463 | 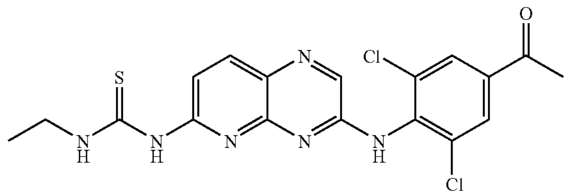 | 1-[3-(4-Acetyl-2,6-dichloro-phenylamino)-pyrido[2,3-b]pyrazin-6-yl]-3-ethyl-thiourea |
| 464 | 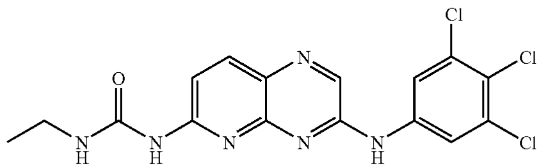 | 1-Ethyl-3-[3-(3,4,5-trichloro-phenylamino)-pyrido[2,3-b]pyrazin-6-yl]-urea |
| 465 | 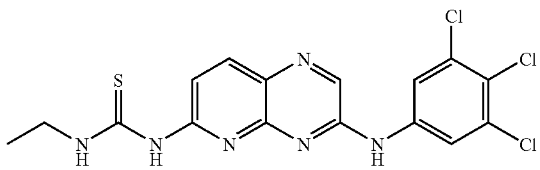 | 1-Ethyl-3-[3-(3,4,5-trichloro-phenylamino)-pyrido[2,3-b]pyrazin-6-yl]-thiourea |
| 466 | 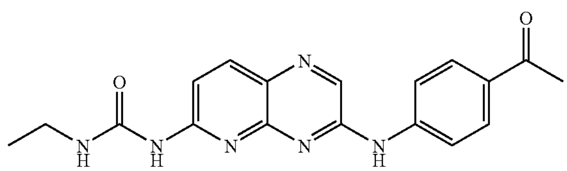 | 1-[3-(4-Acetyl-phenylamino)-pyrido[2,3-b]pyrazin-6-yl]-3-ethyl-urea |
| 467 | 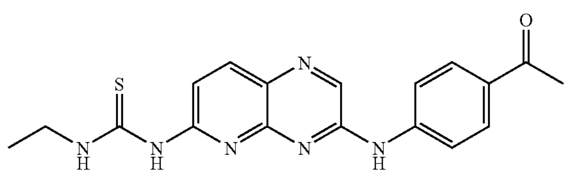 | 1-[3-(4-Acetyl-phenylamino)-pyrido[2,3-b]pyrazin-6-yl]-3-ethyl-thiourea |
| 468 | 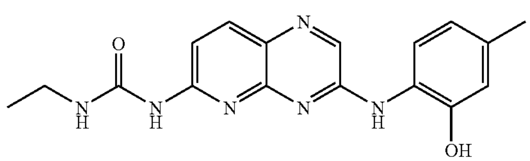 | 1-Ethyl-3-[3-(2-hydroxy-4-methyl-phenylamino)-pyrido[2,3-b]pyrazin-6-yl]-urea |
| 469 | 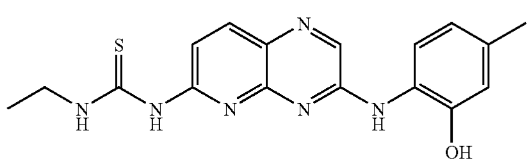 | 1-Ethyl-3-[3-(2-hydroxy-4-methyl-phenylamino)-pyrido[2,3-b]pyrazin-6-yl]-thiourea |
| 470 | 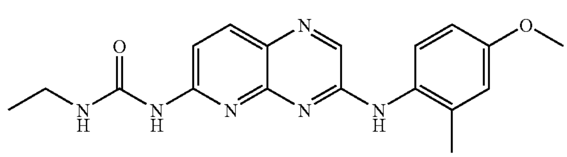 | 1-Ethyl-3-[3-(4-methoxy-2-methyl-phenylamino)-pyrido[2,3-b]pyrazin-6-yl]-urea |
| 471 | 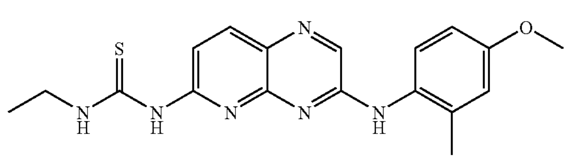 | 1-Ethyl-3-[3-(4-methoxy-2-methyl-phenylamino)-pyrido[2,3-b]pyrazin-6-yl]-thiourea |

-continued

| Compound | Structure | Name |
|---|---|---|
| 472 | 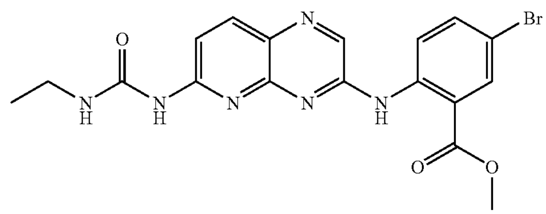 | 5-Bromo-2-[6-(3-ethyl-ureido)pyrido[2,3-b]pyrazin-3-ylamino]-benzoic acid methyl ester |
| 473 | 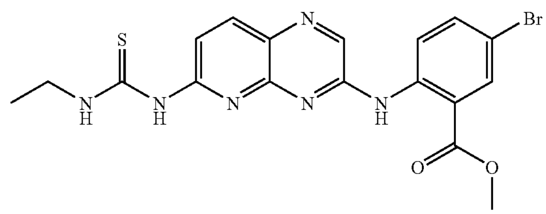 | 5-Bromo-2-[6-(3-ethyl-thioureido)-pyrido[2,3-b]pyrazin-3-ylamino]-benzoic acid methyl ester |
| 474 | 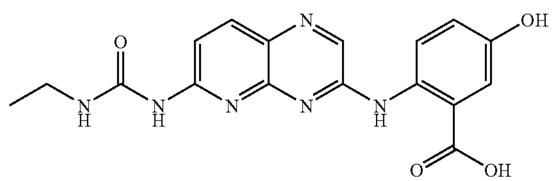 | 2-[6-(3-Ethyl-ureido)-pyrido[2,3-b]pyrazin-3-ylamino]-5-hydroxy-benzoic acid |
| 475 | 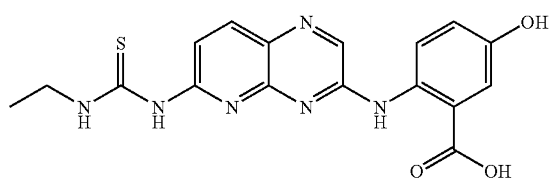 | 2-[6-(3-Ethyl-thioureido)-pyrido[2,3-b]pyrazin-3-ylamino]-5-hydroxy-benzoic acid |
| 476 | 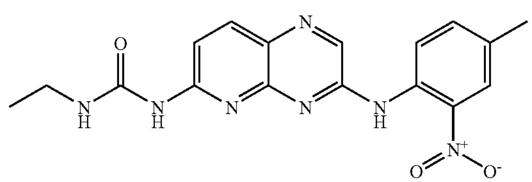 | 1-Ethyl-3-[3-(4-methyl-2-nitro-phenylamino)-pyrido[2,3-b]pyrazin-6-yl]-urea |
| 477 | 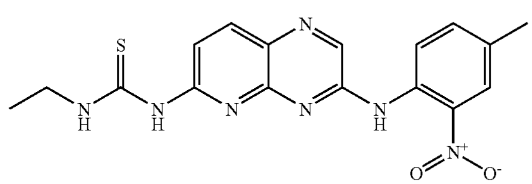 | 1-Ethyl-3-[3-(4-methyl-2-nitro-phenylamino)-pyrido[2,3-b]pyrazin-6-yl]-thiourea |
| 478 | 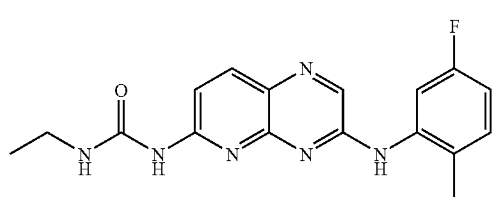 | 1-Ethyl-3-[3-(5-fluoro-2-methyl-phenylamino)-pyrido[2,3-b]pyrazin-6-yl]-urea |
| 479 | 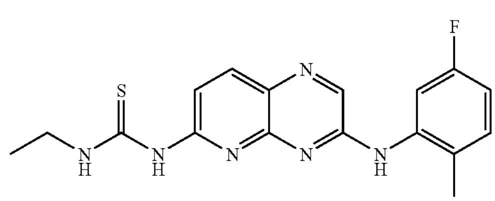 | 1-Ethyl-3-[3-(5-fluoro-2-methyl-phenylamino)-pyrido[2,3-b]pyrazin-6-yl]-thiourea |

-continued

| Compound | Structure | Name |
|---|---|---|
| 480 | 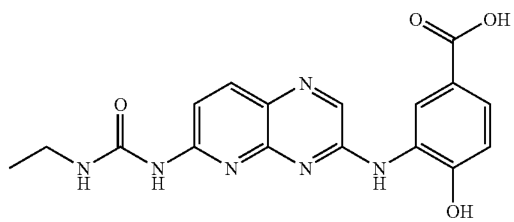 | 3-[6-(3-Ethyl-ureido)-pyrido[2,3-b]pyrazin-3-ylamino]-4-hydroxy-benzoic acid |
| 481 | 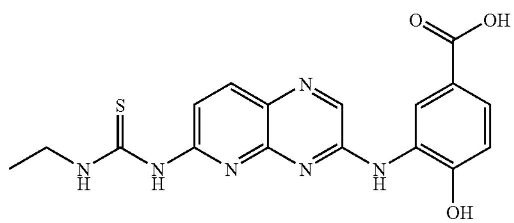 | 3-[6-(3-Ethyl-thioureido)-pyrido[2,3-b]pyrazin-3-ylamino]-4-hydroxy-benzoic acid |
| 482 | 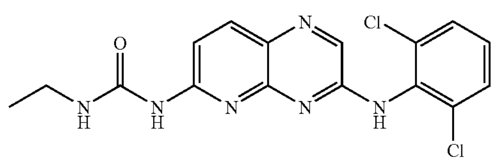 | 1-[3-(2,6-Dichloro-phenylamino)-pyrido[2,3-b]pyrazin-6-yl]-3-ethyl-urea |
| 483 | 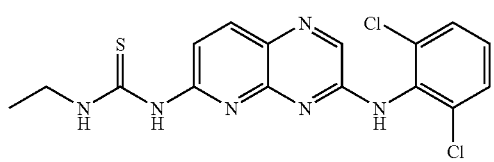 | 1-[3-(2,6-Dichloro-phenylamino)-pyrido[2,3-b]pyrazin-6-yl]-3-ethyl-thiourea |
| 484 | 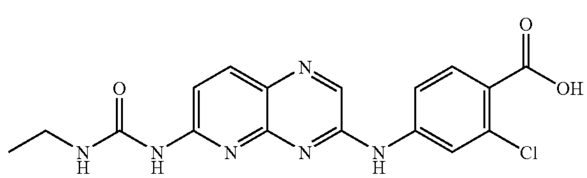 | 2-Chloro-4-[6-(3-ethyl-ureido)-pyrido[2,3-b]pyrazin-3-ylamino]-benzoic acid |
| 485 | 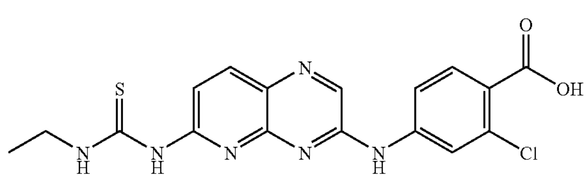 | 2-Chloro-4-[6-(3-ethyl-thioureido)-pyrido[2,3-b]pyrazin-3-ylamino]-benzoic acid |
| 486 | 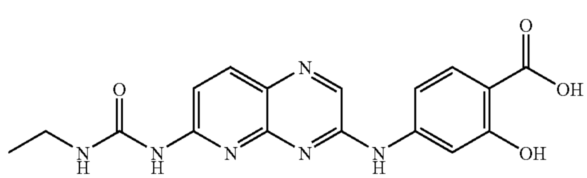 | 4-[6-(3-Ethyl-ureido)-pyrido[2,3-b]pyrazin-3-ylamino]-2-hydroxy-benzoic acid |
| 487 | 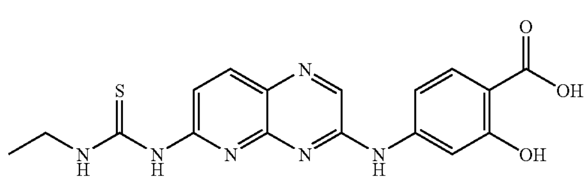 | 4-[6-(3-Ethyl-thioureido)-pyrido[2,3-b]pyrazin-3-ylamino]-2-hydroxy-benzoic acid |

-continued

| Compound | Structure | Name |
|---|---|---|
| 488 | 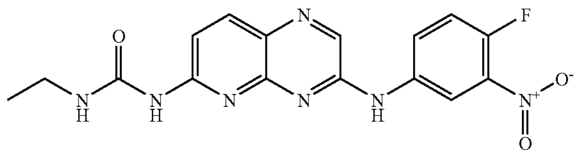 | 1-Ethyl-3-[3-(4-fluoro-3-nitro-phenylamino)-pyrido[2,3-b]pyrazin-6-yl]-urea |
| 489 | 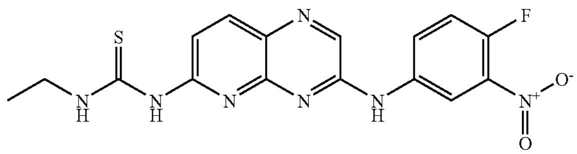 | 1-Ethyl-3-[3-(4-fluoro-3-nitro-phenylamino)-pyrido[2,3-b]pyrazin-6-yl]-thiourea |
| 490 | 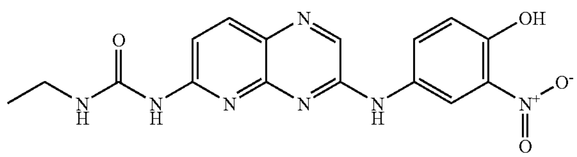 | 1-Ethyl-3-[3-(4-hydroxy-3-nitro-phenylamino)-pyrido[2,3-b]pyrazin-6-yl]-urea |
| 491 | 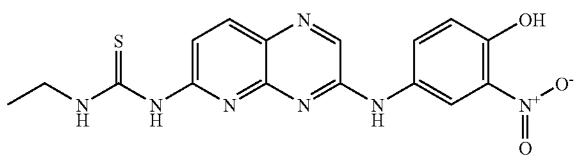 | 1-Ethyl-3-[3-(4-hydroxy-3-nitro-phenylamino)-pyrido[2,3-b]pyrazin-6-yl]-thiourea |
| 492 | 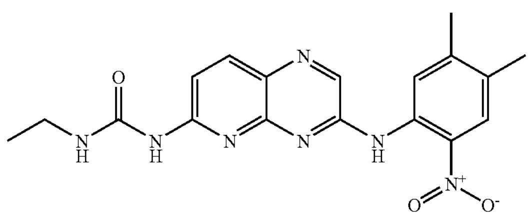 | 1-[3-(4,5-Dimethyl-2-nitro-phenylamino)-pyrido[2,3-b]pyrazin-6-yl]-3-ethyl-urea |
| 493 | 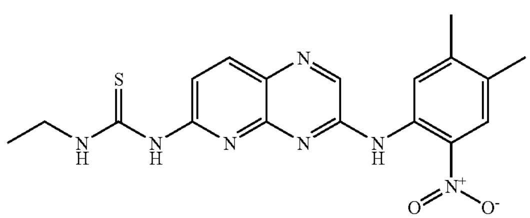 | 1-[3-(4,5-Dimethyl-2-nitro-phenylamino)-pyrido[2,3-b]pyrazin-6-yl]-3-ethyl-thiourea |
| 494 | 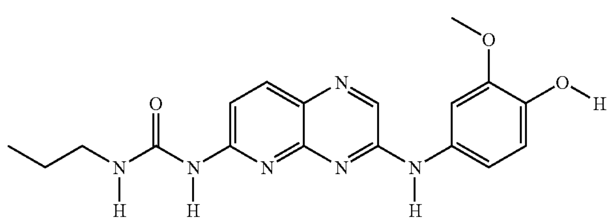 | 1-[3-(4-Hydroxy-3-methoxy-phenylamino)-pyrido[2,3-b]pyrazin-6-yl]-3-propyl-urea |
| 495 | 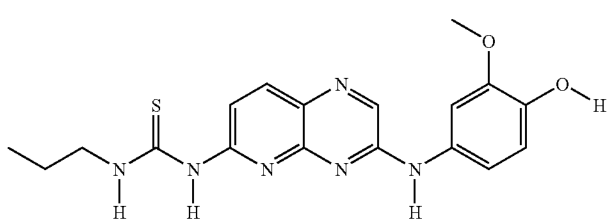 | 1-[3-(4-Hydroxy-3-methoxy-phenylamino)-pyrido[2,3-b]pyrazin-6-yl]-3-propyl-thiourea |

| Compound | Structure | Name |
|---|---|---|
| 496 | 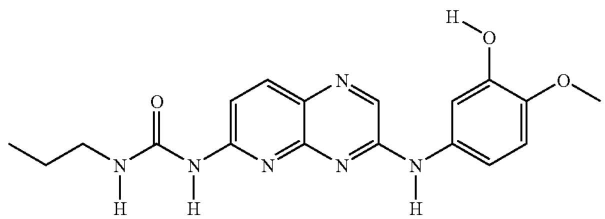 | 1-[3-(3-Hydroxy-4-methoxy-phenylamino)-pyrido[2,3-b]pyrazin-6-yl]-3-propyl-urea |
| 497 | 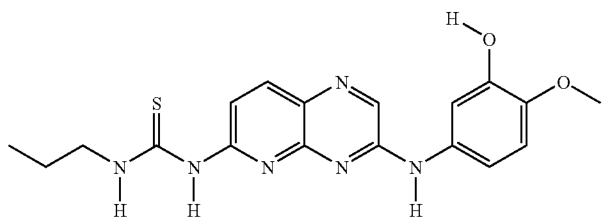 | 1-[3-(3-Hydroxy-4-methoxy-phenylamino)-pyrido[2,3-b]pyrazin-6-yl]-3-propyl-thiourea |
| 498 | 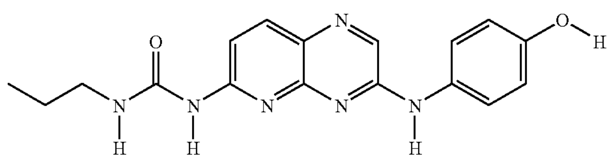 | 1-[3-(4-Hydroxy-phenylamino)-pyrido[2,3-b]pyrazin-6-yl]-3-propyl-urea |
| 499 | 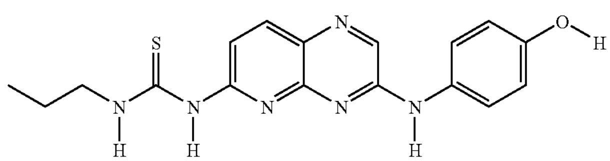 | 1-[3-(4-Hydroxy-phenylamino)-pyrido[2,3-b]pyrazin-6-yl]-3-propyl-thiourea |
| 500 | 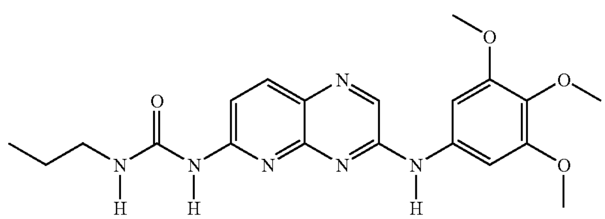 | 1-Propyl-3-[3-(3,4,5-trimethoxy-phenylamino)-pyrido[2,3-b]pyrazin-6-yl]-urea |
| 501 | 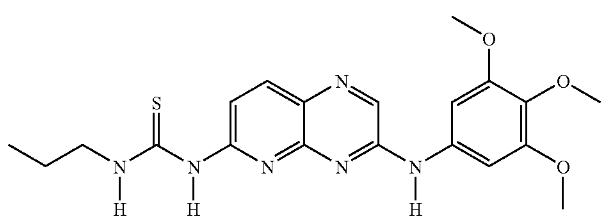 | 1-Propyl-3-[3-(3,4,5-trimethoxy-phenylamino)-pyrido[2,3-b]pyrazin-6-yl]-thiourea |
| 502 | 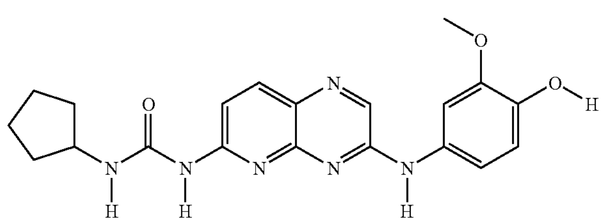 | 1-Cyclopentyl-3-[3-(4-hydroxy-3-methoxy-phenylamino)-pyrido[2,3-b]pyrazin-6-yl]-urea |

-continued

| Compound | Structure | Name |
|---|---|---|
| 503 | 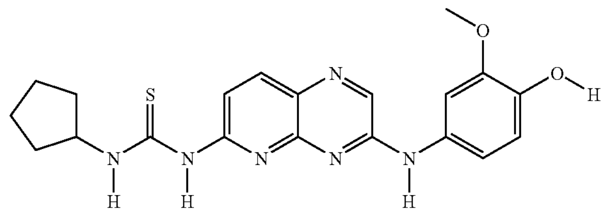 | 1-Cyclopentyl-3-[3-(4-hydroxy-3-methoxy-phenylamino)-pyrido[2,3-b]pyrazin-6-yl]-thiourea |
| 504 | 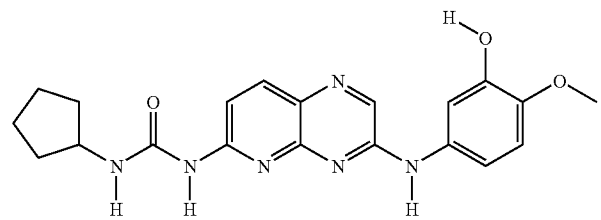 | 1-Cyclopentyl-3-[3-(3-hydroxy-4-methoxy-phenylamino)-pyrido[2,3-b]pyrazin-6-yl]-urea |
| 505 | 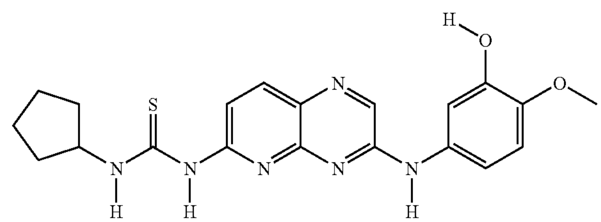 | 1-Cyclopentyl-3-[3-(3-hydroxy-4-methoxy-phenylamino)-pyrido[2,3-b]pyrazin-6-yl]-thiourea |
| 506 | 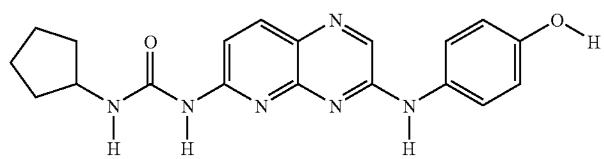 | 1-Cyclopentyl-3-[3-(4-hydroxy-phenylamino)-pyrido[2,3-b]pyrazin-6-yl]-urea |
| 507 | 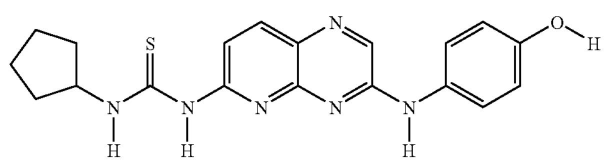 | 1-Cyclopentyl-3-[3-(4-hydroxy-phenylamino)-pyrido[2,3-b]pyrazin-6-yl]-thiourea |
| 508 | 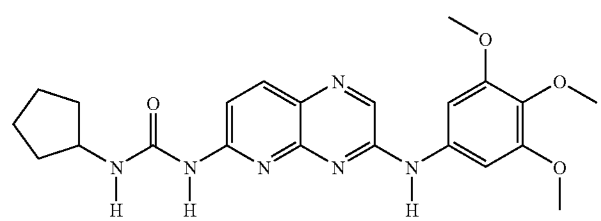 | 1-Cyclopentyl-3-[3-(3,4,5-trimethoxy-phenylamino)-pyrido[2,3-b]pyrazin-6-yl]-urea |
| 509 | 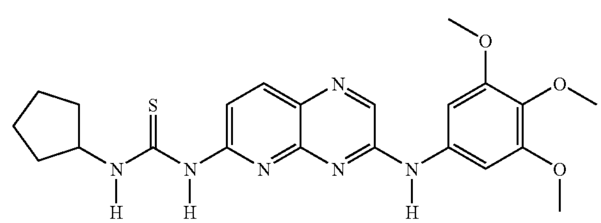 | 1-Cyclopentyl-3-[3-(3,4,5-trimethoxy-phenylamino)-pyrido[2,3-b]pyrazin-6-yl]-thiourea |

| Compound | Structure | Name |
|---|---|---|
| 510 | 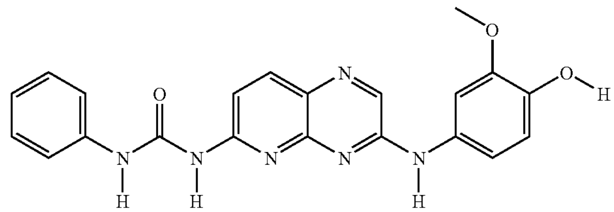 | 1-[3-(4-Hydroxy-3-methoxy-phenylamino)-pyrido[2,3-b]pyrazin-6-yl]-3-phenyl-urea |
| 511 | 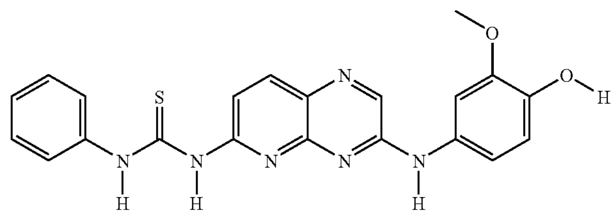 | 1-[3-(4-Hydroxy-3-methoxy-phenylamino)-pyrido[2,3-b]pyrazin-6-yl]-3-phenyl-thiourea |
| 512 | 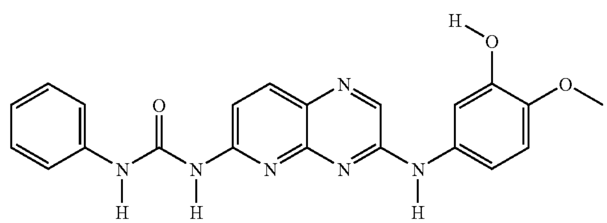 | 1-[3-(3-Hydroxy-4-methoxy-phenylamino)-pyrido[2,3-b]pyrazin-6-yl]-3-phenyl-urea |
| 513 | 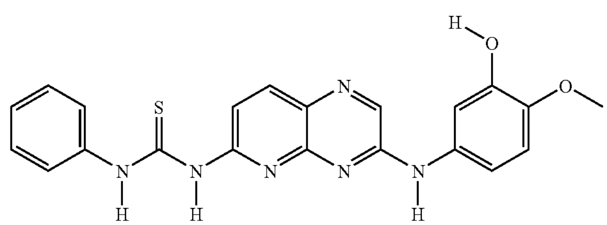 | 1-[3-(3-Hydroxy-4-methoxy-phenylamino)-pyrido[2,3-b]pyrazin-6-yl]-3-phenyl-thiourea |
| 514 | 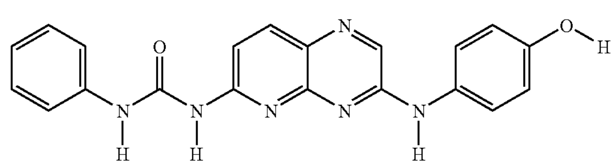 | 1-[3-(4-Hydroxy-phenylamino)-pyrido[2,3-b]pyrazin-6-yl]-3-phenyl-urea |
| 515 | 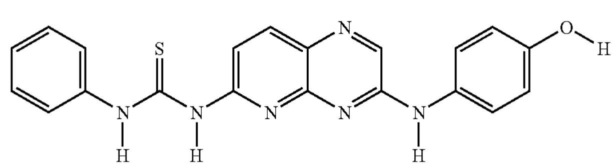 | 1-[3-(4-Hydroxy-phenylamino)-pyrido[2,3-b]pyrazin-6-yl]-3-phenyl-thiourea |
| 516 | 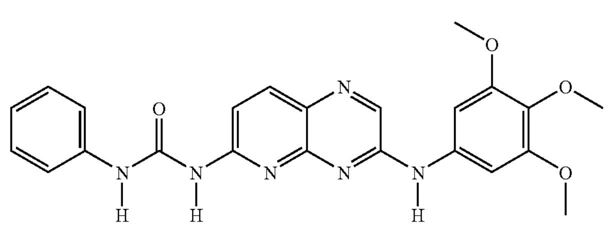 | 1-Phenyl-3-[3-(3,4,5-trimethoxy-phenylamino)-pyrido[2,3-b]pyrazin-6-yl]urea |

-continued

| Compound | Structure | Name |
|---|---|---|
| 517 | 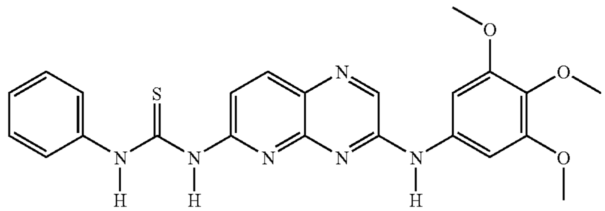 | 1-Phenyl-3-[3-(3,4,5-trimethoxy-phenylamino)-pyrido[2,3-b]pyrazin-6-yl]-thiourea |
| 518 | 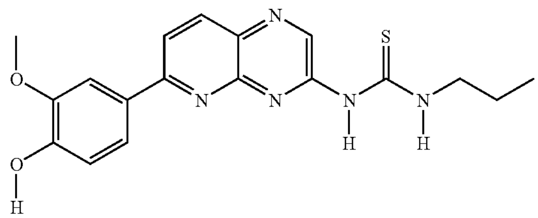 | 1-[6-(4-Hydroxy-3-methoxy-phenyl)-pyrido[2,3-b]pyrazin-3-yl]-3-propyl-thiourea |
| 519 | 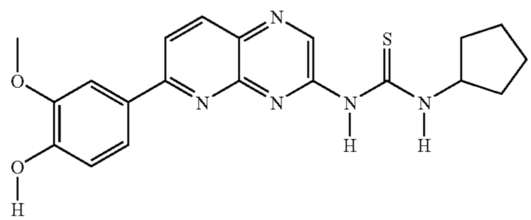 | 1-Cyclopentyl-3-[6-(4-hydroxy-3-methoxy-phenyl)-pyrido[2,3-b]pyrazin-3-yl]-thiourea |
| 520 | 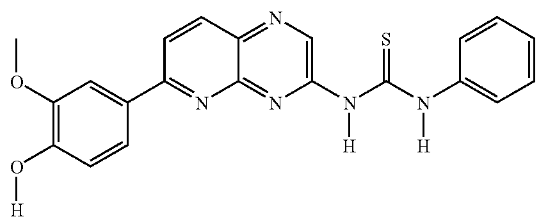 | 1-[6-(4-Hydroxy-3-methoxy-phenyl)-pyrido[2,3-b]pyrazin-3-yl]-3-phenyl-thiourea |
| 521 | 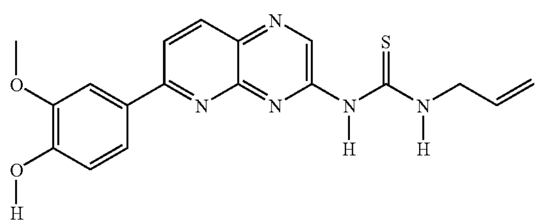 | 1-Allyl-3-[6-(4-hydroxy-3-methoxy-phenyl)-pyrido[2,3-b]pyrazin-3-yl]-thiourea |
| 522 | 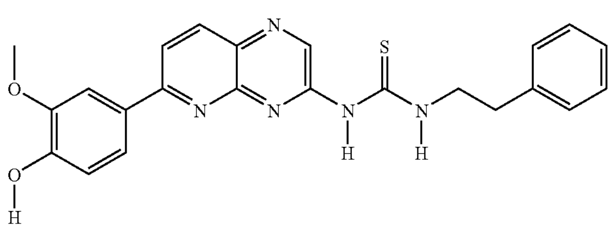 | 1-[6-(4-Hydroxy-3-methoxy-phenyl)-pyrido[2,3-b]pyrazin-3-yl]-3-phenethyl-thiourea |
| 523 | 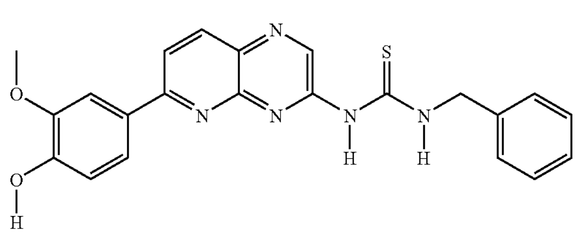 | 1-Benzyl-3-[6-(4-hydroxy-3-methoxy-phenyl)-pyrido[2,3-b]pyrazin-3-yl]-thiourea |

| Compound | Structure | Name |
|---|---|---|
| 524 | 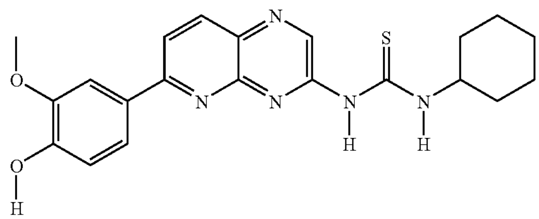 | 1-Cyclohexyl-3-[6-(4-hydroxy-3-methoxy-phenyl)-pyrido[2,3-b]pyrazin-3-yl]-thiourea |
| 525 | 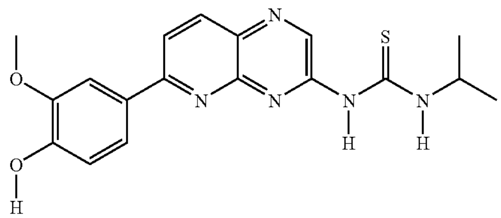 | 1-[6-(4-Hydroxy-3-methoxy-phenyl)-pyrido[2,3-b]pyrazin-3-yl]-3-isopropyl-thiourea |
| 526 | 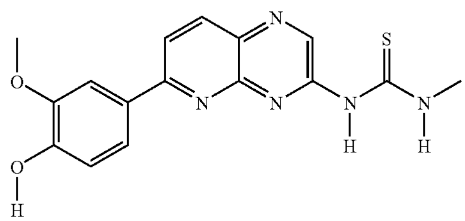 | 1-[6-(4-Hydroxy-3-methoxy-phenyl)-pyrido[2,3-b]pyrazin-3-yl]-3-methyl-thiourea |
| 527 | 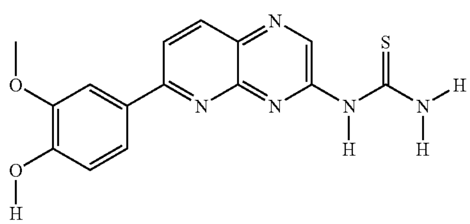 | [6-(4-Hydroxy-3-methoxy-phenyl)-pyrido[2,3-b]pyrazin-3-yl]-thiourea |
| 528 | 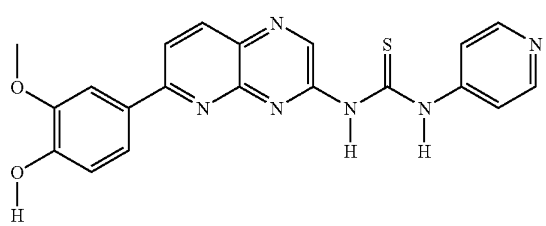 | 1-[6-(4-Hydroxy-3-methoxy-phenyl)-pyrido[2,3-b]pyrazin-3-yl]-3-pyridin-4-yl-thiourea |
| 529 | 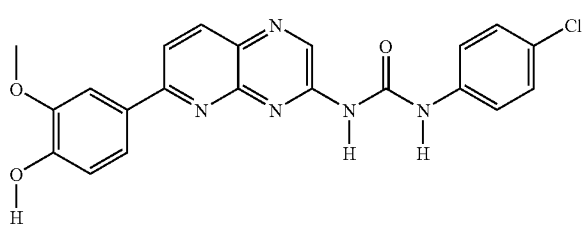 | 1-(4-Chloro-phenyl)-3-[6-(4-hydroxy-3-methoxy-phenyl)-pyrido[2,3-b]pyrazin-3-yl]-urea |
| 530 | 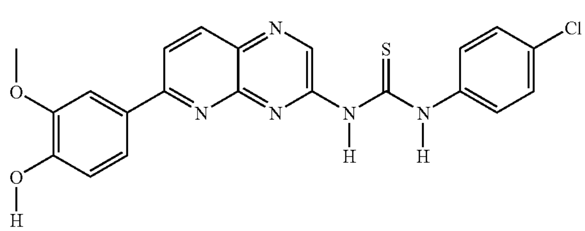 | 1-(4-Chloro-phenyl)-3-[6-(4-hydroxy-3-methoxy-phenyl)-pyrido[2,3-b]pyrazin-3-yl]-thiourea |

| Compound | Structure | Name |
|---|---|---|
| 531 | 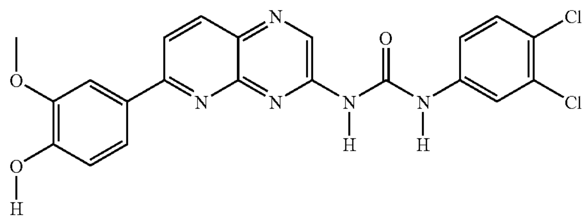 | 1-(3,4-Dichloro-phenyl)-3-[6-(4-hydroxy-3-methoxy-phenyl)-pyrido[2,3-b]pyrazin-3-yl]-urea |
| 532 | 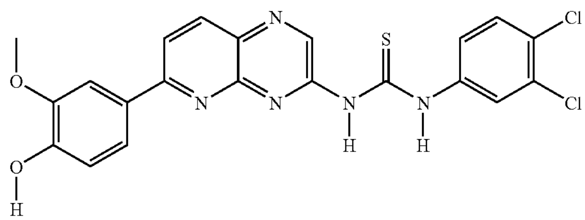 | 1-(3,4-Dichloro-phenyl)-3-[6-(4-hydroxy-3-methoxy-phenyl)-pyrido[2,3-b]pyrazin-3-yl]-thiourea |
| 533 | 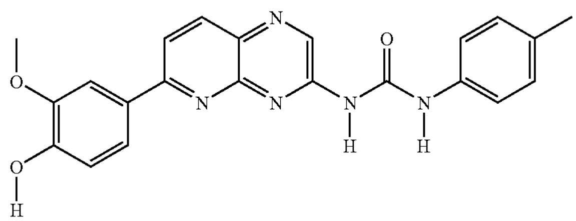 | 1-[6-(4-Hydroxy-3-methoxy-phenyl)-pyrido[2,3-b]pyrazin-3-yl]-3-p-tolyl-urea |
| 534 | 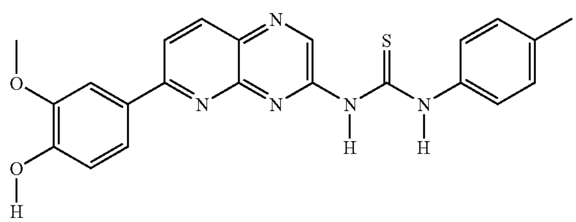 | 1-[6-(4-Hydroxy-3-methoxy-phenyl)-pyrido[2,3-b]pyrazin-3-yl]-3-p-tolyl-thiourea |
| 535 | 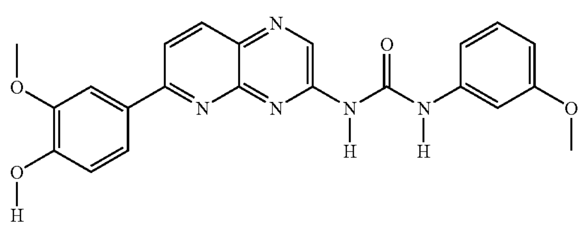 | 1-[6-(4-Hydroxy-3-methoxy-phenyl)-pyrido[2,3-b]pyrazin-3-yl]-3-(3-methoxy-phenyl)-urea |
| 536 | 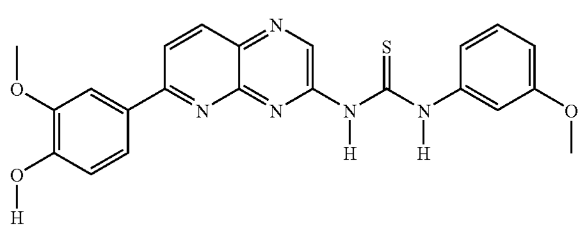 | 1-[6-(4-Hydroxy-3-methoxy-phenyl)-pyrido[2,3-b]pyrazin-3-yl]-3-(3-methoxy-phenyl)-thiourea |
| 537 | 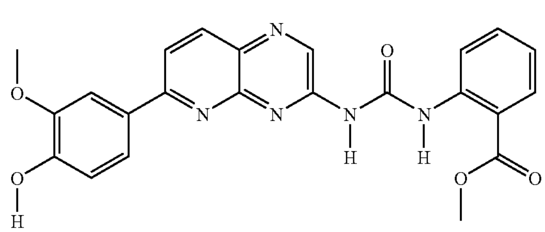 | 2-{3-[6-(4-Hydroxy-3-methoxy-phenyl)-pyrido[2,3-b]pyrazin-3-yl]-ureido}-benzoic acid methyl ester |

| Compound | Structure | Name |
|---|---|---|
| 538 | 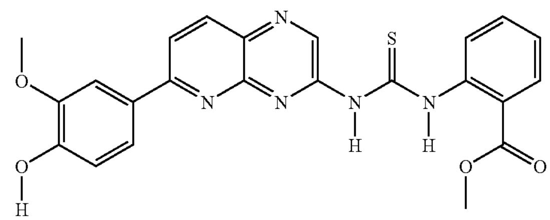 | 2-{3-[6-(4-Hydroxy-3-methoxy-phenyl)-pyrido[2,3-b]pyrazin-3-yl]-thioureido}-benzoic acid methyl ester |
| 539 | 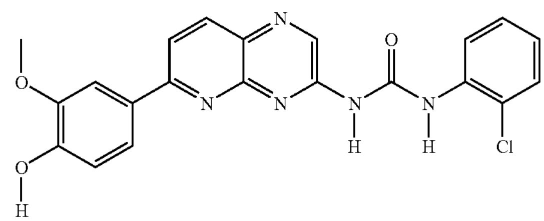 | 1-(2-Chloro-phenyl)-3-[6-(4-hydroxy-3-methoxy-phenyl)-pyrido[2,3-b]pyrazin-3-yl]-urea |
| 540 | 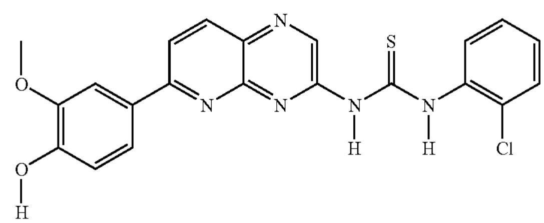 | 1-(2-Chloro-phenyl)-3-[6-(4-hydroxy-3-methoxy-phenyl)-pyrido[2,3-b]pyrazin-3-yl]-thiourea |
| 541 | 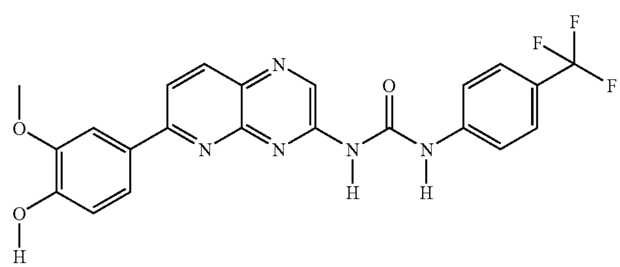 | 1-[6-(4-Hydroxy-3-methoxy-phenyl)-pyrido[2,3-b]pyrazin-3-yl]-3-(4-trifluoromethyl-phenyl)-urea |
| 542 | 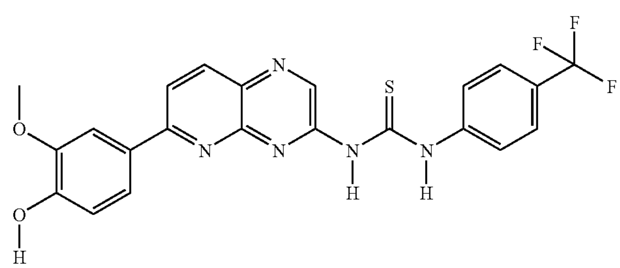 | 1-[6-(4-Hydroxy-3-methoxy-phenyl)-pyrido[2,3-b]pyrazin-3-yl]-3-(4-trifluoromethyl-phenyl)-thiourea |
| 543 | 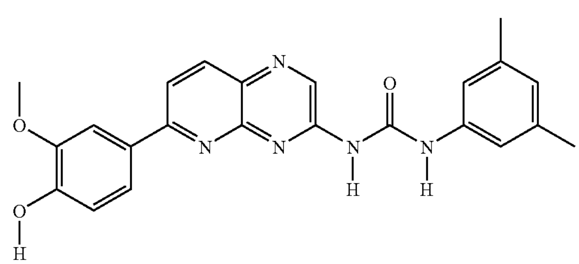 | 1-(3,5-Dimethyl-phenyl)-3-[6-(4-hydroxy-3-methoxy-phenyl)-pyrido[2,3-b]pyrazin-3-yl]-urea |

-continued

| Compound | Structure | Name |
|---|---|---|
| 544 | 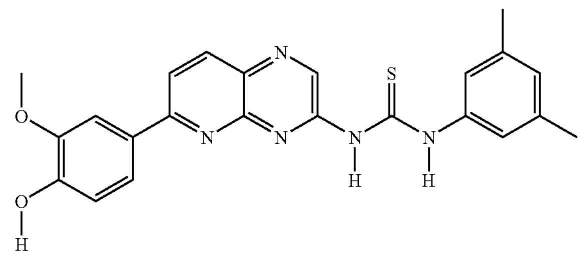 | 1-(3,5-Dimethyl-phenyl)-3-[6-(4-hydroxy-3-methoxy-phenyl)-pyrido[2,3-b]pyrazin-3-yl]-thiourea |
| 545 | 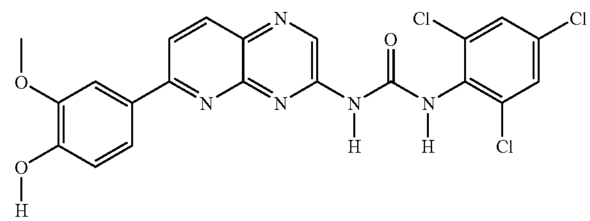 | 1-[6-(4-Hydroxy-3-methoxy-phenyl)-pyrido[2,3-b]pyrazin-3-yl]-3-(2,4,6-trichloro-phenyl)-urea |
| 546 | 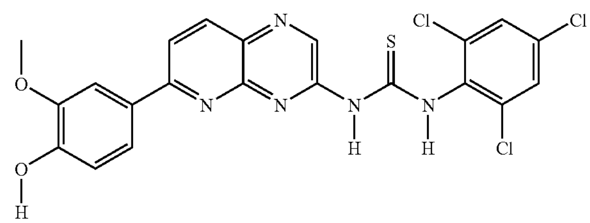 | 1-[6-(4-Hydroxy-3-methoxy-phenyl)-pyrido[2,3-b]pyrazin-3-yl]-3-(2,4,6-trichloro-phenyl)-thiourea |
| 547 | 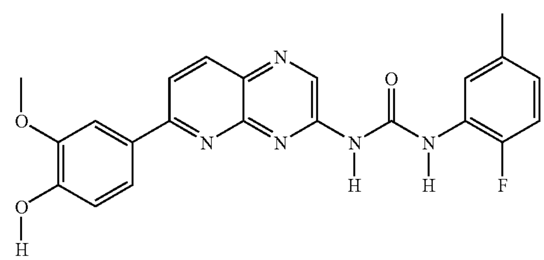 | 1-(2-Fluoro-5-methyl-phenyl)-3-[6-(4-hydroxy-3-methoxy-phenyl)-pyrido[2,3-b]pyrazin-3-yl]-urea |
| 548 | 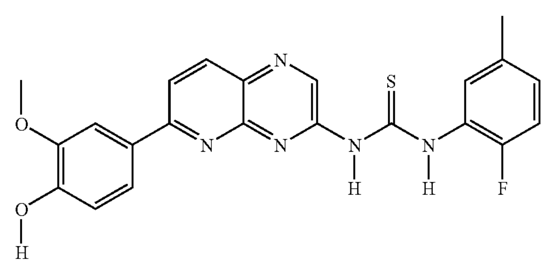 | 1-(2-Fluoro-5-methyl-phenyl)-3-[6-(4-hydroxy-3-methoxy-phenyl)-pyrido[2,3-b]pyrazin-3-yl]-thiourea |
| 549 | 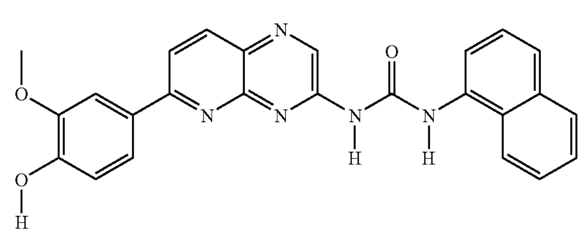 | 1-[6-(4-Hydroxy-3-methoxy-phenyl)-pyrido[2,3-b]pyrazin-3-yl]-3-naphthalen-1-yl-urea |

| Compound | Structure | Name |
|---|---|---|
| 550 | 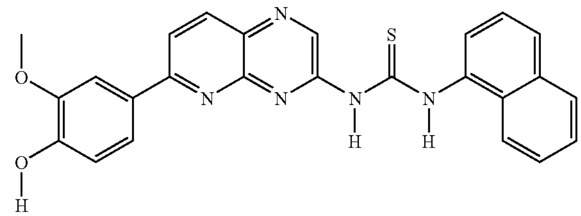 | 1-[6-(4-Hydroxy-3-methoxy-phenyl)-pyrido[2,3-b]pyrazin-3-yl]-3-naphthalen-1-yl-thiourea |
| 551 | 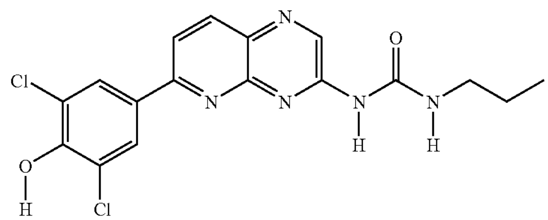 | 1-[6-(3,5-Dichloro-4-hydroxy-phenyl)-pyrido[2,3-b]pyrazin-3-yl]-3-propyl-urea |
| 552 | 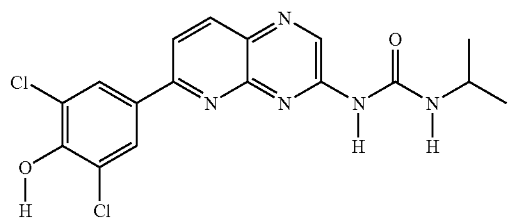 | 1-[6-(3,5-Dichloro-4-hydroxy-phenyl)-pyrido[2,3-b]pyrazin-3-yl]-3-isopropyl-urea |
| 553 | 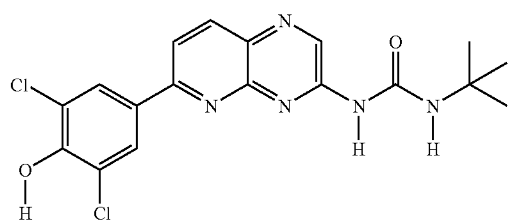 | 1-tert-Butyl-3-[6-(3,5-dichloro-4-hydroxy-phenyl)-pyrido[2,3-b]pyrazin-3-yl]-urea |
| 554 | 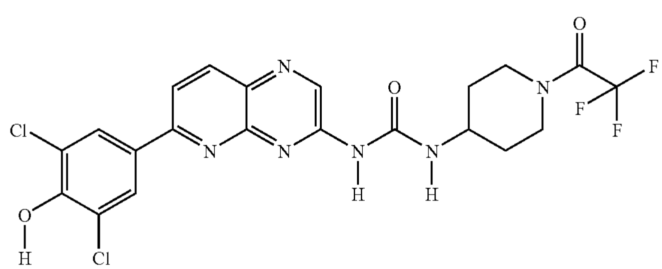 | 1-tert-Butyl-3-[6-(3,5-dichloro-4-hydroxy-phenyl)-pyrido[2,3-b]pyrazin-3-yl]-urea |
| 555 | 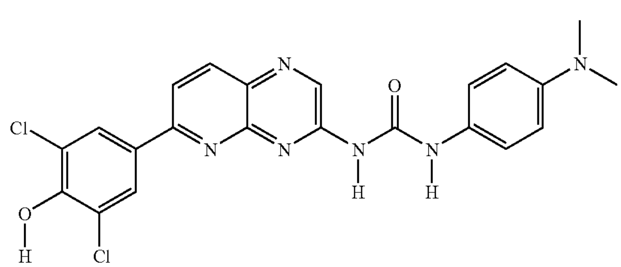 | 1-[6-(3,5-Dichloro-4-hydroxy-phenyl)-pyrido[2,3-b]pyrazin-3-yl]-3-(4-dimethylamino-phenyl)-urea |

-continued

| Compound | Structure | Name |
|---|---|---|
| 556 | 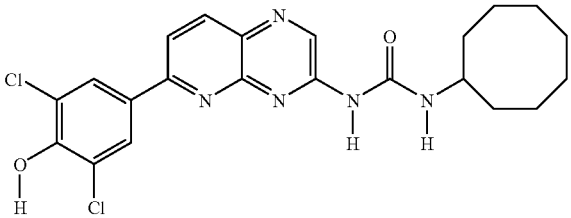 | 1-Cyclooctyl-3-[6-(3,5-dichloro-4-hydroxy-phenyl)-pyrido[2,3-b]pyrazin-3-yl]-urea |
| 557 | 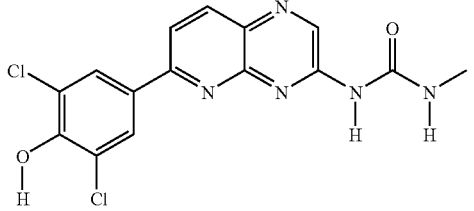 | 1-[6-(3,5-Dichloro-4-hydroxy-phenyl)-pyrido[2,3-b]pyrazin-3-yl]-3-methyl-urea |
| 558 | 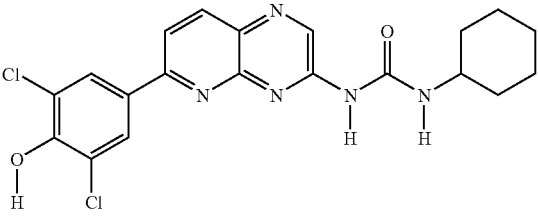 | 1-Cyclohexyl-3-[6-(3,5-dichloro-4-hydroxy-phenyl)-pyrido[2,3-b]pyrazin-3-yl]-urea |
| 559 | 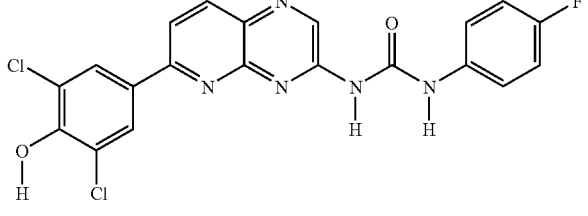 | 1-[6-(3,5-Dichloro-4-hydroxy-phenyl)-pyrido[2,3-b]pyrazin-3-yl]-3-(4-fluoro-phenyl)-urea |
| 560 | 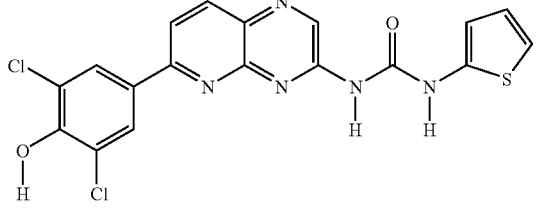 | 1-[6-(3,5-Dichloro-4-hydroxy-phenyl)-pyrido[2,3-b]pyrazin-3-yl]-3-thiophen-2-yl-urea |
| 561 | 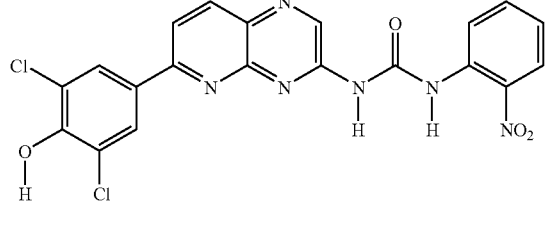 | 1-[6-(3,5-Dichloro-4-hydroxy-phenyl)-pyrido[2,3-b]pyrazin-3-yl]-3-(2-nitro-phenyl)-urea |
| 562 | 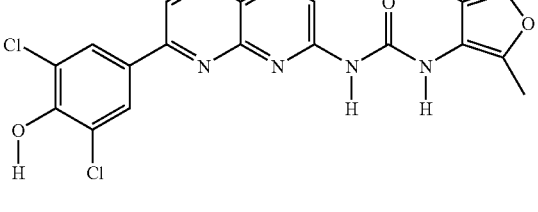 | 1-[6-(3,5-Dichloro-4-hydroxy-phenyl)-pyrido[2,3-b]pyrazin-3-yl]-3-(3,5-dimethyl-isoxazol-4-yl)-urea |

| Compound | Structure | Name |
|---|---|---|
| 563 | 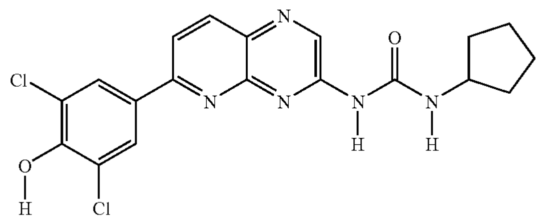 | 1-Cyclopentyl-3-[6-(3,5-dichloro-4-hydroxy-phenyl)-pyrido[2,3-b]pyrazin-3-yl]-urea |
| 564 | 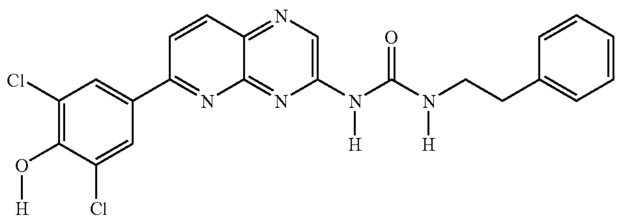 | 1-[6-(3,5-Dichloro-4-hydroxy-phenyl)-pyrido[2,3-b]pyrazin-3-yl]-3-phenethyl-urea |
| 565 | 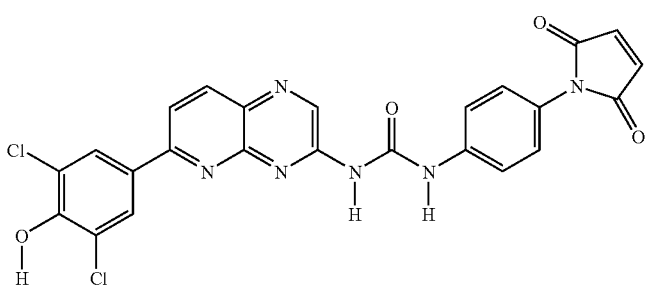 | 1-[6-(3,5-Dichloro-4-hydroxy-phenyl-pyrido[2,3-b]pyrazin-3-yl]-3-[4-(2,5-dioxo-2,5-dihydro-pyrrol-1-yl)-phenyl]-urea |
| 566 | 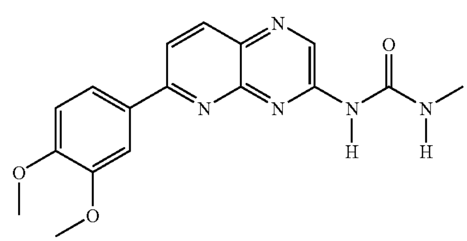 | 1-[6-(3,4-Dimethoxy-phenyl)-pyrido[2,3-b]pyrazin-3-yl]-3-methyl-urea |
| 567 | 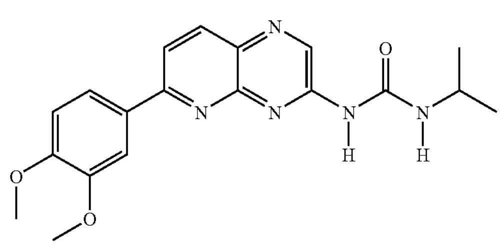 | 1-[6-(3,4-Dimethoxy-phenyl)-pyrido[2,3-b]pyrazin-3-yl]-3-isopropyl-urea |
| 568 | 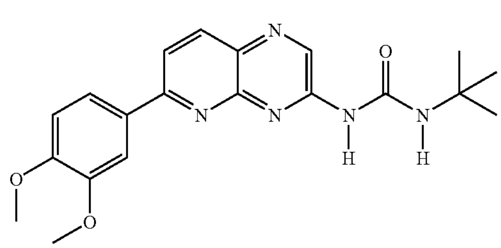 | 1-tert-Butyl-3-[6-(3,4-dimethoxy-phenyl)-pyrido[2,3-b]pyrazin-3-yl]-urea |

-continued

| Compound | Structure | Name |
|---|---|---|
| 569 | 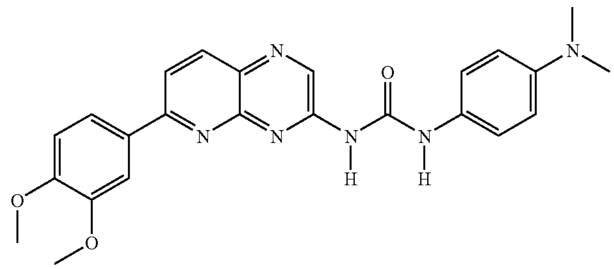 | 1-[6-(3,4-Dimethoxy-phenyl)-pyrido[2,3-b]pyrazin-3-yl]-3-(4-dimethylamino-phenyl)-urea |
| 570 | 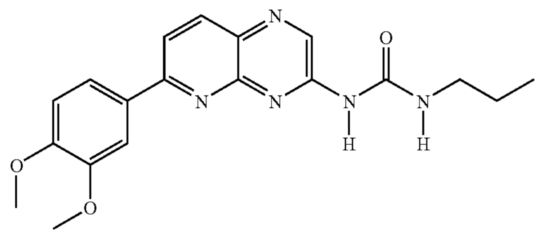 | 1-[6-(3,4-Dimethoxy-phenyl)-pyrido[2,3-b]pyrazin-3-yl]-3-propyl-urea |
| 571 | 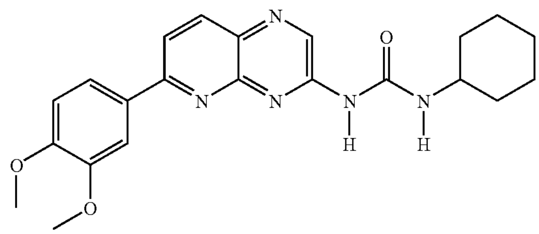 | 1-Cyclohexyl-3-[6-(3,4-dimethoxy-phenyl)-pyrido[2,3-b]pyrazin-3-yl]-urea |
| 572 | 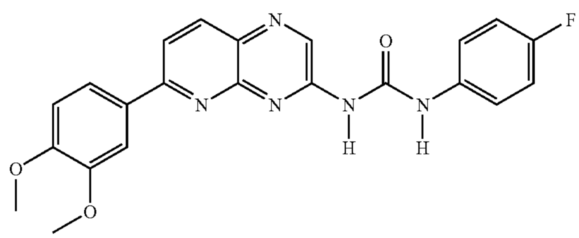 | 1-[6-(3,4-Dimethoxy-phenyl)-pyrido[2,3-b]pyrazin-3-yl]-3-(4-fluoro-phenyl)-urea |
| 573 | 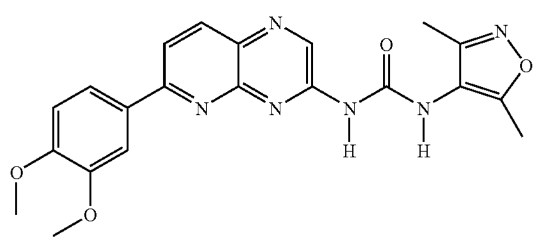 | 1-[6-(3,4-Dimethoxy-phenyl)-pyrido[2,3-b]pyrazin-3-yl]-3-(3,5-dimethyl-isoxazol-4-yl)-urea |
| 574 | 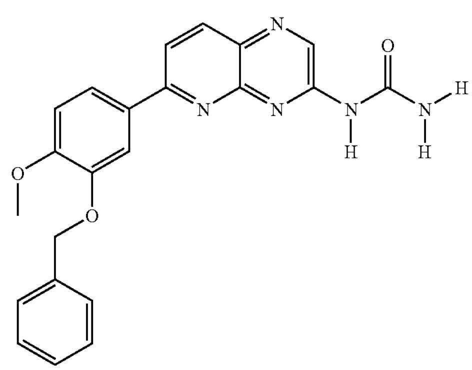 | [6-(4-Benzyloxy-3-methoxy-phenyl)-pyrido[2,3-b]pyrazin-3-yl]-urea |

| Compound | Structure | Name |
|---|---|---|
| 575 | 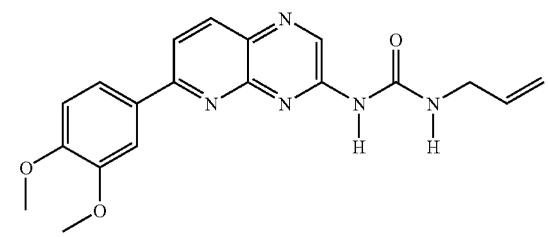 | 1-Allyl-3-[6-(3,4-dimethoxy-phenyl)-pyrido[2,3-b]pyrazin-3-yl]-urea |
| 576 | 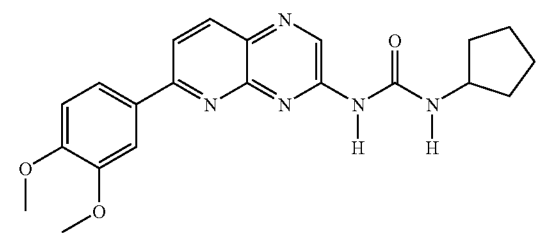 | 1-Cyclopentyl-3-[6-(3,4-dimethoxy-phenyl)-pyrido[2,3-b]pyrazin-3-yl]-urea |
| 577 | 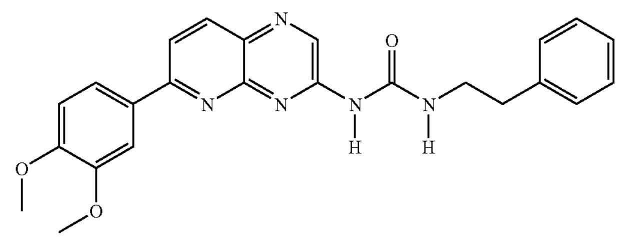 | 1-[6-(3,4-Dimethoxy-phenyl)-pyrido[2,3-b]pyrazin-3-yl]-3-phenethyl-urea |
| 578 | 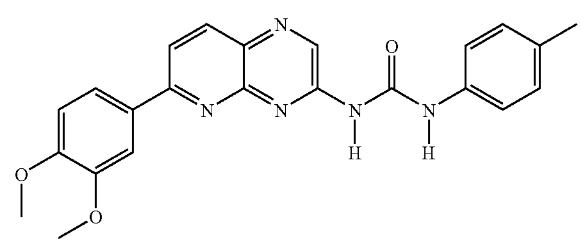 | 1-[6-(3,4-Dimethoxy-phenyl)-pyrido[2,3-b]pyrazin-3-yl]-3-p-tolyl-urea |
| 579 | 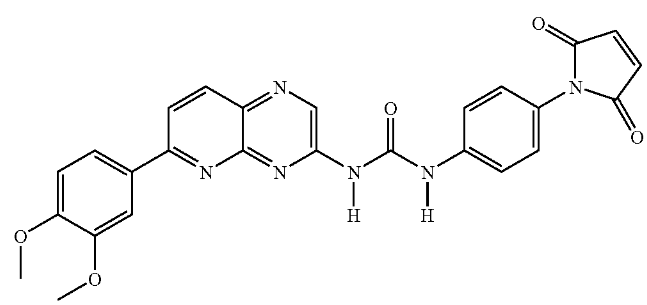 | 1-[6-(3,4-Dimethoxy-phenyl)-pyrido[2,3-b]pyrazin-3-yl]-3-[4-(2,5-dioxo-2,5-dihydro-pyrrol-1-yl)-phenyl]-urea |
| 580 | 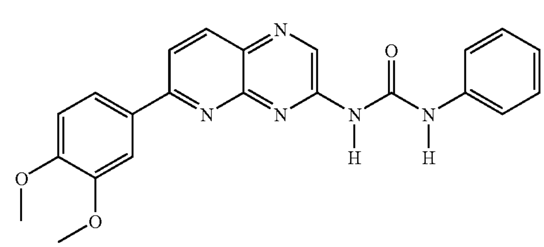 | 1-[6-(3,4-Dimethoxy-phenyl)-pyrido[2,3-b]pyrazin-3-yl]-3-phenyl-urea |

-continued

| Compound | Structure | Name |
| --- | --- | --- |
| 581 | 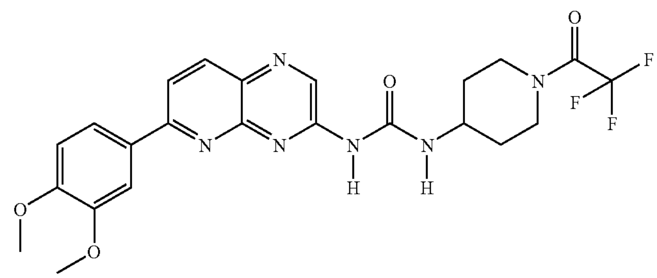 | 1-[6-(3,4-Dimethoxy-phenyl)-pyrido[2,3-b]pyrazin-3-yl]-3-[1-(2,2,2-trifluoro-acetyl)-piperidin-4-yl]-urea |
| 582 | 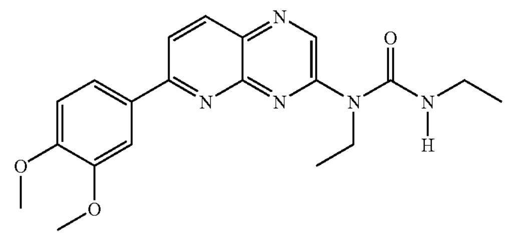 | 1-[6-(3,4-Dimethoxy-phenyl)-pyrido[2,3-b]pyrazin-3-yl]-1,3-diethyl-urea |
| 583 | 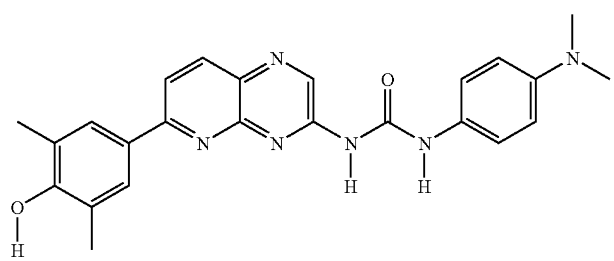 | 1-Ethyl-3-[6-(4-hydroxy-3,5-dimethyl-phenyl)-pyrido[2,3-b]pyrazin-3-yl]-urea |
| 584 | 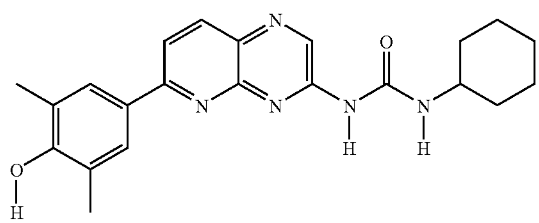 | 1-(4-Dimethylamino-phenyl)-3-[6-(4-hydroxy-3,5-dimethyl-phenyl)-pyrido[2,3-b]pyrazin-3-yl]-urea |
| 585 | 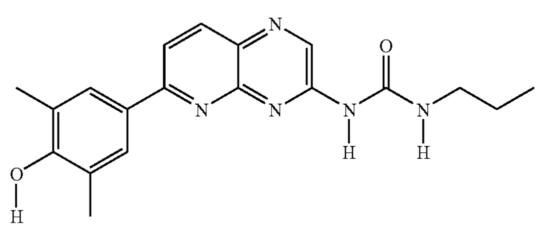 | 1-Cyclohexyl-3-[6-(4-hydroxy-3,5-dimethyl-phenyl)-pyrido[2,3-b]pyrazin-3-yl]-urea |
| 586 | 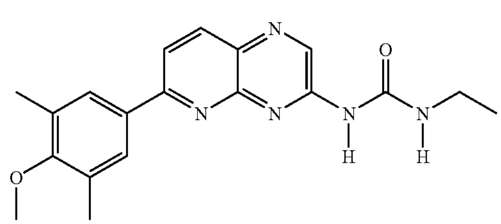 | 1-Ethyl-3-[6-(4-methoxy-3,5-dimethyl-phenyl)-pyrido[2,3-b]pyrazin-3-yl]-urea |

| Compound | Structure | Name |
|---|---|---|
| 587 | 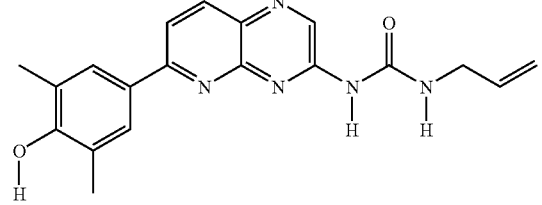 | 1-Allyl-3-[6-(4-hydroxy-3,5-dimethyl-phenyl)-pyrido[2,3-b]pyrazin-3-yl]-urea |
| 588 | 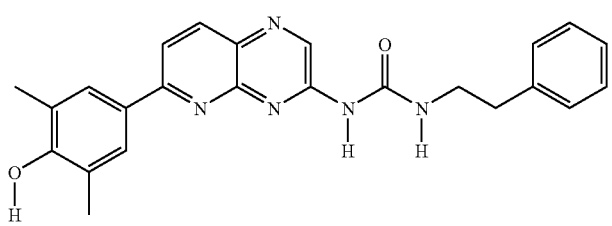 | 1-[6-(4-Hydroxy-3,5-dimethyl-phenyl)-pyrido[2,3-b]pyrazin-3-yl]-3-phenethyl-urea |
| 589 | 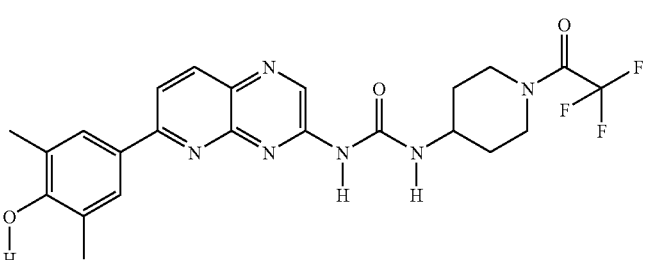 | 1-[6-(4-Hydroxy-3,5-dimethyl-phenyl)-pyrido[2,3-b]pyrazin-3-yl]-3-[1-(2,2,2-trifluoro-acetyl)-piperidin-4-yl]-urea |
| 590 | 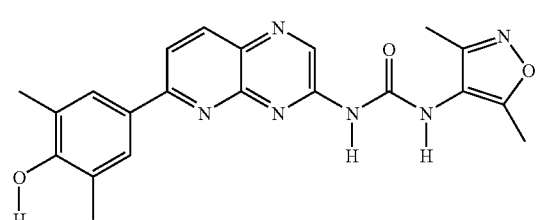 | 1-(3,5-Dimethyl-isoxazol-4-yl)-3-[6-(4-hydroxy-3,5-dimethyl-phenyl)-pyrido[2,3-b]pyrazin-3-yl]-urea |
| 591 | 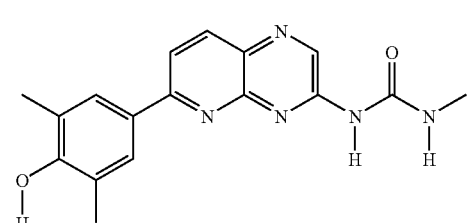 | 1-[6-(4-Hydroxy-3,5-dimethyl-phenyl)-pyrido[2,3-b]pyrazin-3-yl]-3-methyl-urea |
| 592 | 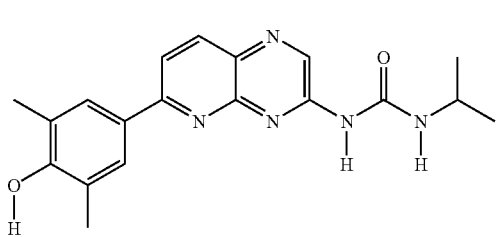 | 1-[6-(4-Hydroxy-3,5-dimethyl-phenyl)-pyrido[2,3-b]pyrazin-3-yl]-3-isopropyl-urea |

-continued

| Compound | Structure | Name |
|---|---|---|
| 593 | 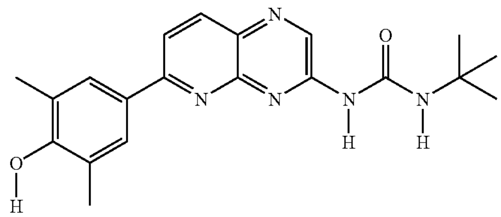 | 1-tert-Butyl-3-[6-(4-hydroxy-3,5-dimethyl-phenyl)-pyrido[2,3-b]pyrazin-3-yl]-urea |
| 594 | 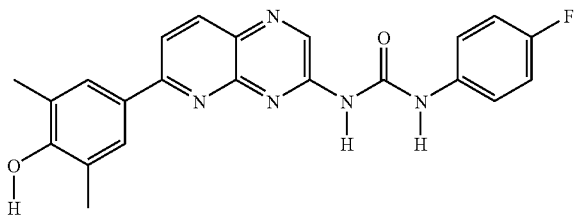 | 1-(4-Fluoro-phenyl)-3-[6-(4-hydroxy-3,5-dimethyl-phenyl)-pyrido[2,3-b]pyrazin-3-yl]-urea |
| 595 | 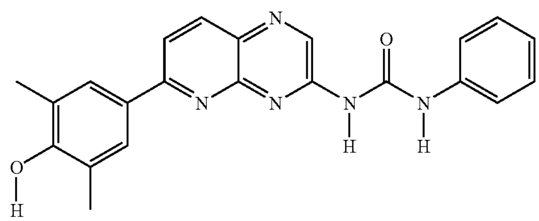 | 1-[6-(4-Hydroxy-3,5-dimethyl-phenyl)-pyrido[2,3-b]pyrazin-3-yl]-3-phenyl-urea |
| 596 | 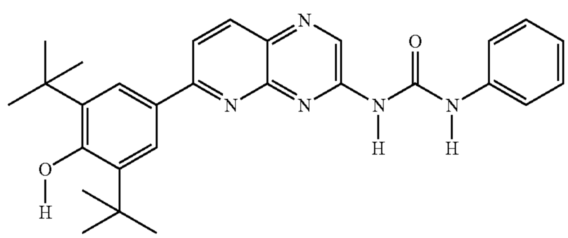 | 1-[6-(3,5-Di-tert-butyl-4-hydroxy-phenyl)-pyrido[2,3-b]pyrazin-3-yl]-3-ethyl-urea |
| 597 | 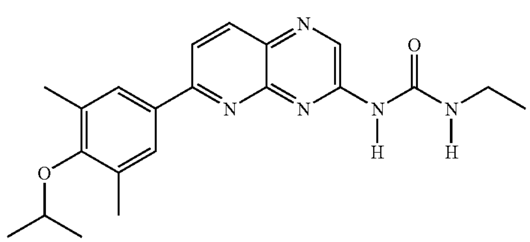 | 1-Ethyl-3-[6-(4-isopropoxy-3,5-dimethyl-phenyl)-pyrido[2,3-b]pyrazin-3-yl]-urea |
| 598 | 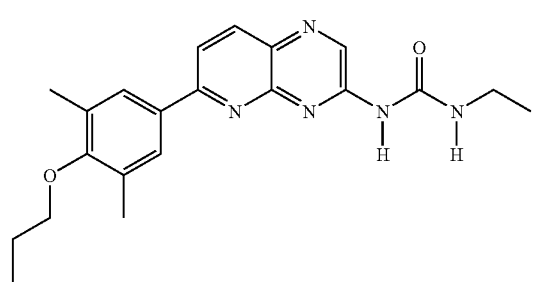 | 1-[6-(3,5-Dimethyl-4-propoxy-phenyl)-pyrido[2,3-b]pyrazin-3-yl]-3-ethyl-urea |

| Compound | Structure | Name |
|---|---|---|
| 599 | 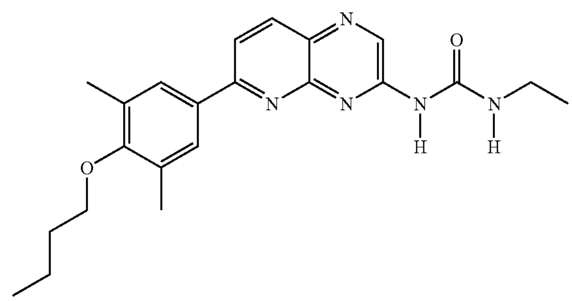 | 1-[6-(4-Butoxy-3,5-dimethyl-phenyl)-pyrido[2,3-b]pyrazin-3-yl]-3-ethyl-urea |
| 600 | 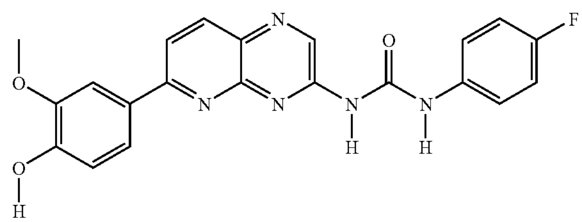 | 1-(4-Fluoro-phenyl)-3-[6-(4-hydroxy-3-methoxy-phenyl)-pyrido[2,3-b]pyrazin-3-yl]-urea |
| 601 | 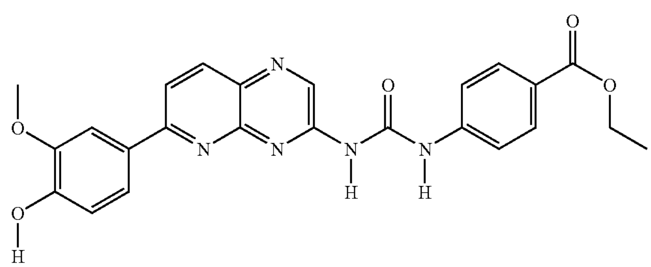 | 4{3-[6-(4-Hydroxy-3-methoxy-phenyl)-pyrido[2,3-b]pyrazin-3-yl]-ureido}-benzoic acid ethyl ester |
| 602 | 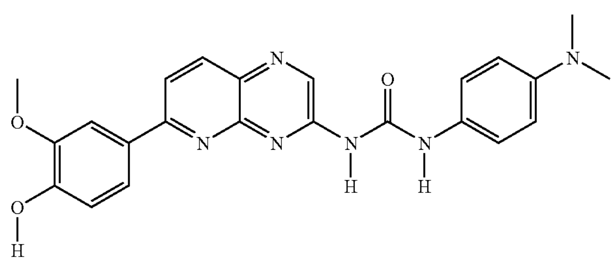 | 1-(4-Dimethylamino-phenyl)-3-[6-(4-hydroxy-3-methoxy-phenyl)-pyrido[2,3-b]pyrazin-3-yl]-urea |
| 603 | 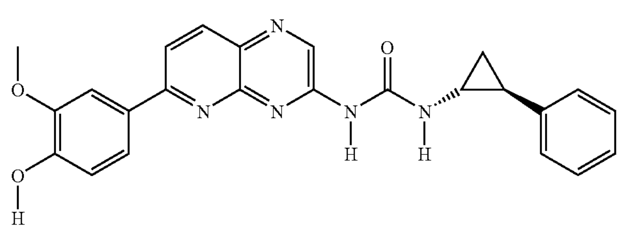 | 1-[6-(4-Hydroxy-3-methoxy-phenyl)-pyrido[2,3-b]pyrazin-3-yl]-3-((1R, 2S)-2-phenyl-cyclopropyl)-urea |
| 604 | 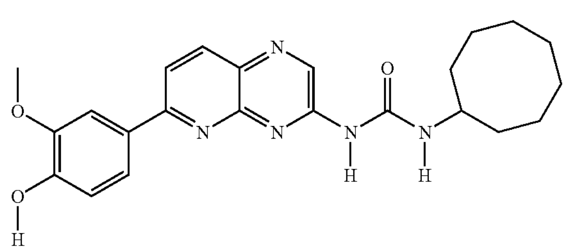 | 1-Cyclooctyl-3-[6-(4-hydroxy-3-methoxy-phenyl)-pyrido[2,3-b]pyrazin-3-yl]-urea |

| Compound | Structure | Name |
|---|---|---|
| 605 | 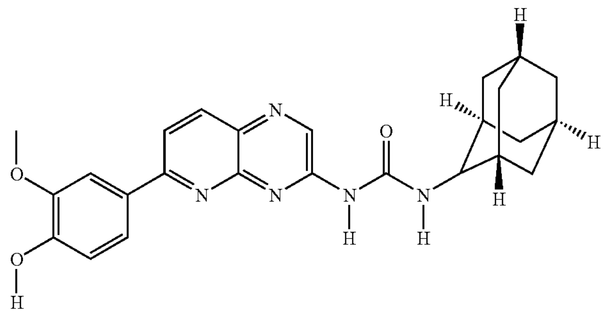 | 1-Adamantan-1-yl-3-[6-(4-hydroxy-3-methoxy-phenyl)-pyrido[2,3-b]pyrazin-3-yl]-urea |
| 606 | 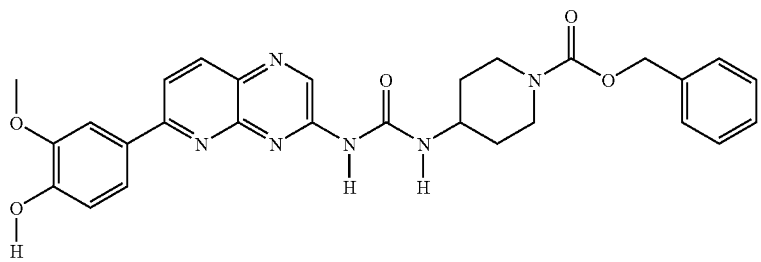 | 4-{3-[6-(4-Hydroxy-3-methoxy-phenyl)-pyrido[2,3-b]pyrazin-3-yl]-ureido}-piperidine-1-carboxylic acid benzyl ester |
| 607 | 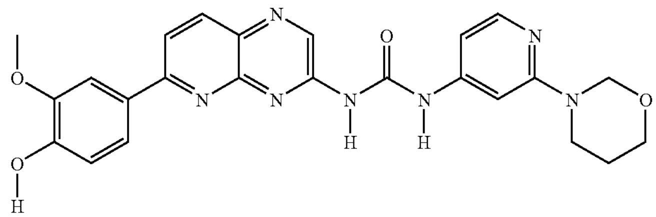 | 1-[6-(4-Hydroxy-3-methoxy-phenyl)-pyrido[2,3-b]pyrazin-3-yl]-3-(2-morpholin-4-yl-pyridin-4-yl)-urea |
| 608 | 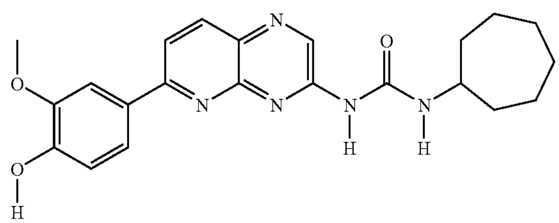 | 1-Cycloheptyl-3-[6-(4-hydroxy-3-methoxy-phenyl)-pyrido[2,3-b]pyrazin-3-yl]-urea |
| 609 | 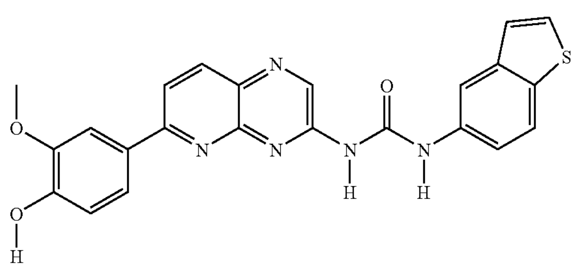 | 1-[6-(4-Hydroxy-3-methoxy-phenyl)-pyrido[2,3-b]pyrazin-3-yl]-3-thiophen-2-yl-urea |
| 610 | 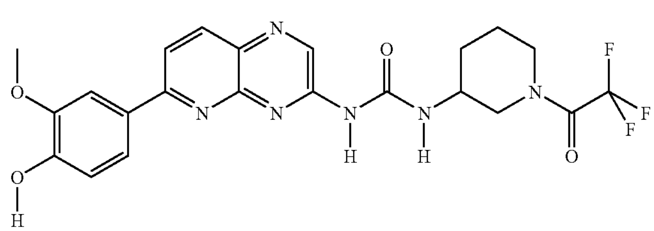 | 1-[6-(4-Hydroxy-3-methoxy-phenyl)-pyrido[2,3-b]pyrazin-3-yl]-3-[1-(2,2,2-trifluoro-acetyl)-piperidin-3-yl]-urea |

-continued

| Compound | Structure | Name |
|---|---|---|
| 611 | 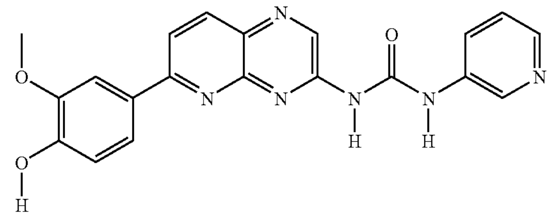 | 1-[6-(4-Hydroxy-3-methoxy-phenyl)-pyrido[2,3-b]pyrazin-3-yl]-3-pyridin-3-yl-urea |
| 612 | 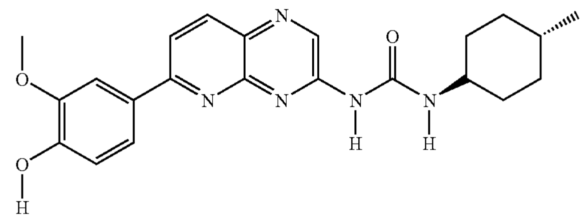 | 1-[6-(4-Hydroxy-3-methoxy-phenyl)-pyrido[2,3-b]pyrazin-3-yl]-3-(4-methyl-cyclohexyl)-urea |
| 613 | 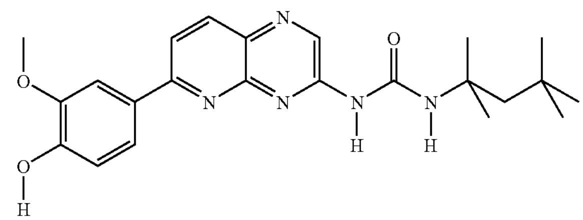 | 1-[6-(4-Hydroxy-3-methoxy-phenyl)-pyrido[2,3-b]pyrazin-3-yl]-3-(1,1,3,3-tetramethyt-butyl)-urea |
| 614 | 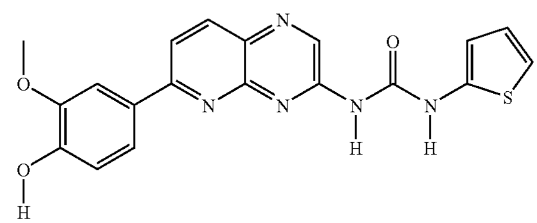 | 1-[6-(4-Hydroxy-3-methoxy-phenyl)-pyrido[2,3-b]pyrazin-3-yl]-3-thiophen-2-yl-urea |
| 615 | 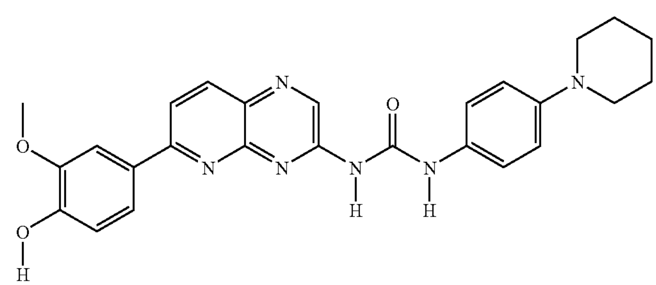 | 1-[6-(4-Hydroxy-3-methoxy-phenyl)-pyrido[2,3-b]pyrazin-3-yl]-3-(4-piperidin-1-yl-phenyl)-urea |
| 616 | 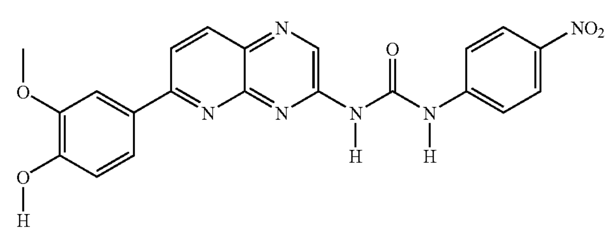 | 1-[6-(4-Hydroxy-3-methoxy-phenyl)-pyrido[2,3-b]pyrazin-3-yl]-3-(4-nitro-phenyl)-urea |

-continued

| Compound | Structure | Name |
|---|---|---|
| 617 | 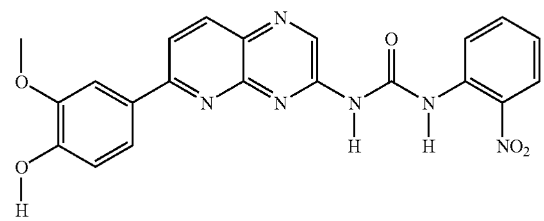 | 1-[6-(4-Hydroxy-3-methoxy-phenyl)-pyrido[2,3-b]pyrazin-3-yl]-3-(2-nitro-phenyl)-urea |
| 618 | 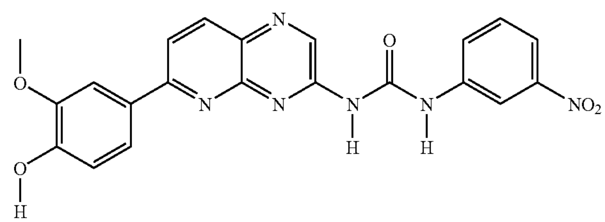 | 1-[6-(4-Hydroxy-3-methoxy-phenyl)-pyrido[2,3-b]pyrazin-3-yl]-3-(3-nitro-phenyl)-urea |
| 619 | 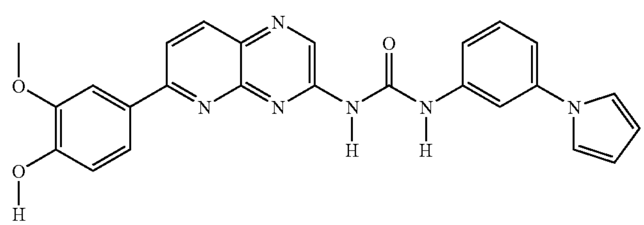 | 1-[6-(4-Hydroxy-3-methoxy-phenyl)-pyrido[2,3-b]pyrazin-3-yl]-3-(3-pyrrol-1-yl-phenyl)-urea |
| 620 | 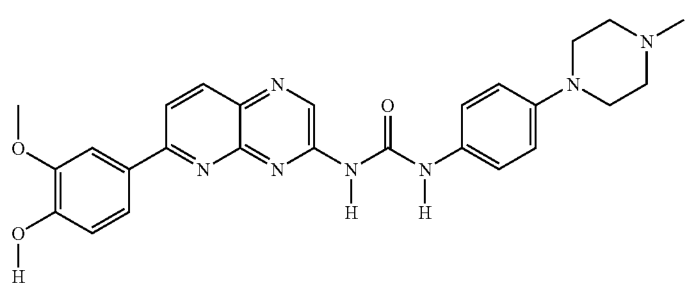 | 1-[6-(4-Hydroxy-3-methoxy-phenyl)-pyrido[2,3-b]pyrazin-3-yl]-3-[4-(4-methyl-piperazin-1-yl)-phenyl]-urea |
| 621 | 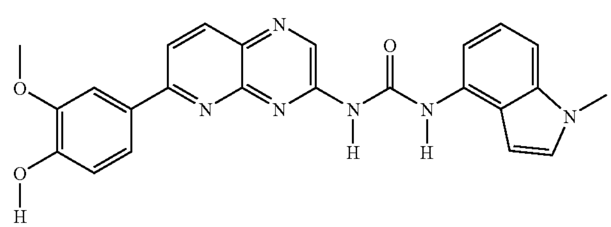 | 1-[6-(4-Hydroxy-3-methoxy-phenyl)-pyrido[2,3-b]pyrazin-3-yl]-3-(1-methyl-1H-indol-4-yl)-urea |
| 622 | 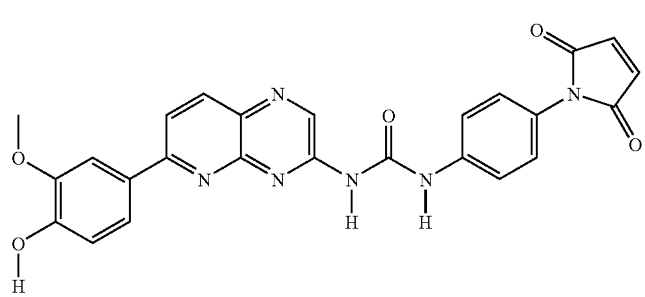 | 1-[4-(2,5-Dioxo-2,5-dihydro-pyrrol-1-yl)-phenyl]-3-[6-(4-hydroxy-3-methoxy-phenyl)-pyrido[2,3-b]pyrazin-3-yl]-urea |

| Compound | Structure | Name |
|---|---|---|
| 623 | 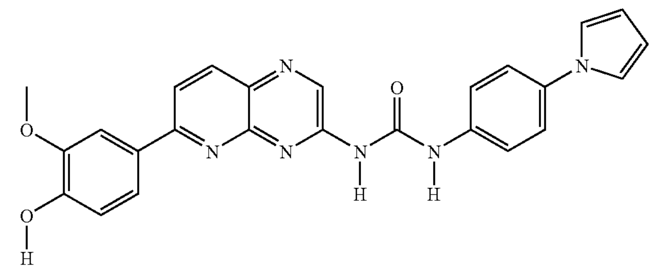 | 1-[6-(4-Hydroxy-3-methoxy-phenyl)-pyrido[2,3-b]pyrazin-3-yl]-3-(4-pyrrol-1-yl-phenyl)-urea |
| 624 | 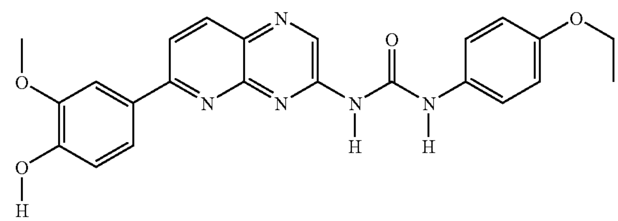 | 1-(4-Ethoxy-phenyl)-3-[6-(4-hydroxy-3-methoxy-phenyl)-pyrido[2,3-b]pyrazin-3-yl]-urea |
| 625 | 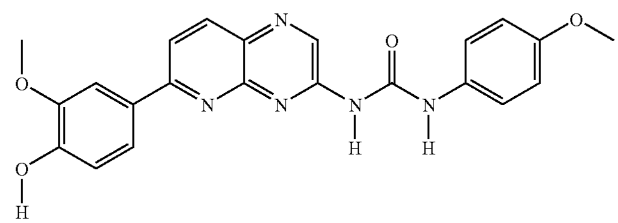 | 1-(4-Methoxy-phenyl)-3-[6-(4-hydroxy-3-methoxy-phenyl)-pyrido[2,3-b]pyrazin-3-yl]-urea |
| 626 | 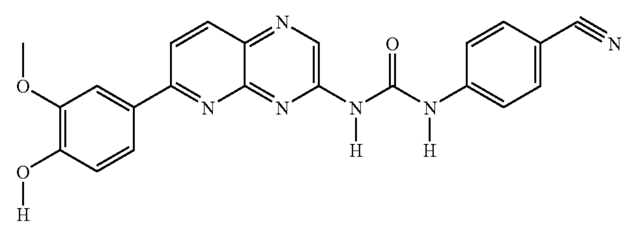 | 1-(4-Cyano-phenyl)-3-[6-(4-hydroxy-3-methoxy-phenyl)-pyrido[2,3-b]pyrazin-3-yl]-urea |
| 627 | 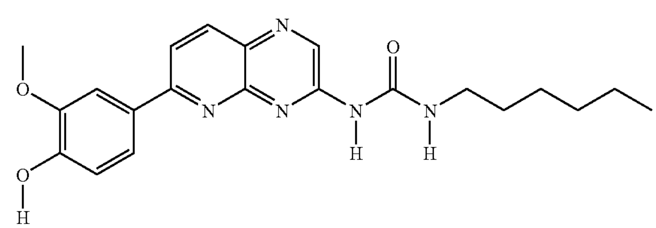 | 1-Hexyl-3-[6-(4-hydroxy-3-methoxy-phenyl)-pyrido[2,3-b]pyrazin-3-yl]-urea |
| 628 | 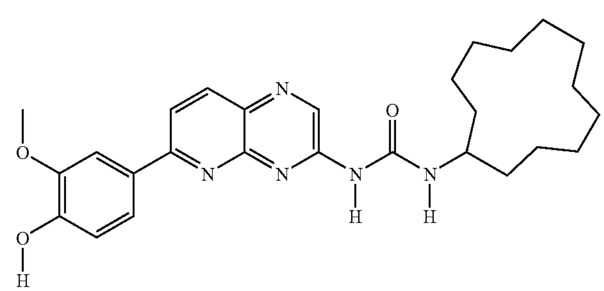 | 1-Cyclododecyl-3-[6-(4-hydroxy-3-methoxy-phenyl)-pyrido[2,3-b]pyrazin-3-yl]-urea |

| Compound | Structure | Name |
|---|---|---|
| 629 | 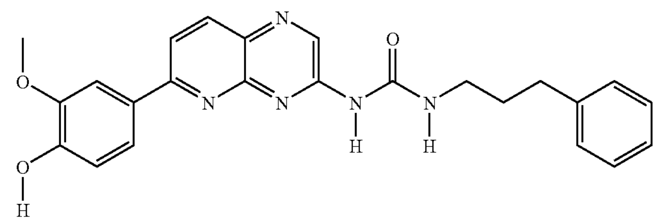 | 1-[6-(4-Hydroxy-3-methoxy-phenyl)-pyrido[2,3-b]pyrazin-3-yl]-3-(3-phenyl-propyl)-urea |
| 630 | 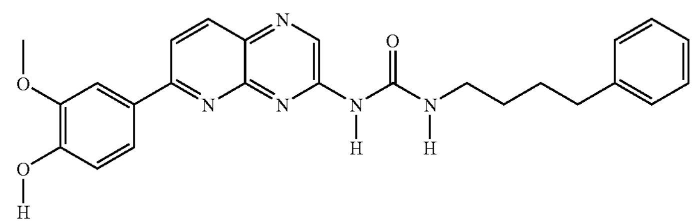 | 1-[6-(4-Hydroxy-3-methoxy-phenyl)-pyrido[2,3-b]pyrazin-3-yl]-3-(4-phenyl-butyl)-urea |
| 631 | 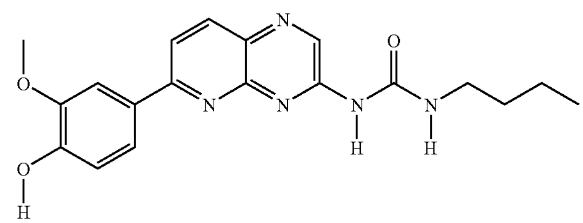 | 1-Butyl-3-[6-(4-hydroxy-3-methoxy-phenyl)-pyrido[2,3-b]pyrazin-3-yl]-urea |
| 632 | 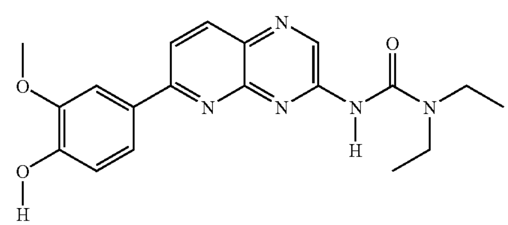 | 1,1-Diethyl-3-[6-(4-hydroxy-3-methoxy-phenyl)-pyrido[2,3-b]pyrazin-3-yl]-urea |
| 633 | 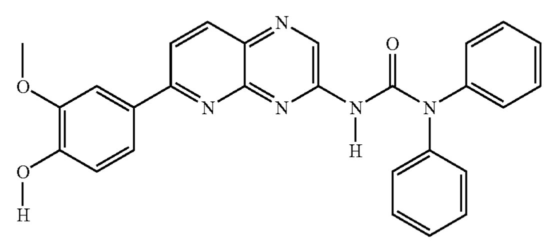 | 3-[6-(4-Hydroxy-3-methoxy-phenyl)-pyrido[2,3-b]pyrazin-3-yl]-1,1-diphenyl-urea |
| 634 | 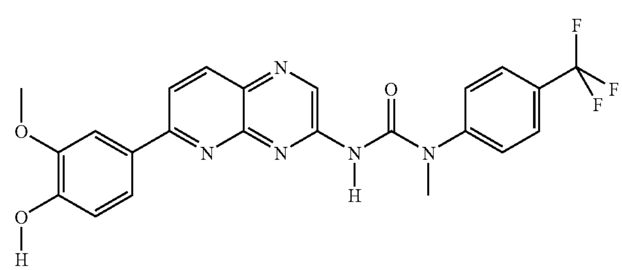 | 3-[6-(4-Hydroxy-3-methoxy-phenyl)-pyrido[2,3-b]pyrazin-3-yl]-1-methyl-1-(4-trifluoromethyl-phenyl)-urea |

| Compound | Structure | Name |
|---|---|---|
| 635 | 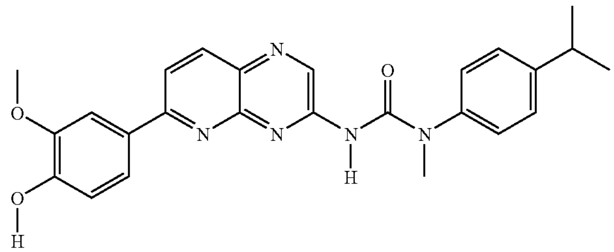 | 3-[6-(4-Hydroxy-3-methoxy-phenyl)-pyrido[2,3-b]pyrazin-3-yl]-1-(4-isopropyl-phenyl)-1-methyl-urea |
| 636 | 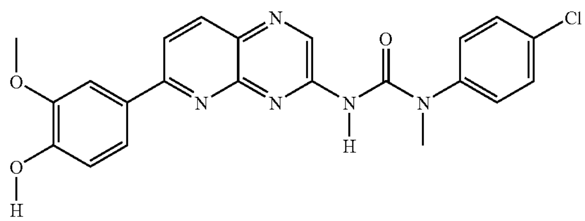 | 1-(4-Chloro-phenyl)-3-[6-(4-hydroxy-3-methoxy-phenyl)-pyrido[2,3-b]pyrazin-3-yl]-1-methyl-urea |
| 637 | 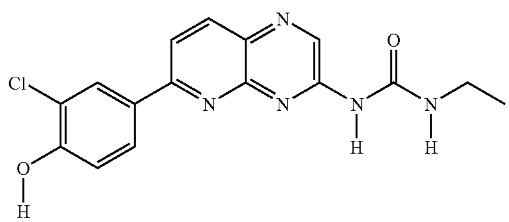 | 1-[6-(3-Chloro-4-hydroxy-phenyl)-pyrido[2,3-b]pyrazin-3-yl]-3-ethyl-urea |
| 638 | 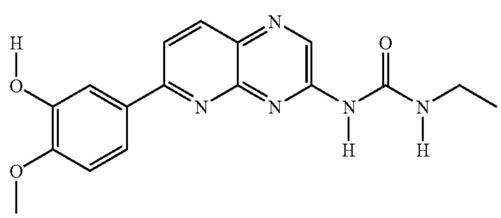 | 1-Ethyl-3-[6-(3-hydroxy-4-methoxy-phenyl)-pyrido[2,3-b]pyrazin-3-yl]-urea |
| 639 | 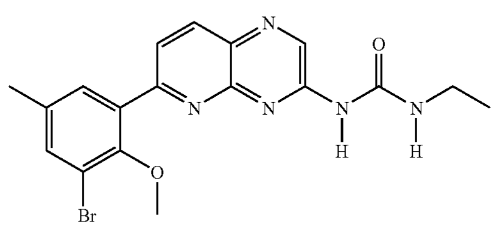 | 1-[6-(3-Bromo-2-methoxy-5-methyl-phenyl)-pyrido[2,3-b]pyrazin-3-yl]-3-ethyl-urea |
| 640 | 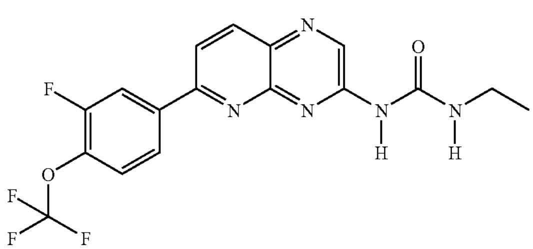 | 1-Ethyl-3-[6-(3-fluoro-4-trifluoromethoxy-phenyl)-pyrido[2,3-b]pyrazin-3-yl]-urea |

-continued

| Compound | Structure | Name |
|---|---|---|
| 641 | 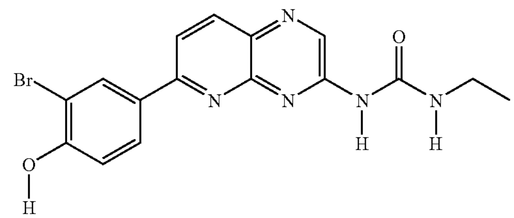 | 1-[6-(3-Bromo-4-hydroxy-phenyl)-pyrido[2,3-b]pyrazin-3-yl]-3-ethyl-urea |
| 642 | 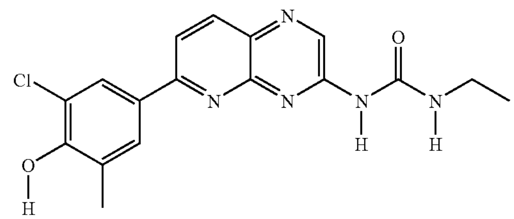 | 1-[6-(3-Chloro-4-hydroxy-5-methyl-phenyl)-pyrido[2,3-b]pyrazin-3-yl]-3-ethyl-urea |
| 643 | 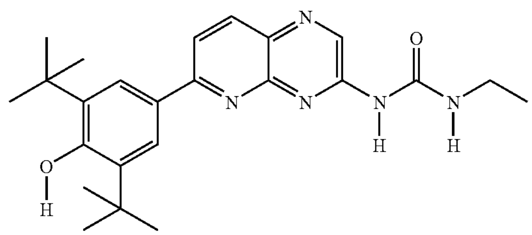 | 1-[6-(3,5-Di-tert-butyl-4-hydroxy-phenyl)-pyrido[2,3-b]pyrazin-3-yl]-3-ethyl-urea |
| 644 | 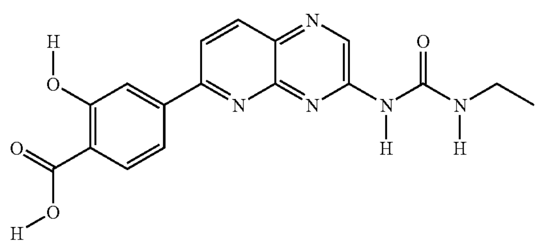 | 4-[3-(3-Ethyl-ureido)-pyrido[2,3-b]pyrazin-6-yl]-2-hydroxy-benzoic acid methyl ester |
| 645 | 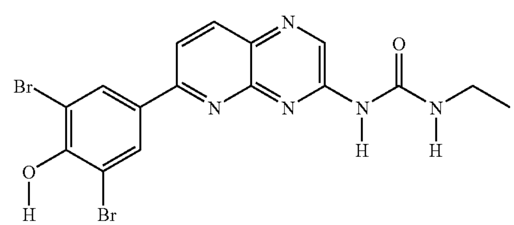 | 1-[6-(3,5-Di-bromo-4-hydroxy-phenyl)-pyrido[2,3-b]pyrazin-3-yl]-3-ethyl-urea |
| 646 | 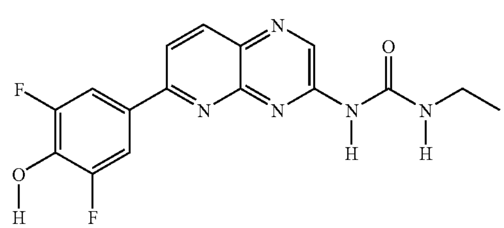 | 1-[6-(3,5-Di-fluoro-4-hydroxy-phenyl)-pyrido[2,3-b]pyrazin-3-yl]-3-ethyl-urea |
| 647 | 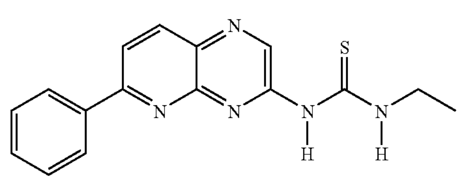 | 1-Ethyl-3-(6-phenyl-pyrido[2,3-b]pyrazin-3-yl)-thiourea |

| Compound | Structure | Name |
|---|---|---|
| 648 | 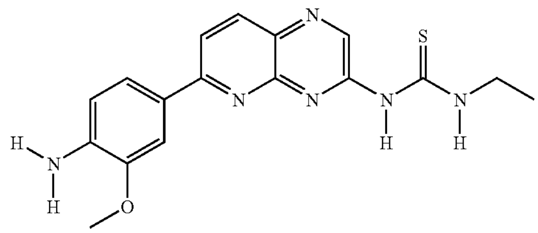 | 1-[6-(4-Amino-3-methoxy-phenyl)-pyrido[2,3-b]pyrazin-3-yl]-3-ethyl-thiourea |
| 649 | 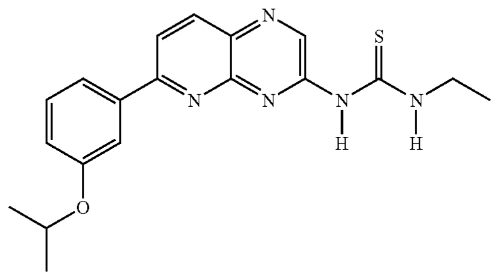 | 1-Ethyl-3-[6-(3-isopropoxy-phenyl)-pyrido[2,3-b]pyrazin-3-yl]-thiourea |
| 650 | 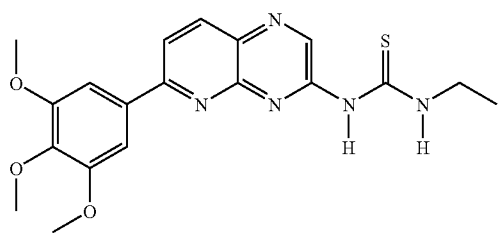 | 1-Ethyl-3-[6-(3,4,5-trimethoxy-phenyl)-pyrido[2,3-b]pyrazin-3-yl]-thiourea |
| 651 | 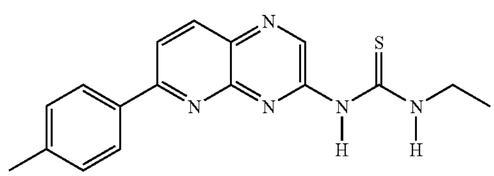 | 1-Ethyl-3-(6-p-tolyl-pyrido[2,3-b]pyrazin-3-yl)-thiourea |
| 652 | 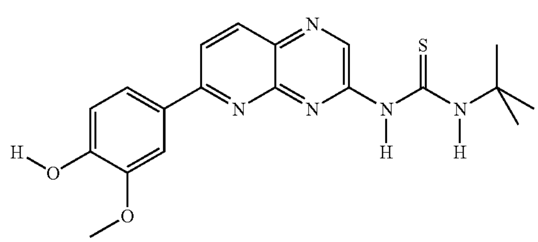 | 1-tert-Butyl-3-[6-(4-hydroxy-3-methoxy-phenyl)-pyrido[2,3-b]pyrazin-3-yl]-thiourea |
| 653 | 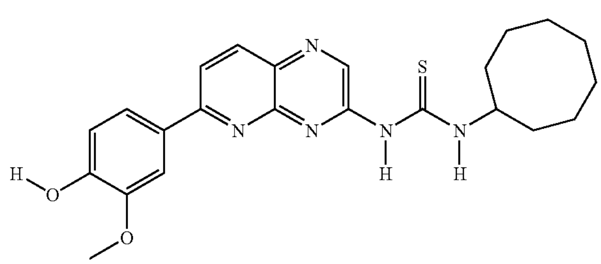 | 1-Cyclooctyl-3-[6-(4-hydroxy-3-methoxy-phenyl)-pyrido[2,3-b]pyrazin-3-yl]-thiourea |

-continued

| Compound | Structure | Name |
|---|---|---|
| 654 | 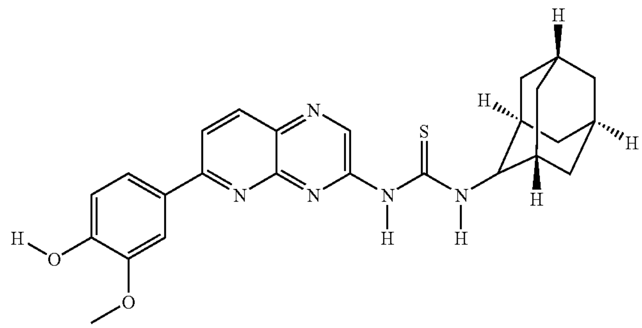 | 1-Adamantan-1-yl-3-[6-(4-hydroxy-3-methoxy-phenyl)-pyrido[2,3-b]pyrazin-3-yl]-thiourea |
| 655 | 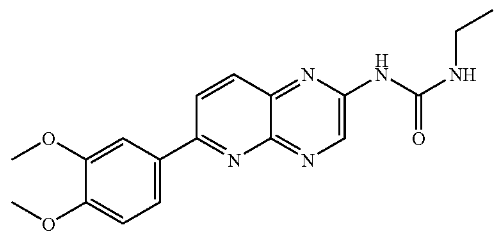 | 1-[6-(3,4-Dimethoxy-phenyl)-pyrido[2,3-b]pyrazin-2-yl]-3-ethyl-urea |
| 656 | 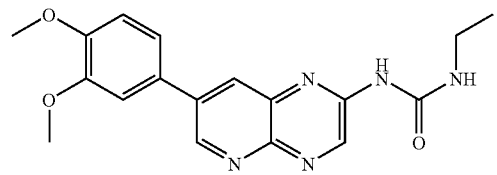 | 1-[7-(3,4-Dimethoxy-phenyl)-pyrido[2,3-b]pyrazin-2-yl]-3-ethyl-urea |
| 657 | 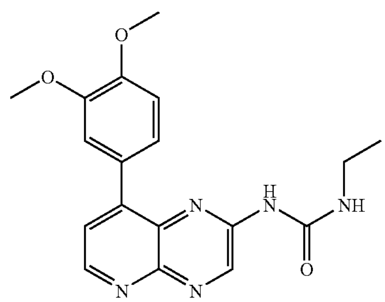 | 1-[8-(3,4-Dimethoxy-phenyl)-pyrido[2,3-b]pyrazin-2-yl]-3-ethyl-urea |
| 658 | 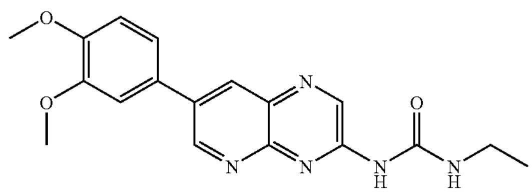 | 1-Ethyl-3-[7-(3,4-Dimethoxy-phenyl)-pyrido[2,3-b]pyrazin-3-yl]-urea |
| 659 | 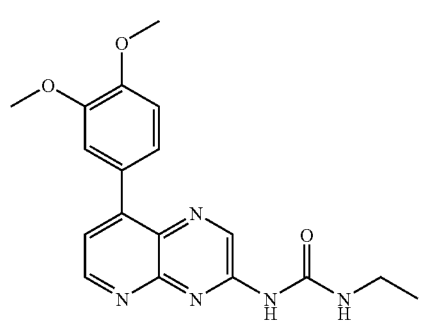 | 1-Ethyl-3-[8-(3,4-Dimethoxy-phenyl)-pyrido[2,3-b]pyrazin-3-yl]-urea |

| Compound | Structure | Name |
|---|---|---|
| 660 | 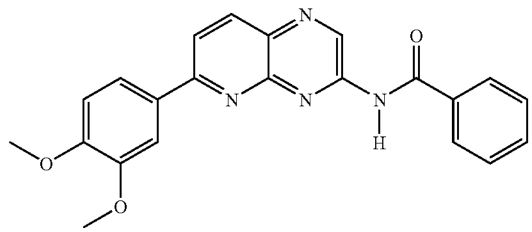 | N-[6-(3,4-Dimethoxy-phenyl)-pyrido[2,3-b]pyrazin-3-yl]-benzamide |
| 661 | 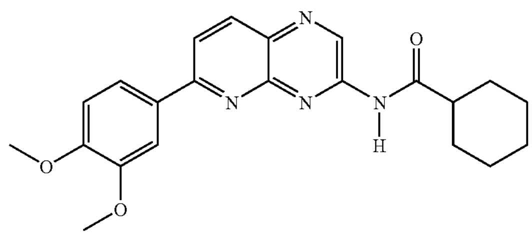 | Cyclohexanecarbox-ylic acid [6-(3,4-dimethoxy-phenyl)-pyrido[2,3-b]pyrazin-3-yl]-amide |
| 662 | 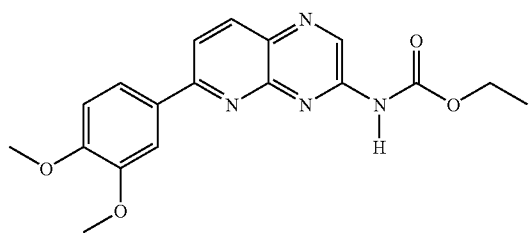 | [6-(3,4-Dimethoxy-phenyl)-pyrido[2,3-b]pyrazin-3-yl]-carbamic acid ethyl ester |
| 663 | 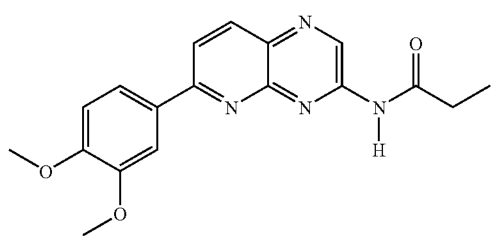 | N-[6-(3,4-Dimethoxy-phenyl)-pyrido[2,3-b]pyrazin-3-yl]-propionamide |
| 664 | 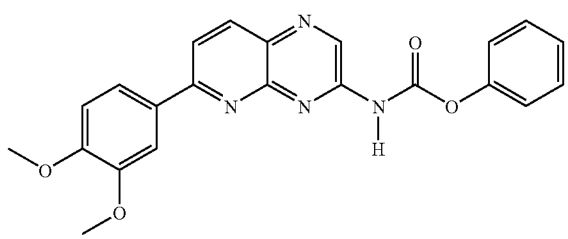 | [6-(3,4-Dimethoxy-phenyl)-pyrido[2,3-b]pyrazin-3-yl]-carbamic acid phenyl ester |
| 665 | 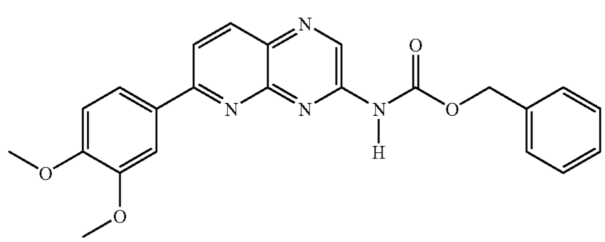 | [6-(3,4-Dimethoxy-phenyl)-pyrido[2,3-b]pyrazin-3-yl]-carbamic acid benzyl ester |

| Compound | Structure | Name |
|---|---|---|
| 666 | 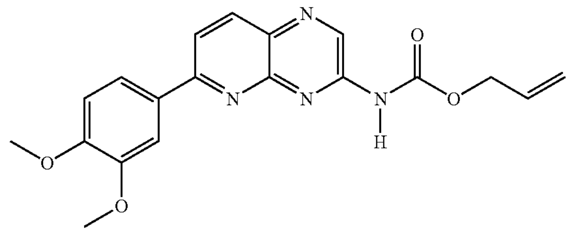 | [6-(3,4-Dimethoxy-phenyl)-pyrido[2,3-b]pyrazin-3-yl]-carbamic acid allyl ester |
| 667 | 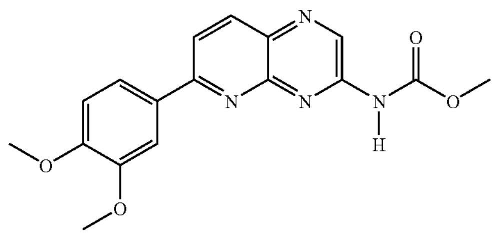 | [6-(3,4-Dimethoxy-phenyl)-pyrido[2,3-b]pyrazin-3-yl]-carbamic acid methyl ester |
| 668 | 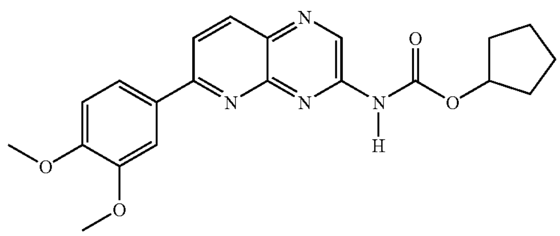 | [6-(3,4-Dimethoxy-phenyl)-pyrido[2,3-b]pyrazin-3-yl]-carbamic acid cyclopentyl ester |
| 669 | 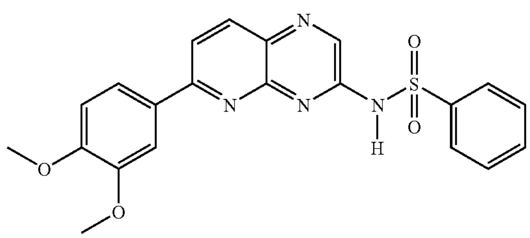 | N-[6-(3,4-Dimethoxy-phenyl)-pyrido[2,3-b]pyrazin-3-yl]-benzenesulfonamide |
| 670 | 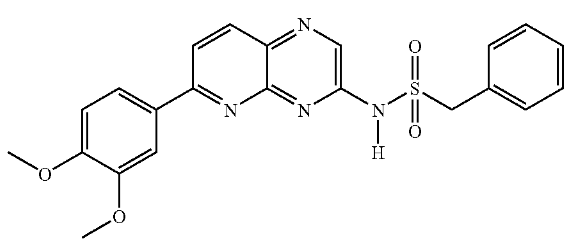 | N-[6-(3,4-Dimethoxy-phenyl)-pyrido[2,3-b]pyrazin-3-yl]-C-phenyl-methanesulfonamide |
| 671 | 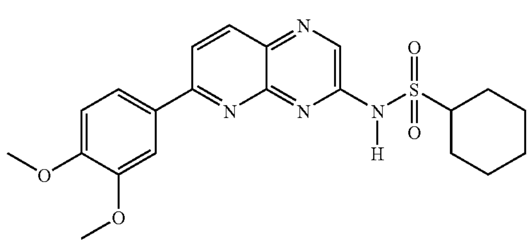 | Cyclohexanesulfonic acid [6-(3,4-dimethoxy-phenyl)-pyrido[2,3-b]pyrazin-3-yl]-amide |

| Compound | Structure | Name |
|---|---|---|
| 672 | 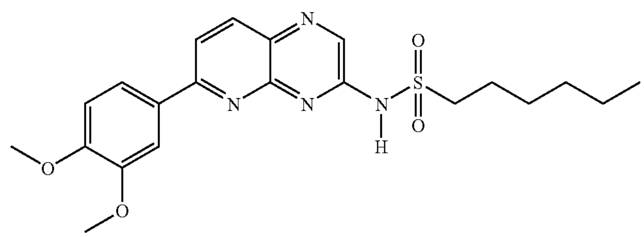 | Hexane-1-sulfonic acid [6-(3,4-dimethoxy-phenyl)-pyrido[2,3-b]pyrazin-3-yl]-amide |
| 673 | 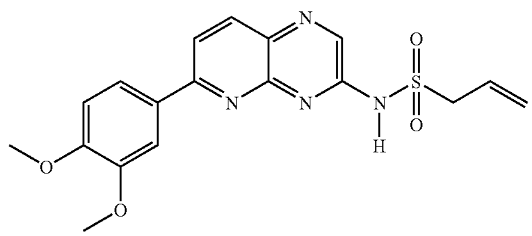 | Prop-2-ene-1-sulfonic acid [6-(3,4-dimethoxy-phenyl)-pyrido[2,3-b]pyrazin-3-yl]-amide |
| 674 | 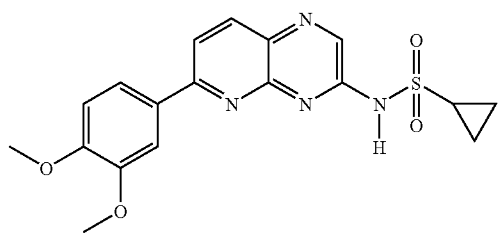 | Cyclopropanesulfonic acid [6-(3,4-dimethoxy-phenyl)-pyrido[2,3-b]pyrazin-3-yl]-amide |
| 675 | 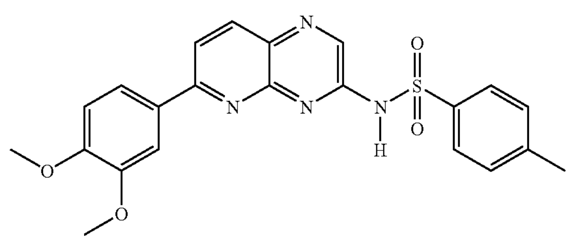 | N-[6-(3,4-Dimethoxy-phenyl)-pyrido[2,3-b]pyrazin-3-yl]-4-methyl-benzenesulfonamide |
| 676 | 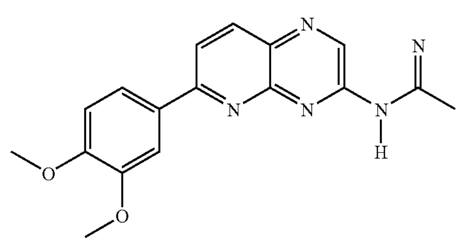 | N-[6-(3,4-Dimethoxy-phenyl)-pyrido[2,3-b]pyrazin-3-yl]-acetamidine |
| 677 | 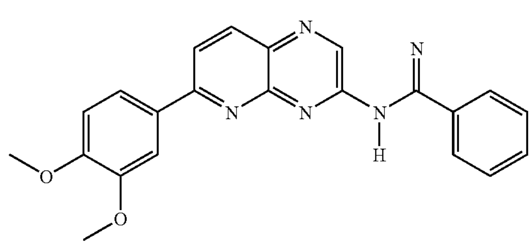 | N-[6-(3,4-Dimethoxy-phenyl)-pyrido[2,3-b]pyrazin-3-yl]-benzamidine |

| Compound | Structure | Name |
|---|---|---|
| 678 | 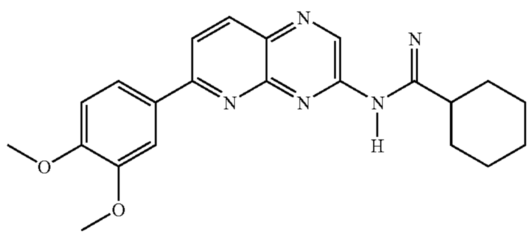 | N-[6-(3,4-Dimethoxy-phenyl)-pyrido[2,3-b]pyrazin-3-yl]-cyclohexanecarboxamidine |
| 679 | 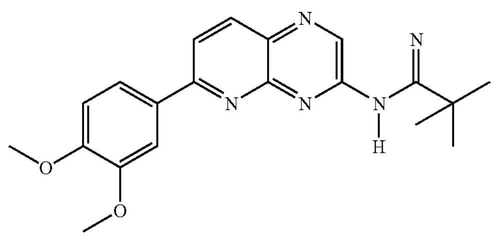 | N-[6-(3,4-Dimethoxy-phenyl)-pyrido[2,3-b]pyrazin-3-yl]-2,2-dimethyl-propionamidine |
| 680 | 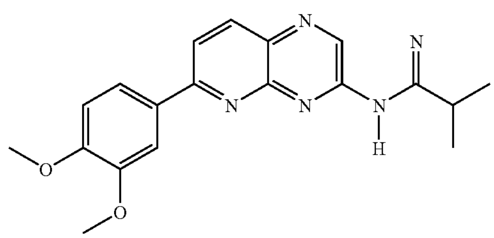 | N-[6-(3,4-Dimethoxy-phenyl)-pyrido[2,3-b]pyrazin-3-yl]-isobutyramidine |
| 681 | 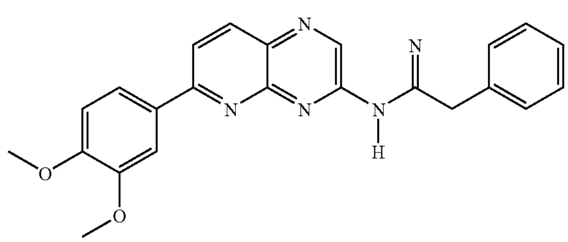 | N-[6-(3,4-Dimethoxy-phenyl)-pyrido[2,3-b]pyrazin-3-yl]-2-phenyl-acetamidine |
| 682 | 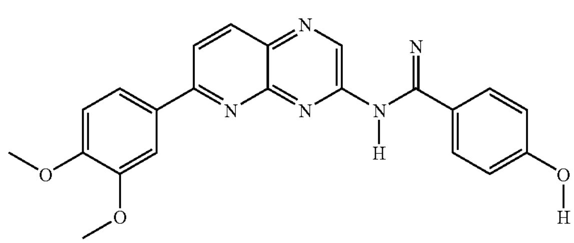 | N-[6-(3,4-Dimethoxy-phenyl)-pyrido[2,3-b]pyrazin-3-yl]-4-hydroxy-benzamidine |
| 683 | 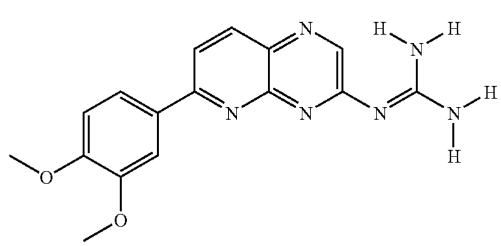 | N-[6-(3,4-Dimethoxy-phenyl)-pyrido[2,3-b]pyrazin-3-yl]-guanidine |

| Compound | Structure | Name |
|---|---|---|
| 684 | 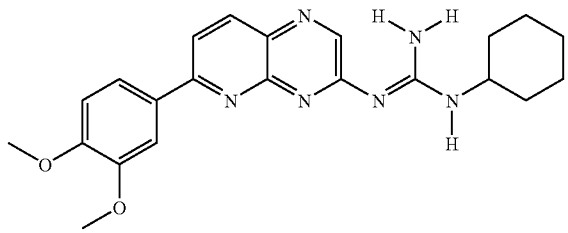 | N-Cyclohexyl-N'-[6-(3,4-dimethoxy-phenyl)-pyrido[2,3-b]pyrazin-3-yl]-guanidine |
| 685 | 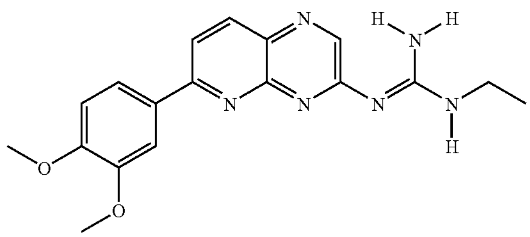 | N-[6-(3,4-Dimethoxy-phenyl)-pyrido[2,3-b]pyrazin-3-yl]-N'-ethyl-guanidine |
| 686 | 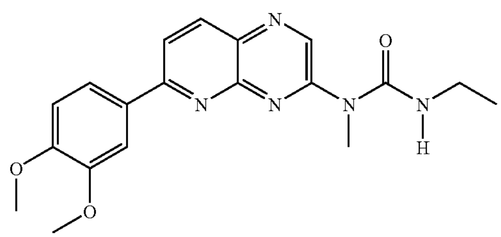 | 1-[6-(3,4-Dimethoxy-phenyl)-pyrido[2,3-b]pyrazin-3-yl]-3-ethyl-1-methyl-urea |
| 687 | 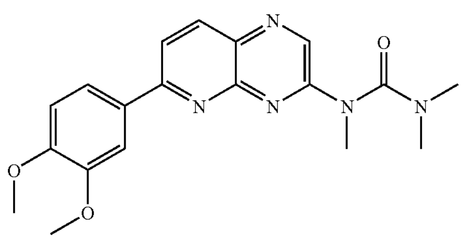 | 1-[6-(3,4-Dimethoxy-phenyl)-pyrido[2,3-b]pyrazin-3-yl]-1,3,3-trimethyl-urea |
| 688 | 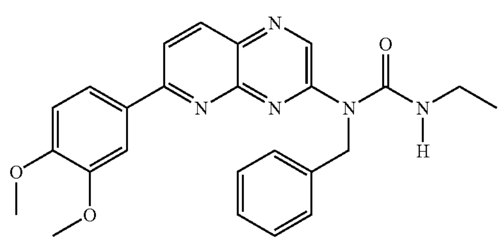 | 1-Benzyl-1-[6-(3,4-dimethoxy-phenyl)-pyrido[2,3-b]pyrazin-3-yl]-3-ethyl-urea |
| 689 | 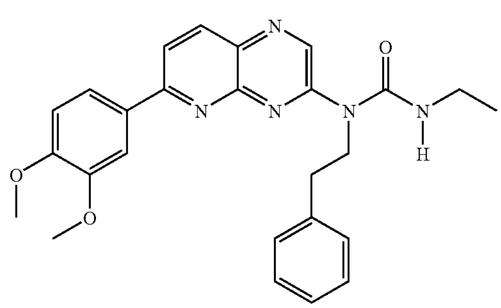 | 1-[6-(3,4-Dimethoxy-phenyl)-pyrido[2,3-b]pyrazin-3-yl]-3-ethyl-1-phenethyl-urea |

| Compound | Structure | Name |
|---|---|---|
| 690 | 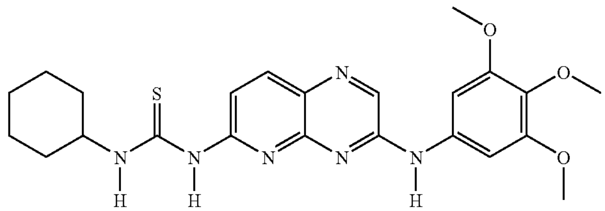 | 1-Cyclohexyl-3-[3-(3,4,5-trimethoxy-phenylamino)-pyrido[2,3-b]pyrazin-6-yl]-thiourea |
| 691 | 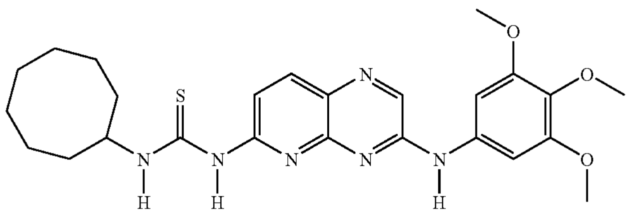 | 1-Cyclooctyl-3-[3-(3,4,5-trimethoxy-phenylamino)-pyrido[2,3-b]pyrazin-6-yl]-thiourea |
| 692 | 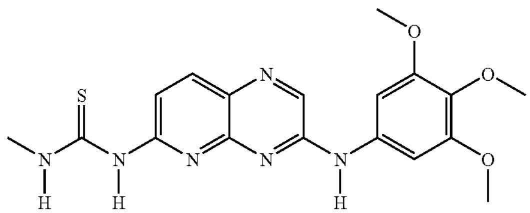 | 1-Methyl-3-[3-(3,4,5-trimethoxy-phenylamino)-pyrido[2,3-b]pyrazin-6-yl]-thiourea |
| 693 | 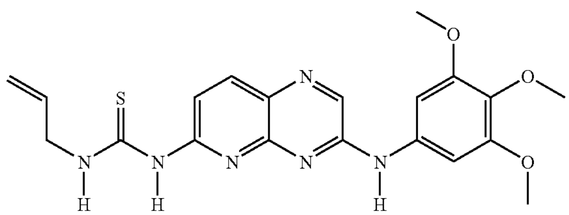 | 1-Allyl-3-[3-(3,4,5-trimethoxy-phenylamino)-pyrido[2,3-b]pyrazin-6-yl]-thiourea |
| 694 | 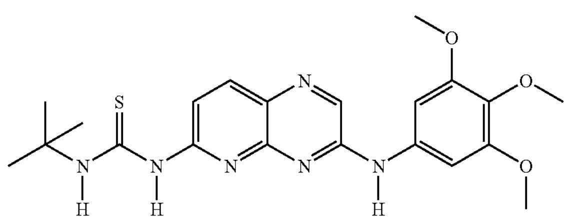 | 1-tert-Butyl-3-[3-(3,4,5-trimethoxy-phenylamino)-pyrido[2,3-b]pyrazin-6-yl]-thiourea |
| 695 | 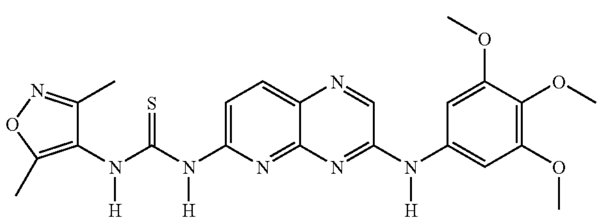 | 1-(3,5-Dimethyl-isoxazol-4-yl)-3-[3-(3,4,5-trimethoxy-phenylamino)-pyrido[2,3-b]pyrazin-6-yl]-thiourea |
| 696 | 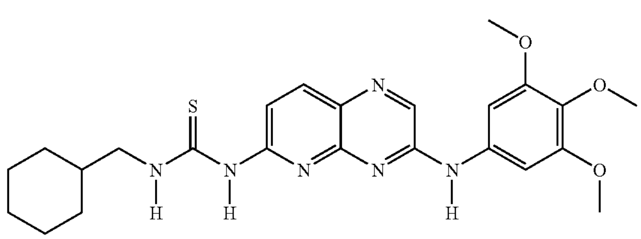 | 1-Cyclohexylmethyl-3-[3-(3,4,5-trimethoxy-phenylamino)-pyrido[2,3-b]pyrazin-6-yl]-thiourea |

-continued

| Compound | Structure | Name |
|---|---|---|
| 697 | 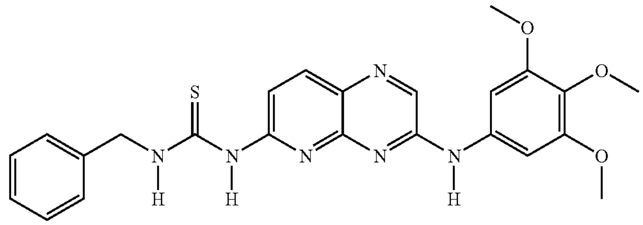 | 1-Benzyl-3-[3-(3,4,5-trimethoxy-phenylamino)-pyrido[2,3-b]pyrazin-6-yl]-thiourea |
| 698 | 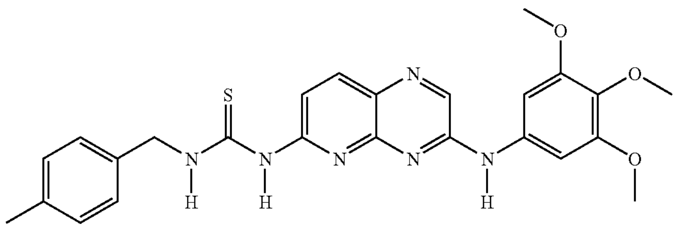 | 1-(4-Methyl-benzyl)-3-[3-(3,4,5-trimethoxy-phenylamino)-pyrido[2,3-b]pyrazin-6-yl]-thiourea |
| 699 | 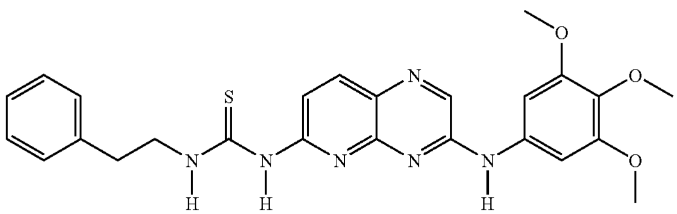 | 1-Phenethyl-3-[3-(3,4,5-trimethoxy-phenylamino)-pyrido[2,3-b]pyrazin-6-yl]-thiourea |
| 700 | 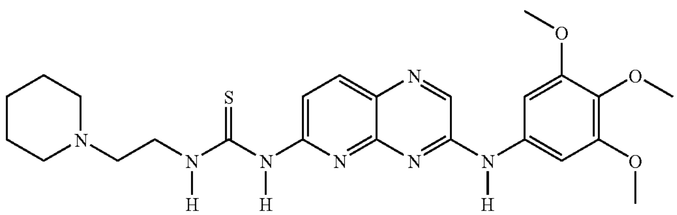 | 1-(2-Piperidin-1-yl-ethyl)-3-[3-(3,4,5-trimethoxy-phenylamino)-pyrido[2,3-b]pyrazin-6-yl]-thiourea |
| 701 | 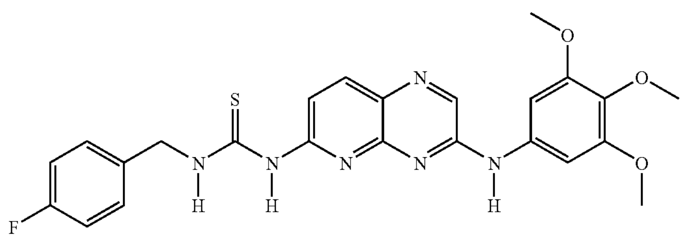 | 1-(4-Fluoro-benzyl)-3-[3-(3,4,5-trimethoxy-phenylamino)-pyrido[2,3-b]pyrazin-6-yl]-thiourea |
| 702 | 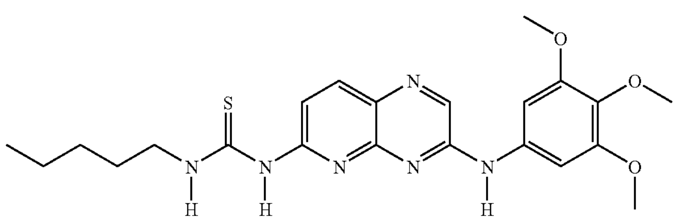 | 1-Pentyl-3-[3-(3,4,5-trimethoxy-phenylamino)-pyrido[2,3-b]pyrazin-6-yl]-thiourea |
| 703 | 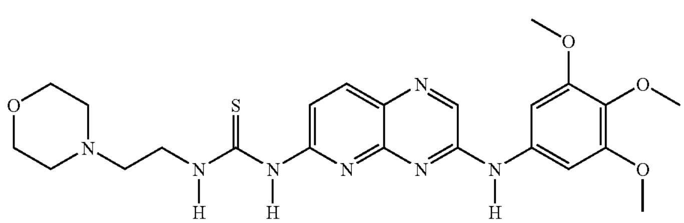 | 1-(2-Morpholin-4-yl-ethyl)-3-[3-(3,4,5-trimethoxy-phenylamino)-pyrido[2,3-b]pyrazin-6-yl]-thiourea |

-continued

| Compound | Structure | Name |
|---|---|---|
| 704 | 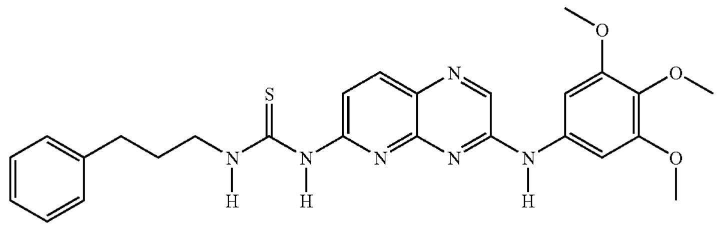 | 1-(3-Phenyl-propyl)-3-[3-(3,4,5-trimethoxy-phenylamino)-pyrido[2,3-b]pyrazin-6-yl]-thiourea |
| 705 | 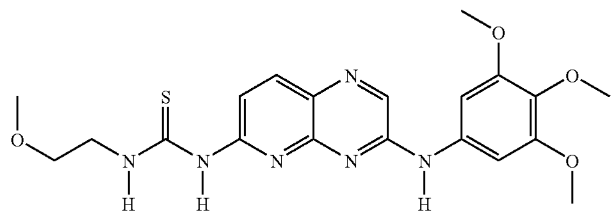 | 1-(2-Methoxy-ethyl)-3-[3-(3,4,5-trimethoxy-phenylamino)-pyrido[2,3-b]pyrazin-6-yl]-thiourea |
| 706 | 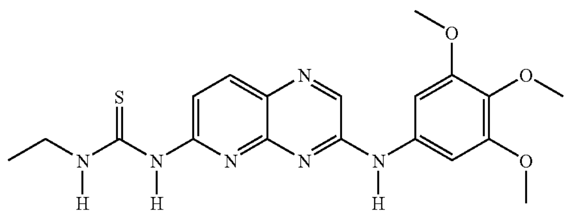 | 1-Ethyl-3-{3-[methyl-(3,4,5-trimethoxy-phenyl)-amino]-pyrido[2,3-b]pyrazin-6-yl}-thiourea |
| 707 | 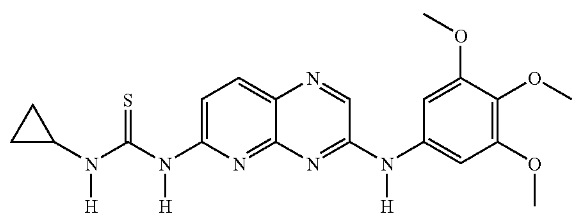 | 1-Cyclopropyl-3-[3-(3,4,5-trimethoxy-phenylamino)-pyrido[2,3-b]pyrazin-6-yl]-thiourea |
| 708 | 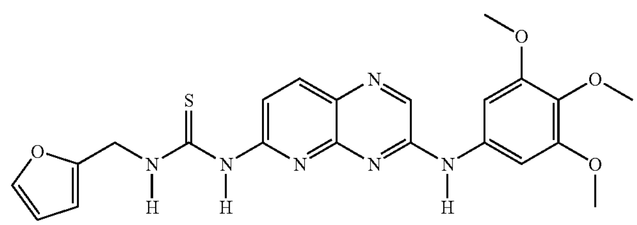 | 1-Furan-2-ylmethyl-3-[3-(3,4,5-trimethoxy-phenylamino)-pyrido[2,3-b]pyrazin-6-yl]-thiourea |
| 709 | 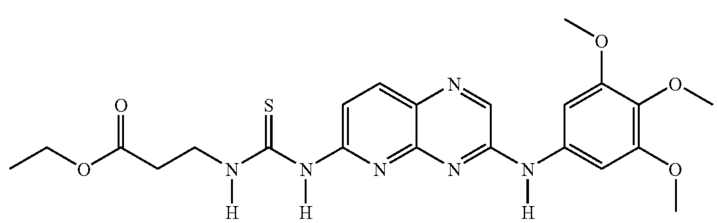 | 3-{3-[3-(3,4,5-Trimethoxy-phenylamino)-pyrido[2,3-b]pyrazin-6-yl]-thioureido}-propionic acid ethyl ester |
| 710 | 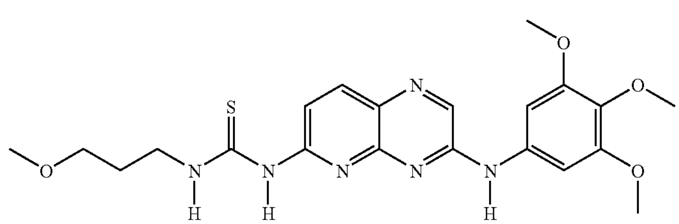 | 1-(3-Methoxy-propyl)-3-[3-(3,4,5-trimethoxy-phenylamino)-pyrido[2,3-b]pyrazin-6-yl]-thiourea |

-continued

| Compound | Structure | Name |
|---|---|---|
| 711 | 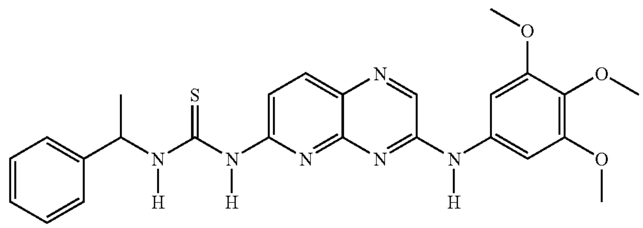 | 1-(1-Phenyl-ethyl)-3-[3-(3,4,5-trimethoxy-phenylamino)-pyrido[2,3-b]pyrazin-6-yl]-thiourea |
| 712 | 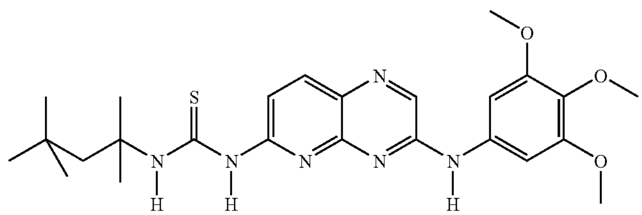 | 1-(1,1,3,3-Tetramethyl-butyl)-3-[3-(3,4,5-trimethoxy-phenylamino)-pyrido[2,3-b]pyrazin-6-yl]-thiourea |
| 713 | 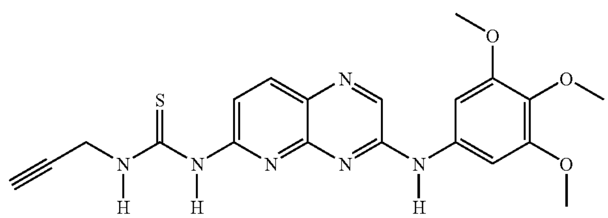 | 1-Prop-2-ynyl-3-[3-(3,4,5-trimethoxy-phenylamino)-pyrido[2,3-b]pyrazin-6-yl]-thiourea |
| 714 | 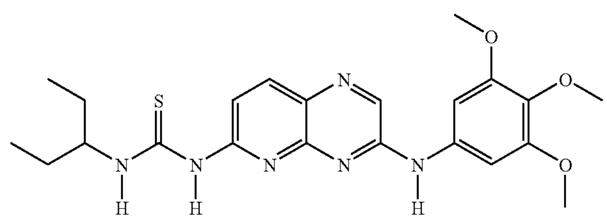 | 1-(1-Ethyl-propyl)-3-[3-(3,4,5-trimethoxy-phenylamino)-pyrido[2,3-b]pyrazin-6-yl]-thiourea |
| 715 | 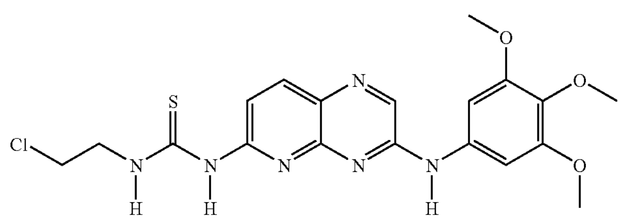 | 1-(2-Chloro-ethyl)-3-[3-(3,4,5-trimethoxy-phenylamino)-pyrido[2,3-b]pyrazin-6-yl]-thiourea |
| 716 | 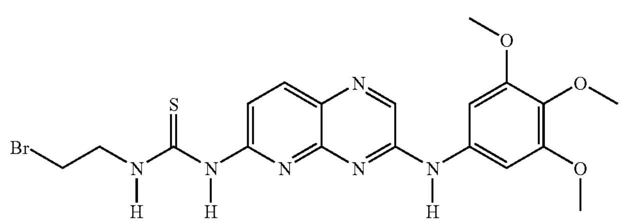 | 1-(2-Bromo-ethyl)-3-[3-(3,4,5-trimethoxy-phenylamino)-pyrido[2,3-b]pyrazin-6-yl]-thiourea |
| 717 | 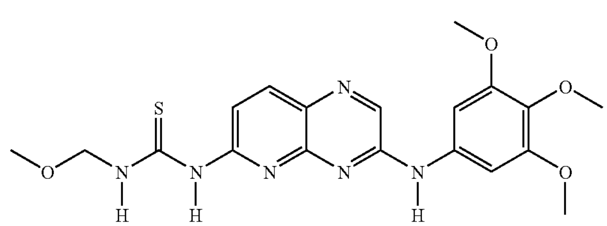 | 1-Methoxymethyl-3-[3-(3,4,5-trimethoxy-phenylamino)-pyrido[2,3-b]pyrazin-6-yl]-thiourea |

| Compound | Structure | Name |
| --- | --- | --- |
| 718 | 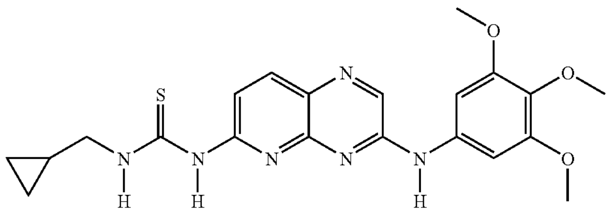 | 1-Cyclopropylmethyl-3-[3-(3,4,5-trimethoxy-phenylamino)-pyrido[2,3-b]pyrazin-6-yl]-thiourea |
| 719 | 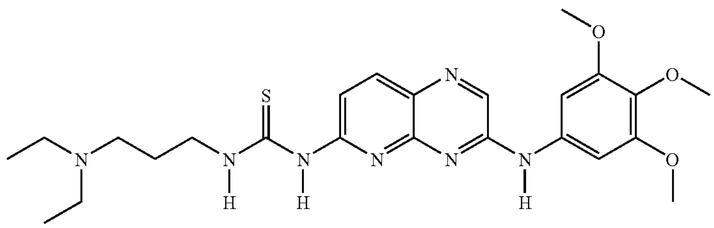 | 1-(3-Diethylamino-propyl)-3-[3-(3,4,5-trimethoxy-phenylamino)-pyrido[2,3-b]pyrazin-6-yl]-thiourea |
| 720 | 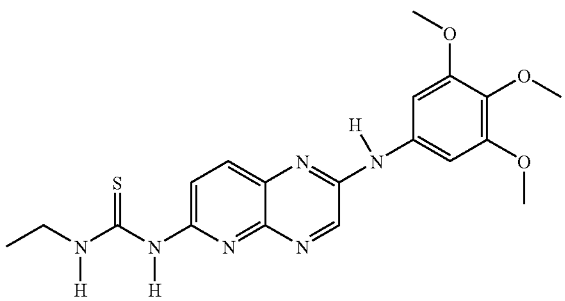 | 1-Ethyl-3-[2-(3,4,5-trimethoxy-phenylamino)-pyrido[2,3-b]pyrazin-6-yl]-thiourea |
| 721 | 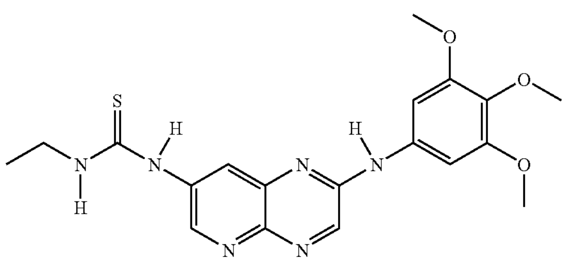 | 1-Ethyl-3-[2-(3,4,5-trimethoxy-phenylamino)-pyrido[2,3-b]pyrazin-7-yl]-thiourea |
| 722 | 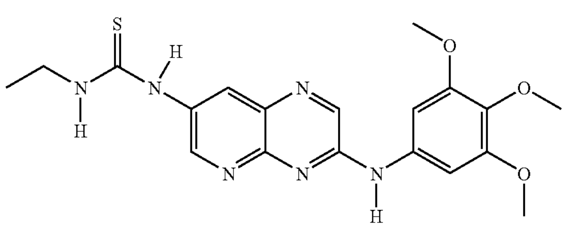 | 1-Ethyl-3-[3-(3,4,5-trimethoxy-phenylamino)-pyrido[2,3-b]pyrazin-7-yl]-thiourea |
| 723 | 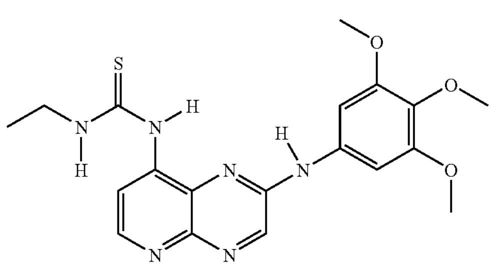 | 1-Ethyl-3-[2-(3,4,5-trimethoxy-phenylamino)-pyrido[2,3-b]pyrazin-8-yl]-thiourea |

| Compound | Structure | Name |
|---|---|---|
| 724 | 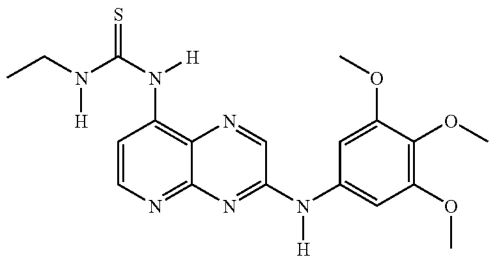 | 1-Ethyl-3-[3-(3,4,5-trimethoxy-phenylamino)-pyrido[2,3-b]pyrazin-8-yl]-thiourea |
| 725 | 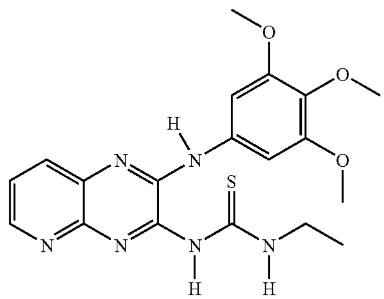 | 1-Ethyl-3-[2-(3,4,5-trimethoxy-phenylamino)-pyrido[2,3-b]pyrazin-3-yl]-thiourea |
| 726 | 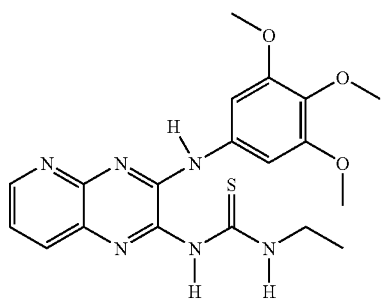 | 1-Ethyl-3-[3-(3,4,5-trimethoxy-phenylamino)-pyrido[2,3-b]pyrazin-2-yl]-thiourea |
| 727 | 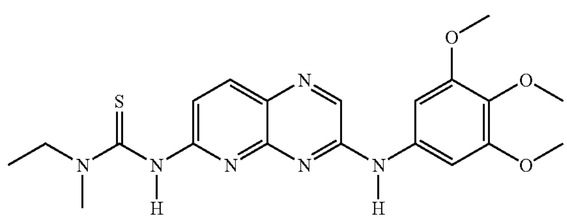 | 1-Ethyl-1-methyl-3-[3-(3,4,5-trimethoxy-phenylamino)-pyrido[2,3-b]pyrazin-6-yl]-thiourea |
| 728 | 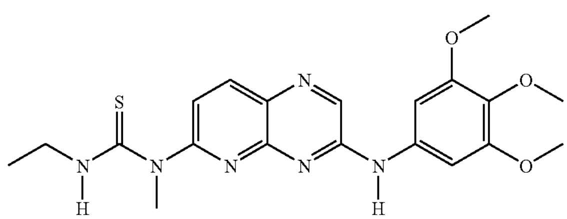 | 3-Ethyl-1-methyl-1-[3-(3,4,5-trimethoxy-phenylamino)-pyrido[2,3-b]pyrazin-6-yl]-thiourea |
| 729 | 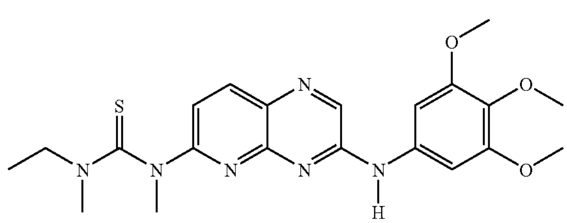 | 1-Ethyl-1,3-dimethyl-3-[3-(3,4,5-trimethoxy-phenylamino)-pyrido[2,3-b]pyrazin-6-yl]-thiourea |

-continued

| Compound | Structure | Name |
|---|---|---|
| 730 | 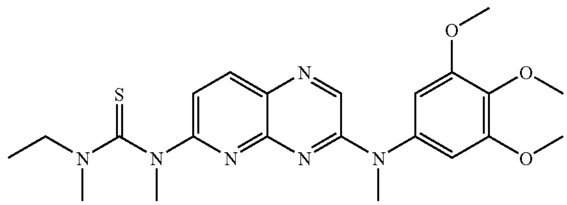 | 1-Ethyl-1,3-dimethyl-3-{3-[methyl-(3,4,5-trimethoxy-phenyl)-amino]-pyrido[2,3-b]pyrazin-6-yl}-thiourea |
| 731 | 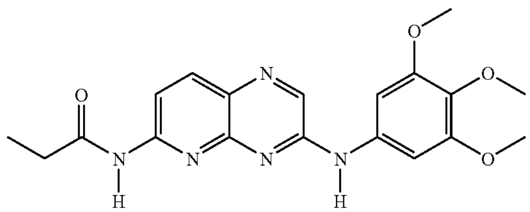 | N-[3-(3,4,5-Trimethoxy-phenylamino)-pyrido[2,3-b]pyrazin-6-yl]-propionamide |
| 732 | 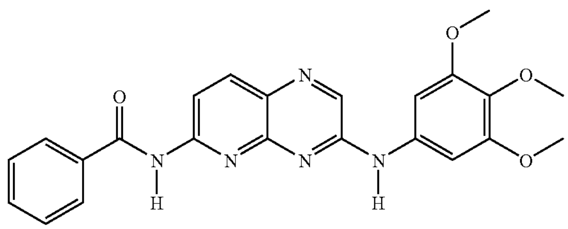 | N-[3-(3,4,5-Trimethoxy-phenylamino)-pyrido[2,3-b]pyrazin-6-yl]-benzamide |
| 733 | 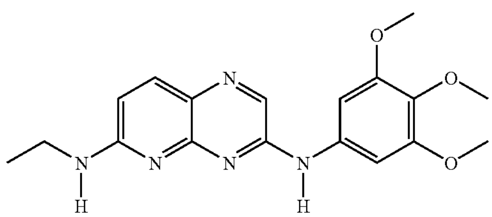 | N*6*-Ethyl-N*3*-(3,4,5-trimethoxy-phenyl)-pyrido[2,3-b]pyrazine-3,6-diamine |
| 734 | 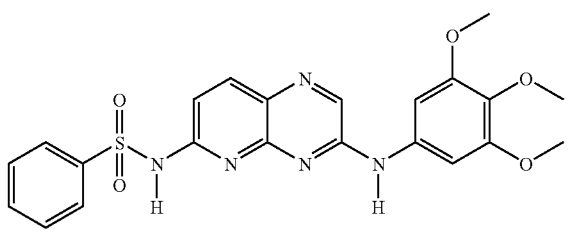 | N-[3-(3,4,5-Trimethoxy-phenylamino)-pyrido[2,3-b]pyrazin-6-yl]-benzenesulfonamide |
| 735 | 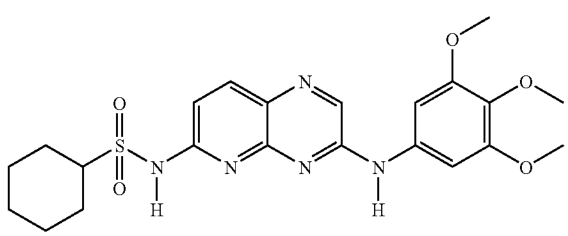 | Cyclohexanesulfonic acid [3-(3,4,5-trimethoxy-phenylamino)-pyrido[2,3-b]pyrazin-6-yl]-amide |
| 736 | 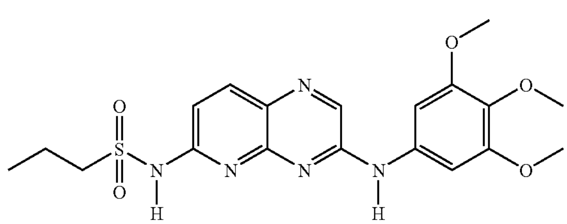 | Propane-1-sulfonic acid [3-(3,4,5-trimethoxy-phenylamino)-pyrido[2,3-b]pyrazin-6-yl]-amide |

| Compound | Structure | Name |
|---|---|---|
| 737 | 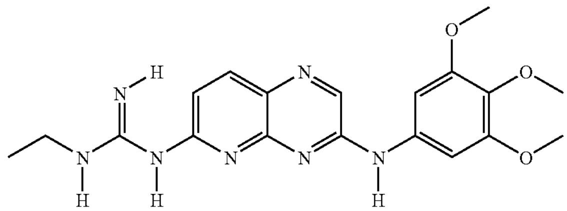 | N-Ethyl-N'-[3-(3,4,5-trimethoxy-phenylamino)-pyrido[2,3-b]pyrazin-6-yl]-guanidine |
| 738 | 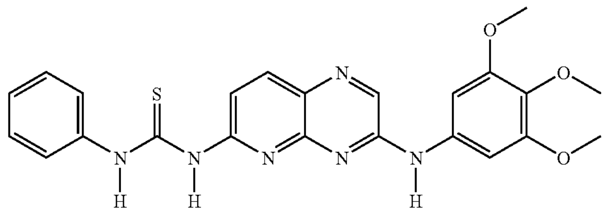 | 1-Phenyl-3-[3-(3,4,5-trimethoxy-phenylamino)-pyrido[2,3-b]pyrazin-6-yl]-thiourea |
| 739 | 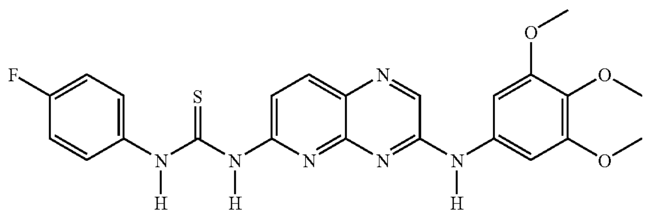 | 1-(4-Fluoro-phenyl)-3-[3-(3,4,5-trimethoxy-phenylamino)-pyrido[2,3-b]pyrazin-6-yl]-thiourea |
| 740 | 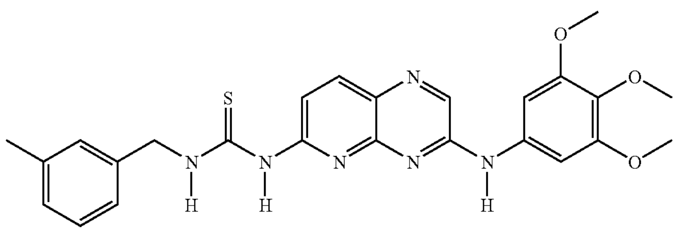 | 1-(3-Methyl-benzyl)-3-[3-(3,4,5-trimethoxy-phenylamino)-pyrido[2,3-b]pyrazin-6-yl]-thiourea |
| 741 | 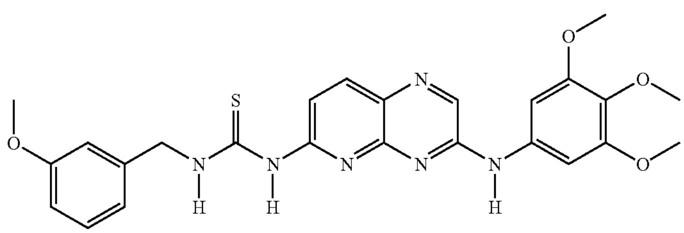 | 1-(3-Methoxy-benzyl)-3-[3-(3,4,5-trimethoxy-phenylamino)-pyrido[2,3-b]pyrazin-6-yl]-thiourea |
| 742 | 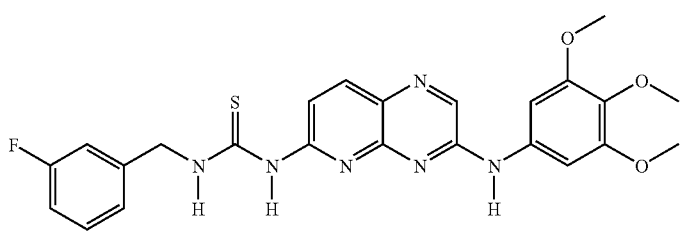 | 1-(3-Fluoro-benzyl)-3-[3-(3,4,5-trimethoxy-phenylamino)-pyrido[2,3-b]pyrazin-6-yl]-thiourea |
| 743 | 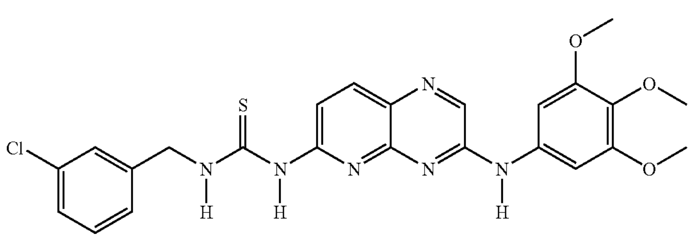 | 1-(3-Chloro-benzyl)-3-[3-(3,4,5-trimethoxy-phenylamino)-pyrido[2,3-b]pyrazin-6-yl]-thiourea |

| Compound | Structure | Name |
|---|---|---|
| 744 | 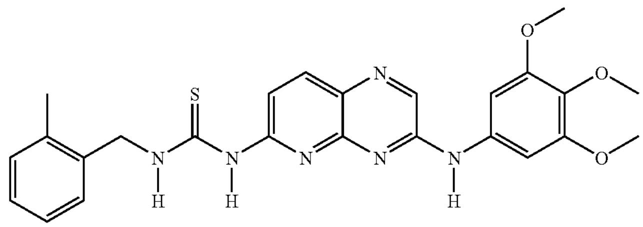 | 1-(2-Methyl-benzyl)-3-[3-(3,4,5-trimethoxy-phenylamino)-pyrido[2,3-b]pyrazin-6-yl]-thiourea |
| 745 | 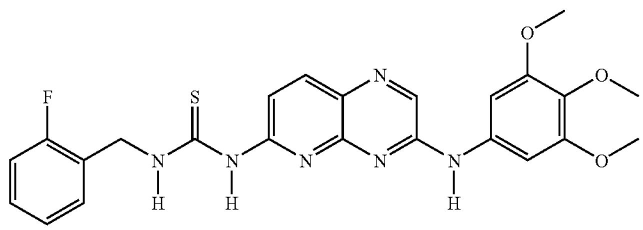 | 1-(2-Fluoro-benzyl)-3-[3-(3,4,5-trimethoxy-phenylamino)-pyrido[2,3-b]pyrazin-6-yl]-thiourea |
| 746 | 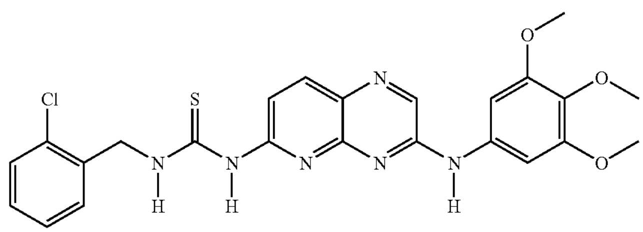 | 1-(2-Chloro-benzyl)-3-[3-(3,4,5-trimethoxy-phenylamino)-pyrido[2,3-b]pyrazin-6-yl]-thiourea |
| 747 | 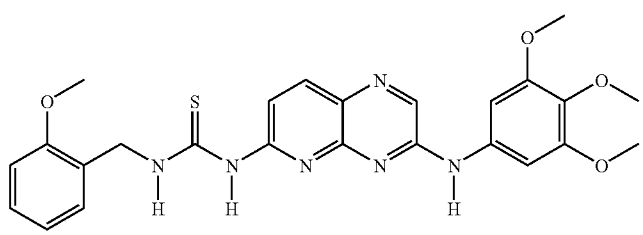 | 1-(2-Methoxy-benzyl)-3-[3-(3,4,5-trimethoxy-phenylamino)-pyrido[2,3-b]pyrazin-6-yl]-thiourea |
| 748 | 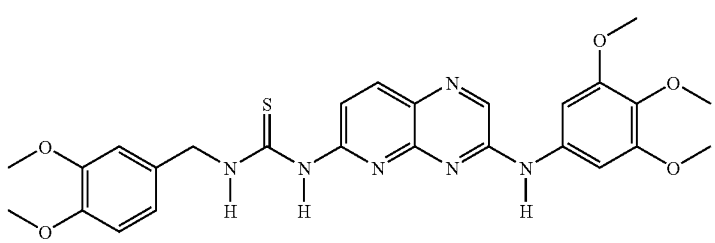 | 1-(3,4-Dimethoxy-benzyl)-3-[3-(3,4,5-trimethoxy-phenylamino)-pyrido[2,3-b]pyrazin-6-yl]-thiourea |
| 749 | 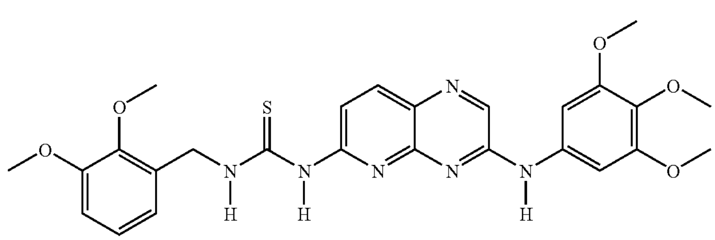 | 1-(2,3-Dimethoxy-benzyl)-3-[3-(3,4,5-trimethoxy-phenylamino)-pyrido[2,3-b]pyrazin-6-yl]-thiourea |

-continued

| Compound | Structure | Name |
|---|---|---|
| 750 | 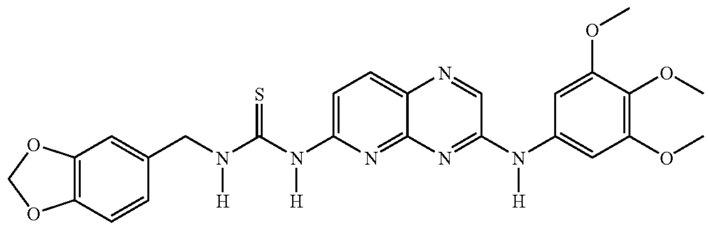 | 1-Benzo[1,3]dioxol-5-ylmethyl-3-[3-(3,4,5-trimethoxy-phenylamino)-pyrido[2,3-b]pyrazin-6-yl]-thiourea |
| 751 | 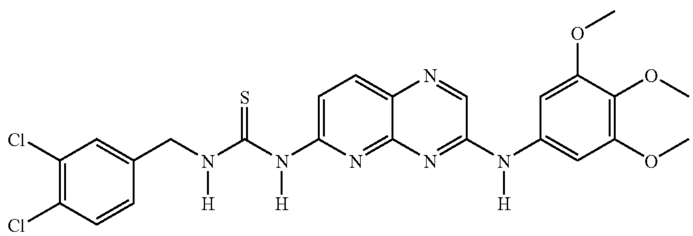 | 1-(3,4-Dichloro-benzyl)-3-[3-(3,4,5-trimethoxy-phenylamino)-pyrido[2,3-b]pyrazin-6-yl]-thiourea |
| 752 | 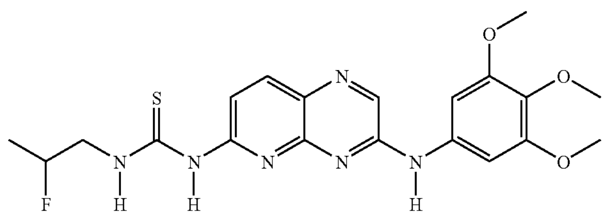 | 1-(2-Fluoro-propyl)-3-[3-(3,4,5-trimethoxy-phenylamino)-pyrido[2,3-b]pyrazin-6-yl]-thiourea |
| 753 | 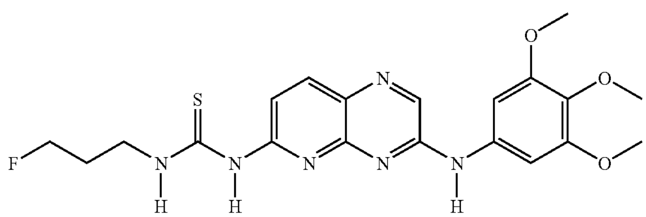 | 1-(3-Fluoro-propyl)-3-[3-(3,4,5-trimethoxy-phenylamino)-pyrido[2,3-b]pyrazin-6-yl]-thiourea |
| 754 | 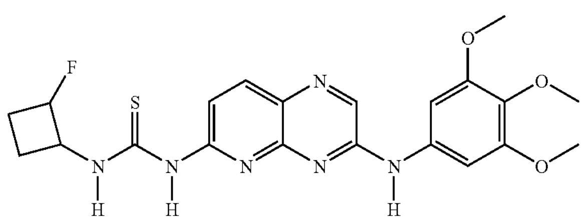 | 1-(2-Fluoro-cyclobutyl)-3-[3-(3,4,5-trimethoxy-phenylamino)-pyrido[2,3-b]pyrazin-6-yl]-thiourea |
| 755 | 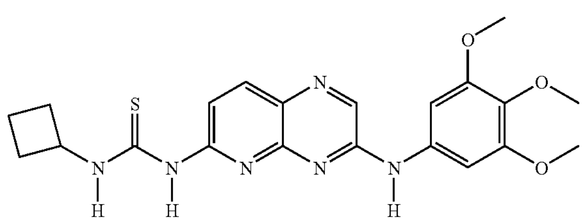 | 1-Cyclobutyl-3-[3-(3,4,5-trimethoxy-phenylamino)-pyrido[2,3-b]pyrazin-6-yl]-thiourea |
| 756 | 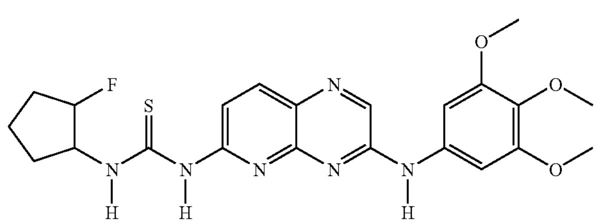 | 1-(2-Fluoro-cyclopentyl)-3-[3-(3,4,5-trimethoxy-phenylamino)-pyrido[2,3-b]pyrazin-6-yl]-thiourea |

| Compound | Structure | Name |
|---|---|---|
| 757 | 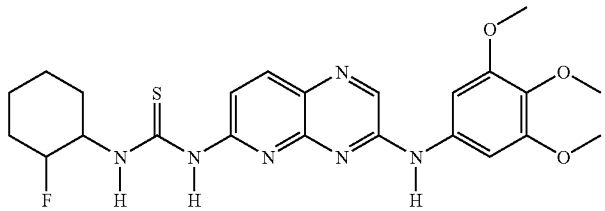 | 1-(2-Fluoro-cyclohexyl)-3-[3-(3,4,5-trimethoxy-phenylamino)-pyrido[2,3-b]pyrazin-6-yl]-thiourea |
| 758 | 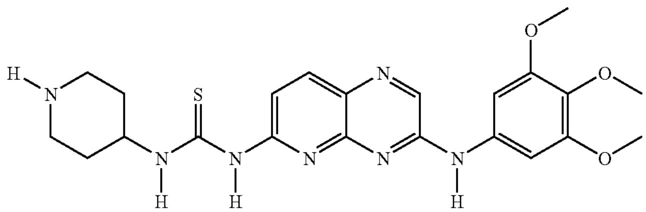 | 1-Piperidin-4-yl-3-[3-(3,4,5-trimethoxy-phenylamino)-pyrido[2,3-b]pyrazin-6-yl]-thiourea |
| 759 | 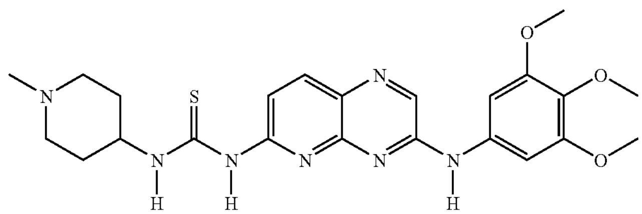 | 1-(1-Methyl-piperidin-4-yl)-3-[3-(3,4,5-trimethoxy-phenylamino)-pyrido[2,3-b]pyrazin-6-yl]-thiourea |
| 760 | 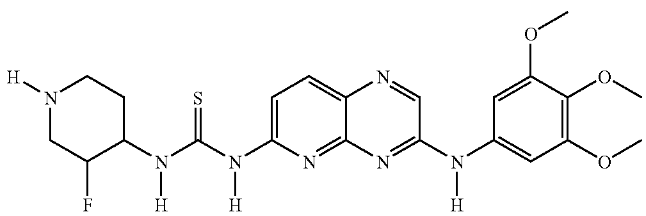 | 1-(3-Fluoro-piperidin-4-yl)-3-[3-(3,4,5-trimethoxy-phenylamino)-pyrido[2,3-b]pyrazin-6-yl]-thiourea |
| 761 | 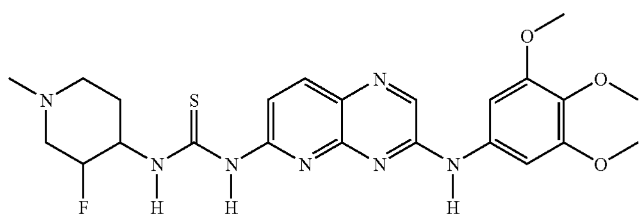 | 1-(3-Fluoro-1-methyl-piperidin-4-yl)-3-[3-(3,4,5-trimethoxy-phenylamino)-pyrido[2,3-b]pyrazin-6-yl]-thiourea |
| 762 | 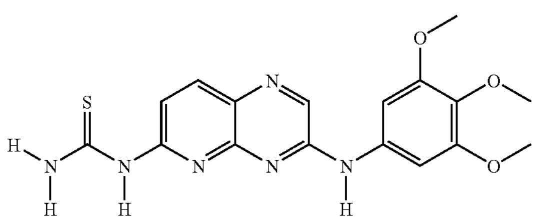 | [3-(3,4,5-Trimethoxy-phenylamino)-pyrido[2,3-b]pyrazin-6-yl]-thiourea |
| 763 | 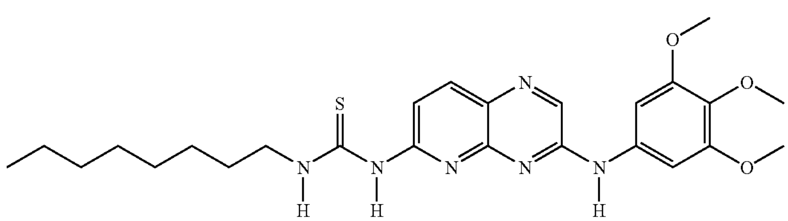 | 1-Octyl-3-[3-(3,4,5-trimethoxy-phenylamino)-pyrido[2,3-b]pyrazin-6-yl]-thiourea |

| Compound | Structure | Name |
|---|---|---|
| 764 | 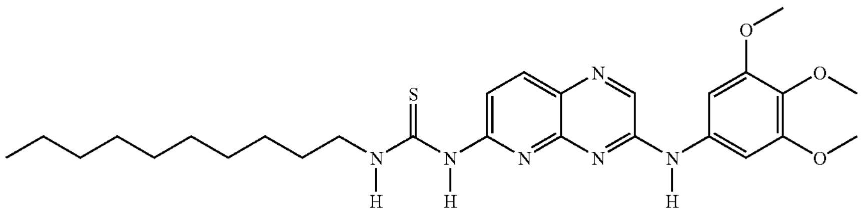 | 1-Decyl-3-[3-(3,4,5-trimethoxy-phenylamino)-pyrido[2,3-b]pyrazin-6-yl]-thiourea |
| 765 | 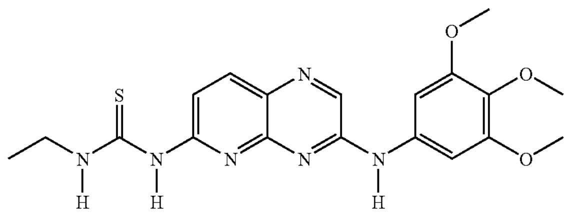 | 1-Ethyl-3-{3-[methyl-(3,4,5-trimethoxy-phenyl)-amino]-pyrido[2,3-b]pyrazin-6-yl}-thiourea |
| 766 | 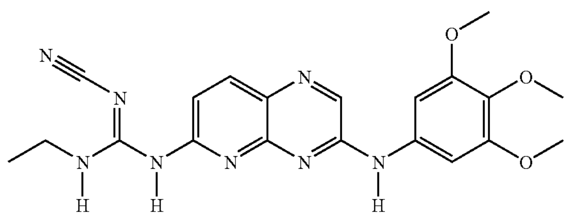 | Namensgebung mit Autonom nicht möglich |
| 767 | 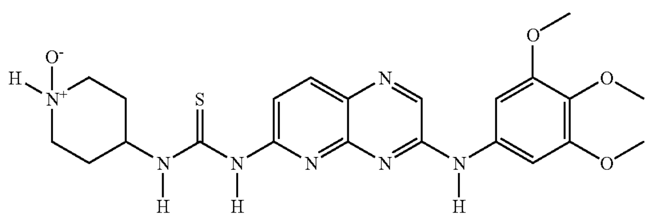 | 1-(1-Oxy-piperidin-4-yl)-3-[3-(3,4,5-trimethoxy-phenylamino)-pyrido[2,3-b]pyrazin-6-yl]-thiourea |
| 768 | 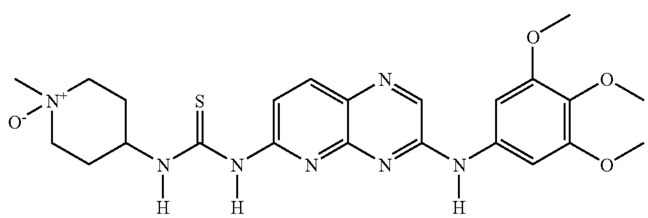 | 1-(1-Methyl-1-oxy-piperidin-4-yl)-3-[3-(3,4,5-trimethoxy-phenylamino)-pyrido[2,3-b]pyrazin-6-yl]-thiourea |
| 769 | 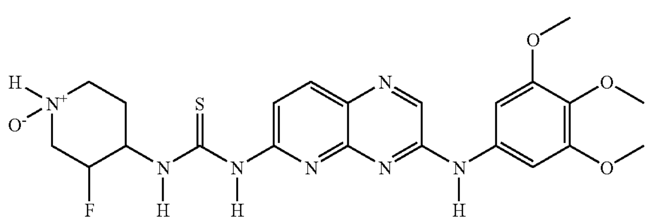 | 1-(3-Fluoro-1-oxy-piperidin-4-yl)-3-[3-(3,4,5-trimethoxy-phenylamino)-pyrido[2,3-b]pyrazin-6-yl]-thiourea |
| 770 | 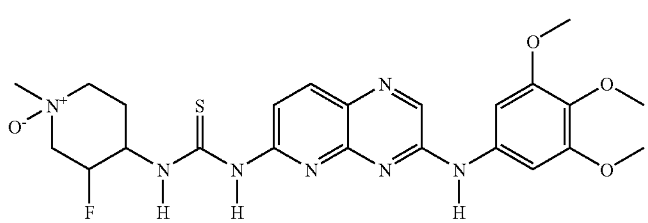 | 1-(3-Fluoro-1-methyl-1-oxy-piperidin-4-yl)-3-[3-(3,4,5-trimethoxy-phenylamino)-pyrido[2,3-b]pyrazin-6-yl]-thiourea |

| Compound | Structure | Name |
|---|---|---|
| 771 | 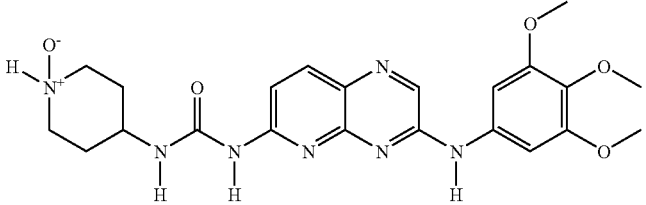 | 1-(1-Oxy-piperidin-4-yl)-3-[3-(3,4,5-trimethoxy-phenylamino)-pyrido[2,3-b]pyrazin-6-yl]-urea |
| 772 | 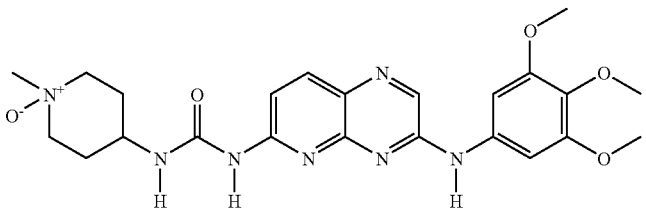 | 1-(1-Methyl-1-oxy-piperidin-4-yl)-3-[3-(3,4,5-trimethoxy-phenylamino)-pyrido[2,3-b]pyrazin-6-yl]-urea |
| 773 | 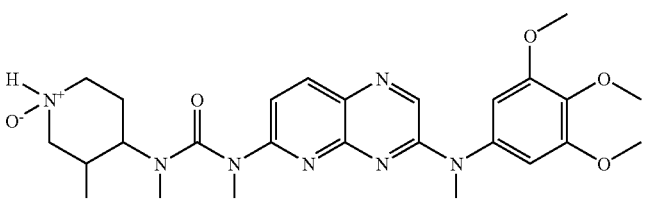 | 1-(3-Fluoro-1-oxy-piperidin-4-yl)-3-[3-(3,4,5-trimethoxy-phenylamino)-pyrido[2,3-b]pyrazin-6-yl]-urea |
| 774 | 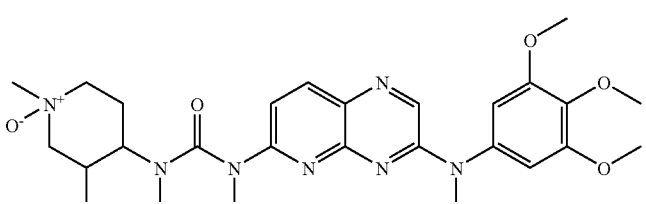 | 1-(3-Fluoro-1-methyl-1-oxy-piperidin-4-yl)-3-[3-(3,4,5-trimethoxy-phenylamino)-pyrido[2,3-b]pyrazin-6-yl]-urea |

For the avoidance of doubt, if chemical name and chemical structure of the above illustrated compounds do not correspond by mistake, the chemical structure is regarded to unambigously define the compound.

All the above generically or explicitly disclosed pyrido[2,3-b]pyrazine derivatives, including preferred subsets/embodiments of general formula (I) and Compounds 1 to 774 are hereinafter referred to as compounds of the (present) invention.

The terms indicated for explanation of the above compounds of the invention always, unless indicated otherwise in the description or in the claims, have the following meanings:

The term "unsubstituted" means that the corresponding radical, group or moiety has no substituents.

The term "substituted" means that the corresponding radical, group or moiety has one or more substituents. Where a radical has a plurality of substituents, and a selection of various substituents is specified, the substituents are selected independently of one another and do not need to be identical.

The term "alkyl" for the purposes of this invention refers to acyclic saturated or unsaturated hydrocarbon radicals which may be branched or straight-chain and have 1 to 8 carbon atoms, i.e. $C_{1-8}$-alkanyls, $C_{2-8}$-alkenyls and $C_{2-8}$-alkynyls. Alkenyls have at least one C—C double bond and alkynyls at least one C—C triple bond. Alkynyls may additionally also have at least one C—C double bond. Examples of suitable alkyl radicals are methyl, ethyl, n-propyl, isopropyl, n-butyl, isobutyl, sec-butyl, tert-butyl, n-pentyl, iso-pentyl, neo-pentyl, tert-pentyl, 2- or 3-methyl-pentyl, n-hexyl, 2-hexyl, iso-hexyl, n-heptyl, n-octyl, n-nonyl, n-decyl, n-undecyl, n-dodecyl, n-tetradecyl, n-hexadecyl, n-octadecyl, n-icosanyl, n-docosanyl, ethylenyl (vinyl), propenyl (—CH$_2$CH═CH$_2$; —CH═CH—CH$_3$, —C(═CH$_2$)—CH$_3$), butenyl, pentenyl, hexenyl, heptenyl, octenyl, octadienyl, octadecenyl, octadec-9-enyl, icosenyl, icos-11-enyl, (Z)-icos-11-enyl, docosnyl, docos-13-enyl, (Z)-docos-13-enyl, ethynyl, propynyl (—CH$_2$—C≡CH, —C≡C—CH$_3$), butynyl, pentynyl, hexynyl, heptynyl, octynyl.

The term "($C_9$-$C_{30}$)alkyl" for the purposes of this invention refers to acyclic saturated or unsaturated hydrocarbon radicals which may be branched or straight-chain and have 9 to 30 carbon atoms, i.e. $C_{9-30}$-alkanyls, $C_{9-30}$-alkenyls and $C_{9-30}$-alkynyls. $C_{9-30}$-Alkenyls have at least one C—C double bond and $C_{9-30}$-alkynyls at least one C—C triple bond. $C_{9-30}$-Alkynyls may additionally also have at least one C—C double bond. Examples of suitable ($C_9$-$C_{30}$)alkyl radicals are tetradecyl, hexadecyl, octadecyl, eicosanyl, cis-13-docosenyl (erucyl), trans-13-docosenyl (brassidyl), cis-15-tetracosenyl (nervonyl) and trans-15-tetracosenyl.

The term "cycloalkyl" for the purposes of this invention refers to saturated and partially unsaturated non-aromatic cyclic hydrocarbon groups/radicals, having 1 to 3 rings, that contain 3 to 20, preferably 3 to 12, most preferably 3 to 8 carbon atoms. The cycloalkyl radical may also be part of a bior polycyclic system, where, for example, the cycloalkyl radical is fused to an aryl, heteroaryl or heterocyclyl radical as defined herein by any possible and desired ring member(s). The bonding to the compounds of the general formula (I) can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl.

The term "heterocyclyl" for the purposes of this invention refers to a mono- or polycyclic system of 3 to 20, preferably 5 or 6 to 14 ring atoms comprising carbon atoms and 1, 2, 3, 4, or 5 heteroatoms, in particular nitrogen, oxygen and/or sulfur which are identical or different. The cyclic system may be saturated, mono- or polyunsaturated but may not be aromatic. In the case of a cyclic system consisting of at least two rings the rings may be fused or spiro- or otherwise connected. Such "heterocyclyl" radicals can be linked via any ring member. The term "heterocyclyl" also includes systems in which the heterocycle is part of a bi- or polycyclic saturated, partially unsaturated and/or aromatic system, such as where the heterocycle is fused to an "aryl", "cycloalkyl", "heteroaryl" or "heterocyclyl" group as defined herein via any desired and possible ring member of the heterocycyl radical. The bonding to the compounds of the general formula (I) can be effected via any possible ring member of the heterocycyl radical. Examples of suitable "heterocyclyl" radicals are pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl.

The term "aryl" for the purposes of this invention refers to aromatic hydrocarbon systems having 3 to 14, preferably 5 to 14, more preferably 6 to 14 carbon atoms. The term "aryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the aryl radical. The bonding to the compounds of the general formula (I) can be effected via any possible ring member of the aryl radical. Examples of suitable "aryl" radicals are phenyl, biphenyl, naphthyl and anthracenyl, but likewise indanyl, indenyl, or 1,2,3,4-tetrahydronaphthyl.

The term "heteroaryl" for the purposes of this invention refers to a 3 to 14, preferably 5 to 14, more preferably 5-, 6- or 7-membered cyclic aromatic hydrocarbon radical which comprises at least 1, where appropriate also 2, 3, 4 or 5 heteroatoms, preferably nitrogen, oxygen and/or sulfur, where the heteroatoms are identical or different. The number of nitrogen atoms is preferably 0, 1, 2, or 3, and that of the oxygen and sulfur atoms is independently 0 or 1. The term "heteroaryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the heteroaryl radical. The bonding to the compounds of the general formula (I) can be effected via any possible ring member of the heteroaryl radical. Examples of suitable "heteroaryl" are pyrrolyl, thienyl, furyl, imidazolyl, thiazolyl, isothiazolyl, oxazolyl, oxadiazolyl, isoxazolyl, pyrazolyl, pyridinyl, pyrimidinyl, pyridazinyl, pyrazinyl, indolyl, quinolinyl, isoquinolinyl, imidazolyl, triazolyl, triazinyl, tetrazolyl, phthalazinyl, indazolyl, indolizinyl, quinoxalinyl, quinazolinyl, pteridinyl, carbazolyl, phenazinyl, phenoxazinyl, phenothiazinyl, acridinyl.

For the purposes of the present invention, the terms "alkyl-cycloalkyl", "cycloalkylalkyl", "alkyl-heterocyclyl", "heterocyclylalkyl", "alkyl-aryl", "arylalkyl", "alkyl-heteroaryl" and "heteroarylalkyl" mean that alkyl, cycloalkyl, heterocycle, aryl and heteroaryl are each as defined above, and the cycloalkyl, heterocyclyl, aryl and heteroaryl radical is bonded to the compounds of the general formula (I) via an alkyl radical, preferably $C_1$-$C_8$-alkyl radical, more preferably $C_1$-$C_4$-alkyl radical.

The term "halogen", "halogen atom" or "halogen substituent" (Hal-) for the purposes of this invention refers to one, where appropriate, a plurality of fluorine (F, fluoro), bromine (Br, bromo), chlorine (Cl, chloro), or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. "Halogen" preferably means a fluorine, chlorine or bromine atom.

All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers.

Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or nonchiral phases or by recrystallization from an optionally optically active solvent or with use of an optically active acid or base or by derivatization with an optically active reagent such as, for example, an optically active alcohol, and subsequent elimination of the radical.

The compounds of the invention may be present in the form of their double bond isomers as "pure" E or Z isomers, or in the form of mixtures of these double bond isomers.

Where possible, the compounds of the invention may be in the form of the tautomers.

It is likewise possible for the compounds of the invention to be in the form of any desired prodrugs such as, for example, esters, carbonates, carbamates, ureas, amides, N-oxides or phosphates, in which cases the actually biologically active form is released only through metabolism. Any compound that can be converted in vivo to provide the bioactive agent (i.e. compounds of the invention) is a prodrug within the scope and spirit of the invention.

Various forms of prodrugs are well known in the art and are described for instance in:
  (i) Wermuth C G et al., Chapter 31:671-696, The Practice of Medicinal Chemistry, Academic Press 1996;
  (ii) Bundgaard H, Design of Prodrugs, Elsevier 1985; and
  (iii) Bundgaard H, Chapter 5:131-191, A Textbook of Drug Design and Development, Harwood Academic Publishers 1991.

Said references are incorporated herein by reference.

It is further known that chemical substances are converted in the body into metabolites which may where appropriate likewise elicit the desired biological effect—in some circumstances even in more pronounced form.

Any biologically active compound that was converted in vivo by metabolism from any of the compounds of the invention is a metabolite within the scope and spirit of the invention.

Corresponding prodrugs and metabolites of the compounds of the invention should be considered to be part of the invention.

The compounds of the invention can, if they have a sufficiently basic group such as, for example, a secondary or tertiary amine, be converted with inorganic and organic acids into salts. The pharmaceutically acceptable salts of the compounds of the invention are preferably formed with hydrochloric acid, hydrobromic acid, iodic acid, sulfuric acid, phosphoric acid, methanesulfonic acid, p-toluenesulfonic acid, carbonic acid, formic acid, acetic acid, sulfoacetic acid, trifluoroacetic acid, oxalic acid, malonic acid, maleic acid, succinic acid, tartaric acid, racemic acid, malic acid, embonic acid, mandelic acid, fumaric acid, lactic acid, citric acid, taurocholic acid, glutaric acid, stearic acid, glutamic acid or aspartic acid. The salts which are formed are, inter alia, hydrochlorides, chlorided, hydrobromides, bromides, iodides, sulfates, phosphates, methanesulfonates, tosylates, carbonates, bicarbonates, formates, acetates, sulfoacetates, triflates, oxalates, malonates, maleates, succinates, tartrates, malates, embonates, mandelates, fumarates, lactates, citrates, glutarates, stearates, aspartates and glutamates. The stoichiometry of the salts formed from the compounds of the invention may moreover be an integral or non-integral multiple of one.

The compounds of the invention can, if they contain a sufficiently acidic group such as, for example, the carboxy, sulfonic acid, phosphoric acid or a phenolic group, be converted with inorganic and organic bases into their physiologically tolerated salts. Examples of suitable inorganic bases are ammonium, sodium hydroxide, potassium hydroxide, calcium hydroxide, and of organic bases are ethanolamine, diethanolamine, triethanolamine, ethylenediamine, t-butylamine, t-octylamine, dehydroabietylamine, cyclohexylamine, dibenzylethylene-diamine and lysine. The stoichiometry of the salts formed from the compounds of the invention can moreover be an integral or non-integral multiple of one.

It is likewise possible for the compounds of the invention to be in the form of their solvates and, in particular, hydrates which can be obtained for example by crystallization from a solvent or from aqueous solution. It is moreover possible for one, two, three or any number of solvate or water molecules to combine with the compounds of the invention to give solvates and hydrates.

It is known that chemical substances form solids which exist in different order states which are referred to as polymorphic forms or modifications. The various modifications of a polymorphic substance may differ greatly in their physical properties. The compounds of the invention can exist in various polymorphic forms and certain modifications may moreover be metastable. All these polymorphic forms of the compounds are to be regarded as belonging to the invention.

It has now been found in a surprising and advantageous manner that the compounds of the invention can also act, i.e. have a modulating or inhibiting effect, on two or more signal transduction pathways or enzymes of such pathways. It has been found that the compounds of the invention act, i.e. modulate or inhibit, with high selectivity.

Such a simultaneous, for example dual, modulation or inhibition of two or more signal transduction pathways, for example ras-Raf-Mek-Erk signal pathway, PI3K-Akt signal pathway and/or SAPK signal pathway, more specifically Erk1/Erk2 and/or PI3K and/or Jnk and/or p38, is advantageous over the only single modulation or inhibition of one signal transduction pathway, since synergistic therapeutic effects can be brought about, for example enhanced apoptosis and more rapid and efficient tumor regression.

The surprising advantageous effects of the compounds of the invention enable multiple therapeutic approaches to be pursued in the physiological and/or pathophysiological states or conditions which are sensitive to the treatment or modulation of, or are mediated by, two or more signal transduction pathways.

It has also been found in a surprising and advantageous manner that the compounds of the invention can also act, i.e. have modulating or inhibiting action, with high selectivity on the ras-Raf-Mek-Erk signal transduction pathway or enzymes thereof, and that the multiple mechanisms of action and therapeutic approaches detailed above can also find use with this signal pathway or enzymes.

It has also been found in a surprising and advantageous manner that the compounds of the invention can also act, i.e. have modulating or inhibiting action, with high selectivity on the PI3K-Akt signal transduction pathway or enzymes thereof, and that the multiple mechanisms of action and therapeutic approaches detailed above can also find use with this signal pathway or enzymes.

It has also been found in a surprising and advantageous manner that the compounds of the invention can also act, i.e. have modulating or inhibiting action, with high selectivity on the SAPK signal transduction pathway or enzymes thereof, and that the multiple mechanisms of action and therapeutic approaches detailed above can also find use with this signal pathway or enzymes.

It has additionally been found in a surprising and advantageous manner that the compounds of the invention can also act, i.e. have a modulating or inhibiting action, with high selectivity on enzymes such as ATM, ATR, mTOR, DNA-PK and/or hSMG-1, and that the multiple mechanisms of action and therapeutic approaches detailed above can also find use with these enzymes.

According to the invention, the term "modulation" is understood to mean the following: "activation, partial activation, inhibition, partial inhibition". It is within the technical knowledge of the average person skilled in the art to measure and to determine such an activation, partial activation, inhibition or partial inhibition by means of the customary measurement and determination methods. For example, a partial activation can be measured and determined in relation to a full activation; and likewise a partial inhibition in relation to a full inhibition.

According to the invention, the term "inhibition" is understood to mean the following: "partial or full inhibition". It is within the technical knowledge of the average person skilled in the art to measure and to determine such a partial or full inhibition by means of the customary measurement and determination methods. For example, partial inhibition can be measured and determined in relation to full inhibition.

The terms "modulation" and "inhibition" relate, in connection with "enzymes" and/or "kinases" in the context of this invention, both to the inactive form (enzymatically inactive) and/or active form (enzymatically active) of the particular enzyme and/or kinase. This means in the context of this invention that a compound of the invention can display its modulating action on the inactive form, active form or both forms of the enzyme and/or kinase.

In a further aspect, the object of the invention has surprisingly been solved by providing the compounds of the present invention or pharmaceutical compositions as described herein for use as a medicament.

In another aspect, the object of the present invention has surprisingly been solved by providing the use of the compounds of the invention or pharmaceutical compositions as described herein for the manufacture of a medicament for the treatment or prophylaxis of the physiological and/or pathological conditions described herein.

In a further aspect, the object of the invention has surprisingly been solved by providing the compounds of the invention for use in the manufacture of a medicament for modulating misdirected cellular signal transduction processes, especially for influencing the function of active and inactive receptor tyrosine kinases, and also cytoplasmic tyrosine, serine/threonine and lipid kinases, such as c-Raf, B-Raf, Mek, MAPKs, PDGFRbeta, Flt-3, IGF1R, PI3K, PKB/Akt1, c-Kit, c-Abl, FGFR1 and KDR.

In a further aspect, the object of the invention has surprisingly been solved by providing the compounds of the invention for use in the manufacture of a medicament for the treatment or prophylaxis of physiological and/or pathophysiological conditions in mammals, that are mediated by one or more signal transduction pathways selected from the group consisting of: "ras-Raf-Mek-Erk signal transduction pathway, PI3K-Akt signal transduction pathway and/or SAPK signal transduction pathway".

In a further aspect, the object of the invention has surprisingly been solved by providing the compounds of the invention for use in the manufacture of a medicament for the treatment or prophylaxis of physiological and/or pathophysiological conditions in mammals mediated by one or more enzymes selected from the group consisting of: "ATM, ATR, mTOR, DNA-PK, hSMG-1".

In a further aspect, the object of the invention has surprisingly been solved by providing the compounds of the invention for use in the manufacture of a medicament for the treatment or prophylaxis of physiological and/or pathophysiological conditions in mammals, where the treatment or prophylaxis is brought about by modification of one or more enzymes selected from the group consisting of: "ATM, ATR, mTOR, DNA-PK, hSMG-1".

In a preferred embodiment, the compounds of the invention are provided for use in the manufacture of a medicament for the treatment or prophylaxis of physiological and/or pathophysiological conditions mediated by ras-Raf-Mek-Erk signal transduction pathway and PI3K-Akt signal transduction pathway in mammals, and/or for the manufacture of a medicament for the treatment or prophylaxis of physiological and/or pathophysiological conditions in mammals, where the treatment or prophylaxis is brought about by modulation of ras-Raf-Mek-Erk signal transduction pathway and of PI3K-Akt signal transduction pathway.

In a further aspect, the object of the invention has surprisingly been solved by providing the compounds of the invention for use in the manufacture of a medicament for the treatment or prophylaxis of physiological and/or pathophysiological conditions mediated by ras-Raf-Mek-Erk signal transduction pathway in mammals.

In a further aspect, the object of the invention has surprisingly been solved by providing the compounds of the invention for use in the manufacture of a medicament for the treatment or prophylaxis of physiological and/or pathophysiological conditions mediated by PI3K-Akt signal transduction pathway in mammals.

In a further aspect, the object of the invention has surprisingly been solved by providing the compounds of the invention for use in the manufacture of a medicament for the treatment or prophylaxis of physiological and/or pathophysiological conditions in mammals, where the treatment or prophylaxis is brought about by modulation of PI3K-Akt signal transduction pathway.

In a preferred embodiment, the compounds of the invention are provided for use in the manufacture of a medicament for the treatment or prophylaxis of physiological and/or pathophysiological conditions mediated by SAPK signal transduction pathway and PI3K-Akt signal transduction pathway in mammals, and/or for the manufacture of a medicament for the treatment or prophylaxis of physiological and/or pathophysiological conditions in mammals, where the treatment or prophylaxis is brought about by modulation of SAPK signal transduction pathway and of PI3K-Akt signal transduction pathway.

In a further aspect, the object of the invention has surprisingly been solved by providing the compounds of the invention for use in the manufacture of a medicament for the treatment or prophylaxis of physiological and/or pathophysiological conditions mediated by SAPK signal transduction pathway in mammals.

In a further aspect, the object of the invention has surprisingly been solved by providing the compounds of the invention for use in the manufacture of a medicament for the treatment or prophylaxis of physiological and/or pathophysiological conditions in mammals, where the treatment or prophylaxis is brought about by modulation of SAPK signal transduction pathway.

In a preferred embodiment, the compounds of the invention are provided for the uses detailed above, where the modulation of ras-Raf-Mek-Erk signal transduction pathway is brought about by modulation of one or more enzymes selected from the group consisting of: "tyrosine kinase, serine/threonine kinase, receptor tyrosine kinase, cytoplasmic tyrosine kinase, cytoplasmic serine/threonine kinase" and preferably selected from the group consisting of "Erk, Erk1, Erk2".

In a further preferred embodiment, the compounds of the invention are provided for the uses as detailed above, where the modulation of PI3K-Akt signal transduction pathway is brought about by modulation of one or more enzymes selected from the group consisting of "lipid kinases" and preferably selected from the group consisting of: "PI3K, PI3Kalpha, PI3 Kbeta, PI3 Kgamma, PI3 Kdelta, PI3K-C2alpha, PI3K-C2beta, PI3K-Vps34p".

In a further preferred embodiment, the compounds of the invention are provided for the uses as detailed above, where the modulation of SAPK signal transduction pathway is brought about by modulation of one or more enzymes selected from the group consisting of: "tyrosine kinase, serine/threonine kinase, receptor tyrosine kinase, cytoplasmatic tyrosine kinase, cytoplasmatic serine/threonine kinase" and preferably selected from the group consisting of: "Jnk, Jnk1, Jnk2, Jnk3, p38, p38alpha, p38beta, p38gamma, p38delta".

In a further aspect, the object of the invention has surprisingly been solved by providing a process of manufacturing the compounds of the invention.

In a further aspect, the object of the invention has surprisingly been solved by providing the compounds of the invention according to the aspects, preferred embodiments and uses detailed above for use in the manufacture of a medicament for the treatment or prophylaxis of physiological and/or pathophysiological conditions in mammals, where the treatment or prophylaxis is brought about by modulation of two or more enzymes.

In a more preferred embodiment, the compounds of the invention are provided for the uses detailed above, where at least one enzyme in the treatment or prophylaxis brought about by modulation of two or more enzymes is selected from the group consisting of:"Erk, Erk1, Erk2" and at least one enzyme is selected from the group consisting of:"PI3K, PI3Kalpha, PI3 Kbeta, PI3 Kgamma, PI3 Kdelta, PI3K-C2alpha, PI3K-C2beta, PI3K-Vps34p".

In a more preferred embodiment, the compounds of the invention are provided for the uses detailed above, where at least one enzyme in the treatment or prophylaxis brought about by modulation of two or more enzymes is selected from the group consisting of:"Jnk, Jnk1, Jnk2, Jnk3, p38, p38alpha, p38beta, p38gamma, p38delta" and at least one enzyme is selected from the group consisting of:"PI3K, PI3Kalpha, PI3 Kbeta, PI3 Kgamma, PI3 Kdelta, PI3K-C2alpha, PI3K-C2beta, PI3K-Vps34p".

In a more preferred embodiment, the compounds of the invention are provided for the uses detailed above, where at least one enzyme in the treatment or prophylaxis brought about by modulation of two or more enzymes is selected from the group consisting of:"Erk, Erk1, Erk2" and at least one enzyme is selected from the group consisting of:"ATM, ATR, mTOR, DNA-PK, hSMG-1".

In a more preferred embodiment, the compounds of the invention are provided for the uses detailed above, where at least one enzyme in the treatment or prophylaxis brought about by modulation of two or more enzymes is selected from the group consisting of:"Jnk, Jnk1, Jnk2, Jnk3, p38, p38alpha, p38beta, p38gamma, p38delta" and at least one enzyme is selected from the group consisting of:"ATM, ATR, mTOR, DNA-PK, hSMG-1".

In a more preferred embodiment, the compounds of the invention are provided for the uses detailed above, where at least one enzyme in the treatment or prophylaxis brought about by modulation of two or more enzymes is selected from the group consisting of:"PI3K, PI3Kalpha, PI3 Kbeta, PI3 Kgamma, PI3 Kdelta, PI3K-C2alpha, PI3K-C2beta, PI3K-Vps34p" and at least one enzyme is selected from the group consisting of:"ATM, ATR, mTOR, DNA-PK, hSMG-1".

In another preferred embodiment, the compounds of the invention are provided for the uses detailed above, where the modulation is an inhibition.

Likewise, corresponding medicaments comprising at least one compound of the invention or at least one pharmaceutical composition as described herein for use in the treatment or prophylaxis of the herein disclosed physiological and/or pathological conditions are also comprised by the present invention.

For the purpose of the present invention, the compounds of the invention may be administered to all known mammals, especially to the human, for treatment and/or prophylaxis.

Preferably, such mammals are selected from the group consisting of "human, domestic animals, cattle, livestock, pets, cow, sheep, pig, goat, horse, pony, donkey, hinny, mule, hare, rabbit, cat, dog, guinea pig, hamster, rat, mouse". More preferably, such mammals are human.

For the purpose of the present invention, the compounds of the invention may be used for the treatment or prophylaxis of all knowri physiological and/or pathophysiological conditions.

In a preferred embodiment, the compounds of the invention are provided for the uses detailed above, where the physiological and/or pathophysiological conditions are selected from the group consisting of:"malignant tumors, benign tumors, inflammatory disorders, inflammations, pain, rheumatic disorders, arthritic disorders, HIV infections, neurological or neurodegenerative disorders, rheumatism, arthritis, AIDS, ARC (AIDS related complex), Kaposi's sarcoma, tumors originating in the brain and/or nervous system and/or meninges (refer to WO 99/01764), dementia, Alzheimer's disease, hyperproliferative disorders, psoriasis, endometriosis, scar formation, benign prostate hyperplasia (BPH), disorders of the immune system, autoimmune disorders, immune deficiency disorders, colon tumor, stomach tumor, intestine tumor, lung tumor, pancreas tumor, ovarian tumor, prostate tumor, leukemia, melanoma, liver tumor, kidney tumor, head tumor, throat tumor, glioma, breast tumor, uterine cancer, endometrial cancer, cervical cancer, brain tumor, adenocanthoma, bladder cancer, colorectal tumor, esophageal cancer, gynecological tumor, ovarian tumor, thyroid cancer, lymphoma, chronic leukemia, acute leukemia, restenosis, diabetes, diabetic nephropathy, fibrotic disorders, cystic fibrosis, malignant nephrosclerosis, thrombotic microangiopathy syndrome, organ transplant rejection, glomerulopathies, disorders of the metabolism, solid tumors, rheumatic arthritis, diabetic retinopathy, asthma, allergies, allergic disorders, chronic obstructive pulmonary disorders, inflammatory bowel disorder, fibrosis, atherosclerosis, cardiac disorders, cardiovascular disorders, disorders of the heart muscle, vascular disorders, angiogenetic disorders, kidney disorders, rhinitis, Grave's disease, focal ischemia, heart failure, ischemia, cardiac hypertrophy, kidney failure, cardiac myocyte dysfunction, high blood pressure, vascular constriction, stroke, anaphylactic shock, blood platelet agglutination, skeletal muscular atrophy, obesity, excess weight, glucose homeostasis, congestive heart failure, angina, heart attack, myocardial infarction, hyperglycemia, hypoglycemia, hypertension".

In a further aspect of the present invention, the object of the invention has surprisingly been solved by providing the compounds of the invention according to the aspects, preferred embodiments and uses detailed above for use in the manufacture of a medicament for the treatment or prophylaxis of physiological and/or pathophysiological conditions in mammals, where the medicament comprises at least one further pharmacologically active substance.

In a further aspect of the present invention, the object of the invention has surprisingly been solved by providing the compounds of the invention according to the aspects, preferred embodiments and uses detailed above for use in the manufacture of a medicament for the treatment or prophylaxis of physiological and/or pathophysiological conditions in mammals, where the medicament is administered before and/or during and/or after the treatment with at least one further pharmacologically active substance.

In a further aspect of the present invention, the object of the invention has surprisingly been solved by providing the compounds of the invention according to the aspects, preferred embodiments and uses detailed above for use in the manufacture of a medicament for the treatment or prophylaxis of physiological and/or pathophysiological conditions in mammals, where the medicament is administered before and/or during and/or after the treatment with radiation therapy and/or surgery.

In the context of the present invention, the compounds of the invention may be administered with all known pharmacologically active substances in a combination therapy as detailed.

In a preferred embodiment, the compounds of the invention are provided for the uses detailed above, where the further pharmacologically active substance is selected from the group consisting of:"DNA topoisomerase I and/or II inhibitors, DNA intercalators, alkylating agents, microtubuli destabilizers, hormone and/or growth factor receptor agonists and/ or antagonists, antibodies against growth factors and their receptors, kinase inhibitors, antimetabolites".

In a preferred embodiment, the compounds of the invention are provided for the above uses, where the further pharmacologically active substance is selected from the group consisting of:"asparaginase, bleomycin, carboplatin, carmustine, chlorambucil, cisplatin, colaspase, cyclophosphamide, cytarabine, dacarbazine, dactinomycin, daunorubicin, doxorubicin (adriamycin), epirubicin, etoposide, 5-fluorouracil, hexamethylmelamine, hydroxyurea, ifosfamide, irinotecan, leiucovorin, lomustine mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, vindesine, aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethynylestradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, oxaliplatin, pentostatin, Nphosphonoacetyl-L-aspartate (PALA), plicamycin, semustine, teniposide, testosterone propionate, thiotepa, trimethylmelamine, uridine, vinorelbine, epothilone, gemcitabine, taxotere, BCNU, CCNU, DTIC, 5-fluorouarcil, herceptin, avastin, erbitux, sorafenib, gleevec, iressa, tarceva, rapamycin, actinomycin D, sunitinib (sutent)".

The compounds of the present invention and/or where appropriate additional pharmacologically active substances or pharmaceutical compositions as described herein can be administered in a known manner. The route of administration may thereby be any route which effectively transports the active compound to the appropriate or desired site of action, for example orally or non-orally, in particular topically, transdermally, pulmonary, rectally, intravaginally, nasally or parenteral or by implantation. Oral administration is preferred.

The compounds of the present invention and/or where appropriate additional pharmacologically active substances or pharmaceutical compositions as described herein can be administered as liquid, semisolid and solid medicinal forms. This takes place in the manner suitable in each case in the form of aerosols, powders, dusting powders and epipastics, tablets including coated tablets, emulsions, foams, solutions, suspensions, gels, ointments, pastes, pills, pastilles, capsules or suppositories. They can be administered in a suitable dosage form to the skin, epicutaneously as solution, suspension, emulsion, foam, ointment, paste or plaster; via the oral and lingual mucosa, buccally, lingually or sublingually as tablet, pastille, coated tablet, linctus or gargle; via the gastric and intestinal mucosa, enterally as tablet, coated tablet, capsule, solution, suspension or emulsion; via the rectal mucosa, rectally as suppository, rectal capsule or ointment; via the nasal mucosa, nasally as drops, ointments or spray; via the bronchial and alveolar epithelium, by the pulmonary route or by inhalation as aerosol or inhalant; via the conjunctiva, conjunctivally as eyedrops, eye ointment, eye tablets, lamellae or eye lotion; via the mucosa of the genital organs, intravaginally as vaginal suppositories, ointments and douche, by the intrauterine route as uterine pessary; via the urinary tract, intraurethrally as irrigation, ointment or bougie; into an artery, intraarterially as injection; into a vein, intravenously as injection or -infusion; into the skin, intracutaneously as injection or implant; under the skin, subcutaneously as injection or implant; into the muscle, intramuscularly as injection or implant; into the abdominal cavity, intraperitoneally as injection or infusion.

As already explained above, the compounds of the invention can also be combined with other pharmaceutically active substances. It is possible for the purpose of a combination therapy to administer the individual active ingredients simultaneously or separately, in particular either by the same route (for example orally) or by separate routes (for example orally and as injection). They may be present and administered in identical or different amounts in a unit dose. It is also possible to use a particular dosage regimen when this appears appropriate. It is also possible in this way to combine a plurality of the novel compounds according to the invention with one another.

The compounds of the invention and/or where appropriate additional pharmacologically active substances are converted into a form which can be administered and are mixed where appropriate with pharmaceutically acceptable carriers and/or auxiliaries and/or diluents. Suitable excipients and carriers are described for example in Zanowiak P, Ullmann's Encyclopedia of Industrial Chemistry 2005, Pharmaceutical Dosage Forms, 1-33; Spiegel A J et al., Journal of Pharmaceutical Sciences 1963, 52:917-927; Czetsch-Lindenwald H, Pharm. Ind. 1961, 2:72-74; Fiedler H P, Lexikon der Hilfsstoffe für Pharmazie, Kosmetik and angrenzende Gebiete 2002, Editio Cantor Verlag, p65-68.

Oral administration can take place for example in solid form as tablet, capsule, gel capsule, coated tablet, granulation or powder, but also in the form of a drinkable solution or emulsion. The compounds of the invention can for oral administration be combined with known and ordinarily used, physiologically acceptable auxiliaries and carriers, such as, for example, gum arabic, talc, starch, sugars such as, for example, mannitol, methylcellulose, lactose, gelatin, surface-active agents, magnesium stearate, cyclodextrins, aqueous or nonaqueous carriers, diluents, dispersants, emulsifiers, lubricants, preservatives and flavorings (e.g. essential oils). The compounds of the invention can also be dispersed in a microparticulate, e.g. nanoparticulate, composition.

Non-oral administration can take place for example by intravenous, subcutaneous, intramuscular injection of sterile aqueous or oily solutions, suspensions or emulsions, by means of implants or by ointments, creams or suppositories. Administration as sustained release form is also possible where appropriate. Implants may comprise inert materials, e.g. biodegradable polymers or synthetic silicones such as, for example, silicone rubber. Intravaginal administration is possible for example by means of vaginal rings. Intrauterine administration is possible for example by means of diaphragms or other suitable intrauterine devices. Transdermal administration is additionally provided, in particular by means of a formulation suitable for this purpose and/or suitable means such as, for example, patches.

The dosage may vary within a wide range depending on type and/or severity of the disease, physiological and/or pathological condition, the mode of administration, the age, gender, bodyweight and sensitivity of the subject to be treated. It is within the ability of a skilled worker to determine a "pharmacologically effective amount" of a compound of the invention and/or additional pharmacologically active substance. Administration can take place in a single dose or a plurality of separate dosages.

A suitable unit dose is, for example, from 0.001 mg to 100 mg of the active ingredient, i.e. at least one compound of the invention and, where appropriate, at least one additional pharmacologically active substance, per kg of a patient's bodyweight.

In another aspect, the present invention relates to a pharmaceutical composition comprising a pharmacologically active amount of at least one compound of the invention, preferably a compound of the invention selected from the group consisting of:
compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 66, 67, 68, 69, 70, 71, 72, 73, 74, 75, 76, 77, 78, 80, 81, 82, 83, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773 and/or compound 774.

In a further aspect, such a pharmaceutical composition additionally comprises at least one pharmaceutically acceptable carrier and/or auxiliary and/or comprises at least one further pharmacologically active substance.

In a preferred embodiment, such further pharmacologically active substance is selected from the group consisting of:"DNA topoisomerase I and/or II inhibitors, DNA intercalators, alkylating agents, microtubuli destabilizers, hormone and/or growth factor receptor agonists and/or antagonists, antibodies against growth factors and their receptors, kinase inhibitors, antimetabolites" and preferably is selected from the group consisting of:"asparaginase, bleomycin, carboplatin, carmustine, chlorambucil, cisplatin, colaspase, cyclophosphamide, cytarabine, dacarbazine, dactinomycin, daunorubicin, doxorubicin (adriamycin), epirubicin, etoposide, 5-fluorouracil, hexamethylmelamine, hydroxyurea, ifosfamide, irinotecan, leucovorin, lomustine mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, vindesine, aminoglutethimide, L-asparaginase, azathioprine, 5-azacytidine cladribine, busulfan, diethylstilbestrol; 2',2'-difluorodeoxycytidine, docetaxel, erythrohydroxynonyladenine, ethynylestradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, oxaliplatin, pentostatin, N-phosphonoacetyl-L-aspartate (PALA), plicamycin, semustine, teniposide, testosterone propionate, thiotepa, trimethylmelamine, uridine, vinorelbine, epothilone, gemcitabine, taxotere, BCNU, CCNU, $DTIC_{1-5}$-fluorouarcil, herceptin, avastin, erbitux, sorafenib, gleevec, iressa, tarceva, rapamycin, actinomycin D, sunitinib (sutent)".

Concerning the pharmaceutical compositions of the invention, at least one of the compounds of the invention is present in a pharmacologically effective amount, preferably in a unit dose, e.g. the aforementioned unit dose, specifically and preferably in an administration form which makes oral administration possible. Furthermore, reference may be made to that already said in connection with the possible uses and administrations of the compounds of the invention.

In a further aspect of the present invention, the object of the invention has surprisingly been solved by providing a kit comprising a pharmacologically active amount of at least one compound of the invention as detailed above and/or at least one pharmaceutical composition as detailed above and a pharmacologically active amount of at least one further pharmacologically active substance as defined above.

General Synthesis Methods for the Compounds of the Invention:

The processes for preparing the substituted pyrido[2,3-b]pyrazine compounds of the invention are illustrated below.

The compounds of the invention are obtainable according to the following schemes (schemes 1-12) and corresponding processes known to those skilled in the art:

The definition of the R1 to R18 and X2, X3, X9 and X41 radicals shown in the following schemes corresponds to the substituents defined above in connection with the general formula (I), for example Z radicals, R radicals, X radicals, Y radicals, etc. The individual assignment can be accomplished in a simple manner by the person skilled in the art on the basis of his or her average technical knowledge.

Scheme 1

1st stage

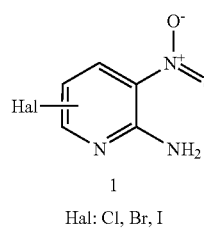

1

Hal: Cl, Br, I

2  3

2nd stage/
LC-chromatography

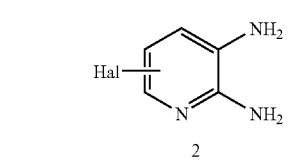 + 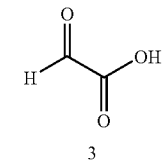

4a  4b

3rd and 4th stage

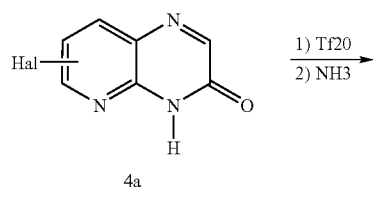

4a

3rd and 4th stage

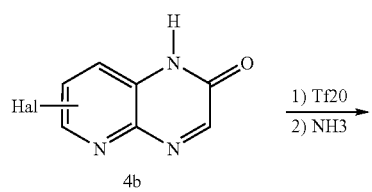

4b

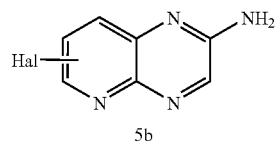

5b

Precursors for selected examples of the compounds of the invention in which the substituent R6 is not to be H are, for example, obtainable by the process in scheme 2 or a corresponding process known to those skilled in the art.

Scheme 2

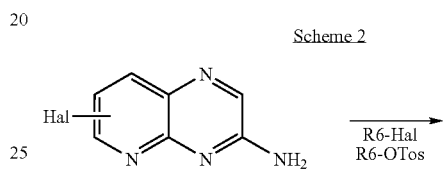

5a

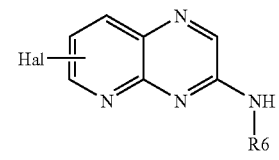

6a

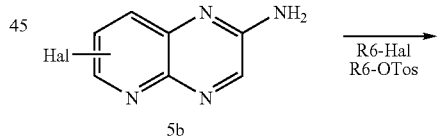

5b

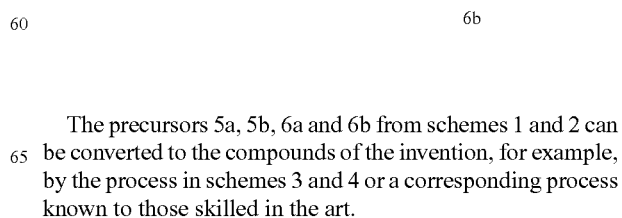

6b

The precursors 5a, 5b, 6a and 6b from schemes 1 and 2 can be converted to the compounds of the invention, for example, by the process in schemes 3 and 4 or a corresponding process known to those skilled in the art.

Scheme 3
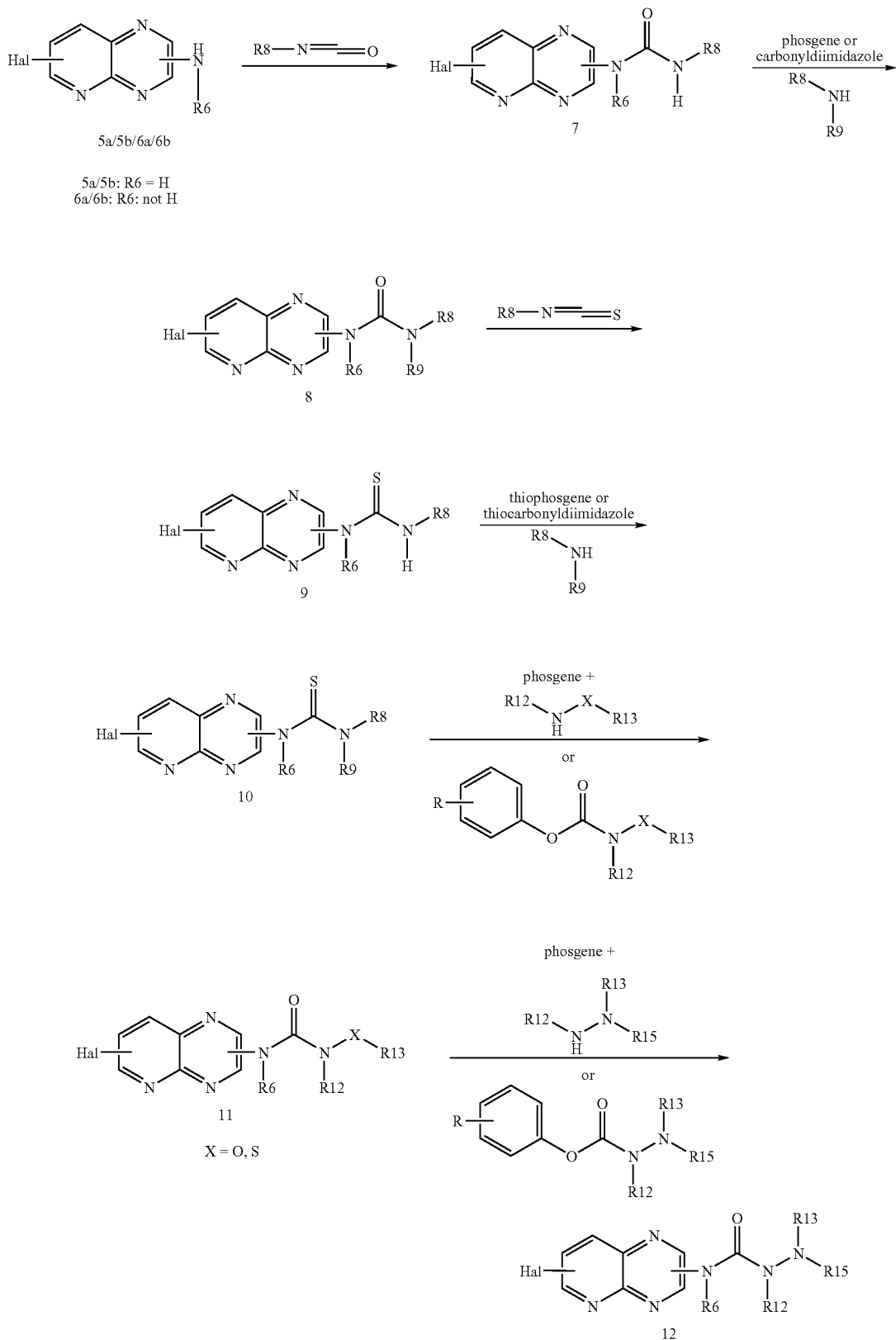

Scheme 4

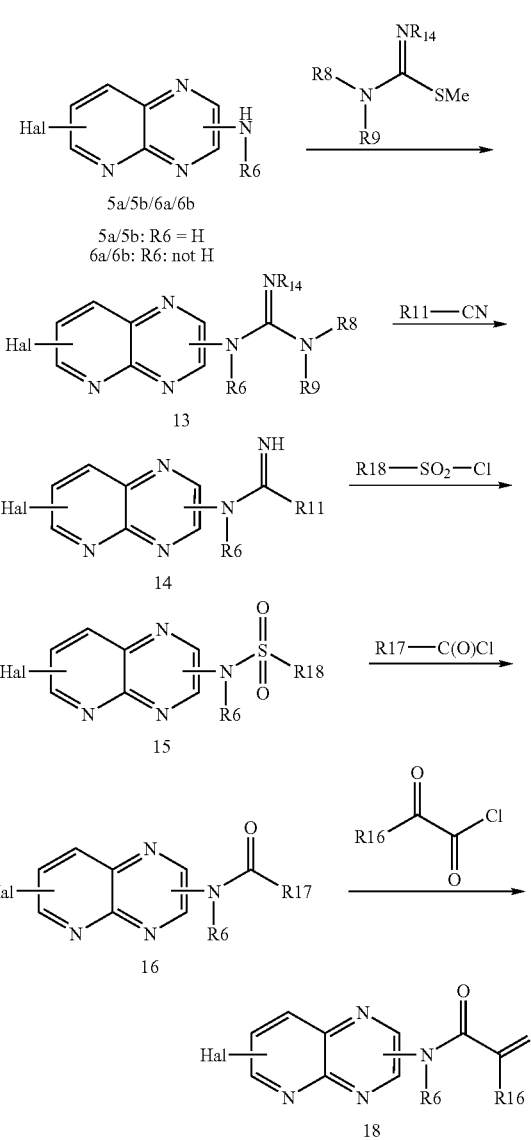

Selected examples of the compounds of the invention in which the substituents R1, R2 and/or R5 may be selected substituted aryl, heteroaryl, alkyl, alkenyl or alkynyl radicals are, for example, obtainable by the process in scheme 5 or corresponding processes known to those skilled in the art.

Scheme 5

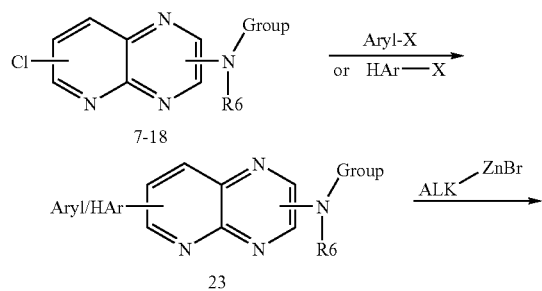

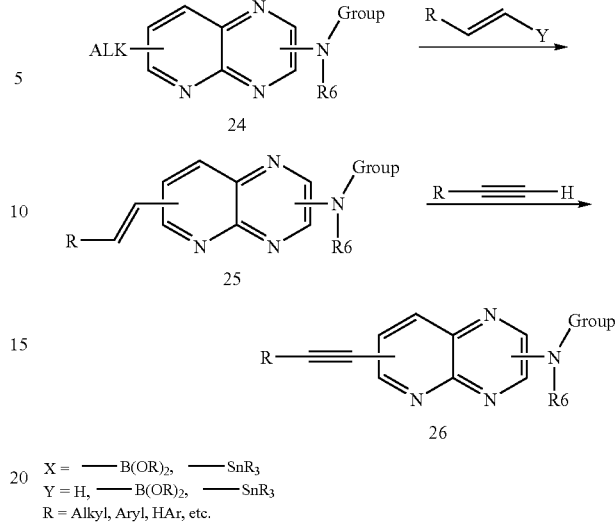

$X = -B(OR)_2, -SnR_3$
$Y = H, -B(OR)_2, -SnR_3$
$R = Alkyl, Aryl, HAr, etc.$

Selected examples of the compounds of the invention in which the substituents R1, R2 and/or R5 may be selected NH2 or NX2X3-substituted radicals are, for example, obtainable by the process in scheme 6 or corresponding processes known to those skilled in the art.

Scheme 6

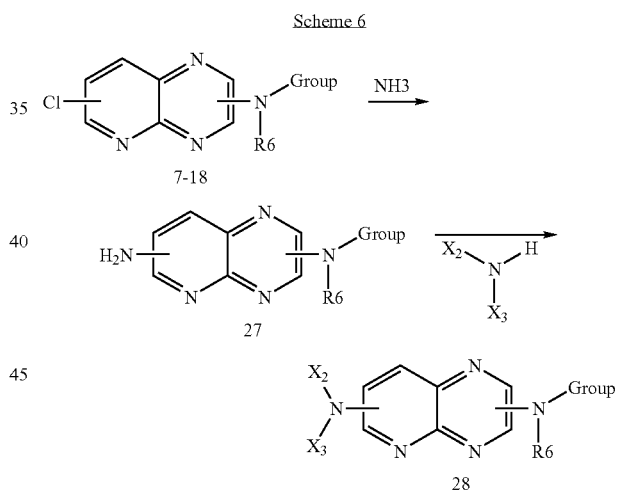

Selected examples of the compounds of the invention in which the substituents R1 may be selected O—X9 or S—X41-substituted radicals are, for example, obtainable by the process in scheme 7 or corresponding processes known to those skilled in the art.

Scheme 7

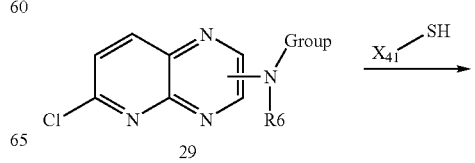

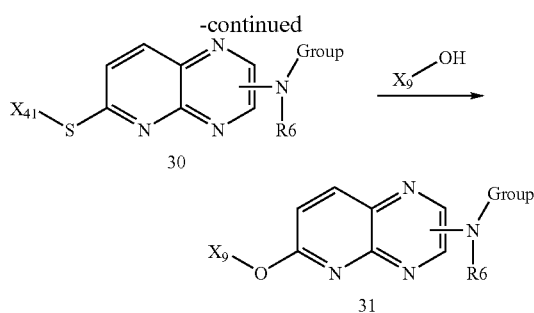
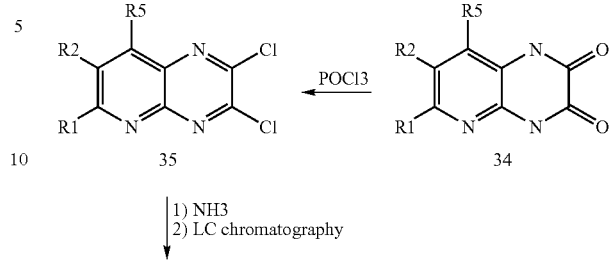

Precursors for selected examples of the compounds of the invention in which the substituents R3 and R4 are to be substituted by hydrogen are, for example, obtainable by the process in scheme 8 or a corresponding process known to those skilled in the art.

Scheme 8

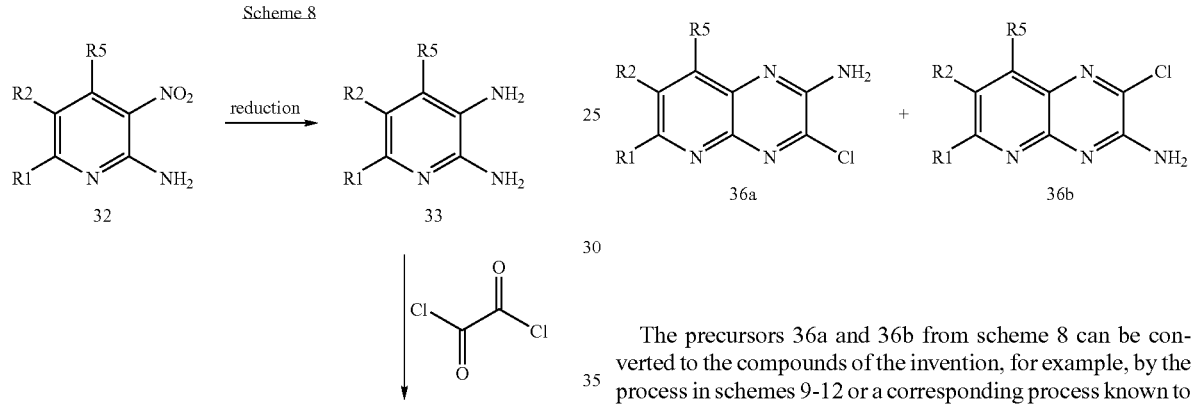

The precursors 36a and 36b from scheme 8 can be converted to the compounds of the invention, for example, by the process in schemes 9-12 or a corresponding process known to those skilled in the art.

Scheme 9

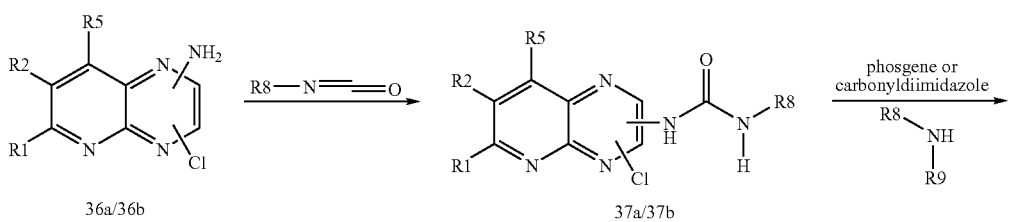

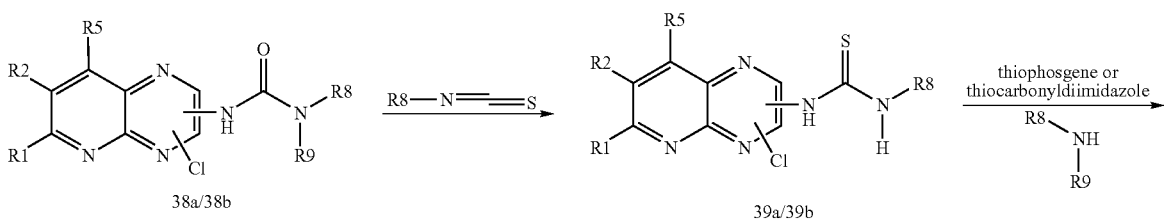

-continued
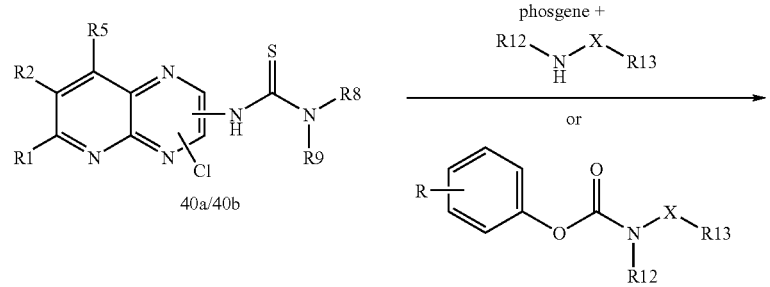
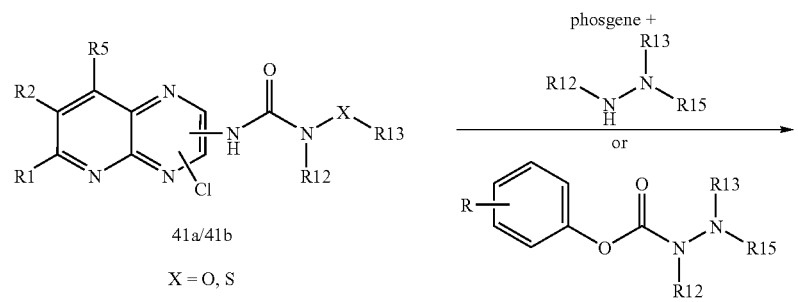
X = O, S
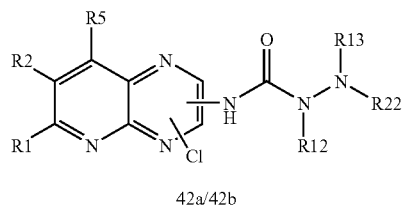
Scheme 10
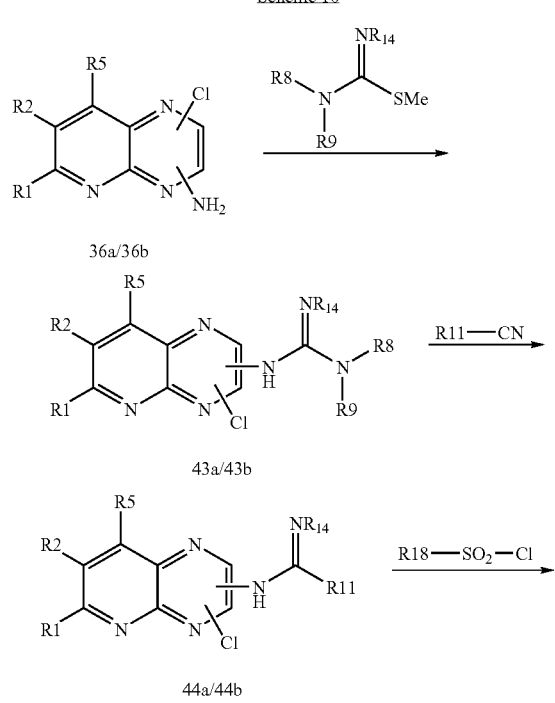
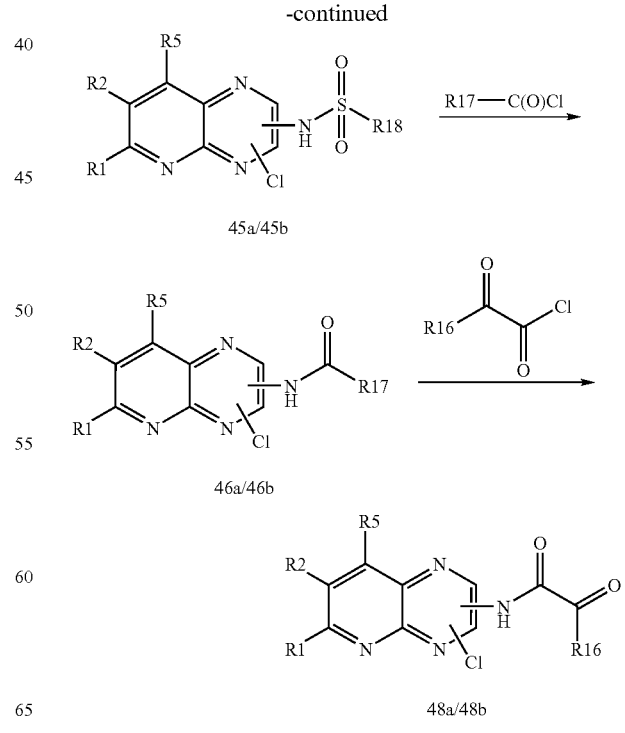

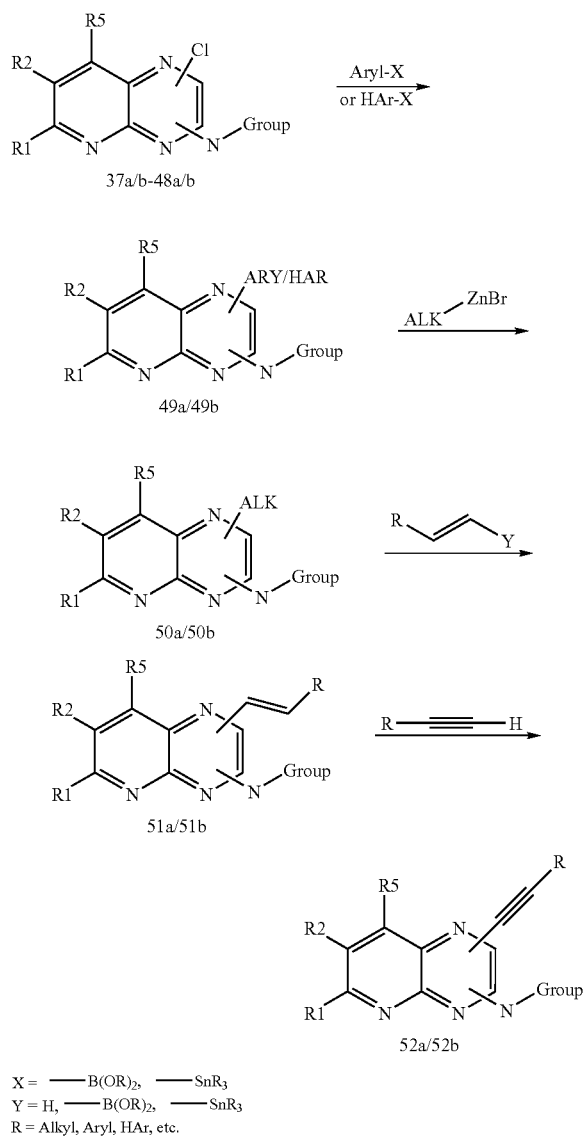

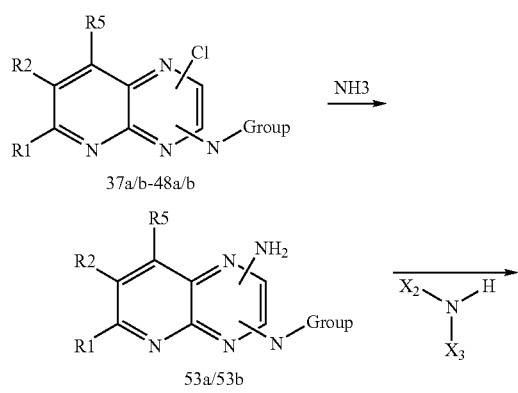

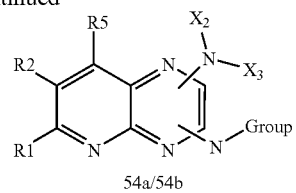

The starting compounds and intermediates are either commercially available or can be prepared by procedures known per se or known to those skilled in the art. The reactants 5-18 and 36-48 are valuable intermediates for the preparation of the compounds of the invention.

For the preparation of the starting compounds, intermediates and the compounds of the invention, reference is made inter alia to the patents WO 2004/104002 and WO 2004/104003, and also, for example, to the following primary literature whose contents are hereby incorporated into the disclosure of the present application:

1) Houben-Weyl, Methoden der Organischen Chemie, volume 4/1a, pp 343-350
2) Houben—Weyl, Methoden der Organischen Chemie, 4th ed., volume E 7b (part 2), p. 579
3) GB 1184848
4) EP 0 735 025
5) D. Catarzi, et al.; *J. Med. Chem.* 1996, 1330-1336
6) J. K. Seydel, et al.; *J. Med. Chem.* 1994, 3016-3022
7) Houben-Weyl, Methods of Organic Chemistry, Volume E 9c, pp. 231-235
8) Houben-Weyl/Science of Synthesis, Volume 16, p. 1269
9) C. L. Leese, H. N. Rydon *J. Chem. Soc.* 1955, 303-309;
10) T. S. Osdene, G. M. Timmis *J. Chem. Soc.* 1955, 2033-2035
11) W. He, et al. *Bioorg. Med. Chem. Lett.* 2003, 13, 3097-3100
12) M. S. A. El-Gaby, et al. *Indian J. Chem. Sect. B* 2001, 40, 195-200
13) M. R. Myers, et al. *Bioorg. Med. Chem. Lett.* 2003, 13, 3091-3096
14) A. R. Renslo, et al. *J. Amer. Chem. Soc.* 1999, 121, 7459-7460
15) C. O. Okafor, et al. *J. Heterocyclic Chem.* 1983, 20, 199-203
16) C. R. Hopkins, et al. *Tet. Lett.* 2004, 45, 8631-8633
17) J. Yin, et al. *Org. Lett.* 2002, 4, 3481-3484
18) O. A. El-Sayed, et al. *Arch. Pharm.* 2002, 335, 403-410
19) C. Temple, et al. *J. Med. Chem.* 1992, 35, 988-993
20) A. M. Thompson, et al. *J. Med. Chem.* 2000, 43, 4200-4211
21) N. A. Dales, et al. *Org. Lett.* 2001, 2313-2316
22) G. Dannhardt, et al. *Arch. Pharm.* 2000, 267-274
23) G. S. Poindexter, et al. *Bioorg. Med. Chem.* 2004, 12, 507-521
24) J.-M. Receveur, et al. *Bioorg. Med. Chem. Lett.* 2004, 14, 5075-5080
25) G. Heinisch, et al. *Arch. Pharm.* 1997, 207-210
26) K. Matsuno, et al. *J. Med. Chem.* 2002, 45, 4513-4523
27) A. M. Papini, et al. *J. Med. Chem.* 2004, 47, 5224-5229
28) J. Mindl, et al. *Collect. Czech. Chem. Commun.* 1983, 48, 900-905
29) S. Sasaki, et al. *J. Med. Chem.* 2003, 46, 113-124
30) B.-B. Zeng, et al. *Bioorg. Med. Chem. Lett.* 2004, 14, 5565-5568
31) Q. Wang, et al. *Synthetic Commun.* 2004, 34, 255-264

32) W. Mederski, et al. *Bioorg. Med. Chem. Lett.* 2003, 13, 13715-3718
33) R. J. Brown, et al. *Tetrahedron* 2004, 60, 4361-4375
34) L. Mao, et al. *Synthesis* 2004, 15, 2535-2539
35) M. Darabantu, et al. *Tetrahedron* 2005, 61, 2897-2905
36) E. Ford, et al. *Tet. Lett.* 2000, 41, 3197-3198
37) T. Shiota, et al. *J. Org. Chem.* 1999, 64, 453-457
38) E. C. Taylor, et al. *Synthetic Commun.* 1987, 17, 1865-1868
39) G. A. Molander, et al. *J. Org. Chem.* 2002, 67, 8424-8429
40) G. Hughes, et al. *Org. & Biomolecular Chem.* 2004, 2, 3363-3367
41) R. P. Tangallapally, et al. *J. Med. Chem.* 2004, 47, 5276-5283
42) R. H. Bradburry, et al. *J. Med. Chem.* 1997, 40, 996-1004
43) X. He, et al. *Bioorg. Med. Chem.* 2004, 12, 4003-4008
44) A. Gopalsamy, et al. *Bioorg. Med. Chem. Lett.* 2005, 15, 1591-1594
45) J.-F. Cheng, et al. *Bioorg. Med. Chem. Lett.* 2004, 14, 2411-2416
46) E. R. Parmee, et al. *Bioorg. Med. Chem. Lett.* 2004, 14, 43-46
47) G. Yang, et al. *Synthetic Commun.* 2006, 36, 5611-5619
48) H. B. Woo, et al. *Bioorg. Med. Chem. Lett.* 2005, 15, 3782-3786
49) J. F. Miravet, et al. *Org. Lett.* 2005, 7, 4791-4794
50) A. L. Castelhano, et al. *Bioorg. Med. Chem. Lett.* 2005, 15, 1501-1504
51) Y. Lu, et al. *Bioorg. Med. Chem. Lett.* 2006, 16, 915-919
52) J. W. Szewczyk, et al. *Bioorg. Med. Chem. Lett.* 2006, 16, 3055-3060
53) J. Li, et al. *Bioorg. Med. Chem. Lett.* 2006, 14, 2209-2224
54) J. E. Dowling, et al. *Bioorg. Med. Chem. Lett.* 2005, 16, 4809-4813.

Under some of the reaction conditions specified, OH, SH and $NH_2$ groups may possibly enter into undesired side reactions. It is therefore preferred to provide them with protecting groups or, in the case of $NH_2$, to replace it with $NO_2$, and then to eliminate the protecting group or to reduce the $NO_2$ group. For instance, in a modification of the above-described processes, at least one OH group in the starting compounds can be replaced, for example, by a benzyloxy group, and/or at least one SH group can be replaced, for example, by an S-benzyl group and/of at least one $NH_2$ group can be replaced, for example, by an NH-benzyl group or by an $NO_2$ group. Subsequently, at least one—preferably all—benzyloxy group(s) or NH-benzyl group(s) can be eliminated, for example, with hydrogen and palladium on carbon, and/or at least one—preferably all —S-benzyl group(s) can be eliminated, for example, with sodium in ammonia, and/or at least one—preferably all —$NO_2$ group(s) can be reduced, for example, with hydrogen and Raney nickel to $NH_2$.

Under some of the reaction conditions mentioned, OH, $NH_2$ and COOH groups may possibly enter into undesired side reactions. It is therefore preferred to convert starting compounds and intermediates which contain at least one OH group and/or at least one $NH_2$ group and/or at least one COOH group to corresponding carboxylic ester and carboxamide derivatives. In a modification of the above-described processes, starting compounds and intermediates which have at least one OH group and/or which have at least one $NH_2$ group can be converted to carboxylic ester or carboxamide derivatives by reaction with an activated carboxylic acid group, for example a carbonyl chloride group. In a modification of the above-described processes, starting compounds and intermediates which contain at least one COOH can be converted to carboxylic ester or carboxamide derivatives by reaction with an activating agent, for example thionyl chloride or carbonyldiimidazole, and subsequent reaction with a suitable alcohol or amine. Subsequently, at least one—preferably all—carboxylic ester or carboxamide group(s) in the starting compounds and intermediates can be detached, for example, with dilute aqueous acids or bases, in order to release one—preferably all —OH group(s) and/or $NH_2$ group(s) and/or COOH group(s).

The compounds of the invention were named using the AutoNom 2000 software (ISIS™/Draw 2.5; MDL).

The contents of all cited references are hereby incorporated by reference in their entirety. The invention is explained in more detail by means of the following examples without, however, being restricted thereto.

EXAMPLES

I) Preparation and Physicochemical Characterization of Selected Compounds of the Invention The general synthesis methods which are based on the synthesis schemes 1-12 were used to synthesize the following compounds of the invention. In addition, their NMR spectroscopy data and mass spectrometry data and melting points are included, respectively.

The precursors used for the preparation of the compounds of the invention can—unless stated otherwise—be synthesized by processes known to those skilled in the art.

The chemicals and solvents used were obtained commercially from the conventional suppliers (Acros, Aldrich, Fluka, Lancaster, Maybridge, Merck, Sigma, TCI, etc.) or synthesized.

Example 1

1-(6-Chloro-pyrido[2,3-b]pyrazin-3-yl)-3-ethyl-urea

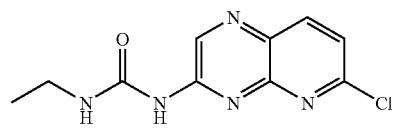

A total of 5.0 g 6-Chloro-pyrido[2,3-b]pyrazin-3-ylamine (27.7 mmol; 1 eq) was suspended in 150 mL of dry 1,4-dioxane. 2.63 g (33.2 mmol; 1.2 eq) ethyl isocyanate was added and the reaction mixture was stirred at 100° C. for 4 hours. Additional 1.97 g (27.7 mmol; 1 eq) of ethyl isocyanate were added and the resulting solution was stirred at 100° C. for further 4 hours. After cooling to room temperature, the precipitate was filtered of and dried in vacuo to afford 6.5 g (93.3% yield) of 1-(6-Chloro-pyrido[2,3-b]pyrazin-3-yl)-3-ethyl-urea.

m.p.:240° C.

ESI-MS:found:252.0 (M+H$^+$); calculated:251.68 g/mol

1H-NMR (DMSO-d6) δ=10.38 (s, 1H), 9.00 (s, 1H), 8.42 (m, 2H), 7.69 (d, 1H), 3.30 (m, 2H), 1.15 (t, 3H) ppm

Example 2

1-(6-Chloro-pyrido[2,3-b]pyrazin-3-yl)-3-ethyl-thiourea

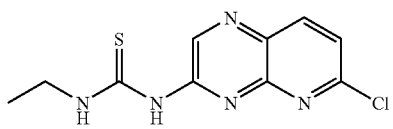

A total of 5.0 g 6-Chloro-pyrido[2,3-b]pyrazin-3-ylamine (27.7 mmol; 1 eq) was dissolved in 150 mL of dry DMF. 1.32 g NaH (60% dispersion in mineral oil; 33.2 mmol; 1.2 eq) was added and the dark brown solution was stirred at room temperature for 1 hour. 2.4 g (27.7 mmol; 1 eq) ethyl isothiocyanate was then added and the resulting mixture was stirred at room temperature for 3 h. The reaction mixture was then poured into 500 mL of water. The solution was neutralized with 1 N HCl whereas the product crystallizes. The brown solid was filtered of and recrystallised from dichloromethane/diethyl ether to afford 3.6 g (48.5% yield) of 1-(6-Chloro-pyrido[2,3-b]pyrazin-3-yl)-3-ethyl-thiourea.
m.p.:215° C.
ESI-MS:found:268.1 (M+H$^+$); calculated:267.74 g/mol
1H-NMR (DMSO-d6) δ=11.55 (s, 1H), 11.40 (s, 1H), 8.88 (s, 1H), 8.44 (d, 1H), 7.75 (d, 1H), 3.75 (m, 2H), 1.30 (t, 3H) ppm

Example 3

4-(3-Amino-pyrido[2,3-b]pyrazin-6-yl)-2-methoxyphenol

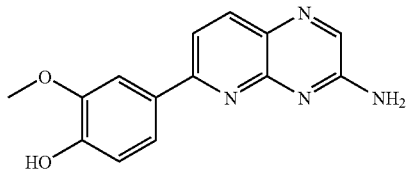

To a suspension of 1.13 g 6-Chloro-pyrido[2,3-b]pyrazin-3-ylamine (5.94 mmol; 1 eq) and 1.67 g 2-Methoxy-4-(4,4,5,5-tetramethyl-[1,3,2]dioxaborolan-2-yl)-phenol (6.55 mmol; 1.1 eq.) in ethylene glycol dimethyl ether (45 mL) under Ar, a solution of 6.29 g sodium carbonate (59.3 mmol; 10 eq.) in water (20 mL) and a suspension of 378 mg FluoroFlash catalyst (0.24 mmol; 0.04 eq.) in undecafluoro(trifluoromethyl)cyclohexane (45 mL) were added. The mixture was heated to 75° C. for 5 hours. Additional 0.76 g (2.97 mmol; 0.5 eq) of 2-Methoxy-4-(4,4,5,5-tetramethyl-[1,3,2]dioxaborolan-2-yl)-phenol were added and the resulting mixture was stirred at 75° C. for 7.5 hours. After cooling to room temperature, the aqueous and organic phase were separated from the fluorous phase and concentrated in vacuo. The residue was dissolved in methanol and methylene dichloride and filtered. The black solution was again concentrated in vacuo. The residue was taken up in water and the resulting solution was neutralized with 1 N HCl whereas the product crystallizes. The brown solid was filtered of, washed with water and dried in vacuo to afford 1.5 g (80.2% yield) of 4-(3-Amino-pyrido[2,3-b]pyrazin-6-yl)-2-methoxy-phenol.

ESI-MS:found:269.0 (M+H$^+$); calculated:268.28 g/mol
1H-NMR (DMSO-d6) δ=9.47 (s, 1H), 8.29 (s, 1H), 8.15 (d, 1H), 7.91 (d, 1H), 7.84 (s, 1H), 7.67 (d, 1H), 7.34 (s, 2H), 6.90 (d, 1H), 3.89 (s, 3H) ppm

Example 4

Compound 1—1-Ethyl-3-(6-p-tolylamino-pyrido[2,3-b]pyrazin-3-yl)-urea

A total of 100 mg 1-(6-Chloro-pyrido[2,3-b]pyrazin-3-yl)-3-ethyl-urea/example 1 (0.40 mmol; 1 eq) was suspended in 3 ml of n-propanole. To this suspension 51 mg p-toluidine (0.48 mmol; 1.2 eq) was added and the reaction mixture was stirred at 100° C. for 5 hours. After cooling to room temperature, the precipitate formed was filtered and washed with diethyl ether. The brown crystals were dissolved in dichloromethane, washed with 0.5 N HCl and NaHCO3. The solution was dried over MgSO4 and the solvent was removed to afford 74 mg (52.4% yield) of 1-Ethyl-3-(6-p-tolylamino-pyrido[2,3-b]pyrazin-3-yl)-urea (compound 1) as yellow powder.
m.p.:235° C.
ESI-MS:found:323.0 (M+H$^+$); calculated:322.37 g/mol
1H-NMR (DMSO-d6) δ=9.97 (s, 1H), 9.14 (s, 1H), 8.72 (s, 1H), 8.23 (s, 1H), 8.00 (d, 1H), 7.86 (d, 2H), 7.16 (d, 2H), 7.09 (d, 1H), 3.27 (m, 2H), 1.18 (t, 3H) ppm

Example 5

Compound 2—1-[6-(4-Amino-3-methoxy-phenyl)-pyrido[2,3-b]pyrazin-3-yl]-3-ethyl-urea To a suspension of 100 mg 1-(6-Chloro-pyrido[2,3-b]pyrazin-3-yl)-3-ethyl-urea/example 1 (0.39 mmol; 1 eq) and 108 mg 2-Methoxy-4-(4,4,5,5-tetramethyl-[1,3,2]dioxaborolan-2-yl)-phenylamine (0.43 mmol; 1.1 eq.) in ethylene glycol dimethyl ether (4 mL) under Ar, a solution of 414 mg sodium carbonate (3.9 mmol; 10 eq.) in water (1.5 mL) and a suspension of 12 mg FluoroFlash catalyst (0.01 mmol; 0.02 eq.) in undecafluoro(trifluoromethyl)cyclohexane (4 mL) were added. The mixture was heated to 60° C. for 4 hours. After cooling to room temperature, the aqueous and organic phase were separated from the fluorous phase and concentrated in vacuo. The residue was dissolved in methanol and methylene dichloride and filtered. The black solution was again concentrated in vacuo. The residue was taken up in water and the resulting solution was neutralized with 1 N HCl whereas the product crystallizes. The brown solid was filtered of, washed with water and dried in vacuo to afford 120 mg (86.4% yield) of 1-[6-(4-Amino-3-methoxy-phenyl)-pyrido[2,3-b]pyrazin-3-yl]-3-ethyl-urea (compound 2).
m.p.:>310° C.
ESI-MS:found:339.1 (M+H$^+$); calculated:338.37 g/mol
1H-NMR (DMSO-d6) δ=10.15 (s, 1H), 8.88 (s, 1H), 8.55 (s, 1H), 8.26 (d, 1H), 8.13 (d, 1H), 7.78 (s, 1H), 7.71 (d, 1H), 6.75 (s, 1H), 5.38 (d, 2H), 3.91 (s, 3H), 3.27 (m, 2H), 1.18 (t, 3H) ppm

Example 6

Compound 3—1-[6-(4-Hydroxy-3-methoxy-phenyl)-pyrido[2,3-b]pyrazin-3-yl]-3-phenyl-urea In dry 1,4-dioxane (6 mL) was stirred 111.3 mg 4-(3-Amino-pyrido[2,3-b]pyrazin-6-yl)-2-methoxy-phenol/example 3 (0.35 mmol; 1 eq.). The mixture was heated to 70° C. 120 mg (0.99 mmol; 2.8 eq) Phenyl isocyanate was added and the reaction mixture was stirred at 70° C. for 4 hours. Additional 64 mg (0.53 mmol; 1.5 eq) of Phenyl isocyanate were added and the resulting mixture was stirred at 70° C. for 4 hours. After cooling to room temperature, the mixture was concentrated in vacuo and the residue was stirred in ethanol. Diethyl ether was added and the product was collected by filtration. The solid was washed with ethanol, methylene dichloride and diethyl ether and dried in vacuo to afford 92.5 mg (67.7% yield) of 1-[6-(4-Hydroxy-3-methoxy-phenyl)-pyrido[2,3-b]pyrazin-3-yl]-3-phenyl-urea (compound 3).

m.p.:240° C.
ESI-MS:found:388.3 (M+H$^+$); calculated:387.40 g/mol
1H-NMR (DMSO-d6) δ=10.98 (s, 1H), 10.45 (s, 1H), 9.62 (s, 1H), 9.07 (s, 1H), 8.40 (d, 1H), 8.26 (d, 1H), 7.96 (s, 1H), 7.82 (d, 1H), 7.61 (d, 2H), 7.39 (t, 2H), 7.11 (t, 1H), 6.96 (d, 1H), 3.94 (s, 3H) ppm The following examples were synthesized according to the Compounds 1-3 and the general schemes 1-12:

Example 7

Compound 4—1-Ethyl-3-(6-phenyl-pyrido[2,3-b]pyrazin-3-yl)-urea

ESI-MS:found:294.1 (M+H$^+$); calculated:293.0 g/mol
$^1$H-NMR (DMSO-d$_6$) δ=10.27 (s, 1H); 8.97 (s, 1H); 8.65 (s, 1H); 8.45 (d, 1H); 8.29 (dd, 2H); 8.26 (d, 1H); 7.53-7.60 (m, 3H); 3.32-3.36 (m, 2H); 1.20 (t, 3H) ppm.

Example 8

Compound 5—1-Ethyl-3-[6-(4-hydroxy-3-methoxy-phenyl)-pyrido[2,3-b]pyrazin-3-yl]-urea ESI-MS:found:340.2 (M+H$^+$); calculated:339.0 g/mol
$^1$H-NMR (DMSO-d$_6$) δ=10.21 (s, 1H); 9.58 (s, 1H); 8.94 (s, 1H); 8.55 (s, 1H); 8.35 (d, 1H); 8.20 (dd, 1H); 7.89 (d, 1H); 7.78 (dd, 1H); 6.94 (d, 1H); 3.92 (s, 3H); 3.29-3.35 (m, 2H); 1.19 (t, 3H) ppm.

Example 9

Compound 6—1-[6-(4-Chloro-phenyl)-pyrido[2,3-b]pyrazin-3-yl]-3-ethyl-urea m.p.:276° C.
ESI-MS:found:328.2 (M+H$^+$); calculated:327.0 g/mol
$^1$H-NMR (DMSO-d$_6$) δ=10.29 (s, 1H); 8.97 (s, 1H); 8.65 (s, 1 H); 8.45 (d, 1H); 8.33 (dd, 1H); 8.27 (d, 1H); 7.64 (d, 2H); 3.31-3.35 (m, 2H); 1.19 (t, 3H) ppm.

Example 10

Compound 7—1-Ethyl-3-(6-pyridin-4-yl-pyrido[2,3-b]pyrazin-3-yl)-urea m.p.:211° C.
ESI-MS:found:295.2 (M+H$^+$); calculated:294.0 g/mol
$^1$H-NMR (DMSO-d$_6$) δ=10.35 (s, 1H); 9.03 (s, 1H); 8.80 (d, 2 H); 8.62 (s, 1H); 8.54 (d, 1H); 8.36 (d, 1H); 8.23 (d, 2H); 3.31-3.36 (m, 2H); 1.20 (t, 3H) ppm.

Example 11

Compound 8—1-[6-(3-Chloro-4-hydroxy-5-methoxy-phenyl)-pyrido[2,3-b]pyrazin-3-yl]-3-ethyl-urea ESI-MS:found:374.3 (M+H$^+$); calculated:373.0 g/mol
$^1$H-NMR (DMSO-d$_6$) δ=10.23 (s, 1H); 10.00 (s, 1H); 8.97 (s, 1H); 8.53 (s, 1 H); 8.38 (d, 1H); 8.28 (d, 1H); 7.94 (d, 1H); 7.87 (d, 1H); 3.98 (s, 3H); 3.31-3.35 (m, 2H); 1.19 (t, 3H) ppm.

Example 12

Compound 9—1-[6-(3,5-Dichloro-4-hydroxy-phenyl)-pyrido[2,3-b]pyrazin-3-yl]-3-ethyl-urea m.p.:>300° C.
ESI-MS:found:378.4 (M+H$^+$); calculated:377.0 g/mol
$^1$H-NMR (DMSO-d$_6$) δ=10.00 (s, 1H); 8.71 (s, 1H); 8.66 (s, 1H); 8.05 (d, 1 H); 8.00 (s, 2H); 7.92 (d, 1H); 3.31-3.35 (m, 2H); 1.18 (t, 3H) ppm.

Example 13

Compound 10—1-Ethyl-3-[6-(1-methyl-1H-pyrazol-4-yl)-pyrido[2,3-b]pyrazin-3-yl]-urea m.p.:211° C.
ESI-MS:found:298.2 (M+H$^+$); calculated:297.0 g/mol
$^1$H-NMR (DMSO-d$_6$) δ=10.17 (s, 1H); 8.85 (s, 1H); 8.65 (s, 1H); 8.51 (s, 1H); 8.29 (d, 1 H); 8.19 (s, 1H); 7.91 (d, 1H); 3.94 (s, 3H); 3.31-3.35 (m, 2H); 1.19 (t, 3H) ppm.

Example 14

Compound 11—1-Ethyl-3-[6-(4-methoxy-phenyl)-pyrido[2,3-b]pyrazin-3-yl]-urea m.p.:244° C.
ESI-MS:found:323.9 (M+H$^+$); calculated:323.0 g/mol
$^1$H-NMR (DMSO-d$_6$) δ=10.22 (s, 1H); 8.92 (s, 1H); 8.65 (s, 1H); 8.38 (d, 1 H); 8.27 (d, 2H); 8.20 (d, 1H); 7.12 (d, 2H); 3.86 (s, 3H); 3.31-3.36 (m, 2H); 1.19 (t, 3H) ppm.

Example 15

Compound 12—1-Ethyl-3-[6-(3-isopropoxy-phenylamino)-pyrido[2,3-b]pyrazin-3-yl]-urea ESI-MS:found:367.0 (M+H$^+$); calculated:366.0 g/mol
$^1$H-NMR (DMSO-d$_6$) δ=10.02 (s, 1H); 9.77 (s, 1H); 8.67 (s, 1H); 8.47 (s, 1 H); 8.03 (d, 1H); 7.97 (s, 1H); 7.20-7.22 (m, 2H); 7.11 (d, 1H); 6.57-6.60 (m, 1H); 4.57-4.63 (m, 1H); 3.26-3.31 (m, 2H); 1.30 (d, 6H); 1.19 (t, 3H) ppm.

Example 16

Compound 13—1-Ethyl-3-(6-phenylamino-pyrido[2,3-b]pyrazin-3-yl)-urea m.p.:202° C.
ESI-MS:found:309.1 (M+H$^+$); calculated:308.0 g/mol
$^1$H-NMR (DMSO-d$_6$) δ=10.00 (s, 1H); 9.81 (s, 1H); 8.74 (s, 1H); 8.22 (s, 1 H); 8.03 (d, 1H); 7.98 (d, 2H); 7.35 (dd, 2H); 7.13 (d, 1H); 7.02 (dd, 1H); 3.24-3.30 (m, 2H); 1.18 (t, 3H) ppm.

Example 17

Compound 14—1-Phenyl-3-(6-phenylamino-pyrido[2,3-b]pyrazin-3-yl)-urea m.p.:251° C.
ESI-MS:found:357.3 (M+H$^+$); calculated:356.0 g/mol
$^1$H-NMR (DMSO-d$_6$) δ=11.13 (s, 1H); 10.31 (s, 1H); 9.90 (s, 1H); 8.75 (s, 1H); 8.08 (d, 1H); 8.06 (d, 2); 7.59 (d, 2H); 7.37-7.42 (m, 4H); 7.18 (d, 1H); 7.09 (dd, 1H); 7.06 (dd, 1H) ppm.

Example 18

Compound 15—1-[6-(3,5-Dichloro-4-hydroxy-phenylamino)-pyrido[2,3-b]pyrazin-3-yl]-3-ethyl-urea m.p.:272° C.
ESI-MS:found:393.3 (M+H$^+$); calculated:392.0 g/mol
$^1$H-NMR (DMSO-d$_6$) δ=10.06 (s, 1H); 9.85 (s, 1H); 9.72 (s, 1H); 8.69 (s, 1H); 8.42 (s, 1H); 8.09 (s, 2H); 8.04 (d, 1H); 7.04 (d, 1H); 3.25-3.30 (m, 2H); 1.22 (t, 3H) ppm.

Example 19

Compound 16—1-[6-(4-Hydroxy-3-methoxy-phenyl)-pyrido[2,3-b]pyrazin-3-yl]-3-propyl-urea m.p.:220-222° C.
ESI-MS:found:354.1 (M+H$^+$); calculated:353.38 g/mol
$^1$H-NMR (DMSO-d$_6$) δ=10.25 (s, 1H), 9.59 (s, 1H), 8.90 (bs, 1H), 8.87 (s, 1H), 8.34 (d, 1H), 8.20 (d, 1H), 7.92 (s, 1H), 7.77 (d, 1H), 6.94 (d, 1H), 3.91 (s, 3H), 3.27-3.33 (m, 2H), 1.60 (m, 2H), 1.04 (t, 3H) ppm

Example 20

Compound 17—1-Cyclohexyl-3-[6-(4-hydroxy-3-methoxy-phenyl)-pyrido[2,3-b]pyrazin-3-yl]-urea m.p.:232-235° C.
ESI-MS:found:394.2 (M+H$^+$); calculated:393.44 g/mol
$^1$H-NMR (DMSO-d$_6$) δ=10.19 (s, 1H), 9.60 (s, 1H), 9.10 (bs, 1H), 8.85 (s, 1H), 8.34 (d, 1H), 8.21 (d, 1H), 7.94 (s, 1H), 7.77 (d, 1H), 6.94 (d, 1H), 3.91 (s, 3H), 3.78 (m, 1H), 1.75-1.85 (m, 4H), 1.40-1.54 (m, 6H) ppm

Example 21

Compound 18—1-Allyl-3-[6-(4-hydroxy-3-methoxy-phenyl)-pyrido[2,3-b]pyrazin-3-yl]-urea m.p.:211-213° C.
ESI-MS:found:352.0 (M+H$^+$); calculated:351.36 g/mol
$^1$H-NMR (DMSO-d$_6$) δ=10.33 (s, 1H), 9.59 (s, 1H), 8.94 (bs, 1H), 8.90 (bs, 1H), 8.35 (d, 1H), 8.21 (d, 1H), 7.89 (s, 1H), 7.77 (d, 1H), 6.94 (d, 1H), 6.00 (m, 1H), 5.38 (d, 1H), 5.19 (d, 1H), 3.97 (t, 2H), 3.91 (s, 3H) ppm

Example 22

Compound 19—1-[6-(4-Hydroxy-3-methoxy-phenyl)-pyrido[2,3-b]pyrazin-3-yl]-3-isopropyl-urea m.p.:212-214° C.
ESI-MS:found:354.0 (M+H$^+$); calculated:353.38 g/mol
$^1$H-NMR (DMSO-d$_6$) δ=10.10 (s, 1H), 9.59 (s, 1H), 8.94 (s, 1H), 8.58 (bs, 1H), 8.34 (d, 1H), 8.21 (d, 1H), 7.92 (s, 1H), 7.77 (d, 1H), 6.94 (d, 1H), 3.92 (m, 1H), 3.91 (s, 3H), 1.24 (d, 6H) ppm

Example 23

Compound 20—1-Cyclopentyl-3-[6-(4-hydroxy-3-methoxy-phenyl)-pyrido[2,3-b]pyrazin-3-yl]-urea m.p.:222-225° C.
ESI-MS:found:380.1 (M+H$^+$); calculated:379.42 g/mol
$^1$H-NMR (DMSO-d$_6$) δ=10.15 (s, 1H), 9.60 (s, 1H), 9.09 (bs, 1H), 8.85 (s, 1H), 8.34 (d, 1H), 8.20 (d, 1H), 7.96 (s, 1H), 7.77 (d, 1H), 6.94 (d, 1H), 4.15 (m, 1H), 3.91 (s, 3H), 1.92 (m, 2H), 1.81 (m, 2H), 1.66 (m, 2H), 1.57 (m, 2H) ppm

Example 24

Compound 21—1-Ethyl-3-[6-(4-hydroxy-3-methoxy-phenylamino)-pyrido[2,3-b]pyrazin-3-yl]-urea m.p.:255° C.
ESI-MS:found:355.0 (M+H$^+$); calculated:354.37 g/mol
$^1$H-NMR (DMSO-d$_6$) δ=9.94 (bs, 1H), 9.59 (s, 1H), 8.68 (bs, 2H), 8.55 (s, 1H), 7.95 (d, 1H), 7.83 (s, 1H), 7.19 (d, 1H), 7.04 (d, 1H), 6.75 (d, 1H), 3.82 (s, 3H), 3.27 (m, 2H), 1.15 (t, 3H) ppm

Example 25

Compound 22—1-[6-(3,4-Dimethoxy-phenyl)-pyrido[2,3-b]pyrazin-3-yl]-3-ethyl-urea m.p.:>235° C.
ESI-MS:found:354.1 (M+H$^+$); calculated:353.38 g/mol
$^1$H-NMR (DMSO-d$_6$) δ=10.23 (s, 1H), 8.98 (s, 1H), 8.53 (bs, 1H), 8.38 (d, 1H), 8.25 (d, 1H), 7.90 (s, 1H), 7.88 (d, 1H), 7.14 (d, 1H), 3:91 (s, 3H), 3.86 (s, 3H), 3.32 (m, 2H), 1.19 (t, 3H) ppm

Example 26

Compound 23—1-Ethyl-3-[6-(3,4,5-trimethoxy-phenyl)-pyrido[2,3-b]pyrazin-3-yl]-urea m.p.:>230° C.
ESI-MS:found:384.1 (M+H$^+$); calculated:383.41 g/mol
$^1$H-NMR (DMSO-d$_6$) δ=10.25 (s, 1H), 9.03 (s, 1H), 8.44 (bs, 1H), 8.42 (d, 1H), 8.32 (d, 1H), 7.60 (s, 2H), 3.93 (s, 6H), 3.76 (s, 3H), 3.32 (m, 2H), 1.19 (t, 3H) ppm

Example 27

Compound 24—1-Ethyl-3-[6-(4-hydroxy-phenylamino)-pyrido[2,3-b]pyrazin-3-yl]-urea m.p.:277° C.
ESI-MS:found:325.1 (M+H$^+$); calculated:324.34 g/mol
$^1$H-NMR (DMSO-d$_6$) δ=9.92 (s, 1H), 9.59 (s, 1H), 9.16 (bs, 1H), 8.65 (s, 1H), 8.34 (bs, 1H), 7.94 (d, 1H), 7.70 (d, 2H), 7.04 (d, 1H), 6.76 (d, 2H), 3.26 (m, 2H), 1.16 (t, 3H) ppm

Example 28

Compound 25—1-Ethyl-3-(6-p-tolylamino-pyrido[2,3-b]pyrazin-3-yl)-thiourea m.p.:195° C.
ESI-MS:found:339.0 (M+H$^+$); calculated:338.44 g/mol
$^1$H-NMR (DMSO-d$_6$) δ=11.97 (t, 1H), 11.14 (s, 1H), 9.81 (s, 1H), 8.48 (s, 1H), 8.02 (d, 1H), 7.87 (d, 2H), 7.13-7.15 (d, 3H), 3.67 (m, 2H), 2.29 (s, 3H), 1.36 (t, 3H) ppm

Example 29

Compound 26—1-[6-(4-Hydroxy-3-methoxy-phenyl)-pyrido[2,3-b]pyrazin-3-yl]-3-phenethyl-urea m.p.:235-237° C.
ESI-MS:found:416.2 (M+H$^+$); calculated:415.46 g/mol
$^1$H-NMR (DMSO-d6) δ=10.26 (s, 1H), 9.59 (s, 1H), 8.89 (s, 1H), 8.74 (s, 1H), 8.35 (d, 1H), 8.22 (d, 1H), 7.93 (s, 1H), 7.80 (d, 1H), 7.44 (d, 2H), 7.27 (t, 2H), 7.18 (t, 1H), 6.95 (d, 1H), 3.88 (s, 3H), 3.53 (m, 2H), 2.92 (t, 2H) ppm

Example 30

Compound 27—1-(3,5-Dimethyl-isoxazol-4-yl)-3-[6-(4-hydroxy-3-methoxy-phenyl)-pyrido[2,3-b]pyrazin-3-yl]-urea m.p.:249-252° C.
ESI-MS:found:407.2 (M+H$^+$); calculated:406.40 g/mol
1H-NMR (DMSO-d6) δ=10.64 (s, 1H), 10.10 (s, 1H), 9.61 (s, 1H), 9.01 (s, 1H), 8.40 (d, 1H), 8.26 (d, 1H), 7.90 (s, 1H), 7.79 (d, 1H), 6.94 (d, 1H), 3.91 (s, 3H), 2.40 (s, 3H), 2.25 (s, 3H) ppm

Example 31

Compound 28—1-tert-Butyl-3-[6-(4-hydroxy-3-methoxy-phenyl)-pyrido[2,3-b]pyrazin-3-yl]-urea m.p.:219-222° C.
ESI-MS:found:368.1 (M+H$^+$); calculated:367.41 g/mol.
1H-NMR (DMSO-d6) δ=10.01 (s, 1H), 9.58 (s, 1H), 8.96 (s, 1H), 8.86 (s, 1H), 8.33 (d, 1H), 8.20 (d, 1H), 7.94 (s, 1H), 7.77 (d, 1H), 6.93 (d, 1H), 3.90 (s, 3H), 1.43 (s, 9H) ppm

Example 32

Compound 29—1-Benzyl-3-[6-(4-hydroxy-3-methoxy-phenyl)-pyrido[2,3-b]pyrazin-3-yl]-urea m.p.:229-231° C.
ESI-MS:found:402.2 (M+H$^+$); calculated:401.43 g/mol
1H-NMR (DMSO-d6) δ=10.36 (s, 1H), 9.58 (s, 1H), 9.11 (s, 1H), 8.94 (s, 1H), 8.35 (d, 1H), 8.20 (d, 1H), 7.85 (s, 1H), 7.75 (d, 1H), 7.43 (d, 2H), 7.38 (t, 2H), 7.29 (t, 1H), 6.93 (d, 1H), 4.54 (d, 2H), 3.88 (s, 3H) ppm

Example 33

Compound 30—1-[6-(4-Hydroxy-3-methoxy-phenyl)-pyrido[2,3-b]pyrazin-3-yl]-3-[1-(2,2,2-trifluoro-acetyl)-piperidin-4-yl]-urea m.p.:236-239° C.
ESI-MS:found:491.2 (M+H$^+$); calculated:490.45 g/mol
1H-NMR (DMSO-d6) δ=10.29 (s, 1H), 9.60 (s, 1H), 9.19 (s, 1H), 8.89 (s, 1H), 8.35 (d, 1H), 8.22 (d, 1H), 7.92 (s, 1H), 7.76 (d, 1H), 6.92 (d, 1H), 4.04 (m, 2H), 3.88 (s, 3H), 3.83 (m, 1H), 3.57 (m, 1H), 3.48 (m, 1H), 2.06 (m, 2H), 1.63 (m, 2H) ppm

Example 34

Compound 31—1-[6-(3-Chloro-4-hydroxy-phenylamino)-pyrido[2,3-b]pyrazin-3-yl]-3-ethyl-urea m.p:277-280° C.
ESI-MS:found:359.1 (M+H$^+$); calculated:358.79 g/mol
1H-NMR (DMSO-d6) δ=10.00 (s, 1H), 9.78 (s, 1H), 9.71 (s, 1H), 8.65 (s, 1H), 8.46 (s, 1H), 7.99 (d, 1H), 7.35 (m, 1H), 7.05 (d, 1H), 6.94 (d, 1H), 3.26 (m, 2H), 1.20 (m, 3H) ppm

Example 35

Compound 32—1-Ethyl-3-[6-(quinolin-3-ylamino)-pyrido[2,3-b]pyrazin-3-yl]-urea m.p.:265-270° C.
ESI-MS:found:360.4 (M+H$^+$); calculated:359.39 g/mol
1H-NMR (DMSO-d6) δ=10.31 (s, 1H), 10.09 (s, 1H), 9.34 (d, 1H), 9.05 (d, 1H), 8.75 (s, 1H), 8.52 (s, 1H), 8.14 (d, 1H), 7.96 (d, 1H), 7.84 (d, 1H), 7.60 (m, 2H), 7.25 (d, 1H), 3.33 (m, 2H), 1.26 (m, 3H) ppm

Example 36

Compound 33

ESI-MS:found:760.5 (M+H$^+$); calculated:759.79 g/mol

Example 37

Compound 34 m.p.:182-184° C.
ESI-MS:found:476.3 (M+H$^+$); calculated:475.44 g/mol

Example 38

Compound 35 m.p.:245-247° C.
ESI-MS:found:365.2 (M+H$^+$); calculated:364.41 g/mol

Example 39

Compound 36 m.p.:177° C.
ESI-MS:found:338.3 (M+H$^+$); calculated:337.38 g/mol

Example 40

Compound 37 m.p.:247-249° C.
ESI-MS:found:452.2 (M+H$^+$); calculated:451.89 g/mol

Example 41

Compound 38

ESI-MS:found:368.2 (M+H$^+$); calculated:367.41 g/mol.
Example 42

Compound 39

ESI-MS:found:402.2 (M+H$^+$); calculated:401.85 g/mol.

Example 43

Compound 40 m.p.:>240° C.
ESI-MS:found:441.4 (M+H$^+$); calculated:440.46 g/mol.

Example 44

Compound 41 m.p.:>350° C.
ESI-MS:found:420.3 (M+H$^+$); calculated:463.30 g/mol.

Example 45

Compound 42 m.p.:238-241° C.
ESI-MS:found:389.3 (M+H$^+$); calculated:388.33 g/mol.

Example 46

Compound 43 m.p.:246-249° C.
ESI-MS:found:418.2 (M+H$^+$); calculated:417.44 g/mol.

Example 47

Compound 44 m.p.:>330° C.
ESI-MS:found:529.3 (M+H$^+$); calculated:528.56 g/mol.

Example 48

Compound 45

ESI-MS:found:367.2 (M+H$^+$); calculated:366.38 g/mol.

Example 49

Compound 46 m.p.:>270° C.
ESI-MS:found:340.3 (M+H$^+$); calculated:339.35 g/mol.

Example 50

Compound 47 m.p.:337-339° C.
ESI-MS:found:390.2, 388.3 (M+H$^+$); calculated:388.22 g/mol.

Example 51

Compound 48 m.p.:276-279° C.
ESI-MS:found:422.3 (M+H$^+$); calculated:421.46 g/mol.

Example 52

Compound 49 m.p.:134° C.
ESI-MS:found:379.4 (M+H$^+$); calculated:378.43 g/mol.

Example 53

Compound 50 m.p.:195-200° C.
ESI-MS:found:383.2 (M+H$^+$); calculated:382.38 g/mol.

Example 54

Compound 51 m.p.:231-232° C.
ESI-MS:found:353.1 (M+H$^+$); calculated:352.40 g/mol.

Example 55

Compound 52 m.p.:218-220° C.
ESI-MS:found:284.1 (M+H$^+$); calculated:283.29 g/mol.

Example 56

Compound 53 m.p.:257-259° C.
ESI-MS:found:298.3 (M+H$^+$); calculated:297.32 g/mol.

Example 57

Compound 54 m.p.:227-229° C.
ESI-MS:found:382.1 (M+H$^+$); calculated:381.39 g/mol.

Example 58

Compound 55 m.p.:243-246° C.
ESI-MS:found:325.2 (M+H$^+$); calculated:324.34 g/mol.

Example 59

Compound 56 m.p.:270-273° C.
ESI-MS:found:325.3 (M+H$^+$); calculated:324.34 g/mol.

Example 60

Compound 57 m.p.:181-183° C.
ESI-MS:found:400.3 (M+H$^+$); calculated:399.45 g/mol.

Example 61

Compound 58 m.p.:258-261° C.
ESI-MS:found:374.2 (M+H$^+$); calculated:373.42 g/mol.

Example 62

Compound 59 m.p.:189-191° C.
ESI-MS:found:340.3 (M+H$^+$); calculated:339.40 g/mol.

Example 63

Compound 60 m.p.:223-226° C.
ESI-MS:found:397.3 (M+H$^+$); calculated:396.45 g/mol.

Example 64

Compound 61 m.p.:270-274° C.
ESI-MS:found:334.2 (M+H$^+$); calculated:333.35 g/mol.

Example 65

Compound 62 m.p.:179-181° C.
ESI-MS:found:366.2 (M+H$^+$); calculated:365.43 g/mol.

Example 66

Compound 63 m.p.:225-227° C.
ESI-MS:found:467.3 (M+H$^+$); calculated:466.54 g/mol.

Example 67

Compound 64 m.p.:229-231° C.
ESI-MS:found:309.2 (M+H$^+$); calculated:308.34 g/mol.

Example 68

Compound 65

ESI-MS:found:480.3 (M+H$^+$); calculated:479.58 g/mol.

Example 69

Compound 66 m.p.:276-279° C.
ESI-MS:found:351.2 (M+H$^+$); calculated:350.38 g/mol.

Example 70

Compound 67 m.p.:200-202° C.
ESI-MS:found:432.0 (M+H$^+$); calculated:430.30 g/mol.

Example 71

Compound 68 m.p.:182-185° C.
ESI-MS:found:354.1 (M+H$^+$); calculated:353.38 g/mol.

Example 73

Compound 70 m.p.:>300° C.
ESI-MS:found:333.2 (M+H$^+$); calculated:332.37 g/mol.

Example 74

Compound 71 m.p.:>300° C.
ESI-MS:found:384.2 (M+H$^+$); calculated:383.41 g/mol.

Example 75

Compound 72 m.p.:>300° C.
ESI-MS:found:311.0 (M+H$^+$); calculated:310.32 g/mol.

Example 76

Compound 73

ESI-MS:found:375.2 (M+H$^+$); calculated:374.35 g/mol.

Example 77

Compound 74

ESI-MS:found:456.2 (M+H$^+$); calculated:455.54 g/mol.

Example 78

Compound 75

ESI-MS:found:356.2 (M+H$^+$); calculated:355.42 g/mol.

Example 79

Compound 76 m.p.:253° C.
ESI-MS:found:423.2 (M+H$^+$); calculated:422.44 g/mol.

Example 80

Compound 77 m.p.:>300° C.
ESI-MS:found:381.2 (M+H$^+$); calculated:380.41 g/mol.

Example 81

Compound 78 m.p.:>350° C.
ESI-MS:found:354.2 (M+H$^+$); calculated:353.34 g/mol.

Example 82

Compound 79 m.p.:238.1-241.8° C.
ESI-MS:found:354.2 (M+H$^+$); calculated:353.36 g/mol.

Example 83

Compound 80 m.p.:255.3-258.2° C.
ESI-MS:found:351.8 (M+H$^+$); calculated:351.41 g/mol.

Example 84

Compound 81 m.p.:305.4-307.2° C.
ESI-MS:found:348.2 (M+H$^+$); calculated:347.30 g/mol.

Example 85

Compound 82 m.p.:255.3-257.9° C.
ESI-MS:found:321.8 (M+H$^+$); calculated:321.38 g/mol.

Example 86

Compound 83 m.p.:247.8-252.4° C.
ESI-MS:found:326.2 (M+H$^+$); calculated:325.35 g/mol.

Example 87

Compound 84 m.p.:263.9-265.6° C.
ESI-MS:found:388.3 (M+H$^+$); calculated:387.42 g/mol.

Example 88

Compound 85 m.p.:253.3-256.2° C.
ESI-MS:found:353.2 (M+H$^+$); calculated:352.35 g/mol.

Example 89

Compound 86 m.p.:277-280° C.
ESI-MS:found:339.3 (M+H$^+$); calculated:338.37 g/mol.

Example 90

Compound 87 m.p.:256-259° C.
ESI-MS:found:397.2 (M+H$^+$); calculated:396.40 g/mol.

Example 91

Compound 88 m.p.:240-242° C.
ESI-MS:found:306.5 (M+H$^+$); calculated:610.68 g/mol.

Example 92

Compound 89 m.p.:216-219° C.
ESI-MS:found:339.0 (M+H$^+$); calculated:338.37 g/mol.

Example 93

Compound 90 m.p.:298-305° C.
ESI-MS:found:362.3 (M+H$^+$); calculated:362.22 g/mol.

Example 94

Compound 91 m.p.:254-257° C.
ESI-MS:found:358.1 (M+H$^+$); calculated:357.80 g/mol.

Example 95

Compound 92 m.p.:264-269° C.
ESI-MS:found:362.2 (M+H$^+$); calculated:362.22 g/mol.

Example 96

Compound 93 m.p.:253-258° C.
ESI-MS:found:342.1 (M+H$^+$); calculated:341.34 g/mol.

Example 97

Compound 94 m.p.:270-274° C.
ESI-MS:found:386.2 (M+H$^+$); calculated:386.25 g/mol.

Example 98

Compound 95 m.p.:259-262° C.
ESI-MS:found:330.3 (M+H$^+$); calculated:329.31 g/mol.

Example 99

Compound 96 m.p.:258-259° C.
ESI-MS:found:360.2 (M+H$^+$); calculated:359.79 g/mol.

Example 100

Compound 97 m.p.:240-243° C.
ESI-MS:found:361.9 (M+H$^+$); calculated:361.33 g/mol.

Example 101

Compound 98 m.p.:223-225° C.
ESI-MS:found:338.0 (M+H$^+$); calculated:337.38 g/mol.

Example 102

Compound 99 m.p.:275° C.
ESI-MS:found:346.2 (M+H$^+$); calculated:345.76 g/mol.

Example 103

Compound 100 m.p.:232-234° C.
ESI-MS:found:307.9 (M+H$^+$); calculated:307.36 g/mol.

Example 104

Compound 101 m.p.:249-253° C.
ESI-MS:found:339.1 (M+H$^+$); calculated:338.33 g/mol.

Example 105

Compound 102 m.p.:220-222° C.
ESI-MS:found:337.8 (M+H$^+$); calculated:337.38 g/mol.

Example 106

Compound 103 m.p.:226-228° C.
ESI-MS:found:311.8 (M+H$^+$); calculated:311.32 g/mol.

Example 107

Compound 104 m.p.:310° C.
ESI-MS:found:328.2 (M+H$^+$); calculated:327.77 g/mol.

Example 108

Compound 105 m.p.:218-220° C.
ESI-MS:found:307.9 (M+H$^+$); calculated:307.36 g/mol.

Example 109

Compound 106 m.p.:270° C.
ESI-MS:found:326.0 (M+H$^+$); calculated:325.35 g/mol.

Example 110

Compound 107 m.p.:260° C.
ESI-MS:found:321.9 (M+H$^+$); calculated:321.38 g/mol.

Example 111

Compound 108 m.p.:>350° C.
ESI-MS:found:362.2 (M+H$^+$); calculated:362.22 g/mol.

Example 112

Compound 109 m.p.:236-238° C.
ESI-MS:found:494.0, 492.0 (M+H$^+$); calculated:492.37 g/mol.

Example 113

Compound 110 m.p.:228-230° C.
ESI-MS:found:417.9, 416.1 (M+H$^+$); calculated:416.28 g/mol.

Example 114

Compound 111 m.p.:262-264° C.
ESI-MS:found:328.1 (M+H$^+$); calculated:327.77 g/mol.

Example 115

Compound 112 m.p.:229-231° C.
ESI-MS:found:356.1 (M+H$^+$); calculated:355.37 g/mol.

Example 116

Compound 113 m.p.:242° C.
ESI-MS:found:314.2 (M+H$^+$); calculated:313.39 g/mol.

Example 117

Compound 114 m.p.:253-257° C.
ESI-MS:found:318.9 (M+H$^+$); calculated:318.34 g/mol.

Example 118

Compound 115 m.p.:200-202° C.
ESI-MS:found:323.9 (M+H$^+$); calculated:323.35 g/mol.

Example 119

Compound 116 m.p.:251-255° C.
ESI-MS:found:370.3 (M+H$^+$); calculated:369.43 g/mol.

Example 120

Compound 117 m.p.:221-224° C.
ESI-MS:found:340.0 (M+H$^+$); calculated:339.42 g/mol.

Example 121

Compound 118 m.p.:239-240° C.
ESI-MS:found:378.1 (M+H$^+$); calculated:377.32 g/mol.

Example 122

Compound 119 m.p.:222-223° C.
ESI-MS:found:366.0 (M+H$^+$); calculated:365.39 g/mol.

Example 123

Compound 120 m.p.:224-228° C.
ESI-MS:found:387.1 (M+H$^+$); calculated:386.43 g/mol.

Example 124

Compound 121 m.p.:212-217° C.
ESI-MS:found:460.1 (M+H$^+$); calculated:459.50 g/mol.

Example 125

Compound 122 m.p.:244-247° C.
ESI-MS:found:328.0 (M+H$^+$); calculated:327.77 g/mol.

Example 126

Compound 123 m.p.:280° C.
ESI-MS:found:370.2 (M+H$^+$); calculated:369.43 g/mol.

Example 127

Compound 124 m.p.:246° C.
ESI-MS:found:324.0 (M+H$^+$); calculated:323.42 g/mol.

Example 128

Compound 125 m.p.:244° C.
ESI-MS:found:354.2 (M+H$^+$); calculated:353.45 g/mol.

Example 129

Compound 126 m.p.:278° C.
ESI-MS:found:339.1 (M+H$^+$); calculated:338.44 g/mol.

Example 130

Compound 127 m.p.:227° C.
ESI-MS:found:368.0 (M+H$^+$); calculated:367.47 g/mol.

Example 131

Compound 128 m.p.:269-273° C.
ESI-MS:found:461.4 (M+H$^+$); calculated:460.54 g/mol.

Example 132

Compound 129 m.p.:283-286° C.
ESI-MS:found:311.9 (M+H$^+$); calculated:311.32 g/mol.

Example 133

Compound 130 m.p.:220-223° C.
ESI-MS:found:337.8 (M+H$^+$); calculated:337.38 g/mol.

Example 134

Compound 131 m.p.:>350° C.
ESI-MS:found:339.1 (M+H$^+$); calculated:338.33 g/mol.

Example 135

Compound 132 m.p.:260° C.
ESI-MS:found:351.9 (M+H$^+$); calculated:351.36 g/mol.

Example 136

Compound 133 m.p.:258.7° C.
ESI-MS:found:351.8 (M+H$^+$); calculated:351.41 g/mol.

Example 137

Compound 134 m.p.:230° C.
ESI-MS:found:400.3 (M+H$^+$); calculated:399.47 g/mol.

Example 138

Compound 135 m.p.:182-185° C.
ESI-MS:found:340.0 (M+H$^+$); calculated:339.42 g/mol.

Example 139

Compound 136 m.p.:256-260° C.
ESI-MS:found:319.1 (M+H$^+$); calculated:318.34 g/mol.

Example 140

Compound 137 m.p.:236-239° C.
ESI-MS:found:342.0 (M+H$^+$); calculated:341.34 g/mol.

Example 141

Compound 138

ESI-MS:found:394.4 (M+H$^+$); calculated:394.28 g/mol.

Example 142

Compound 139

ESI-MS:found:390.3 (M+H$^+$); calculated:389.87 g/mol.

Example 143

Compound 140

ESI-MS:found:355.3 (M+H$^+$); calculated:354.44 g/mol.

Example 144

Compound 141 m.p.:250° C.
ESI-MS:found:299.9 (M+H$^+$); calculated:299.36 g/mol.

Example 145

Compound 142 m.p.:247-249° C.
ESI-MS:found:321.9 (M+H$^+$); calculated:321.38 g/mol.

Example 146

Compound 143 m.p.:250-252° C.
ESI-MS:found:370.2 (M+H$^+$); calculated:369.35 g/mol.

Example 147

Compound 144 m.p.:240-244° C.
ESI-MS:found:336.9 (M+H$^+$); calculated:336.40 g/mol.

Example 148

Compound 145 m.p.:207-209° C.
ESI-MS:found:353.9 (M+H$^+$); calculated:353.38 g/mol.

Example 149

Compound 146 m.p.:202-204° C.
ESI-MS:found:356.0 (M+H$^+$); calculated:355.37 g/mol.

Example 150

Compound 147 m.p.:272° C.
ESI-MS:found:371.3 (M+H$^+$); calculated:370.44 g/mol.

Example 151

Compound 148 m.p.:285° C.
ESI-MS:found:325.1 (M+H$^+$); calculated:324.41 g/mol.

Example 152

Compound 149 m.p.:280° C.
ESI-MS:found:341.2 (M+H$^+$); calculated:340.41 g/mol.

Example 153

Compound 150 m.p.:269° C.
ESI-MS:found:371.1 (M+H$^+$); calculated:370.44 g/mol.

Example 154

Compound 151 m.p.:228-233° C.
ESI-MS:found:335.7 (M+H$^+$); calculated:335.41 g/mol.

Example 155

Compound 152 m.p.:227-228° C.
ESI-MS:found:300.0 (M+H$^+$); calculated:299.36 g/mol.

Example 156

Compound 153 m.p.:225° C.
ESI-MS:found:339.0 (M+H$^+$); calculated:338.37 g/mol.

Example 157

Compound 154 m.p.:238° C.
ESI-MS:found:339.0 (M+H$^+$); calculated:338.37 g/mol.

Example 158

Compound 155 m.p.:230° C.
ESI-MS:found:401.0 (M+H$^+$); calculated:400.44 g/mol.

Example 159

Compound 156 m.p.:281° C.
ESI-MS:found:355.1 (M+H$^+$); calculated:354.37 g/mol.

Example 160

Compound 157 m.p.:265° C.
ESI-MS:found:385.1 (M+H$^+$); calculated:384.46 g/mol.

Example 161

Compound 158

ESI-MS:found:375.1 (M+H$^+$); calculated:374.85 g/mol.

Example 162

Compound 159 m.p.:276° C.
ESI-MS:found:389.1 (M+H$^+$); calculated:388.88 g/mol.

Example 163

Compound 160 m.p.:268° C.
ESI-MS:found:415.1 (M+H$^+$); calculated:414.49 g/mol.

Example 164

Compound 161 m.p.:262° C.
ESI-MS:found:341.1 (M+H$^+$); calculated:340.41 g/mol.

Example 165

Compound 162 m.p.:288° C.
ESI-MS:found:369.1 (M+H$^+$); calculated:368.46 g/mol.

Example 166

Compound 163 m.p.:238° C.
ESI-MS:found:383.1 (M+H$^+$); calculated:382.49 g/mol.

Example 167

Compound 164 m.p.:294° C.
ESI-MS:found:392.2 (M+H$^+$); calculated:391.46 g/mol.

Example 168

Compound 165 m.p.:268° C.
ESI-MS:found:432.2 (M+H$^+$); calculated:431.54 g/mol.

Example 169

Compound 166 m.p.:278° C.
ESI-MS:found:409.4 (M+H$^+$); calculated:409.30 g/mol.

Example 170

Compound 167 m.p.:253° C.
ESI-MS:found:343.0 (M+H$^+$); calculated:342.79 g/mol.

Example 171

Compound 168 m.p.:289° C.
ESI-MS:found:375.4 (M+H$^+$); calculated:374.47 g/mol.

Example 172

Compound 169 m.p.:228° C.
ESI-MS:found:351.8 (M+H$^+$); calculated:351.41 g/mol.

Example 173

Compound 170 m.p.:243° C.
ESI-MS:found:350.9 (M+H$^+$); calculated:350.38 g/mol.

Example 174

Compound 172 m.p.:242-244° C.
ESI-MS:found:326.1 (M+H$^+$); calculated:325.33 g/mol.

Example 175

Compound 173 m.p.:215-218° C.
ESI-MS:found:374.1 (M+H$^+$); calculated:373.80 g/mol.

Example 176

Compound 176 m.p.:234-237° C.
ESI-MS:found:389.2 (M+H$^+$); calculated:388.39 g/mol.

Example 177

Compound 177 m.p.:234-237° C.
ESI-MS:found:351.9 (M+H$^+$); calculated:351.41 g/mol.

Example 178

Compound 178 m.p.:227-228° C.
ESI-MS:found:308.0 (M+H$^+$); calculated:307.36 g/mol.

Example 179

Compound 179 m.p.:>320° C.
ESI-MS:found:309.2 (M+H$^+$); calculated:308.34 g/mol.

Example 180

Compound 180 m.p.:>320° C.
ESI-MS:found:323.0 (M+H$^+$); calculated:322.37 g/mol.

Example 181

Compound 181 m.p.:>240° C.
ESI-MS:found:338.2 (M+H$^+$); calculated:337.38 g/mol.

Example 182

Compound 182 m.p.:277-279° C.
ESI-MS:found:310.2 (M+H$^+$); calculated:309.33 g/mol.

Example 183

Compound 183 m.p.:>250° C.
ESI-MS:found:342.8 (M+H$^+$); calculated:341.39 g/mol.

Example 184

Compound 194 m.p.:305-308° C.
ESI-MS:found:367.2 (M+H$^+$); calculated:366.38 g/mol.

Example 185

Compound 195 m.p.:248° C.
ESI-MS:found:383.2 (M+H$^+$); calculated:382.45 g/mol.

Example 186

Compound 197 m.p.:211° C.
ESI-MS:found:341.2 (M+H$^+$); calculated:340.41 g/mol.

Example 187

Compound 198 m.p.:258° C.
ESI-MS:found:341.1 (M+H$^+$); calculated:340.41 g/mol.

Example 188

Compound 200 m.p.:238° C.
ESI-MS:found:415.3 (M+H$^+$); calculated:414.49 g/mol.

Example 189

Compound 201 m.p.:260° C.
ESI-MS:found:373.1 (M+H$^+$); calculated:372.81 g/mol.

Example 190

Compound 202 m.p.:225° C.
ESI-MS:found:389.2 (M+H$^+$); calculated:388.88 g/mol.

Example 191

Compound 203 m.p.:166° C.
ESI-MS:found:371.2 (M+H$^+$); calculated:370.44 g/mol.

Example 192

Compound 205 m.p.:166° C.
ESI-MS:found:371.2 (M+H$^+$); calculated:370.44 g/mol.

Example 193

Compound 207 m.p.:236° C.
ESI-MS:found:432.2 (M+H$^+$); calculated:431.54 g/mol.

Example 194

Compound 208 m.p.:203° C.
ESI-MS:found:375.2 (M+H$^+$); calculated:374.85 g/mol.

Example 195

Compound 209 m.p.:255° C.
ESI-MS:found:353.1 (M+H$^+$); calculated:352.40 g/mol.

Example 196

Compound 210 m.p.:148° C.
ESI-MS:found:369.0 (M+H$^+$); calculated:368.46 g/mol.

Example 197

Compound 217 m.p.:185° C.
ESI-MS:found:359.0 (M+H$^+$); calculated:358.86 g/mol.

Example 198

Compound 221 m.p.:189° C.
ESI-MS:found:355.2 (M+H$^+$); calculated:354.44 g/mol.

Example 199

Compound 225 m.p.:243-245° C.
ESI-MS:found:303.2 (M+H$^+$); calculated:302.34 g/mol.

Example 200

Compound 227 m.p.:214-216° C.
ESI-MS:found:316.3 (M+H$^+$); calculated:315.34 g/mol.

Example 201

Compound 231 m.p.:201-203° C.
ESI-MS:found:287.1 (M+H$^+$); calculated:286.34 g/mol.

Example 202

Compound 233 m.p.:199-201° C.
ESI-MS:found:330.3 (M+H$^+$); calculated:329.41 g/mol.

Example 203

Compound 235 m.p.:249-251° C.
ESI-MS:found:317.2 (M+H$^+$); calculated:316.36 g/mol.

Example 204

Compound 239 m.p.:211-213° C.
ESI-MS:found:323.2 (M+H$^+$); calculated:322.37 g/mol.

Example 205

Compound 241

ESI-MS:found:337.2 (M+H$^+$); calculated:336.40 g/mol.

Example 206

Compound 255

ESI-MS:found:392.4 (M+H$^+$); calculated:391.50 g/mol.

Example 207

Compound 257 m.p.:216° C.
ESI-MS:found:418.1 (M+H$^+$); calculated:417.54 g/mol.

Example 208

Compound 329 m.p.:>220° C.
ESI-MS:found:359.3 (M+H$^+$); calculated:358.86 g/mol.

Example 209

Compound 331 m.p.:258° C.
ESI-MS:found:355.3 (M+H$^+$); calculated:354.44 g/mol.

Example 210

Compound 332 m.p.:232° C.
ESI-MS:found:355.1 (M+H$^+$); calculated:354.44 g/mol.

Example 211

Compound 336 m.p.:255° C.
ESI-MS:found:381.2 (M+H$^+$)—free Base; calculated: 416.91 g/mol.

Example 212

Compound 341 m.p.:235° C.
ESI-MS:found:477.4 (M+H$^+$)—free base; calculated: 513.00 g/mol.

Example 213

Compound 374 m.p.:215° C.
ESI-MS:found:352.0 (M+H$^+$); calculated:351.41 g/mol.

Example 214

Compound 378 m.p.:225° C.
ESI-MS:found:336.8 (M+H$^+$); calculated:336.44 g/mol.

Example 215

Compound 380

ESI-MS:found:339.2 (M+H$^+$); calculated:338.37 g/mol.

Example 216

Compound 394 m.p.:272° C.
ESI-MS:found:339.2 (M+H$^+$); calculated:338.37 g/mol.

Example 217

Compound 398 m.p.:210° C.
ESI-MS:found:336.8 (M+H$^+$); calculated:336.40 g/mol.

Example 218

Compound 399 m.p.:215° C.
ESI-MS:found:353.1 (M+H$^+$); calculated:352.46 g/mol.

Example 219

Compound 433 m.p.:265° C.
ESI-MS:found:361.2 (M+H$^+$); calculated:360.39 g/mol.

Example 220

Compound 434 m.p.:324-329° C.
ESI-MS:found 387.1 (M+H$^+$); calculated:386.80 g/mol.

Example 221

Compound 441 m.p.:220° C.
ESI-MS:found:375.3 (M+H$^+$); calculated:374.85 g/mol.

Example 222

Compound 443 m.p.:270° C.
ESI-MS:found:394.1 (M+H$^+$); calculated:393.30 g/mol.

Example 223

Compound 446 m.p.:222° C.
ESI-MS:found:353.0 (M+H$^+$); calculated:352.40 g/mol.

Example 224

Compound 465 m.p.:277° C.
ESI-MS:found:428.3 (M+H$^+$); calculated:427.75 g/mol.

Example 225

Compound 467 m.p.:232° C.
ESI-MS:found:367.1 (M+H$^+$); calculated:366.45 g/mol.

Example 226

Compound 489 m.p.:260° C.
ESI-MS:found:388.2 (M+H$^+$); calculated:387.40 g/mol.

Example 227

Compound 491 m.p.:250° C.
ESI-MS:found:386.4 (M+H$^+$); calculated:385.41 g/mol.

Example 228

Compound 501 m.p.:243° C.
ESI-MS:found:429.2 (M+H$^+$); calculated:428.51 g/mol.

Example 229

Compound 509 m.p.:246° C.
ESI-MS:found:455.1 (M+H$^+$); calculated:454.55 g/mol.

Example 230

Compound 518 m.p.:245-238° C.
ESI-MS:found:370.4 (M+H$^+$); calculated:369.45 g/mol.

Example 231

Compound 519 m.p.:233-235° C.
ESI-MS:found:396.3 (M+H$^+$); calculated:395.48 g/mol.

Example 232

Compound 521 m.p.:261-262° C.
ESI-MS:found:368.2 (M+H$^+$); calculated:367.43 g/mol.

Example 233

Compound 524 m.p.:253-254° C.
ESI-MS:found:410.4 (M+H$^+$); calculated:409.51 g/mol.

Example 234

Compound 526 m.p.:279-280° C.
ESI-MS:found:342.0 (M+H$^+$); calculated:341.39 g/mol.

Example 235

Compound 529 m.p.:224-226° C.
ESI-MS:found:422.3 (M+H$^+$); calculated:421.84 g/mol.

Example 236

Compound 533

ESI-MS:found:402.4 (M+H$^+$); calculated:401.42 g/mol.

Example 237

Compound 541

ESI-MS:found:456.4 (M+H$^+$); calculated:455.39 g/mol.

Example 238

Compound 551 m.p.:265-268° C.
ESI-MS:found:392.2 (M+H$^+$); calculated:392.24 g/mol.

Example 239

Compound 552 m.p.:259-261° C.
ESI-MS:found:392.2 (M+H$^+$); calculated:392.24 g/mol.

Example 240

Compound 553 m.p.:251-253° C.
ESI-MS:found:406.2 (M+H$^+$); calculated:406.27 g/mol.

Example 241

Compound 554 m.p.:226-230° C.
ESI-MS:found:530.2 (M+H$^+$); calculated:529.30 g/mol.

Example 242

Compound 555 m.p.:259-262° C.
ESI-MS:found:469.3 (M+H$^+$); calculated:469.33 g/mol.

Example 243

Compound 556 m.p.:261-263° C.
ESI-MS:found:460.3 (M+H$^+$); calculated:460.36 g/mol.

Example 244

Compound 557 m.p.:247-249° C.
ESI-MS:found:364.2 (M+H$^+$); calculated:364.19 g/mol.

Example 245

Compound 558 m.p.:272-275° C.
ESI-MS:found:432.2 (M+H$^+$); calculated:432.31 g/mol.

Example 246

Compound 559 m.p.:289-291° C.
ESI-MS:found:444.3 (M+H$^+$); calculated:444.25 g/mol.

Example 247

Compound 560 m.p.:253-255° C.
ESI-MS:found:432.3 (M+H$^+$); calculated:432.29 g/mol.

Example 248

Compound 561 m.p.:>300° C.
ESI-MS:found:471.0 (M+H$^+$); calculated:471.26 g/mol.

Example 249

Compound 562 m.p.:257-260° C.
ESI-MS:found:445.1 (M+H$^+$); calculated:445.26 g/mol.

Example 250

Compound 563 m.p.:262-264° C.
ESI-MS:found:418.1 (M+H$^+$); calculated:418.28 g/mol.

Example 251

Compound 564 m.p.:280-282° C.
ESI-MS:found:454.3 (M+H$^+$); calculated:454.32 g/mol.

Example 252

Compound 565 m.p.:>300° C.
ESI-MS:found:521.3 (M+H$^+$); calculated:521.32 g/mol.

Example 253

Compound 566 m.p.:253-255° C.
ESI-MS:found:340.1 (M+H$^+$); calculated:339.35 g/mol.

Example 254

Compound 567 m.p.:233-236° C.
ESI-MS:found:368.2 (M+H$^+$); calculated:367.41 g/mol.

Example 255

Compound 568 m.p.:230-233° C.
ESI-MS:found:382.2 (M+H$^+$); calculated:381.43 g/mol.

Example 256

Compound 569 m.p.:262-263° C.
ESI-MS:found:445.3 (M+H$^+$); calculated:444.49 g/mol.

Example 257

Compound 570 m.p.:246-248° C.
ESI-MS:found:368.2 (M+H$^+$); calculated:367.41 g/mol.

Example 258

Compound 571 m.p.:262-264° C.
ESI-MS:found:408.3 (M+H$^+$); calculated:407.47 g/mol.

Example 259

Compound 572 m.p.:269-271° C.
ESI-MS:found:420.4 (M+H$^+$); calculated:419.41 g/mol.

Example 260

Compound 573 m.p.:265-267° C.
ESI-MS:found:421.3 (M+H$^+$); calculated:420.43 g/mol.

Example 261

Compound 574 m.p.:188-191° C.
ESI-MS:found:402.2 (M+H$^+$); calculated:401.42 g/mol.

Example 262

Compound 575 m.p.:236-238° C.
ESI-MS:found:366.1 (M+H$^+$); calculated:365.39 g/mol.

Example 263

Compound 576 m.p.:261-264° C.
ESI-MS:found:394.3 (M+H$^+$); calculated:393.44 g/mol.

Example 264

Compound 577 m.p.:254-257° C.
ESI-MS:found:430.2 (M+H$^+$); calculated:429.48 g/mol.

Example 265

Compound 578 m.p.:263-266° C.
ESI-MS:found:416.2 (M+H$^+$); calculated:415.48 g/mol.

Example 266

Compound 579 m.p.:279-283° C.
ESI-MS:found:497.1 (M+H$^+$); calculated:496.48 g/mol.

Example 267

Compound 580 m.p.:248-251° C.
ESI-MS:found:402.1 (M+H$^+$); calculated:401.42 g/mol.

Example 268

Compound 581 m.p.:239-242° C.
ESI-MS:found:505.0 (M+H$^+$); calculated:504.47 g/mol.

Example 269

Compound 582

ESI-MS:found:382.3 (M+H$^+$); calculated:381.43 g/mol.

Example 270

Compound 583 m.p.:273-275° C.
ESI-MS:found:429.2 (M+H$^+$); calculated:428.49 g/mol.

Example 271

Compound 584 m.p.:247-250° C.
ESI-MS:found:392.4 (M+H$^+$); calculated:391.47 g/mol.

Example 272

Compound 585

ESI-MS:found:351.9 (M+H$^+$); calculated:351.41 g/mol.

Example 273

Compound 586 m.p.:240-241° C.
ESI-MS:found:351.9 (M+H$^+$); calculated:351.41 g/mol.

Example 274

Compound 587 m.p.:210-212° C.
ESI-MS:found:350.1 (M+H$^+$); calculated:349.39 g/mol.

Example 275

Compound 588 m.p.:267-269° C.
ESI-MS:found:414.2 (M+H$^+$); calculated:413.48 g/mol.

Example 276

Compound 589 m.p.:251-253° C.
ESI-MS:found:489.0 (M+H$^+$); calculated:488.47 g/mol.

Example 277

Compound 590 m.p.:242-244° C.
ESI-MS:found:405.2 (M+H$^+$); calculated:404.43 g/mol.

Example 278

Compound 591

ESI-MS:found:324.1 (M+H$^+$); calculated:323.35 g/mol.

Example 279

Compound 592

ESI-MS:found:351.9 (M+H$^+$); calculated:351.41 g/mol.

Example 280

Compound 593

ESI-MS:found:366.0 (M+H$^+$); calculated:365.43 g/mol.

Example 281

Compound 594

ESI-MS:found:404.3 (M+H$^+$); calculated:403.42 g/mol.

Example 282

Compound 595 m.p.:271-273° C.
ESI-MS:found:386.2 (M+H$^+$); calculated:385.43 g/mol.

Example 283

Compound 596 m.p.:263° C.
ESI-MS:found:422.2 (M+H$^+$); calculated:421.54 g/mol.

Example 284

Compound 597 m.p.:221° C.
ESI-MS:found:380.2 (M+H$^+$); calculated:379.46 g/mol.

Example 285

Compound 598 m.p.:232° C.
ESI-MS:found:380.1 (M+H$^+$); calculated:379.46 g/mol.

Example 286

Compound 599 m.p.:233° C.
ESI-MS:found:394.1 (M+H$^+$); calculated:393.49 g/mol.

Example 287

Compound 600 m.p.:244-246° C.
ESI-MS:found:406.3 (M+H$^+$); calculated:405.39 g/mol.

Example 288

Compound 601

ESI-MS:found:460.5 (M+H$^+$); calculated:459.46 g/mol.

Example 289

Compound 602 m.p.:287-290° C.
ESI-MS:found:431.2 (M+H$^+$); calculated:430.47 g/mol.

Example 290

Compound 603 m.p.:233-236° C.
ESI-MS:found:428.3 (M+H$^+$); calculated:427.46 g/mol.

Example 291

Compound 604 m.p.:232-234° C.
ESI-MS:found:422.4 (M+H$^+$); calculated:421.50 g/mol.

Example 292

Compound 605 m.p.:252-254° C.
ESI-MS:found:446.4 (M+H$^+$); calculated:445.52 g/mol.

Example 293

Compound 606 m.p.:210-212° C.
ESI-MS:found:529.4 (M+H$^+$); calculated:528.57 g/mol.

Example 294

Compound 607 m.p.:260-263° C.
ESI-MS:found:474.5 (M+H$^+$); calculated:473.49 g/mol.

Example 295

Compound 608

ESI-MS:found:408.4 (M+H$^+$); calculated:407.47 g/mol.

Example 296

Compound 609 m.p.:257-259° C.
ESI-MS:found:444.3 (M+H$^+$); calculated:443.49 g/mol.

Example 297

Compound 610

ESI-MS:found:491.5 (M+H$^+$); calculated:490.44 g/mol.

Example 298

Compound 611 m.p.:245-248° C.
ESI-MS:found:389.4 (M+H$^+$); calculated:388.39 g/mol.

Example 299

Compound 612 m.p.:272-273° C.
ESI-MS:found:408.4 (M+H$^+$); calculated:407.47 g/mol.

Example 300

Compound 613 m.p.:232-236° C.
ESI-MS:found:424.4 (M+H$^+$); calculated:423.51 g/mol.

Example 301

Compound 614 m.p.:216-219° C.
ESI-MS:found:394.4 (M+H$^+$); calculated:393.43 g/mol.

Example 302

Compound 615

ESI-MS:found:471.4 (M+H$^+$); calculated:470.53 g/mol.

Example 303

Compound 616 m.p.:247-250° C.
ESI-MS:found:433.3 (M+H$^+$); calculated:432.39 g/mol.

Example 304

Compound 617 m.p.:220-222° C.
ESI-MS:found:433.4 (M+H$^+$); calculated:432.39 g/mol.

Example 305

Compound 618 m.p.:274-276° C.
ESI-MS:found:433.1 (M+H$^+$); calculated:432.39 g/mol.

Example 306

Compound 619 m.p.:214-217° C.
ESI-MS:found:453.4 (M+H$^+$); calculated:452.43 g/mol.

Example 307

Compound 620 m.p.:207-210° C.
ESI-MS:found:486.3 (M+H$^+$); calculated:485.55 g/mol.

Example 308

Compound 621 m.p.:248-251° C.
ESI-MS:found:441.5 (M+H$^+$); calculated:440.46 g/mol.

Example 309

Compound 622 m.p.:290-293° C.
ESI-MS:found:483.5 (M+H$^+$); calculated:482.45 g/mol.

Example 310

Compound 623 m.p.:263-265° C.
ESI-MS:found:453.4 (M+H$^+$); calculated:452.47 g/mol.

Example 311

Compound 624 m.p.:242-245° C.
ESI-MS:found:432.2 (M+H$^+$); calculated:431.45 g/mol.

Example 312

Compound 625 m.p.:235-238° C.
ESI-MS:found:418.1 (M+H$^+$); calculated:417.42 g/mol.

Example 313

Compound 626 m.p.:259-261° C.
ESI-MS:found:413.3 (M+H$^+$); calculated:412.41 g/mol.

Example 314

Compound 627 m.p.:234-235° C.
ESI-MS:found:396.4 (M+H$^+$); calculated:395.46 g/mol.

Example 315

Compound 628 m.p.:233-235° C.
ESI-MS:found:478.4 (M+H$^+$); calculated:477.61 g/mol.

Example 316

Compound 629 m.p.:233-236° C.
ESI-MS:found:430.3 (M+H$^+$); calculated:429.48 g/mol.

Example 317

Compound 630 m.p.:208-210° C.
ESI-MS:found:444.4 (M+H$^+$); calculated:443.50 g/mol.

Example 318

Compound 631 m.p.:223-226° C.
ESI-MS:found:368.2 (M+H$^+$); calculated:367.41 g/mol.

Example 319

Compound 632 m.p.:214-216° C.
ESI-MS:found:368.2 (M+H$^+$); calculated:367.41 g/mol.

Example 320

Compound 633

ESI-MS:found:464.4 (M+H$^+$); calculated:463.49 g/mol.

Example 321

Compound 634

ESI-MS:found:470.1 (M+H$^+$); calculated:469.42 g/mol.

Example 322

Compound 635 m.p.:226-228° C.
ESI-MS:found:444.1 (M+H$^+$); calculated:443.50 g/mol.

Example 323

Compound 636

ESI-MS:found:436.1 (M+H$^+$); calculated:435.87 g/mol.

Example 324

Compound 637 m.p.:>270° C.
ESI-MS:found:344.6 (M+H$^+$); calculated:343.77 g/mol.

Example 325

Compound 638

ESI-MS:found:340.1 (M+H$^+$); calculated:339.35 g/mol.

Example 326

Compound 639 m.p.:250-252° C.
ESI-MS:found:416.9 (M+H$^+$); calculated:416.77 g/mol.

Example 327

Compound 640 m.p.:262° C.
ESI-MS:found:396.2 (M+H$^+$); calculated:395.31 g/mol.

Example 328

Compound 641 m.p.:291° C.
ESI-MS:found:388.2 (M+H$^+$); calculated:388.22 g/mol.

Example 329

Compound 642 m.p.:266° C.
ESI-MS:found:358.2 (M+H$^+$); calculated:357.80 g/mol.

Example 330

Compound 643 m.p.:263° C.
ESI-MS:found:422.2 (M+H$^+$); calculated:421.54 g/mol.

Example 331

Compound 644 m.p.:225° C.
ESI-MS:found:354.1 (M+H$^+$); calculated:353.34 g/mol.

Example 332

Compound 647

ESI-MS:found:310.2 (M+H$^+$); calculated:309.40 g/mol.

Example 333

Compound 648

ESI-MS:found:355.3 (M+H$^+$); calculated:354.44 g/mol.

Example 334

Compound 649

ESI-MS:found:368.1 (M+H$^+$); calculated:367.47 g/mol.

Example 335

Compound 650 m.p.:218-219° C.
ESI-MS:found:400.2 (M+H$^+$); calculated:399.47 g/mol.

Example 336

Compound 651 m.p.:230-231° C.
ESI-MS:found:324.1 (M+H$^+$); calculated:323.42 g/mol.

Example 337

Compound 652 m.p.:213-215° C.
ESI-MS:found:384.3 (M+H$^+$); calculated:383.47 g/mol.

Example 338

Compound 653 m.p.:250-251° C.
ESI-MS:found:438.4 (M+H$^+$); calculated:437.57 g/mol.

Example 339

Compound 654 m.p.:238-240° C.
ESI-MS:found:462.4 (M+H$^+$); calculated:461.59 g/mol.

Example 340

Compound 655

ESI-MS:found:354.0 (M+H$^+$); calculated:353.38 g/mol.

Example 341

Compound 660 m.p.:168-170° C.
ESI-MS:found:387.1 (M+H$^+$); calculated:386.41 g/mol.

Example 342

Compound 661

ESI-MS:found:393.3 (M+H$^+$); calculated:392.46 g/mol.

Example 343

Compound 686

ESI-MS:found:368.1 (M+H$^+$); calculated:367.41 g/mol.

Example 344

Compound 690 m.p.:248° C.
ESI-MS:found:469.2 (M+H$^+$); calculated:468.58 g/mol.

Example 345

Compound 691 m.p.:250° C.
ESI-MS:found:497.3 (M+H$^+$); calculated:496.63 g/mol.

Example 346

Compound 692 m.p.:258-261° C.
ESI-MS:found:401.1 (M+H$^+$); calculated:400.46 g/mol.

Example 347

Compound 693 m.p.:230-234° C.
ESI-MS:found:427.3 (M+H$^+$); calculated:426.50 g/mol.

Example 348

Compound 694 m.p.:218-220° C.
ESI-MS:found:443.2 (M+H$^+$); calculated:442.54 g/mol.

Example 349

Compound 695 m.p.:247° C.
ESI-MS:found:482.3 (M+H$^+$); calculated:481.53 g/mol.

Example 350

Compound 696 m.p.:347° C.
ESI-MS:found:483.1 (M+H$^+$); calculated:482.61 g/mol.

Example 351

Compound 697 m.p.:250-252° C.
ESI-MS:found:477.0 (M+H$^+$); calculated:476.56 g/mol.

Example 352

Compound 698 m.p.:248-250° C.
ESI-MS:found:491.1 (M+H$^+$); calculated:490.59 g/mol.

Example 353

Compound 699 m.p.:197-200° C.
ESI-MS:found:491.3 (M+H$^+$); calculated:490.59 g/mol.

Example 354

Compound 700 m.p.:206° C.
ESI-MS:found:498.1 (M+H$^+$); calculated:497.62 g/mol.

Example 355

Compound 701 m.p.:255° C.
ESI-MS:found:495.1 (M+H$^+$); calculated:494.55 g/mol.

Example 356

Compound 702 m.p.:210° C.
ESI-MS:found:457.4 (M+H$^+$); calculated:456.57 g/mol.

Example 357

Compound 703 m.p.:196° C.
ESI-MS:found:500.2 (M+H$^+$); calculated:499.59 g/mol.

Example 358

Compound 704 m.p.:195-198° C.
ESI-MS:found:505.3 (M+H$^+$); calculated:504.61 g/mol.

Example 359

Compound 705 m.p.: 243-245° C.
ESI-MS: found: 445.4 (M+H⁺); calculated: 444.51 g/mol.

Example 359

Compound 706 m.p.: 222° C.
ESI-MS: found: 428.9 (M+H⁺); calculated: 428.51 g/mol.

Example 360

Compound 707 m.p.: 248° C.
ESI-MS: found: 427.3 (M+H⁺); calculated: 426.50 g/mol.

Example 361

Compound 708 m.p.: 228° C.
ESI-MS: found: 467.3 (M+H⁺); calculated: 466.52 g/mol.

Example 362

Compound 709 m.p.: 244° C.
ESI-MS: found: 487.2 (M+H⁺); calculated: 486.55 g/mol.

Example 363

Compound 710 m.p.: 246° C.
ESI-MS: found: 459.4 (M+H⁺); calculated: 458.54 g/mol.

Example 364

Compound 711 m.p.: 248° C.
ESI-MS: found: 491.4 (M+H⁺); calculated: 490.59 g/mol.

Example 365

Compound 733 m.p.: 110° C.
ESI-MS: found: 356.0 (M+H⁺); calculated: 355.40 g/mol.

II) Biological Effects of the Compounds of the Invention

II.1) Cell-Free Kinase Assays (by Means of ALPHA Technology)

The inhibitory effect of the compounds of the invention was tested on various human serine/threonine kinases, tyrosine kinases and lipid kinases in enzymatic assays. Recombinant human kinases, for example PI3Kalpha, -beta, -gamma, -delta, Erk2, p38alpha, p38gamma, Jnk1, Jnk2 and others were used, in some cases as full-length kinases, in some cases as truncated fragments—but at least consisting of the functional kinase domains. The commercial kinase proteins (Proqinase, Upstate) were used as recombinant fusion proteins with GST (glutathione S-transferase) tag or His tag. Depending on the substrate type, the different kinase reactions were quantified by suitable ALPHA™ beads (PerkinElmer).

Testing

The kinase assays for PI3K and Erk are described in detail and selected test results are cited below. To determine the $IC_{50}$ value, the potential inhibitor substances were investigated at 10 half-logarithmically graduated concentrations of 3.16 nM-100 μM.

a) PI3K-ALPHA (e.g. PI3Kalpha): The test substance, 1 ng of PI3Kalpha (#14-602, Upstate), 100 μM ATP and 20 μM $PIP_2$ substrate (#P4508, Echelon) were incubated on a 384-well Optiplate (Perkin Elmer) for 60 minutes in 50 mM Hepes, 50 mM NaCl, 5 mM $MgCl_2$, 0.05% Chaps, 5 mM DTT at pH 7.4. Subsequently, the kinase reaction was stopped by adding the ALPHA bead mix (10 μg/ml, #6760603/PerkinElmer), preincubated with 1 nM GST:Grp1 fusion protein (Upstate) and 15 nM biotinylated PIP3 (#C-39B6/Echelon) in 50 mM Hepes, 50 mM NaCl, 50 mM EDTA and 0.1% BSA, and left to stand overnight.

b) Erk2-ALPHA: The test substance, 0.625 ng of Erk2 (#14-173, Upstate), 10 μM ATP and 15 nM biotinylated MBP (myelin basic protein) substrate were incubated on a 384-well Optiplate (Perkin Elmer) in a volume of 15 μl for 1 h in 25 mM Tris, 10 mM $MgCl_2$, 0.1% Tween-20, 100 μM $NaVO_4$, 2 mM DTT at pH 7.5. The kinase reaction was stopped by adding 10 μl of the ALPHA bead mix (10 μg/ml, #6760617/PerkinElmer), pre-incubated with anti-phospho MBP antibody (320 pM, #05-429/Upstate), in 25 mM Tris, 200 mM NaCl, 100 mM EDTA and 0.3% BSA, and left to stand overnight.

The luminiscence was detected the next morning in a Fusion™ alpha instrument (Perkin Elmer).

Evaluation

The calculation of % inhibition values per substance concentration was done by means of the following formula from the raw data determined in the Fusion™ alpha:

$$\% \text{ kinase } inhibition_{(sample)} = 100 - \left(100 \times \frac{mean_{(sample)} - mean_{(0\% \text{ control})}}{mean_{(100\% \text{ control})} - mean_{(0\% \text{ control})}}\right)$$

The controls were determined 8 fold and the substance samples 2 fold. 0% control contained neither any ATP nor any substrate. The 100% control contained no test substance. The $IC_{50}$ values were determined with GraphPadPrism.

The compounds of the invention exhibited effective inhibition of PI3Kalpha, Erk2, p38alpha and Jnk1+Jnk2 with $IC_{50}$ values of <500 nM (see Table 1).

TABLE 1

PI3Kalpha and MAPK kinase assay test results ($IC_{50}$ [μM] at 10 μM or 100 μM* ATP)

| Compound | PI3Kalpha* | Erk2 | p38alpha | Jnk1 + Jnk2 |
|---|---|---|---|---|
| 5 | <0.5 | >100 | >100 | >10 |
| 20 | <1 | >100 | >100 | >100 |
| 30 | <1 | <10 | <10 | <31.6 |
| 46 | <5 | <0.5 | >100 | <1 |
| 50 | <1 | >100 | >100 | >100 |

TABLE 1-continued

PI3Kalpha and MAPK kinase assay test results (IC$_{50}$ [µM] at 10 µM or 100 µM* ATP)

| Compound | PI3Kalpha* | Erk2 | p38alpha | Jnk1 + Jnk2 |
|---|---|---|---|---|
| 54  | <5 | <0.5  | >100  | <31.6 |
| 55  | <5 | >100  | <10   | >100  |
| 56  | <5 | <10   | <10   | >10   |
| 73  | <5 | >100  | >10   | >100  |
| 147 | <1 | >100  | >100  | >31.6 |
| 160 | <1 | <31.6 | <50   | >100  |
| 173 | <1 | <50   | <50   | <31.6 |
| 176 | <1 | >31.6 | <50   | <50   |
| 181 | <5 | >100  | <50   | >100  |
| 509 | <1 | >100  | >100  | >100  |
| 526 | <1 | >100  | <50   | >100  |
| 553 | <5 | >100  | >100  | <100  |
| 563 | <1 | >100  | —     | —     |
| 566 | <5 | >100  | >31.6 | >100  |
| 614 | <1 | <31.6 | <10   | <31.6 |
| 637 | <5 | >100  | >100  | >100  |

Especially compound 5 and derivatives are characterized by low IC$_{50}$ values against PI3K and high selectivity against the other kinases.

Also pyridopyrazines, substituted by —NH-heteroaryl at the pyrazine ring (for example, compounds 50, 55, 56 and 73), show PI3K inhibition, but no or only moderate MAPK inhibition.

Pyridopyrazines, substituted by heteroaryl at the pyrazine ring (for example, compounds 46 and 54) exhibit a dual mode of kinase inhibition at least, namely an inhibition of PI3K and Erk2.

II.2) Cellular Assay:Testing for Anti-Proliferate Activity (XTT Assay)

The principle of this test is based on the intracellular reduction of the tetrazolium dye XTT (sodium 3'-[1-(phenylaminocarbonyl)-3,4-tetrazolium]bis(4-methoxy-6-nitro)benzenesulphonic acid, Sigma) to a formazan dye by mitochondrial dehydrogenases. The dye is formed only by metabolically active cells. Its photometrically measurable intensity is a quantitative indicator for the presence of living cells. The reduction in the dye formation as a result of incubation of the cells with substances serves as a parameter for the anti-proliferative activity.

Testing

The tumour cell lines (ATCC) were seeded in 96-well microtitre plates in a defined cell count (5000 cells/well for Hct116; 10000 cells/well for MDA MB468), and incubated overnight at 37° C., 5% CO$_2$ and 95% air humidity. The test substances were made up as stock solutions (10 mM) in DMSO. To determine the EC$_{50}$ values, the potential inhibitor substances were added to the cells in quarter-logarithmically graded dilutions, so as to result in final concentrations of 0.28 µM-50 µM. The cell plates were then incubated for 45 h at 37° C., 5% CO$_2$ and 95% air humidity.

For the detection reaction, the XTT substrate was mixed with PMS (N-methyldibenzopyrazine methylsulphate, Sigma) and added to the cells, to result in a final concentration of 325 µg of XTT/ml and 2.5 µg PMS/ml. The mixture was then incubated for 3 h at 37° C., 95% air humidity. Subsequently the formazan salt formed by cellular dehydrogenases was quantified at an absorption of 490 nm.

Evaluation

The evaluation of the % inhibition values was done by means of the following formula from the values for the optical densities measured in each case at 490 nm:

$$\% \text{ inhibition of cell } proliferation_{(sample)} = 100 - \left(100 \times \frac{mean_{(sample)} - mean_{(0\% \, control)}}{mean_{(100\% \, control)} - mean_{(0\% \, control)}}\right)$$

The controls were determined 8 fold, the substance samples 2 fold. 0% control contained no cells and the 100% control contained no test substance. The EC$_{50}$ values were determined with GraphPadPrism.

The compounds of the invention exhibited effective inhibition of cell proliferation in some cases with EC$_{50}$ values <1 µM (see Table 2).

TABLE 2

XTT assay test results (EC50 [µM])

| Compound | MDA-MB468 | Hct116 |
|---|---|---|
| 5   | <1  | <2  |
| 46  | <10 | <10 |
| 50  | <10 | <5  |
| 54  | <5  | <5  |
| 55  | <5  | <5  |
| 56  | <5  | <10 |
| 73  | <5  | <5  |
| 89  | <5  | <5  |
| 113 | <5  | <5  |
| 126 | <5  | <5  |
| 134 | <5  | <5  |
| 138 | <10 | <10 |
| 140 | <5  | <5  |
| 147 | <5  | <5  |
| 148 | <5  | <10 |
| 150 | <5  | <5  |
| 152 | <10 | <10 |
| 160 | <1  | <1  |
| 173 | <1  | <1  |
| 176 | <1  | <1  |
| 181 | <10 | <10 |
| 509 | <5  | <5  |
| 526 | <1  | <5  |
| 553 | <5  | <5  |
| 563 | <1  | <1  |
| 566 | <5  | <5  |
| 614 | <5  | <5  |
| 637 | <10 | <10 |

Especially compound 5 and derivatives display high antiproliferative potencies against human tumor cell lines, as they show EC$_{50}$ values in the nanomolar range II.3) Cellular Assay:Testing of Substrate Inhibition (Western Blotting)

This method enables a statement of whether the kinase modulator investigated achieves the desired effect in a cellular context too, i.e., in this case, a substrate protein downstream of the target kinase is examined for its phosphorylation status. To this end, the cells incubated with substance are lysed and the overall protein is separated on a reducing polyacrylamide gel. Subsequently, the proteins are transferred to a PVDF membrane by Western blotting and the substrate bands sought are made visible with specific antibodies and a suitable detection method. The substrate proteins downstream of the target kinases are detected simultaneously with an anti-phospho antibody which is specific in each case and a total antibody which recognizes the substrate total protein. The duplex technology of the ODYSSEY imager (LiCOR) enables this simultaneous measurement. The intensity of the total substrate bands is employed to normalize and quantify the phosphorylation inhibition or activation.

Testing

Suitable tumor cell lines (e.g. BxPC3, Hct116 or MDA MB468) were seeded into 6-well microtitre plates in a defined cell count (e.g. 350 000 cells/well for BxPC3 and Hct116) in the particular standard complete media and then incubated overnight at 37° C., 5% $CO_2$ and 95% air humidity. Afterwards, the cells were incubated for 24 h under serum-reduced conditions, i.e. in the particular medium except at only 0.25% serum. The test substances were made up as stock solutions (10 mM) in DMSO and incubated with the cells at final concentrations of 5, 15.8 and 50 µM for 5 h. This was followed by cell lysis in 25 mM Tris, 150 mM NaCl, 10 mM sodium pyrophosphate, 2 mM EGTA, 25 mM beta-glycerophosphate, 25 mM NaF, 10% glycerol, 0.75% NP-40, 100 µM $NaVO_4$ buffer. After protein quantification using the BCA (bicinchonic acid protein assay kit, Sigma) assay, amounts of protein of about 20 µg per track were separated on a Lammli polyacrylamide gel and then transferred onto a PVDF membrane (Millipore) by semi-dry Western blotting at 0.8 $mA/cm^2$ for 1 h. This was followed by prehybridization of the membrane for 1 hour in I-block reagent (Applied Biosystems) and overnight simultaneous incubation with the specific antibodies. To determine the Erk and PI3K inhibition, the next substrates Rskl downstream were detected with the total antibody (Rsk #sc-231g C-21, Santa Cruz) and the phospho antibody (Phospho-p90RSK (S380) #9341, NEB Cell Signalling) and Akt with the total antibody (Akt1 #sc-1618 C-20, Santa Cruz) and the phospho antibody (Phospho-Akt (Ser 473) #9271, NEB Cell Signaling). After the membrane had been washed, the secondary antibodies were incubated with anti-rabbit IR Dye 800 (#611-732-127, Rockland) for the phospho antibodies and anti-goat Alexa Fluor 680 (#A-21081, Molecular samples) for the total protein antibodies. After incubation for 30 min at room temperature in the dark, the hybridization of the detection antibody was detected on the membrane by scanning in an ODYSSEY imager (Li-COR).

Evaluation

At concentrations of 5-50 µM, the compounds of the invention exhibited selective inhibition of PI3K or dual inhibition of Erk (MAPK1/2) and of PI3K (see Table 3), which is indicated by inhibition of the phospho-band intensity of the downstream substrates Rsk1 and Akt.

TABLE 3

| Inhibition of cellular substrate phosphorylation (at 50 µM) | | |
|---|---|---|
| Compound | PI3K → pAkt | Erk → pRsk |
| 5 | 100% | 0% |
| 46 | 40% | 100% |
| 50 | 100% | 0% |
| 54 | 100% | 90% |
| 55 | 90% | 0% |
| 56 | 100% | 0% |

Especially, pyridopyrazines such as compound 5 show total inhibition of cellular phospho-Akt at compound concentrations <50 µM. The Raf-Mek-Erk pathway is not affected by these derivatives, as phospho-Rsk is not inhibited.

Also, pyridopyrazines, substituted by —NH-heteroaryl at the pyrazine ring (for example, compounds 50, 55 and 56), exhibit cellular PI3K selectivity, as they do not block the Raf-Mek-Erk pathway or show inhibition of phospho-Rsk respectively.

Pyridopyrazines, substituted by heteroaryl at the pyrazine ring (for example, compounds 46 and 54) exhibit a dual mode of kinase inhibition, as they inhibit both, the PI3K-Akt and the Raf-Mek-Erk-Rsk pathways.

ABBREVIATIONS

Akt from:murine Akt8 retrovirus or protein kinase B (PKB)
Ask1 apoptosis signal-regulating kinase
ATR ataxia-telangiectasia and Rad3-related
ATM ataxia-telangiectasia mutated
Bag1 Bcl-2 associated athanogene-1
Bcl-2 B-cell leukaemia/lymhoma-2 gene
DNA-PK DNA-dependent protein kinase
Erk extracellular signal-regulated kinase
Flt-3 fms like tyrosine kinase 3
GSK-3 glycogen synthase kinase-3
hSMG-1 human orthologue of product of seven nematode gene-1
JAK-3 Janus kinase 3
JNK c-jun N-terminal kinase
MAPK mitogen activated protein kinase
Mek MAP or Erk kinase
mTOR mammalian target of rapamycin
PDGFR platelet derived growth factor receptor
PI3K phosphoinositol 3-kinase
PIKK phosphoinositol 3-kinase related kinase
$PIP_2$ phosphatidylinositol biphosphate.
$PIP_3$ phosphatidylinositol triphosphate
PtdIns phosphatidylinositol
Raf rapid accelerated fibrosarcoma
Ras rat sarcoma
RTK receptor tyrosine kinase
SAPK stress-activated protein kinase
Ser serine
Syk spleen tyrosine kinase
Thr threonine
Tyr tyrosine
VEGFR vascular endothelial growth factor receptor

The invention claimed is:

1. A pyrido[2,3-b]pyrazine compound according to formula (Ia)

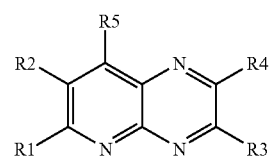

(Ia)

wherein:
R1 is thiourea substituted with cyclobutyl, ethyl, or allyl;
R2 and R5 are hydrogen;
R3 and R4 are different and are hydrogen or NR6R7, wherein R6 and R7 are different and are hydrogen or trimethoxyphenyl.

2. The pyrido[2,3-b]pyrazine compound according to claim 1, which is a stereoisomer, a geometric isomer, or a tautomer.

3. The pyrido[2,3-b]pyrazine compound of claim 1, which is 1-ethyl-3-[3-(3,4,5-trimethoxy-phenylamino)-pyrido[2,3-b]pyrazin-6-yl]-thiourea.

4. The pyrido[2,3-b]pyrazine compound of claim 1, which is 1-allyl-3-[3-(3,4,5-trimethoxy-phenylamino)-pyrido[2,3-b]pyrazin-6-yl]-thiourea.

5. The pyrido[2,3-b]pyrazine compound of claim 1, which is 1-cyclobutyl -3-[3-(3,4,5-trimethoxy-phenylamino)-pyrido[2,3-b]pyrazin-6-yl]-thiourea.

6. A composition comprising at least one compound according to claim 1; and a pharmaceutically acceptable carrier and/or pharmaceutically acceptable auxilary.

7. The composition according to claim 6, wherein the at least one compound is present in a unit dose of from 0.001 mg to 100 mg per kg of body weight of a patient.

8. A composition comprising the pyrido[2,3-b]pyrazine compound according to claim 2; and a pharmaceutically acceptable carrier and/or pharmaceutically acceptable auxilary.

9. The composition according to claim 8, wherein the compound is present in a unit dose of from 0.001 mg to 100 mg per kg of body weight of a patient.

10. A composition comprising the compound according to claim 3; and a pharmaceutically acceptable carrier and/or pharmaceutically acceptable auxilary.

11. The composition according to claim 10, wherein the compound is present in a unit dose of from 0.001 mg to 100 mg per kg of body weight of a patient.

12. The pyrido[2,3-b]pyrazine compound according to claim 3, which is a stereoisomer, a geometric isomer, or a tautomer.

13. A composition comprising the pyrido[2,3-b]pyrazine compound according to claim 12; and a pharmaceutically acceptable carrier and/or pharmaceutically acceptable auxilary.

14. The composition according to claim 13, wherein the compound is present in a unit dose of from 0.001 mg to 100 mg per kg of body weight of a patient.

15. A composition comprising the compound according to claim 4; and a pharmaceutically acceptable carrier and/or pharmaceutically acceptable auxilary.

16. The composition according to claim 15, wherein the compound is present in a unit dose of from 0.001 mg to 100 mg per kg of body weight of a patient.

17. The pyrido[2,3-b]pyrazine compound according to claim 4, which is a stereoisomer, a geometric isomer, or a tautomer.

18. A composition comprising the pyrido[2,3-b]pyrazine compound according to claim 17; and a pharmaceutically acceptable carrier and/or pharmaceutically acceptable auxilary.

19. The composition according to claim 18, wherein the compound is present in a unit dose of from 0.001 mg to 100 mg per kg of body weight of a patient.

20. A composition comprising the compound according to claim 5; and a pharmaceutically acceptable carrier and/or pharmaceutically acceptable auxilary.

21. The composition according to claim 20, wherein the at least one compound is present in a unit dose of from 0.001 mg to 100 mg per kg of body weight of a patient.

22. The pyrido[2,3-b]pyrazine compound according to claim 5, which is a stereoisomer, a geometric isomer, or a tautomer.

23. A composition comprising the pyrido[2,3-b]pyrazine compound according to claim 22; and a pharmaceutically acceptable carrier and/or pharmaceutically acceptable auxilary.

24. The composition according to claim 23, wherein the compound is present in a unit dose of from 0.001 mg to 100 mg per kg of body weight of a patient.

* * * * *